United States Patent [19]

Christensen

[11] Patent Number: 4,906,283

[45] Date of Patent: Mar. 6, 1990

[54] HERBICIDAL SULFONAMIDES

[75] Inventor: Joel R. Christensen, Wilmington, Del.

[73] Assignee: E. I. Du Pont de Nemours and Company, Wilmington, Del.

[21] Appl. No.: 186,041

[22] Filed: Apr. 25, 1988

Related U.S. Application Data

[60] Division of Ser. No. 52,611, May 21, 1987, Pat. No. 4,759,790, which is a division of Ser. No. 788,711, Oct. 23, 1985, Pat. No. 4,690,705, which is a continuation-in-part of Ser. No. 676,891, Nov. 30, 1984, abandoned.

[51] Int. Cl.$^4$ ............ A01N 43/54; C07D 239/69; C07D 401/12; C07D 409/12
[52] U.S. Cl. ............................................. 71/92; 71/90; 544/122; 544/123; 544/320; 544/321; 544/323; 544/332; 544/324; 544/331
[58] Field of Search ............... 71/92, 90; 544/122, 544/123, 320, 321, 323, 332, 324, 331

[56] References Cited

U.S. PATENT DOCUMENTS

| | | |
|---|---|---|
| 4,127,405 | 11/1978 | Levitt ............................ 71/93 |
| 4,169,719 | 10/1979 | Levitt ............................ 71/92 |
| 4,370,480 | 1/1983 | Levitt et al. ............... 544/320 |
| 4,394,506 | 7/1983 | Levitt ........................ 544/321 |
| 4,424,073 | 1/1984 | Levitt ............................ 71/92 |
| 4,481,029 | 11/1984 | Levitt ............................ 71/93 |
| 4,491,467 | 1/1985 | Petersen ........................ 71/93 |
| 4,545,808 | 10/1985 | Levitt ............................ 71/92 |
| 4,666,501 | 5/1987 | Hay et al. ..................... 71/90 |
| 4,668,279 | 5/1987 | Rorer ............................ 71/92 |

FOREIGN PATENT DOCUMENTS

| | | |
|---|---|---|
| 116518 | 8/1984 | European Pat. Off. |
| 44209 | 10/1984 | European Pat. Off. |
| 141777 | 6/1985 | European Pat. Off. |
| 161211 | 11/1985 | European Pat. Off. |
| 838416 | 5/1984 | South Africa |
| 2126586 | 3/1984 | United Kingdom |

Primary Examiner—John M. Ford

[57] ABSTRACT

This invention relates to herbicidally active sulfonamide compounds having a heterocyclic carbonyl group ortho to the sulfonyl bridge.

27 Claims, No Drawings

HERBICIDAL SULFONAMIDES

This application is a divisional application of U.S. Ser. No. 052,611 filed May 21, 1987 which is now U.S. Pat. No. 4,759,790, which is a divisional application of U.S. Ser. No. 788,711 filed Oct. 23, 1985 which is now U.S. Pat. No. 4,690,705 which is a continuation-in-part of U.S. Ser. No. 676,891 filed Nov. 30, 1984, now abandoned.

BACKGROUND OF THE INVENTION

This invention relates to herbicidally active sulfonamide compounds, agriculturally suitable compositions thereof and a method of their use as general and/or selective herbicides or plant growth regulators. More specifically, this invention relates to herbicidally active sulfonamides having an ortho-acyl group or a derivative thereof ortho to the sulfonyl bridge.

In the most common situation, the control of undesired vegetation is desired to permit the growth of useful crops such as cotton, rice, corn, wheat and soybeans, to name a few. Unchecked weed growth in such useful crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

U.S. Pat. Nos. 4,169,719 and 4,127,405 disclose herbicidal benzenesulfonamides having a substituent ortho to the sulfonyl group.

U.S. Pat. No. 4,370,480 discloses herbicidal benzenesulfonamides of formula

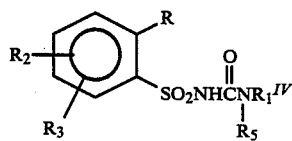

wherein
R is

T is O; and
R is alkyl or substituted alkyl.

U.S. Pat No. 4,481,029 discloses, in part, thiophenesulfonamides of formula

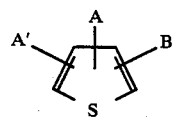

wherein
A is

$R^{II}$ is alkyl, alkenyl, phenyl, benzyl or substituted phenyl or benzyl; and
B is

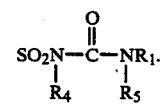

U.S. Pat. No. 4,491,467 discloses, in part, herbicidal benzenesulfonamides of formula

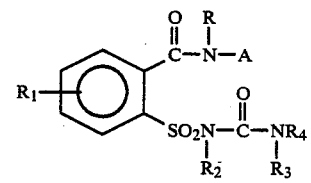

wherein
A is a 5- or 6-membered aromatic heterocycle, a 5-or 5-membered dihydroaromatic heterocycle or a 6-membered tetrahydroaromatic heterocycle which contains 1-4 heteroatoms selected from 0-1 oxygen atoms, 0-1 sulfur atoms, and/or 0-4 nitrogen atoms; the heterocycles may be optionally substituted with 1-4$CH_3$, 1-2$OCH_3$, 0-1 $SCH_3$, 0-1 Cl, 0-1 $N(CH_3)_2$ or 0-1 CN groups.

U.S. Pat. No. 4,394,506 discloses, in part, herbicidal sulfonylureas of the formula

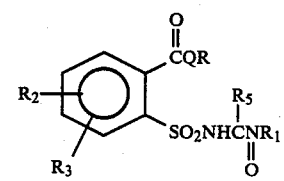

wherein
Q is O, S or $NR_6$;
R is H, $C_1$-$C_{12}$ alkyl, etc.;
$R_6$ is H, $C_1$-$C_6$ alkyl, allyl, etc.; or
R and $R_6$ can be taken together to form $-(CH_2)_4-$, $-(CH_2)_5-$, $-(CH_2)_6-$, $-CH_2CH_2OCH_2CH_2-$ or $-CH_2CH_2NCH_2CH_2-$.
$\phantom{-CH_2CH_2OCH_2CH_2- or -CH_2CH_2N}|$
$\phantom{-CH_2CH_2OCH_2CH_2- or -CH_2CH_2N}CH_3$ South African Patent Application No. 83/8416 (published 5/12/84; Swiss priority 11/12/82) discloses herbicidal sulfonylureas of formula

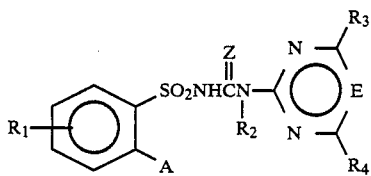

wherein, in part,
A is an unsaturated or only partially saturated 5- or 6-membered heterocyclic ring system which is bonded through a carbon atom and contains 1, 2 or 3 heteroatoms and which may be substituted by $C_1$-$C_4$ alkyl, $C_1$-$C_4$ haloalkyl, $C_1$-$C_4$ alkoxy, $C_1$-$C_4$ alkylthio, $C_2$-$C_8$ alkoxyalkyl, di($C_1$-$C_4$ alkyl)amino, halogen, cyano or nitro.

EP-A-141,777 (published 5/15/85; Swiss priority 9/9/83) discloses herbicidal sulfonylureas of the formula

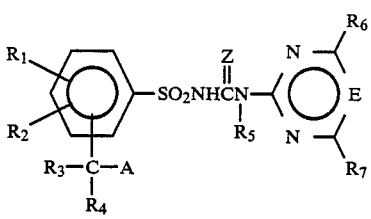

wherein
$R_3$ is H, alkyl, haloalkyl or CN;
$R_4$ is H or alkyl;
A is $Y(CH_2)_nR_{17}$ or

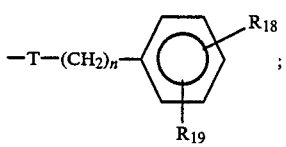

Y is O, S or a single bond;
n is 0 or 1; and
$R_{17}$ is a 5- or 6-membered saturated heterocycle.

EP-A-116,518 (published 8/22/84; Swiss priority 2/4/83) discloses herbicidal sulfonylureas of the formula

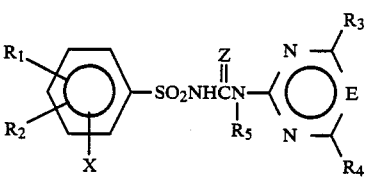

wherein
X is $NR_6R_7$, $N(SO_2R_9)_2$ or

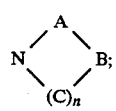

A is CO, $SO_2$, $CONR_{23}$ or $CO_2$;
B is $C_1$-$C_4$ alkylene or $C_2$-$C_4$ alkylene; and
C is CO, $CR_{21}R_{22}$ or $SO_2$.

SUMMARY OF THE INVENTION

This invention comprises novel compounds of Formula I, agriculturally suitable compositions containing them and their method-of-use as general and/or selective preemergent and/or post-emergent herbicides or plant growth regulants.

$$JSO_2NHC(W)NA \quad \text{I}$$
$$\phantom{JSO_2NHC(W)N}R$$

wherein
W is O or S;
J is

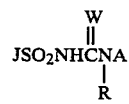 J-1

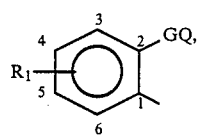 J-2

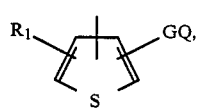 J-3

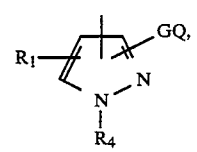 J-4

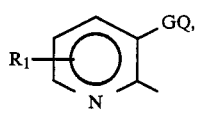 J-5

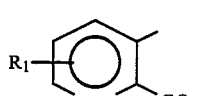 J-6

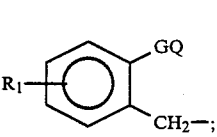

Q is a saturated 5- or 6-membered ring containing 1 or 2 heteroatoms selected from 0–1 oxygen, 0–1 sulfur and 0–1 nitrogen, or Q is an unsaturated or partially unsaturated 5- or 6-membered ring containing 1–3 heteroatoms selected from 0–1 sulfur, 0–1 oxygen and 0–3 nitrogen; or Q is a saturated 3- or 4-membered heterocyclic ring containing one nitrogen atom and is bonded to G through said nitrogen; and Q may be optionally substituted by 1–4 groups selected from L;

G is a $C_1$-$C_3$ alkyl radical in which one of the carbons must be substituted with $R_2$ and/or $R_3$, and the remaining carbon atoms may optionally be substituted with 1 or 2 substituents selected from $CH_3$, F and Cl;

R is H or $CH_3$;

$R_1$ is H, $C_1$–$C_3$ alkyl, $C_1$–$C_3$ haloalkyl, halogen, nitro, $C_1$–$C_3$ alkoxy, $SO_2NR^IR^{II}$, $C_1$–$C_3$ alkylthio, $C_1$–$C_3$ alkylsulfinyl, $C_1$–$C_3$ alkylsulfonyl, $CO_2R^{III}$, $CH_2OCH_3$, $CH_2SCH_3$, $CH_2CN$, $NH_2$, $NHCH_3$ or $N(CH_3)_2$;

$R_2$ is OH, $OCH_3$ or $OC_2H_5$;

$R_3$ is $OCH_3$ or $OC_2H_5$; or $R_2$ and $R_3$ can be taken together to form a carbonyl group, or the 5- or 6-membered ring ketal or thioketal thereof;

$R^I$ is H, $C_1$–$C_4$ alkyl, $C_2$–$C_3$ cyanoalyl, methoxy or ethoxy;

$R^{II}$ is H, $C_1$–$C_4$ alkyl or $C_3$–$C_4$ alkenyl; or $R^I$ and $R^{II}$ may be taken together as $-(CH_2)_3-$, $-(CH_2)_4-$, $-(CH_2)_5-$ or $-CH_2CH_2OCH_2CH_2-$;

$R^{III}$ is $C_1$–$C_4$ alkyl, $C_3$–$C_4$ alkenyl, $C_3$–$C_4$ alkynyl, $C_2$–$C_4$ haloalkyl, $C_2$–$C_3$ cyanoalkyl, $C_5$–$C_6$ cycloalkyl, $C_4$–$C_7$ cycloalkylalkyl or $C_2$–$C_4$ alkoxyalkyl;

L is $C_1$–$C_4$ alkyl, $C_1$–$C_3$ haloalkyl, halogen, $C_1$–$C_3$ alkoxy, $C_1$–$C_3$ alkylthio, $C_3$–$C_4$ alkenyloxy, $C_3$–$C_4$ alkenylthio, $C_1$–$C_2$ haloalkoxy or $C_1$–$C_2$ haloalkylthio;

A is

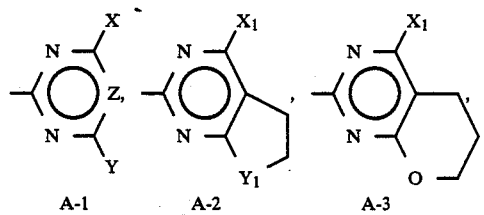

A-1  A-2  A-3

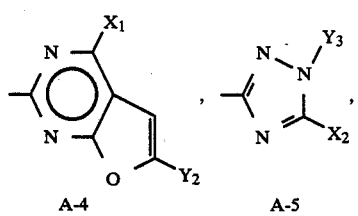

A-4  A-5

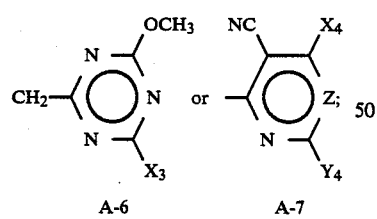

A-6  A-7

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_1$–$C_4$ haloalkyl, $C_3$–$C_5$ cycloalkyl, $C_2$–$C_4$ alkynyl, $C(O)R_4$,

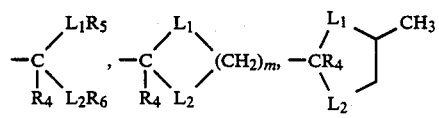

or $N(OCH_3)CH_3$;

m is 2 or 3;

$L_1$ and $L_2$ are independently O or S;

$R_5$ and $R_6$ are independently $C_1$–$C_2$ alkyl;

$R_4$ is H or $CH_3$;

Z is CH or N;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$;

$Y_3$ is $CH_3$, $CH_2CH_3$ or $CH_2CF_3$;

$X_3$ is $CH_3$ or $OCH_3$;

$X_4$ is $CH_3$, $OCH_3$, $OC_2H_5$, $CH_2OCH_3$ or Cl; and $Y_4$ is $CH_3$, $OCH_3$ or $OC_2H_5$;

and their agriculturally suitable salts; provided that (a) when X is Cl, F, Br or I, then Z is CH and Y is $OCH_3$, $OCH_2CH_3$, $N(OCH_3)CH_3$, $NHCH_3$, $N(CH_3)_2$ or $OCF_2H$;

(b) when X or Y is $OCF_2H$, then Z is CH;

(c) when J is J-2 or J-3, then GQ and the sulfonylurea bridge must be on adjacent carbon atoms;

(d) when Q is bonded to G through nitrogen, then the adjacent carbon atom of G cannot be substituted with OH, F or Cl;

(e) when G is $C_1$ alkyl in the form of a carbonyl group, then Q is other than

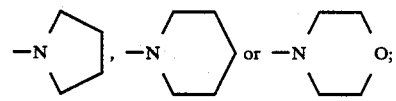

(f) when the total number of carbon atoms of X and Y is greater than four, then the total number of carbon atoms of $R_1$ and GQ must be less than or equal to ten;

(g) when W is S, then A is A-1, R is H, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$ or $CH(OCH_3)_2$; and (h) when $R_3$ is $OCH_3$ or $OC_2H_5$, then $R_2$ is other than OH.

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy or isopropoxy.

Alkenyl denotes straight chain or branched alkenes, e.g., vinyl, 1-propenyl, 2-propenyl, 3-propenyl or the different butenyl isomers.

Alkynyl denotes straight chain or branched alkynes, e.g., ethynyl, 1-propynyl, 2-propynyl and the different butynyl isomers.

Alkylsulfonyl denotes methylsulfonyl, ethylsulfonyl or the different propylsulfonyl isomers.

Alkylthio, alkylsulfinyl, alkylamino, etc. are defined in an analogous manner.

Cycloalkyl means cyclopropyl, cyclobutyl or cyclopentyl.

The term "halogen", either alone or in compound words such as "haloalkyl", denotes fluorine, chlorine, bromine or iodine.

The total number of carbon atoms in a substituent group is indicated by the $C_i$-$C_j$ prefix where i and j are numbers from 1 to 7. For example, $C_1$-$C_3$ alkylsulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$. The term $C_4$-$C_7$ cycloalkylalkyl is meant to define cyclopropylmethyl through cyclohexylmethyl or cyclopropylbutyl and the various structural isomers embraced therein.

Compounds preferred for reasons of increased ease of synthesis and/or greater herbicidal efficacy are:

(1) Compounds of Formula I where
W is O; and
R is H;

(2) Compounds of Preferred 1 where Q is

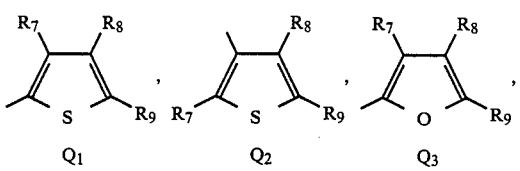

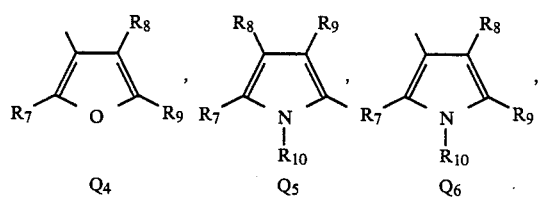

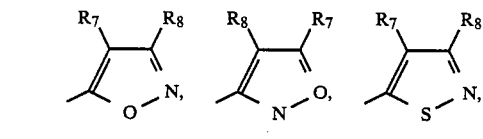

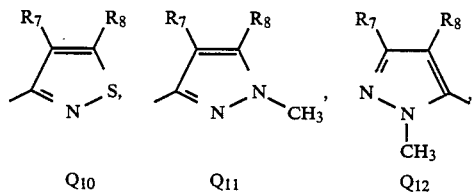

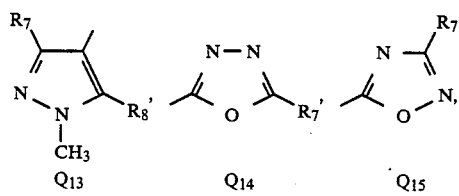

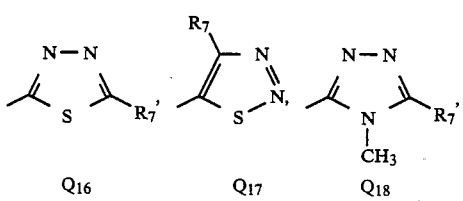

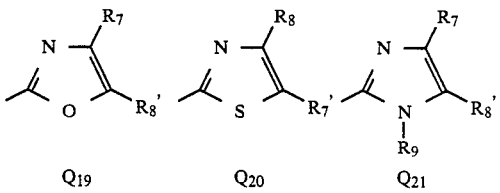

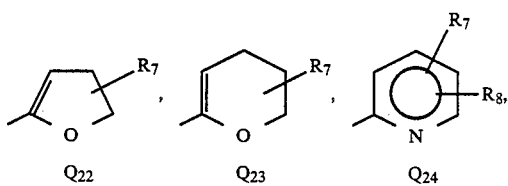

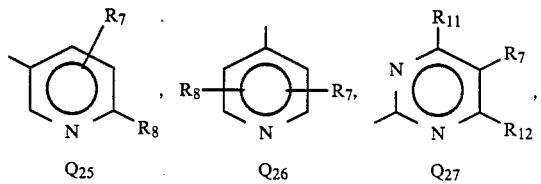

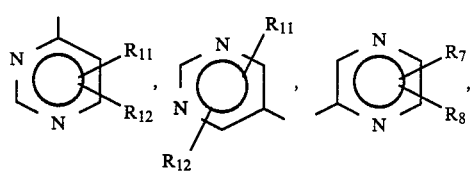

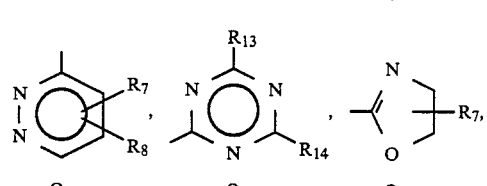

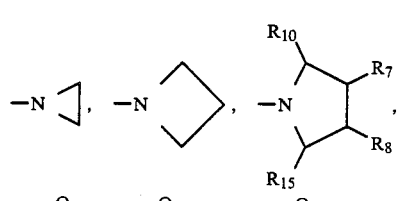

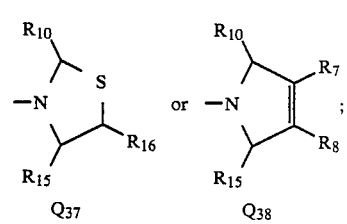

$R_7$, $R_8$ and $R_9$ are independently R, $CH_3$, Cl or Br;
$R_{10}$, $R_{15}$ and $R_{16}$ are independently H or $CH_3$;
$R_{11}$ and $R_{12}$ are independently H, $CH_3$ or $OCH_3$; and
$R_{13}$ and $R_{14}$ are independently $CH_3$ or $OCH_3$;

(3) Compounds of Preferred 2 where
G is a carbonyl group, or is a single carbon atom substituted with OH, $OCH_3$ or $OC_2H_5$; and
$R_1$ is H, $CH_3$, $OCH_3$, $SCH_3$, $SO_2CH_3$, F, Cl, Br, $NO_2$, $CH_2CN$, $CF_3$ or $OCF_2H$;

(4) Compounds of Preferred 3 where
X is CH$_3$, OCH$_3$, OCH$_2$CH$_3$, Cl, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br; and
Y is H, C$_1$-C$_3$ alkyl, OCH$_3$, OC$_2$H$_5$, CH$_2$OCH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, SCF$_2$H, C(O)R$_4$,

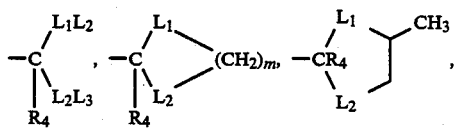

OCF$_2$H, cyclopropyl, C≡CH or C≡CCH$_3$;
(5) Compounds of Preferred 4 where
A is A-1;
R$_1$ is H, CH$_3$, OCH$_3$, SCH$_3$ or Cl; and
G is a carbonyl group or a single carbon atom substituted with OH;
(6) Compounds of Preferred 5 where
X is CH$_3$, OCH$_3$, Cl or OCF$_2$H; and
Y is CH$_3$, OCH$_3$, C$_2$H$_5$, CH$_2$OCH$_3$, CH(CH$_3$)$_2$, NHCH$_3$, CH(OCH$_3$)$_2$ or cyclopropyl;
(7) Compounds of Preferred 6 where
J is J-1; and
R$_1$ is in the 5-position;
(8) Compounds of Preferred 6 where
J is J-2; and
R$_1$ is H;
(9) Compounds of Preferred 6 where
J is J-3; and
R$_1$ is H;
(10) Compounds of Preferred 6 where
J is J-4; and
R$_1$ is H;
(11) Compounds of Preferred 6 where
J is J-5; and
R$_1$ is H;
(12) Compounds of Preferred 6 where
J is J-6; and
R$_1$ is H;
(13) Compounds of Preferred 7 where Q is Q$_1$;
(14) Compounds of Preferred 7 where Q is Q$_2$;
(15) Compounds of Preferred 7 where Q is Q$_3$;
(16) Compounds of Preferred 7 where Q is Q$_4$;
(17) Compounds of Preferred 7 where Q is Q$_5$;
(18) Compounds of Preferred 7 where Q is Q$_6$;
(19) Compounds of Preferred 7 where Q is Q$_7$;
(20) Compounds of Preferred 7 where Q is Q$_8$;
(21) Compounds of Preferred 7 where Q is Q$_9$;
(22) Compounds of Preferred 7 where Q is Q$_{10}$;
(23) Compounds of Preferred 7 where Q is Q$_{11}$;
(24) Compounds of Preferred 7 where Q is Q$_{12}$;
(25) Compounds of Preferred 7 where Q is Q$_{13}$;
(26) Compounds of Preferred 7 where Q is Q$_{14}$;
(27) Compounds of Preferred 7 where Q is Q$_{15}$;
(28) Compounds of Preferred 7 where Q is Q$_{16}$;
(29) Compounds of Preferred 7 where Q is Q$_{17}$;
(30) Compounds of Preferred 7 where Q is Q$_{18}$;
(31) Compounds of Preferred 7 where Q is Q$_{19}$;
(32) Compounds of Preferred 7 where Q is Q$_{20}$;
(33) Compounds of Preferred 7 where Q is Q$_{21}$;
(34) Compounds of Preferred 7 where Q is Q$_{22}$;
(35) Compounds of Preferred 7 where Q is Q$_{23}$;
(36) Compounds of Preferred 7 where Q is Q$_{24}$;
(37) Compounds of Preferred 7 where Q is Q$_{25}$;
(38) Compounds of Preferred 7 where Q is Q$_{26}$;
(39) Compounds of Preferred 7 where Q is Q$_{27}$;
(40) Compounds of Preferred 7 where Q is Q$_{28}$;
(41) Compounds of Preferred 7 where Q is Q$_{29}$;
(42) Compounds of Preferred 7 where Q is Q$_{30}$;
(43) Compounds of Preferred 7 where Q is Q$_{31}$;
(44) Compounds of Preferred 7 where Q is Q$_{32}$;
(45) Compounds of Preferred 7 where Q is Q$_{33}$;
(46) Compounds of Preferred 7 where Q is Q$_{34}$;
(47) Compounds of Preferred 7 where Q is Q$_{35}$;
(48) Compounds of Preferred 7 where Q is Q$_{36}$;
(49) Compounds of Preferred 7 where Q is Q$_{37}$;
(50) Compounds of Preferred 7 where Q is Q$_{38}$;

Also preferred are compounds of Formula I wherein
Q is a saturated 5- or 6-membered ring which is bonded through a carbon atom and contains 1 heteroatom selected from oxygen or sulfur, or an unsaturated or partially unsaturated 5- or 6-membered ring which is bonded through a carbon atom and contains 1-3 heteroatoms selected from 0-1 sulfur, 0-1 oxygen or 0-3 nitrogen; and Q may be optionally substituted by 1-4 groups selected from L;
G is a carbonyl group or CHR$_2$;
R$_1$ is H, C$_1$-C$_3$ alkyl, C$_1$-C$_3$ haloalkyl, halogen, nitro, C$_1$-C$_3$ alkoxy, SO$_2$NR$^I$R$^{II}$. C$_1$-C$_3$ alkylthio, C$_1$-C$_3$ alkylsulfinyl, C$_1$-C$_3$ alkylsulfonyl or CO$_2$R$^{III}$; and
A is A-1, A-2, A-3, A-4, A-5 or A-6.

The most preferred compounds for reasons of greatest ease of synthesis and/or greatest herbicidal efficacy are: N-[(4,6-dimethoxypyrimidin-2-yl)aminocarbonyl]-2-(2-thienylcarbonyl)benzenesulfonamide, m.p. 173°-177° C.; N-[(4-methoxy-6-methyl-1,3,5-triazin-2-yl)aminocarbonyl]-2-(2-thienylcarbonyl)benzenesulfonamide, m.p. 181°-188° C.; and N-[(4,6-dimethoxypyrimidin-2-yl)aminocarbonyl]-2-[hydroxy(2-thienyl)methyl]benzenesulfonamide, m.p. 152°-154° C.

DETAILED DESCRIPTION OF THE INVENTION

Synthesis

Compounds of Formula I can be synthesized by one or both of the methods shown below in Equation 1 and 2.

Equation 1 illustrates the reaction of sulfonyl isocyanates II with the appropriate heterocyclic amines of Formula III to give the desired sulfonylureas I.

Equation I

wherein
J, R, and A are as previously defined provided R$_2$ is not OH.

The reaction of Equation 1 is best carried out in an inert aprotic solvent such as methylene chloride, tetrahydrofuran or acetonitrile at a temperature between 0° and 82° C. A catalytic amount of 1,4-diaz abicyclo[2,2,2]octane (DABCO) may be used to accelerate the reaction. In cases in which the products are insoluble in the reaction solvent, they may be isolated by simple filtration. When the products are soluble, they can be isolated by evaporation of the solvent and trituration of the residue with solvents such as 1-chlorobutane, diethyl ether or ethyl acetate, and filtration.

Compounds of Formula I can be prepared as shown below in Equation 2 by the reaction of sulfonamides IV with the phenyl ester of the appropriate carbamic acid, V, in the presence of an equimolar quantity of a tertiary amine base such as 1,8-diazabicyclo[5.4.0]undec-7-ene (DBU) when X is H, or an equimolar quantity of fluoride ion when X is Si(CH$_3$)$_2$(t—C$_4$H$_9$).

Equation 2

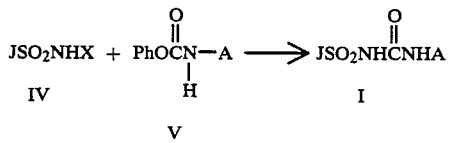

X = H, Si(CH$_3$)$_2$(t-C$_4$H$_9$)

when X is H, the methods described in U.S. Pat. No. 4,443,245 are employed. When X is Si(CH$_3$)$_2$-(t—C$_4$H$_9$) the reaction is best carried out at 0° C. in acetonitrile with one equivalent of a fluoride ion source such as tetrabutylammonium fluoride or cesium fluoride. The desired products of Formula I can be conveniently isolated by acidifying the reaction solution with aqueous hydrochloric acid and filtering.

A judicious choice of the appropriate methods for preparing compounds of Formula I must take into account the nature of the substituents contained within the J values (J$_1$–J$_6$), namely Q and R$_1$, and their chemical compatability with the reaction conditions of Equations 1 and 2.

Sulfonyl isocyanates of Formula II can be prepared as shown in Equation 3 by the reaction of sulfonamides of the general structure IV with phosgene in the presence of n-butyl isocyanate and a catalytic amount of 1,4-diazabicyclo[2.2.2]octane (DABCO).

Equation 3

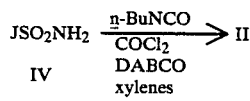

wherein
J is as previously defined, provided R$_2$ is not OH.

The reaction depicted in Equation 3 is best carried out according to the procedure described in U.S. Pat. No. 4,238,621.

Alternatively, sulfonyl isocyanates II can be prepared via phosgenation of the preformed n-butylureas of Formula VI as represented in Equation 4.

Equation 4

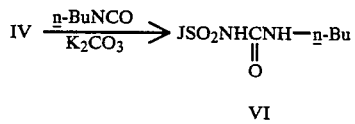

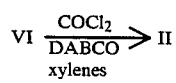

wherein
J is as previously defined, provided R$_2$ is not OH.

The compounds of Formula VI are conveniently prepared by stirring a mixture of the appropriate sulfonamide IV, anhydrous potassium carbonate, and n-butyl isocyanate in a suitable solvent such as acetone or methyl ethyl ketone at 25° to 80° C. until all of the isocyanate has reacted. The products are isolated by quenching in dilute aqueous acid and recrystallizing the insoluble solid. The n-butylureas VI are then treated with phosgene and a catalytic amount of DABCO in refluxing xylenes or chlorobenzene in a manner analogous to that described in the reference cited for Equation 3.

Alternatively, treatment of the sulfonamides of Formula IV with thionyl chloride gives intermediate N-sulfinylsulfonamides VII, which afford sulfonylisocyanates II upon exposure to phosgene in the presence of a catalytic amount of pyridine.

Equation 5

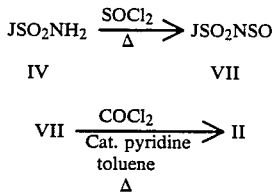

wherein
R$_2$ is not OH.

The reaction of Equation 5 can best be performed according to the procedure of H. Ulrich, B. Tucker and A. Sayigh, *J. Org. Chem.*, 34, 3200 (1969).

A judicious choice of the appropriate method for preparing compounds of Formula II must take into account the nature of the substituents contained within the J values (J$_1$–J$_6$), namely Q and R$_1$, and their chemical compatability with reaction conditions of Equation 3–5.

The required sulfonamides of Formula IV can be synthesized by one or more of the methods shown below in Equations 6, 7 and 8.

Equation 6 depicts the reaction of sulfonyl chlorides of Formula VIII with ammonia to give sulfonamides of Formula IVa.

Equation 6

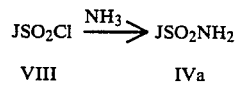

wherein
J is as previously defined.

The amination of Equation 6 can be effected by adding at least two molar equivalents of either anhydrous ammonia or concentrated ammonium hydroxide to a solution of the sulfonyl chloride VIII in a solvent such as diethyl ether, methylene chloride, or tetrahydrofuran at temperatures between −30° and 25° C. The sulfonamides of Formula IVa are isolated either by filtration, in which case the ammonium chloride by-product is removed by washing with water, or extraction into an organic solvent such as methylene chloride. Drying and evaporation of the solvent affords the sulfonamides IVa, which are usually sufficiently pure to be carried directly on to the next step.

Sulfonamides of Formula IVb can be prepared as depicted in Equation 7 by treatment of the corresponding N-t-butylsulfonamides IX with an appropriate acid such as trifluoroacetic (TFA), polyphosphoric (PPA), or p-toluenesulfonic acid (p-TSA).

Equation 7

$$JSO_2NH-\underline{t}-Bu \xrightarrow[p-TSA]{TFA, PPA \text{ or}} JSO_2NH_2$$

$$IX \qquad\qquad\qquad IVb$$

wherein

J is as previously defined, provided $R_2$ is not OH.

The reaction of Equation 7 is conveniently carried out by stirring a solution of the compound of Formula IX in excess trifluoracetic acid (approximately 0.3M) at about 25° C. for 1-24 hours. The desired sulfonamides of Formula IVb are then isolated by removal of the volatiles in vacuo and recrystallization from a solvent such as ethyl acetate, diethyl ether, or 1-chlorobutane. Alternatively, the N-t-butylsulfonamides of Formula IX can be treated with a catalytic amount of p-toluene sulfonic acid monohydrate in a solvent such as toluene or xylenes at reflux temperature for 1-6 hours. The desired products are then isolated in a manner analogous to the one described above. For use of PPA in the deprotection of N-t-butylsulfonamides, see J. G. Lombardino, *J. Org. Chem.*, 36, 1843 (1971); for use of TFA, see J. O. Catt and W. L. Matier, *J. Org. Chem.*, 39, 566 (1974).

The carbinol sulfonamides of Formula IVd can be prepared by reduction of the corresponding ketosulfonamides IVc with lithium or sodium tetrahydridoborate. The carbinols, IVd, can be alkylated with iodomethane or ethane under basic conditions using conventional procedures. Equation 8 depicts these reactions.

Equation 8

$$JSO_2NH_2 \xrightarrow{LiBH_4 / THF} JSO_2NH_2$$

$$IVc \qquad\qquad\qquad IVd$$

$$(R_2/R_3 \text{ are } C=O) \qquad (R_2 = OH, R_3 = H)$$

$$IVd \xrightarrow[CH_3I \text{ or } CH_3CH_2I]{2 \text{ eq. base (NaOH, NaH, etc.)}} J-SO_2NH_2$$

$$IVe$$

$$(R_2 \text{ is } OCH_3 \text{ or } OCH_2CH_3, R_3 \text{ is } H)$$

wherein

J is as previously defined.

The reaction of Equation 8 is best carried out by the addition of lithium or sodium tetrahydridoborate to a solution of compounds of Formula IVc dissolved in tetrahydrofuran. After stirring at room temperature for 0.25 to 2 hours, the reaction mixture is quenched with water, acidified with aqueous hydrochloric acid, and extracted with methylene chloride. The organic layer is washed with saturated sodium bicarbonate, dried, and evaporated to afford the sulfonamides IVd, which are usually sufficiently pure to be carried directly on to the next step.

Sulfonyl chlorides of Formula VIII can be prepared by one or more of the methods shown below in Equations 9, 10, 11 and 12.

Diazotization of appropriately substituted aniline derivatives of Formula X, as shown in Equation 9, and subsequent coupling with sulfur dioxide in the presence of either cupric or cuprous chloride give the desired products of Formula VIII.

Equation 9

$$J-NH_2 \xrightarrow[(2) SO_2, CuCl_2 \text{ or } CuCl, HOAc]{(1) NaNO_2, HCl} JSO_2Cl$$

$$X \qquad\qquad\qquad VIII$$

wherein

J is $J_1-J_5$.

The reaction of Equation 9 can be affected by analogous methods described in EP-A-Nos. 83,975 and 85,476 (published Aug. 10, 1983). In Equation 9, a substituted aniline X, in concentratred hydrochloric acid is treated with a solution of sodium nitrate in water at −5° to 5° C. After being stirred for 10-30 minutes at about 0° C., the solution is added to a mixture of excess sulfur dioxide and a catalytic amount of cupric or cuprous chloride in acetic acid at about 10° C. After stirring for 0.25 to 24 hours at temperatures between 10° to 25° C., the solution is poured into a large excess of ice water. The sulfonyl chlorides VIII can be isolated by filtration, or by extraction into a solvent such as methylene chloride or diethyl ether, followed by drying and evaporation of the solvent.

Sulfonyl chlorides of Formula VIIIa can be prepared as shown below in Equation 10 by metal halogen exchange or directed lithiation of appropriately substituted aryl or heterocyclic substrates XI, and trapping with sulfuryl chloride.

Equation 10

$$J-Br \xrightarrow[\substack{-78° C. \\ (2) SO_2Cl_2/\text{Hexanes}}]{(1) \underline{n}-BuLi; Et_2O \text{ or } THF} JSO_2Cl$$

$$(H)$$

$$XI \qquad\qquad\qquad VIIIa$$

wherein

J is as previously described provided that the combination of $R_2$ and $R_3$ is not C=O and $R_1$ is not $CO_2R^{III}$.

The lithiation shown in Equation 10 can be performed according to the procedure of S. H. Bhattacharya, et al., *J. Chem. Soc.* (C), 1265 (1968) or by procedures reviewed by H. Gschwend and H. Rodriquez in *Organic Reactions*, Vol. 26, Wiley, N.Y., 1979, and references cited within.

Compounds of Formula VIII can be prepared via oxidative chlorination of the appropriate thioethers of Formula XII as represented in Equation 11.

Equation 11

$$J-SR_{17} \xrightarrow[H_2O, HOAC]{Cl_2} JSO_2Cl$$

$$XII \qquad\qquad\qquad VIII$$

wherein

J is as previously defined and $R_{15}$ is $C_2$–$C_4$ alkyl or benzyl and $R_1$ is not $C_1$–$C_3$ alkylthio or $C_1$–$C_3$ alkylsulfinyl and $R_2$ is not OH.

The reaction of Equation 11 can be carried out by treating a solution of the thioether XII in a solvent such as acetic acid in the presence of at least 2.5 equivalents of water and at least 3.0 equivalents of chlorine at 0°–30° C. for 0.25 to 5 hours. The reaction is poured into ice-water and the product is isolated by extraction with a suitable solvent such as methylene chloride, dried, and the solvent evaporated to yield a product sufficiently pure to be carried directly on to the next step.

Benzenemethanesulfonyl chlorides of Formula VIIIb ($J=J_6$) can be prepared from appropriately substituted benzyl chlorides or bromides of Formula XIII by a simple two-step procedure outlined in Equation 12.

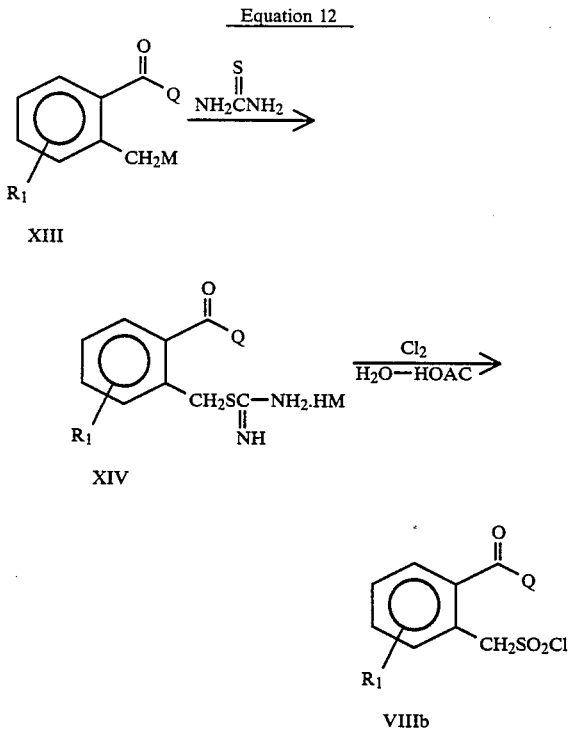

wherein
$R_1$ and Q are as previously defined except $R_1$ is not $C_1$–$C_3$ alkylthio or $C_1$–$C_3$ alkylsulfinyl, and M is Cl or Br.

The conversion of alkyl halides of Formula XIII to isothiouronium salts of Formula XIV can be carried out by the procedure or T. B. Johnson and J. M. Sprague, *J. Am. Chem. Soc.*, 58, 1348 (1936); 59 1837 and 2439 (1937); 61 176 (1939). Oxidative chlorination of isothouronium salts such as XIV to afford sulfonyl chlorides of Formula VIIIb is best carried out according to the procedure of Johnson as described in *J. Am. Chem. Soc.*, 61, 2548 (1939).

The requisite aniline derivatives of Formula X can be prepared by reduction of the corresponding nitro compounds of Formula XV as depicted in Equation 13.

Equation 13

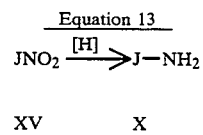

XV          X wherein
J is as previously described.

The reduction reactions of Equation 13 can be accomplished by methods known in the literature by those skilled in the art. For details see, for example, EP-A No. 83,975 and references cited therein.

The required thioethers of Formula XII can be prepared by nucleophilic displacement of activated halo or nitro compounds of Formula XVI by the sodium or potassium salt of the appropriate mercaptan as depicted in Equation 14.

Equation 14

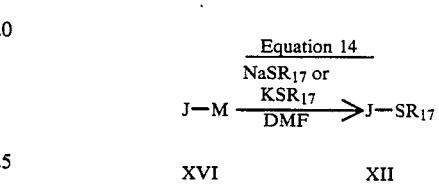

XVI          XII wherein
J is as previously defined provided that the carbonyl moiety of G is directly attached to J and/or $R_1$ is a sufficiently strong electron with drawing group to promote displacement. $R_{17}$ is $C_2$–$C_4$ alkyl or benzyl and M is Cl, Br or $NO_2$.

The reaction of Equation 14 can be accomplished by the addition of compounds of Formula XVI to a solution of the mercaptide salt, prepared by the action of a base such as sodium hydroxide or potassium t-butoxide on the corresponding mercaptan in dimethylformamide, at temperatures between 0° and 100° C. for 1 to 72 hours. The reaction mixture is poured into ice-water and the product isolated by filtration or by extraction into a suitable solvent such as diethyl ether or methylene chloride followed by drying and evaporation of the solvent. If necessary, purification can be effected by recrystallization, vacuum distillation or chromatographic procedures.

The benzyl halides of Formula XIII can be prepared as shown below in Equation 15 by treatment of the appropriately substituted toluene derivatives XVII, with either N-bromosuccinimide (NBS) or N-chlorosuccinimide (NCS).

Equation 15

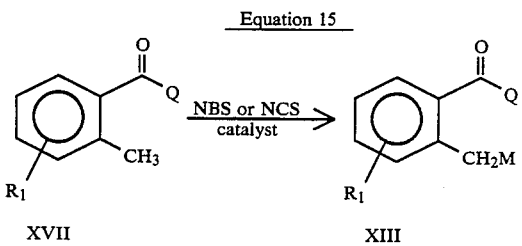

XVII          XIII wherein
G and $R_1$ are as previously defined except $R_1$ is not $C_1$–$C_3$ alkylthio or $C_1$–$C_3$ alkylsulfinyl, M is Br or Cl.

The reaction of Equation 15 can be conveniently carried out by heating a solution of XVII and N- bromosuccinimide or N-chlorosuccinimide in a suitable solvent such as carbon tetrachloride at reflux temperature. A free radical catalyst such as azoisobutyronitrile or benzoyl peroxide is usually employed to initiate the reaction, when complete, the cooled solution is filtered to remove the by-product succinimide and the filtrate concentrated in vacuo. The benzyl halides are normally obtained sufficiently pure for further transformation, however, may be purified by procedures known to those skilled in the art.

The compounds of Formula XVI, where $R_2$ and $R_3$ are taken together to form carbonyl, can be synthesized by one or more of the following methods depicted in Equations 16, 17, 18, 19 and 20.

Equation 16 depicts a Friedel-Crafts acylation procedure which can be utilized to prepare compounds of Formula XV and XVI, where J is $J_1$, $J_2$ and $J_3$.

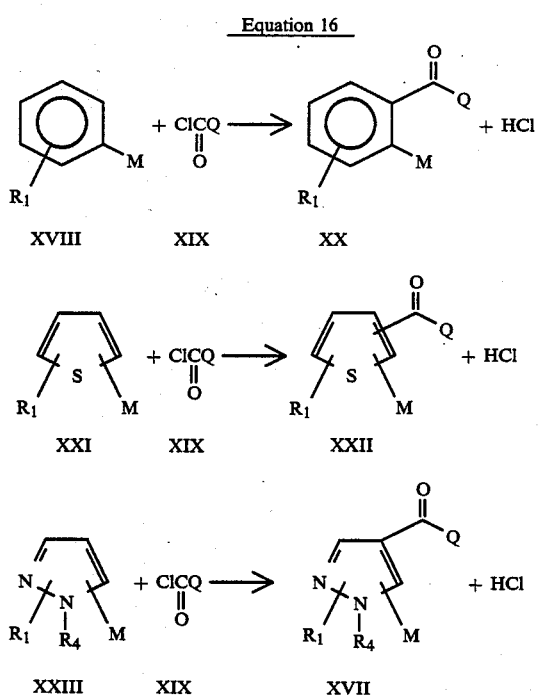

wherein
$R_1$ and $R_4$ are as previously defined;
Q is $Q_1-Q_{21}$, $Q_{24}-Q_{32}$ and $Q_{34}-Q_{38}$;
M is Cl, Br or $NO_2$.

The acylation reactions depicted in Equation 16 can be carried out utilizing the heterocyclic acid chlorides of Formula XIX by one or more of the numerous procedures reviewed in *Friedel-Crafts and Related Reactions* (G. A. Olah, ed.) Vol. 3, pp. 1–381, Interscience, New York, 1964 and references cited within. Depending upon the procedure, the free carboxylic acid of Formula XIX can also be employed. The C-acylation of 1,3-dialkylpyrazole and pyrazolones can best be carried by procedures taught by D. E. Butler and H. A. DeWald in *J. Org. Chem.*, 36, 2542–2547 (1971) and by H. A. DeWald, S. Lobbestael, and B. P. H. Poshel in *J. Med. Chem.*, 24, 982–987 (1981). Depending on the substitution pattern of compounds of Formulae XVIII, XXI and XXIII, the acylations depicted in Equation 16 can give rise to isomeric products. Isomer separation can be effected by procedures known to those skilled in the art.

The compounds of Formulae XVIII, XIX, XXI and XXIII may be prepared according to literature methods known in the art, such as those reviewed in *The Chemistry of Heterocyclic Compounds*, a series published by Interscience Publ., New York and London, the teachings of which are incorporated herein by reference.

Analogously, a reversed component acylation can be employed as illustrated in Equation 17 for the preparation of XX.

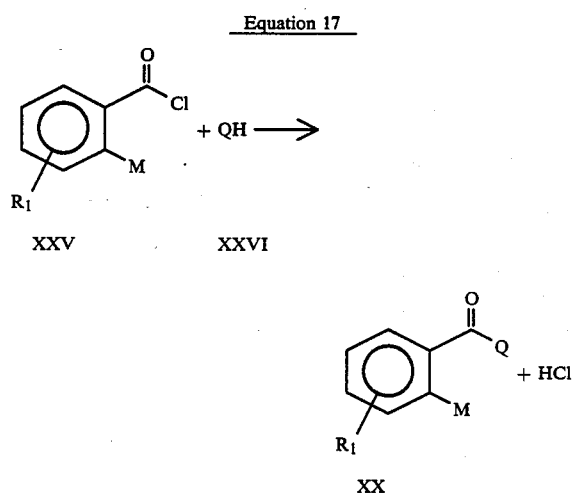

wherein
$R_1$ is as previously described, Q is $Q_1$, $Q_3$ $Q_6$ and $Q_{34}-Q_{38}$; M is Cl, Br or $NO_2$.

The schemes outlined in equations 16 and 17 can be employed for the synthesis of compounds of general Formula XVI provided that the carbonyl moiety contained in the alkyl bridge, as defined by G, is directly attached to Q or the aromtic nucleus to which the sulfonylurea bridged is attached.

U.S. Pat. No. 4,394,506 describes the preparation of ortho-amide type sulfonylureas. With slight modifications, the procedures describe therein can be utilized to prepare compounds of the Formula I where Q is $Q_{34}-Q_{38}$.

As an alternate to the acylation procedures described in Equation 16 and 17, phenyl or heterocyclic lithium reagents can be reacted with heterocyclic aldehydes to give intermediate carbinols, which upon oxidation affords ketones of Formula XXX.

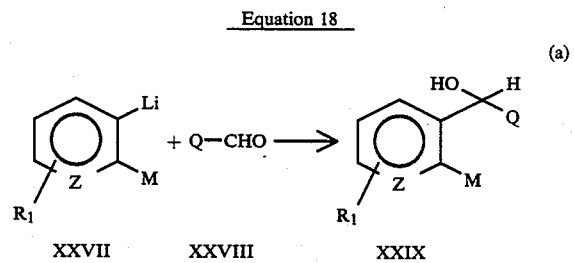

-continued
Equation 18

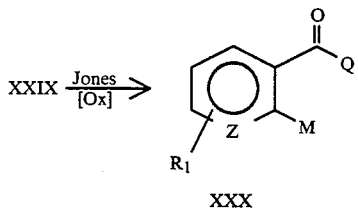
(b)

wherein
$R_1$ is H, Cl, $C_1$-$C_3$ alkoxy, $C_2$-$C_3$ alkylthio; $R_1$ is not $CO_2R^{III}$ or $CH_2CN$;
M is Cl, $SO_2$NH-t-butyl; or $SO_2$N-HSi(CH$_3$)$_2$C(CH$_3$)$_3$;
Z is CH or N.

Equation 18a illustrates the reaction of a phenyl- or pyridyl-lithium compound with heterocyclic aldehydes; however, this approach can also be used for thienyl- and pyrazyl-lithium compounds.

The oxidation of carbinols of Formula XXIX, as depicted in Equation 18b, can be conveniently carried out with Jones reagent in an acetone solvent. See, for example, M. J. Ashton et al. in *J. Med. Chem.*, 27, 1245-1253 (1984).

Heterocyclic nitriles can be used in place of the aldehydes to give intermediate imines which are easily hydrolyzed in aqueous acid to provide ketones of Formula XXX as shown in Equations 19a and 19b.

Equation 19

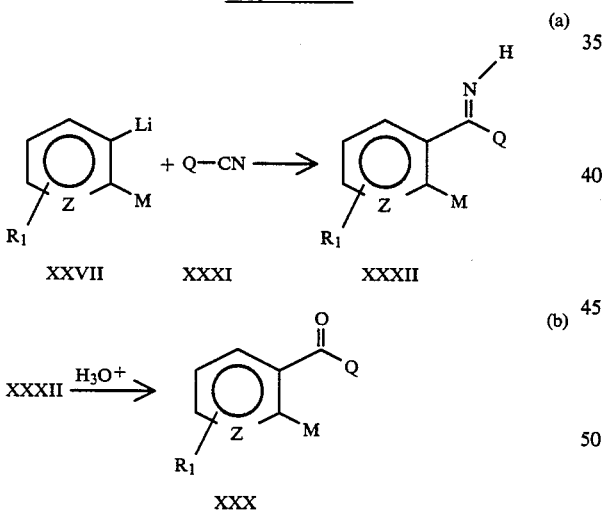

wherein
$R_1$ is H, Cl, $C_1$-$C_3$ alkoxy, or $C_2$-$C_3$ alkylthio;
M is Cl, Br or $SO_{NH-t-butyl}$; and
Z is CH or N.

Thienyl and pyrazyl-lithium compounds may also be employed in the approach depicted in Equation 19a.

The reactions of Equation 18a and 19a, including the preparation of the requisite lithium compounds, can be performed according to one or more of the procedures reviewed by H. G. Schwend and H. Rodriquez in *Organic Reactions*, Vol. 26, Wiley, New York, 1979, and references cited within. See also D. E. Butler and H. A. DeWald, *J. Org. Chem.*, 36, 2542-2547 (1971) for a discussion of the metallation of substituted pyrazoles.

The reversal of the compounds of Equations 18a and 19a provides an alternative, although similar preparative route as depicted in Equation 20.

Equation 20

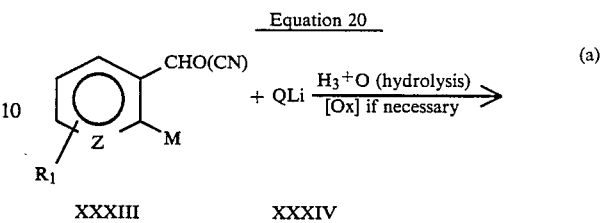
(a)

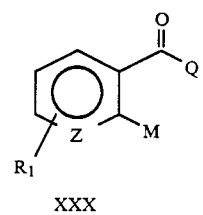

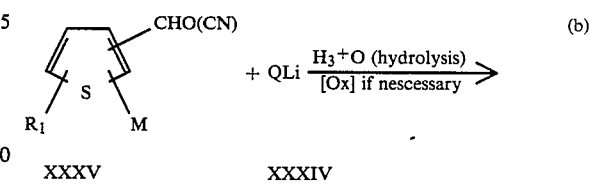
(b)

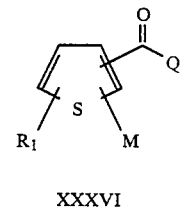

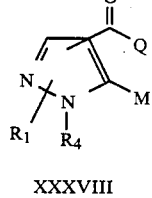
(c)

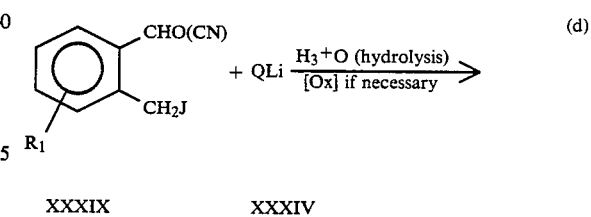
(d)

-continued
Equation 20

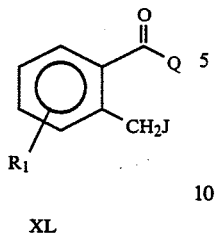

XL wherein
$Q_1$ and $R_4$ are as previously defined;
$R_1$ is H, Cl, Br, $C_1$–$C_3$ alkyl, $C_2$–$C_3$ thioalkyl or $NO_2$;
M is Cl, Br or $C_2$–$C_4$ alkyl- or benzylthio;
Z=CH or N; and
J=H or Cl.

The reactions of Equation 20, and the preparation of compounds of Formulae XXXIII through XL can be performed according to references cited for Equations 18 and 19.

The methodology described in equations 18, 19, and 20 is readily applicable to various aldehydes and nitrile compounds and thus provides considerable flexibility in the synthesis of the intermediate requisite carbinols and ketones.

It should be noted that the chemical compatibility of the wide variety of reactions and reaction conditions described throughout this disclosure with J, $R_1$, Q, and G must be taken into account and as such requires a judicious choice of the appropriate methods for preparing compounds described within this disclosure. In addition, circumvention of instances of incompatibility may be achieved by the suitable selection of a protecting group, obvious to one skilled in the art. For a compilation of references describing the wide variety of protecting groups available, see T. W. Greene, "Protective Groups in Organic Synthesis", John Wiley and Sons, Inc., New York, 1981.

The heterocyclic amines of Formula III in Equation 3 above can be prepared by methods known in the literature, or simple modifications thereof, by those skilled in the art. For instance, EP-A No. 84,224 (published July 27, 1983) and W. Braker et al., J. Chem. Soc., 69, 3072 (1947) describes methods for preparing aminopyridines and triazines substituted by acetal groups such as dialkoxymethyl or 1,3-dioxolan-2-yl, among other groups. Also, for example, South African patent application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, or $OCF_2H$, among other groups. South African patent application No. 83/7434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2,3-d]pyrimidine-2-amines, the cyclopenta[d]pyrimidines-2-amines (III, A is A-2) and the 6,7-dihydro-5H-pyrano[2,3-d]pyrimidin-2-amines (III, A is A-3) can be prepared as described in EP-A No. 15,683. The furo[2,3-d]pyrimidin-2-amines (III, A is A-4) are described in EP-A No. 46,677.

Compounds of Formula III, where A is A-5, are described in EP-A-73,562. Compounds of Formula III, where A is A-6, are described in EP-A-94,260.

In addition, general methods for preparing aminopyrimidines and triazines have been reviewed in the following publications:
"The Chemistry of Heterocyclic Compounds", a series published by Interscience Publishers, Inc., New York and London;
"Pyrimidines", Vol. 16 of the same series by D. J. Brown;
"s-Triazines and Derivatives", Vol. 13 of the same series of E. M. Smolin and L. Rappoport; and
F. C. Schaefer, U.S. Pat. No. 3,154,547 and K. R. Huffman and F. C. Schaefer, J. Org. Chem., 28, 1812 (1963), which describes the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

1-(2-chlorophenyl)-1-(2-thienyl)methanone

To a cooled solution of 58 mL of o-chlorobenzoyl chloride and 24 mL of thiophene in 700 mL of carbon disulfide, cooled to 0° C. under a nitrogen atmosphere, was added 134 g of aluminum trichloride portionwise over a 20-minute period. A delayed exotherm was noted and the resulting deep red mixture was stirred for one hour at room temperature. Reaction mixture was poured into 4.0 kg of ice-water, extracted with methylene chloride and the organic layer washed three times with 1N NaOH followed by a final water wash. The organic layer was dried ($MgSO_4$), filtered and concentrated to a dark oil. Distillation under vacuum provided 55 g of the subject compound as a light green viscous liquid, B.P. 160° C. at 1.6 mm.

EXAMPLE 2

1-(2-propylthiophenyl)-1-(2-thienyl)methanone

To a cloudy solution of 400 mL of dry dimethylformamide containing 22.4 g or potassium-t-butoxide, cooled to 0° under a nitrogen atmosphere, was added 18 mL of n-propanethiol dropwise at such a rate to maintain the temperature below 5° C. The resulting mixture was stirred for 5 minutes and then a solution of 44 g of the product of Example 1 dissolved in 100 mL of dimethylformamide was added. The reaction mixture was stirred for 24 hours at room temperature, poured into 2 L of ice-water and extracted with methylene chloride. The organic layer was separated, washed with 1N NaOH (aq), water, and dried (MgSO$_4$). Filtration, followed by concentration of the filtrate in vacuo gave a dark residue which after column chromatography on silica (methylene chloride as eluant) provided 40 g of the subject compound as a red oil.

NMR (CDCl$_3$) ppm 7.75 (m, 1H, Ar), 7.3 (m, 5H, Ar), 7.0 (m, 1H, Ar), 2.8 (m, 2H, SCH$_2$), 1.5 (m, 2H, CH$_2$), 0.9 (t, 3H, CH$_3$).

IR (neat) 1630 cm$^{-1}$ (C=O).

EXAMPLE 3

2-(2-thienylcarbonyl)benzenesulfonamide

Chlorine gas was bubbled into a stirring solution of 19 g of the product of Example 2 in 150 ml of acetic acid containing 3.75 mL of water at a temperature of 15° for 10 minutes. After an additional 5 minutes of stirring, the reaction mixture was poured into 2.5 L of ice-water and extracted with methylene chloride. The organic layer was separated, washed with aqueous saturated sodium bicarbonate and dried (MgSO$_4$). The magnesium sulfate was filtered off, the filtrate cooled to 0°, and 10 mL of liquid ammonia was added dropwise with stirring under a nitrogen atmosphere. After 1 hour at 0° C., the reaction mixture was filtered and concentrated in vacuo to give a dark oil. Column chromatography on silica (95% methylene chloride, 5% methanol as eluant) gave a green oil which after trituation with n-chlorobutane crystallized. This solid was triturated again with ethanol and air dried to afford 7.0 g of the subject compound, m.p. 122°-25°

NMR (CDCl$_3$-DMSO): ppm 7.1-8.2 (m, 7H, Ar), 6.8 (s, 2H, NH$_2$).

IR (Nujol) 1620 cm$^{-1}$ (C=O).

EXAMPLE 4

N-[4,6-dimethoxypyrimidin-2-yl)aminocarbonyl]-2-(2-thienylcarbonyl)benzenesulfonamide To a solution of 0.27 g of the product of Example 3 and 0.28 g of phenyl(4,6-dimethoxypyrimidin-2-yl)carbamate in 10 mL of p-dioxane was added 0.15 mL of 1,5-diazabicyclo[5.4.0]undec-5-ene (DBU). The solution was stirred for 2 hours at room temperature, diluted with 30 mL of ice-water and acidified with 5 drops of concentrated hydrochloric acid. The resulting precipitate was filtered off, and dried in vacuo at 60° overnight to afford 0.23 g of the subject compound, m.p. 173°-77°.

NMR (CDCl$_3$) ppm 12.6 (bs, 1H, NH), 8.4 (m, 1H, Ar), 7.65-7.8 (m, 7H, Ar-H and NH), 5.8 (s, 1H, py-H).

IR (Nujol) 1690 cm$^{-1}$ (C=O).

EXAMPLE 5

N-[4,6-dimethoxy-1,3,5-triazin-2-yl)aminocarbonyl]-2-(2-thienylcarbonyl)benzenesulfonamide By the procedure of Example 4, 0.27 g of the product of Example 3 was reacted with 0.27 g of phenyl-4,6-dimethoxy-1,3,5-triazin-2-yl)carbamate and 0.15 mL of "DBU" in 10 mL of p-dioxane. Work-up provided 0.2 g of the subject compound, m.p., 193°-96°

NMR (DMSO-D$_6$) ppm 12.2 (s, 1H, NH), 11.0 (s, 1H, NH), 7.05-8.2 (m, 7H, Ar), 3.93 (s, 6H, OCH$_3$).

IR (Nujol) 1705 cm$^{-1}$ (C=O).

EXAMPLE 6

2-[hydroxy(2-thienyl)methyl]benzenesulfonamide

To a solution, at room temperature, of 0.5 g of the product of Example 3 dissolved in 30 mL of dry tetrahydrofuran was added 0.1 g of lithium tetrahydridoborate (LiBH$_4$). After stirring for 0.5 hour, 30 mL of water was carefully added following by acidification with concentrated hydrochloric acid. The reaction was extracted with methylene chloride, washed with water and brine and dried (MgSO$_4$). Filtration and concentration of the filtrate in vacuo afforded 0.5 g of the subject compound as a light green oil which was used as such in the following example.

EXAMPLE 7

N-[(4,6-dimethoxypyrimidin-2-yl)aminocarbonyl]-2-[hydroxy(2-thienyl)methyl]benzenesulfonamide To 0.5 g of the product of Example 6, dissolved in 30 mL of p-dioxane, was added 0.51 g of phenyl(4,6-dimethoxypyrimidin-2-yl)carbamate followed by 0.27 mL of "DBU". The reaction was stirred for 1.5 hours, diluted with 45 mL of ice-water and acidified with 10 drops of concentrated hydrochloric acid to obtain an oily precipitate. The water was decanted from the oil and the oily residue was dissolved in methylene chloride, washed with water and brine, and finally dried (MgSO$_4$). Filtration and concentration of the filtrate, in vacuo, yielded an oil. Trituration with a 10:1 mixture of n-chlorbutane and methylene chloride provided 0.3 g of the subject compound as an off-white solid, m.p. 152°-54°.

NMR (CDCl$_3$) ppm 12.5 (s, 1H, NH), 8.22 (dd, 1H, Ar), 7.5-7.9 (m, 3H, Ar), 7.2 (bs, 1H), 7.1 (bs, 1H), 7.06 (d, -1H), 6.7 (m, 1H, Ar), 6.6 (d, 1H, CH), 5.74 (s, 1H, Py-H), 3.98 (s, 6H, OCH$_3$), 3.22 (d, 1H, OH).

IR (Nujol) 3370 & 1690 cm$^{-1}$ (C=O).

EXAMPLE 8

1-(3,4-dibromo-2-thienyl)-1-(2-thienyl)methanone

To a solution of 30 g of 3,4-dibromothiophene and 13.5 mL of thiophene-2-carbonylchloride in 120 mL of carbon disulfide was added 16.5 g aluminum trichloride portionwise over 10 minutes. The mixture was stirred for 3 hours, poured into 900 g of ice-water and extracted with methylene chloride. The organic layer was washed with 1N NaOH (aq), water, and dried (MgSO$_4$). Filtration and concentration of the filtrate, in vacuo, afforded an oil which crystallized upon trituration with n-chorobutane to yield 32 g of the subject compound as an off-white solid, m.p. 105°-109° C.

EXAMPLE 9

1-[4-bromo-3-(propylthio)-2-thienyl]-1-(2-thienyl)methane

To a cloudy solution of 80 mL of dimethylformamide containing 3.7 g of potassium-t-butoxide, under a nitrogen blanket and cooled to 0°, was added 3.0 mL of n-propanethiol. This mixture was stirred for 5 minutes and then 12 g of the product of Example 8 was added in one portion. After stirring for 3 hours at room temperature, the mixture was poured into 400 mL of ice-water and extracted with methylene chloride. The organic layer was washed with 1N NaOH (aq), water and dried (MgSO$_4$). Filtration and concentration of the filtrate in vacuo afforded 7.5 g of the subject compound as a dark oil.

EXAMPLE 10

4-bromo-2-(2-thienylcarbonyl)-3-thiophenesulfonamide

Chlorine gas was bubbled into a stirring solution of 12.0 g of the product of example 9 in 90 mL of acetic acid containing 0.6 mL of water at a temperature of 10° C. for 10 minutes. After an additional 15 minutes, the reaction mixture was poured into 1 L of ice-water and extracted with methylene chloride. The organic layer was washed with saturated sodium bicarbonate, dried (MgSO$_4$), and filtered. To the filtrate was added 6 mL of concentrated ammonium hydroxide and stirred for 1 hour. The mixture was filtered and the filtrate was concentrated in vacuo to afford a semisolid which was triturated with n-chlorobutane to yield 3.0 of the subject compound as a tan solid.

NMR (CDCl$_3$) ppm 7.82 (d, 1H, Ar), 7.54 (s, 1H, Ar), 7.17 (m, 1H, Ar), 6.5 (dd, 1H, Ar), 5.46 (bs, 2H, NH$_2$).

EXAMPLE 11

4-bromo-N-[(4-methoxy-6-methylpyrimidin-2-yl)aminocarbonyl]-2-(2-thienylcarbonyl)-3-thiophenesulfonamide To a solution of 0.35 g of the product of Example 10 and 0.26 g of phenyl(4-methoxy-6-methylpyrimidin-2-yl)carbamate in 10 mL of p-dioxane was added 0.15 mL of "DBU". The solution was stirred for 1 hour at room temperature, diluted with 30 mL of ice-water and acidified with 5 drops of concentrated hydrochloric acid. The precipitate was filtered off, washed with a little water and dried in vacuo at 60° overnight to afford 0.32 g of the subject compound as a brown solid, m.p. 106° with decomposition.

NMR (CDCl$_3$) ppm 13.4 (bs, 1H, NH), 7.79–7.84 (m, 2H, Ar), 7.49 (s, 1H, Ar), 7.44 (bs, 1H, NH), 7.15 (s, 1H, NH), 6.3 (s, 1H, py-H), 3.95 (s, 3H, OCH$_3$), 2.42 (s, 3H, CH$_3$).

IR (Nujol) 1720 cm$^{-1}$ (C=O's).

EXAMPLE 12

4-bromo-N-[(4,6-dimethoxy-1,3,5-triazine-2-yl)aminocarbonyl]-2-(2-thienylcarbonyl)-3-thiophenesulfonamide By the procedure of Example 11, 0.35 g of the product of Example 10 was reacted with 0.27 g of phenyl(4,6-dimethoxy-1,3,5-triazin-2-yl)carbamate and 0.15 mL of "DBU" in 10 mL of p-dioxane and worked up to afford 0.4 g of the subject compound as a brown solid, m.p. 115° with decomposition.

NMR (CDCl$_3$) ppm 12.4 (bs, 1H, NH), 7.8 (m, 1H, Ar), 7.68 (m, 2H, Ar, H and NH), 7.51 (s, 1H, Ar), 7.13 (m, 1H, Ar), 4.00 (s, CH, OCH$_3$).

IR (Nujol) br 1720 cm$^{-1}$ (C=O's).

Using the techniques described in Equations 1–20 and Examples 4, 5, 7, 11 and 12, or simple modifications thereof, the following compounds in Tables I–XXIII can be made by those skilled in the art.

General Formulae for Tables I–XXV

Table I 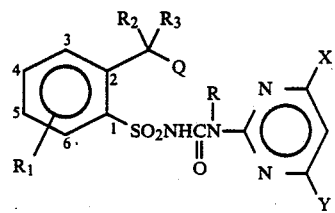

Table II 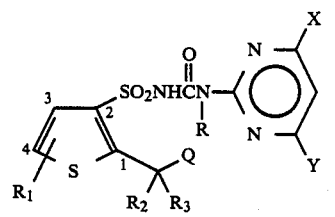

Table III 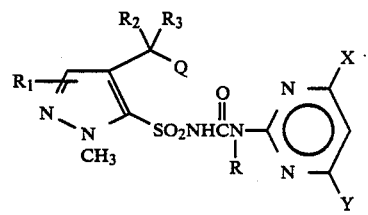

Table IV 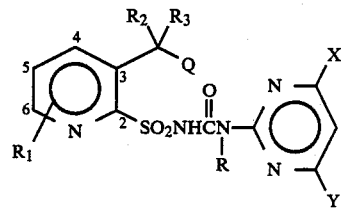

Table V 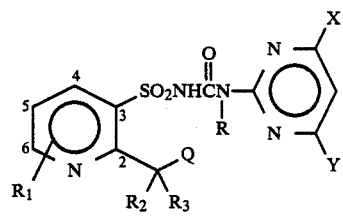

Table VI 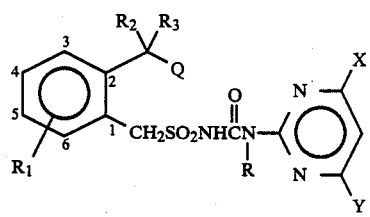

-continued
| General Formulae for Tables I–XXV | | General Formulae for Tables I–XXV |
|---|---|---|
| Table VII 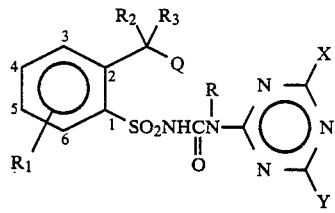 | | Table XIV 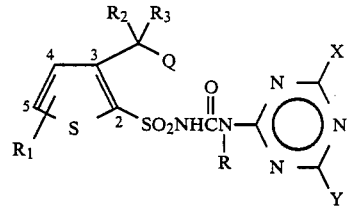 |
| Table VIII 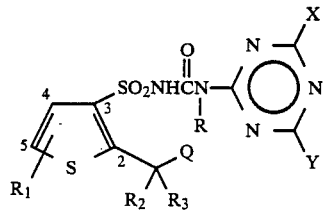 | | Table XV 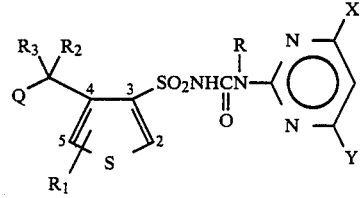 |
| Table IX 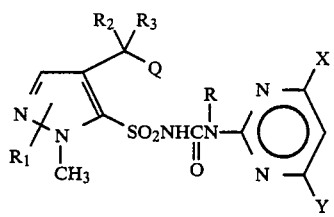 | | Table XVI 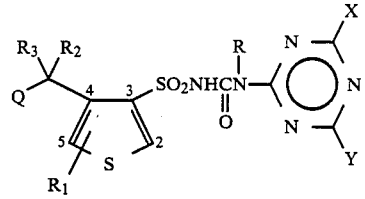 |
| Table X 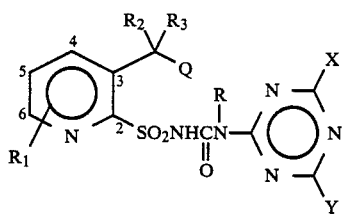 | | Table XVII 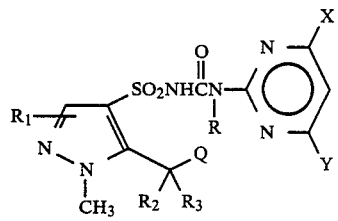 |
| Table XI 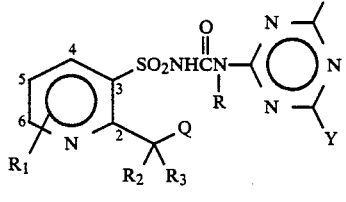 | | Table XVIII 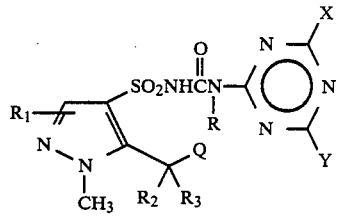 |
| Table XII 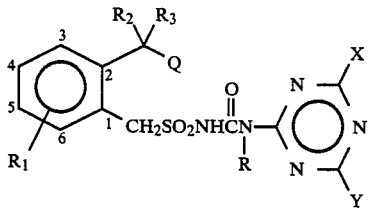 | | Table XIX 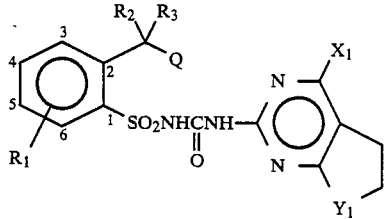 |
| Table XIII 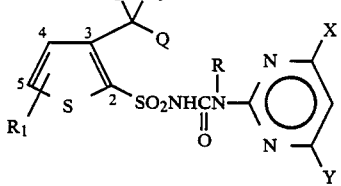 | | Table XX 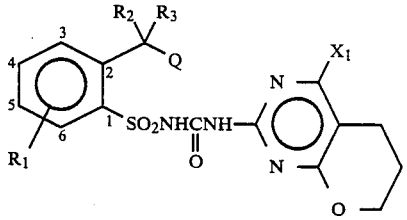 |

-continued
General Formulae for Tables I-XXV

Table XXI
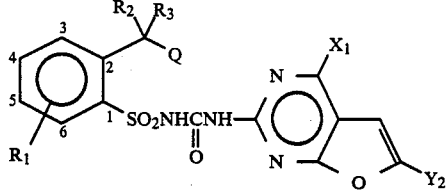

Table XXII
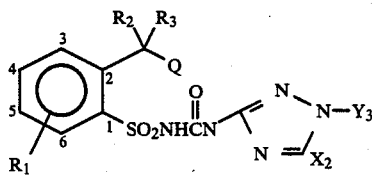

Table XXIII
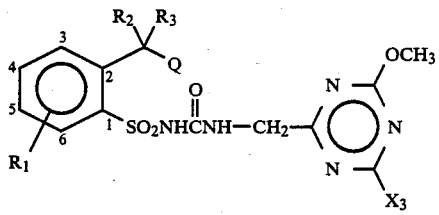

-continued
General Formulae for Tables I-XXV

Table XXIV
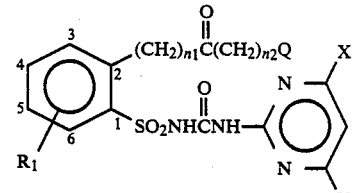

Table XXV
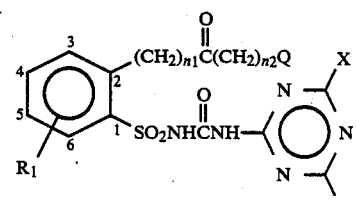

TABLE I
General Formula I

| Q | R | $R_1$ | $R_2$ | $R_3$ | X | Y | m.p. (°C.) |
|---|---|---|---|---|---|---|---|
| $Q_1(R_7=H,R_8=H,R_9=H)$ | H | H | | C=O | $CH_3$ | $CH_3$ | 156-163 |
| $Q_1(R_7=H,R_8=H,R_9=H)$ | H | H | | C=O | $CH_3$ | $OCH_3$ | 166-167 |
| $Q_1(R_7=H,R_8=H,R_9=H)$ | H | H | | C=O | $OCH_3$ | $OCH_3$ | 173-177 |
| $Q_1(R_7=H,R_8=H,R_9=H)$ | H | H | | C=O | Cl | $OCH_3$ | |
| $Q_1(R_7=H,R_8=H,R_9=H)$ | H | H | OH | H | $CH_3$ | $CH_3$ | |
| $Q_1(R_7=H,R_8=H,R_9=H)$ | H | H | OH | H | $CH_3$ | $OCH_3$ | |
| $Q_1(R_7=H,R_8=H,R_9=H)$ | H | H | OH | H | $OCH_3$ | $OCH_3$ | 152-154 |
| $Q_1(R_7=H,R_8=H,R_9=H)$ | H | H | OH | H | Cl | $OCH_3$ | |
| $Q_1(R_7=H,R_8=H,R_9=H)$ | $CH_3$ | H | $OCH_3$ | H | $OCH_3$ | $OCH_3$ | |
| $Q_1(R_7=H,R_8=H,R_9=H)$ | H | H | $OCH_2CH_3$ | H | $OCH_3$ | $OCH_3$ | |
| $Q_1(R_7=H,R_8=H,R_9=H)$ | H | H | $OCH_3$ | $OCH_3$ | $OCH_3$ | $OCH_3$ | |
| $Q_1(R_7=H,R_8=H,R_9=H)$ | H | H | —O(CH$_2$)$_3$O— | | $OCH_3$ | $OCH_3$ | |
| $Q_2(R_7=H,R_8=H,R_9=H)$ | H | H | | C=O | $OCF_2H$ | $CH_3$ | |
| $Q_2(R_7=H,R_8=H,R_9=H)$ | H | H | | C=O | $CH_3$ | $OCH_3$ | |
| $Q_2(R_7=H,R_8=H,R_9=H)$ | H | H | | C=O | $OCH_3$ | $OCH_3$ | |
| $Q_2(R_7=H,R_8=H,R_9=H)$ | H | H | | C=O | Cl | $OCH_3$ | |
| $Q_2(R_7=H,R_8=H,R_9=H)$ | H | H | OH | H | $CH_3$ | $CH_3$ | |
| $Q_2(R_7=H,R_8=H,R_9=H)$ | H | H | OH | H | $CH_3$ | $OCH_3$ | |
| $Q_2(R_7=H,R_8=H,R_9=H)$ | H | H | OH | H | $OCH_3$ | $OCH_3$ | |
| $Q_2(R_7=H,R_8=H,R_9=H)$ | H | H | OH | H | Cl | $OCH_3$ | |
| $Q_2(R_7=H,R_8=H,R_9=H)$ | H | H | $OCH_3$ | H | $CH_3$ | $CH_3$ | |
| $Q_2(R_7=H,R_8=H,R_9=H)$ | H | H | $OCH_2CH_3$ | H | $CH_3$ | $CH_3$ | |
| $Q_3(R_7=H,R_8=H,R_9=H)$ | H | H | | C=O | $CH_3$ | $CH_3$ | |
| $Q_3(R_7=H,R_8=H,R_9=H)$ | H | H | | C=O | $CH_3$ | $OCH_3$ | |
| $Q_3(R_7=H,R_8=H,R_9=H)$ | H | H | | C=O | $OCH_3$ | $OCH_3$ | |
| $Q_3(R_7=H,R_8=H,R_9=H)$ | H | H | | C=O | Cl | $OCH_3$ | |
| $Q_3(R_7=H,R_8=H,R_9=H)$ | H | H | OH | H | $CH_3$ | $CH_3$ | |
| $Q_3(R_7=H,R_8=H,R_9=H)$ | H | H | OH | H | $CH_3$ | $OCH_3$ | |
| $Q_3(R_7=H,R_8=H,R_9=H)$ | H | H | OH | H | $OCH_3$ | $OCH_3$ | |
| $Q_3(R_7=H,R_8=H,R_9=H)$ | H | H | OH | H | Cl | $OCH_3$ | |
| $Q_3(R_7=H,R_8=H,R_9=Cl)$ | H | H | | C=O | $OCH_3$ | $OCH_3$ | |
| $Q_3(R_7=H,R_8=H,R_9=CH_3)$ | H | H | | C=O | $OCH_3$ | $OCH_3$ | |
| $Q_3(R_7=H,R_8=H,R_9=CH_3)$ | H | H | OH | H | $OCH_3$ | $OCH_3$ | |
| $Q_3(R_7=H,R_8=H,R_9=H_3)$ | H | H | $OCH_3$ | $OCH_3$ | $OCH_3$ | $OCH_3$ | |
| $Q_3(R_7=H,R_8=H,R_9=H_3)$ | H | H | —O(CH$_2$)$_3$O— | | $OCH_3$ | $OCH_3$ | |
| $Q_4(R_7=H,R_8=H,R_9=H)$ | H | H | | C=O | $CH_3$ | $CH_3$ | |
| $Q_4(R_7=H,R_8=H,R_9=H)$ | H | H | | C=O | $CH_3$ | $OCH_3$ | |
| $Q_4(R_7=H,R_8=H,R_9=H)$ | H | H | | C=O | $OCH_3$ | $OCH_3$ | |
| $Q_4(R_7=H,R_8=H,R_9=H)$ | H | H | | C=O | Cl | $OCH_3$ | |
| $Q_4(R_7=H,R_8=H,R_9=H)$ | H | H | OH | H | $CH_3$ | $CH_3$ | |
| $Q_4(R_7=H,R_8=H,R_9=H)$ | H | H | OH | H | $OCH_3$ | $OCH_3$ | |
| $Q_4(R_7=H,R_8=H,R_9=H)$ | H | H | OH | H | Cl | $OCH_3$ | |
| $Q_5(R_7=H,R_8=H,R_9=H,R_{10}=CH_3)$ | H | $CH_2CH_3$ | OH | H | $CH_3$ | $CH_3$ | |
| $Q_5(R_7=H,R_8=H,R_9=H,R_{10}=CH_3)$ | H | H | | C=O | $CH_3$ | $OCH_3$ | |

TABLE I-continued

General Formula I

| Q | R | $R_1$ | $R_2$ | $R_3$ | X | Y | m.p. (°C.) |
|---|---|---|---|---|---|---|---|
| $Q_5(R_7=H,R_8=H,R_9=H,R_{10}=CH_3)$ | H | H | C=O | | $OCH_3$ | $OCH_3$ | |
| $Q_5(R_7=H,R_8=H,R_9=H,R_{10}=CH_3)$ | H | H | C=O | | Cl | $OCH_3$ | |
| $Q_5(R_7=H,R_8=H,R_9=H,R_{10}=CH_3)$ | H | H | OH | H | $CH_3$ | $CH_3$ | |
| $Q_5(R_7=H,R_8=H,R_9=H,R_{10}=CH_3)$ | H | H | OH | H | $CH_3$ | $OCH_3$ | |
| $Q_5(R_7=H,R_8=H,R_9=H,R_{10}=CH_3)$ | H | H | OH | H | $OCH_3$ | $OCH_3$ | |
| $Q_5(R_7=H,R_8=H,R_9=H,R_{10}=CH_3)$ | H | H | OH | H | Cl | $OCH_3$ | |
| $Q_5(R_7=H,R_8=H,R_9=H,R_{10}=CH_3)$ | H | H | $OCH_3$ | H | Cl | $OCH_3$ | |
| $Q_5(R_7=H,R_8=H,R_9=H,R_{10}=CH_3)$ | H | H | $OCH_2CH_3$ | H | $OCH_3$ | $OCH_3$ | |
| $Q_6(R_7=H,R_8=H,R_9=H,R_{10}=CH_3)$ | H | H | C=O | | $CH_3$ | $CH_3$ | |
| $Q_6(R_7=H,R_8=H,R_9=H,R_{10}=CH_3)$ | H | H | C=O | | $CH_3$ | $OCH_3$ | |
| $Q_6(R_7=H,R_8=H,R_9=H,R_{10}=CH_3)$ | H | H | C=O | | $OCH_3$ | $OCH_3$ | |
| $Q_6(R_7=H,R_8=H,R_9=H,R_{10}=CH_3)$ | H | H | C=O | | Cl | $OCH_3$ | |
| $Q_6(R_7=H,R_8=H,R_9=H,R_{10}=CH_3)$ | H | H | OH | H | $CH_3$ | $CH_3$ | |
| $Q_6(R_7=H,R_8=H,R_9=H,R_{10}=CH_3)$ | H | H | OH | H | $CH_3$ | $OCH_3$ | |
| $Q_6(R_7=H,R_8=H,R_9=H,R_{10}=CH_3)$ | H | H | OH | H | $OCH_3$ | $OCH_3$ | |
| $Q_6(R_7=H,R_8=H,R_9=H,R_{10}=CH_3)$ | H | H | OH | H | Cl | $OCH_3$ | |
| $Q_7(R_7=H,R_8=H)$ | H | H | C=O | | $CH_3$ | $CH_3$ | |
| $Q_7(R_7=H,R_8=H)$ | H | H | C=O | | $CH_3$ | $OCH_3$ | |
| $Q_7(R_7=H,R_8=H)$ | H | H | C=O | | $OCH_3$ | $OCH_3$ | |
| $Q_7(R_7=H,R_8=H)$ | H | H | C=O | | Cl | $OCH_3$ | |
| $Q_7(R_7=H,R_8=H)$ | H | H | OH | H | $CH_3$ | $CH_3$ | |
| $Q_7(R_7=H,R_8=H)$ | H | H | OH | H | $CH_3$ | $OCH_3$ | |
| $Q_7(R_7=H,R_8=H)$ | H | H | OH | H | $OCH_3$ | $OCH_3$ | |
| $Q_7(R_7=H,R_8=H)$ | H | H | OH | H | Cl | $OCH_3$ | |
| $Q_7(R_7=H,R_8=H)$ | H | H | $OCH_3$ | $OCH_3$ | $OCH_3$ | $OCH_3$ | |
| $Q_7(R_7=H,R_8=H)$ | H | H | —O(CH$_2$)$_3$O— | | $OCH_3$ | $OCH_3$ | |
| $Q_8(R_7=H,R_8=H)$ | H | H | C=O | | $OCH_3$ | $OCH_3$ | |
| $Q_8(R_7=H,R_8=H)$ | H | H | C=O | | Cl | $OCH_3$ | |
| $Q_8(R_7=H,R_8=H)$ | H | H | OH | H | Cl | $CH_3$ | |
| $Q_8(R_7=H,R_8=H)$ | H | H | OH | H | $OCH_3$ | $CH_3$ | |
| $Q_8(R_7=H,R_8=H)$ | H | H | $OCH_3$ | $OCH_3$ | $OCH_3$ | $OCH_3$ | |
| $Q_8(R_7=H,R_8=H)$ | H | H | —O(CH$_2$)$_3$O— | | $OCH_3$ | $OCH_3$ | |
| $Q_9(R_7=H,R_8=H)$ | H | H | C=O | | $CH_3$ | $CH_3$ | |
| $Q_9(R_7=H,R_8=H)$ | H | H | C=O | | $CH_3$ | $OCH_3$ | |
| $Q_9(R_7=H,R_8=H)$ | H | H | C=O | | $OCH_3$ | $OCH_3$ | |
| $Q_9(R_7=H,R_8=H)$ | H | H | C=O | | Cl | $OCH_3$ | |
| $Q_9(R_7=H,R_8=H)$ | H | H | OH | H | $CH_3$ | $CH_3$ | |
| $Q_9(R_7=H,R_8=H)$ | H | H | OH | H | $CH_3$ | $OCH_3$ | |
| $Q_9(R_7=H,R_8=H)$ | H | H | OH | H | $OCH_3$ | $OCH_3$ | |
| $Q_9(R_7=H,R_8=H)$ | H | H | OH | H | Cl | $OCH_3$ | |
| $Q_9(R_7=H,R_8=H)$ | H | H | $OCH_3$ | $OCH_3$ | $OCH_3$ | $OCH_3$ | |
| $Q_9(R_7=H,R_8=H)$ | H | H | —O(CH$_2$)$_3$O— | | $OCH_3$ | $OCH_3$ | |
| $Q_{10}(R_7=H,R_8=H)$ | H | H | C=O | | $CH_3$ | $CH_3$ | |
| $Q_{10}(R_7=H,R_8=H)$ | H | H | C=O | | $OCH_3$ | $OCH_3$ | |
| $Q_{10}(R_7=H,R_8=H)$ | H | H | C=O | | Cl | $OCH_3$ | |
| $Q_{10}(R_7=H,R_8=H)$ | H | H | OH | H | $CH_3$ | $CH_3$ | |
| $Q_{10}(R_7=H,R_8=H)$ | H | H | OH | H | $OCH_3$ | $OCH_3$ | |
| $Q_{10}(R_7=H,R_8=H)$ | H | H | OH | H | Cl | $OCH_3$ | |
| $Q_{10}(R_7=H,R_8=H)$ | H | H | $OCH_3$ | $OCH_3$ | $OCH_3$ | $OCH_3$ | |
| $Q_{10}(R_7=H,R_8=H)$ | H | H | —O(CH$_2$)$_3$O— | | $OCH_3$ | $OCH_3$ | |
| $Q_{11}(R_7=H,R_8=H)$ | H | H | C=O | | $CH_3$ | $CH_3$ | |
| $Q_{11}(R_7=H,R_8=H)$ | H | H | C=O | | $CH_3$ | $OCH_3$ | |
| $Q_{11}(R_7=H,R_8=H)$ | H | H | C=O | | $OCH_3$ | $OCH_3$ | |
| $Q_{11}(R_7=H,R_8=H)$ | H | H | C=O | | Cl | $OCH_3$ | |
| $Q_{11}(R_7=H,R_8=H)$ | H | H | OH | H | $CH_3$ | $CH_3$ | |
| $Q_{11}(R_7=H,R_8=H)$ | H | H | OH | H | $CH_3$ | $OCH_3$ | |
| $Q_{11}(R_7=H,R_8=H)$ | H | H | OH | H | $OCH_3$ | $OCH_3$ | |
| $Q_{11}(R_7=H,R_8=H)$ | H | H | OH | H | Cl | $OCH_3$ | |
| $Q_{11}(R_7=H,R_8=H)$ | H | H | $OCH_3$ | $OCH_3$ | $OCH_3$ | $OCH_3$ | |
| $Q_{11}(R_7=H,R_8=H)$ | H | H | —O(CH$_2$)$_3$O— | | $OCH_3$ | $OCH_3$ | |
| $Q_{12}(R_7=H,R_8=H)$ | H | H | C=O | | $CH_3$ | $CH_3$ | |
| $Q_{12}(R_7=H,R_8=H)$ | H | H | C=O | | $CH_3$ | $OCH_3$ | |
| $Q_{12}(R_7=H,R_8=H)$ | H | H | C=O | | $OCH_3$ | $OCH_3$ | |
| $Q_{12}(R_7=H,R_8=H)$ | H | H | C=O | | Cl | $OCH_3$ | |
| $Q_{12}(R_7=H,R_8=H)$ | H | H | OH | H | $CH_3$ | $CH_3$ | |
| $Q_{12}(R_7=H,R_8=H)$ | H | H | OH | H | $CH_3$ | $OCH_3$ | |
| $Q_{12}(R_7=H,R_8=H)$ | H | H | OH | H | $OCH_3$ | $OCH_3$ | |
| $Q_{12}(R_7=H,R_8=H)$ | H | H | OH | H | Cl | $OCH_3$ | |
| $Q_{12}(R_7=H,R_8=H)$ | H | H | $OCH_3$ | H | $OCH_3$ | $OCH_3$ | |
| $Q_{13}(R_7=H,R_8=H)$ | H | H | C=O | | $CH_3$ | $CH_3$ | |
| $Q_{13}(R_7=H,R_8=H)$ | H | H | C=O | | $CH_3$ | $OCH_3$ | |
| $Q_{13}(R_7=H,R_8=H)$ | H | H | C=O | | $OCH_3$ | $OCH_3$ | |
| $Q_{13}(R_7=H,R_8=H)$ | H | H | C=O | | Cl | $OCH_3$ | |
| $Q_{13}(R_7=H,R_8=H)$ | H | H | OH | H | $CH_3$ | $CH_3$ | |
| $Q_{13}(R_7=H,R_8=H)$ | H | H | OH | H | $CH_3$ | $OCH_3$ | |
| $Q_{13}(R_7=H,R_8=H)$ | H | H | OH | H | $OCH_3$ | $OCH_3$ | |
| $Q_{13}(R_7=H,R_8=H)$ | H | H | OH | H | Cl | $OCH_3$ | |
| $Q_{14}(R_7=H)$ | H | H | C=O | | $CH_3$ | $CH_3$ | |
| $Q_{14}(R_7=H)$ | H | H | C=O | | $CH_3$ | $OCH_3$ | |

TABLE I-continued

General Formula I

| Q | R | $R_1$ | $R_2$ | $R_3$ | X | Y | m.p. (°C.) |
|---|---|---|---|---|---|---|---|
| $Q_{14}(R_7=H)$ | H | H | C=O | | $OCH_3$ | $OCH_3$ | |
| $Q_{14}(R_7=H)$ | H | H | C=O | | Cl | $OCH_3$ | |
| $Q_{14}(R_7=H)$ | H | H | OH | H | $CH_3$ | $CH_3$ | |
| $Q_{14}(R_7=H)$ | H | H | OH | H | $CH_3$ | $OCH_3$ | |
| $Q_{14}(R_7=H)$ | H | H | OH | H | $OCH_3$ | $OCH_3$ | |
| $Q_{14}(R_7=H)$ | H | H | OH | H | Cl | $OCH_3$ | |
| $Q_{14}(R_7=H)$ | H | H | $OCH_3$ | $OCH_3$ | $OCH_3$ | $OCH_3$ | |
| $Q_{14}(R_7=H)$ | H | H | —O(CH$_2$)$_3$O— | | $OCH_3$ | $OCH_3$ | |
| $Q_{15}(R_7=H)$ | H | H | C=O | | $CH_3$ | $CH_3$ | |
| $Q_{15}(R_7=H)$ | H | H | C=O | | $CH_3$ | $OCH_3$ | |
| $Q_{15}(R_7=H)$ | H | H | C=O | | $OCH_3$ | $OCH_3$ | |
| $Q_{15}(R_7=H)$ | H | H | C=O | | Cl | $OCH_3$ | |
| $Q_{15}(R_7=H)$ | H | H | OH | H | $CH_3$ | $CH_3$ | |
| $Q_{15}(R_7=H)$ | H | H | OH | H | $CH_3$ | $OCH_3$ | |
| $Q_{15}(R_7=H)$ | H | H | OH | H | $OCH_3$ | $OCH_3$ | |
| $Q_{15}(R_7=H)$ | H | H | OH | H | Cl | $OCH_3$ | |
| $Q_{16}(R_7=H)$ | H | H | C=O | | $CH_3$ | $CH_3$ | |
| $Q_{16}(R_7=H)$ | H | H | C=O | | $CH_3$ | $OCH_3$ | |
| $Q_{16}(R_7=H)$ | H | H | C=O | | $OCH_3$ | $OCH_3$ | |
| $Q_{16}(R_7=H)$ | H | H | C=O | | Cl | $OCH_3$ | |
| $Q_{16}(R_7=H)$ | H | H | OH | H | $CH_3$ | $CH_3$ | |
| $Q_{16}(R_7=H)$ | H | H | OH | H | $CH_3$ | $OCH_3$ | |
| $Q_{16}(R_7=H)$ | H | H | OH | H | $OCH_3$ | $OCH_3$ | |
| $Q_{16}(R_7=H)$ | H | H | OH | H | Cl | $OCH_3$ | |
| $Q_{16}(R_7=H)$ | H | H | $OCH_3$ | $OCH_3$ | $OCH_3$ | $OCH_3$ | |
| $Q_{16}(R_7=H)$ | H | H | —O(CH$_2$)$_3$O— | | $OCH_3$ | $OCH_3$ | |
| $Q_{17}(R_7=CH_3)$ | H | H | C=O | | $CH_3$ | $CH_3$ | |
| $Q_{17}(R_7=CH_3)$ | H | H | C=O | | $CH_3$ | $OCH_3$ | |
| $Q_{17}(R_7=CH_3)$ | H | H | C=O | | $OCH_3$ | $OCH_3$ | |
| $Q_{17}(R_7=CH_3)$ | H | H | C=O | | Cl | $OCH_3$ | |
| $Q_{17}(R_7=CH_3)$ | H | H | OH | H | $CH_3$ | $CH_3$ | |
| $Q_{17}(R_7=CH_3)$ | H | H | OH | H | $CH_3$ | $OCH_3$ | |
| $Q_{17}(R_7=CH_3)$ | H | H | OH | H | $OCH_3$ | $OCH_3$ | |
| $Q_{17}(R_7=CH_3)$ | H | H | OH | H | Cl | $OCH_3$ | |
| $Q_{17}(R_7=CH_3)$ | H | H | $OCH_3$ | $OCH_3$ | $OCH_3$ | $OCH_3$ | |
| $Q_{17}(R_7=CH_3)$ | H | H | —O(CH$_2$)$_3$O— | | $OCH_3$ | $OCH_3$ | |
| $Q_{18}(R_7=H)$ | H | H | C=O | | $CH_3$ | $CH_3$ | |
| $Q_{18}(R_7=H)$ | H | H | C=O | | $CH_3$ | $OCH_3$ | |
| $Q_{18}(R_7=H)$ | H | H | C=O | | $OCH_3$ | $OCH_3$ | |
| $Q_{18}(R_7=H)$ | H | H | C=O | | Cl | $OCH_3$ | |
| $Q_{18}(R_7=H)$ | H | H | OH | H | $CH_3$ | $CH_3$ | |
| $Q_{18}(R_7=H)$ | H | H | OH | H | $CH_3$ | $OCH_3$ | |
| $Q_{18}(R_7=H)$ | H | H | OH | H | $OCH_3$ | $OCH_3$ | |
| $Q_{18}(R_7=H)$ | H | H | OH | H | Cl | $OCH_3$ | |
| $Q_{19}(R_7=H,R_8=H)$ | H | H | C=O | | $CH_3$ | $CH_3$ | |
| $Q_{19}(R_7=H,R_8=H)$ | H | H | C=O | | $CH_3$ | $OCH_3$ | |
| $Q_{19}(R_7=H,R_8=H)$ | H | H | C=O | | $OCH_3$ | $OCH_3$ | |
| $Q_{19}(R_7=H,R_8=H)$ | H | H | C=O | | Cl | $OCH_3$ | |
| $Q_{19}(R_7=H,R_8=H)$ | H | H | OH | H | $CH_3$ | $CH_3$ | |
| $Q_{19}(R_7=H,R_8=H)$ | H | H | OH | H | $CH_3$ | $OCH_3$ | |
| $Q_{19}(R_7=H,R_8=H)$ | H | H | OH | H | $OCH_3$ | $OCH_3$ | |
| $Q_{19}(R_7=H,R_8=H)$ | H | H | OH | H | Cl | $OCH_3$ | |
| $Q_{19}(R_7=H,R_8=H)$ | H | H | $OCH_3$ | $OCH_3$ | $OCH_3$ | $OCH_3$ | |
| $Q_{19}(R_7=H,R_8=H)$ | H | H | —O(CH$_2$)$_3$O— | | $OCH_3$ | $OCH_3$ | |
| $Q_{20}(R_7=H,R_8=H)$ | H | H | C=O | | $CH_3$ | $CH_3$ | |
| $Q_{20}(R_7=H,R_8=H)$ | H | H | C=O | | $CH_3$ | $OCH_3$ | |
| $Q_{20}(R_7=H,R_8=H)$ | H | H | C=O | | $OCH_3$ | $OCH_3$ | |
| $Q_{20}(R_7=H,R_8=H)$ | H | H | C=O | | Cl | $OCH_3$ | |
| $Q_{20}(R_7=H,R_8=H)$ | H | H | OH | H | $CH_3$ | $CH_3$ | |
| $Q_{20}(R_7=H,R_8=H)$ | H | H | OH | H | $CH_3$ | $OCH_3$ | |
| $Q_{20}(R_7=H,R_8=H)$ | H | H | OH | H | $OCH_3$ | $OCH_3$ | |
| $Q_{20}(R_7=H,R_8=H)$ | H | H | OH | H | Cl | $OCH_3$ | |
| $Q_{20}(R_7=H,R_8=H)$ | H | H | $OCH_3$ | $OCH_3$ | $OCH_3$ | $OCH_3$ | |
| $Q_{20}(R_7=H,R_8=H)$ | H | H | —O(CH$_2$)$_3$O— | | $OCH_3$ | $OCH_3$ | |
| $Q_{21}(R_7=H,R_8=H,R_9=CH_3)$ | H | H | C=O | | $CH_3$ | $CH_3$ | |
| $Q_{21}(R_7=H,R_8=H,R_9=CH_3)$ | H | H | C=O | | $CH_3$ | $OCH_3$ | |
| $Q_{21}(R_7=H,R_8=H,R_9=CH_3)$ | H | H | C=O | | $OCH_3$ | $OCH_3$ | |
| $Q_{21}(R_7=H,R_8=H,R_9=CH_3)$ | H | H | C=O | | Cl | $OCH_3$ | |
| $Q_{21}(R_7=H,R_8=H,R_9=CH_3)$ | H | H | OH | H | $CH_3$ | $CH_3$ | |
| $Q_{21}(R_7=H,R_8=H,R_9=CH_3)$ | H | H | OH | H | $CH_3$ | $OCH_3$ | |
| $Q_{21}(R_7=H,R_8=H,R_9=CH_3)$ | H | H | OH | H | $OCH_3$ | $OCH_3$ | |
| $Q_{21}(R_7=H,R_8=H,R_9=CH_3)$ | H | H | OH | H | Cl | $OCH_3$ | |
| $Q_{21}(R_7=H,R_8=H,R_9=CH_3)$ | H | H | $OCH_3$ | $OCH_3$ | $OCH_3$ | $OCH_3$ | |
| $Q_{21}(R_7=H,R_8=H,R_9=CH_3)$ | H | H | —O(CH$_2$)$_3$O— | | $OCH_3$ | $OCH_3$ | |
| $Q_{22}(R_7=H)$ | H | H | C=O | | $CH_3$ | $CH_3$ | |
| $Q_{22}(R_7=H)$ | H | H | C=O | | $CH_3$ | $OCH_3$ | |
| $Q_{22}(R_7=H)$ | H | H | C=O | | $OCH_3$ | $OCH_3$ | |
| $Q_{22}(R_7=H)$ | H | H | C=O | | Cl | $OCH_3$ | |
| $Q_{22}(R_7=H)$ | H | H | OH | H | $CH_3$ | $CH_3$ | |

TABLE I-continued

General Formula I

| Q | R | $R_1$ | $R_2$ | $R_3$ | X | Y | m.p. (°C.) |
|---|---|---|---|---|---|---|---|
| $Q_{22}(R_7=H)$ | H | H | OH | H | $CH_3$ | $OCH_3$ | |
| $Q_{22}(R_7=H)$ | H | H | OH | H | $OCH_3$ | $OCH_3$ | |
| $Q_{22}(R_7=H)$ | H | H | OH | H | Cl | $OCH_3$ | |
| $Q_{23}(R_7=H)$ | H | H | C=O | | $CH_3$ | $CH_3$ | |
| $Q_{23}(R_7=H)$ | H | H | C=O | | $CH_3$ | $OCH_3$ | |
| $Q_{23}(R_7=H)$ | H | H | C=O | | $OCH_3$ | $OCH_3$ | |
| $Q_{23}(R_7=H)$ | H | H | C=O | | Cl | $OCH_3$ | |
| $Q_{23}(R_7=H)$ | H | H | OH | H | $CH_3$ | $CH_3$ | |
| $Q_{23}(R_7=H)$ | H | H | OH | H | $CH_3$ | $OCH_3$ | |
| $Q_{23}(R_7=H)$ | H | H | OH | H | $OCH_3$ | $OCH_3$ | |
| $Q_{23}(R_7=H)$ | H | H | OH | H | Cl | $OCH_3$ | |
| $Q_{24}(R_7=H,R_8=H)$ | H | H | C=O | | $CH_3$ | $CH_3$ | |
| $Q_{24}(R_7=H,R_8=H)$ | H | H | C=O | | $CH_3$ | $OCH_3$ | |
| $Q_{24}(R_7=H,R_8=H)$ | H | H | C=O | | $OCH_3$ | $OCH_3$ | |
| $Q_{24}(R_7=H,R_8=H)$ | H | H | C=O | | Cl | $OCH_3$ | |
| $Q_{24}(R_7=H,R_8=H)$ | H | H | OH | H | $CH_3$ | $CH_3$ | |
| $Q_{24}(R_7=H,R_8=H)$ | H | H | OH | H | $CH_3$ | $OCH_3$ | |
| $Q_{24}(R_7=H,R_8=H)$ | H | H | OH | H | $OCH_3$ | $OCH_3$ | |
| $Q_{24}(R_7=H,R_8=H)$ | H | H | OH | H | Cl | $OCH_3$ | |
| $Q_{24}(R_7=H,R_8=H)$ | H | H | $OCH_3$ | $OCH_3$ | $OCH_3$ | $OCH_3$ | |
| $Q_{24}(R_7=H,R_8=H)$ | H | H | —O(CH$_2$)$_3$O— | | $OCH_3$ | $OCH_3$ | |
| $Q_{25}(R_7=H,R_8=H)$ | H | H | C=O | | $CH_3$ | $CH_3$ | |
| $Q_{25}(R_7=H,R_8=H)$ | H | H | C=O | | $CH_3$ | $OCH_3$ | |
| $Q_{25}(R_7=H,R_8=H)$ | H | H | C=O | | $OCH_3$ | $OCH_3$ | |
| $Q_{25}(R_7=H,R_8=H)$ | H | H | C=O | | Cl | $OCH_3$ | |
| $Q_{25}(R_7=H,R_8=H)$ | H | H | OH | H | $CH_3$ | $CH_3$ | |
| $Q_{25}(R_7=H,R_8=H)$ | H | H | OH | H | $CH_3$ | $OCH_3$ | |
| $Q_{25}(R_7=H,R_8=H)$ | H | H | OH | H | $OCH_3$ | $OCH_3$ | |
| $Q_{25}(R_7=H,R_8=H)$ | H | H | OH | H | Cl | $OCH_3$ | |
| $Q_{26}(R_7=H,R_8=H)$ | H | H | C=O | | $CH_3$ | $CH_3$ | |
| $Q_{26}(R_7=H,R_8=H)$ | H | H | C=O | | $CH_3$ | $OCH_3$ | |
| $Q_{26}(R_7=H,R_8=H)$ | H | H | C=O | | $OCH_3$ | $OCH_3$ | |
| $Q_{26}(R_7=H,R_8=H)$ | H | H | C=O | | Cl | $OCH_3$ | |
| $Q_{26}(R_7=H,R_8=H)$ | H | H | OH | H | $CH_3$ | $CH_3$ | |
| $Q_{26}(R_7=H,R_8=H)$ | H | H | OH | H | $CH_3$ | $OCH_3$ | |
| $Q_{26}(R_7=H,R_8=H)$ | H | H | OH | H | $OCH_3$ | $OCH_3$ | |
| $Q_{26}(R_7=H,R_8=H)$ | H | H | OH | H | Cl | $OCH_3$ | |
| $Q_{27}(R_7=H,R_{11}=H,R_{12}=H)$ | H | H | C=O | | $CH_3$ | $CH_3$ | |
| $Q_{27}(R_7=H,R_{11}=H,R_{12}=H)$ | H | H | C=O | | $CH_3$ | $OCH_3$ | |
| $Q_{27}(R_7=H,R_{11}=H,R_{12}=H)$ | H | H | C=O | | $OCH_3$ | $OCH_3$ | |
| $Q_{27}(R_7=H,R_{11}=H,R_{12}=H)$ | H | H | C=O | | Cl | $OCH_3$ | |
| $Q_{27}(R_7=H,R_{11}=H,R_{12}=H)$ | H | H | OH | H | $CH_3$ | $CH_3$ | |
| $Q_{27}(R_7=H,R_{11}=H,R_{12}=H)$ | H | H | OH | H | $CH_3$ | $OCH_3$ | |
| $Q_{27}(R_7=H,R_{11}=H,R_{12}=H)$ | H | H | OH | H | $OCH_3$ | $OCH_3$ | |
| $Q_{27}(R_7=H,R_{11}=H,R_{12}=H)$ | H | H | OH | H | Cl | $OCH_3$ | |
| $Q_{27}(R_7=H,R_{11}=H,R_{12}=H)$ | H | H | $OCH_3$ | $OCH_3$ | $OCH_3$ | $OCH_3$ | |
| $Q_{27}(R_7=H,R_{11}=H,R_{12}=H)$ | H | H | —O(CH$_2$)$_3$O— | | $OCH_3$ | $OCH_3$ | |
| $Q_{28}(R_{11}=H,R_{12}=H)$ | H | H | C=O | | $CH_3$ | $CH_3$ | |
| $Q_{28}(R_{11}=H,R_{12}=H)$ | H | H | C=O | | $CH_3$ | $OCH_3$ | |
| $Q_{28}(R_{11}=H,R_{12}=H)$ | H | H | C=O | | $OCH_3$ | $OCH_3$ | |
| $Q_{28}(R_{11}=H,R_{12}=H)$ | H | H | C=O | | Cl | $OCH_3$ | |
| $Q_{28}(R_{11}=H,R_{12}=H)$ | H | H | OH | H | $CH_3$ | $CH_3$ | |
| $Q_{28}(R_{11}=H,R_{12}=H)$ | H | H | OH | H | $CH_3$ | $OCH_3$ | |
| $Q_{28}(R_{11}=H,R_{12}=H)$ | H | H | OH | H | $OCH_3$ | $OCH_3$ | |
| $Q_{28}(R_{11}=H,R_{12}=H)$ | H | H | OH | H | Cl | $OCH_3$ | |
| $Q_{29}(R_{11}=H,R_{12}=H)$ | H | H | C=O | | $CH_3$ | $CH_3$ | |
| $Q_{29}(R_{11}=H,R_{12}=H)$ | H | H | C=O | | $CH_3$ | $OCH_3$ | |
| $Q_{29}(R_{11}=H,R_{12}=H)$ | H | H | C=O | | $OCH_3$ | $OCH_3$ | |
| $Q_{29}(R_{11}=H,R_{12}=H)$ | H | H | C=O | | Cl | $OCH_3$ | |
| $Q_{29}(R_{11}=H,R_{12}=H)$ | H | H | OH | H | $CH_3$ | $CH_3$ | |
| $Q_{29}(R_{11}=H,R_{12}=H)$ | H | H | OH | H | $CH_3$ | $OCH_3$ | |
| $Q_{29}(R_{11}=H,R_{12}=H)$ | H | H | OH | H | $OCH_3$ | $OCH_3$ | |
| $Q_{29}(R_{11}=H,R_{12}=H)$ | H | H | OH | H | Cl | $OCH_3$ | |
| $Q_{30}(R_7=H,R_8=H)$ | H | H | C=O | | $CH_3$ | $CH_3$ | |
| $Q_{30}(R_7=H,R_8=H)$ | H | H | C=O | | $CH_3$ | $OCH_3$ | |
| $Q_{30}(R_7=H,R_8=H)$ | H | H | C=O | | $OCH_3$ | $OCH_3$ | |
| $Q_{30}(R_7=H,R_8=H)$ | H | H | C=O | | Cl | $OCH_3$ | |
| $Q_{30}(R_7=H,R_8=H)$ | H | H | OH | H | $CH_3$ | $CH_3$ | |
| $Q_{30}(R_7=H,R_8=H)$ | H | H | OH | H | $CH_3$ | $OCH_3$ | |
| $Q_{30}(R_7=H,R_8=H)$ | H | H | OH | H | $OCH_3$ | $OCH_3$ | |
| $Q_{30}(R_7=H,R_8=H)$ | H | H | OH | H | Cl | $OCH_3$ | |
| $Q_{30}(R_7=H,R_8=H)$ | H | H | $OCH_3$ | $OCH_3$ | $OCH_3$ | $OCH_3$ | |
| $Q_{30}(R_7=H,R_8=H)$ | H | H | —O(CH$_2$)$_3$O— | | $OCH_3$ | $OCH_3$ | |
| $Q_{31}(R_7=H,R_8=H)$ | H | H | C=O | | $CH_3$ | $CH_3$ | |
| $Q_{31}(R_7=H,R_8=H)$ | H | H | C=O | | $CH_3$ | $OCH_3$ | |
| $Q_{31}(R_7=H,R_8=H)$ | H | H | C=O | | $OCH_3$ | $OCH_3$ | |
| $Q_{31}(R_7=H,R_8=H)$ | H | H | C=O | | Cl | $OCH_3$ | |
| $Q_{31}(R_7=H,R_8=H)$ | H | H | OH | H | $CH_3$ | $CH_3$ | |
| $Q_{31}(R_7=H,R_8=H)$ | H | H | OH | H | $CH_3$ | $OCH_3$ | |

TABLE I-continued

General Formula I

| Q | R | R₁ | R₂ | R₃ | X | Y | m.p. (°C.) |
|---|---|---|---|---|---|---|---|
| Q₃₁(R₇=H,R₈=H) | H | H | OH | H | OCH₃ | OCH₃ | |
| Q₃₁(R₇=H,R₈=H) | H | H | OH | H | Cl | OCH₃ | |
| Q₃₁(R₇=H,R₈=H) | H | H | OCH₃ | OCH₃ | OCH₃ | OCH₃ | |
| Q₃₁(R₇=H,R₈=H) | H | H | —O(CH₂)₃O— | | OCH₃ | OCH₃ | |
| Q₃₂(R₁₃=OCH₃,R₁₄=OCH₃) | H | H | | C=O | CH₃ | CH₃ | |
| Q₃₂(R₁₃=OCH₃,R₁₄=OCH₃) | H | H | | C=O | CH₃ | OCH₃ | |
| Q₃₂(R₁₃=OCH₃,R₁₄=OCH₃) | H | H | | C=O | OCH₃ | OCH₃ | |
| Q₃₂(R₁₃=OCH₃,R₁₄=OCH₃) | H | H | | C=O | Cl | OCH₃ | |
| Q₃₂(R₁₃=OCH₃,R₁₄=OCH₃) | H | H | OH | H | CH₃ | CH₃ | |
| Q₃₂(R₁₃=OCH₃,R₁₄=OCH₃) | H | H | OH | H | CH₃ | OCH₃ | |
| Q₃₂(R₁₃=OCH₃,R₁₄=OCH₃) | H | H | OH | H | OCH₃ | OCH₃ | |
| Q₃₂(R₁₃=OCH₃,R₁₄=OCH₃) | H | H | OH | H | Cl | OCH₃ | |
| Q₃₃(R₇=H) | H | H | | C=O | CH₃ | CH₃ | |
| Q₃₃(R₇=H) | H | H | | C=O | CH₃ | OCH₃ | |
| Q₃₃(R₇=H) | H | H | | C=O | OCH₃ | OCH₃ | |
| Q₃₃(R₇=H) | H | H | | C=O | Cl | OCH₃ | |
| Q₃₃(R₇=H) | H | H | OH | H | CH₃ | CH₃ | |
| Q₃₃(R₇=H) | H | H | OH | H | CH₃ | OCH₃ | |
| Q₃₃(R₇=H) | H | H | OH | H | OCH₃ | OCH₃ | |
| Q₃₃(R₇=H) | H | H | OH | H | Cl | OCH₃ | |
| Q₃₄ | H | H | | C=O | OCH₃ | OCH₃ | |
| Q₃₄ | H | H | | C=O | CH₃ | CH₃ | |
| Q₃₅ | H | H | | C=O | OCH₃ | OCH₃ | 190–90.5 |
| Q₃₅ | H | H | | C=O | OCH₂CH₃ | OCH₂CH₃ | 193–96 |
| Q₃₆(R₁₀=CH₃ and R₇=R₈=R₁₅=H) | H | H | | C=O | OCH₂CH₃ | OCH₂CH₃ | 199–202 |
| Q₃₆(R₁₀=CH₃ and R₇=R₈=R₁₅=H) | H | H | | C=O | OCH₃ | OCH₃ | |
| Q₃₆(R₁₀=R₇=R₁₅=H R₈=CH₃) | H | H | | C=O | OCH₃ | OCH₃ | |
| Q₃₆(R₁₀=R₇=R₁₅=H R₈=CH₃) | H | H | | C=O | OCH₂CH₃ | OCH₂CH₃ | 151–55 |
| Q₃₆(R₁₀=R₁₅=H; R₇=R₈=Br) | H | H | | C=O | OCH₃ | OCH₃ | 113–15 |
| Q₃₆(R₁₀=R₁₅=H; R₇=R₈=Br) | H | H | | C=O | CH₃ | CH₃ | 190–91.5 |
| Q₃₆(R₁₀=R₁₅=H; R₇=R₈=Br) | H | H | | C=O | CH₃ | OCH₃ | 125–30 |
| Q₃₆(R₁₀=R₁₅=H; R₇=R₈=Br) | H | H | | C=O | Cl | OCH₃ | 116–19 |
| Q₃₇(R₁₀=R₁₆=R₁₅=H) | H | H | | C=O | OCH₃ | OCH₃ | |
| Q₃₇(R₁₀=R₁₆=R₁₅=H) | H | H | | C=O | OCH₂CH₃ | OCH₂CH₃ | 198–200 |
| Q₃₈(R₁₀=R₇=R₈=R₁₅=H) | H | H | | C=O | OCH₃ | OCH₃ | 191–92 |
| Q₃₈(R₁₀=R₇=R₈=R₁₅=H) | H | 3-CH₃ | | C=O | OCH₃ | OCH₃ | 184–88 |
| Q₃₈(R₁₀=R₇=R₈=R₁₅=H) | H | H | | C=O | CH₃ | OCH₃ | 198–200 |
| Q₃₈(R₁₀=R₇=R₈=R₁₅=H) | H | H | | C=O | Cl | OCH₃ | |
| Q₁(R₇=H,R₈=H,R₉=H) | H | 5-CH₃ | | C=O | OCH₃ | OCH₃ | |
| Q₁(R₇=H,R₈=H,R₉=H) | H | 5-CH₂CH₃ | | C=O | OCH₃ | OCH₃ | |
| Q₁(R₇=H,R₈=H,R₉=H) | H | 5-OCH₃ | | C=O | OCH₃ | OCH₃ | |
| Q₁(R₇=H,R₈=H,R₉=H) | H | 5-OCH₂CH₃ | | C=O | OCH₃ | OCH₃ | |
| Q₁(R₇=H,R₈=H,R₉=H) | H | 5-Cl | | C=O | OCH₃ | OCH₃ | |
| Q₁(R₇=H,R₈=H,R₉=H) | H | 5-Br | | C=O | OCH₃ | OCH₃ | |
| Q₁(R₇=H,R₈=H,R₉=H) | H | 5-F | | C=O | OCH₃ | OCH₃ | |
| Q₁(R₇=H,R₈=H,R₉=H) | H | 5-I | | C=O | OCH₃ | OCH₃ | |
| Q₁(R₇=H,R₈=H,R₉=H) | H | 5-NO₂ | | C=O | OCH₃ | OCH₃ | |
| Q₁(R₇=H,R₈=H,R₉=H) | H | 5-CH₂Cl | | C=O | OCH₃ | OCH₃ | |
| Q₁(R₇=H,R₈=H,R₉=H) | H | 5-CF₃ | | C=O | OCH₃ | OCH₃ | |
| Q₁(R₇=H,R₈=H,R₉=H) | H | 5-SCH₃ | | C=O | OCH₃ | OCH₃ | |
| Q₁(R₇=H,R₈=H,R₉=H) | H | 5-SCH₃CH₂CH₃ | | C=O | OCH₃ | OCH₃ | |
| Q₁(R₇=H,R₈=H,R₉=H) | H | 5-SO₂CH₃ | | C=O | OCH₃ | OCH₃ | |
| Q₁(R₇=H,R₈=H,R₉=H) | H | 5-N(CH₃)₂ | | C=O | OCH₃ | OCH₃ | |
| Q₁(R₇=H,R₈=H,R₉=H) | H | 5-SO₂CH₂CH₃ | | C=O | OCH₃ | OCH₃ | |
| Q₁(R₇=H,R₈=H,R₉=H) | H | 3-Cl | | C=O | OCH₃ | OCH₃ | |
| Q₁(R₇=H,R₈=H,R₉=H) | H | 6-Cl | | C=O | OCH₃ | OCH₃ | |
| Q₁(R₇=H,R₈=H,R₉=H) | H | 6-CH₃ | | C=O | OCH₃ | OCH₃ | |
| Q₁(R₇=H,R₈=H,R₉=H) | H | 5-SOCH₃ | | C=O | OCH₃ | OCH₃ | |
| Q₁(R₇=H,R₈=H,R₉=H) | H | 5-SOCH₂CH₂CH₃ | | C=O | OCH₃ | OCH₃ | |
| Q₁(R₇=H,R₈=H,R₉=H) | H | 3-SO₂N(CH₂)₃ | | C=O | OCH₃ | OCH₃ | |
| Q₁(R₇=H,R₈=H,R₉=Cl) | H | 5-CO₂CH₃ | | C=O | OCH₃ | OCH₃ | |
| Q₁(R₇=H,R₈=H,R₉=Cl) | H | 5-CO₂CH₂CH₃ | | C=O | OCH₃ | OCH₃ | |
| Q₁(R₇=H,R₈=H,R₉=Cl) | H | 5-CO₂CH₂CH=CH₂ | | C=O | OCH₃ | OCH₃ | |
| Q₁(R₇=H,R₈=H,R₉=Cl) | H | 5-CO₂CH₂C≡CH | | C=O | OCH₃ | OCH₃ | |
| Q₁(R₇=H,R₈=H,R₉=Cl) | H | 5-CO₂CH₂CF₃ | | C=O | OCH₃ | OCH₃ | |
| Q₁(R₇=H,R₈=H,R₉=Cl) | H | 5-CO₂CH₂CN | | C=O | OCH₃ | OCH₃ | |

TABLE I-continued

General Formula I

| Q | R | R₁ | R₂ | R₃ | X | Y | m.p. (°C.) |
|---|---|---|---|---|---|---|---|
| $Q_1(R_7=H,R_8=H,R_9=Cl)$ | H | 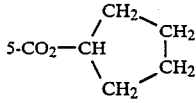 | | C=O | OCH₃ | OCH₃ | |
| $Q_1(R_7=H,R_8=H,R_9=Cl)$ | H | 5-CO₂CH₂OCH₃ | | C=O | OCH₃ | OCH₃ | |
| $Q_1(R_7=H,R_8=H,R_9=Cl)$ | H | H | | C=O | CH₂CH₃ | OCH₃ | |
| $Q_1(R_7=H,R_8=H,R_9=Cl)$ | H | H | | C=O | OCH₂CH₃ | OCH₃ | |
| $Q_1(R_7=H,R_8=H,R_9=Cl)$ | H | H | | C=O | OCH₂F | OCH₃ | |
| $Q_1(R_7=H,R_8=H,R_9=Cl)$ | H | H | | C=O | OCH₂CF₃ | OCH₃ | |
| $Q_1(R_7=H,R_8=H,R_9=Cl)$ | H | H | | C=O | OCH₂CHF₂ | OCH₃ | |
| $Q_1(R_7=H,R_8=H,R_9=Cl)$ | H | H | | C=O | NH₂ | OCH₃ | |
| $Q_1(R_7=H,R_8=H,R_9=Cl)$ | H | H | | C=O | OCH₂CH₂F | OCH₃ | |
| $Q_1(R_7=H,R_8=H,R_9=Cl)$ | H | H | | C=O | CF₃ | OCH₃ | |
| $Q_1(R_7=H,R_8=H,R_9=Cl)$ | H | H | | C=O | F | OCH₃ | |
| $Q_1(R_7=H,R_8=H,R_9=Cl)$ | H | H | | C=O | OCH₃ | H | |
| $Q_1(R_7=H,R_8=H,R_9=Cl)$ | H | H | | C=O | Cl | OCH₂CH₃ | |
| $Q_1(R_7=H,R_8=H,R_9=Cl)$ | H | H | | C=O | OCH₃ | CH₂OCH₃ | |
| $Q_1(R_7=H,R_8=H,R_9=Cl)$ | H | H | | C=O | Cl | NHCH₃ | |
| $Q_1(R_7=H,R_8=H,R_9=Cl)$ | H | H | | C=O | OCH₂CH₃ | N(OCH₃)CH₃ | |
| $Q_1(R_7=H,R_8=H,R_9=Cl)$ | H | H | | C=O | OCH₃ | CH₂CH₃ | |
| $Q_1(R_7=H,R_8=H,R_9=Cl)$ | H | H | | C=O | CF₃ | CF₃ | |
| $Q_1(R_7=H,R_8=H,R_9=Cl)$ | H | H | | C=O | CH₃ | SCH₃ | |
| $Q_1(R_7=H,R_8=H,R_9=Cl)$ | H | H | | C=O | OCH₃ | OCH₂CH=CH₂ | |
| $Q_1(R_7=H,R_8=H,R_9=Cl)$ | H | H | | C=O | CH₃ | CH₂OCH₂CH₃ | |
| $Q_1(R_7=H,R_8=H,R_9=Cl)$ | H | H | | C=O | CH₃ | CH₂OCH₂OCH₃ | |
| $Q_1(R_7=H,R_8=H,R_9=Cl)$ | H | H | | C=O | CH₃ | CH₂SCH₃ | |
| $Q_1(R_7=H,R_8=H,R_9=Cl)$ | H | H | | C=O | CH₃ | CHO | |
| $Q_1(R_7=H,R_8=H,R_9=Cl)$ | H | H | | C=O | CH₃ | C(O)CH₃ | |
| $Q_1(R_7=H,R_8=H,R_9=Cl)$ | H | H | | C=O | OCH₃ | CH(OCH₃)₂ | |
| $Q_1(R_7=H,R_8=H,R_9=Cl)$ | H | H | | C=O | OCH₃ | CH(OCH₂CH₃)₂ | |
| $Q_1(R_7=H,R_8=H,R_9=Cl)$ | H | H | | C=O | OCH₃ | CH(SCH₃)₂ | |
| $Q_1(R_7=H,R_8=H,R_9=Cl)$ | H | H | | C=O | OCH₃ | C(CH₃)(OCH₃)₂ | |
| $Q_1(R_7=H,R_8=H,R_9=Cl)$ | H | H | | C=O | OCH₃ | 1,3-dioxolan-2-yl | |
| $Q_1(R_7=H,R_8=H,R_9=Cl)$ | H | H | | C=O | OCH₃ | 1,3-dioxan-2-yl | |
| $Q_1(R_7=H,R_8=H,R_9=Cl)$ | H | H | | C=O | OCH₃ | 1,3-dithiolan-2-yl | |
| $Q_1(R_7=H,R_8=H,R_9=Cl)$ | H | H | | C=O | OCH₃ | 1,3-oxathiolan-2-yl | |
| $Q_1(R_7=H,R_8=H,R_9=Cl)$ | H | H | | C=O | OCH₃ | 2-methyl-1,3-dioxolan-2-yl | |

TABLE II

General Formula II

| Q | R | R₁ | R₂ | R₃ | X | Y | m.p. (°C.) |
|---|---|---|---|---|---|---|---|
| $Q_1(R_7=H,R_8=H,R_9=H)$ | H | 4-Br | C=O | | CH₃ | CH₃ | 114(d) |
| $Q_1(R_7=H,R_8=H,R_9=H)$ | H | 4-Br | C=O | | CH₃ | OCH₃ | 106(d) |
| $Q_1(R_7=H,R_8=H,R_9=H)$ | H | 4-Br | C=O | | CH₃ | OCH₃ | 111(d) |
| $Q_1(R_7=H,R_8=H,R_9=H)$ | H | H | C=O | | CH₃ | OCH₃ | |
| $Q_1(R_7=H,R_8=H,R_9=H)$ | H | H | OH | H | OCF₂H | CH₃ | |
| $Q_1(R_7=H,R_8=H,R_9=H)$ | H | H | OH | H | CH₃ | OCH₃ | |
| $Q_1(R_7=H,R_8=H,R_9=H)$ | H | H | OH | H | OCH₃ | OCH₃ | |
| $Q_1(R_7=H,R_8=H,R_9=H)$ | H | H | OH | H | Cl | OCH₃ | |
| $Q_1(R_7=H,R_8=H,R_9=H)$ | H | H | OCH₃ | H | OCH₃ | OCH₃ | |
| $Q_1(R_7=H,R_8=H,R_9=H)$ | H | H | OCH₂CH₃ | H | OCH₃ | OCH₃ | |
| $Q_2(R_7=H,R_8=H,R_9=H)$ | H | H | C=O | | CH₃ | CH₃ | |
| $Q_2(R_7=H,R_8=H,R_9=H)$ | H | H | C=O | | CH₃ | OCH₃ | |
| $Q_2(R_7=H,R_8=H,R_9=H)$ | H | H | C=O | | OCH₃ | OCH₃ | |
| $Q_2(R_7=H,R_8=H,R_9=H)$ | H | H | C=O | | Cl | OCH₃ | |
| $Q_2(R_7=H,R_8=H,R_9=H)$ | H | H | OH | H | CH₃ | CH₃ | |
| $Q_2(R_7=H,R_8=H,R_9=H)$ | H | H | OH | H | CH₃ | OCH₃ | |
| $Q_2(R_7=H,R_8=H,R_9=H)$ | H | H | OH | H | OCH₃ | OCH₃ | |
| $Q_2(R_7=H,R_8=H,R_9=H)$ | H | H | OH | H | Cl | OCH₃ | |
| $Q_2(R_7=H,R_8=H,R_9=H)$ | H | H | OCH₃ | H | CH₃ | OCH₃ | |
| $Q_2(R_7=H,R_8=H,R_9=H)$ | H | H | OCH₂CH₃ | H | CH₃ | CH₃ | |
| $Q_3(R_7=H,R_8=H,R_9=H)$ | H | H | C=O | | CH₃ | CH₃ | |
| $Q_3(R_7=H,R_8=H,R_9=H)$ | H | H | C=O | | CH₃ | OCH₃ | |
| $Q_3(R_7=H,R_8=H,R_9=H)$ | H | H | C=O | | OCH₃ | OCH₃ | |
| $Q_3(R_7=H,R_8=H,R_9=H)$ | H | H | C=O | | Cl | OCH₃ | |
| $Q_3(R_7=H,R_8=H,R_9=H)$ | H | H | OH | H | CH₃ | CH₃ | |
| $Q_3(R_7=H,R_8=H,R_9=H)$ | H | H | OH | H | OCH₃ | OCH₃ | |
| $Q_3(R_7=H,R_8=H,R_9=H)$ | H | H | OH | H | Cl | OCH₃ | |
| $Q_3(R_7=H,R_8=H,R_9=Cl)$ | H | H | C=O | | OCH₃ | OCH₃ | |
| $Q_3(R_7=H,R_8=H,R_9=CH_3)$ | H | H | C=O | | OCH₃ | OCH₃ | |
| $Q_3(R_7=H,R_8=H,R_9=CH_3)$ | H | H | OH | H | OCH₃ | OCH₃ | |
| $Q_4(R_7=H,R_8=H,R_9=H)$ | H | H | C=O | | CH₃ | CH₃ | |

TABLE II-continued

General Formula II

| Q | R | $R_1$ | $R_2$ | $R_3$ | X | Y | m.p. (°C.) |
|---|---|---|---|---|---|---|---|
| $Q_4(R_7=H,R_8=H,R_9=H)$ | H | H | C=O | | $CH_3$ | $OCH_3$ | |
| $Q_4(R_7=H,R_8=H,R_9=H)$ | H | H | C=O | | $OCH_3$ | $OCH_3$ | |
| $Q_4(R_7=H,R_8=H,R_9=H)$ | H | H | C=O | | Cl | $OCH_3$ | |
| $Q_4(R_7=H,R_8=H,R_9=H)$ | H | H | OH | H | $CH_3$ | $CH_3$ | |
| $Q_4(R_7=H,R_8=H,R_9=H)$ | H | H | OH | H | $CH_3$ | $OCH_3$ | |
| $Q_4(R_7=H,R_8=H,R_9=H)$ | H | H | OH | H | $OCH_3$ | $OCH_3$ | |
| $Q_4(R_7=H,R_8=H,R_9=H)$ | H | H | OH | H | Cl | $OCH_3$ | |
| $Q_5(R_7=H,R_8=H,R_9=H,R_{10}=CH_3)$ | H | H | C=O | | $CH_3$ | $CH_3$ | |
| $Q_5(R_7=H,R_8=H,R_9=H,R_{10}=CH_3)$ | H | H | C=O | | $CH_3$ | $OCH_3$ | |
| $Q_5(R_7=H,R_8=H,R_9=H,R_{10}=CH_3)$ | H | H | C=O | | $OCH_3$ | $OCH_3$ | |
| $Q_5(R_7=H,R_8=H,R_9=H,R_{10}=CH_3)$ | H | H | C=O | | Cl | $OCH_3$ | |
| $Q_5(R_7=H,R_8=H,R_9=H,R_{10}=CH_3)$ | H | H | OH | H | $CH_3$ | $CH_3$ | |
| $Q_5(R_7=H,R_8=H,R_9=H,R_{10}=CH_3)$ | H | H | OH | H | $CH_3$ | $OCH_3$ | |
| $Q_5(R_7=H,R_8=H,R_9=H,R_{10}=CH_3)$ | H | H | OH | H | $OCH_3$ | $OCH_3$ | |
| $Q_5(R_7=H,R_8=H,R_9=H,R_{10}=CH_3)$ | H | H | OH | H | Cl | $OCH_3$ | |
| $Q_5(R_7=H,R_8=H,R_9=H,R_{10}=CH_3)$ | H | H | $OCH_3$ | H | Cl | $OCH_3$ | |
| $Q_5(R_7=H,R_8=H,R_9=H,R_{10}=CH_3)$ | H | H | $OCH_2CH_3$ | H | $OCH_3$ | $OCH_3$ | |
| $Q_6(R_7=H,R_8=H,R_9=H,R_{10}=CH_3)$ | H | H | C=O | | $CH_3$ | $CH_3$ | |
| $Q_6(R_7=H,R_8=H,R_9=H,R_{10}=CH_3)$ | H | H | C=O | | $CH_3$ | $OCH_3$ | |
| $Q_6(R_7=H,R_8=H,R_9=H,R_{10}=CH_3)$ | H | H | C=O | | $OCH_3$ | $OCH_3$ | |
| $Q_6(R_7=H,R_8=H,R_9=H,R_{10}=CH_3)$ | H | H | C=O | | Cl | $OCH_3$ | |
| $Q_6(R_7=H,R_8=H,R_9=H,R_{10}=CH_3)$ | H | H | OH | H | $CH_3$ | $CH_3$ | |
| $Q_6(R_7=H,R_8=H,R_9=H,R_{10}=CH_3)$ | H | H | OH | H | $CH_3$ | $OCH_3$ | |
| $Q_6(R_7=H,R_8=H,R_9=H,R_{10}=CH_3)$ | H | H | OH | H | $OCH_3$ | $OCH_3$ | |
| $Q_6(R_7=H,R_8=H,R_9=H,R_{10}=CH_3)$ | H | H | OH | H | Cl | $OCH_3$ | |
| $Q_7(R_7=H,R_8=H)$ | H | H | C=O | | $CH_3$ | $CH_3$ | |
| $Q_7(R_7=H,R_8=H)$ | H | H | C=O | | $CH_3$ | $OCH_3$ | |
| $Q_7(R_7=H,R_8=H)$ | H | H | C=O | | $OCH_3$ | $OCH_3$ | |
| $Q_7(R_7=H,R_8=H)$ | H | H | C=O | | Cl | $OCH_3$ | |
| $Q_7(R_7=H,R_8=H)$ | H | H | OH | H | $CH_3$ | $CH_3$ | |
| $Q_7(R_7=H,R_8=H)$ | H | H | OH | H | $CH_3$ | $OCH_3$ | |
| $Q_7(R_7=H,R_8=H)$ | H | H | OH | H | $OCH_3$ | $OCH_3$ | |
| $Q_7(R_7=H,R_8=H)$ | H | H | OH | H | Cl | $OCH_3$ | |
| $Q_8(R_7=H,R_8=H)$ | H | H | C=O | | $OCH_3$ | $OCH_3$ | |
| $Q_8(R_7=H,R_8=H)$ | H | H | C=O | | Cl | $OCH_3$ | |
| $Q_8(R_7=H,R_8=H)$ | H | H | OH | H | Cl | $OCH_3$ | |
| $Q_8(R_7=H,R_8=H)$ | H | H | OH | H | $OCH_3$ | $OCH_3$ | |
| $Q_9(R_7=H,R_8=H)$ | H | H | C=O | | $CH_3$ | $CH_3$ | |
| $Q_9(R_7=H,R_8=H)$ | H | H | C=O | | $CH_3$ | $OCH_3$ | |
| $Q_9(R_7=H,R_8=H)$ | H | H | C=O | | $OCH_3$ | $OCH_3$ | |
| $Q_9(R_7=H,R_8=H)$ | H | H | C=O | | Cl | $OCH_3$ | |
| $Q_9(R_7=H,R_8=H)$ | H | H | OH | H | $CH_3$ | $CH_3$ | |
| $Q_9(R_7=H,R_8=H)$ | H | H | OH | H | $CH_3$ | $OCH_3$ | |
| $Q_9(R_7=H,R_8=H)$ | H | H | OH | H | $OCH_3$ | $OCH_3$ | |
| $Q_9(R_7=H,R_8=H)$ | H | H | OH | H | Cl | $OCH_3$ | |
| $Q_{10}(R_7=H,R_8=H)$ | H | H | C=O | | $CH_3$ | $OCH_3$ | |
| $Q_{10}(R_7=H,R_8=H)$ | H | H | C=O | | $OCH_3$ | $OCH_3$ | |
| $Q_{10}(R_7=H,R_8=H)$ | H | H | C=O | | Cl | $OCH_3$ | |
| $Q_{10}(R_7=H,R_8=H)$ | H | H | OH | H | $CH_3$ | $CH_3$ | |
| $Q_{10}(R_7=H,R_8=H)$ | H | H | OH | H | $OCH_3$ | $OCH_3$ | |
| $Q_{10}(R_7=H,R_8=H)$ | H | H | OH | H | Cl | $OCH_3$ | |
| $Q_{11}(R_7=H,R_8=H)$ | H | H | C=O | | $CH_3$ | $CH_3$ | |
| $Q_{11}(R_7=H,R_8=H)$ | H | H | C=O | | $CH_3$ | $OCH_3$ | |
| $Q_{11}(R_7=H,R_8=H)$ | H | H | C=O | | $OCH_3$ | $OCH_3$ | |
| $Q_{11}(R_7=H,R_8=H)$ | H | H | C=O | | Cl | $OCH_3$ | |
| $Q_{11}(R_7=H,R_8=H)$ | H | H | OH | H | $CH_3$ | $CH_3$ | |
| $Q_{11}(R_7=H,R_8=H)$ | H | H | OH | H | $CH_3$ | $OCH_3$ | |
| $Q_{11}(R_7=H,R_8=H)$ | H | H | OH | H | $OCH_3$ | $OCH_3$ | |
| $Q_{11}(R_7=H,R_8=H)$ | H | H | OH | H | Cl | $OCH_3$ | |
| $Q_{12}(R_7=H,R_8=H)$ | H | H | C=O | | $CH_3$ | $CH_3$ | |
| $Q_{12}(R_7=H,R_8=H)$ | H | H | C=O | | $CH_3$ | $OCH_3$ | |
| $Q_{12}(R_7=H,R_8=H)$ | H | H | C=O | | $OCH_3$ | $OCH_3$ | |
| $Q_{12}(R_7=H,R_8=H)$ | H | H | C=O | | Cl | $OCH_3$ | |
| $Q_{12}(R_7=H,R_8=H)$ | H | H | OH | H | $CH_3$ | $CH_3$ | |
| $Q_{12}(R_7=H,R_8=H)$ | H | H | OH | H | $CH_3$ | $OCH_3$ | |
| $Q_{12}(R_7=H,R_8=H)$ | H | H | OH | H | $OCH_3$ | $OCH_3$ | |
| $Q_{12}(R_7=H,R_8=H)$ | H | H | OH | H | Cl | $OCH_3$ | |
| $Q_{12}(R_7=H,R_8=H)$ | H | H | $OCH_3$ | H | $OCH_3$ | $OCH_3$ | |
| $Q_{13}(R_7=H,R_8=H)$ | H | H | C=O | | $CH_3$ | $CH_3$ | |
| $Q_{13}(R_7=H,R_8=H)$ | H | H | C=O | | $CH_3$ | $OCH_3$ | |
| $Q_{13}(R_7=H,R_8=H)$ | H | H | C=O | | $OCH_3$ | $OCH_3$ | |
| $Q_{13}(R_7=H,R_8=H)$ | H | H | C=O | | Cl | $OCH_3$ | |
| $Q_{13}(R_7=H,R_8=H)$ | H | H | OH | H | $CH_3$ | $CH_3$ | |
| $Q_{13}(R_7=H,R_8=H)$ | H | H | OH | H | $CH_3$ | $OCH_3$ | |
| $Q_{13}(R_7=H,R_8=H)$ | H | H | OH | H | $OCH_3$ | $OCH_3$ | |
| $Q_{13}(R_7=H,R_8=H)$ | H | H | OH | H | Cl | $OCH_3$ | |
| $Q_{14}(R_7=H)$ | H | H | C=O | | $CH_3$ | $CH_3$ | |
| $Q_{14}(R_7=H)$ | H | H | C=O | | $CH_3$ | $OCH_3$ | |
| $Q_{14}(R_7=H)$ | H | H | C=O | | $OCH_3$ | $OCH_3$ | |
| $Q_{14}(R_7=H)$ | H | H | C=O | | Cl | $OCH_3$ | |

TABLE II-continued

| | General Formula II | | | | | | |
|---|---|---|---|---|---|---|---|
| Q | R | $R_1$ | $R_2$ | $R_3$ | X | Y | m.p. (°C.) |
| $Q_{14}(R_7=H)$ | H | H | OH | H | $CH_3$ | $CH_3$ | |
| $Q_{14}(R_7=H)$ | H | H | OH | H | $CH_3$ | $OCH_3$ | |
| $Q_{14}(R_7=H)$ | H | H | OH | H | $OCH_3$ | $OCH_3$ | |
| $Q_{14}(R_7=H)$ | H | H | OH | H | Cl | $OCH_3$ | |
| $Q_{15}(R_7=H)$ | H | H | C=O | | $CH_3$ | $CH_3$ | |
| $Q_{15}(R_7=H)$ | H | H | C=O | | $CH_3$ | $OCH_3$ | |
| $Q_{15}(R_7=H)$ | H | H | C=O | | $OCH_3$ | $OCH_3$ | |
| $Q_{15}(R_7=H)$ | H | H | C=O | | Cl | $OCH_3$ | |
| $Q_{15}(R_7=H)$ | H | H | OH | H | $CH_3$ | $CH_3$ | |
| $Q_{15}(R_7=H)$ | H | H | OH | H | $CH_3$ | $OCH_3$ | |
| $Q_{15}(R_7=H)$ | H | H | OH | H | $OCH_3$ | $OCH_3$ | |
| $Q_{15}(R_7=H)$ | H | H | OH | H | Cl | $OCH_3$ | |
| $Q_{16}(R_7=H)$ | H | H | C=O | | $CH_3$ | $CH_3$ | |
| $Q_{16}(R_7=H)$ | H | H | C=O | | $CH_3$ | $OCH_3$ | |
| $Q_{16}(R_7=H)$ | H | H | C=O | | $OCH_3$ | $OCH_3$ | |
| $Q_{16}(R_7=H)$ | H | H | C=O | | Cl | $OCH_3$ | |
| $Q_{16}(R_7=H)$ | H | H | OH | H | $CH_3$ | $CH_3$ | |
| $Q_{16}(R_7=H)$ | H | H | OH | H | $CH_3$ | $OCH_3$ | |
| $Q_{16}(R_7=H)$ | H | H | OH | H | $OCH_3$ | $OCH_3$ | |
| $Q_{16}(R_7=H)$ | H | H | OH | H | Cl | $OCH_3$ | |
| $Q_{17}(R_7=CH_3)$ | H | H | C=O | | $CH_3$ | $CH_3$ | |
| $Q_{17}(R_7=CH_3)$ | H | H | C=O | | $CH_3$ | $OCH_3$ | |
| $Q_{17}(R_7=CH_3)$ | H | H | C=O | | $OCH_3$ | $OCH_3$ | |
| $Q_{17}(R_7=CH_3)$ | H | H | C=O | | Cl | $OCH_3$ | |
| $Q_{17}(R_7=CH_3)$ | H | H | OH | H | $CH_3$ | $CH_3$ | |
| $Q_{17}(R_7=CH_3)$ | H | H | OH | H | $CH_3$ | $OCH_3$ | |
| $Q_{17}(R_7=CH_3)$ | H | H | OH | H | $OCH_3$ | $OCH_3$ | |
| $Q_{17}(R_7=CH_3)$ | H | H | OH | H | Cl | $OCH_3$ | |
| $Q_{18}(R_7=H)$ | H | H | C=O | | $CH_3$ | $CH_3$ | |
| $Q_{18}(R_7=H)$ | H | H | C=O | | $CH_3$ | $OCH_3$ | |
| $Q_{18}(R_7=H)$ | H | H | C=O | | $OCH_3$ | $OCH_3$ | |
| $Q_{18}(R_7=H)$ | H | H | C=O | | Cl | $OCH_3$ | |
| $Q_{18}(R_7=H)$ | H | H | OH | H | $CH_3$ | $CH_3$ | |
| $Q_{18}(R_7=H)$ | H | H | OH | H | $CH_3$ | $OCH_3$ | |
| $Q_{18}(R_7=H)$ | H | H | OH | H | $OCH_3$ | $OCH_3$ | |
| $Q_{18}(R_7=H)$ | H | H | OH | H | Cl | $OCH_3$ | |
| $Q_{19}(R_7=H,R_8=H)$ | H | H | C=O | | $CH_3$ | $CH_3$ | |
| $Q_{19}(R_7=H,R_8=H)$ | H | H | C=O | | $CH_3$ | $OCH_3$ | |
| $Q_{19}(R_7=H,R_8=H)$ | H | H | C=O | | $OCH_3$ | $OCH_3$ | |
| $Q_{19}(R_7=H,R_8=H)$ | H | H | C=O | | Cl | $OCH_3$ | |
| $Q_{19}(R_7=H,R_8=H)$ | H | H | OH | H | $CH_3$ | $CH_3$ | |
| $Q_{19}(R_7=H,R_8=H)$ | H | H | OH | H | $CH_3$ | $OCH_3$ | |
| $Q_{19}(R_7=H,R_8=H)$ | H | H | OH | H | $OCH_3$ | $OCH_3$ | |
| $Q_{19}(R_7=H,R_8=H)$ | H | H | OH | H | Cl | $OCH_3$ | |
| $Q_{20}(R_7=H,R_8=H)$ | H | H | C=O | | $CH_3$ | $CH_3$ | |
| $Q_{20}(R_7=H,R_8=H)$ | H | H | C=O | | $CH_3$ | $OCH_3$ | |
| $Q_{20}(R_7=H,R_8=H)$ | H | H | C=O | | $OCH_3$ | $OCH_3$ | |
| $Q_{20}(R_7=H,R_8=H)$ | H | H | C=O | | Cl | $OCH_3$ | |
| $Q_{20}(R_7=H,R_8=H)$ | H | H | OH | H | $CH_3$ | $CH_3$ | |
| $Q_{20}(R_7=H,R_8=H)$ | H | H | OH | H | $CH_3$ | $OCH_3$ | |
| $Q_{20}(R_7=H,R_8=H)$ | H | H | OH | H | $OCH_3$ | $OCH_3$ | |
| $Q_{20}(R_7=H,R_8=H)$ | H | H | OH | H | Cl | $OCH_3$ | |
| $Q_{21}(R_7=H,R_8=H,R_9=CH_3)$ | H | H | C=O | | $CH_3$ | $CH_3$ | |
| $Q_{21}(R_7=H,R_8=H,R_9=CH_3)$ | H | H | C=O | | $CH_3$ | $OCH_3$ | |
| $Q_{21}(R_7=H,R_8=H,R_9=CH_3)$ | H | H | C=O | | $OCH_3$ | $OCH_3$ | |
| $Q_{21}(R_7=H,R_8=H,R_9=CH_3)$ | H | H | C=O | | Cl | $OCH_3$ | |
| $Q_{21}(R_7=H,R_8=H,R_9=CH_3)$ | H | H | OH | H | $CH_3$ | $CH_3$ | |
| $Q_{21}(R_7=H,R_8=H,R_9=CH_3)$ | H | H | OH | H | $CH_3$ | $OCH_3$ | |
| $Q_{21}(R_7=H,R_8=H,R_9=CH_3)$ | H | H | OH | H | $OCH_3$ | $OCH_3$ | |
| $Q_{21}(R_7=H,R_8=H,R_9=CH_3)$ | H | H | OH | H | Cl | $OCH_3$ | |
| $Q_{22}(R_7=H)$ | H | H | C=O | | $CH_3$ | $CH_3$ | |
| $Q_{22}(R_7=H)$ | H | H | C=O | | $CH_3$ | $OCH_3$ | |
| $Q_{22}(R_7=H)$ | H | H | C=O | | $OCH_3$ | $OCH_3$ | |
| $Q_{22}(R_7=H)$ | H | H | C=O | | Cl | $OCH_3$ | |
| $Q_{22}(R_7=H)$ | H | H | OH | H | $CH_3$ | $CH_3$ | |
| $Q_{22}(R_7=H)$ | H | H | OH | H | $CH_3$ | $OCH_3$ | |
| $Q_{22}(R_7=H)$ | H | H | OH | H | $OCH_3$ | $OCH_3$ | |
| $Q_{22}(R_7=H)$ | H | H | OH | H | Cl | $OCH_3$ | |
| $Q_{23}(R_7=H)$ | H | H | C=O | | $CH_3$ | $CH_3$ | |
| $Q_{23}(R_7=H)$ | H | H | C=O | | $CH_3$ | $OCH_3$ | |
| $Q_{23}(R_7=H)$ | H | H | C=O | | $OCH_3$ | $OCH_3$ | |
| $Q_{23}(R_7=H)$ | H | H | C=O | | Cl | $OCH_3$ | |
| $Q_{23}(R_7=H)$ | H | H | OH | H | $CH_3$ | $CH_3$ | |
| $Q_{23}(R_7=H)$ | H | H | OH | H | $CH_3$ | $OCH_3$ | |
| $Q_{23}(R_7=H)$ | H | H | OH | H | $OCH_3$ | $OCH_3$ | |
| $Q_{23}(R_7=H)$ | H | H | OH | H | Cl | $OCH_3$ | |
| $Q_{24}(R_7=H,R_8=H)$ | H | H | C=O | | $CH_3$ | $CH_3$ | |
| $Q_{24}(R_7=H,R_8=H)$ | H | H | C=O | | $CH_3$ | $OCH_3$ | |
| $Q_{24}(R_7=H,R_8=H)$ | H | H | C=O | | $OCH_3$ | $OCH_3$ | |
| $Q_{24}(R_7=H,R_8=H)$ | H | H | C=O | | Cl | $OCH_3$ | |

TABLE II-continued

General Formula II

| Q | R | R₁ | R₂ | R₃ | X | Y | m.p. (°C.) |
|---|---|----|----|----|---|---|-----------|
| Q₂₄(R₇=H,R₈=H) | H | H | OH | H | CH₃ | CH₃ | |
| Q₂₄(R₇=H,R₈=H) | H | H | OH | H | CH₃ | OCH₃ | |
| Q₂₄(R₇=H,R₈=H) | H | H | OH | H | OCH₃ | OCH₃ | |
| Q₂₄(R₇=H,R₈=H) | H | H | OH | H | Cl | OCH₃ | |
| Q₂₅(R₇=H,R₈=H) | H | H | C=O | | CH₃ | CH₃ | |
| Q₂₅(R₇=H,R₈=H) | H | H | C=O | | CH₃ | OCH₃ | |
| Q₂₅(R₇=H,R₈=H) | H | H | C=O | | OCH₃ | OCH₃ | |
| Q₂₅(R₇=H,R₈=H) | H | H | C=O | | Cl | OCH₃ | |
| Q₂₅(R₇=H,R₈=H) | H | H | OH | H | CH₃ | CH₃ | |
| Q₂₅(R₇=H,R₈=H) | H | H | OH | H | CH₃ | OCH₃ | |
| Q₂₅(R₇=H,R₈=H) | H | H | OH | H | OCH₃ | OCH₃ | |
| Q₂₅(R₇=H,R₈=H) | H | H | OH | H | Cl | OCH₃ | |
| Q₂₆(R₇=H,R₈=H) | H | H | C=O | | CH₃ | CH₃ | |
| Q₂₆(R₇=H,R₈=H) | H | H | C=O | | CH₃ | OCH₃ | |
| Q₂₆(R₇=H,R₈=H) | H | H | C=O | | OCH₃ | OCH₃ | |
| Q₂₆(R₇=H,R₈=H) | H | H | C=O | | Cl | OCH₃ | |
| Q₂₆(R₇=H,R₈=H) | H | H | OH | H | CH₃ | CH₃ | |
| Q₂₆(R₇=H,R₈=H) | H | H | OH | H | CH₃ | OCH₃ | |
| Q₂₆(R₇=H,R₈=H) | H | H | OH | H | OCH₃ | OCH₃ | |
| Q₂₆(R₇=H,R₈=H) | H | H | OH | H | Cl | OCH₃ | |
| Q₂₇(R₇=H,R₁₁=H,R₁₂=H) | H | H | C=O | | CH₃ | CH₃ | |
| Q₂₇(R₇=H,R₁₁=H,R₁₂=H) | H | H | C=O | | CH₃ | OCH₃ | |
| Q₂₇(R₇=H,R₁₁=H,R₁₂=H) | H | H | C=O | | OCH₃ | OCH₃ | |
| Q₂₇(R₇=H,R₁₁=H,R₁₂=H) | H | H | C=O | | Cl | OCH₃ | |
| Q₂₇(R₇=H,R₁₁=H,R₁₂=H) | H | H | OH | H | CH₃ | CH₃ | |
| Q₂₇(R₇=H,R₁₁=H,R₁₂=H) | H | H | OH | H | CH₃ | OCH₃ | |
| Q₂₇(R₇=H,R₁₁=H,R₁₂=H) | H | H | OH | H | OCH₃ | OCH₃ | |
| Q₂₇(R₇=H,R₁₁=H,R₁₂=H) | H | H | OH | H | Cl | OCH₃ | |
| Q₂₈(R₁₁=H,R₁₂=H) | H | H | C=O | | CH₃ | CH₃ | |
| Q₂₈(R₁₁=H,R₁₂=H) | H | H | C=O | | CH₃ | OCH₃ | |
| Q₂₈(R₁₁=H,R₁₂=H) | H | H | C=O | | OCH₃ | OCH₃ | |
| Q₂₈(R₁₁=H,R₁₂=H) | H | H | C=O | | Cl | OCH₃ | |
| Q₂₈(R₁₁=H,R₁₂=H) | H | H | OH | H | CH₃ | CH₃ | |
| Q₂₈(R₁₁=H,R₁₂=H) | H | H | OH | H | CH₃ | OCH₃ | |
| Q₂₈(R₁₁=H,R₁₂=H) | H | H | OH | H | OCH₃ | OCH₃ | |
| Q₂₈(R₁₁=H,R₁₂=H) | H | H | OH | H | Cl | OCH₃ | |
| Q₂₉(R₁₁=H,R₁₂=H) | H | H | C=O | | CH₃ | CH₃ | |
| Q₂₉(R₁₁=H,R₁₂=H) | H | H | C=O | | CH₃ | OCH₃ | |
| Q₂₉(R₁₁=H,R₁₂=H) | H | H | C=O | | OCH₃ | OCH₃ | |
| Q₂₉(R₁₁=H,R₁₂=H) | H | H | C=O | | Cl | OCH₃ | |
| Q₂₉(R₁₁=H,R₁₂=H) | H | H | OH | H | CH₃ | CH₃ | |
| Q₂₉(R₁₁=H,R₁₂=H) | H | H | OH | H | CH₃ | OCH₃ | |
| Q₂₉(R₁₁=H,R₁₂=H) | H | H | OH | H | OCH₃ | OCH₃ | |
| Q₂₉(R₁₁=H,R₁₂=H) | H | H | OH | H | Cl | OCH₃ | |
| Q₃₀(R₇=H,R₈=H) | H | H | C=O | | CH₃ | CH₃ | |
| Q₃₀(R₇=H,R₈=H) | H | H | C=O | | CH₃ | OCH₃ | |
| Q₃₀(R₇=H,R₈=H) | H | H | C=O | | OCH₃ | OCH₃ | |
| Q₃₀(R₇=H,R₈=H) | H | H | C=O | | Cl | OCH₃ | |
| Q₃₀(R₇=H,R₈=H) | H | H | OH | H | CH₃ | CH₃ | |
| Q₃₀(R₇=H,R₈=H) | H | H | OH | H | CH₃ | OCH₃ | |
| Q₃₀(R₇=H,R₈=H) | H | H | OH | H | OCH₃ | OCH₃ | |
| Q₃₀(R₇=H,R₈=H) | H | H | OH | H | Cl | OCH₃ | |
| Q₃₁(R₇=H,R₈=H) | H | H | C=O | | CH₃ | CH₃ | |
| Q₃₁(R₇=H,R₈=H) | H | H | C=O | | CH₃ | OCH₃ | |
| Q₃₁(R₇=H,R₈=H) | H | H | C=O | | OCH₃ | OCH₃ | |
| Q₃₁(R₇=H,R₈=H) | H | H | C=O | | Cl | OCH₃ | |
| Q₃₁(R₇=H,R₈=H) | H | H | OH | H | CH₃ | CH₃ | |
| Q₃₁(R₇=H,R₈=H) | H | H | OH | H | CH₃ | OCH₃ | |
| Q₃₁(R₇=H,R₈=H) | H | H | OH | H | OCH₃ | OCH₃ | |
| Q₃₁(R₇=H,R₈=H) | H | H | OH | H | Cl | OCH₃ | |
| Q₃₂(R₁₃=OCH₃,R₁₄=OCH₃) | H | H | C=O | | CH₃ | CH₃ | |
| Q₃₂(R₁₃=OCH₃,R₁₄=OCH₃) | H | H | C=O | | CH₃ | OCH₃ | |
| Q₃₂(R₁₃=OCH₃,R₁₄=OCH₃) | H | H | C=O | | OCH₃ | OCH₃ | |
| Q₃₂(R₁₃=OCH₃,R₁₄=OCH₃) | H | H | C=O | | Cl | OCH₃ | |
| Q₃₂(R₁₃=OCH₃,R₁₄=OCH₃) | H | H | OH | H | CH₃ | CH₃ | |
| Q₃₂(R₁₃=OCH₃,R₁₄=OCH₃) | H | H | OH | H | CH₃ | OCH₃ | |
| Q₃₂(R₁₃=OCH₃,R₁₄=OCH₃) | H | H | OH | H | OCH₃ | OCH₃ | |
| Q₃₂(R₁₃=OCH₃,R₁₄=OCH₃) | H | H | OH | H | Cl | OCH₃ | |
| Q₃₃(R₇=H) | H | H | C=O | | CH₃ | CH₃ | |
| Q₃₃(R₇=H) | H | H | C=O | | CH₃ | OCH₃ | |
| Q₃₃(R₇=H) | H | H | C=O | | OCH₃ | OCH₃ | |
| Q₃₃(R₇=H) | H | H | C=O | | Cl | OCH₃ | |
| Q₃₃(R₇=H) | H | H | OH | H | CH₃ | CH₃ | |
| Q₃₃(R₇=H) | H | H | OH | H | CH₃ | OCH₃ | |
| Q₃₃(R₇=H) | H | H | OH | H | OCH₃ | OCH₃ | |
| Q₃₃(R₇=H) | H | H | OH | H | Cl | OCH₃ | |

TABLE III

General Formula III

| Q | R | R$_1$ | R$_2$ | R$_3$ | X | Y | m.p. (°C.) |
|---|---|---|---|---|---|---|---|
| Q$_1$(R$_7$=H,R$_8$=H,R$_9$=H) | H | H | C=O | | CH$_3$ | CH$_3$ | |
| Q$_1$(R$_7$=H,R$_8$=H,R$_9$=H) | H | H | C=O | | CH$_3$ | OCH$_3$ | |
| Q$_1$(R$_7$=H,R$_8$=H,R$_9$=H) | H | H | C=O | | —CH$_2$CH$_2$CH$_3$ | OCH$_3$ | |
| Q$_1$(R$_7$=H,R$_8$=H,R$_9$=H) | H | H | C=O | | Cl | OCH$_3$ | |
| Q$_1$(R$_7$=H,R$_8$=H,R$_9$=H) | H | H | OH | H | CH$_3$ | CH$_3$ | |
| Q$_1$(R$_7$=H,R$_8$=H,R$_9$=H) | H | H | OH | H | CH$_3$ | OCH$_3$ | |
| Q$_1$(R$_7$=H,R$_8$=H,R$_9$=H) | H | H | OH | H | OCH$_3$ | OCH$_3$ | |
| Q$_1$(R$_7$=H,R$_8$=H,R$_9$=H) | H | H | OH | H | Cl | OCH$_3$ | |
| Q$_1$(R$_7$=H,R$_8$=H,R$_9$=H) | H | H | OCH$_3$ | H | OCH$_3$ | OCH$_3$ | |
| Q$_1$(R$_7$=H,R$_8$=H,R$_9$=H) | H | H | OCH$_2$CH$_3$ | H | OCH$_3$ | OCH$_3$ | |
| Q$_2$(R$_7$=H,R$_8$=H,R$_9$=H) | H | H | C=O | | CH$_3$ | CH$_3$ | |
| Q$_2$(R$_7$=H,R$_8$=H,R$_9$=H) | H | H | C=O | | CH$_3$ | OCH$_3$ | |
| Q$_2$(R$_7$=H,R$_8$=H,R$_9$=H) | H | H | C=O | | OCH$_3$ | OCH$_3$ | |
| Q$_2$(R$_7$=H,R$_8$=H,R$_9$=H) | H | H | C=O | | Cl | OCH$_3$ | |
| Q$_2$(R$_7$=H,R$_8$=H,R$_9$=H) | H | H | OH | H | CH$_3$ | CH$_3$ | |
| Q$_2$(R$_7$=H,R$_8$=H,R$_9$=H) | H | H | OH | H | CH$_3$ | OCH$_3$ | |
| Q$_2$(R$_7$=H,R$_8$=H,R$_9$=H) | H | H | OH | H | OCH$_3$ | OCH$_3$ | |
| Q$_2$(R$_7$=H,R$_8$=H,R$_9$=H) | H | H | OH | H | Cl | OCH$_3$ | |
| Q$_2$(R$_7$=H,R$_8$=H,R$_9$=H) | H | H | OCH$_3$ | H | CH$_3$ | OCH$_3$ | |
| Q$_2$(R$_7$=H,R$_8$=H,R$_9$=H) | H | H | OCH$_2$CH$_3$ | H | CH$_3$ | CH$_3$ | |
| Q$_3$(R$_7$=H,R$_8$=H,R$_9$=H) | H | H | C=O | | CH$_3$ | CH$_3$ | |
| Q$_3$(R$_7$=H,R$_8$=H,R$_9$=H) | H | H | C=O | | CH$_3$ | OCH$_3$ | |
| Q$_3$(R$_7$=H,R$_8$=H,R$_9$=H) | H | H | C=O | | OCH$_3$ | OCH$_3$ | |
| Q$_3$(R$_7$=H,R$_8$=H,R$_9$=H) | H | H | C=O | | Cl | OCH$_3$ | |
| Q$_3$(R$_7$=H,R$_8$=H,R$_9$=H) | H | H | OH | H | CH$_3$ | CH$_3$ | |
| Q$_3$(R$_7$=H,R$_8$=H,R$_9$=H) | H | H | OH | H | CH$_3$ | OCH$_3$ | |
| Q$_3$(R$_7$=H,R$_8$=H,R$_9$=H) | H | H | OH | H | OCH$_3$ | OCH$_3$ | |
| Q$_3$(R$_7$=H,R$_8$=H,R$_9$=H) | H | H | OH | H | Cl | OCH$_3$ | |
| Q$_3$(R$_7$=H,R$_8$=H,R$_9$=Cl) | H | H | C=O | | OCH$_3$ | OCH$_3$ | |
| Q$_3$(R$_7$=H,R$_8$=H,R$_9$=CH$_3$) | H | H | C=O | | OCH$_3$ | OCH$_3$ | |
| Q$_3$(R$_7$=H,R$_8$=H,R$_9$=CH$_3$) | H | H | OH | H | OCH$_3$ | OCH$_3$ | |
| Q$_4$(R$_7$=H,R$_8$=H,R$_9$=H) | H | H | C=O | | CH$_3$ | CH$_3$ | |
| Q$_4$(R$_7$=H,R$_8$=H,R$_9$=H) | H | H | C=O | | CH$_3$ | OCH$_3$ | |
| Q$_4$(R$_7$=H,R$_8$=H,R$_9$=H) | H | H | C=O | | OCH$_3$ | OCH$_3$ | |
| Q$_4$(R$_7$=H,R$_8$=H,R$_9$=H) | H | H | C=O | | Cl | OCH$_3$ | |
| Q$_4$(R$_7$=H,R$_8$=H,R$_9$=H) | H | H | OH | H | CH$_3$ | CH$_3$ | |
| Q$_4$(R$_7$=H,R$_8$=H,R$_9$=H) | H | H | OH | H | CH$_3$ | OCH$_3$ | |
| Q$_4$(R$_7$=H,R$_8$=H,R$_9$=H) | H | H | OH | H | OCH$_3$ | OCH$_3$ | |
| Q$_4$(R$_7$=H,R$_8$=H,R$_9$=H) | H | H | OH | H | Cl | OCH$_3$ | |
| Q$_5$(R$_7$=H,R$_8$=H,R$_9$=H,R$_{10}$=CH$_3$) | H | H | C=O | | CH$_3$ | CH$_3$ | |
| Q$_5$(R$_7$=H,R$_8$=H,R$_9$=H,R$_{10}$=CH$_3$) | H | H | C=O | | CH$_3$ | OCH$_3$ | |
| Q$_5$(R$_7$=H,R$_8$=H,R$_9$=H,R$_{10}$=CH$_3$) | H | H | C=O | | OCH$_3$ | OCH$_3$ | |
| Q$_5$(R$_7$=H,R$_8$=H,R$_9$=H,R$_{10}$=CH$_3$) | H | H | C=O | | Cl | OCH$_3$ | |
| Q$_5$(R$_7$=H,R$_8$=H,R$_9$=H,R$_{10}$=CH$_3$) | H | H | OH | H | CH$_3$ | CH$_3$ | |
| Q$_5$(R$_7$=H,R$_8$=H,R$_9$=H,R$_{10}$=CH$_3$) | H | H | OH | H | CH$_3$ | OCH$_3$ | |
| Q$_5$(R$_7$=H,R$_8$=H,R$_9$=H,R$_{10}$=CH$_3$) | H | H | OH | H | OCH$_3$ | OCH$_3$ | |
| Q$_5$(R$_7$=H,R$_8$=H,R$_9$=H,R$_{10}$=CH$_3$) | H | H | OH | H | Cl | OCH$_3$ | |
| Q$_5$(R$_7$=H,R$_8$=H,R$_9$=H,R$_{10}$=CH$_3$) | H | H | OCH$_3$ | H | Cl | OCH$_3$ | |
| Q$_5$(R$_7$=H,R$_8$=H,R$_9$=H,R$_{10}$=CH$_3$) | H | H | OCH$_2$CH$_3$ | H | OCH$_3$ | OCH$_3$ | |
| Q$_6$(R$_7$=H,R$_8$=H,R$_9$=H,R$_{10}$=CH$_3$) | H | H | C=O | | CH$_3$ | CH$_3$ | |
| Q$_6$(R$_7$=H,R$_8$=H,R$_9$=H,R$_{10}$=CH$_3$) | H | H | C=O | | CH$_3$ | OCH$_3$ | |
| Q$_6$(R$_7$=H,R$_8$=H,R$_9$=H,R$_{10}$=CH$_3$) | H | H | C=O | | OCH$_3$ | OCH$_3$ | |
| Q$_6$(R$_7$=H,R$_8$=H,R$_9$=H,R$_{10}$=CH$_3$) | H | H | C=O | | Cl | OCH$_3$ | |
| Q$_6$(R$_7$=H,R$_8$=H,R$_9$=H,R$_{10}$=CH$_3$) | H | H | OH | O | CH$_3$ | CH$_3$ | |
| Q$_6$(R$_7$=H,R$_8$=H,R$_9$=H,R$_{10}$=CH$_3$) | H | H | OH | H | CH$_3$ | OCH$_3$ | |
| Q$_6$(R$_7$=H,R$_8$=H,R$_9$=H,R$_{10}$=CH$_3$) | H | H | OH | H | OCH$_3$ | OCH$_3$ | |
| Q$_6$(R$_7$=H,R$_8$=H,R$_9$=H,R$_{10}$=CH$_3$) | H | H | OH | H | Cl | OCH$_3$ | |
| Q$_7$(R$_7$=H,R$_8$=H) | H | H | C=O | | CH$_3$ | CH$_3$ | |
| Q$_7$(R$_7$=H,R$_8$=H) | H | H | C=O | | CH$_3$ | OCH$_3$ | |
| Q$_7$(R$_7$=H,R$_8$=H) | H | H | C=O | | OCH$_3$ | OCH$_3$ | |
| Q$_7$(R$_7$=H,R$_8$=H) | H | H | C=O | | Cl | OCH$_3$ | |
| Q$_7$(R$_7$=H,R$_8$=H) | H | H | OH | H | CH$_3$ | CH$_3$ | |
| Q$_7$(R$_7$=H,R$_8$=H) | H | H | OH | H | CH$_3$ | OCH$_3$ | |
| Q$_7$(R$_7$=H,R$_8$=H) | H | H | OH | H | OCH$_3$ | OCH$_3$ | |
| Q$_7$(R$_7$=H,R$_8$=H) | H | H | OH | H | Cl | OCH$_3$ | |
| Q$_8$(R$_7$=H,R$_8$=H) | H | H | C=O | | OCH$_3$ | OCH$_3$ | |
| Q$_8$(R$_7$=H,R$_8$=H) | H | H | C=O | | Cl | OCH$_3$ | |
| Q$_9$(R$_7$=H,R$_8$=H) | H | H | OH | H | Cl | OCH$_3$ | |
| Q$_8$(R$_7$=H,R$_8$=H) | H | H | OH | H | OCH$_3$ | OCH$_3$ | |
| Q$_8$(R$_7$=H,R$_8$=H) | H | H | C=O | | CH$_3$ | CH$_3$ | |
| Q$_9$(R$_7$=H,R$_8$=H) | H | H | C=O | | CH$_3$ | OCH$_3$ | |
| Q$_9$(R$_7$=H,R$_8$=H) | H | H | C=O | | OCH$_3$ | OCH$_3$ | |
| Q$_9$(R$_7$=H,R$_8$=H) | H | H | C=O | | Cl | OCH$_3$ | |
| Q$_9$(R$_7$=H,R$_8$=H) | H | H | OH | H | CH$_3$ | CH$_3$ | |
| Q$_9$(R$_7$=H,R$_8$=H) | H | H | OH | H | CH$_3$ | OCH$_3$ | |
| Q$_9$(R$_7$=H,R$_8$=H) | H | H | OH | H | OCH$_3$ | OCH$_3$ | |
| Q$_9$(R$_7$=H,R$_8$=H) | H | H | OH | H | Cl | OCH$_3$ | |
| Q$_{10}$(R$_7$=H,R$_8$=H) | H | H | C=O | | CH$_3$ | OCH$_3$ | |
| Q$_{10}$(R$_7$=H,R$_8$=H) | H | H | C=O | | OCH$_3$ | OCH$_3$ | |
| Q$_{10}$(R$_7$=H,R$_8$=H) | H | H | C=O | | Cl | OCH$_3$ | |

TABLE III-continued

General Formula III

| Q | R | R₁ | R₂ | | R₃ | X | Y | m.p. (°C.) |
|---|---|---|---|---|---|---|---|---|
| Q₁₀(R₇=H,R₈=H) | H | H | OH | | H | CH₃ | CH₃ | |
| Q₁₀(R₇=H,R₈=H) | H | H | OH | | H | OCH₃ | OCH₃ | |
| Q₁₀(R₇=H,R₈=H) | H | H | OH | | H | Cl | OCH₃ | |
| Q₁₁(R₇=H,R₈=H) | H | H | | C=O | | CH₃ | CH₃ | |
| Q₁₁(R₇=H,R₈=H) | H | H | | C=O | | CH₃ | OCH₃ | |
| Q₁₁(R₇=H,R₈=H) | H | H | | C=O | | OCH₃ | OCH₃ | |
| Q₁₁(R₇=H,R₈=H) | H | H | | C=O | | Cl | OCH₃ | |
| Q₁₁(R₇=H,R₈=H) | H | H | OH | | H | CH₃ | CH₃ | |
| Q₁₁(R₇=H,R₈=H) | H | H | OH | | H | CH₃ | OCH₃ | |
| Q₁₁(R₇=H,R₈=H) | H | H | OH | | H | OCH₃ | OCH₃ | |
| Q₁₁(R₇=H,R₈=H) | H | H | OH | | H | Cl | OCH₃ | |
| Q₁₂(R₇=H,R₈=H) | H | H | | C=O | | CH₃ | CH₃ | |
| Q₁₂(R₇=H,R₈=H) | H | H | | C=O | | CH₃ | OCH₃ | |
| Q₁₂(R₇=H,R₈=H) | H | H | | C=O | | OCH₃ | OCH₃ | |
| Q₁₂(R₇=H,R₈=H) | H | H | | C=O | | Cl | OCH₃ | |
| Q₁₂(R₇=H,R₈=H) | H | H | OH | | H | CH₃ | CH₃ | |
| Q₁₂(R₇=H,R₈=H) | H | H | OH | | H | CH₃ | OCH₃ | |
| Q₁₂(R₇=H,R₈=H) | H | H | OH | | H | OCH₃ | OCH₃ | |
| Q₁₂(R₇=H,R₈=H) | H | H | OH | | H | Cl | OCH₃ | |
| Q₁₂(R₇=H,R₈=H) | H | H | OCH₃ | | H | OCH₃ | OCH₃ | |
| Q₁₃(R₇=H,R₈=H) | H | H | | C=O | | CH₃ | CH₃ | |
| Q₁₃(R₇=H,R₈=H) | H | H | | C=O | | CH₃ | OCH₃ | |
| Q₁₃(R₇=H,R₈=H) | H | H | | C=O | | OCH₃ | OCH₃ | |
| Q₁₃(R₇=H,R₈=H) | H | H | | C=O | | Cl | OCH₃ | |
| Q₁₃(R₇=H,R₈=H) | H | H | OH | | H | CH₃ | CH₃ | |
| Q₁₃(R₇=H,R₈=H) | H | H | OH | | H | CH₃ | OCH₃ | |
| Q₁₃(R₇=H,R₈=H) | H | H | OH | | H | OCH₃ | OCH₃ | |
| Q₁₃(R₇=H,R₈=H) | H | H | OH | | H | Cl | OCH₃ | |
| Q₁₄(R₇=H) | H | H | | C=O | | CH₃ | CH₃ | |
| Q₁₄(R₇=H) | H | H | | C=O | | CH₃ | OCH₃ | |
| Q₁₄(R₇=H) | H | H | | C=O | | OCH₃ | OCH₃ | |
| Q₁₄(R₇=H) | H | H | | C=O | | Cl | OCH₃ | |
| Q₁₄(R₇=H) | H | H | OH | | H | CH₃ | CH₃ | |
| Q₁₄(R₇=H) | H | H | OH | | H | CH₃ | OCH₃ | |
| Q₁₄(R₇=H) | H | H | OH | | H | OCH₃ | OCH₃ | |
| Q₁₄(R₇=H) | H | H | OH | | H | Cl | OCH₃ | |
| Q₁₅(R₇=H) | H | H | | C=O | | CH₃ | CH₃ | |
| Q₁₅(R₇=H) | H | H | | C=O | | CH₃ | OCH₃ | |
| Q₁₅(R₇=H) | H | H | | C=O | | OCH₃ | OCH₃ | |
| Q₁₅(R₇=H) | H | H | | C=O | | Cl | OCH₃ | |
| Q₁₅(R₇=H) | H | H | OH | | H | CH₃ | CH₃ | |
| Q₁₅(R₇=H) | H | H | OH | | H | CH₃ | OCH₃ | |
| Q₁₅(R₇=H) | H | H | OH | | H | OCH₃ | OCH₃ | |
| Q₁₅(R₇=H) | H | H | OH | | H | Cl | OCH₃ | |
| Q₁₆(R₇=H) | H | H | | C=O | | CH₃ | CH₃ | |
| Q₁₆(R₇=H) | H | H | | C=O | | CH₃ | OCH₃ | |
| Q₁₆(R₇=H) | H | H | | C=O | | OCH₃ | OCH₃ | |
| Q₁₆(R₇=H) | H | H | | C=O | | Cl | OCH₃ | |
| Q₁₆(R₇=H) | H | H | OH | | H | CH₃ | CH₃ | |
| Q₁₆(R₇=H) | H | H | OH | | H | CH₃ | OCH₃ | |
| Q₁₆(R₇=H) | H | H | OH | | H | OCH₃ | OCH₃ | |
| Q₁₆(R₇=H) | H | H | OH | | H | Cl | OCH₃ | |
| Q₁₇(R₇=CH₃) | H | H | | C=O | | CH₃ | CH₃ | |
| Q₁₇(R₇=CH₃) | H | H | | C=O | | CH₃ | OCH₃ | |
| Q₁₇(R₇=CH₃) | H | H | | C=O | | OCH₃ | OCH₃ | |
| Q₁₇(R₇=CH₃) | H | H | | C=O | | Cl | OCH₃ | |
| Q₁₇(R₇=CH₃) | H | H | OH | | H | CH₃ | CH₃ | |
| Q₁₇(R₇=CH₃) | H | H | OH | | H | CH₃ | OCH₃ | |
| Q₁₇(R₇=CH₃) | H | H | OH | | H | OCH₃ | OCH₃ | |
| Q₁₇(R₇=CH₃) | H | H | OH | | H | Cl | OCH₃ | |
| Q₁₈(R₇=H) | H | H | | C=O | | CH₃ | CH₃ | |
| Q₁₈(R₇=H) | H | H | | C=O | | CH₃ | OCH₃ | |
| Q₁₈(R₇=H) | H | H | | C=O | | OCH₃ | OCH₃ | |
| Q₁₈(R₇=H) | H | H | | C=O | | Cl | OCH₃ | |
| Q₁₈(R₇=H) | H | H | OH | | H | CH₃ | CH₃ | |
| Q₁₈(R₇=H) | H | H | OH | | H | CH₃ | OCH₃ | |
| Q₁₈(R₇=H) | H | H | OH | | H | OCH₃ | OCH₃ | |
| Q₁₈(R₇=H) | H | H | OH | | H | Cl | OCH₃ | |
| Q₁₉(R₇=H,R₈=H) | H | H | | C=O | | CH₃ | CH₃ | |
| Q₁₉(R₇=H,R₈=H) | H | H | | C=O | | CH₃ | OCH₃ | |
| Q₁₉(R₇=H,R₈=H) | H | H | | C=O | | OCH₃ | OCH₃ | |
| Q₁₉(R₇=H,R₈=H) | H | H | | C=O | | Cl | OCH₃ | |
| Q₁₉(R₇=H,R₈=H) | H | H | OH | | H | CH₃ | CH₃ | |
| Q₁₉(R₇=H,R₈=H) | H | H | OH | | H | CH₃ | OCH₃ | |
| Q₁₉(R₇=H,R₈=H) | H | H | OH | | H | OCH₃ | OCH₃ | |
| Q₁₉(R₇=H,R₈=H) | H | H | OH | | H | Cl | OCH₃ | |
| Q₂₀(R₇=H,R₈=H) | H | H | | C=O | | CH₃ | CH₃ | |
| Q₂₀(R₇=H,R₈=H) | H | H | | C=O | | CH₃ | OCH₃ | |
| Q₂₀(R₇=H,R₈=H) | H | H | | C=O | | OCH₃ | OCH₃ | |
| Q₂₀(R₇=H,R₈=H) | H | H | | C=O | | Cl | OCH₃ | |

TABLE III-continued

General Formula III

| Q | R | R₁ | R₂ | R₃ | X | Y | m.p. (°C.) |
|---|---|----|----|----|----|---|-----------|
| Q₂₀(R₇=H,R₈=H) | H | H | OH | H | CH₃ | CH₃ | |
| Q₂₀(R₇=H,R₈=H) | H | H | OH | H | CH₃ | OCH₃ | |
| Q₂₀(R₇=H,R₈=H) | H | H | OH | H | OCH₃ | OCH₃ | |
| Q₂₀(R₇=H,R₈=H) | H | H | OH | H | Cl | OCH₃ | |
| Q₂₁(R₇=H,R₈=H,R₉=CH₃) | H | H | C=O | | CH₃ | CH₃ | |
| Q₂₁(R₇=H,R₈=H,R₉=CH₃) | H | H | C=O | | CH₃ | OCH₃ | |
| Q₂₁(R₇=H,R₈=H,R₉=CH₃) | H | H | C=O | | OCH₃ | OCH₃ | |
| Q₂₁(R₇=H,R₈=H,R₉=CH₃) | H | H | C=O | | Cl | OCH₃ | |
| Q₂₁(R₇=H,R₈=H,R₉=CH₃) | H | H | OH | H | CH₃ | CH₃ | |
| Q₂₁(R₇=H,R₈=H,R₉=CH₃) | H | H | OH | H | CH₃ | OCH₃ | |
| Q₂₁(R₇=H,R₈=H,R₉=CH₃) | H | H | OH | H | OCH₃ | OCH₃ | |
| Q₂₁(R₇=H,R₈=H,R₉=CH₃) | H | H | OH | H | Cl | OCH₃ | |
| Q₂₂(R₇=H) | H | H | C=O | | CH₃ | CH₃ | |
| Q₂₂(R₇=H) | H | H | C=O | | CH₃ | OCH₃ | |
| Q₂₂(R₇=H) | H | H | C=O | | OCH₃ | OCH₃ | |
| Q₂₂(R₇=H) | H | H | C=O | | Cl | OCH₃ | |
| Q₂₂(R₇=H) | H | H | OH | H | CH₃ | CH₃ | |
| Q₂₂(R₇=H) | H | H | OH | H | CH₃ | OCH₃ | |
| Q₂₂(R₇=H) | H | H | OH | H | OCH₃ | OCH₃ | |
| Q₂₂(R₇=H) | H | H | OH | H | Cl | OCH₃ | |
| Q₂₃(R₇=H) | H | H | C=O | | CH₃ | CH₃ | |
| Q₂₃(R₇=H) | H | H | C=O | | CH₃ | OCH₃ | |
| Q₂₃(R₇=H) | H | H | C=O | | OCH₃ | OCH₃ | |
| Q₂₃(R₇=H) | H | H | C=O | | Cl | OCH₃ | |
| Q₂₃(R₇=H) | H | H | OH | H | CH₃ | CH₃ | |
| Q₂₃(R₇=H) | H | H | OH | H | CH₃ | OCH₃ | |
| Q₂₃(R₇=H) | H | H | OH | H | OCH₃ | OCH₃ | |
| Q₂₃(R₇=H) | H | H | OH | H | Cl | OCH₃ | |
| Q₂₄(R₇=H,R₈=H) | H | H | C=O | | CH₃ | CH₃ | |
| Q₂₄(R₇=H,R₈=H) | H | H | C=O | | CH₃ | OCH₃ | |
| Q₂₄(R₇=H,R₈=H) | H | H | C=O | | OCH₃ | OCH₃ | |
| Q₂₄(R₇=H,R₈=H) | H | H | C=O | | Cl | OCH₃ | |
| Q₂₄(R₇=H,R₈=H) | H | H | OH | H | CH₃ | CH₃ | |
| Q₂₄(R₇=H,R₈=H) | H | H | OH | H | CH₃ | OCH₃ | |
| Q₂₄(R₇=H,R₈=H) | H | H | OH | H | OCH₃ | OCH₃ | |
| Q₂₄(R₇=H,R₈=H) | H | H | OH | H | Cl | OCH₃ | |
| Q₂₅(R₇=H,R₈=H) | H | H | C=O | | CH₃ | CH₃ | |
| Q₂₅(R₇=H,R₈=H) | H | H | C=O | | CH₃ | OCH₃ | |
| Q₂₅(R₇=H,R₈=H) | H | H | C=O | | OCH₃ | OCH₃ | |
| Q₂₅(R₇=H,R₈=H) | H | H | C=O | | Cl | OCH₃ | |
| Q₂₅(R₇=H,R₈=H) | H | H | OH | H | CH₃ | CH₃ | |
| Q₂₅(R₇=H,R₈=H) | H | H | OH | H | CH₃ | OCH₃ | |
| Q₂₅(R₇=H,R₈=H) | H | H | OH | H | OCH₃ | OCH₃ | |
| Q₂₅(R₇=H,R₈=H) | H | H | OH | H | Cl | OCH₃ | |
| Q₂₆(R₇=H,R₈=H) | H | H | C=O | | CH₃ | CH₃ | |
| Q₂₆(R₇=H,R₈=H) | H | H | C=O | | CH₃ | OCH₃ | |
| Q₂₆(R₇=H,R₈=H) | H | H | C=O | | OCH₃ | OCH₃ | |
| Q₂₆(R₇=H,R₈=H) | H | H | C=O | | Cl | OCH₃ | |
| Q₂₆(R₇=H,R₈=H) | H | H | OH | H | CH₃ | CH₃ | |
| Q₂₆(R₇=H,R₈=H) | H | H | OH | H | CH₃ | OCH₃ | |
| Q₂₆(R₇=H,R₈=H) | H | H | OH | H | OCH₃ | OCH₃ | |
| Q₂₆(R₇=H,R₈=H) | H | H | OH | H | Cl | OCH₃ | |
| Q₂₇(R₇=H,R₁₁=H,R₁₂=H) | H | H | C=O | | CH₃ | CH₃ | |
| Q₂₇(R₇=H,R₁₁=H,R₁₂=H) | H | H | C=O | | CH₃ | OCH₃ | |
| Q₂₇(R₇=H,R₁₁=H,R₁₂=H) | H | H | C=O | | OCH₃ | OCH₃ | |
| Q₂₇(R₇=H,R₁₁=H,R₁₂=H) | H | H | C=O | | Cl | OCH₃ | |
| Q₂₇(R₇=H,R₁₁=H,R₁₂=H) | H | H | OH | H | CH₃ | CH₃ | |
| Q₂₇(R₇=H,R₁₁=H,R₁₂=H) | H | H | OH | H | CH₃ | OCH₃ | |
| Q₂₇(R₇=H,R₁₁=H,R₁₂=H) | H | H | OH | H | OCH₃ | OCH₃ | |
| Q₂₇(R₇=H,R₁₁=H,R₁₂=H) | H | H | OH | H | Cl | OCH₃ | |
| Q₂₈(R₁₁=H,R₁₂=H) | H | H | C=O | | CH₃ | CH₃ | |
| Q₂₈(R₁₁=H,R₁₂=H) | H | H | C=O | | CH₃ | OCH₃ | |
| Q₂₈(R₁₁=H,R₁₂=H) | H | H | C=O | | OCH₃ | OCH₃ | |
| Q₂₈(R₁₁=H,R₁₂=H) | H | H | C=O | | Cl | OCH₃ | |
| Q₂₈(R₁₁=H,R₁₂=H) | H | H | OH | H | CH₃ | CH₃ | |
| Q₂₈(R₁₁=H,R₁₂=H) | H | H | OH | H | CH₃ | OCH₃ | |
| Q₂₈(R₁₁=H,R₁₂=H) | H | H | OH | H | OCH₃ | OCH₃ | |
| Q₂₈(R₁₁=H,R₁₂=H) | H | H | OH | H | Cl | OCH₃ | |
| Q₂₉(R₁₁=H,R₁₂=H) | H | H | C=O | | CH₃ | CH₃ | |
| Q₂₉(R₁₁=H,R₁₂=H) | H | H | C=O | | CH₃ | OCH₃ | |
| Q₂₉(R₁₁=H,R₁₂=H) | H | H | C=O | | OCH₃ | OCH₃ | |
| Q₂₉(R₁₁=H,R₁₂=H) | H | H | C=O | | Cl | OCH₃ | |
| Q₂₉(R₁₁=H,R₁₂=H) | H | H | OH | H | CH₃ | CH₃ | |
| Q₂₉(R₁₁=H,R₁₂=H) | H | H | OH | H | CH₃ | OCH₃ | |
| Q₂₉(R₁₁=H,R₁₂=H) | H | H | OH | H | OCH₃ | OCH₃ | |
| Q₂₉(R₁₁=H,R₁₂=H) | H | H | OH | H | Cl | OCH₃ | |
| Q₃₀(R₇=H,R₈=H) | H | H | C=O | | CH₃ | CH₃ | |
| Q₃₀(R₇=H,R₈=H) | H | H | C=O | | CH₃ | OCH₃ | |
| Q₃₀(R₇=H,R₈=H) | H | H | C=O | | OCH₃ | OCH₃ | |
| Q₃₀(R₇=H,R₈=H) | H | H | C=O | | Cl | OCH₃ | |

TABLE III-continued

General Formula III

| Q | R | $R_1$ | $R_2$ | $R_3$ | X | Y | m.p. (°C.) |
|---|---|---|---|---|---|---|---|
| $Q_{30}(R_7=H,R_8=H)$ | H | H | OH | H | $CH_3$ | $CH_3$ | |
| $Q_{30}(R_7=H,R_8=H)$ | H | H | OH | H | $CH_3$ | $OCH_3$ | |
| $Q_{30}(R_7=H,R_8=H)$ | H | H | OH | H | $OCH_3$ | $OCH_3$ | |
| $Q_{30}(R_7=H,R_8=H)$ | H | H | OH | H | Cl | $OCH_3$ | |
| $Q_{31}(R_7=H,R_8=H)$ | H | H | C=O | | $CH_3$ | $CH_3$ | |
| $Q_{31}(R_7=H,R_8=H)$ | H | H | C=O | | $CH_3$ | $OCH_3$ | |
| $Q_{31}(R_7=H,R_8=H)$ | H | H | C=O | | $OCH_3$ | $OCH_3$ | |
| $Q_{31}(R_7=H,R_8=H)$ | H | H | C=O | | Cl | $OCH_3$ | |
| $Q_{31}(R_7=H,R_8=H)$ | H | H | OH | H | $CH_3$ | $CH_3$ | |
| $Q_{31}(R_7=H,R_8=H)$ | H | H | OH | H | $CH_3$ | $OCH_3$ | |
| $Q_{31}(R_7=H,R_8=H)$ | H | H | OH | H | $OCH_3$ | $OCH_3$ | |
| $Q_{31}(R_7=H,R_8=H)$ | H | H | OH | H | Cl | $OCH_3$ | |
| $Q_{32}(R_{13}=OCH_3,R_{14}=OCH_3)$ | H | H | C=O | | $CH_3$ | $CH_3$ | |
| $Q_{32}(R_{13}=OCH_3,R_{14}=OCH_3)$ | H | H | C=O | | $CH_3$ | $OCH_3$ | |
| $Q_{32}(R_{13}=OCH_3,R_{14}=OCH_3)$ | H | H | C=O | | $OCH_3$ | $OCH_3$ | |
| $Q_{32}(R_{13}=OCH_3,R_{14}=OCH_3)$ | H | H | C=O | | Cl | $OCH_3$ | |
| $Q_{32}(R_{13}=OCH_3,R_{14}=OCH_3)$ | H | H | OH | H | $CH_3$ | $CH_3$ | |
| $Q_{32}(R_{13}=OCH_3,R_{14}=OCH_3)$ | H | H | OH | H | $CH_3$ | $OCH_3$ | |
| $Q_{32}(R_{13}=OCH_3,R_{14}=OCH_3)$ | H | H | OH | H | $OCH_3$ | $OCH_3$ | |
| $Q_{32}(R_{13}=OCH_3,R_{14}=OCH_3)$ | H | H | OH | H | Cl | $OCH_3$ | |
| $Q_{33}(R_7=H)$ | H | H | C=O | | $CH_3$ | $CH_3$ | |
| $Q_{33}(R_7=H)$ | H | H | C=O | | $CH_3$ | $OCH_3$ | |
| $Q_{33}(R_7=H)$ | H | H | C=O | | $OCH_3$ | $OCH_3$ | |
| $Q_{33}(R_7=H)$ | H | H | C=O | | Cl | $OCH_3$ | |
| $Q_{33}(R_7=H)$ | H | H | OH | H | $CH_3$ | $CH_3$ | |
| $Q_{33}(R_7=H)$ | H | H | OH | H | $CH_3$ | $OCH_3$ | |
| $Q_{33}(R_7=H)$ | H | H | OH | H | $OCH_3$ | $OCH_3$ | |
| $Q_{33}(R_7=H)$ | H | H | OH | H | Cl | $OCH_3$ | |

TABLE IV

General Formula IV

| $Q_1$ | R | $R_1$ | $R_2$ | $R_3$ | X | Y | m.p. (°C.) |
|---|---|---|---|---|---|---|---|
| $Q_1(R_7 = H, R_8 = H, R_9 = H)$ | H | H | C=O | | $CH_3$ | $CH_3$ | |
| $Q_1(R_7 = H, R_8 = H, R_9 = H)$ | H | H | C=O | | $CH_3$ | $OCH_3$ | |
| $Q_1(R_7 = H, R_8 = H, R_9 = H)$ | H | H | C=O | | $OCH_3$ | $OCH_3$ | |
| $Q_1(R_7 = H, R_8 = H, R_9 = H)$ | H | H | C=O | | Cl | $OCH_3$ | |
| $Q_1(R_7 = H, R_8 = H, R_9 = H)$ | H | H | OH | H | $CH_3$ | $CH_3$ | |
| $Q_1(R_7 = H, R_8 = H, R_9 = H)$ | H | H | OH | H | $CH_3$ | $OCH_3$ | |
| $Q_1(R_7 = H, R_8 = H, R_9 = H)$ | H | H | OH | H | $OCH_3$ | $OCH_3$ | |
| $Q_1(R_7 = H, R_8 = H, R_9 = H)$ | H | H | OH | H | Cl | $OCH_3$ | |
| $Q_1(R_7 = H, R_8 = H, R_9 = H)$ | H | H | $OCH_3$ | H | $OCH_3$ | $OCH_3$ | |
| $Q_1(R_7 = H, R_8 = H, R_9 = H)$ | H | H | $OCH_2CH_3$ | H | $OCH_3$ | $OCH_3$ | |
| $Q_2(R_7 = H, R_8 = H, R_9 = H)$ | H | H | C=O | | $CH_3$ | $CH_3$ | |
| $Q_2(R_7 = H, R_8 = H, R_9 = H)$ | H | H | C=O | | $CH_3$ | $OCH_3$ | |
| $Q_2(R_7 = H, R_8 = H, R_9 = H)$ | H | H | C=O | | $OCH_3$ | $OCH_3$ | |
| $Q_2(R_7 = H, R_8 = H, R_9 = H)$ | H | H | C=O | | Cl | $OCH_3$ | |
| $Q_2(R_7 = H, R_8 = H, R_9 = H)$ | H | H | OH | H | $CH_3$ | $CH_3$ | |
| $Q_2(R_7 = H, R_8 = H, R_9 = H)$ | H | H | OH | H | $CH_3$ | $OCH_3$ | |
| $Q_2(R_7 = H, R_8 = H, R_9 = H)$ | H | H | OH | H | $OCH_3$ | $OCH_3$ | |
| $Q_2(R_7 = H, R_8 = H, R_9 = H)$ | H | H | OH | H | Cl | $OCH_3$ | |
| $Q_2(R_7 = H, R_8 = H, R_9 = H)$ | H | H | $OCH_3$ | H | $CH_3$ | $CH_3$ | |
| $Q_2(R_7 = H, R_8 = H, R_9 = H)$ | H | H | $OCH_2CH_3$ | H | $CH_3$ | $CH_3$ | |
| $Q_3(R_7 = H, R_8 = H, R_9 = H)$ | H | H | C=O | | $CH_3$ | $CH_3$ | |
| $Q_3(R_7 = H, R_8 = H, R_9 = H)$ | H | H | C=O | | $CH_3$ | $OCH_3$ | |
| $Q_3(R_7 = H, R_8 = H, R_9 = H)$ | H | H | C=O | | $OCH_3$ | $OCH_3$ | |
| $Q_3(R_7 = H, R_8 = H, R_9 = H)$ | H | H | C=O | | Cl | $OCH_3$ | |
| $Q_3(R_7 = H, R_8 = H, R_9 = H)$ | H | H | OH | H | $CH_3$ | $CH_3$ | |
| $Q_3(R_7 = H, R_8 = H, R_9 = H)$ | H | H | OH | H | $CH_3$ | $OCH_3$ | |
| $Q_3(R_7 = H, R_8 = H, R_9 = H)$ | H | H | OH | H | $OCH_3$ | $OCH_3$ | |
| $Q_3(R_7 = H, R_8 = H, R_9 = H)$ | H | H | OH | H | Cl | $OCH_3$ | |
| $Q_3(R_7 = H, R_8 = H, R_9 = Cl)$ | H | H | C=O | | $OCH_3$ | $OCH_3$ | |
| $Q_3(R_7 = H, R_8 = H, R_9 = CH_3)$ | H | H | C=O | | $OCH_3$ | $OCH_3$ | |
| $Q_3(R_7 = H, R_8 = H, R_9 = CH_3)$ | H | H | OH | H | $OCH_3$ | $OCH_3$ | |
| $Q_4(R_7 = H, R_8 = H, R_9 = H)$ | H | H | C=O | | $CH_3$ | $CH_3$ | |
| $Q_4(R_7 = H, R_8 = H, R_9 = H)$ | H | H | C=O | | $CH_3$ | $OCH_3$ | |
| $Q_4(R_7 = H, R_8 = H, R_9 = H)$ | H | H | C=O | | $OCH_3$ | $OCH_3$ | |
| $Q_4(R_7 = H, R_8 = H, R_9 = H)$ | H | H | C=O | | Cl | $OCH_3$ | |
| $Q_4(R_7 = H, R_8 = H, R_9 = H)$ | H | H | OH | H | $CH_3$ | $CH_3$ | |
| $Q_4(R_7 = H, R_8 = H, R_9 = H)$ | H | H | OH | H | $CH_3$ | $OCH_3$ | |
| $Q_4(R_7 = H, R_8 = H, R_9 = H)$ | H | H | OH | H | $OCH_3$ | $OCH_3$ | |
| $Q_4(R_7 = H, R_8 = H, R_9 = H)$ | H | H | OH | H | Cl | $OCH_3$ | |
| $Q_5(R_7 = H, R_8 = H, R_9 = H, R_{10} = CH_3)$ | H | H | C=O | | $CH_3$ | $CH_3$ | |
| $Q_5(R_7 = H, R_8 = H, R_9 = H, R_{10} = CH_3)$ | H | H | C=O | | $CH_3$ | $OCH_3$ | |
| $Q_5(R_7 = H, R_8 = H, R_9 = H, R_{10} = CH_3)$ | H | H | C=O | | $OCH_3$ | $OCH_3$ | |
| $Q_5(R_7 = H, R_8 = H, R_9 = H, R_{10} = CH_3)$ | H | H | C=O | | Cl | $OCH_3$ | |
| $Q_5(R_7 = H, R_8 = H, R_9 = H, R_{10} = CH_3)$ | H | H | OH | H | $CH_3$ | $CH_3$ | |
| $Q_5(R_7 = H, R_8 = H, R_9 = H, R_{10} = CH_3)$ | H | H | OH | H | $CH_3$ | $OCH_3$ | |

TABLE IV-continued

General Formula IV

| $Q_1$ | R | $R_1$ | $R_2$ | $R_3$ | X | Y | m.p. (°C.) |
|---|---|---|---|---|---|---|---|
| $Q_5(R_7 = H, R_8 = H, R_9 = H, R_{10} = CH_3)$ | H | H | OH | H | $OCH_3$ | $OCH_3$ | |
| $Q_5(R_7 = H, R_8 = H, R_9 = H, R_{10} = CH_3)$ | H | H | OH | H | Cl | $OCH_3$ | |
| $Q_5(R_7 = H, R_8 = H, R_9 = H, R_{10} = CH_3)$ | H | H | $OCH_3$ | H | Cl | $OCH_3$ | |
| $Q_5(R_7 = H, R_8 = H, R_9 = H, R_{10} = CH_3)$ | H | H | $OCH_2CH_3$ | H | $OCH_3$ | $OCH_3$ | |
| $Q_6(R_7 = H, R_8 = H, R_9 = H, R_{10} = CH_3)$ | H | H | C=O | | $CH_3$ | $CH_3$ | |
| $Q_6(R_7 = H, R_8 = H, R_9 = H, R_{10} = CH_3)$ | H | H | C=O | | $CH_3$ | $OCH_3$ | |
| $Q_6(R_7 = H, R_8 = H, R_9 = H, R_{10} = CH_3)$ | H | H | C=O | | $OCH_3$ | $OCH_3$ | |
| $Q_6(R_7 = H, R_8 = H, R_9 = H, R_{10} = CH_3)$ | H | H | C=O | | Cl | $OCH_3$ | |
| $Q_6(R_7 = H, R_8 = H, R_9 = H, R_{10} = CH_3)$ | H | H | OH | H | $CH_3$ | $CH_3$ | |
| $Q_6(R_7 = H, R_8 = H, R_9 = H, R_{10} = CH_3)$ | H | H | OH | H | $CH_3$ | $OCH_3$ | |
| $Q_6(R_7 = H, R_8 = H, R_9 = H, R_{10} = CH_3)$ | H | H | OH | H | $OCH_3$ | $OCH_3$ | |
| $Q_6(R_7 = H, R_8 = H, R_9 = H, R_{10} = CH_3)$ | H | H | OH | H | Cl | $OCH_3$ | |
| $Q_7(R_7 = H, R_8 = H)$ | H | H | C=O | | $CH_3$ | $CH_3$ | |
| $Q_7(R_7 = H, R_8 = H)$ | H | H | C=O | | $CH_3$ | $OCH_3$ | |
| $Q_7(R_7 = H, R_8 = H)$ | H | H | C=O | | $OCH_3$ | $OCH_3$ | |
| $Q_7(R_7 = H, R_8 = H)$ | H | H | C=O | | Cl | $OCH_3$ | |
| $Q_7(R_7 = H, R_8 = H)$ | H | H | OH | H | $CH_3$ | $CH_3$ | |
| $Q_7(R_7 = H, R_8 = H)$ | H | H | OH | H | $CH_3$ | $OCH_3$ | |
| $Q_7(R_7 = H, R_8 = H)$ | H | H | OH | H | $OCH_3$ | $OCH_3$ | |
| $Q_7(R_7 = H, R_8 = H)$ | H | H | OH | H | Cl | $OCH_3$ | |
| $Q_8(R_7 = H, R_8 = H)$ | H | H | C=O | | $OCH_3$ | $OCH_3$ | |
| $Q_8(R_7 = H, R_8 = H)$ | H | H | C=O | | Cl | $OCH_3$ | |
| $Q_8(R_7 = H, R_8 = H)$ | H | H | OH | H | Cl | $OCH_3$ | |
| $Q_8(R_7 = H, R_8 = H)$ | H | H | OH | H | $OCH_3$ | $OCH_3$ | |
| $Q_9(R_7 = H, R_8 = H)$ | H | H | C=O | | $CH_3$ | $CH_3$ | |
| $Q_9(R_7 = H, R_8 = H)$ | H | H | C=O | | $CH_3$ | $OCH_3$ | |
| $Q_9(R_7 = H, R_8 = H)$ | H | H | C=O | | $OCH_3$ | $OCH_3$ | |
| $Q_9(R_7 = H, R_8 = H)$ | H | H | C=O | | Cl | $OCH_3$ | |
| $Q_9(R_7 = H, R_8 = H)$ | H | H | OH | H | $CH_3$ | $CH_3$ | |
| $Q_9(R_7 = H, R_8 = H)$ | H | H | OH | H | $CH_3$ | $OCH_3$ | |
| $Q_9(R_7 = H, R_8 = H)$ | H | H | OH | H | $OCH_3$ | $OCH_3$ | |
| $Q_9(R_7 = H, R_8 = H)$ | H | H | OH | H | Cl | $OCH_3$ | |
| $Q_{10}(R_7 = H, R_8 = H)$ | H | H | C=O | | $CH_3$ | $OCH_3$ | |
| $Q_{10}(R_7 = H, R_8 = H)$ | H | H | C=O | | $OCH_3$ | $OCH_3$ | |
| $Q_{10}(R_7 = H, R_8 = H)$ | H | H | C=O | | Cl | $OCH_3$ | |
| $Q_{10}(R_7 = H, R_8 = H)$ | H | H | OH | H | $CH_3$ | $CH_3$ | |
| $Q_{10}(R_7 = H, R_8 = H)$ | H | H | OH | H | $OCH_3$ | $OCH_3$ | |
| $Q_{10}(R_7 = H, R_8 = H)$ | H | H | OH | H | Cl | $OCH_3$ | |
| $Q_{11}(R_7 = H, R_8 = H)$ | H | H | C=O | | $CH_3$ | $CH_3$ | |
| $Q_{11}(R_7 = H, R_8 = H)$ | H | H | C=O | | $CH_3$ | $OCH_3$ | |
| $Q_{11}(R_7 = H, R_8 = H)$ | H | H | C=O | | $OCH_3$ | $OCH_3$ | |
| $Q_{11}(R_7 = H, R_8 = H)$ | H | H | C=O | | Cl | $OCH_3$ | |
| $Q_{11}(R_7 = H, R_8 = H)$ | H | H | OH | H | $CH_3$ | $CH_3$ | |
| $Q_{11}(R_7 = H, R_8 = H)$ | H | H | OH | H | $CH_3$ | $OCH_3$ | |
| $Q_{11}(R_7 = H, R_8 = H)$ | H | H | OH | H | $OCH_3$ | $OCH_3$ | |
| $Q_{11}(R_7 = H, R_8 = H)$ | H | H | OH | H | Cl | $OCH_3$ | |
| $Q_{12}(R_7 = H, R_8 = H)$ | H | H | C=O | | $CH_3$ | $CH_3$ | |
| $Q_{12}(R_7 = H, R_8 = H)$ | H | H | C=O | | $CH_3$ | $OCH_3$ | |
| $Q_{12}(R_7 = H, R_8 = H)$ | H | H | C=O | | $OCH_3$ | $OCH_3$ | |
| $Q_{12}(R_7 = H, R_8 = H)$ | H | H | C=O | | Cl | $OCH_3$ | |
| $Q_{12}(R_7 = H, R_8 = H)$ | H | H | OH | H | $CH_3$ | $CH_3$ | |
| $Q_{12}(R_7 = H, R_8 = H)$ | H | H | OH | H | $CH_3$ | $OCH_3$ | |
| $Q_{12}(R_7 = H, R_8 = H)$ | H | H | OH | H | $OCH_3$ | $OCH_3$ | |
| $Q_{12}(R_7 = H, R_8 = H)$ | H | H | OH | H | Cl | $OCH_3$ | |
| $Q_{12}(R_7 = H, R_8 = H)$ | H | H | $OCH_3$ | H | $OCH_3$ | $OCH_3$ | |
| $Q_{13}(R_7 = H, R_8 = H)$ | H | H | C=O | | $CH_3$ | $CH_3$ | |
| $Q_{13}(R_7 = H, R_8 = H)$ | H | H | C=O | | $CH_3$ | $OCH_3$ | |
| $Q_{13}(R_7 = H, R_8 = H)$ | H | H | C=O | | $OCH_3$ | $OCH_3$ | |
| $Q_{13}(R_7 = H, R_8 = H)$ | H | H | C=O | | Cl | $OCH_3$ | |
| $Q_{13}(R_7 = H, R_8 = H)$ | H | H | OH | H | $CH_3$ | $CH_3$ | |
| $Q_{13}(R_7 = H, R_8 = H)$ | H | H | OH | H | $CH_3$ | $OCH_3$ | |
| $Q_{13}(R_7 = H, R_8 = H)$ | H | H | OH | H | $OCH_3$ | $OCH_3$ | |
| $Q_{13}(R_7 = H, R_8 = H)$ | H | H | OH | H | Cl | $OCH_3$ | |
| $Q_{14}(R_7 = H)$ | H | H | C=O | | $CH_3$ | $CH_3$ | |
| $Q_{14}(R_7 = H)$ | H | H | C=O | | $CH_3$ | $OCH_3$ | |
| $Q_{14}(R_7 = H)$ | H | H | C=O | | $OCH_3$ | $OCH_3$ | |
| $Q_{14}(R_7 = H)$ | H | H | C=O | | Cl | $OCH_3$ | |
| $Q_{14}(R_7 = H)$ | H | H | OH | H | $CH_3$ | $CH_3$ | |
| $Q_{14}(R_7 = H)$ | H | H | OH | H | $CH_3$ | $OCH_3$ | |
| $Q_{14}(R_7 = H)$ | H | H | OH | H | $OCH_3$ | $OCH_3$ | |
| $Q_{14}(R_7 = H)$ | H | H | OH | H | Cl | $OCH_3$ | |
| $Q_{15}(R_7 = H)$ | H | H | C=O | | $CH_3$ | $CH_3$ | |
| $Q_{15}(R_7 = H)$ | H | H | C=O | | $CH_3$ | $OCH_3$ | |
| $Q_{15}(R_7 = H)$ | H | H | C=O | | $OCH_3$ | $OCH_3$ | |
| $Q_{15}(R_7 = H)$ | H | H | C=O | | Cl | $OCH_3$ | |
| $Q_{15}(R_7 = H)$ | H | H | OH | H | $CH_3$ | $CH_3$ | |
| $Q_{15}(R_7 = H)$ | H | H | OH | H | $CH_3$ | $OCH_3$ | |
| $Q_{15}(R_7 = H)$ | H | H | OH | H | $OCH_3$ | $OCH_3$ | |
| $Q_{15}(R_7 = H)$ | H | H | OH | H | Cl | $OCH_3$ | |
| $Q_{16}(R_7 = H)$ | H | H | C=O | | $CH_3$ | $CH_3$ | |

TABLE IV-continued

General Formula IV

| $Q_1$ | R | $R_1$ | $R_2$ | $R_3$ | X | Y | m.p. (°C.) |
|---|---|---|---|---|---|---|---|
| $Q_{16}(R_7 = H)$ | H | H | C=O | | $CH_3$ | $CH_3$ | |
| $Q_{16}(R_7 = H)$ | H | H | C=O | | $OCH_3$ | $OCH_3$ | |
| $Q_{16}(R_7 = H)$ | H | H | C=O | | Cl | $OCH_3$ | |
| $Q_{16}(R_7 = H)$ | H | H | OH | H | $CH_3$ | $CH_3$ | |
| $Q_{16}(R_7 = H)$ | H | H | OH | H | $CH_3$ | $OCH_3$ | |
| $Q_{16}(R_7 = H)$ | H | H | OH | H | $OCH_3$ | $OCH_3$ | |
| $Q_{16}(R_7 = H)$ | H | H | OH | H | Cl | $OCH_3$ | |
| $Q_{17}(R_7 = CH_3)$ | H | H | C=O | | $CH_3$ | $CH_3$ | |
| $Q_{17}(R_7 = CH_3)$ | H | H | C=O | | $CH_3$ | $OCH_3$ | |
| $Q_{17}(R_7 = CH_3)$ | H | H | C=O | | $OCH_3$ | $OCH_3$ | |
| $Q_{17}(R_7 = CH_3)$ | H | H | C=O | | Cl | $OCH_3$ | |
| $Q_{17}(R_7 = CH_3)$ | H | H | OH | H | $CH_3$ | $CH_3$ | |
| $Q_{17}(R_7 = CH_3)$ | H | H | OH | H | $CH_3$ | $OCH_3$ | |
| $Q_{17}(R_7 = CH_3)$ | H | H | OH | H | $OCH_3$ | $OCH_3$ | |
| $Q_{17}(R_7 = CH_3)$ | H | H | OH | H | Cl | $OCH_3$ | |
| $Q_{18}(R_7 = H)$ | H | H | C=O | | $CH_3$ | $CH_3$ | |
| $Q_{18}(R_7 = H)$ | H | H | C=O | | $CH_3$ | $OCH_3$ | |
| $Q_{18}(R_7 = H)$ | H | H | C=O | | $OCH_3$ | $OCH_3$ | |
| $Q_{18}(R_7 = H)$ | H | H | C=O | | Cl | $OCH_3$ | |
| $Q_{18}(R_7 = H)$ | H | H | OH | H | $CH_3$ | $CH_3$ | |
| $Q_{18}(R_7 = H)$ | H | H | OH | H | $CH_3$ | $OCH_3$ | |
| $Q_{18}(R_7 = H)$ | H | H | OH | H | $OCH_3$ | $OCH_3$ | |
| $Q_{18}(R_7 = H)$ | H | H | OH | H | Cl | $OCH_3$ | |
| $Q_{19}(R_7 = H, R_8 = H)$ | H | H | C=O | | $CH_3$ | $CH_3$ | |
| $Q_{19}(R_7 = H, R_8 = H)$ | H | H | C=O | | $CH_3$ | $OCH_3$ | |
| $Q_{19}(R_7 = H, R_8 = H)$ | H | H | C=O | | $OCH_3$ | $OCH_3$ | |
| $Q_{19}(R_7 = H, R_8 = H)$ | H | H | C=O | | Cl | $OCH_3$ | |
| $Q_{19}(R_7 = H, R_8 = H)$ | H | H | OH | H | $CH_3$ | $CH_3$ | |
| $Q_{19}(R_7 = H, R_8 = H)$ | H | H | OH | H | $CH_3$ | $OCH_3$ | |
| $Q_{19}(R_7 = H, R_8 = H)$ | H | H | OH | H | $OCH_3$ | $OCH_3$ | |
| $Q_{19}(R_7 = H, R_8 = H)$ | H | H | OH | H | Cl | $OCH_3$ | |
| $Q_{20}(R_7 = H, R_8 = H)$ | H | H | C=O | | $CH_3$ | $CH_3$ | |
| $Q_{20}(R_7 = H, R_8 = H)$ | H | H | C=O | | $CH_3$ | $OCH_3$ | |
| $Q_{20}(R_7 = H, R_8 = H)$ | H | H | C=O | | $OCH_3$ | $OCH_3$ | |
| $Q_{20}(R_7 = H, R_8 = H)$ | H | H | C=O | | Cl | $OCH_3$ | |
| $Q_{20}(R_7 = H, R_8 = H)$ | H | H | OH | H | $CH_3$ | $CH_3$ | |
| $Q_{20}(R_7 = H, R_8 = H)$ | H | H | OH | H | $CH_3$ | $OCH_3$ | |
| $Q_{20}(R_7 = H, R_8 = H)$ | H | H | OH | H | $OCH_3$ | $OCH_3$ | |
| $Q_{20}(R_7 = H, R_8 = H)$ | H | H | OH | H | Cl | $OCH_3$ | |
| $Q_{21}(R_7 = H, R_8 = H, R_9 = CH_3)$ | H | H | C=O | | $CH_3$ | $CH_3$ | |
| $Q_{21}(R_7 = H, R_8 = H, R_9 = CH_3)$ | H | H | C=O | | $CH_3$ | $OCH_3$ | |
| $Q_{21}(R_7 = H, R_8 = H, R_9 = CH_3)$ | H | H | C=O | | $OCH_3$ | $OCH_3$ | |
| $Q_{21}(R_7 = H, R_8 = H, R_9 = CH_3)$ | H | H | C=O | | Cl | $OCH_3$ | |
| $Q_{21}(R_7 = H, R_8 = H, R_9 = CH_3)$ | H | H | OH | H | $CH_3$ | $CH_3$ | |
| $Q_{21}(R_7 = H, R_8 = H, R_9 = CH_3)$ | H | H | OH | H | $CH_3$ | $OCH_3$ | |
| $Q_{21}(R_7 = H, R_8 = H, R_9 = CH_3)$ | H | H | OH | H | $OCH_3$ | $OCH_3$ | |
| $Q_{21}(R_7 = H, R_8 = H, R_9 = CH_3)$ | H | H | OH | H | Cl | $OCH_3$ | |
| $Q_{22}(R_7 = H)$ | H | H | C=O | | $CH_3$ | $CH_3$ | |
| $Q_{22}(R_7 = H)$ | H | H | C=O | | $CH_3$ | $OCH_3$ | |
| $Q_{22}(R_7 = H)$ | H | H | C=O | | $OCH_3$ | $OCH_3$ | |
| $Q_{22}(R_7 = H)$ | H | H | C=O | | Cl | $OCH_3$ | |
| $Q_{22}(R_7 = H)$ | H | H | OH | H | $CH_3$ | $CH_3$ | |
| $Q_{22}(R_7 = H)$ | H | H | OH | H | $CH_3$ | $OCH_3$ | |
| $Q_{22}(R_7 = H)$ | H | H | OH | H | $OCH_3$ | $OCH_3$ | |
| $Q_{22}(R_7 = H)$ | H | H | OH | H | Cl | $OCH_3$ | |
| $Q_{23}(R_7 = H)$ | H | H | C=O | | $CH_3$ | $CH_3$ | |
| $Q_{23}(R_7 = H)$ | H | H | C=O | | $CH_3$ | $OCH_3$ | |
| $Q_{23}(R_7 = H)$ | H | H | C=O | | $OCH_3$ | $OCH_3$ | |
| $Q_{23}(R_7 = H)$ | H | H | C=O | | Cl | $OCH_3$ | |
| $Q_{23}(R_7 = H)$ | H | H | OH | H | $CH_3$ | $CH_3$ | |
| $Q_{23}(R_7 = H)$ | H | H | OH | H | $CH_3$ | $OCH_3$ | |
| $Q_{23}(R_7 = H)$ | H | H | OH | H | $OCH_3$ | $OCH_3$ | |
| $Q_{23}(R_7 = H)$ | H | H | OH | H | Cl | $OCH_3$ | |
| $Q_{24}(R_7 = H, R_8 = H)$ | H | H | C=O | | $CH_3$ | $CH_3$ | |
| $Q_{24}(R_7 = H, R_8 = H)$ | H | H | C=O | | $CH_3$ | $OCH_3$ | |
| $Q_{24}(R_7 = H, R_8 = H)$ | H | H | C=O | | $OCH_3$ | $OCH_3$ | |
| $Q_{24}(R_7 = H, R_8 = H)$ | H | H | C=O | | Cl | $OCH_3$ | |
| $Q_{24}(R_7 = H, R_8 = H)$ | H | H | OH | H | $CH_3$ | $CH_3$ | |
| $Q_{24}(R_7 = H, R_8 = H)$ | H | H | OH | H | $CH_3$ | $OCH_3$ | |
| $Q_{24}(R_7 = H, R_8 = H)$ | H | H | OH | H | $OCH_3$ | $OCH_3$ | |
| $Q_{24}(R_7 = H, R_8 = H)$ | H | H | OH | H | Cl | $OCH_3$ | |
| $Q_{25}(R_7 = H, R_8 = H)$ | H | H | C=O | | $CH_3$ | $CH_3$ | |
| $Q_{25}(R_7 = H, R_8 = H)$ | H | H | C=O | | $CH_3$ | $OCH_3$ | |
| $Q_{25}(R_7 = H, R_8 = H)$ | H | H | C=O | | $OCH_3$ | $OCH_3$ | |
| $Q_{25}(R_7 = H, R_8 = H)$ | H | H | C=O | | Cl | $OCH_3$ | |
| $Q_{25}(R_7 = H, R_8 = H)$ | H | H | OH | H | $CH_3$ | $CH_3$ | |
| $Q_{25}(R_7 = H, R_8 = H)$ | H | H | OH | H | $CH_3$ | $OCH_3$ | |
| $Q_{25}(R_7 = H, R_8 = H)$ | H | H | OH | H | $OCH_3$ | $OCH_3$ | |
| $Q_{25}(R_7 = H, R_8 = H)$ | H | H | OH | H | Cl | $OCH_3$ | |
| $Q_{26}(R_7 = H, R_8 = H)$ | H | H | C=O | | $CH_3$ | $CH_3$ | |

TABLE IV-continued

General Formula IV

| Q1 | R | R1 | R2 | | R3 | X | Y | m.p. (°C.) |
|---|---|---|---|---|---|---|---|---|
| Q26(R7 = H, R8 = H) | H | H | C=O | | | CH3 | OCH3 | |
| Q26(R7 = H, R8 = H) | H | H | C=O | | | OCH3 | OCH3 | |
| Q26(R7 = H, R8 = H) | H | H | C=O | | | Cl | OCH3 | |
| Q26(R7 = H, R8 = H) | H | H | OH | | H | CH3 | CH3 | |
| Q26(R7 = H, R8 = H) | H | H | OH | | H | CH3 | OCH3 | |
| Q26(R7 = H, R8 = H) | H | H | OH | | H | OCH3 | OCH3 | |
| Q26(R7 = H, R8 = H) | H | H | OH | | H | Cl | OCH3 | |
| Q27(R7 = H, R11 = H, R12 = H) | H | H | C=O | | | CH3 | CH3 | |
| Q27(R7 = H, R11 = H, R12 = H) | H | H | C=O | | | CH3 | OCH3 | |
| Q27(R7 = H, R11 = H, R12 = H) | H | H | C=O | | | OCH3 | OCH3 | |
| Q27(R7 = H, R11 = H, R12 = H) | H | H | C=O | | | Cl | OCH3 | |
| Q27(R7 = H, R11 = H, R12 = H) | H | H | OH | | H | CH3 | CH3 | |
| Q27(R7 = H, R11 = H, R12 = H) | H | H | OH | | H | CH3 | OCH3 | |
| Q27(R7 = H, R11 = H, R12 = H) | H | H | OH | | H | OCH3 | OCH3 | |
| Q27(R7 = H, R11 = H, R12 = H) | H | H | OH | | H | Cl | OCH3 | |
| Q28(R11 = H, R12 = H) | H | H | C=O | | | CH3 | CH3 | |
| Q28(R11 = H, R12 = H) | H | H | C=O | | | CH3 | OCH3 | |
| Q28(R11 = H, R12 = H) | H | H | C=O | | | OCH3 | OCH3 | |
| Q28(R11 = H, R12 = H) | H | H | C=O | | | Cl | OCH3 | |
| Q28(R11 = H, R12 = H) | H | H | OH | | H | CH3 | CH3 | |
| Q28(R11 = H, R12 = H) | H | H | OH | | H | CH3 | OCH3 | |
| Q28(R11 = H, R12 = H) | H | H | OH | | H | OCH3 | OCH3 | |
| Q28(R11 = H, R12 = H) | H | H | OH | | H | Cl | OCH3 | |
| Q29(R11 = H, R12 = H) | H | H | C=O | | | CH3 | CH3 | |
| Q29(R11 = H, R12 = H) | H | H | C=O | | | CH3 | OCH3 | |
| Q29(R11 = H, R12 = H) | H | H | C=O | | | OCH3 | OCH3 | |
| Q29(R11 = H, R12 = H) | H | H | C=O | | | Cl | OCH3 | |
| Q29(R11 = H, R12 = H) | H | H | OH | | H | CH3 | CH3 | |
| Q29(R11 = H, R12 = H) | H | H | OH | | H | CH3 | OCH3 | |
| Q29(R11 = H, R12 = H) | H | H | OH | | H | OCH3 | OCH3 | |
| Q29(R11 = H, R12 = H) | H | H | OH | | H | Cl | OCH3 | |
| Q30(R7 = H, R8 = H) | H | H | C=O | | | CH3 | CH3 | |
| Q30(R7 = H, R8 = H) | H | H | C=O | | | CH3 | OCH3 | |
| Q30(R7 = H, R8 = H) | H | H | C=O | | | OCH3 | OCH3 | |
| Q30(R7 = H, R8 = H) | H | H | C=O | | | Cl | OCH3 | |
| Q30(R7 = H, R8 = H) | H | H | OH | | H | CH3 | CH3 | |
| Q30(R7 = H, R8 = H) | H | H | OH | | H | CH3 | OCH3 | |
| Q30(R7 = H, R8 = H) | H | H | OH | | H | OCH3 | OCH3 | |
| Q30(R7 = H, R8 = H) | H | H | OH | | H | Cl | OCH3 | |
| Q31(R7 = H, R8 = H) | H | H | C=O | | | CH3 | CH3 | |
| Q31(R7 = H, R8 = H) | H | H | C=O | | | CH3 | OCH3 | |
| Q31(R7 = H, R8 = H) | H | H | C=O | | | OCH3 | OCH3 | |
| Q31(R7 = H, R8 = H) | H | H | C=O | | | Cl | OCH3 | |
| Q31(R7 = H, R8 = H) | H | H | OH | | H | CH3 | CH3 | |
| Q31(R7 = H, R8 = H) | H | H | OH | | H | CH3 | OCH3 | |
| Q31(R7 = H, R8 = H) | H | H | OH | | H | OCH3 | OCH3 | |
| Q31(R7 = H, R8 = H) | H | H | OH | | H | Cl | OCH3 | |
| Q32(R13 = OCH3, R14 = OCH3) | H | H | C=O | | | CH3 | CH3 | |
| Q32(R13 = OCH3, R14 = OCH3) | H | H | C=O | | | CH3 | OCH3 | |
| Q32(R13 = OCH3, R14 = OCH3) | H | H | C=O | | | OCH3 | OCH3 | |
| Q32(R13 = OCH3, R14 = OCH3) | H | H | C=O | | | Cl | OCH3 | |
| Q32(R13 = OCH3, R14 = OCH3) | H | H | OH | | H | CH3 | CH3 | |
| Q32(R13 = OCH3, R14 = OCH3) | H | H | OH | | H | CH3 | OCH3 | |
| Q32(R13 = OCH3, R14 = OCH3) | H | H | OH | | H | OCH3 | OCH3 | |
| Q32(R13 = OCH3, R14 = OCH3) | H | H | OH | | H | Cl | OCH3 | |
| Q33(R7 = H) | H | H | C=O | | | CH3 | CH3 | |
| Q33(R7 = H) | H | H | C=O | | | CH3 | OCH3 | |
| Q33(R7 = H) | H | H | C=O | | | OCH3 | OCH3 | |
| Q33(R7 = H) | H | H | C=O | | | Cl | OCH3 | |
| Q33(R7 = H) | H | H | OH | | H | CH3 | CH3 | |
| Q33(R7 = H) | H | H | OH | | H | CH3 | OCH3 | |
| Q33(R7 = H) | H | H | OH | | H | OCH3 | OCH3 | |
| Q33(R7 = H) | H | H | OH | | H | Cl | OCH3 | |

TABLE V

General Formula V

| Q | R | R1 | R2 | | R3 | X | Y | m.p. (°C.) |
|---|---|---|---|---|---|---|---|---|
| Q1(R7 = H, R8 = H, R9 = H) | H | H | C=O | | | CH3 | CH3 | |
| Q1(R7 = H, R8 = H, R9 = H) | H | H | C=O | | | CH3 | OCH3 | |
| Q1(R7 = H, R8 = H, R9 = H) | H | H | C=O | | | OCH3 | OCH3 | |
| Q1(R7 = H, R8 = H, R9 = H) | H | H | C=O | | | Cl | OCH3 | |
| Q1(R7 = H, R8 = H, R9 = H) | H | H | OH | | H | CH3 | CH3 | |
| Q1(R7 = H, R8 = H, R9 = H) | H | H | OH | | H | CH3 | OCH3 | |
| Q1(R7 = H, R8 = H, R9 = H) | H | H | OH | | H | OCH3 | OCH3 | |
| Q1(R7 = H, R8 = H, R9 = H) | H | H | OH | | H | Cl | OCH3 | |
| Q1(R7 = H, R8 = H, R9 = H) | H | H | OCH3 | | H | OCH3 | OCH3 | |
| Q1(R7 = H, R8 = H, R9 = H) | H | H | OCH2CH3 | | H | OCH3 | OCH3 | |

TABLE V-continued

| | General Formula V | | | | | | |
|---|---|---|---|---|---|---|---|
| Q | R | $R_1$ | $R_2$ | $R_3$ | X | Y | m.p. (°C.) |
| $Q_2(R_7 = H, R_8 = H, R_9 = H)$ | H | H | C=O | | $CH_3$ | $CH_3$ | |
| $Q_2(R_7 = H, R_8 = H, R_9 = H)$ | H | H | C=O | | $CH_3$ | $OCH_3$ | |
| $Q_2(R_7 = H, R_8 = H, R_9 = H)$ | H | H | C=O | | $OCH_3$ | $OCH_3$ | |
| $Q_2(R_7 = H, R_8 = H, R_9 = H)$ | H | H | C=O | | Cl | $OCH_3$ | |
| $Q_2(R_7 = H, R_8 = H, R_9 = H)$ | H | H | OH | H | $CH_3$ | $CH_3$ | |
| $Q_2(R_7 = H, R_8 = H, R_9 = H)$ | H | H | OH | H | $CH_3$ | $OCH_3$ | |
| $Q_2(R_7 = H, R_8 = H, R_9 = H)$ | H | H | OH | H | $OCH_3$ | $OCH_3$ | |
| $Q_2(R_7 = H, R_8 = H, R_9 = H)$ | H | H | OH | H | Cl | $OCH_3$ | |
| $Q_2(R_7 = H, R_8 = H, R_9 = H)$ | H | H | $OCH_3$ | H | $CH_3$ | $CH_3$ | |
| $Q_2(R_7 = H, R_8 = H, R_9 = H)$ | H | H | $OCH_2CH_3$ | H | $CH_3$ | $CH_3$ | |
| $Q_3(R_7 = H, R_8 = H, R_9 = H)$ | H | H | C=O | | $CH_3$ | $CH_3$ | |
| $Q_3(R_7 = H, R_8 = H, R_9 = H)$ | H | H | C=O | | $CH_3$ | $OCH_3$ | |
| $Q_3(R_7 = H, R_8 = H, R_9 = H)$ | H | H | C=O | | $OCH_3$ | $OCH_3$ | |
| $Q_3(R_7 = H, R_8 = H, R_9 = H)$ | H | H | C=O | | Cl | $OCH_3$ | |
| $Q_3(R_7 = H, R_8 = H, R_9 = H)$ | H | H | OH | H | $CH_3$ | $CH_3$ | |
| $Q_3(R_7 = H, R_8 = H, R_9 = H)$ | H | H | OH | H | $CH_3$ | $OCH_3$ | |
| $Q_3(R_7 = H, R_8 = H, R_9 = H)$ | H | H | OH | H | $OCH_3$ | $OCH_3$ | |
| $Q_3(R_7 = H, R_8 = H, R_9 = H)$ | H | H | OH | H | Cl | $OCH_3$ | |
| $Q_3(R_7 = H, R_8 = H, R_9 = Cl)$ | H | H | C=O | | $OCH_3$ | $OCH_3$ | |
| $Q_3(R_7 = H, R_8 = H, R_9 = CH_3)$ | H | H | C=O | | $OCH_3$ | $OCH_3$ | |
| $Q_3(R_7 = H, R_8 = H, R_9 = CH_3)$ | H | H | OH | H | $OCH_3$ | $OCH_3$ | |
| $Q_4(R_7 = H, R_8 = H, R_9 = H)$ | H | H | C=O | | $CH_3$ | $CH_3$ | |
| $Q_4(R_7 = H, R_8 = H, R_9 = H)$ | H | H | C=O | | $CH_3$ | $OCH_3$ | |
| $Q_4(R_7 = H, R_8 = H, R_9 = H)$ | H | H | C=O | | $OCH_3$ | $OCH_3$ | |
| $Q_4(R_7 = H, R_8 = H, R_9 = H)$ | H | H | C=O | | Cl | $OCH_3$ | |
| $Q_4(R_7 = H, R_8 = H, R_9 = H)$ | H | H | OH | H | $CH_3$ | $CH_3$ | |
| $Q_4(R_7 = H, R_8 = H, R_9 = H)$ | H | H | OH | H | $CH_3$ | $OCH_3$ | |
| $Q_4(R_7 = H, R_8 = H, R_9 = H)$ | H | H | OH | H | $OCH_3$ | $OCH_3$ | |
| $Q_4(R_7 = H, R_8 = H, R_9 = H)$ | H | H | OH | H | Cl | $OCH_3$ | |
| $Q_5(R_7 = H, R_8 = H, R_9 = H, R_{10} = CH_3)$ | H | H | C=O | | $CH_3$ | $CH_3$ | |
| $Q_5(R_7 = H, R_8 = H, R_9 = H, R_{10} = CH_3)$ | H | H | C=O | | $CH_3$ | $OCH_3$ | |
| $Q_5(R_7 = H, R_8 = H, R_9 = H, R_{10} = CH_3)$ | H | H | C=O | | $OCH_3$ | $OCH_3$ | |
| $Q_5(R_7 = H, R_8 = H, R_9 = H, R_{10} = CH_3)$ | H | H | C=O | | Cl | $OCH_3$ | |
| $Q_5(R_7 = H, R_8 = H, R_9 = H, R_{10} = CH_3)$ | H | H | OH | H | $CH_3$ | $CH_3$ | |
| $Q_5(R_7 = H, R_8 = H, R_9 = H, R_{10} = CH_3)$ | H | H | OH | H | $CH_3$ | $OCH_3$ | |
| $Q_5(R_7 = H, R_8 = H, R_9 = H, R_{10} = CH_3)$ | H | H | OH | H | $OCH_3$ | $OCH_3$ | |
| $Q_5(R_7 = H, R_8 = H, R_9 = H, R_{10} = CH_3)$ | H | H | OH | H | Cl | $OCH_3$ | |
| $Q_5(R_7 = H, R_8 = H, R_9 = H, R_{10} = CH_3)$ | H | H | $OCH_3$ | H | Cl | $OCH_3$ | |
| $Q_5(R_7 = H, R_8 = H, R_9 = H, R_{10} = CH_3)$ | H | H | $OCH_2CH_3$ | H | $OCH_3$ | $OCH_3$ | |
| $Q_6(R_7 = H, R_8 = H, R_9 = H, R_{10} = CH_3)$ | H | H | C=O | | $CH_3$ | $CH_3$ | |
| $Q_6(R_7 = H, R_8 = H, R_9 = H, R_{10} = CH_3)$ | H | H | C=O | | $CH_3$ | $OCH_3$ | |
| $Q_6(R_7 = H, R_8 = H, R_9 = H, R_{10} = CH_3)$ | H | H | C=O | | $OCH_3$ | $OCH_3$ | |
| $Q_6(R_7 = H, R_8 = H, R_9 = H, R_{10} = CH_3)$ | H | H | C=O | | Cl | $OCH_3$ | |
| $Q_6(R_7 = H, R_8 = H, R_9 = H, R_{10} = CH_3)$ | H | H | OH | H | $CH_3$ | $CH_3$ | |
| $Q_6(R_7 = H, R_8 = H, R_9 = H, R_{10} = CH_3)$ | H | H | OH | H | $CH_3$ | $OCH_3$ | |
| $Q_6(R_7 = H, R_8 = H, R_9 = H, R_{10} = CH_3)$ | H | H | OH | H | $OCH_3$ | $OCH_3$ | |
| $Q_6(R_7 = H, R_8 = H, R_9 = H, R_{10} = CH_3)$ | H | H | OH | H | Cl | $OCH_3$ | |
| $Q_7(R_7 = H, R_8 = H)$ | H | H | C=O | | $CH_3$ | $CH_3$ | |
| $Q_7(R_7 = H, R_8 = H)$ | H | H | C=O | | $CH_3$ | $OCH_3$ | |
| $Q_7(R_7 = H, R_8 = H)$ | H | H | C=O | | $OCH_3$ | $OCH_3$ | |
| $Q_7(R_7 = H, R_8 = H)$ | H | H | C=O | | Cl | $OCH_3$ | |
| $Q_7(R_7 = H, R_8 = H)$ | H | H | OH | H | $CH_3$ | $CH_3$ | |
| $Q_7(R_7 = H, R_8 = H)$ | H | H | OH | H | $CH_3$ | $OCH_3$ | |
| $Q_7(R_7 = H, R_8 = H)$ | H | H | OH | H | $OCH_3$ | $OCH_3$ | |
| $Q_7(R_7 = H, R_8 = H)$ | H | H | OH | H | Cl | $OCH_3$ | |
| $Q_8(R_7 = H, R_8 = H)$ | H | H | C=O | | $OCH_3$ | $OCH_3$ | |
| $Q_8(R_7 = H, R_8 = H)$ | H | H | C=O | | Cl | $OCH_3$ | |
| $Q_8(R_7 = H, R_8 = H)$ | H | H | OH | H | Cl | $OCH_3$ | |
| $Q_8(R_7 = H, R_8 = H)$ | H | H | OH | H | $OCH_3$ | $OCH_3$ | |
| $Q_9(R_7 = H, R_8 = H)$ | H | H | C=O | | $CH_3$ | $CH_3$ | |
| $Q_9(R_7 = H, R_8 = H)$ | H | H | C=O | | $CH_3$ | $OCH_3$ | |
| $Q_9(R_7 = H, R_8 = H)$ | H | H | C=O | | $OCH_3$ | $OCH_3$ | |
| $Q_9(R_7 = H, R_8 = H)$ | H | H | C=O | | Cl | $OCH_3$ | |
| $Q_9(R_7 = H, R_8 = H)$ | H | H | OH | H | $CH_3$ | $CH_3$ | |
| $Q_9(R_7 = H, R_8 = H)$ | H | H | OH | H | $CH_3$ | $OCH_3$ | |
| $Q_9(R_7 = H, R_8 = H)$ | H | H | OH | H | $OCH_3$ | $OCH_3$ | |
| $Q_9(R_7 = H, R_8 = H)$ | H | H | OH | H | Cl | $OCH_3$ | |
| $Q_{10}(R_7 = H, R_8 = H)$ | H | H | C=O | | $CH_3$ | $OCH_3$ | |
| $Q_{10}(R_7 = H, R_8 = H)$ | H | H | C=O | | $OCH_3$ | $OCH_3$ | |
| $Q_{10}(R_7 = H, R_8 = H)$ | H | H | C=O | | Cl | $OCH_3$ | |
| $Q_{10}(R_7 = H, R_8 = H)$ | H | H | OH | H | $CH_3$ | $OCH_3$ | |
| $Q_{10}(R_7 = H, R_8 = H)$ | H | H | OH | H | $OCH_3$ | $OCH_3$ | |
| $Q_{10}(R_7 = H, R_8 = H)$ | H | H | OH | H | Cl | $OCH_3$ | |
| $Q_{11}(R_7 = H, R_8 = H)$ | H | H | C=O | | $CH_3$ | $CH_3$ | |
| $Q_{11}(R_7 = H, R_8 = H)$ | H | H | C=O | | $CH_3$ | $OCH_3$ | |
| $Q_{11}(R_7 = H, R_8 = H)$ | H | H | C=O | | $OCH_3$ | $OCH_3$ | |
| $Q_{11}(R_7 = H, R_8 = H)$ | H | H | C=O | | Cl | $OCH_3$ | |
| $Q_{11}(R_7 = H, R_8 = H)$ | H | H | OH | H | $CH_3$ | $CH_3$ | |
| $Q_{11}(R_7 = H, R_8 = H)$ | H | H | OH | H | $CH_3$ | $OCH_3$ | |
| $Q_{11}(R_7 = H, R_8 = H)$ | H | H | OH | H | $OCH_3$ | $OCH_3$ | |

TABLE V-continued

General Formula V

| Q | R | $R_1$ | $R_2$ | $R_3$ | X | Y | m.p. (°C.) |
|---|---|---|---|---|---|---|---|
| $Q_{11}(R_7 = H, R_8 = H)$ | H | H | OH | H | Cl | $OCH_3$ | |
| $Q_{12}(R_7 = H, R_8 = H)$ | H | H | C=O | | $CH_3$ | $CH_3$ | |
| $Q_{12}(R_7 = H, R_8 = H)$ | H | H | C=O | | $CH_3$ | $OCH_3$ | |
| $Q_{12}(R_7 = H, R_8 = H)$ | H | H | C=O | | $OCH_3$ | $OCH_3$ | |
| $Q_{12}(R_7 = H, R_8 = H)$ | H | H | C=O | | Cl | $OCH_3$ | |
| $Q_{12}(R_7 = H, R_8 = H)$ | H | H | OH | H | $CH_3$ | $CH_3$ | |
| $Q_{12}(R_7 = H, R_8 = H)$ | H | H | OH | H | $CH_3$ | $OCH_3$ | |
| $Q_{12}(R_7 = H, R_8 = H)$ | H | H | OH | H | $OCH_3$ | $OCH_3$ | |
| $Q_{12}(R_7 = H, R_8 = H)$ | H | H | OH | H | Cl | $OCH_3$ | |
| $Q_{12}(R_7 = H, R_8 = H)$ | H | H | $OCH_3$ | H | $OCH_3$ | $OCH_3$ | |
| $Q_{13}(R_7 = H, R_8 = H)$ | H | H | C=O | | $CH_3$ | $CH_3$ | |
| $Q_{13}(R_7 = H, R_8 = H)$ | H | H | C=O | | $CH_3$ | $OCH_3$ | |
| $Q_{13}(R_7 = H, R_8 = H)$ | H | H | C=O | | $OCH_3$ | $OCH_3$ | |
| $Q_{13}(R_7 = H, R_8 = H)$ | H | H | C=O | | Cl | $OCH_3$ | |
| $Q_{13}(R_7 = H, R_8 = H)$ | H | H | OH | H | $CH_3$ | $CH_3$ | |
| $Q_{13}(R_7 = H, R_8 = H)$ | H | H | OH | H | $CH_3$ | $OCH_3$ | |
| $Q_{13}(R_7 = H, R_8 = H)$ | H | H | OH | H | $OCH_3$ | $OCH_3$ | |
| $Q_{13}(R_7 = H, R_8 = H)$ | H | H | OH | H | Cl | $OCH_3$ | |
| $Q_{14}(R_7 = H)$ | H | H | C=O | | $CH_3$ | $CH_3$ | |
| $Q_{14}(R_7 = H)$ | H | H | C=O | | $CH_3$ | $OCH_3$ | |
| $Q_{14}(R_7 = H)$ | H | H | C=O | | $OCH_3$ | $OCH_3$ | |
| $Q_{14}(R_7 = H)$ | H | H | C=O | | Cl | $OCH_3$ | |
| $Q_{14}(R_7 = H)$ | H | H | OH | H | $CH_3$ | $CH_3$ | |
| $Q_{14}(R_7 = H)$ | H | H | OH | H | $CH_3$ | $OCH_3$ | |
| $Q_{14}(R_7 = H)$ | H | H | OH | H | $OCH_3$ | $OCH_3$ | |
| $Q_{14}(R_7 = H)$ | H | H | OH | H | Cl | $OCH_3$ | |
| $Q_{15}(R_7 = H)$ | H | H | C=O | | $CH_3$ | $CH_3$ | |
| $Q_{15}(R_7 = H)$ | H | H | C=O | | $CH_3$ | $OCH_3$ | |
| $Q_{15}(R_7 = H)$ | H | H | C=O | | $OCH_3$ | $OCH_3$ | |
| $Q_{15}(R_7 = H)$ | H | H | C=O | | Cl | $OCH_3$ | |
| $Q_{15}(R_7 = H)$ | H | H | OH | H | $CH_3$ | $CH_3$ | |
| $Q_{15}(R_7 = H)$ | H | H | OH | H | $CH_3$ | $OCH_3$ | |
| $Q_{15}(R_7 = H)$ | H | H | OH | H | $OCH_3$ | $OCH_3$ | |
| $Q_{15}(R_7 = H)$ | H | H | OH | H | Cl | $OCH_3$ | |
| $Q_{16}(R_7 = H)$ | H | H | C=O | | $CH_3$ | $CH_3$ | |
| $Q_{16}(R_7 = H)$ | H | H | C=O | | $CH_3$ | $OCH_3$ | |
| $Q_{16}(R_7 = H)$ | H | H | C=O | | $OCH_3$ | $OCH_3$ | |
| $Q_{16}(R_7 = H)$ | H | H | C=O | | Cl | $OCH_3$ | |
| $Q_{16}(R_7 = H)$ | H | H | OH | H | $CH_3$ | $CH_3$ | |
| $Q_{16}(R_7 = H)$ | H | H | OH | H | $CH_3$ | $OCH_3$ | |
| $Q_{16}(R_7 = H)$ | H | H | OH | H | $OCH_3$ | $OCH_3$ | |
| $Q_{16}(R_7 = H)$ | H | H | OH | H | Cl | $OCH_3$ | |
| $Q_{17}(R_7 = CH_3)$ | H | H | C=O | | $CH_3$ | $CH_3$ | |
| $Q_{17}(R_7 = CH_3)$ | H | H | C=O | | $CH_3$ | $OCH_3$ | |
| $Q_{17}(R_7 = CH_3)$ | H | H | C=O | | $OCH_3$ | $OCH_3$ | |
| $Q_{17}(R_7 = CH_3)$ | H | H | C=O | | Cl | $OCH_3$ | |
| $Q_{17}(R_7 = CH_3)$ | H | H | OH | H | $CH_3$ | $CH_3$ | |
| $Q_{17}(R_7 = CH_3)$ | H | H | OH | H | $CH_3$ | $OCH_3$ | |
| $Q_{17}(R_7 = CH_3)$ | H | H | OH | H | $OCH_3$ | $OCH_3$ | |
| $Q_{17}(R_7 = CH_3)$ | H | H | OH | H | Cl | $OCH_3$ | |
| $Q_{18}(R_7 = H)$ | H | H | C=O | | $CH_3$ | $CH_3$ | |
| $Q_{18}(R_7 = H)$ | H | H | C=O | | $CH_3$ | $OCH_3$ | |
| $Q_{18}(R_7 = H)$ | H | H | C=O | | $OCH_3$ | $OCH_3$ | |
| $Q_{18}(R_7 = H)$ | H | H | C=O | | Cl | $OCH_3$ | |
| $Q_{18}(R_7 = H)$ | H | H | OH | H | $CH_3$ | $CH_3$ | |
| $Q_{18}(R_7 = H)$ | H | H | OH | H | $CH_3$ | $OCH_3$ | |
| $Q_{18}(R_7 = H)$ | H | H | OH | H | $OCH_3$ | $OCH_3$ | |
| $Q_{18}(R_7 = H)$ | H | H | OH | H | Cl | $OCH_3$ | |
| $Q_{19}(R_7 = H, R_8 = H)$ | H | H | C=O | | $CH_3$ | $CH_3$ | |
| $Q_{19}(R_7 = H, R_8 = H)$ | H | H | C=O | | $CH_3$ | $OCH_3$ | |
| $Q_{19}(R_7 = H, R_8 = H)$ | H | H | C=O | | $OCH_3$ | $OCH_3$ | |
| $Q_{19}(R_7 = H, R_8 = H)$ | H | H | C=O | | Cl | $OCH_3$ | |
| $Q_{19}(R_7 = H, R_8 = H)$ | H | H | OH | H | $CH_3$ | $CH_3$ | |
| $Q_{19}(R_7 = H, R_8 = H)$ | H | H | OH | H | $CH_3$ | $OCH_3$ | |
| $Q_{19}(R_7 = H, R_8 = H)$ | H | H | OH | H | $OCH_3$ | $OCH_3$ | |
| $Q_{19}(R_7 = H, R_8 = H)$ | H | H | OH | H | Cl | $OCH_3$ | |
| $Q_{20}(R_7 = H, R_8 = H)$ | H | H | C=O | | $CH_3$ | $CH_3$ | |
| $Q_{20}(R_7 = H, R_8 = H)$ | H | H | C=O | | $CH_3$ | $OCH_3$ | |
| $Q_{20}(R_7 = H, R_8 = H)$ | H | H | C=O | | $OCH_3$ | $OCH_3$ | |
| $Q_{20}(R_7 = H, R_8 = H)$ | H | H | C=O | | Cl | $OCH_3$ | |
| $Q_{20}(R_7 = H, R_8 = H)$ | H | H | OH | H | $CH_3$ | $CH_3$ | |
| $Q_{20}(R_7 = H, R_8 = H)$ | H | H | OH | H | $CH_3$ | $OCH_3$ | |
| $Q_{20}(R_7 = H, R_8 = H)$ | H | H | OH | H | $OCH_3$ | $OCH_3$ | |
| $Q_{20}(R_7 = H, R_8 = H)$ | H | H | OH | H | Cl | $OCH_3$ | |
| $Q_{21}(R_7 = H, R_8 = H, R_9 = CH_3)$ | H | H | C=O | | $CH_3$ | $CH_3$ | |
| $Q_{21}(R_7 = H, R_8 = H, R_9 = CH_3)$ | H | H | C=O | | $CH_3$ | $OCH_3$ | |
| $Q_{21}(R_7 = H, R_8 = H, R_9 = CH_3)$ | H | H | C=O | | $OCH_3$ | $OCH_3$ | |
| $Q_{21}(R_7 = H, R_8 = H, R_9 = CH_3)$ | H | H | C=O | | Cl | $OCH_3$ | |
| $Q_{21}(R_7 = H, R_8 = H, R_9 = CH_3)$ | H | H | OH | H | $CH_3$ | $CH_3$ | |
| $Q_{21}(R_7 = H, R_8 = H, R_9 = CH_3)$ | H | H | OH | H | $CH_3$ | $OCH_3$ | |

TABLE V-continued

| | General Formula V | | | | | | |
|---|---|---|---|---|---|---|---|
| Q | R | R$_1$ | R$_2$ | R$_3$ | X | Y | m.p. (°C.) |
| Q$_{21}$(R$_7$ = H, R$_8$ = H, R$_9$ = CH$_3$) | H | H | OH | H | OCH$_3$ | OCH$_3$ | |
| Q$_{21}$(R$_7$ = H, R$_8$ = H, R$_9$ = CH$_3$) | H | H | OH | H | Cl | OCH$_3$ | |
| Q$_{22}$(R$_7$ = H) | H | H | C=O | | CH$_3$ | CH$_3$ | |
| Q$_{22}$(R$_7$ = H) | H | H | C=O | | CH$_3$ | OCH$_3$ | |
| Q$_{22}$(R$_7$ = H) | H | H | C=O | | OCH$_3$ | OCH$_3$ | |
| Q$_{22}$(R$_7$ = H) | H | H | C=O | | Cl | OCH$_3$ | |
| Q$_{22}$(R$_7$ = H) | H | H | OH | H | CH$_3$ | CH$_3$ | |
| Q$_{22}$(R$_7$ = H) | H | H | OH | H | CH$_3$ | OCH$_3$ | |
| Q$_{22}$(R$_7$ = H) | H | H | OH | H | OCH$_3$ | OCH$_3$ | |
| Q$_{22}$(R$_7$ = H) | H | H | OH | H | Cl | OCH$_3$ | |
| Q$_{23}$(R$_7$ = H) | H | H | C=O | | CH$_3$ | CH$_3$ | |
| Q$_{23}$(R$_7$ = H) | H | H | C=O | | CH$_3$ | OCH$_3$ | |
| Q$_{23}$(R$_7$ = H) | H | H | C=O | | OCH$_3$ | OCH$_3$ | |
| Q$_{23}$(R$_7$ = H) | H | H | C=O | | Cl | OCH$_3$ | |
| Q$_{23}$(R$_7$ = H) | H | H | OH | H | CH$_3$ | CH$_3$ | |
| Q$_{23}$(R$_7$ = H) | H | H | OH | H | CH$_3$ | OCH$_3$ | |
| Q$_{23}$(R$_7$ = H) | H | H | OH | H | OCH$_3$ | OCH$_3$ | |
| Q$_{23}$(R$_7$ = H) | H | H | OH | H | Cl | OCH$_3$ | |
| Q$_{24}$(R$_7$ = H, R$_8$ = H) | H | H | C=O | | CH$_3$ | CH$_3$ | |
| Q$_{24}$(R$_7$ = H, R$_8$ = H) | H | H | C=O | | CH$_3$ | OCH$_3$ | |
| Q$_{24}$(R$_7$ = H, R$_8$ = H) | H | H | C=O | | OCH$_3$ | OCH$_3$ | |
| Q$_{24}$(R$_7$ = H, R$_8$ = H) | H | H | C=O | | Cl | OCH$_3$ | |
| Q$_{24}$(R$_7$ = H, R$_8$ = H) | H | H | OH | H | CH$_3$ | CH$_3$ | |
| Q$_{24}$(R$_7$ = H, R$_8$ = H) | H | H | OH | H | CH$_3$ | OCH$_3$ | |
| Q$_{24}$(R$_7$ = H, R$_8$ = H) | H | H | OH | H | OCH$_3$ | OCH$_3$ | |
| Q$_{24}$(R$_7$ = H, R$_8$ = H) | H | H | OH | H | Cl | OCH$_3$ | |
| Q$_{25}$(R$_7$ = H, R$_8$ = H) | H | H | C=O | | CH$_3$ | CH$_3$ | |
| Q$_{25}$(R$_7$ = H, R$_8$ = H) | H | H | C=O | | CH$_3$ | OCH$_3$ | |
| Q$_{25}$(R$_7$ = H, R$_8$ = H) | H | H | C=O | | OCH$_3$ | OCH$_3$ | |
| Q$_{25}$(R$_7$ = H, R$_8$ = H) | H | H | C=O | | Cl | OCH$_3$ | |
| Q$_{25}$(R$_7$ = H, R$_8$ = H) | H | H | OH | H | CH$_3$ | CH$_3$ | |
| Q$_{25}$(R$_7$ = H, R$_8$ = H) | H | H | OH | H | CH$_3$ | OCH$_3$ | |
| Q$_{25}$(R$_7$ = H, R$_8$ = H) | H | H | OH | H | OCH$_3$ | OCH$_3$ | |
| Q$_{25}$(R$_7$ = H, R$_8$ = H) | H | H | OH | H | Cl | OCH$_3$ | |
| Q$_{26}$(R$_7$ = H, R$_8$ = H) | H | H | C=O | | CH$_3$ | CH$_3$ | |
| Q$_{26}$(R$_7$ = H, R$_8$ = H) | H | H | C=O | | CH$_3$ | OCH$_3$ | |
| Q$_{26}$(R$_7$ = H, R$_8$ = H) | H | H | C=O | | OCH$_3$ | OCH$_3$ | |
| Q$_{26}$(R$_7$ = H, R$_8$ = H) | H | H | C=O | | Cl | OCH$_3$ | |
| Q$_{26}$(R$_7$ = H, R$_8$ = H) | H | H | OH | H | CH$_3$ | CH$_3$ | |
| Q$_{26}$(R$_7$ = H, R$_8$ = H) | H | H | OH | H | CH$_3$ | OCH$_3$ | |
| Q$_{26}$(R$_7$ = H, R$_8$ = H) | H | H | OH | H | OCH$_3$ | OCH$_3$ | |
| Q$_{26}$(R$_7$ = H, R$_8$ = H) | H | H | OH | H | Cl | OCH$_3$ | |
| Q$_{27}$(R$_7$ = H, R$_{11}$ = H, R$_{12}$ = H) | H | H | C=O | | CH$_3$ | CH$_3$ | |
| Q$_{27}$(R$_7$ = H, R$_{11}$ = H, R$_{12}$ = H) | H | H | C=O | | CH$_3$ | OCH$_3$ | |
| Q$_{27}$(R$_7$ = H, R$_{11}$ = H, R$_{12}$ = H) | H | H | C=O | | OCH$_3$ | OCH$_3$ | |
| Q$_{27}$(R$_7$ = H, R$_{11}$ = H, R$_{12}$ = H) | H | H | C=O | | Cl | OCH$_3$ | |
| Q$_{27}$(R$_7$ = H, R$_{11}$ = H, R$_{12}$ = H) | H | H | OH | H | CH$_3$ | CH$_3$ | |
| Q$_{27}$(R$_7$ = H, R$_{11}$ = H, R$_{12}$ = H) | H | H | OH | H | CH$_3$ | OCH$_3$ | |
| Q$_{27}$(R$_7$ = H, R$_{11}$ = H, R$_{12}$ = H) | H | H | OH | H | OCH$_3$ | OCH$_3$ | |
| Q$_{27}$(R$_7$ = H, R$_{11}$ = H, R$_{12}$ = H) | H | H | OH | H | Cl | OCH$_3$ | |
| Q$_{28}$(R$_{11}$ = H, R$_{12}$ = H) | H | H | C=O | | CH$_3$ | CH$_3$ | |
| Q$_{28}$(R$_{11}$ = H, R$_{12}$ = H) | H | H | C=O | | CH$_3$ | OCH$_3$ | |
| Q$_{28}$(R$_{11}$ = H, R$_{12}$ = H) | H | H | C=O | | OCH$_3$ | OCH$_3$ | |
| Q$_{28}$(R$_{11}$ = H, R$_{12}$ = H) | H | H | C=O | | Cl | OCH$_3$ | |
| Q$_{28}$(R$_{11}$ = H, R$_{12}$ = H) | H | H | OH | H | CH$_3$ | CH$_3$ | |
| Q$_{28}$(R$_{11}$ = H, R$_{12}$ = H) | H | H | OH | H | CH$_3$ | OCH$_3$ | |
| Q$_{28}$(R$_{11}$ = H, R$_{12}$ = H) | H | H | OH | H | OCH$_3$ | OCH$_3$ | |
| Q$_{28}$(R$_{11}$ = H, R$_{12}$ = H) | H | H | OH | H | Cl | OCH$_3$ | |
| Q$_{29}$(R$_{11}$ = H, R$_{12}$ = H) | H | H | C=O | | CH$_3$ | CH$_3$ | |
| Q$_{29}$(R$_{11}$ = H, R$_{12}$ = H) | H | H | C=O | | CH$_3$ | OCH$_3$ | |
| Q$_{29}$(R$_{11}$ = H, R$_{12}$ = H) | H | H | C=O | | OCH$_3$ | OCH$_3$ | |
| Q$_{29}$(R$_{11}$ = H, R$_{12}$ = H) | H | H | C=O | | Cl | OCH$_3$ | |
| Q$_{29}$(R$_{11}$ = H, R$_{12}$ = H) | H | H | OH | H | CH$_3$ | CH$_3$ | |
| Q$_{29}$(R$_{11}$ = H, R$_{12}$ = H) | H | H | OH | H | CH$_3$ | OCH$_3$ | |
| Q$_{29}$(R$_{11}$ = H, R$_{12}$ = H) | H | H | OH | H | OCH$_3$ | OCH$_3$ | |
| Q$_{29}$(R$_{11}$ = H, R$_{12}$ = H) | H | H | OH | H | Cl | OCH$_3$ | |
| Q$_{30}$(R$_7$ = H, R$_8$ = H) | H | H | C=O | | CH$_3$ | CH$_3$ | |
| Q$_{30}$(R$_7$ = H, R$_8$ = H) | H | H | C=O | | CH$_3$ | OCH$_3$ | |
| Q$_{30}$(R$_7$ = H, R$_8$ = H) | H | H | C=O | | OCH$_3$ | OCH$_3$ | |
| Q$_{30}$(R$_7$ = H, R$_8$ = H) | H | H | C=O | | Cl | OCH$_3$ | |
| Q$_{30}$(R$_7$ = H, R$_8$ = H) | H | H | OH | H | CH$_3$ | CH$_3$ | |
| Q$_{30}$(R$_7$ = H, R$_8$ = H) | H | H | OH | H | CH$_3$ | OCH$_3$ | |
| Q$_{30}$(R$_7$ = H, R$_8$ = H) | H | H | OH | H | OCH$_3$ | OCH$_3$ | |
| Q$_{30}$(R$_7$ = H, R$_8$ = H) | H | H | OH | H | Cl | OCH$_3$ | |
| Q$_{31}$(R$_7$ = H, R$_8$ = H) | H | H | C=O | | CH$_3$ | CH$_3$ | |
| Q$_{31}$(R$_7$ = H, R$_8$ = H) | H | H | C=O | | CH$_3$ | OCH$_3$ | |
| Q$_{31}$(R$_7$ = H, R$_8$ = H) | H | H | C=O | | OCH$_3$ | OCH$_3$ | |
| Q$_{31}$(R$_7$ = H, R$_8$ = H) | H | H | C=O | | Cl | OCH$_3$ | |
| Q$_{31}$(R$_7$ = H, R$_8$ = H) | H | H | OH | H | CH$_3$ | CH$_3$ | |
| Q$_{31}$(R$_7$ = H, R$_8$ = H) | H | H | OH | H | CH$_3$ | OCH$_3$ | |

TABLE V-continued

| Q | General Formula V | | | | | | | |
|---|---|---|---|---|---|---|---|---|
| | R | R₁ | R₂ | | R₃ | X | Y | m.p. (°C.) |
| Q₃₁(R₇ = H, R₈ = H) | H | H | OH | | H | OCH₃ | OCH₃ | |
| Q₃₁(R₇ = H, R₈ = H) | H | H | OH | | H | Cl | OCH₃ | |
| Q₃₂(R₁₃ = OCH₃, R₁₄ = OCH₃) | H | H | | C=O | | CH₃ | CH₃ | |
| Q₃₂(R₁₃ = OCH₃, R₁₄ = OCH₃) | H | H | | C=O | | CH₃ | OCH₃ | |
| Q₃₂(R₁₃ = OCH₃, R₁₄ = OCH₃) | H | H | | C=O | | OCH₃ | OCH₃ | |
| Q₃₂(R₁₃ = OCH₃, R₁₄ = OCH₃) | H | H | | C=O | | Cl | OCH₃ | |
| Q₃₂(R₁₃ = OCH₃, R₁₄ = OCH₃) | H | H | OH | | H | CH₃ | CH₃ | |
| Q₃₂(R₁₃ = OCH₃, R₁₄ = OCH₃) | H | H | OH | | H | CH₃ | OCH₃ | |
| Q₃₂(R₁₃ = OCH₃, R₁₄ = OCH₃) | H | H | OH | | H | OCH₃ | OCH₃ | |
| Q₃₂(R₁₃ = OCH₃, R₁₄ = OCH₃) | H | H | OH | | H | Cl | OCH₃ | |
| Q₃₃(R₇ = H) | H | H | | C=O | | CH₃ | CH₃ | |
| Q₃₃(R₇ = H) | H | H | | C=O | | CH₃ | OCH₃ | |
| Q₃₃(R₇ = H) | H | H | | C=O | | OCH₃ | OCH₃ | |
| Q₃₃(R₇ = H) | H | H | | C=O | | Cl | OCH₃ | |
| Q₃₃(R₇ = H) | H | H | OH | | H | CH₃ | CH₃ | |
| Q₃₃(R₇ = H) | H | H | OH | | H | CH₃ | OCH₃ | |
| Q₃₃(R₇ = H) | H | H | OH | | H | OCH₃ | OCH₃ | |
| Q₃₃(R₇ = H) | H | H | OH | | H | Cl | OCH₃ | |

TABLE VI

| Q | General Formula VI | | | | | | | |
|---|---|---|---|---|---|---|---|---|
| | R | R₁ | R₂ | | R₃ | X | Y | m.p. (°C.) |
| Q₁(R₇ = H, R₈ = H, R₉ = H) | H | H | | C=O | | CH₃ | CH₃ | |
| Q₁(R₇ = H, R₈ = H, R₉ = H) | H | H | | C=O | | CH₃ | OCH₃ | |
| Q₁(R₇ = H, R₈ = H, R₉ = H) | H' | H | | C=O | | OCH₃ | OCH₃ | |
| Q₁(R₇ = H, R₈ = H, R₉ = H) | H | H | | C=O | | Cl | OCH₃ | |
| Q₁(R₇ = H, R₈ = H, R₉ = H) | H | H | OH | | H | CH₃ | CH₃ | |
| Q₁(R₇ = H, R₈ = H, R₉ = H) | H | H | OH | | H | CH₃ | OCH₃ | |
| Q₁(R₇ = H, R₈ = H, R₉ = H) | H | H | OH | | H | OCH₃ | OCH₃ | |
| Q₁(R₇ = H, R₈ = H, R₉ = H) | H | H | OH | | H | Cl | OCH₃ | |
| Q₁(R₇ = H, R₈ = H, R₉ = H) | H | H | OCH₃ | | H | OCH₃ | OCH₃ | |
| Q₁(R₇ = H, R₈ = H, R₉ = H) | H | H | OCH₂CH₃ | | H | OCH₃ | OCH₃ | |
| Q₂(R₇ = H, R₈ = H, R₉ = H) | H | H | | C=O | | CH₃ | CH₃ | |
| Q₂(R₇ = H, R₈ = H, R₉ = H) | H | H | | C=O | | CH₃ | OCH₃ | |
| Q₂(R₇ = H, R₈ = H, R₉ = H) | H | H | | C=O | | OCH₃ | OCH₃ | |
| Q₂(R₇ = H, R₈ = H, R₉ = H) | H | H | | C=O | | Cl | OCH₃ | |
| Q₂(R₇ = H, R₈ = H, R₉ = H) | H | H | OH | | H | CH₃ | CH₃ | |
| Q₂(R₇ = H, R₈ = H, R₉ = H) | H | H | OH | | H | CH₃ | OCH₃ | |
| Q₂(R₇ = H, R₈ = H, R₉ = H) | H | H | OH | | H | OCH₃ | OCH₃ | |
| Q₂(R₇ = H, R₈ = H, R₉ = H) | H | H | OH | | H | Cl | OCH₃ | |
| Q₂(R₇ = H, R₈ = H, R₉ = H) | H | H | OCH₃ | | H | CH₃ | OCH₃ | |
| Q₂(R₇ = H, R₈ = H, R₉ = H) | H | H | OCH₂CH₃ | | H | CH₃ | CH₃ | |
| Q₃(R₇ = H, R₈ = H, R₉ = CH₃) | H | H | | C=O | | CH₃ | CH₃ | |
| Q₃(R₇ = H, R₈ = H, R₉ = H) | H | H | | C=O | | CH₃ | OCH₃ | |
| Q₃(R₇ = H, R₈ = H, R₉ = H) | H | H | | C=O | | OCH₃ | OCH₃ | |
| Q₃(R₇ = H, R₈ = H, R₉ = H) | H | H | | C=O | | Cl | OCH₃ | |
| Q₃(R₇ = H, R₈ = H, R₉ = H) | H | H | OH | | H | CH₃ | CH₃ | |
| Q₃(R₇ = H, R₈ = H, R₉ H) | H | H | OH | | H | CH₃ | OCH₃ | |
| Q₃(R₇ = H, R₈ = H, R₉ H) | H | H | OH | | H | OCH₃ | OCH₃ | |
| Q₃(R₇ = H, R₈ = H, R₉ H) | H | H | OH | | H | Cl | OCH₃ | |
| Q₃(R₇ = H, R₈ = H, R₉ = Cl) | H | H | | C=O | | OCH₃ | OCH₃ | |
| Q₃(R₇ = H, R₈ = H, R₉ CH₃) | H | H | | C=O | | OCH₃ | OCH₃ | |
| Q₃(R₇ = H, R₈ = H, R₉ = | H | H | OH | | H | OCH₃ | OCH₃ | |
| Q₄(R₇ = H, R₈ = H, R₉ = H) | H | H | | C=O | | CH₃ | CH₃ | |
| Q₄(R₇ = H, R₈ = H, R₉ = H) | H | H | | C=O | | CH₃ | OCH₃ | |
| Q₄(R₇ = H, R₈ = H, R₉ = H) | H | H | | C=O | | OCH₃ | OCH₃ | |
| Q₄(R₇ = H, R₈ = H, R₉ = H) | H | H | | C=O | | Cl | OCH₃ | |
| Q₄(R₇ = H, R₈ = H, R₉ = H) | H | H | OH | | H | CH₃ | CH₃ | |
| Q₄(R₇ = H, R₈ = H, R₉ = H) | H | H | OH | | H | CH₃ | OCH₃ | |
| Q₄(R₇ = H, R₈ = H, R₉ = H) | H | H | OH | | H | OCH₃ | OCH₃ | |
| Q₄(R₇ = H, R₈ = H, R₉ = H) | H | H | OH | | H | Cl | OCH₃ | |
| Q₅(R₇ = H, R₈ = H, R₉ = H, R₁₀ = CH₃) | H | H | | C=O | | CH₃ | CH₃ | |
| Q₅(R₇ = H, R₈ = H, R₉ = H, R₁₀ = CH₃) | H | H | | C=O | | CH₃ | OCH₃ | |
| Q₅(R₇ = H, R₈ = H, R₉ = H, R₁₀ = CH₃) | H | H | | C=O | | OCH₃ | OCH₃ | |
| Q₅(R₇ = H, R₈ = H, R₉ = H, R₁₀ = CH₃) | H | H | | C=O | | Cl | OCH₃ | |
| Q₅(R₇ = H, R₈ = H, R₉ = H, R₁₀ = CH₃) | H | H | OH | | H | CH₃ | CH₃ | |
| Q₅(R₇ = H, R₈ = H, R₉ = H, R₁₀ = CH₃) | H | H | OH | | H | CH₃ | OCH₃ | |
| Q₅(R₇ = H, R₈ = H, R₉ = H, R₁₀ = CH₃) | H | H | OH | | H | OCH₃ | OCH₃ | |
| Q₅(R₇ = H, R₈ = H, R₉ = H, R₁₀ = CH₃) | H | H | OH | | H | Cl | OCH₃ | |
| Q₅(R₇ = H, R₈ = H, R₉ = H, R₁₀ = CH₃) | H | H | OCH₃ | | H | Cl | OCH₃ | |
| Q₅(R₇ = H, R₈ = H, R₉ = H, R₁₀ = CH₃) | H | H | OCH₂CH₃ | | H | OCH₃ | OCH₃ | |
| Q₆(R₇ = H, R₈ = H, R₉ = H, R₁₀ = CH₃) | H | H | | C=O | | CH₃ | CH₃ | |
| Q₆(R₇ = H, R₈ = H, R₉ = H, R₁₀ = CH₃) | H | H | | C=O | | CH₃ | OCH₃ | |
| Q₆(R₇ = H, R₈ = H, R₉ = H, R₁₀ = CH₃) | H | H | | C=O | | OCH₃ | OCH₃ | |
| Q₆(R₇ = H, R₈ = H, R₉ = H, R₁₀ = CH₃) | H | H | | C=O | | Cl | OCH₃ | |
| Q₆(R₇ = H, R₈ = H, R₉ = H, R₁₀ = CH₃) | H | H | OH | | H | CH₃ | CH₃ | |
| Q₆(R₇ = H, R₈ = H, R₉ = H, R₁₀ = CH₃) | H | H | OH | | H | CH₃ | OCH₃ | |

TABLE VI-continued

| | General Formula VI | | | | | | | |
|---|---|---|---|---|---|---|---|---|
| Q | R | $R_1$ | $R_2$ | | $R_3$ | X | Y | m.p. (°C.) |
| $Q_6(R_7 = H, R_8 = H, R_9 = H, R_{10} = CH_3)$ | H | H | OH | | H | $OCH_3$ | $OCH_3$ | |
| $Q_6(R_7 = H, R_8 = H, R_9 = H, R_{10} = CH_3)$ | H | H | OH | | H | Cl | $OCH_3$ | |
| $Q_7(R_7 = H, R_8 = H)$ | H | H | | C=O | | $CH_3$ | $CH_3$ | |
| $Q_7(R_7 = H, R_8 = H)$ | H | H | | C=O | | $CH_3$ | $OCH_3$ | |
| $Q_7(R_7 = H, R_8 = H)$ | H | H | | C=O | | $OCH_3$ | $OCH_3$ | |
| $Q_7(R_7 = H, R_8 = H)$ | H | H | | C=O | | Cl | $OCH_3$ | |
| $Q_7(R_7 = H, R_8 = H)$ | H | H | OH | | H | $CH_3$ | $CH_3$ | |
| $Q_7(R_7 = H, R_8 = H)$ | H | H | OH | | H | $CH_3$ | $OCH_3$ | |
| $Q_7(R_7 = H, R_8 = H)$ | H | H | OH | | H | $OCH_3$ | $OCH_3$ | |
| $Q_7(R_7 = H, R_8 = H)$ | H | H | OH | | H | Cl | $OCH_3$ | |
| $Q_8(R_7 = H, R_8 = H)$ | H | H | | C=O | | $OCH_3$ | $OCH_3$ | |
| $Q_8(R_7 = H, R_8 = H)$ | H | H | | C=O | | Cl | $OCH_3$ | |
| $Q_8(R_7 = H, R_8 = H)$ | H | H | OH | | H | Cl | $OCH_3$ | |
| $Q_8(R_7 = H, R_8 = H)$ | H | H | OH | | H | $OCH_3$ | $OCH_3$ | |
| $Q_9(R_7 = H, R_8 = H)$ | H | H | | C=O | | $CH_3$ | $CH_3$ | |
| $Q_9(R_7 = H, R_8 = H)$ | H | H | | C=O | | $CH_3$ | $OCH_3$ | |
| $Q_9(R_7 = H, R_8 = H)$ | H | H | | C=O | | $OCH_3$ | $OCH_3$ | |
| $Q_9(R_7 = H, R_8 = H)$ | H | H | | C=O | | Cl | $OCH_3$ | |
| $Q_9(R_7 = H, R_8 = H)$ | H | H | OH | | H | $CH_3$ | $CH_3$ | |
| $Q_9(R_7 = H, R_8 = H)$ | H | H | OH | | H | $CH_3$ | $OCH_3$ | |
| $Q_9(R_7 = H, R_8 = H)$ | H | H | OH | | H | $OCH_3$ | $OCH_3$ | |
| $Q_9(R_7 = H, R_8 = H)$ | H | H | OH | | H | Cl | $OCH_3$ | |
| $Q_{10}(R_7 = H, R_8 = H)$ | H | H | | C=O | | $CH_3$ | $OCH_3$ | |
| $Q_{10}(R_7 = H, R_8 = H)$ | H | H | | C=O | | $OCH_3$ | $OCH_3$ | |
| $Q_{10}(R_7 = H, R_8 = H)$ | H | H | | C=O | | Cl | $OCH_3$ | |
| $Q_{10}(R_7 = H, R_8 = H)$ | H | H | OH | | H | $CH_3$ | $CH_3$ | |
| $Q_{10}(R_7 = H, R_8 = H)$ | H | H | OH | | H | $OCH_3$ | $OCH_3$ | |
| $Q_{10}(R_7 = H, R_8 = H)$ | H | H | OH | | H | Cl | $OCH_3$ | |
| $Q_{11}(R_7 = H, R_8 = H)$ | H | H | | C=O | | $CH_3$ | $CH_3$ | |
| $Q_{11}(R_7 = H, R_8 = H)$ | H | H | | C=O | | $CH_3$ | $OCH_3$ | |
| $Q_{11}(R_7 = H, R_8 = H)$ | H | H | | C=O | | $OCH_3$ | $OCH_3$ | |
| $Q_{11}(R_7 = H, R_8 = H)$ | H | H | | C=O | | Cl | $OCH_3$ | |
| $Q_{11}(R_7 = H, R_8 = H)$ | H | H | OH | | H | $CH_3$ | $CH_3$ | |
| $Q_{11}(R_7 = H, R_8 = H)$ | H | H | OH | | H | $CH_3$ | $OCH_3$ | |
| $Q_{11}(R_7 = H, R_8 = H)$ | H | H | OH | | H | $OCH_3$ | $OCH_3$ | |
| $Q_{11}(R_7 = H, R_8 = H)$ | H | H | OH | | H | Cl | $OCH_3$ | |
| $Q_{12}(R_7 = H, R_8 = H)$ | H | H | | C=O | | $CH_3$ | $CH_3$ | |
| $Q_{12}(R_7 = H, R_8 = H)$ | H | H | | C=O | | $CH_3$ | $OCH_3$ | |
| $Q_{12}(R_7 = H, R_8 = H)$ | H | H | | C=O | | $OCH_3$ | $OCH_3$ | |
| $Q_{12}(R_7 = H, R_8 = H)$ | H | H | | C=O | | Cl | $OCH_3$ | |
| $Q_{12}(R_7 = H, R_8 = H)$ | H | H | OH | | H | $CH_3$ | $CH_3$ | |
| $Q_{12}(R_7 = H, R_8 = H)$ | H | H | OH | | H | $CH_3$ | $OCH_3$ | |
| $Q_{12}(R_7 = H, R_8 = H)$ | H | H | OH | | H | $OCH_3$ | $OCH_3$ | |
| $Q_{12}(R_7 = H, R_8 = H)$ | H | H | OH | | H | Cl | $OCH_3$ | |
| $Q_{12}(R_7 = H, R_8 = H)$ | H | H | $OCH_3$ | | H | $OCH_3$ | $OCH_3$ | |
| $Q_{13}(R_7 = H, R_8 = H)$ | H | H | | C=O | | $CH_3$ | $CH_3$ | |
| $Q_{13}(R_7 = H, R_8 = H)$ | H | H | | C=O | | $CH_3$ | $OCH_3$ | |
| $Q_{13}(R_7 = H, R_8 = H)$ | H | H | | C=O | | $OCH_3$ | $OCH_3$ | |
| $Q_{13}(R_7 = H, R_8 = H)$ | H | H | | C=O | | Cl | $OCH_3$ | |
| $Q_{13}(R_7 = H, R_8 = H)$ | H | H | OH | | H | $CH_3$ | $CH_3$ | |
| $Q_{13}(R_7 = H, R_8 = H)$ | H | H | OH | | H | $CH_3$ | $OCH_3$ | |
| $Q_{13}(R_7 = H, R_8 = H)$ | H | H | OH | | H | $OCH_3$ | $OCH_3$ | |
| $Q_{13}(R_7 = H, R_8 = H)$ | H | H | OH | | H | Cl | $OCH_3$ | |
| $Q_{14}(R_7 = H)$ | H | H | | C=O | | $CH_3$ | $CH_3$ | |
| $Q_{14}(R_7 = H)$ | H | H | | C=H | | $CH_3$ | $OCH_3$ | |
| $Q_{14}(R_7 = H)$ | H | H | | C=H | | $OCH_3$ | $OCH_3$ | |
| $Q_{14}(R_7 = H)$ | H | H | | C=H | | Cl | $OCH_3$ | |
| $Q_{14}(R_7 = H)$ | H | H | OH | | H | $CH_3$ | $CH_3$ | |
| $Q_{14}(R_7 = H)$ | H | H | OH | | H | $CH_3$ | $OCH_3$ | |
| $Q_{14}(R_7 = H)$ | H | H | OH | | H | $OCH_3$ | $OCH_3$ | |
| $Q_{14}(R_7 = H)$ | H | H | OH | | H | Cl | $OCH_3$ | |
| $Q_{15}(R_7 = H)$ | H | H | | C=O | | $CH_3$ | $CH_3$ | |
| $Q_{15}(R_7 = H)$ | H | H | | C=O | | $CH_3$ | $OCH_3$ | |
| $Q_{15}(R_7 = H)$ | H | H | | C=O | | $OCH_3$ | $OCH_3$ | |
| $Q_{15}(R_7 = H)$ | H | H | | C=O | | Cl | $OCH_3$ | |
| $Q_{15}(R_7 = H)$ | H | H | OH | | H | $CH_3$ | $CH_3$ | |
| $Q_{15}(R_7 = H)$ | H | H | OH | | H | $CH_3$ | $OCH_3$ | |
| $Q_{15}(R_7 = H)$ | H | H | OH | | H | $OCH_3$ | $OCH_3$ | |
| $Q_{15}(R_7 = H)$ | H | H | OH | | H | Cl | $OCH_3$ | |
| $Q_{16}(R_7 = H)$ | H | H | | C=O | | $CH_3$ | $CH_3$ | |
| $Q_{16}(R_7 = H)$ | H | H | | C=O | | $CH_3$ | $OCH_3$ | |
| $Q_{16}(R_7 = H)$ | H | H | | C=O | | $OCH_3$ | $OCH_3$ | |
| $Q_{16}(R_7 = H)$ | H | H | | C=O | | Cl | $OCH_3$ | |
| $Q_{16}(R_7 = H)$ | H | H | OH | | H | $CH_3$ | $CH_3$ | |
| $Q_{16}(R_7 = H)$ | H | H | OH | | H | $CH_3$ | $OCH_3$ | |
| $Q_{16}(R_7 = H)$ | H | H | OH | | H | $OCH_3$ | $OCH_3$ | |
| $Q_{16}(R_7 = H)$ | H | H | OH | | H | Cl | $OCH_3$ | |
| $Q_{17}(R_7 = CH_3)$ | H | H | | C=O | | $CH_3$ | $CH_3$ | |
| $Q_{17}(R_7 = CH_3)$ | H | H | | C=O | | $CH_3$ | $OCH_3$ | |
| $Q_{17}(R_7 = CH_3)$ | H | H | | C=O | | $OCH_3$ | $OCH_3$ | |

TABLE VI-continued

General Formula VI

| Q | R | R₁ | R₂ | R₃ | X | Y | m.p. (°C.) |
|---|---|----|----|----|----|----|-----------|
| $Q_{17}(R_7 = CH_3)$ | H | H | C=O | | Cl | OCH₃ | |
| $Q_{17}(R_7 = CH_3)$ | H | H | OH | H | CH₃ | CH₃ | |
| $Q_{17}(R_7 = CH_3)$ | H | H | OH | H | CH₃ | OCH₃ | |
| $Q_{17}(R_7 = CH_3)$ | H | H | OH | H | OCH₃ | OCH₃ | |
| $Q_{17}(R_7 = CH_3)$ | H | H | OH | H | Cl | OCH₃ | |
| $Q_{18}(R_7 = H)$ | H | H | C=O | | CH₃ | CH₃ | |
| $Q_{18}(R_7 = H)$ | H | H | C=O | | CH₃ | OCH₃ | |
| $Q_{18}(R_7 = H)$ | H | H | C=O | | OCH₃ | OCH₃ | |
| $Q_{18}(R_7 = H)$ | H | H | C=O | | Cl | OCH₃ | |
| $Q_{18}(R_7 = H)$ | H | H | OH | H | CH₃ | CH₃ | |
| $Q_{18}(R_7 = H)$ | H | H | OH | H | CH₃ | OCH₃ | |
| $Q_{18}(R_7 = H)$ | H | H | OH | H | OCH₃ | OCH₃ | |
| $Q_{18}(R_7 = H)$ | H | H | OH | H | Cl | OCH₃ | |
| $Q_{19}(R_7 = H, R_8 = H)$ | H | H | C=O | | CH₃ | CH₃ | |
| $Q_{19}(R_7 = H, R_8 = H)$ | H | H | C=O | | CH₃ | OCH₃ | |
| $Q_{19}(R_7 = H, R_8 = H)$ | H | H | C=O | | OCH₃ | OCH₃ | |
| $Q_{19}(R_7 = H, R_8 = H)$ | H | H | C=O | | Cl | OCH₃ | |
| $Q_{19}(R_7 = H, R_8 = H)$ | H | H | OH | H | CH₃ | CH₃ | |
| $Q_{19}(R_7 = H, R_8 = H)$ | H | H | OH | H | CH₃ | OCH₃ | |
| $Q_{19}(R_7 = H, R_8 = H)$ | H | H | OH | H | OCH₃ | OCH₃ | |
| $Q_{19}(R_7 = H, R_8 = H)$ | H | H | OH | H | Cl | OCH₃ | |
| $Q_{20}(R_7 = H, R_8 = H)$ | H | H | C=O | | CH₃ | CH₃ | |
| $Q_{20}(R_7 = H, R_8 = H)$ | H | H | C=O | | CH₃ | OCH₃ | |
| $Q_{20}(R_7 = H, R_8 = H)$ | H | H | C=O | | OCH₃ | OCH₃ | |
| $Q_{20}(R_7 = H, R_8 = H)$ | H | H | C=O | | Cl | OCH₃ | |
| $Q_{20}(R_7 = H, R_8 = H)$ | H | H | OH | H | CH₃ | CH₃ | |
| $Q_{20}(R_7 = H, R_8 = H)$ | H | H | OH | H | CH₃ | OCH₃ | |
| $Q_{20}(R_7 = H, R_8 = H)$ | H | H | OH | H | OCH₃ | OCH₃ | |
| $Q_{20}(R_7 = H, R_8 = H)$ | H | H | OH | H | Cl | OCH₃ | |
| $Q_{21}(R_7 = H, R_8 = H, R_9 = CH_3)$ | H | H | C=O | | CH₃ | CH₃ | |
| $Q_{21}(R_7 = H, R_8 = H, R_9 = CH_3)$ | H | H | C=O | | CH₃ | OCH₃ | |
| $Q_{21}(R_7 = H, R_8 = H, R_9 = CH_3)$ | H | H | C=O | | OCH₃ | OCH₃ | |
| $Q_{21}(R_7 = H, R_8 = H, R_9 = CH_3)$ | H | H | C=O | | Cl | OCH₃ | |
| $Q_{21}(R_7 = H, R_8 = H, R_9 = CH_3)$ | H | H | OH | H | CH₃ | CH₃ | |
| $Q_{21}(R_7 = H, R_8 = H, R_9 = CH_3)$ | H | H | OH | H | CH₃ | OCH₃ | |
| $Q_{21}(R_7 = H, R_8 = H, R_9 = CH_3)$ | H | H | OH | H | OCH₃ | OCH₃ | |
| $Q_{21}(R_7 = H, R_8 = H, R_9 = CH_3)$ | H | H | OH | H | Cl | OCH₃ | |
| $Q_{22}(R_7 = H)$ | H | H | C=O | | CH₃ | CH₃ | |
| $Q_{22}(R_7 = H)$ | H | H | C=O | | CH₃ | OCH₃ | |
| $Q_{22}(R_7 = H)$ | H | H | C=O | | OCH₃ | OCH₃ | |
| $Q_{22}(R_7 = H)$ | H | H | C=O | | Cl | OCH₃ | |
| $Q_{22}(R_7 = H)$ | H | H | OH | H | CH₃ | CH₃ | |
| $Q_{22}(R_7 = H)$ | H | H | OH | H | CH₃ | OCH₃ | |
| $Q_{22}(R_7 = H)$ | H | H | OH | H | OCH₃ | OCH₃ | |
| $Q_{22}(R_7 = H)$ | H | H | OH | H | Cl | OCH₃ | |
| $Q_{23}(R_7 = H)$ | H | H | C=O | | CH₃ | CH₃ | |
| $Q_{23}(R_7 = H)$ | H | H | C=O | | CH₃ | OCH₃ | |
| $Q_{23}(R_7 = H)$ | H | H | C=O | | OCH₃ | OCH₃ | |
| $Q_{23}(R_7 = H)$ | H | H | C=O | | Cl | OCH₃ | |
| $Q_{23}(R_7 = H)$ | H | H | OH | H | CH₃ | CH₃ | |
| $Q_{23}(R_7 = H)$ | H | H | OH | H | CH₃ | OCH₃ | |
| $Q_{23}(R_7 = H)$ | H | H | OH | H | OCH₃ | OCH₃ | |
| $Q_{23}(R_7 = H)$ | H | H | OH | H | Cl | OCH₃ | |
| $Q_{24}(R_7 = H, R_8 = H)$ | H | H | C=O | | CH₃ | CH₃ | |
| $Q_{24}(R_7 = H, R_8 = H)$ | H | H | C=O | | CH₃ | OCH₃ | |
| $Q_{24}(R_7 = H, R_8 = H)$ | H | H | C=O | | OCH₃ | OCH₃ | |
| $Q_{24}(R_7 = H, R_8 = H)$ | H | H | C=O | | Cl | OCH₃ | |
| $Q_{24}(R_7 = H, R_8 = H)$ | H | H | OH | H | CH₃ | CH₃ | |
| $Q_{24}(R_7 = H, R_8 = H)$ | H | H | OH | H | CH₃ | OCH₃ | |
| $Q_{24}(R_7 = H, R_8 = H)$ | H | H | OH | H | OCH₃ | OCH₃ | |
| $Q_{24}(R_7 = H, R_8 = H)$ | H | H | OH | H | Cl | OCH₃ | |
| $Q_{25}(R_7 = H, R_8 = H)$ | H | H | C=O | | CH₃ | CH₃ | |
| $Q_{25}(R_7 = H, R_8 = H)$ | H | H | C=O | | CH₃ | OCH₃ | |
| $Q_{25}(R_7 = H, R_8 = H)$ | H | H | C=O | | OCH₃ | OCH₃ | |
| $Q_{25}(R_7 = H, R_8 = H)$ | H | H | C=O | | Cl | OCH₃ | |
| $Q_{25}(R_7 = H, R_8 = H)$ | H | H | OH | H | CH₃ | CH₃ | |
| $Q_{25}(R_7 = H, R_8 = H)$ | H | H | OH | H | CH₃ | OCH₃ | |
| $Q_{25}(R_7 = H, R_8 = H)$ | H | H | OH | H | OCH₃ | OCH₃ | |
| $Q_{25}(R_7 = H, R_8 = H)$ | H | H | OH | H | Cl | OCH₃ | |
| $Q_{26}(R_7 = H, R_8 = H)$ | H | H | C=O | | CH₃ | CH₃ | |
| $Q_{26}(R_7 = H, R_8 = H)$ | H | H | C=O | | CH₃ | OCH₃ | |
| $Q_{26}(R_7 = H, R_8 = H)$ | H | H | C=O | | OCH₃ | OCH₃ | |
| $Q_{26}(R_7 = H, R_8 = H)$ | H | H | C=O | | Cl | OCH₃ | |
| $Q_{26}(R_7 = H, R_8 = H)$ | H | H | OH | H | CH₃ | CH₃ | |
| $Q_{26}(R_7 = H, R_8 = H)$ | H | H | OH | H | CH₃ | OCH₃ | |
| $Q_{26}(R_7 = H, R_8 = H)$ | H | H | OH | H | OCH₃ | OCH₃ | |
| $Q_{26}(R_7 = H, R_8 = H)$ | H | H | OH | H | Cl | OCH₃ | |
| $Q_{27}(R_7 = H, R_{11} = H, R_{12} = H)$ | H | H | C=O | | CH₃ | CH₃ | |
| $Q_{27}(R_7 = H, R_{11} = H, R_{12} = H)$ | H | H | C=O | | CH₃ | OCH₃ | |
| $Q_{27}(R_7 = H, R_{11} = H, R_{12} = H)$ | H | H | C=O | | OCH₃ | OCH₃ | |

TABLE VI-continued

General Formula VI

| Q | R | $R_1$ | $R_2$ | $R_3$ | X | Y | m.p. (°C.) |
|---|---|---|---|---|---|---|---|
| $Q_{27}(R_7 = H, R_{11} = H, R_{12} = H)$ | H | H | | C=O | Cl | $OCH_3$ | |
| $Q_{27}(R_7 = H, R_{11} = H, R_{12} = H)$ | H | H | OH | H | $CH_3$ | $CH_3$ | |
| $Q_{27}(R_7 = H, R_{11} = H, R_{12} = H)$ | H | H | OH | H | $CH_3$ | $OCH_3$ | |
| $Q_{27}(R_7 = H, R_{11} = H, R_{12} = H)$ | H | H | OH | H | $OCH_3$ | $OCH_3$ | |
| $Q_{27}(R_7 = H, R_{11} = H, R_{12} = H)$ | H | H | OH | H | Cl | $OCH_3$ | |
| $Q_{28}(R_{11} = H, R_{12} = H, R_{12} = H)$ | H | H | | C=O | $CH_3$ | $CH_3$ | |
| $Q_{28}(R_{11} = H, R_{12} = H)$ | H | H | | C=O | $CH_3$ | $OCH_3$ | |
| $Q_{28}(R_{11} = H, R_{12} = H)$ | H | H | | C=O | $OCH_3$ | $OCH_3$ | |
| $Q_{28}(R_{11} = H, R_{12} = H)$ | H | H | | C=O | Cl | $OCH_3$ | |
| $Q_{28}(R_{11} = H, R_{12} = H)$ | H | H | OH | H | $CH_3$ | $CH_3$ | |
| $Q_{28}(R_{11} = H, R_{12} = H)$ | H | H | OH | H | $CH_3$ | $OCH_3$ | |
| $Q_{28}(R_{11} = H, R_{12} = H)$ | H | H | OH | H | $OCH_3$ | $OCH_3$ | |
| $Q_{28}(R_{11} = H, R_{12} = H)$ | H | H | OH | H | Cl | $OCH_3$ | |
| $Q_{29}(R_{11} = H, R_{12} = H)$ | H | H | | C=O | $CH_3$ | $CH_3$ | |
| $Q_{29}(R_{11} = H, R_{12} = H)$ | H | H | | C=O | $CH_3$ | $OCH_3$ | |
| $Q_{29}(R_{11} = H, R_{12} = H)$ | H | H | | C=O | $OCH_3$ | $OCH_3$ | |
| $Q_{29}(R_{11} = H, R_{12} = H)$ | H | H | | C=O | Cl | $OCH_3$ | |
| $Q_{29}(R_{11} = H, R_{12} = H)$ | H | H | OH | H | $CH_3$ | $CH_3$ | |
| $Q_{29}(R_{11} = H, R_{12} = H)$ | H | H | OH | H | $CH_3$ | $OCH_3$ | |
| $Q_{29}(R_{11} = H, R_{12} = H)$ | H | H | OH | H | $OCH_3$ | $OCH_3$ | |
| $Q_{29}(R_{11} = H, R_{12} = H)$ | H | H | OH | H | Cl | $OCH_3$ | |
| $Q_{30}(R_7 = H, R_8 = H)$ | H | H | | C=O | $CH_3$ | $CH_3$ | |
| $Q_{30}(R_7 = H, R_8 = H)$ | H | H | | C=O | $CH_3$ | $OCH_3$ | |
| $Q_{30}(R_7 = H, R_8 = H)$ | H | H | | C=O | $OCH_3$ | $OCH_3$ | |
| $Q_{30}(R_7 = H, R_8 = H)$ | H | H | | C=O | Cl | $OCH_3$ | |
| $Q_{30}(R_7 = H, R_8 = H)$ | H | H | OH | H | $CH_3$ | $CH_3$ | |
| $Q_{30}(R_7 = H, R_8 = H)$ | H | H | OH | H | $CH_3$ | $OCH_3$ | |
| $Q_{30}(R_7 = H, R_8 = H)$ | H | H | OH | H | $OCH_3$ | $OCH_3$ | |
| $Q_{30}(R_7 = H, R_8 = H)$ | H | H | OH | H | Cl | $OCH_3$ | |
| $Q_{31}(R_7 = H, R_8 = H)$ | H | H | | C=O | $CH_3$ | $CH_3$ | |
| $Q_{31}(R_7 = H, R_8 = H)$ | H | H | | C=O | $CH_3$ | $OCH_3$ | |
| $Q_{31}(R_7 = H, R_8 = H)$ | H | H | | C=O | $OCH_3$ | $OCH_3$ | |
| $Q_{31}(R_7 = H, R_8 = H)$ | H | H | | C=O | Cl | $OCH_3$ | |
| $Q_{31}(R_7 = H, R_8 = H)$ | H | H | OH | H | $CH_3$ | $CH_3$ | |
| $Q_{31}(R_7 = H, R_8 = H)$ | H | H | OH | H | $CH_3$ | $OCH_3$ | |
| $Q_{31}(R_7 = H, R_8 = H)$ | H | H | OH | H | $OCH_3$ | $OCH_3$ | |
| $Q_{31}(R_7 = H, R_8 = H)$ | H | H | OH | H | Cl | $OCH_3$ | |
| $Q_{32}(R_{13} = OCH_3, R_{14} = OCH_3)$ | H | H | | C=O | $CH_3$ | $CH_3$ | |
| $Q_{32}(R_{13} = OCH_3, R_{14} = OCH_3)$ | H | H | | C=O | $CH_3$ | $OCH_3$ | |
| $Q_{32}(R_{13} = OCH_3, R_{14} = OCH_3)$ | H | H | | C=O | $OCH_3$ | $OCH_3$ | |
| $Q_{32}(R_{13} = OCH_3, R_{14} = OCH_3)$ | H | H | | C=O | Cl | $OCH_3$ | |
| $Q_{32}(R_{13} = OCH_3, R_{14} = OCH_3)$ | H | H | OH | H | $CH_3$ | $CH_3$ | |
| $Q_{32}(R_{13} = OCH_3, R_{14} = OCH_3)$ | H | H | OH | H | $OCH_3$ | $OCH_3$ | |
| $Q_{32}(R_{13} = OCH_3, R_{14} = OCH_3)$ | H | H | OH | H | Cl | $OCH_3$ | |
| $Q_{33}(R_7 = H)$ | H | H | | C=O | $CH_3$ | $CH_3$ | |
| $Q_{33}(R_7 = H)$ | H | H | | C=O | $CH_3$ | $OCH_3$ | |
| $Q_{33}(R_7 = H)$ | H | H | | C=O | $OCH_3$ | $OCH_3$ | |
| $Q_{33}(R_7 = H)$ | H | H | | C=O | Cl | $OCH_3$ | |
| $Q_{33}(R_7 = H)$ | H | H | OH | H | $CH_3$ | $CH_3$ | |
| $Q_{33}(R_7 = H)$ | H | H | OH | H | $CH_3$ | $OCH_3$ | |
| $Q_{33}(R_7 = H)$ | H | H | OH | H | $OCH_3$ | $OCH_3$ | |
| $Q_{33}(R_7 = H)$ | H | H | OH | H | Cl | $OCH_3$ | |

TABLE VII

General Formula VII

| Q | R | $R_1$ | $R_2$ | $R_3$ | X | Y | m.p. (°C.) |
|---|---|---|---|---|---|---|---|
| $Q_1(R_7=H, R_8=H, R_9=H)$ | H | H | | C=O | $CH_3$ | $CH_3$ | 176–179 |
| $Q_1(R_7=H, R_8=H, R_9=H)$ | H | H | | C=O | $CH_3$ | $OCH_3$ | 181–188 |
| $Q_1(R_7=H, R_8=H, R_9=H)$ | H | H | | C=O | $OCH_3$ | $OCH_3$ | 193–196 |
| $Q_1(R_7=H, R_8=H, R_9=H)$ | H | H | | C=O | Cl | $OCH_3$ | |
| $Q_1(R_7=H, R_8=H, R_9=H)$ | H | H | OH | H | $CH_3$ | $CH_3$ | |
| $Q_1(R_7=H, R_8=H, R_9=H)$ | H | H | OH | H | $CH_3$ | $OCH_3$ | |
| $Q_1(R_7=H, R_8=H, R_9=H)$ | H | H | OH | H | $OCH_3$ | $OCH_3$ | |
| $Q_1(R_7=H, R_8=H, R_9=H)$ | H | H | OH | H | Cl | $OCH_3$ | |
| $Q_1(R_7=H, R_8=H, R_9=H)$ | H | H | $OCH_3$ | H | $OCH_3$ | $OCH_3$ | |
| $Q_1(R_7=H, R_8=H, R_9=H)$ | H | H | $OCH_2CH_3$ | H | $OCH_3$ | $OCH_3$ | |
| $Q_1(R_7=H, R_8=H, R_9=H)$ | H | H | $OCH_3$ | $OCH_3$ | $OCH_3$ | $OCH_3$ | |
| $Q_1(R_7=H, R_8=H, R_9=H)$ | H | H | —O(CH$_2$)$_3$O— | | $OCH_3$ | $OCH_3$ | |
| $Q_2(R_7=H, R_8=H, R_9=H)$ | H | H | | C=O | $CH_3$ | $CH_3$ | |
| $Q_2(R_7=H, R_8=H, R_9=H)$ | H | H | | C=O | $CH_3$ | $OCH_3$ | |
| $Q_2(R_7=H, R_8=H, R_9=H)$ | H | H | | C=O | $OCH_3$ | $OCH_3$ | |
| $Q_2(R_7=H, R_8=H, R_9=H)$ | H | H | | C=O | Cl | $OCH_3$ | |
| $Q_2(R_7=H, R_8=H, R_9=H)$ | H | H | OH | H | $CH_3$ | $CH_3$ | |
| $Q_2(R_7=H, R_8=H, R_9=H)$ | H | H | OH | H | $CH_3$ | $OCH_3$ | |
| $Q_2(R_7=H, R_8=H, R_9=H)$ | H | H | OH | H | $OCH_3$ | $OCH_3$ | |
| $Q_2(R_7=H, R_8=H, R_9=H)$ | H | H | OH | H | Cl | $OCH_3$ | |

TABLE VII-continued

General Formula VII

| Q | R | $R_1$ | $R_2$ | $R_3$ | X | Y | m.p. (°C.) |
|---|---|---|---|---|---|---|---|
| $Q_2(R_7=H, R_8=H, R_9=H)$ | H | H | $OCH_3$ | H | $CH_3$ | $OCH_3$ | |
| $Q_2(R_7=H, R_8=H, R_9=H)$ | H | H | $OCH_2CH_3$ | H | $CH_3$ | $CH_3$ | |
| $Q_3(R_7=H, R_8=H, R_9=H)$ | H | H | C=O | | $CH_3$ | $CH_3$ | |
| $Q_3(R_7=H, R_8=H, R_9=H)$ | H | H | C=O | | $CH_3$ | $OCH_3$ | |
| $Q_3(R_7=H, R_8=H, R_9=H)$ | H | H | C=O | | $OCH_3$ | $OCH_3$ | |
| $Q_3(R_7=H, R_8=H, R_9=H)$ | H | H | C=O | | Cl | $OCH_3$ | |
| $Q_3(R_7=H, R_8=H, R_9=H)$ | H | H | OH | H | $CH_3$ | $CH_3$ | |
| $Q_3(R_7=H, R_8=H, R_9=H)$ | H | H | OH | H | $CH_3$ | $OCH_3$ | |
| $Q_3(R_7=H, R_8=H, R_9=H)$ | H | H | OH | H | $OCH_3$ | $OCH_3$ | |
| $Q_3(R_7=H, R_8=H, R_9=H)$ | H | H | OH | H | Cl | $OCH_3$ | |
| $Q_3(R_7=H, R_8=H, R_9=Cl)$ | H | H | C=O | | $OCH_3$ | $OCH_3$ | |
| $Q_3(R_7=H, R_8=H, R_9=CH_3)$ | H | H | C=O | | $OCH_3$ | $OCH_3$ | |
| $Q_3(R_7=H, R_8=H, R_9=CH_3)$ | H | H | OH | H | $OCH_3$ | $OCH_3$ | |
| $Q_3(R_7=H, R_8=H, R_9=CH_3)$ | H | H | $OCH_3$ | $OCH_3$ | $OCH_3$ | $OCH_3$ | |
| $Q_3(R_7=H, R_8=H, R_9=CH_3)$ | H | H | —O(CH$_2$)$_3$O— | | $OCH_3$ | $OCH_3$ | |
| $Q_4(R_7=H, R_8=H, R_9=H)$ | H | H | C=O | | $CH_3$ | $CH_3$ | |
| $Q_4(R_7=H, R_8=H, R_9=H)$ | H | H | C=O | | $CH_3$ | $OCH_3$ | |
| $Q_4(R_7=H, R_8=H, R_9=H)$ | H | H | C=O | | $OCH_3$ | $OCH_3$ | |
| $Q_4(R_7=H, R_8=H, R_9=H)$ | H | H | C=O | | Cl | $OCH_3$ | |
| $Q_4(R_7=H, R_8=H, R_9=H)$ | H | H | OH | H | $CH_3$ | $CH_3$ | |
| $Q_4(R_7=H, R_8=H, R_9=H)$ | H | H | OH | H | $CH_3$ | $OCH_3$ | |
| $Q_4(R_7=H, R_8=H, R_9=H)$ | H | H | OH | H | $OCH_3$ | $OCH_3$ | |
| $Q_4(R_7=H, R_8=H, R_9=H)$ | H | H | OH | H | Cl | $OCH_3$ | |
| $Q_5(R_7=H, R_8=H, R_9=H, R_{10}=CH_3)$ | H | H | C=O | | $CH_3$ | $CH_3$ | |
| $Q_5(R_7=H, R_8=H, R_9=H, R_{10}=CH_3)$ | H | H | C=O | | $CH_3$ | $OCH_3$ | |
| $Q_5(R_7=H, R_8=H, R_9=H, R_{10}=CH_3)$ | H | H | C=O | | $OCH_3$ | $OCH_3$ | |
| $Q_5(R_7=H, R_8=H, R_9=H, R_{10}=CH_3)$ | H | H | C=O | | Cl | $OCH_3$ | |
| $Q_5(R_7=H, R_8=H, R_9=H, R_{10}=CH_3)$ | H | H | OH | H | $CH_3$ | $CH_3$ | |
| $Q_5(R_7=H, R_8=H, R_9=H, R_{10}=CH_3)$ | H | H | OH | H | $CH_3$ | $OCH_3$ | |
| $Q_5(R_7=H, R_8=H, R_9=H, R_{10}=CH_3)$ | H | H | OH | H | $OCH_3$ | $OCH_3$ | |
| $Q_5(R_7=H, R_8=H, R_9=H, R_{10}=CH_3)$ | H | H | OH | H | Cl | $OCH_3$ | |
| $Q_5(R_7=H, R_8=H, R_9=H, R_{10}=CH_3)$ | H | H | $OCH_3$ | H | Cl | $OCH_3$ | |
| $Q_5(R_7=H, R_8=H, R_9=H, R_{10}=CH_3)$ | H | H | $OCH_2CH_3$ | H | $OCH_3$ | $OCH_3$ | |
| $Q_6(R_7=H, R_8=H, R_9=H, R_{10}=CH_3)$ | H | H | C=O | | $CH_3$ | $CH_3$ | |
| $Q_6(R_7=H, R_8=H, R_9=H, R_{10}=CH_3)$ | H | H | C=O | | $CH_3$ | $OCH_3$ | |
| $Q_6(R_7=H, R_8=H, R_9=H, R_{10}=CH_3)$ | H | H | C=O | | $OCH_3$ | $OCH_3$ | |
| $Q_6(R_7=H, R_8=H, R_9=H, R_{10}=CH_3)$ | H | H | C=O | | Cl | $OCH_3$ | |
| $Q_6(R_7=H, R_8=H, R_9=H, R_{10}=CH_3)$ | H | H | OH | H | $CH_3$ | $CH_3$ | |
| $Q_6(R_7=H, R_8=H, R_9=H, R_{10}=CH_3)$ | H | H | OH | H | $CH_3$ | $OCH_3$ | |
| $Q_6(R_7=H, R_8=H, R_9=H, R_{10}=CH_3)$ | H | H | OH | H | $OCH_3$ | $OCH_3$ | |
| $Q_6(R_7=H, R_8=H, R_9=H, R_{10}=CH_3)$ | H | H | OH | H | Cl | $OCH_3$ | |
| $Q_7(R_7=H, R_8=H)$ | H | H | C=O | | $CH_3$ | $CH_3$ | |
| $Q_7(R_7=H, R_8=H)$ | H | H | C=O | | $CH_3$ | $OCH_3$ | |
| $Q_7(R_7=H, R_8=H)$ | H | H | C=O | | $OCH_3$ | $OCH_3$ | |
| $Q_7(R_7=H, R_8=H)$ | H | H | C=O | | Cl | $OCH_3$ | |
| $Q_7(R_7=H, R_8=H)$ | H | H | OH | H | $CH_3$ | $CH_3$ | |
| $Q_7(R_7=H, R_8=H)$ | H | H | OH | H | $CH_3$ | $OCH_3$ | |
| $Q_7(R_7=H, R_8=H)$ | H | H | OH | H | $OCH_3$ | $OCH_3$ | |
| $Q_7(R_7=H, R_8=H)$ | H | H | OH | H | Cl | $OCH_3$ | |
| $Q_7(R_7=H, R_8=H)$ | H | H | $OCH_3$ | $OCH_3$ | $OCH_3$ | $OCH_3$ | |
| $Q_7(R_7=H, R_8=H)$ | H | H | —O(CH$_2$)$_3$O— | | $OCH_3$ | $OCH_3$ | |
| $Q_8(R_7=H, R_8=H)$ | H | H | C=O | | $OCH_3$ | $OCH_3$ | |
| $Q_8(R_7=H, R_8=H)$ | H | H | C=O | | Cl | $OCH_3$ | |
| $Q_8(R_7=H, R_8=H)$ | H | H | OH | H | Cl | $OCH_3$ | |
| $Q_8(R_7=H, R_8=H)$ | H | H | OH | H | $OCH_3$ | $OCH_3$ | |
| $Q_8(R_7=H, R_8=H)$ | H | H | $OCH_3$ | $OCH_3$ | $OCH_3$ | $OCH_3$ | |
| $Q_8(R_7=H, R_8=H)$ | H | H | —O(CH$_2$)$_3$O— | | $OCH_3$ | $OCH_3$ | |
| $Q_9(R_7=H, R_8=H)$ | H | H | C=O | | $CH_3$ | $CH_3$ | |
| $Q_9(R_7=H, R_8=H)$ | H | H | C=O | | $CH_3$ | $OCH_3$ | |
| $Q_9(R_7=H, R_8=H)$ | H | H | C=O | | $OCH_3$ | $OCH_3$ | |
| $Q_9(R_7=H, R_8=H)$ | H | H | C=O | | Cl | $OCH_3$ | |
| $Q_9(R_7=H, R_8=H)$ | H | H | OH | H | $CH_3$ | $CH_3$ | |
| $Q_9(R_7=H, R_8=H)$ | H | H | OH | H | $CH_3$ | $OCH_3$ | |
| $Q_9(R_7=H, R_8=H)$ | H | H | OH | H | $OCH_3$ | $OCH_3$ | |
| $Q_9(R_7=H, R_8=H)$ | H | H | OH | H | Cl | $OCH_3$ | |
| $Q_9(R_7=H, R_8=H)$ | H | H | $OCH_3$ | $OCH_3$ | $OCH_3$ | $OCH_3$ | |
| $Q_9(R_7=H, R_8=H)$ | H | H | —O(CH$_2$)$_3$O— | | $OCH_3$ | $OCH_3$ | |
| $Q_{10}(R_7=H, R_8=H)$ | H | H | C=O | | $CH_3$ | $CH_3$ | |
| $Q_{10}(R_7=H, R_8=H)$ | H | H | C=O | | $OCH_3$ | $OCH_3$ | |
| $Q_{10}(R_7=H, R_8=H)$ | H | H | C=O | | Cl | $OCH_3$ | |
| $Q_{10}(R_7=H, R_8=H)$ | H | H | OH | H | $CH_3$ | $CH_3$ | |
| $Q_{10}(R_7=H, R_8=H)$ | H | H | OH | H | $OCH_3$ | $OCH_3$ | |
| $Q_{10}(R_7=H, R_8=H)$ | H | H | OH | H | Cl | $OCH_3$ | |
| $Q_{10}(R_7=H, R_8=H)$ | H | H | $OCH_3$ | $OCH_3$ | $OCH_3$ | $OCH_3$ | |
| $Q_{10}(R_7=H, R_8=H)$ | H | H | —O(CH$_2$)$_3$O— | | $OCH_3$ | $OCH_3$ | |
| $Q_{11}(R_7=H, R_8=H)$ | H | H | C=O | | $CH_3$ | $CH_3$ | |
| $Q_{11}(R_7=H, R_8=H)$ | H | H | C=O | | $CH_3$ | $OCH_3$ | |
| $Q_{11}(R_7=H, R_8=H)$ | H | H | C=O | | $OCH_3$ | $OCH_3$ | |
| $Q_{11}(R_7=H, R_8=H)$ | H | H | C=O | | Cl | $OCH_3$ | |

TABLE VII-continued

General Formula VII

| Q | R | R$_1$ | R$_2$ | R$_3$ | X | Y | m.p. (°C.) |
|---|---|---|---|---|---|---|---|
| Q$_{11}$(R$_7$=H, R$_8$=H) | H | H | OH | H | CH$_3$ | CH$_3$ | |
| Q$_{11}$(R$_7$=H, R$_8$=H) | H | H | OH | H | CH$_3$ | OCH$_3$ | |
| Q$_{11}$(R$_7$=H, R$_8$=H) | H | H | OH | H | OCH$_3$ | OCH$_3$ | |
| Q$_{11}$(R$_7$=H, R$_8$=H) | H | H | OH | H | Cl | OCH$_3$ | |
| Q$_{11}$(R$_7$=H, R$_8$=H) | H | H | OCH$_3$ | OCH$_3$ | OCH$_3$ | OCH$_3$ | |
| Q$_{11}$(R$_7$=H, R$_8$=H) | H | H | —O(CH$_2$)$_3$O— | | OCH$_3$ | OCH$_3$ | |
| Q$_{12}$(R$_7$=H, R$_8$=H) | H | H | C=O | | CH$_3$ | CH$_3$ | |
| Q$_{12}$(R$_7$=H, R$_8$=H) | H | H | C=O | | CH$_3$ | OCH$_3$ | |
| Q$_{12}$(R$_7$=H, R$_8$=H) | H | H | C=O | | OCH$_3$ | OCH$_3$ | |
| Q$_{12}$(R$_7$=H, R$_8$=H) | H | H | C=O | | Cl | OCH$_3$ | |
| Q$_{12}$(R$_7$=H, R$_8$=H) | H | H | OH | H | CH$_3$ | CH$_3$ | |
| Q$_{12}$(R$_7$=H, R$_8$=H) | H | H | OH | H | CH$_3$ | OCH$_3$ | |
| Q$_{12}$(R$_7$=H, R$_8$=H) | H | H | OH | H | OCH$_3$ | OCH$_3$ | |
| Q$_{12}$(R$_7$=H, R$_8$=H) | H | H | OH | H | Cl | OCH$_3$ | |
| Q$_{12}$(R$_7$=H, R$_8$=H) | H | H | OCH$_3$ | H | OCH$_3$ | OCH$_3$ | |
| Q$_{13}$(R$_7$=H, R$_8$=H) | H | H | C=O | | CH$_3$ | CH$_3$ | |
| Q$_{13}$(R$_7$=H, R$_8$=H) | H | H | C=O | | CH$_3$ | OCH$_3$ | |
| Q$_{13}$(R$_7$=H, R$_8$=H) | H | H | C=O | | OCH$_3$ | OCH$_3$ | |
| Q$_{13}$(R$_7$=H, R$_8$=H) | H | H | C=O | | Cl | OCH$_3$ | |
| Q$_{13}$(R$_7$=H, R$_8$=H) | H | H | OH | H | CH$_3$ | CH$_3$ | |
| Q$_{13}$(R$_7$=H, R$_8$=H) | H | H | OH | H | CH$_3$ | OCH$_3$ | |
| Q$_{13}$(R$_7$=H, R$_8$=H) | H | H | OH | H | OCH$_3$ | OCH$_3$ | |
| Q$_{13}$(R$_7$=H, R$_8$=H) | H | H | OH | H | Cl | OCH$_3$ | |
| Q$_{14}$(R$_7$=H) | H | H | C=O | | CH$_3$ | CH$_3$ | |
| Q$_{14}$(R$_7$=H) | H | H | C=O | | CH$_3$ | OCH$_3$ | |
| Q$_{14}$(R$_7$=H) | H | H | C=O | | OCH$_3$ | OCH$_3$ | |
| Q$_{14}$(R$_7$=H) | H | H | C=O | | Cl | OCH$_3$ | |
| Q$_{14}$(R$_7$=H) | H | H | OH | H | CH$_3$ | CH$_3$ | |
| Q$_{14}$(R$_7$=H) | H | H | OH | H | CH$_3$ | OCH$_3$ | |
| Q$_{14}$(R$_7$=H) | H | H | OH | H | OCH$_3$ | OCH$_3$ | |
| Q$_{14}$(R$_7$=H) | H | H | OH | H | Cl | OCH$_3$ | |
| Q$_{14}$(R$_7$=H) | H | H | OCH$_3$ | OCH$_3$ | OCH$_3$ | OCH$_3$ | |
| Q$_{14}$(R$_7$=H) | H | H | —O(CH$_2$)$_3$O— | | OCH$_3$ | OCH$_3$ | |
| Q$_{15}$(R$_7$=H) | H | H | C=O | | CH$_3$ | CH$_3$ | |
| Q$_{15}$(R$_7$=H) | H | H | C=O | | CH$_3$ | OCH$_3$ | |
| Q$_{15}$(R$_7$=H) | H | H | C=O | | OCH$_3$ | OCH$_3$ | |
| Q$_{15}$(R$_7$=H) | H | H | C=O | | Cl | OCH$_3$ | |
| Q$_{15}$(R$_7$=H) | H | H | OH | H | CH$_3$ | CH$_3$ | |
| Q$_{15}$(R$_7$=H) | H | H | OH | H | CH$_3$ | OCH$_3$ | |
| Q$_{15}$(R$_7$=H) | H | H | OH | H | OCH$_3$ | OCH$_3$ | |
| Q$_{15}$(R$_7$=H) | H | H | OH | H | Cl | OCH$_3$ | |
| Q$_{16}$(R$_7$=H) | H | H | C=O | | CH$_3$ | CH$_3$ | |
| Q$_{16}$(R$_7$=H) | H | H | C=O | | CH$_3$ | OCH$_3$ | |
| Q$_{16}$(R$_7$=H) | H | H | C=O | | OCH$_3$ | OCH$_3$ | |
| Q$_{16}$(R$_7$=H) | H | H | C=O | | Cl | OCH$_3$ | |
| Q$_{16}$(R$_7$=H) | H | H | OH | H | CH$_3$ | CH$_3$ | |
| Q$_{16}$(R$_7$=H) | H | H | OH | H | CH$_3$ | OCH$_3$ | |
| Q$_{16}$(R$_7$=H) | H | H | OH | H | OCH$_3$ | OCH$_3$ | |
| Q$_{16}$(R$_7$=H) | H | H | OH | H | Cl | OCH$_3$ | |
| Q$_{16}$(R$_7$=H) | H | H | OCH$_3$ | OCH$_3$ | OCH$_3$ | OCH$_3$ | |
| Q$_{16}$(R$_7$=H) | H | H | —O(CH$_2$)$_3$O— | | OCH$_3$ | OCH$_3$ | |
| Q$_{17}$(R$_7$=CH$_3$) | H | H | C=O | | CH$_3$ | CH$_3$ | |
| Q$_{17}$(R$_7$=CH$_3$) | H | H | C=O | | CH$_3$ | OCH$_3$ | |
| Q$_{17}$(R$_7$=CH$_3$) | H | H | C=O | | OCH$_3$ | OCH$_3$ | |
| Q$_{17}$(R$_7$=CH$_3$) | H | H | C=O | | Cl | OCH$_3$ | |
| Q$_{17}$(R$_7$=CH$_3$) | H | H | OH | H | CH$_3$ | CH$_3$ | |
| Q$_{17}$(R$_7$=CH$_3$) | H | H | OH | H | CH$_3$ | OCH$_3$ | |
| Q$_{17}$(R$_7$=CH$_3$) | H | H | OH | H | OCH$_3$ | OCH$_3$ | |
| Q$_{17}$(R$_7$=CH$_3$) | H | H | OH | H | Cl | OCH$_3$ | |
| Q$_{17}$(R$_7$=CH$_3$) | H | H | OCH$_3$ | OCH$_3$ | OCH$_3$ | OCH$_3$ | |
| Q$_{17}$(R$_7$=CH$_3$) | H | H | —O(CH$_2$)$_3$O— | | OCH$_3$ | OCH$_3$ | |
| Q$_{18}$(R$_7$=H) | H | H | C=O | | CH$_3$ | CH$_3$ | |
| Q$_{18}$(R$_7$=H) | H | H | C=O | | CH$_3$ | OCH$_3$ | |
| Q$_{18}$(R$_7$=H) | H | H | C=O | | OCH$_3$ | OCH$_3$ | |
| Q$_{18}$(R$_7$=H) | H | H | C=O | | Cl | OCH$_3$ | |
| Q$_{18}$(R$_7$=H) | H | H | OH | H | CH$_3$ | CH$_3$ | |
| Q$_{18}$(R$_7$=H) | H | H | OH | H | CH$_3$ | OCH$_3$ | |
| Q$_{18}$(R$_7$=H) | H | H | OH | H | OCH$_3$ | OCH$_3$ | |
| Q$_{18}$(R$_7$=H) | H | H | OH | H | Cl | OCH$_3$ | |
| Q$_{19}$(R$_7$=H, R$_8$=H) | H | H | C=O | | CH$_3$ | CH$_3$ | |
| Q$_{19}$(R$_7$=H, R$_8$=H) | H | H | C=O | | CH$_3$ | OCH$_3$ | |
| Q$_{19}$(R$_7$=H, R$_8$=H) | H | H | C=O | | OCH$_3$ | OCH$_3$ | |
| Q$_{19}$(R$_7$=H, R$_8$=H) | H | H | C=O | | Cl | OCH$_3$ | |
| Q$_{19}$(R$_7$=H, R$_8$=H) | H | H | OH | H | CH$_3$ | CH$_3$ | |
| Q$_{19}$(R$_7$=H, R$_8$=H) | H | H | OH | H | CH$_3$ | OCH$_3$ | |
| Q$_{19}$(R$_7$=H, R$_8$=H) | H | H | OH | H | OCH$_3$ | OCH$_3$ | |
| Q$_{19}$(R$_7$=H, R$_8$=H) | H | H | OH | H | Cl | OCH$_3$ | |
| Q$_{20}$(R$_7$=H, R$_8$=H) | H | H | C=O | | CH$_3$ | CH$_3$ | |
| Q$_{20}$(R$_7$=H, R$_8$=H) | H | H | C=O | | CH$_3$ | OCH$_3$ | |

TABLE VII-continued

General Formula VII

| Q | R | $R_1$ | $R_2$ | $R_3$ | X | Y | m.p. (°C.) |
|---|---|---|---|---|---|---|---|
| $Q_{20}(R_7=H, R_8=H)$ | H | H | | C=O | $OCH_3$ | $OCH_3$ | |
| $Q_{20}(R_7=H, R_8=H)$ | H | H | | C=O | Cl | $OCH_3$ | |
| $Q_{20}(R_7=H, R_8=H)$ | H | H | OH | H | $CH_3$ | $CH_3$ | |
| $Q_{20}(R_7=H, R_8=H)$ | H | H | OH | H | $CH_3$ | $OCH_3$ | |
| $Q_{20}(R_7=H, R_8=H)$ | H | H | OH | H | $OCH_3$ | $OCH_3$ | |
| $Q_{20}(R_7=H, R_8=H)$ | H | H | OH | H | Cl | $OCH_3$ | |
| $Q_{21}(R_7=H, R_8=H, R_9=CH_3)$ | H | H | | C=O | $CH_3$ | $CH_3$ | |
| $Q_{21}(R_7=H, R_8=H, R_9=CH_3)$ | H | H | | C=O | $CH_3$ | $OCH_3$ | |
| $Q_{21}(R_7=H, R_8=H, R_9=CH_3)$ | H | H | | C=O | $OCH_3$ | $OCH_3$ | |
| $Q_{21}(R_7=H, R_8=H, R_9=CH_3)$ | H | H | | C=O | Cl | $OCH_3$ | |
| $Q_{21}(R_7=H, R_8=H, R_9=CH_3)$ | H | H | OH | H | $CH_3$ | $CH_3$ | |
| $Q_{21}(R_7=H, R_8=H, R_9=CH_3)$ | H | H | OH | H | $CH_3$ | $OCH_3$ | |
| $Q_{21}(R_7=H, R_8=H, R_9=CH_3)$ | H | H | OH | H | $OCH_3$ | $OCH_3$ | |
| $Q_{21}(R_7=H, R_8=H, R_9=CH_3)$ | H | H | OH | H | Cl | $OCH_3$ | |
| $Q_{21}(R_7=H, R_8=H, R_9=CH_3)$ | H | H | $OCH_3$ | $OCH_3$ | $OCH_3$ | $OCH_3$ | |
| $Q_{21}(R_7=H, R_8=H, R_9=CH_3)$ | H | H | —O(CH_2)_3O— | | $OCH_3$ | $OCH_3$ | |
| $Q_{22}(R_7=H)$ | H | H | | C=O | $CH_3$ | $CH_3$ | |
| $Q_{22}(R_7=H)$ | H | H | | C=O | $CH_3$ | $OCH_3$ | |
| $Q_{22}(R_7=H)$ | H | H | | C=O | $OCH_3$ | $OCH_3$ | |
| $Q_{22}(R_7=H)$ | H | H | | C=O | Cl | $OCH_3$ | |
| $Q_{22}(R_7=H)$ | H | H | OH | H | $CH_3$ | $CH_3$ | |
| $Q_{22}(R_7=H)$ | H | H | OH | H | $CH_3$ | $OCH_3$ | |
| $Q_{22}(R_7=H)$ | H | H | OH | H | $OCH_3$ | $OCH_3$ | |
| $Q_{22}(R_7=H)$ | H | H | OH | H | Cl | $OCH_3$ | |
| $Q_{23}(R_7=H)$ | H | H | | C=O | $CH_3$ | $CH_3$ | |
| $Q_{23}(R_7=H)$ | H | H | | C=O | $CH_3$ | $OCH_3$ | |
| $Q_{23}(R_7=H)$ | H | H | | C=O | $OCH_3$ | $OCH_3$ | |
| $Q_{23}(R_7=H)$ | H | H | | C=O | Cl | $OCH_3$ | |
| $Q_{23}(R_7=H)$ | H | H | OH | H | $CH_3$ | $CH_3$ | |
| $Q_{23}(R_7=H)$ | H | H | OH | H | $CH_3$ | $OCH_3$ | |
| $Q_{23}(R_7=H)$ | H | H | OH | H | $OCH_3$ | $OCH_3$ | |
| $Q_{23}(R_7=H)$ | H | H | OH | H | Cl | $OCH_3$ | |
| $Q_{24}(R_7=H, R_8=H)$ | H | H | | C=O | $CH_3$ | $CH_3$ | |
| $Q_{24}(R_7=H, R_8=H)$ | H | H | | C=O | $CH_3$ | $OCH_3$ | |
| $Q_{24}(R_7=H, R_8=H)$ | H | H | | C=O | $OCH_3$ | $OCH_3$ | |
| $Q_{24}(R_7=H, R_8=H)$ | H | H | | C=O | Cl | $OCH_3$ | |
| $Q_{24}(R_7=H, R_8=H)$ | H | H | OH | H | $CH_3$ | $CH_3$ | |
| $Q_{24}(R_7=H, R_8=H)$ | H | H | OH | H | $CH_3$ | $OCH_3$ | |
| $Q_{24}(R_7=H, R_8=H)$ | H | H | OH | H | $OCH_3$ | $OCH_3$ | |
| $Q_{24}(R_7=H, R_8=H)$ | H | H | OH | H | Cl | $OCH_3$ | |
| $Q_{24}(R_7=H, R_8=H)$ | H | H | $OCH_3$ | $OCH_3$ | $OCH_3$ | $OCH_3$ | |
| $Q_{24}(R_7=H, R_8=H)$ | H | H | —O(CH_2)_3O— | | $OCH_3$ | $OCH_3$ | |
| $Q_{25}(R_7=H, R_8=H)$ | H | H | | C=O | $CH_3$ | $CH_3$ | |
| $Q_{25}(R_7=H, R_8=H)$ | H | H | | C=O | $CH_3$ | $OCH_3$ | |
| $Q_{25}(R_7=H, R_8=H)$ | H | H | | C=O | $OCH_3$ | $OCH_3$ | |
| $Q_{25}(R_7=H, R_8=H)$ | H | H | | C=O | Cl | $OCH_3$ | |
| $Q_{25}(R_7=H, R_8=H)$ | H | H | OH | H | $CH_3$ | $CH_3$ | |
| $Q_{25}(R_7=H, R_8=H)$ | H | H | OH | H | $CH_3$ | $OCH_3$ | |
| $Q_{25}(R_7=H, R_8=H)$ | H | H | OH | H | $OCH_3$ | $OCH_3$ | |
| $Q_{25}(R_7=H, R_8=H)$ | H | H | OH | H | Cl | $OCH_3$ | |
| $Q_{26}(R_7=H, R_8=H)$ | H | H | | C=O | $CH_3$ | $CH_3$ | |
| $Q_{26}(R_7=H, R_8=H)$ | H | H | | C=O | $CH_3$ | $OCH_3$ | |
| $Q_{26}(R_7=H, R_8=H)$ | H | H | | C=O | $OCH_3$ | $OCH_3$ | |
| $Q_{26}(R_7=H, R_8=H)$ | H | H | | C=O | Cl | $OCH_3$ | |
| $Q_{26}(R_7=H, R_8=H)$ | H | H | OH | H | $CH_3$ | $CH_3$ | |
| $Q_{26}(R_7=H, R_8=H)$ | H | H | OH | H | $CH_3$ | $OCH_3$ | |
| $Q_{26}(R_7=H, R_8=H)$ | H | H | OH | H | $OCH_3$ | $OCH_3$ | |
| $Q_{26}(R_7=H, R_8=H)$ | H | H | OH | H | Cl | $OCH_3$ | |
| $Q_{27}(R_7=H, R_{11}=H, R_{12}=H)$ | H | H | | C=O | $CH_3$ | $CH_3$ | |
| $Q_{27}(R_7=H, R_{11}=H, R_{12}=H)$ | H | H | | C=O | $CH_3$ | $OCH_3$ | |
| $Q_{27}(R_7=H, R_{11}=H, R_{12}=H)$ | H | H | | C=O | $OCH_3$ | $OCH_3$ | |
| $Q_{27}(R_7=H, R_{11}=H, R_{12}=H)$ | H | H | | C=O | Cl | $OCH_3$ | |
| $Q_{27}(R_7=H, R_{11}=H, R_{12}=H)$ | H | H | OH | H | $CH_3$ | $CH_3$ | |
| $Q_{27}(R_7=H, R_{11}=H, R_{12}=H)$ | H | H | OH | H | $CH_3$ | $OCH_3$ | |
| $Q_{27}(R_7=H, R_{11}=H, R_{12}=H)$ | H | H | OH | H | $OCH_3$ | $OCH_3$ | |
| $Q_{27}(R_7=H, R_{11}=H, R_{12}=H)$ | H | H | OH | H | Cl | $OCH_3$ | |
| $Q_{27}(R_7=H, R_{11}=H, R_{12}=H)$ | H | H | $OCH_3$ | $OCH_3$ | $OCH_3$ | $OCH_3$ | |
| $Q_{27}(R_7=H, R_{11}=H, R_{12}=H)$ | H | H | —O(CH_2)_3O— | | $OCH_3$ | $OCH_3$ | |
| $Q_{28}(R_{11}=H, R_{12}=H)$ | H | H | | C=O | $CH_3$ | $CH_3$ | |
| $Q_{28}(R_{11}=H, R_{12}=H)$ | H | H | | C=O | $CH_3$ | $OCH_3$ | |
| $Q_{28}(R_{11}=H, R_{12}=H)$ | H | H | | C=O | $OCH_3$ | $OCH_3$ | |
| $Q_{28}(R_{11}=H, R_{12}=H)$ | H | H | | C=O | Cl | $OCH_3$ | |
| $Q_{28}(R_{11}=H, R_{12}=H)$ | H | H | OH | H | $CH_3$ | $CH_3$ | |
| $Q_{28}(R_{11}=H, R_{12}=H)$ | H | H | OH | H | $CH_3$ | $OCH_3$ | |
| $Q_{28}(R_{11}=H, R_{12}=H)$ | H | H | OH | H | $OCH_3$ | $OCH_3$ | |
| $Q_{28}(R_{11}=H, R_{12}=H)$ | H | H | OH | H | Cl | $OCH_3$ | |
| $Q_{29}(R_{11}=H, R_{12}=H)$ | H | H | | C=O | $CH_3$ | $CH_3$ | |
| $Q_{29}(R_{11}=H, R_{12}=H)$ | H | H | | C=O | $CH_3$ | $OCH_3$ | |
| $Q_{29}(R_{11}=H, R_{12}=H)$ | H | H | | C=O | $OCH_3$ | $OCH_3$ | |

TABLE VII-continued

General Formula VII

| Q | R | R₁ | R₂ | R₃ | X | Y | m.p. (°C.) |
|---|---|---|---|---|---|---|---|
| Q$_{29}$(R$_{11}$=H, R$_{12}$=H) | H | H | | C=O | Cl | OCH$_3$ | |
| Q$_{29}$(R$_{11}$=H, R$_{12}$=H) | H | H | OH | H | CH$_3$ | CH$_3$ | |
| Q$_{29}$(R$_{11}$=H, R$_{12}$=H) | H | H | OH | H | CH$_3$ | OCH$_3$ | |
| Q$_{29}$(R$_{11}$=H, R$_{12}$=H) | H | H | OH | H | OCH$_3$ | OCH$_3$ | |
| Q$_{29}$(R$_{11}$=H, R$_{12}$=H) | H | H | OH | H | Cl | OCH$_3$ | |
| Q$_{30}$(R$_7$=H, R$_8$=H) | H | H | | C=O | CH$_3$ | CH$_3$ | |
| Q$_{30}$(R$_7$=H, R$_8$=H) | H | H | | C=O | CH$_3$ | OCH$_3$ | |
| Q$_{30}$(R$_7$=H, R$_8$=H) | H | H | | C=O | OCH$_3$ | OCH$_3$ | |
| Q$_{30}$(R$_7$=H, R$_8$=H) | H | H | | C=O | Cl | OCH$_3$ | |
| Q$_{30}$(R$_7$=H, R$_8$=H) | H | H | OH | H | CH$_3$ | CH$_3$ | |
| Q$_{30}$(R$_7$=H, R$_8$=H) | H | H | OH | H | CH$_3$ | OCH$_3$ | |
| Q$_{30}$(R$_7$=H, R$_8$=H) | H | H | OH | H | OCH$_3$ | OCH$_3$ | |
| Q$_{30}$(R$_7$=H, R$_8$=H) | H | H | OH | H | Cl | OCH$_3$ | |
| Q$_{30}$(R$_7$=H, R$_8$=H) | H | H | OCH$_3$ | OCH$_3$ | OCH$_3$ | OCH$_3$ | |
| Q$_{30}$(R$_7$=H, R$_8$=H) | H | H | —O(CH$_2$)$_3$O— | | OCH$_3$ | OCH$_3$ | |
| Q$_{31}$(R$_7$=H, R$_8$=H) | H | H | | C=O | CH$_3$ | CH$_3$ | |
| Q$_{31}$(R$_7$=H, R$_8$=H) | H | H | | C=O | CH$_3$ | OCH$_3$ | |
| Q$_{31}$(R$_7$=H, R$_8$=H) | H | H | | C=O | OCH$_3$ | OCH$_3$ | |
| Q$_{31}$(R$_7$=H, R$_8$=H) | H | H | | C=O | Cl | OCH | |
| Q$_{31}$(R$_7$=H, R$_8$=H) | H | H | OH | H | CH$_3$ | CH$_3$ | |
| Q$_{31}$(R$_7$=H, R$_8$=H) | H | H | OH | H | CH$_3$ | OCH$_3$ | |
| Q$_{31}$(R$_7$=H, R$_8$=H) | H | H | OH | H | OCH$_3$ | OCH$_3$ | |
| Q$_{31}$(R$_7$=H, R$_8$=H) | H | H | OH | H | Cl | OCH$_3$ | |
| Q$_{31}$(R$_7$=H, R$_8$=H) | H | H | OCH$_3$ | OCH$_3$ | OCH$_3$ | OCH$_3$ | |
| Q$_{31}$(R$_7$=H, R$_8$=H) | H | H | —O(CH$_2$)$_3$O— | | OCH$_3$ | OCH$_3$ | |
| Q$_{32}$(R$_{13}$=OCH$_3$, R$_{14}$=OCH$_3$) | H | H | | C=O | CH$_3$ | CH$_3$ | |
| Q$_{32}$(R$_{13}$=OCH$_3$, R$_{14}$=OCH$_3$) | H | H | | C=O | CH$_3$ | OCH$_3$ | |
| Q$_{32}$(R$_{13}$=OCH$_3$, R$_{14}$=OCH$_3$) | H | H | | C=O | OCH$_3$ | OCH$_3$ | |
| Q$_{32}$(R$_{13}$=OCH$_3$, R$_{14}$=OCH$_3$) | H | H | | C=O | Cl | OCH$_3$ | |
| Q$_{32}$(R$_{13}$=OCH$_3$, R$_{14}$=OCH$_3$) | H | H | OH | H | CH$_3$ | CH$_3$ | |
| Q$_{32}$(R$_{13}$=OCH$_3$, R$_{14}$=OCH$_3$) | H | H | OH | H | CH$_3$ | OCH$_3$ | |
| Q$_{32}$(R$_{13}$=OCH$_3$, R$_{14}$=OCH$_3$) | H | H | OH | H | OCH$_3$ | OCH$_3$ | |
| Q$_{32}$(R$_{13}$=OCH$_3$, R$_{14}$=OCH$_3$) | H | H | OH | H | Cl | OCH$_3$ | |
| Q$_{33}$(R$_7$=H) | H | H | | C=O | CH$_3$ | CH$_3$ | |
| Q$_{33}$(R$_7$=H) | H | H | | C=O | CH$_3$ | OCH$_3$ | |
| Q$_{33}$(R$_7$=H) | H | H | | C=O | OCH$_3$ | OCH$_3$ | |
| Q$_{33}$(R$_7$=H) | H | H | | C=O | Cl | OCH$_3$ | |
| Q$_{33}$(R$_7$=H) | H | H | OH | H | CH$_3$ | CH$_3$ | |
| Q$_{33}$(R$_7$=H) | H | H | OH | H | CH$_3$ | OCH$_3$ | |
| Q$_{33}$(R$_7$=H) | H | H | OH | H | OCH$_3$ | OCH$_3$ | |
| Q$_{33}$(R$_7$=H) | H | H | OH | H | Cl | OCH$_3$ | |
| Q$_{34}$ | H | H | | C=O | OCH$_3$ | OCH$_3$ | |
| Q$_{35}$ | H | H | | C=O | OCH$_3$ | OCH$_3$ | |
| Q$_{36}$(R$_{10}$=R$_{15}$=H; R$_7$=R$_8$=Br) | H | H | | C=O | OCH$_3$ | OCH$_3$ | 142.5-44 |
| Q$_{36}$(R$_{10}$=R$_{15}$=H; R$_7$=R$_8$=Br) | H | H | | C=O | CH$_3$ | OCH$_3$ | 187.5-89 |
| Q$_{37}$(R$_{10}$=R$_{16}$=R$_{15}$=H) | H | H | | C=O | OCH$_3$ | OCH$_3$ | |
| Q$_{38}$(R$_{10}$=R$_{15}$=R$_7$=R$_8$=H) | H | H | | C=O | OCH$_3$ | OCH$_3$ | 185.5-87 |
| Q$_{38}$(R$_{10}$=R$_{15}$=R$_7$=R$_8$=H) | H | H | | C=O | CH$_3$ | OCH$_3$ | 185-7 |
| Q$_{38}$(R$_{10}$=R$_{15}$=R$_7$=R$_8$=H) | H | 3-CH$_3$ | | C=O | OCH$_3$ | OCH$_3$ | 170-74.5 |
| Q$_1$(R$_7$=H, R$_8$=H, R$_9$=H) | H | 5-CH$_3$ | | C=O | OCH$_3$ | OCH$_3$ | |
| Q$_1$(R$_7$=H, R$_8$=H, R$_9$=H) | H | 5-CH$_2$CH$_3$ | | C=O | OCH$_3$ | OCH$_3$ | |
| Q$_1$(R$_7$=H, R$_8$=H, R$_9$=H) | H | 5-OCH$_3$ | | C=O | OCH$_3$ | OCH$_3$ | |
| Q$_1$(R$_7$=H, R$_8$=H, R$_9$=H) | H | 5-OCH$_2$CH$_3$ | | C=O | OCH$_3$ | OCH$_3$ | |
| Q$_1$(R$_7$=H, R$_8$=H, R$_9$=H) | H | 5-Cl | | C=O | OCH$_3$ | OCH$_3$ | |
| Q$_1$(R$_7$=H, R$_8$=H, R$_9$=H) | H | 5-Br | | C=O | OCH$_3$ | OCH$_3$ | |
| Q$_1$(R$_7$=H, R$_8$=H, R$_9$=H) | H | 5-F | | C=O | OCH$_3$ | OCH$_3$ | |
| Q$_1$(R$_7$=H, R$_8$=H, R$_9$=H) | H | 5-I | | C=O | OCH$_3$ | OCH$_3$ | |
| Q$_1$(R$_7$=H, R$_8$=H, R$_9$=H) | H | 5-NO$_2$ | | C=O | OCH$_3$ | OCH$_3$ | |
| Q$_1$(R$_7$=H, R$_8$=H, R$_9$=H) | H | 5-CH$_2$Cl | | C=O | OCH$_3$ | OCH$_3$ | |
| Q$_1$(R$_7$=H, R$_8$=H, R$_9$=H) | H | 5-N(CH$_3$)$_2$ | | C=O | OCH$_3$ | OCH$_3$ | |
| Q$_1$(R$_7$=H, R$_8$=H, R$_9$=H) | H | 5-CF$_3$ | | C=O | OCH$_3$ | OCH$_3$ | |
| Q$_1$(R$_7$=H, R$_8$=H, R$_9$=H) | H | 5-SCH$_3$ | | C=O | OCH$_3$ | OCH$_3$ | |
| Q$_1$(R$_7$=H, R$_8$=H, R$_9$=H) | H | 5-SCH$_2$CH$_2$CH$_3$ | | C=O | OCH$_3$ | OCH$_3$ | |
| Q$_1$(R$_7$=H, R$_8$=H, R$_9$=H) | H | 5-SO$_2$CH$_3$ | | C=O | OCH$_3$ | OCH$_3$ | |
| Q$_1$(R$_7$=H, R$_8$=H, R$_9$=H) | H | 5-SO$_2$CH$_2$CH$_3$ | | C=O | OCH$_3$ | OCH$_3$ | |
| Q$_1$(R$_7$=H, R$_8$=H, R$_9$=H) | H | 3-Cl | | C=O | OCH$_3$ | OCH$_3$ | |
| Q$_1$(R$_7$=H, R$_8$=H, R$_9$=H) | H | 6-Cl | | C=O | OCH$_3$ | OCH$_3$ | |
| Q$_1$(R$_7$=H, R$_8$=H, R$_9$=H) | H | 6-CH$_3$ | | C=O | OCH$_3$ | OCH$_3$ | |
| Q$_1$(R$_7$=H, R$_8$=H, R$_9$=H) | H | 5-SOCH$_3$ | | C=O | OCH$_3$ | OCH$_3$ | |
| Q$_1$(R$_7$=H, R$_8$=H, R$_9$=H) | H | 5-SOCH$_2$CH$_2$CH$_3$ | | C=O | OCH$_3$ | OCH$_3$ | |
| Q$_1$(R$_7$=H, R$_8$=H, R$_9$=H) | H | 3-SO$_2$N(CH$_3$)$_2$ | | C=O | OCH$_3$ | OCH$_3$ | |
| Q$_1$(R$_7$=H, R$_8$=H, R$_9$=H) | H | 3-SO$_2$N(CH$_3$)(OCH$_3$) | | C=O | OCH$_3$ | OCH$_3$ | |
| Q$_1$(R$_7$=H, R$_8$=H, R$_9$=H) | H | 3-SO$_2$N(CH$_3$)(CH$_2$CN) | | C=O | OCH$_3$ | OCH$_3$ | |
| Q$_1$(R$_7$=H, R$_8$=H, R$_9$=Cl) | H | 5-CO$_2$CH$_3$ | | C=O | OCH$_3$ | OCH$_3$ | |
| Q$_1$(R$_7$=H, R$_8$=H, R$_9$=Cl) | H | 5-CO$_2$CH$_2$CH$_3$ | | C=O | OCH$_3$ | OCH$_3$ | |
| Q$_1$(R$_7$=H, R$_8$=H, R$_9$=Cl) | H | 5-CO$_2$CH$_2$CH=CH$_2$ | | C=O | OCH$_3$ | OCH$_3$ | |
| Q$_1$(R$_7$=H, R$_8$=H, R$_9$=Cl) | H | 5-CO$_2$CH$_2$C≡CH | | C=O | OCH$_3$ | OCH$_3$ | |
| Q$_1$(R$_7$=H, R$_8$=H, R$_9$=Cl) | H | 5-CO$_2$CH$_2$CF$_3$ | | C=O | OCH$_3$ | OCH$_3$ | |
| Q$_1$(R$_7$=H, R$_8$=H, R$_9$=Cl) | H | 5-CO$_2$CH$_2$CN | | C=O | OCH$_3$ | OCH$_3$ | |

TABLE VII-continued

General Formula VII

| Q | R | $R_1$ | $R_2$ | $R_3$ | X | Y | m.p. (°C.) |
|---|---|---|---|---|---|---|---|
| $Q_1(R_7=H, R_8=H, R_9=Cl)$ | H | 5-CO$_2$—CH(CH$_2$CH$_2$CH$_2$CH$_2$) (cyclopentyl) | | C=O | OCH$_3$ | OCH$_3$ | |
| $Q_1(R_7=H, R_8=H, R_9=Cl)$ | H | 5-CO$_2$CH$_2$OCH$_3$ | | C=O | OCH$_3$ | OCH$_3$ | |
| $Q_1(R_7=H, R_8=H, R_9=Cl)$ | H | H | | C=O | CH$_2$CH$_3$ | OCH$_3$ | |
| $Q_1(R_7=H, R_8=H, R_9=Cl)$ | H | H | | C=O | OCH$_2$CH$_3$ | OCH$_3$ | |
| $Q_1(R_7=H, R_8=H, R_9=Cl)$ | H | H | | C=O | OCH$_2$F | OCH$_3$ | |
| $Q_1(R_7=H, R_8=H, R_9=Cl)$ | H | H | | C=O | OCH$_2$CF$_3$ | OCH$_3$ | |
| $Q_1(R_7=H, R_8=H, R_9=Cl)$ | H | H | | C=O | OCH$_2$CHF$_2$ | OCH$_3$ | |
| $Q_1(R_7=H, R_8=H, R_9=Cl)$ | H | H | | C=O | NH$_2$ | OCH$_3$ | |
| $Q_1(R_7=H, R_8=H, R_9=Cl)$ | H | H | | C=O | OCH$_2$CH$_2$F | OCH$_3$ | |
| $Q_1(R_7=H, R_8=H, R_9=Cl)$ | H | H | | C=O | CF$_3$ | OCH$_3$ | |
| $Q_1(R_7=H, R_8=H, R_9=Cl)$ | H | H | | C=O | F | OCH$_3$ | |
| $Q_1(R_7=H, R_8=H, R_9=Cl)$ | H | H | | C=O | OCH$_3$ | H | |
| $Q_1(R_7=H, R_8=H, R_9=Cl)$ | H | H | | C=O | Cl | OCH$_2$CH$_3$ | |
| $Q_1(R_7=H, R_8=H, R_9=Cl)$ | H | H | | C=O | OCH$_3$ | CH$_2$OCH$_3$ | |
| $Q_1(R_7=H, R_8=H, R_9=Cl)$ | H | H | | C=O | Cl | NHCH$_3$ | |
| $Q_1(R_7=H, R_8=H, R_9=Cl)$ | H | H | | C=O | OCH$_2$CH$_3$ | N(OCH$_3$)CH$_3$ | |
| $Q_1(R_7=H, R_8=H, R_9=Cl)$ | H | H | | C=O | OCH$_3$ | CH$_2$CH$_3$ | |
| $Q_1(R_7=H, R_8=H, R_9=Cl)$ | H | H | | C=O | CF$_3$ | CF$_3$ | |
| $Q_1(R_7=H, R_8=H, R_9=Cl)$ | H | H | | C=O | CH$_3$ | SCH$_3$ | |
| $Q_1(R_7=H, R_8=H, R_9=Cl)$ | H | H | | C=O | OCH$_3$ | OCH$_2$CH=CH$_2$ | |
| $Q_1(R_7=H, R_8=H, R_9=Cl)$ | H | H | | C=O | CH$_3$ | CH$_2$OCH$_2$CH$_3$ | |
| $Q_1(R_7=H, R_8=H, R_9=Cl)$ | H | H | | C=O | CH$_3$ | OCH$_2$CH$_2$OCH$_3$ | |
| $Q_1(R_7=H, R_8=H, R_9=Cl)$ | H | H | | C=O | CH$_3$ | CH$_2$SCH$_3$ | |
| $Q_1(R_7=H, R_8=H, R_9=Cl)$ | H | H | | C=O | CH$_3$ | CHO | |
| $Q_1(R_7=H, R_8=H, R_9=Cl)$ | H | H | | C=O | CH$_3$ | C(O)CH$_3$ | |
| $Q_1(R_7=H, R_8=H, R_9=Cl)$ | H | H | | C=O | OCH$_3$ | CH(OCH$_3$)$_2$ | |
| $Q_1(R_7=H, R_8=H, R_9=Cl)$ | H | H | | C=O | OCH$_3$ | CH(OCH$_2$CH$_3$)$_2$ | |
| $Q_1(R_7=H, R_8=H, R_9=Cl)$ | H | H | | C=O | OCH$_3$ | CH(SCH$_3$)$_2$ | |
| $Q_1(R_7=H, R_8=H, R_9=Cl)$ | H | H | | C=O | OCH$_3$ | C(CH$_3$)(OCH$_3$)$_2$ | |
| $Q_1(R_7=H, R_8=H, R_9=Cl)$ | H | H | | C=O | OCH$_3$ | 1,3-dioxolan-2-yl | |
| $Q_1(R_7=H, R_8=H, R_9=Cl)$ | H | H | | C=O | OCH$_3$ | 1,3-dioxan-2-yl | |
| $Q_1(R_7=H, R_8=H, R_9=Cl)$ | H | H | | C=O | OCH$_3$ | 1,3-dithiolan-2-yl | |
| $Q_1(R_7=H, R_8=H, R_9=Cl)$ | H | H | | C=O | OCH$_3$ | 1,3-oxathiolan-2-yl | |
| $Q_1(R_7=H, R_8=H, R_9=Cl)$ | H | H | | C=O | OCH$_3$ | 2-methyl-1,3-dithian-2-yl | |

TABLE VIII

General Formula VIII

| Q | R | $R_1$ | $R_2$ | $R_3$ | X | Y | m.p. (°C.) |
|---|---|---|---|---|---|---|---|
| $Q_1(R_7=H, R_8=H, R_9=H)$ | H | 4-Br | C=O | | CH$_3$ | CH$_3$ | |
| $Q_1(R_7=H, R_8=H, R_9=H)$ | H | 4-Br | C=O | | CH$_3$ | OCH$_3$ | 104(d) |
| $Q_1(R_7=H, R_8=H, R_9=H)$ | H | 4-Br | C=O | | OCH$_3$ | OCH$_3$ | 115(d) |
| $Q_1(R_7=H, R_8=H, R_9=H)$ | H | H | C=O | | Cl | OCH$_3$ | |
| $Q_1(R_7=H, R_8=H, R_9=H)$ | H | H | OH | H | CH$_3$ | CH$_3$ | |
| $Q_1(R_7=H, R_8=H, R_9=H)$ | H | H | OH | H | CH$_3$ | OCH$_3$ | |
| $Q_1(R_7=H, R_8=H, R_9=H)$ | H | H | OH | H | OCH$_3$ | OCH$_3$ | |
| $Q_1(R_7=H, R_8=H, R_9=H)$ | H | H | OH | H | Cl | OCH$_3$ | |
| $Q_1(R_7=H, R_8=H, R_9=H)$ | H | H | OCH$_3$ | H | OCH$_3$ | OCH$_3$ | |
| $Q_1(R_7=H, R_8=H, R_9=H)$ | H | H | OCH$_2$CH$_3$ | H | OCH$_3$ | OCH$_3$ | |
| $Q_2(R_7=H, R_8=H, R_9=H)$ | H | H | C=O | | CH$_3$ | CH$_3$ | |
| $Q_2(R_7=H, R_8=H, R_9=H)$ | H | H | C=O | | CH$_3$ | OCH$_3$ | |
| $Q_2(R_7=H, R_8=H, R_9=H)$ | H | H | C=O | | OCH$_3$ | OCH$_3$ | |
| $Q_2(R_7=H, R_8=H, R_9=H)$ | H | H | C=O | | Cl | OCH$_3$ | |
| $Q_2(R_7=H, R_8=H, R_9=H)$ | H | H | OH | H | CH$_3$ | CH$_3$ | |
| $Q_2(R_7=H, R_8=H, R_9=H)$ | H | H | OH | H | OCH$_3$ | OCH$_3$ | |
| $Q_2(R_7=H, R_8=H, R_9=H)$ | H | H | OH | H | Cl | OCH$_3$ | |
| $Q_2(R_7=H, R_8=H, R_9=H)$ | H | H | OCH$_3$ | H | CH$_3$ | CH$_3$ | |
| $Q_2(R_7=H, R_8=H, R_9=H)$ | H | H | OCH$_2$CH$_3$ | H | CH$_3$ | CH$_3$ | |
| $Q_3(R_7=H, R_8=H, R_9=H)$ | H | H | C=O | | CH$_3$ | CH$_3$ | |
| $Q_3(R_7=H, R_8=H, R_9=H)$ | H | H | C=O | | CH$_3$ | OCH$_3$ | |
| $Q_3(R_7=H, R_8=H, R_9=H)$ | H | H | C=O | | OCH$_3$ | OCH$_3$ | |
| $Q_3(R_7=H, R_8=H, R_9=H)$ | H | H | C=O | | Cl | OCH$_3$ | |
| $Q_3(R_7=H, R_8=H, R_9=H)$ | H | H | OH | H | CH$_3$ | CH$_3$ | |
| $Q_3(R_7=H, R_8=H, R_9=H)$ | H | H | OH | H | CH$_3$ | OCH$_3$ | |
| $Q_3(R_7=H, R_8=H, R_9=H)$ | H | H | OH | H | OCH$_3$ | OCH$_3$ | |
| $Q_3(R_7=H, R_8=H, R_9=H)$ | H | H | OH | H | Cl | OCH$_3$ | |
| $Q_3(R_7=H, R_8=H, R_9=Cl)$ | H | H | C=O | | OCH$_3$ | OCH$_3$ | |
| $Q_3(R_7=H, R_8=H, R_9=CH_3)$ | H | H | C=O | | OCH$_3$ | OCH$_3$ | |
| $Q_3(R_7=H, R_8=H, R_9=CH_3)$ | H | H | OH | H | OCH$_3$ | OCH$_3$ | |

TABLE VIII-continued

General Formula VIII

| Q | R | R$_1$ | R$_2$ | R$_3$ | X | Y | m.p. (°C.) |
|---|---|---|---|---|---|---|---|
| Q$_4$(R$_7$ = H, R$_8$ = H, R$_9$ = H) | H | H | C=O | | CH$_3$ | CH$_3$ | |
| Q$_4$(R$_7$ = H, R$_8$ = H, R$_9$ = H) | H | H | C=O | | CH$_3$ | OCH$_3$ | |
| Q$_4$(R$_7$ = H, R$_8$ = H, R$_9$ = H) | H | H | C=O | | OCH$_3$ | OCH$_3$ | |
| Q$_4$(R$_7$ = H, R$_8$ = H, R$_9$ = H) | H | H | C=O | | Cl | OCH$_3$ | |
| Q$_4$(R$_7$ = H, R$_8$ = H, R$_9$ = H) | H | H | OH | H | CH$_3$ | CH$_3$ | |
| Q$_4$(R$_7$ = H, R$_8$ = H, R$_9$ = H) | H | H | OH | H | CH$_3$ | OCH$_3$ | |
| Q$_4$(R$_7$ = H, R$_8$ = H, R$_9$ = H) | H | H | OH | H | CH$_3$ | OCH$_3$ | |
| Q$_4$(R$_7$ = H, R$_8$ = H, R$_9$ = H) | H | H | OH | H | Cl | OCH$_3$ | |
| Q$_5$(R$_7$ = H, R$_8$ = H, R$_9$ = H, R$_{10}$ = CH$_3$) | H | H | C=O | | CH$_3$ | CH$_3$ | |
| Q$_5$(R$_7$ = H, R$_8$ = H, R$_9$ = H, R$_{10}$ = CH$_3$) | H | H | C=O | | CH$_3$ | OCH$_3$ | |
| Q$_5$(R$_7$ = H, R$_8$ = H, R$_9$ = H, R$_{10}$ = CH$_3$) | H | H | C=O | | OCH$_3$ | OCH$_3$ | |
| Q$_5$(R$_7$ = H, R$_8$ = H, R$_9$ = H, R$_{10}$ = CH$_3$) | H | H | C=O | | Cl | OCH$_3$ | |
| Q$_5$(R$_7$ = H, R$_8$ = H, R$_9$ = H, R$_{10}$ = CH$_3$) | H | H | OH | H | CH$_3$ | CH$_3$ | |
| Q$_5$(R$_7$ = H, R$_8$ = H, R$_9$ = H, R$_{10}$ = CH$_3$) | H | H | OH | H | CH$_3$ | OCH$_3$ | |
| Q$_5$(R$_7$ = H, R$_8$ = H, R$_9$ = H, R$_{10}$ = CH$_3$) | H | H | OH | H | OCH$_3$ | OCH$_3$ | |
| Q$_5$(R$_7$ = H, R$_8$ = H, R$_9$ = H, R$_{10}$ = CH$_3$) | H | H | OH | H | Cl | OCH$_3$ | |
| Q$_5$(R$_7$ = H, R$_8$ = H, R$_9$ = H, R$_{10}$ = CH$_3$) | H | H | OCH$_3$ | H | Cl | OCH$_3$ | |
| Q$_5$(R$_7$ = H, R$_8$ = H, R$_9$ = H, R$_{10}$ = CH$_3$) | H | H | OCH$_2$CH$_3$ | H | OCH$_3$ | OCH$_3$ | |
| Q$_6$(R$_7$ = H, R$_8$ = H, R$_9$ = H, R$_{10}$ = CH$_3$) | H | H | C=O | | CH$_3$ | CH$_3$ | |
| Q$_6$(R$_7$ = H, R$_8$ = H, R$_9$ = H, R$_{10}$ = CH$_3$) | H | H | C=O | | CH$_3$ | OCH$_3$ | |
| Q$_6$(R$_7$ = H, R$_8$ = H, R$_9$ = H, R$_{10}$ = CH$_3$) | H | H | C=O | | OCH$_3$ | OCH$_3$ | |
| Q$_6$(R$_7$ = H, R$_8$ = H, R$_9$ = H, R$_{10}$ = CH$_3$) | H | H | C=O | | Cl | OCH$_3$ | |
| Q$_6$(R$_7$ = H, R$_8$ = H, R$_9$ = H, R$_{10}$ = CH$_3$) | H | H | OH | H | CH$_3$ | CH$_3$ | |
| Q$_6$(R$_7$ = H, R$_8$ = H, R$_9$ = H, R$_{10}$ = CH$_3$) | H | H | OH | H | CH$_3$ | OCH$_3$ | |
| Q$_6$(R$_7$ = H, R$_8$ = H, R$_9$ = H, R$_{10}$ = CH$_3$) | H | H | OH | H | OCH$_3$ | OCH$_3$ | |
| Q$_6$(R$_7$ = H, R$_8$ = H, R$_9$ = H, R$_{10}$ = CH$_3$) | H | H | OH | H | Cl | OCH$_3$ | |
| Q$_7$(R$_7$ = H, R$_8$ = H) | H | H | C=O | | CH$_3$ | CH$_3$ | |
| Q$_7$(R$_7$ = H, R$_8$ = H) | H | H | C=O | | CH$_3$ | OCH$_3$ | |
| Q$_7$(R$_7$ = H, R$_8$ = H) | H | H | C=O | | OCH$_3$ | OCH$_3$ | |
| Q$_7$(R$_7$ = H, R$_8$ = H) | H | H | C=O | | Cl | OCH$_3$ | |
| Q$_7$(R$_7$ = H, R$_8$ = H) | H | H | OH | H | CH$_3$ | CH$_3$ | |
| Q$_7$(R$_7$ = H, R$_8$ = H) | H | H | OH | H | CH$_3$ | OCH$_3$ | |
| Q$_7$(R$_7$ = H, R$_8$ = H) | H | H | OH | H | OCH$_3$ | OCH$_3$ | |
| Q$_7$(R$_7$ = H, R$_8$ = H) | H | H | OH | H | Cl | OCH$_3$ | |
| Q$_8$(R$_7$ = H, R$_8$ = H) | H | H | C=O | | OCH$_3$ | OCH$_3$ | |
| Q$_8$(R$_7$ = H, R$_8$ = H) | H | H | C=O | | Cl | OCH$_3$ | |
| Q$_8$(R$_7$ = H, R$_8$ = H) | H | H | OH | H | Cl | OCH$_3$ | |
| Q$_8$(R$_7$ = H, R$_8$ = H) | H | H | OH | H | OCH$_3$ | OCH$_3$ | |
| Q$_9$(R$_7$ = H, R$_8$ = H) | H | H | C=O | | CH$_3$ | CH$_3$ | |
| Q$_9$(R$_7$ = H, R$_8$ = H) | H | H | C=O | | CH$_3$ | OCH$_3$ | |
| Q$_9$(R$_7$ = H, R$_8$ = H) | H | H | C=O | | OCH$_3$ | OCH$_3$ | |
| Q$_9$(R$_7$ = H, R$_8$ = H) | H | H | C=O | | Cl | OCH$_3$ | |
| Q$_9$(R$_7$ = H, R$_8$ = H) | H | H | OH | H | CH$_3$ | CH$_3$ | |
| Q$_9$(R$_7$ = H, R$_8$ = H) | H | H | OH | H | CH$_3$ | OCH$_3$ | |
| Q$_9$(R$_7$ = H, R$_8$ = H) | H | H | OH | H | OCH$_3$ | OCH$_3$ | |
| Q$_9$(R$_7$ = H, R$_8$ = H) | H | H | OH | H | Cl | OCH$_3$ | |
| Q$_{10}$(R$_7$ = H, R$_8$ = H) | H | H | C=O | | CH$_3$ | OCH$_3$ | |
| Q$_{10}$(R$_7$ = H, R$_8$ = H) | H | H | C=O | | OCH$_3$ | OCH$_3$ | |
| Q$_{10}$(R$_7$ = H, R$_8$ = H) | H | H | C=O | | Cl | OCH$_3$ | |
| Q$_{10}$(R$_7$ = H, R$_8$ = H) | H | H | OH | H | CH$_3$ | CH$_3$ | |
| Q$_{10}$(R$_7$ = H, R$_8$ = H) | H | H | OH | H | OCH$_3$ | OCH$_3$ | |
| Q$_{10}$(R$_7$ = H, R$_8$ = H) | H | H | OH | H | Cl | OCH$_3$ | |
| Q$_{11}$(R$_7$ = H, R$_8$ = H) | H | H | C=O | | CH$_3$ | CH$_3$ | |
| Q$_{11}$(R$_7$ = H, R$_8$ = H) | H | H | C=O | | CH$_3$ | OCH$_3$ | |
| Q$_{11}$(R$_7$ = H, R$_8$ = H) | H | H | C=O | | OCH$_3$ | OCH$_3$ | |
| Q$_{11}$(R$_7$ = H, R$_8$ = H) | H | H | C=O | | Cl | OCH$_3$ | |
| Q$_{11}$(R$_7$ = H, R$_8$ = H) | H | H | OH | H | CH$_3$ | CH$_3$ | |
| Q$_{11}$(R$_7$ = H, R$_8$ = H) | H | H | OH | H | CH$_3$ | OCH$_3$ | |
| Q$_{11}$(R$_7$ = H, R$_8$ = H) | H | H | OH | H | OCH$_3$ | OCH$_3$ | |
| Q$_{11}$(R$_7$ = H, R$_8$ = H) | H | H | OH | H | Cl | OCH$_3$ | |
| Q$_{12}$(R$_7$ = H, R$_8$ = H) | H | H | C=O | | CH$_3$ | CH$_3$ | |
| Q$_{12}$(R$_7$ = H, R$_8$ = H) | H | H | C=O | | CH$_3$ | OCH$_3$ | |
| Q$_{12}$(R$_7$ = H, R$_8$ = H) | H | H | C=O | | OCH$_3$ | OCH$_3$ | |
| Q$_{12}$(R$_7$ = H, R$_8$ = H) | H | H | C=O | | Cl | OCH$_3$ | |
| Q$_{12}$(R$_7$ = H, R$_8$ = H) | H | H | OH | H | CH$_3$ | CH$_3$ | |
| Q$_{12}$(R$_7$ = H, R$_8$ = H) | H | H | OH | H | CH$_3$ | OCH$_3$ | |
| Q$_{12}$(R$_7$ = H, R$_8$ = H) | H | H | OH | H | OCH$_3$ | OCH$_3$ | |
| Q$_{12}$(R$_7$ = H, R$_8$ = H) | H | H | OH | H | Cl | OCH$_3$ | |
| Q$_{12}$(R$_7$ = H, R$_8$ = H) | H | H | OCH$_3$ | H | OCH$_3$ | OCH$_3$ | |
| Q$_{13}$(R$_7$ = H, R$_8$ = H) | H | H | C=O | | CH$_3$ | CH$_3$ | |
| Q$_{13}$(R$_7$ = H, R$_8$ = H) | H | H | C=O | | CH$_3$ | OCH$_3$ | |
| Q$_{13}$(R$_7$ = H, R$_8$ = H) | H | H | C=O | | OCH$_3$ | OCH$_3$ | |
| Q$_{13}$(R$_7$ = H, R$_8$ = H) | H | H | C=O | | Cl | OCH$_3$ | |
| Q$_{13}$(R$_7$ = H, R$_8$ = H) | H | H | OH | H | CH$_3$ | CH$_3$ | |
| Q$_{13}$(R$_7$ = H, R$_8$ = H) | H | H | OH | H | CH$_3$ | OCH$_3$ | |
| Q$_{13}$(R$_7$ = H, R$_8$ = H) | H | H | OH | H | OCH$_3$ | OCH$_3$ | |
| Q$_{13}$(R$_7$ = H, R$_8$ = H) | H | H | OH | H | Cl | OCH$_3$ | |
| Q$_{14}$(R$_7$ = H) | H | H | C=O | | CH$_3$ | CH$_3$ | |
| Q$_{14}$(R$_7$ = H) | H | H | C=O | | CH$_3$ | OCH$_3$ | |
| Q$_{14}$(R$_7$ = H) | H | H | C=O | | OCH$_3$ | OCH$_3$ | |

TABLE VIII-continued

| Q | General Formula VIII | | | | | | m.p. (°C.) |
|---|---|---|---|---|---|---|---|
| | R | R$_1$ | R$_2$ | R$_3$ | X | Y | |
| Q$_{14}$(R$_7$ = H) | H | H | C=O | | Cl | OCH$_3$ | |
| Q$_{14}$(R$_7$ = H) | H | H | OH | H | CH$_3$ | CH$_3$ | |
| Q$_{14}$(R$_7$ = H) | H | H | OH | H | CH$_3$ | OCH$_3$ | |
| Q$_{14}$(R$_7$ = H) | H | H | OH | H | OCH$_3$ | OCH$_3$ | |
| Q$_{14}$(R$_7$ = H) | H | H | OH | H | Cl | OCH$_3$ | |
| Q$_{15}$(R$_7$ = H) | H | H | C=O | | CH$_3$ | CH$_3$ | |
| Q$_{15}$(R$_7$ = H) | H | H | C=O | | CH$_3$ | OCH$_3$ | |
| Q$_{15}$(R$_7$ = H) | H | H | C=O | | OCH$_3$ | OCH$_3$ | |
| Q$_{15}$(R$_7$ = H) | H | H | C=O | | Cl | OCH$_3$ | |
| Q$_{15}$(R$_7$ = H) | H | H | OH | H | CH$_3$ | CH$_3$ | |
| Q$_{15}$(R$_7$ = H) | H | H | OH | H | CH$_3$ | OCH$_3$ | |
| Q$_{15}$(R$_7$ = H) | H | H | OH | H | OCH$_3$ | OCH$_3$ | |
| Q$_{15}$(R$_7$ = H) | H | H | OH | H | Cl | OCH$_3$ | |
| Q$_{16}$(R$_7$ = H) | H | H | C=O | | CH$_3$ | CH$_3$ | |
| Q$_{16}$(R$_7$ = H) | H | H | C=O | | CH$_3$ | OCH$_3$ | |
| Q$_{16}$(R$_7$ = H) | H | H | C=O | | OCH$_3$ | OCH$_3$ | |
| Q$_{16}$(R$_7$ = H) | H | H | C=O | | Cl | OCH$_3$ | |
| Q$_{16}$(R$_7$ = H) | H | H | OH | H | CH$_3$ | CH$_3$ | |
| Q$_{16}$(R$_7$ = H) | H | H | OH | H | CH$_3$ | OCH$_3$ | |
| Q$_{16}$(R$_7$ = H) | H | H | OH | H | OCH$_3$ | OCH$_3$ | |
| Q$_{16}$(R$_7$ = H) | H | H | OH | H | Cl | OCH$_3$ | |
| Q$_{17}$(R$_7$ = CH$_3$) | H | H | C=O | | CH$_3$ | CH$_3$ | |
| Q$_{17}$(R$_7$ = CH$_3$) | H | H | C=O | | CH$_3$ | OCH$_3$ | |
| Q$_{17}$(R$_7$ = CH$_3$) | H | H | C=O | | OCH$_3$ | OCH$_3$ | |
| Q$_{17}$(R$_7$ = CH$_3$) | H | H | C=O | | Cl | OCH$_3$ | |
| Q$_{17}$(R$_7$ = CH$_3$) | H | H | OH | H | CH$_3$ | CH$_3$ | |
| Q$_{17}$(R$_7$ = CH$_3$) | H | H | OH | H | CH$_3$ | OCH$_3$ | |
| Q$_{17}$(R$_7$ = CH$_3$) | H | H | OH | H | OCH$_3$ | OCH$_3$ | |
| Q$_{17}$(R$_7$ = CH$_3$) | H | H | OH | H | Cl | OCH$_3$ | |
| Q$_{18}$(R$_7$ = H) | H | H | C=O | | CH$_3$ | CH$_3$ | |
| Q$_{18}$(R$_7$ = H) | H | H | C=O | | CH$_3$ | OCH$_3$ | |
| Q$_{18}$(R$_7$ = H) | H | H | C=O | | OCH$_3$ | OCH$_3$ | |
| Q$_{18}$(R$_7$ = H) | H | H | C=O | | Cl | OCH$_3$ | |
| Q$_{18}$(R$_7$ = H) | H | H | OH | H | CH$_3$ | CH$_3$ | |
| Q$_{18}$(R$_7$ = H) | H | H | OH | H | CH$_3$ | OCH$_3$ | |
| Q$_{18}$(R$_7$ = H) | H | H | OH | H | OCH$_3$ | OCH$_3$ | |
| Q$_{18}$(R$_7$ = H) | H | H | OH | H | Cl | OCH$_3$ | |
| Q$_{19}$(R$_7$ = H, R$_8$ = H) | H | H | C=O | | CH$_3$ | CH$_3$ | |
| Q$_{19}$(R$_7$ = H, R$_8$ = H) | H | H | C=O | | CH$_3$ | OCH$_3$ | |
| Q$_{19}$(R$_7$ = H, R$_8$ = H) | H | H | C=O | | OCH$_3$ | OCH$_3$ | |
| Q$_{19}$(R$_7$ = H, R$_8$ = H) | H | H | C=O | | Cl | OCH$_3$ | |
| Q$_{19}$(R$_7$ = H, R$_8$ = H) | H | H | OH | H | CH$_3$ | CH$_3$ | |
| Q$_{19}$(R$_7$ = H, R$_8$ = H) | H | H | OH | H | CH$_3$ | OCH$_3$ | |
| Q$_{19}$(R$_7$ = H, R$_8$ = H) | H | H | OH | H | OCH$_3$ | OCH$_3$ | |
| Q$_{19}$(R$_7$ = H, R$_8$ = H) | H | H | OH | H | Cl | OCH$_3$ | |
| Q$_{20}$(R$_7$ = H, R$_8$ = H) | H | H | C=O | | CH$_3$ | CH$_3$ | |
| Q$_{20}$(R$_7$ = H, R$_8$ = H) | H | H | C=O | | CH$_3$ | OCH$_3$ | |
| Q$_{20}$(R$_7$ = H, R$_8$ = H) | H | H | C=O | | OCH$_3$ | OCH$_3$ | |
| Q$_{20}$(R$_7$ = H, R$_8$ = H) | H | H | C=O | | Cl | OCH$_3$ | |
| Q$_{20}$(R$_7$ = H, R$_8$ = H) | H | H | OH | H | CH$_3$ | CH$_3$ | |
| Q$_{20}$(R$_7$ = H, R$_8$ = H) | H | H | OH | H | CH$_3$ | OCH$_3$ | |
| Q$_{20}$(R$_7$ = H, R$_8$ = H) | H | H | OH | H | OCH$_3$ | OCH$_3$ | |
| Q$_{20}$(R$_7$ = H, R$_8$ = H) | H | H | OH | H | Cl | OCH$_3$ | |
| Q$_{21}$(R$_7$ = H, R$_8$ = H, R$_9$ = CH$_3$) | H | H | C=O | | CH$_3$ | CH$_3$ | |
| Q$_{21}$(R$_7$ = H, R$_8$ = H, R$_9$ = CH$_3$) | H | H | C=O | | CH$_3$ | OCH$_3$ | |
| Q$_{21}$(R$_7$ = H, R$_8$ = H, R$_9$ = CH$_3$) | H | H | C=O | | OCH$_3$ | OCH$_3$ | |
| Q$_{21}$(R$_7$ = H, R$_8$ = H, R$_9$ = CH$_3$) | H | H | C=O | | Cl | OCH$_3$ | |
| Q$_{21}$(R$_7$ = H, R$_8$ = H, R$_9$ = CH$_3$) | H | H | OH | H | CH$_3$ | CH$_3$ | |
| Q$_{21}$(R$_7$ = H, R$_8$ = H, R$_9$ = CH$_3$) | H | H | OH | H | CH$_3$ | OCH$_3$ | |
| Q$_{21}$(R$_7$ = H, R$_8$ = H, R$_9$ = CH$_3$) | H | H | OH | H | OCH$_3$ | OCH$_3$ | |
| Q$_{21}$(R$_7$ = H, R$_8$ = H, R$_9$ = CH$_3$) | H | H | OH | H | Cl | OCH$_3$ | |
| Q$_{22}$(R$_7$ = H) | H | H | C=O | | CH$_3$ | CH$_3$ | |
| Q$_{22}$(R$_7$ = H) | H | H | C=O | | CH$_3$ | OCH$_3$ | |
| Q$_{22}$(R$_7$ = H) | H | H | C=O | | OCH$_3$ | OCH$_3$ | |
| Q$_{22}$(R$_7$ = H) | H | H | C=O | | Cl | OCH$_3$ | |
| Q$_{22}$(R$_7$ = H) | H | H | OH | H | CH$_3$ | CH$_3$ | |
| Q$_{22}$(R$_7$ = H) | H | H | OH | H | CH$_3$ | OCH$_3$ | |
| Q$_{22}$(R$_7$ = H) | H | H | OH | H | OCH$_3$ | OCH$_3$ | |
| Q$_{22}$(R$_7$ = H) | H | H | OH | H | Cl | OCH$_3$ | |
| Q$_{23}$(R$_7$ = H) | H | H | C=O | | CH$_3$ | CH$_3$ | |
| Q$_{23}$(R$_7$ = H) | H | H | C=O | | CH$_3$ | OCH$_3$ | |
| Q$_{23}$(R$_7$ = H) | H | H | C=O | | OCH$_3$ | OCH$_3$ | |
| Q$_{23}$(R$_7$ = H) | H | H | C=O | | Cl | OCH$_3$ | |
| Q$_{24}$(R$_7$ = H, R$_8$ = H) | H | H | C=O | | CH$_3$ | CH$_3$ | |
| Q$_{24}$(R$_7$ = H, R$_8$ = H) | H | H | C=O | | CH$_3$ | OCH$_3$ | |
| Q$_{24}$(R$_7$ = H, R$_8$ = H) | H | H | C=O | | OCH$_3$ | OCH$_3$ | |
| Q$_{24}$(R$_7$ = H, R$_8$ = H) | H | H | C=O | | Cl | OCH$_3$ | |
| Q$_{24}$(R$_7$ = H, R$_8$ = H) | H | H | OH | H | CH$_3$ | CH$_3$ | |
| Q$_{24}$(R$_7$ = H, R$_8$ = H) | H | H | OH | H | CH$_3$ | OCH$_3$ | |
| Q$_{24}$(R$_7$ = H, R$_8$ = H) | H | H | OH | H | OCH$_3$ | OCH$_3$ | |

TABLE VIII-continued

General Formula VIII

| Q | R | R$_1$ | R$_2$ | R$_3$ | X | Y | m.p. (°C.) |
|---|---|---|---|---|---|---|---|
| Q$_{24}$(R$_7$ = H, R$_8$ = H) | H | H | OH | H | Cl | OCH$_3$ | |
| Q$_{25}$(R$_7$ = H, R$_8$ = H) | H | H | C=O | | CH$_3$ | CH$_3$ | |
| Q$_{25}$(R$_7$ = H, R$_8$ = H) | H | H | C=O | | CH$_3$ | OCH$_3$ | |
| Q$_{25}$(R$_7$ = H, R$_8$ = H) | H | H | C=O | | OCH$_3$ | OCH$_3$ | |
| Q$_{25}$(R$_7$ = H, R$_8$ = H) | H | H | C=O | | Cl | OCH$_3$ | |
| Q$_{25}$(R$_7$ = H, R$_8$ = H) | H | H | OH | H | CH$_3$ | CH$_3$ | |
| Q$_{25}$(R$_7$ = H, R$_8$ = H) | H | H | OH | H | CH$_3$ | OCH$_3$ | |
| Q$_{25}$(R$_7$ = H, R$_8$ = H) | H | H | OH | H | OCH$_3$ | OCH$_3$ | |
| Q$_{25}$(R$_7$ = H, R$_8$ = H) | H | H | OH | H | Cl | OCH$_3$ | |
| Q$_{26}$(R$_7$ = H, R$_8$ = H) | H | H | C=O | | CH$_3$ | CH$_3$ | |
| Q$_{26}$(R$_7$ = H, R$_8$ = H) | H | H | C=O | | CH$_3$ | OCH$_3$ | |
| Q$_{26}$(R$_7$ = H, R$_8$ = H) | H | H | C=O | | OCH$_3$ | OCH$_3$ | |
| Q$_{26}$(R$_7$ = H, R$_3$ = H) | H | H | C=O | | Cl | OCH$_3$ | |
| Q$_{26}$(R$_7$ = H, R$_8$ = H) | H | H | OH | H | CH$_3$ | CH$_3$ | |
| Q$_{26}$(R$_7$ = H, R$_8$ = H) | H | H | OH | H | CH$_3$ | OCH$_3$ | |
| Q$_{26}$(R$_7$ = H, R$_8$ = H) | H | H | OH | H | OCH$_3$ | OCH$_3$ | |
| Q$_{26}$(R$_7$ = H, R$_8$ = H) | H | H | OH | H | Cl | OCH$_3$ | |
| Q$_{27}$(R$_7$ = H, R$_{11}$ = H, R$_{12}$ = H) | H | H | C=O | | CH$_3$ | CH$_3$ | |
| Q$_{27}$(R$_7$ = H, R$_{11}$ = H, R$_{12}$ = H) | H | H | C=O | | CH$_3$ | OCH$_3$ | |
| Q$_{27}$(R$_7$ = H, R$_{11}$ = H, R$_{12}$ = H) | H | H | C=O | | OCH$_3$ | OCH$_3$ | |
| Q$_{27}$(R$_7$ = H, R$_{11}$ = H, R$_{12}$ = H) | H | H | C=O | | Cl | OCH$_3$ | |
| Q$_{27}$(R$_7$ = H, R$_{11}$ = H, R$_{12}$ = H) | H | H | OH | H | CH$_3$ | CH$_3$ | |
| Q$_{27}$(R$_7$ = H, R$_{11}$ = H, R$_{12}$ = H) | H | H | OH | H | CH$_3$ | OCH$_3$ | |
| Q$_{27}$(R$_7$ = H, R$_{11}$ = H, R$_{12}$ = H) | H | H | OH | H | OCH$_3$ | OCH$_3$ | |
| Q$_{27}$(R$_7$ = H, R$_{11}$ = H, R$_{12}$ = H) | H | H | OH | H | Cl | OCH$_3$ | |
| Q$_{28}$(R$_{11}$ = H, R$_{12}$ = H) | H | H | C=O | | CH$_3$ | CH$_3$ | |
| Q$_{28}$(R$_{11}$ = H, R$_{12}$ = H) | H | H | C=O | | CH$_3$ | OCH$_3$ | |
| Q$_{28}$(R$_{11}$ = H, R$_{12}$ = H) | H | H | C=O | | OCH$_3$ | OCH$_3$ | |
| Q$_{28}$(R$_{11}$ = H, R$_{12}$ = H) | H | H | C=O | | Cl | OCH$_3$ | |
| Q$_{28}$(R$_{11}$ = H, R$_{12}$ = H) | H | H | OH | H | CH$_3$ | CH$_3$ | |
| Q$_{28}$(R$_{11}$ = H, R$_{12}$ = H) | H | H | OH | H | CH$_3$ | OCH$_3$ | |
| Q$_{28}$(R$_{11}$ = H, R$_{12}$ = H) | H | H | OH | H | OCH$_3$ | OCH$_3$ | |
| Q$_{28}$(R$_{11}$ = H, R$_{12}$ = H) | H | H | OH | H | Cl | OCH$_3$ | |
| Q$_{29}$(R$_{11}$ = H, R$_{12}$ = H) | H | H | C=O | | CH$_3$ | CH$_3$ | |
| Q$_{29}$(R$_{11}$ = H, R$_{12}$ = H) | H | H | C=O | | CH$_3$ | OCH$_3$ | |
| Q$_{29}$(R$_{11}$ = H, R$_{12}$ = H) | H | H | C=O | | OCH$_3$ | OCH$_3$ | |
| Q$_{29}$(R$_{11}$ = H, R$_{12}$ = H) | H | H | C=O | | Cl | OCH$_3$ | |
| Q$_{29}$(R$_{11}$ = H, R$_{12}$ = H) | H | H | OH | H | CH$_3$ | CH$_3$ | |
| Q$_{29}$(R$_{11}$ = H, R$_{12}$ = H) | H | H | OH | H | CH$_3$ | OCH$_3$ | |
| Q$_{29}$(R$_{11}$ = H, R$_{12}$ = H) | H | H | OH | H | OCH$_3$ | OCH$_3$ | |
| Q$_{29}$(R$_{11}$ = H, R$_{12}$ = H) | H | H | OH | H | Cl | OCH$_3$ | |
| Q$_{30}$(R$_7$ = H, R$_8$ = H) | H | H | C=O | | CH$_3$ | CH$_3$ | |
| Q$_{30}$(R$_7$ = H, R$_8$ = H) | H | H | C=O | | CH$_3$ | OCH$_3$ | |
| Q$_{30}$(R$_7$ = H, R$_8$ = H) | H | H | C=O | | OCH$_3$ | OCH$_3$ | |
| Q$_{30}$(R$_7$ = H, R$_8$ = H) | H | H | C=O | | Cl | OCH$_3$ | |
| Q$_{30}$(R$_7$ = H, R$_8$ = H) | H | H | OH | H | CH$_3$ | CH$_3$ | |
| Q$_{30}$(R$_7$ = H, R$_8$ = H) | H | H | OH | H | CH$_3$ | OCH$_3$ | |
| Q$_{30}$(R$_7$ = H, R$_8$ = H) | H | H | OH | H | OCH$_3$ | OCH$_3$ | |
| Q$_{30}$(R$_7$ = H, R$_8$ = H) | H | H | OH | H | Cl | OCH$_3$ | |
| Q$_{31}$(R$_7$ = H, R$_8$ = H) | H | H | C=O | | CH$_3$ | CH$_3$ | |
| Q$_{31}$(R$_7$ = H, R$_8$ = H) | H | H | C=O | | CH$_3$ | OCH$_3$ | |
| Q$_{31}$(R$_7$ = H, R$_8$ = H) | H | H | C=O | | OCH$_3$ | OCH$_3$ | |
| Q$_{31}$(R$_7$ = H, R$_8$ = H) | H | H | C=O | | Cl | OCH$_3$ | |
| Q$_{31}$(R$_7$ = H, R$_8$ = H) | H | H | OH | H | CH$_3$ | CH$_3$ | |
| Q$_{31}$(R$_7$ = H, R$_8$ = H) | H | H | OH | H | CH$_3$ | OCH$_3$ | |
| Q$_{31}$(R$_7$ = H, R$_8$ = H) | H | H | OH | H | OCH$_3$ | OCH$_3$ | |
| Q$_{31}$(R$_7$ = H, R$_8$ = H) | H | H | OH | H | Cl | OCH$_3$ | |
| Q$_{32}$(R$_{13}$ = OCH$_3$, R$_{14}$ = OCH$_3$) | H | H | C=O | | CH$_3$ | CH$_3$ | |
| Q$_{32}$(R$_{13}$ = OCH$_3$, R$_{14}$ = OCH$_3$) | H | H | C=O | | CH$_3$ | OCH$_3$ | |
| Q$_{32}$(R$_{13}$ = OCH$_3$, R$_{14}$ = OCH$_3$) | H | H | C=O | | OCH$_3$ | OCH$_3$ | |
| Q$_{32}$(R$_{13}$ = OCH$_3$, R$_{14}$ = OCH$_3$) | H | H | C=O | | Cl | OCH$_3$ | |
| Q$_{32}$(R$_{13}$ = OCH$_3$, R$_{14}$ = OCH$_3$) | H | H | OH | H | CH$_3$ | CH$_3$ | |
| Q$_{32}$(R$_{13}$ = OCH$_3$, R$_{14}$ = OCH$_3$) | H | H | OH | H | CH$_3$ | OCH$_3$ | |
| Q$_{32}$(R$_{13}$ = OCH$_3$, R$_{14}$ = OCH$_3$) | H | H | OH | H | OCH$_3$ | OCH$_3$ | |
| Q$_{32}$(R$_{13}$ = OCH$_3$, R$_{14}$ = OCH$_3$) | H | H | OH | H | Cl | OCH$_3$ | |
| Q$_{33}$(R$_7$ = H) | H | H | C=O | | CH$_3$ | CH$_3$ | |
| Q$_{33}$(R$_7$ = H) | H | H | C=O | | CH$_3$ | OCH$_3$ | |
| Q$_{33}$(R$_7$ = H) | H | H | C=O | | OCH$_3$ | OCH$_3$ | |
| Q$_{33}$(R$_7$ = H) | H | H | C=O | | Cl | OCH$_3$ | |
| Q$_{33}$(R$_7$ = H) | H | H | OH | H | CH$_3$ | CH$_3$ | |
| Q$_{33}$(R$_7$ = H) | H | H | OH | H | CH$_3$ | OCH$_3$ | |
| Q$_{33}$(R$_7$ = H) | H | H | OH | H | OCH$_3$ | OCH$_3$ | |
| Q$_{33}$(R$_7$ = H) | H | H | OH | H | Cl | OCH$_3$ | |

TABLE IX

General Formula IX

| Q | R | R₁ | R₂ | R₃ | X | Y | m.p. (°C.) |
|---|---|---|---|---|---|---|---|
| $Q_1(R_7 = H, R_8 = H, R_9 = H)$ | H | H | C=O |  | $CH_3$ | $CH_3$ |  |
| $Q_1(R_7 = H, R_8 = H, R_9 = H)$ | H | H | C=O |  | $CH_3$ | $OCH_3$ |  |
| $Q_1(R_7 = H, R_8 = H, R_9 = H)$ | H | H | C=O |  | $OCH_3$ | $OCH_3$ |  |
| $Q_1(R_7 = H, R_8 = H, R_9 = H)$ | H | H | C=O |  | Cl | $OCH_3$ |  |
| $Q_1(R_7 = H, R_8 = H, R_9 = H)$ | H | H | OH | H | $CH_3$ | $CH_3$ |  |
| $Q_1(R_7 = H, R_8 = H, R_9 = H)$ | H | H | OH | H | $CH_3$ | $OCH_3$ |  |
| $Q_1(R_7 = H, R_8 = H, R_9 = H)$ | H | H | OH | H | $OCH_3$ | $OCH_3$ |  |
| $Q_1(R_7 = H, R_8 = H, R_9 = H)$ | H | H | OH | H | Cl | $OCH_3$ |  |
| $Q_1(R_7 = H, R_8 = H, R_9 = H)$ | H | H | $OCH_3$ | H | $OCH_3$ | $OCH_3$ |  |
| $Q_1(R_7 = H, R_8 = H, R_9 = H)$ | H | H | $OCH_2CH_3$ | H | $OCH_3$ | $OCH_3$ |  |
| $Q_2(R_7 = H, R_8 = H, R_9 = H)$ | H | H | C=O |  | $CH_3$ | $CH_3$ |  |
| $Q_2(R_7 = H, R_8 = H, R_9 = H)$ | H | H | C=O |  | $CH_3$ | $OCH_3$ |  |
| $Q_2(R_7 = H, R_8 = H, R_9 = H)$ | H | H | C=O |  | $OCH_3$ | $OCH_3$ |  |
| $Q_2(R_7 = H, R_8 = H, R_9 = H)$ | H | H | C=O |  | Cl | $OCH_3$ |  |
| $Q_2(R_7 = H, R_8 = H, R_9 = H)$ | H | H | OH | H | $CH_3$ | $CH_3$ |  |
| $Q_2(R_7 = H, R_8 = H, R_9 = H)$ | H | H | OH | H | $CH_3$ | $OCH_3$ |  |
| $Q_2(R_7 = H, R_8 = H, R_9 = H)$ | H | H | OH | H | $OCH_3$ | $OCH_3$ |  |
| $Q_2(R_7 = H, R_8 = H, R_9 = H)$ | H | H | OH | H | Cl | $OCH_3$ |  |
| $Q_2(R_7 = H, R_8 = H, R_9 = H)$ | H | H | $OCH_3$ | H | $CH_3$ | $OCH_3$ |  |
| $Q_2(R_7 = H, R_8 = H, R_9 = H)$ | H | H | $OCH_2CH_3$ | H | $CH_3$ | $CH_3$ |  |
| $Q_3(R_7 = H, R_8 = H, R_9 = H)$ | H | H | C=O |  | $CH_3$ | $CH_3$ |  |
| $Q_3(R_7 = H, R_8 = H, R_9 = H)$ | H | H | C=O |  | $CH_3$ | $OCH_3$ |  |
| $Q_3(R_7 = H, R_8 = H, R_9 = H)$ | H | H | C=O |  | $OCH_3$ | $OCH_3$ |  |
| $Q_3(R_7 = H, R_8 = H, R_9 = H)$ | H | H | C=O |  | Cl | $OCH_3$ |  |
| $Q_3(R_7 = H, R_8 = H, R_9 = H)$ | H | H | OH | H | $CH_3$ | $CH_3$ |  |
| $Q_3(R_7 = H, R_8 = H, R_9 = H)$ | H | H | OH | H | $CH_3$ | $OCH_3$ |  |
| $Q_3(R_7 = H, R_8 = H, R_9 = H)$ | H | H | OH | H | $OCH_3$ | $OCH_3$ |  |
| $Q_3(R_7 = H, R_8 = H, R_9 = H)$ | H | H | OH | H | Cl | $OCH_3$ |  |
| $Q_3(R_7 = H, R_8 = H, R_9 = Cl)$ | H | H | C=O |  | $OCH_3$ | $OCH_3$ |  |
| $Q_3(R_7 = H, R_8 = H, R_9 = CH_3)$ | H | H | C=O |  | $OCH_3$ | $OCH_3$ |  |
| $Q_3(R_7 = H, R_8 = H, R_9 = CH_3)$ | H | H | OH | H | $OCH_3$ | $OCH_3$ |  |
| $Q_4(R_7 = H, R_8 = H, R_9 = H)$ | H | H | C=O |  | $CH_3$ | $CH_3$ |  |
| $Q_4(R_7 = H, R_8 = H, R_9 = H)$ | H | H | C=O |  | $CH_3$ | $OCH_3$ |  |
| $Q_4(R_7 = H, R_8 = H, R_9 = H)$ | H | H | C=O |  | $OCH_3$ | $OCH_3$ |  |
| $Q_4(R_7 = H, R_8 = H, R_9 = H)$ | H | H | C=O |  | Cl | $OCH_3$ |  |
| $Q_4(R_7 = H, R_8 = H, R_9 = H)$ | H | H | OH | H | $CH_3$ | $CH_3$ |  |
| $Q_4(R_7 = H, R_8 = H, R_9 = H)$ | H | H | OH | H | $CH_3$ | $OCH_3$ |  |
| $Q_4(R_7 = H, R_8 = H, R_9 = H)$ | H | H | OH | H | $OCH_3$ | $OCH_3$ |  |
| $Q_4(R_7 = H, R_8 = H, R_9 = H)$ | H | H | OH | H | Cl | $OCH_3$ |  |
| $Q_5(R_7 = H, R_8 = H, R_9 = H, R_{10} = CH_3)$ | H | H | C=O |  | $CH_3$ | $CH_3$ |  |
| $Q_5(R_7 = H, R_8 = H, R_9 = H, R_{10} = CH_3)$ | H | H | C=O |  | $CH_3$ | $OCH_3$ |  |
| $Q_5(R_7 = H, R_8 = H, R_9 = H, R_{10} = CH_3)$ | H | H | C=O |  | $OCH_3$ | $OCH_3$ |  |
| $Q_5(R_7 = H, R_8 = H, R_9 = H, R_{10} = CH_3)$ | H | H | C=O |  | Cl | $OCH_3$ |  |
| $Q_5(R_7 = H, R_8 = H, R_9 = H, R_{10} = CH_3)$ | H | H | OH | H | $CH_3$ | $CH_3$ |  |
| $Q_5(R_7 = H, R_8 = H, R_9 = H, R_{10} = CH_3)$ | H | H | OH | H | $CH_3$ | $OCH_3$ |  |
| $Q_5(R_7 = H, R_8 = H, R_9 = H, R_{10} = CH_3)$ | H | H | OH | H | $OCH_3$ | $OCH_3$ |  |
| $Q_5(R_7 = H, R_8 = H, R_9 = H, R_{10} = CH_3)$ | H | H | OH | H | Cl | $OCH_3$ |  |
| $Q_5(R_7 = H, R_8 = H, R_9 = H, R_{10} = CH_3)$ | H | H | $OCH_3$ | H | Cl | $OCH_3$ |  |
| $Q_5(R_7 = H, R_8 = H, R_9 = H, R_{10} = CH_3)$ | H | H | $OCH_2CH_3$ | H | $OCH_3$ | $OCH_3$ |  |
| $Q_6(R_7 = H, R_8 = H, R_9 = H, R_{10} = CH_3)$ | H | H | C=O |  | $CH_3$ | $CH_3$ |  |
| $Q_6(R_7 = H, R_8 = H, R_9 = H, R_{10} = CH_3)$ | H | H | C=O |  | $CH_3$ | $OCH_3$ |  |
| $Q_6(R_7 = H, R_8 = H, R_9 = H, R_{10} = CH_3)$ | H | H | C=O |  | $OCH_3$ | $OCH_3$ |  |
| $Q_6(R_7 = H, R_8 = H, R_9 = H, R_{10} = CH_3)$ | H | H | C=O |  | Cl | $OCH_3$ |  |
| $Q_6(R_7 = H, R_8 = H, R_9 = H, R_{10} = CH_3)$ | H | H | OH | H | $CH_3$ | $CH_3$ |  |
| $Q_6(R_7 = H, R_8 = H, R_9 = H, R_{10} = CH_3)$ | H | H | OH | H | $CH_3$ | $OCH_3$ |  |
| $Q_6(R_7 = H, R_8 = H, R_9 = H, R_{10} = CH_3)$ | H | H | OH | H | $OCH_3$ | $OCH_3$ |  |
| $Q_6(R_7 = H, R_8 = H, R_9 = H, R_{10} = CH_3)$ | H | H | OH | H | Cl | $OCH_3$ |  |
| $Q_7(R_7 = H, R_8 = H)$ | H | H | C=O |  | $CH_3$ | $CH_3$ |  |
| $Q_7(R_7 = H, R_8 = H)$ | H | H | C=O |  | $CH_3$ | $OCH_3$ |  |
| $Q_7(R_7 = H, R_8 = H)$ | H | H | C=O |  | $OCH_3$ | $OCH_3$ |  |
| $Q_7(R_7 = H, R_8 = H)$ | H | H | C=O |  | Cl | $OCH_3$ |  |
| $Q_7(R_7 = H, R_8 = H)$ | H | H | OH | H | $CH_3$ | $CH_3$ |  |
| $Q_7(R_7 = H, R_8 = H)$ | H | H | OH | H | $CH_3$ | $OCH_3$ |  |
| $Q_7(R_7 = H, R_8 = H)$ | H | H | OH | H | $OCH_3$ | $OCH_3$ |  |
| $Q_7(R_7 = H, R_8 = H)$ | H | H | OH | H | Cl | $OCH_3$ |  |
| $Q_8(R_7 = H, R_8 = H)$ | H | H | C=O |  | $OCH_3$ | $OCH_3$ |  |
| $Q_8(R_7 = H, R_8 = H)$ | H | H | C=O |  | Cl | $OCH_3$ |  |
| $Q_8(R_7 = H, R_8 = H)$ | H | H | OH | H | Cl | $OCH_3$ |  |
| $Q_8(R_7 = H, R_8 = H)$ | H | H | OH | H | $OCH_3$ | $OCH_3$ |  |
| $Q_9(R_7 = H, R_8 = H)$ | H | H | C=O |  | $CH_3$ | $CH_3$ |  |
| $Q_9(R_7 = H, R_8 = H)$ | H | H | C=O |  | $CH_3$ | $OCH_3$ |  |
| $Q_9(R_7 = H, R_8 = H)$ | H | H | C=O |  | $OCH_3$ | $OCH_3$ |  |
| $Q_9(R_7 = H, R_8 = H)$ | H | H | C=O |  | Cl | $OCH_3$ |  |
| $Q_9(R_7 = H, R_8 = H)$ | H | H | OH | H | $CH_3$ | $CH_3$ |  |
| $Q_9(R_7 = H, R_8 = H)$ | H | H | OH | H | $CH_3$ | $OCH_3$ |  |
| $Q_9(R_7 = H, R_8 = H)$ | H | H | OH | H | $OCH_3$ | $OCH_3$ |  |
| $Q_9(R_7 = H, R_8 = H)$ | H | H | OH | H | Cl | $OCH_3$ |  |
| $Q_{10}(R_7 = H, R_8 = H)$ | H | H | C=O |  | $CH_3$ | $OCH_3$ |  |
| $Q_{10}(R_7 = H, R_8 = H)$ | H | H | C=O |  | $OCH_3$ | $OCH_3$ |  |
| $Q_{10}(R_7 = H, R_8 = H)$ | H | H | C=O |  | Cl | $OCH_3$ |  |

TABLE IX-continued

General Formula IX

| Q | R | $R_1$ | $R_2$ | | $R_3$ | X | Y | m.p. (°C.) |
|---|---|---|---|---|---|---|---|---|
| $Q_{10}(R_7 = H, R_8 = H)$ | H | H | OH | | H | $CH_3$ | $CH_3$ | |
| $Q_{10}(R_7 = H, R_8 = H)$ | H | H | OH | | H | $OCH_3$ | $OCH_3$ | |
| $Q_{10}(R_7 = H, R_8 = H)$ | H | H | OH | | H | Cl | $OCH_3$ | |
| $Q_{11}(R_7 = H, R_8 = H)$ | H | H | | C=O | | $CH_3$ | $CH_3$ | |
| $Q_{11}(R_7 = H, R_8 = H)$ | H | H | | C=O | | $CH_3$ | $OCH_3$ | |
| $Q_{11}(R_7 = H, R_8 = H)$ | H | H | | C=O | | $OCH_3$ | $OCH_3$ | |
| $Q_{11}(R_7 = H, R_8 = H)$ | H | H | | C=O | | Cl | $OCH_3$ | |
| $Q_{11}(R_7 = H, R_8 = H)$ | H | H | OH | | H | $CH_3$ | $CH_3$ | |
| $Q_{11}(R_7 = H, R_8 = H)$ | H | H | OH | | H | $CH_3$ | $OCH_3$ | |
| $Q_{11}(R_7 = H, R_8 = H)$ | H | H | OH | | H | $OCH_3$ | $OCH_3$ | |
| $Q_{11}(R_7 = H, R_8 = H)$ | H | H | OH | | H | Cl | $OCH_3$ | |
| $Q_{12}(R_7 = H, R_8 = H)$ | H | H | | C=O | | $CH_3$ | $CH_3$ | |
| $Q_{12}(R_7 = H, R_8 = H)$ | H | H | | C=O | | $CH_3$ | $OCH_3$ | |
| $Q_{12}(R_7 = H, R_8 = H)$ | H | H | | C=O | | $OCH_3$ | $OCH_3$ | |
| $Q_{12}(R_7 = H, R_8 = H)$ | H | H | | C=O | | Cl | $OCH_3$ | |
| $Q_{12}(R_7 = H, R_8 = H)$ | H | H | OH | | H | $CH_3$ | $CH_3$ | |
| $Q_{12}(R_7 = H, R_8 = H)$ | H | H | OH | | H | $CH_3$ | $OCH_3$ | |
| $Q_{12}(R_7 = H, R_8 = H)$ | H | H | OH | | H | $OCH_3$ | $OCH_3$ | |
| $Q_{12}(R_7 = H, R_8 = H)$ | H | H | OH | | H | Cl | $OCH_3$ | |
| $Q_{12}(R_7 = H, R_8 = H)$ | H | H | $OCH_3$ | | H | $OCH_3$ | $OCH_3$ | |
| $Q_{13}(R_7 = H, R_8 = H)$ | H | H | | C=O | | $CH_3$ | $CH_3$ | |
| $Q_{13}(R_7 = H, R_8 = H)$ | H | H | | C=O | | $CH_3$ | $OCH_3$ | |
| $Q_{13}(R_7 = H, R_8 = H)$ | H | H | | C=O | | $OCH_3$ | $OCH_3$ | |
| $Q_{13}(R_7 = H, R_8 = H)$ | H | H | | C=O | | Cl | $OCH_3$ | |
| $Q_{13}(R_7 = H, R_8 = H)$ | H | H | OH | | H | $CH_3$ | $CH_3$ | |
| $Q_{13}(R_7 = H, R_8 = H)$ | H | H | OH | | H | $CH_3$ | $OCH_3$ | |
| $Q_{13}(R_7 = H, R_8 = H)$ | H | H | OH | | H | $OCH_3$ | $OCH_3$ | |
| $Q_{13}(R_7 = H, R_8 = H)$ | H | H | OH | | H | Cl | $OCH_3$ | |
| $Q_{14}(R_7 = H)$ | H | H | | C=O | | $CH_3$ | $CH_3$ | |
| $Q_{14}(R_7 = H)$ | H | H | | C=O | | $CH_3$ | $OCH_3$ | |
| $Q_{14}(R_7 = H)$ | H | H | | C=O | | $OCH_3$ | $OCH_3$ | |
| $Q_{14}(R_7 = H)$ | H | H | | C=O | | Cl | $OCH_3$ | |
| $Q_{14}(R_7 = H)$ | H | H | OH | | H | $CH_3$ | $CH_3$ | |
| $Q_{14}(R_7 = H)$ | H | H | OH | | H | $CH_3$ | $OCH_3$ | |
| $Q_{14}(R_7 = H)$ | H | H | OH | | H | $OCH_3$ | $OCH_3$ | |
| $Q_{14}(R_7 = H)$ | H | H | OH | | H | Cl | $OCH_3$ | |
| $Q_{15}(R_7 = H)$ | H | H | | C=O | | $CH_3$ | $CH_3$ | |
| $Q_{15}(R_7 = H)$ | H | H | | C=O | | $CH_3$ | $OCH_3$ | |
| $Q_{15}(R_7 = H)$ | H | H | | C=O | | $OCH_3$ | $OCH_3$ | |
| $Q_{15}(R_7 = H)$ | H | H | | C=O | | Cl | $OCH_3$ | |
| $Q_{15}(R_7 = H)$ | H | H | OH | | H | $CH_3$ | $CH_3$ | |
| $Q_{15}(R_7 = H)$ | H | H | OH | | H | $CH_3$ | $OCH_3$ | |
| $Q_{15}(R_7 = H)$ | H | H | OH | | H | $OCH_3$ | $OCH_3$ | |
| $Q_{15}(R_7 = H)$ | H | H | OH | | H | Cl | $OCH_3$ | |
| $Q_{16}(R_7 = H)$ | H | H | | C=O | | $CH_3$ | $CH_3$ | |
| $Q_{16}(R_7 = H)$ | H | H | | C=O | | $CH_3$ | $OCH_3$ | |
| $Q_{16}(R_7 = H)$ | H | H | | C=O | | $OCH_3$ | $OCH_3$ | |
| $Q_{16}(R_7 = H)$ | H | H | | C=O | | Cl | $OCH_3$ | |
| $Q_{16}(R_7 = H)$ | H | H | OH | | H | $CH_3$ | $CH_3$ | |
| $Q_{16}(R_7 = H)$ | H | H | OH | | H | $CH_3$ | $OCH_3$ | |
| $Q_{16}(R_7 = H)$ | H | H | OH | | H | $OCH_3$ | $OCH_3$ | |
| $Q_{16}(R_7 = H)$ | H | H | OH | | H | Cl | $OCH_3$ | |
| $Q_{17}(R_7 = CH_3)$ | H | H | | C=O | | $CH_3$ | $CH_3$ | |
| $Q_{17}(R_7 = CH_3)$ | H | H | | C=O | | $CH_3$ | $OCH_3$ | |
| $Q_{17}(R_7 = CH_3)$ | H | H | | C=O | | $OCH_3$ | $OCH_3$ | |
| $Q_{17}(R_7 = CH_3)$ | H | H | | C=O | | Cl | $OCH_3$ | |
| $Q_{17}(R_7 = CH_3)$ | H | H | OH | | H | $CH_3$ | $CH_3$ | |
| $Q_{17}(R_7 = CH_3)$ | H | H | OH | | H | $CH_3$ | $OCH_3$ | |
| $Q_{17}(R_7 = CH_3)$ | H | H | OH | | H | $OCH_3$ | $OCH_3$ | |
| $Q_{17}(R_7 = CH_3)$ | H | H | OH | | H | Cl | $OCH_3$ | |
| $Q_{18}(R_7 = H)$ | H | H | | C=O | | $CH_3$ | $CH_3$ | |
| $Q_{18}(R_7 = H)$ | H | H | | C=O | | $CH_3$ | $OCH_3$ | |
| $Q_{18}(R_7 = H)$ | H | H | | C=O | | $OCH_3$ | $OCH_3$ | |
| $Q_{18}(R_7 = H)$ | H | H | | C=O | | Cl | $OCH_3$ | |
| $Q_{18}(R_7 = H)$ | H | H | OH | | H | $CH_3$ | $CH_3$ | |
| $Q_{18}(R_7 = H)$ | H | H | OH | | H | $CH_3$ | $OCH_3$ | |
| $Q_{18}(R_7 = H)$ | H | H | OH | | H | $OCH_3$ | $OCH_3$ | |
| $Q_{18}(R_7 = H)$ | H | H | OH | | H | Cl | $OCH_3$ | |
| $Q_{19}(R_7 = H, R_8 = H)$ | H | H | | C=O | | $CH_3$ | $CH_3$ | |
| $Q_{19}(R_7 = H, R_8 = H)$ | H | H | | C=O | | $CH_3$ | $OCH_3$ | |
| $Q_{19}(R_7 = H, R_8 = H)$ | H | H | | C=O | | $OCH_3$ | $OCH_3$ | |
| $Q_{19}(R_7 = H, R_8 = H)$ | H | H | | C=O | | Cl | $OCH_3$ | |
| $Q_{19}(R_7 = H, R_8 = H)$ | H | H | OH | | H | $CH_3$ | $CH_3$ | |
| $Q_{19}(R_7 = H, R_8 = H)$ | H | H | OH | | H | $CH_3$ | $OCH_3$ | |
| $Q_{19}(R_7 = H, R_8 = H)$ | H | H | OH | | H | $OCH_3$ | $OCH_3$ | |
| $Q_{19}(R_7 = H, R_8 = H)$ | H | H | OH | | H | Cl | $OCH_3$ | |
| $Q_{20}(R_7 = H, R_8 = H)$ | H | H | | C=O | | $CH_3$ | $CH_3$ | |
| $Q_{20}(R_7 = H, R_8 = H)$ | H | H | | C=O | | $CH_3$ | $OCH_3$ | |
| $Q_{20}(R_7 = H, R_8 = H)$ | H | H | | C=O | | $OCH_3$ | $OCH_3$ | |
| $Q_{20}(R_7 = H, R_8 = H)$ | H | H | | C=O | | Cl | $OCH_3$ | |

TABLE IX-continued

General Formula IX

| Q | R | R₁ | R₂ | R₃ | X | Y | m.p. (°C.) |
|---|---|---|---|---|---|---|---|
| Q₂₀(R₇ = H, R₈ = H) | H | H | OH | H | CH₃ | CH₃ | |
| Q₂₀(R₇ = H, R₈ = H) | H | H | OH | H | CH₃ | OCH₃ | |
| Q₂₀(R₇ = H, R₈ = H) | H | H | OH | H | OCH₃ | OCH₃ | |
| Q₂₀(R₇ = H, R₈ = H) | H | H | OH | H | Cl | OCH₃ | |
| Q₂₁(R₇ = H, R₈ = H, R₉ = CH₃) | H | H | C=O | | CH₃ | CH₃ | |
| Q₂₁(R₇ = H, R₈ = H, R₉ = CH₃) | H | H | C=O | | CH₃ | OCH₃ | |
| Q₂₁(R₇ = H, R₈ = H, R₉ = CH₃) | H | H | C=O | | OCH₃ | OCH₃ | |
| Q₂₁(R₇ = H, R₈ = H, R₉ = CH₃) | H | H | C=O | | Cl | OCH₃ | |
| Q₂₁(R₇ = H, R₈ = H, R₉ = CH₃) | H | H | OH | H | CH₃ | CH₃ | |
| Q₂₁(R₇ = H, R₈ = H, R₉ = CH₃) | H | H | OH | H | CH₃ | OCH₃ | |
| Q₂₁(R₇ = H, R₈ = H, R₉ = CH₃) | H | H | OH | H | OCH₃ | OCH₃ | |
| Q₂₁(R₇ = H, R₈ = H, R₉ = CH₃) | H | H | OH | H | Cl | OCH₃ | |
| Q₂₂(R₇ = H) | H | H | C=O | | CH₃ | CH₃ | |
| Q₂₂(R₇ = H) | H | H | C=O | | CH₃ | OCH₃ | |
| Q₂₂(R₇ = H) | H | H | C=O | | OCH₃ | OCH₃ | |
| Q₂₂(R₇ = H) | H | H | C=O | | Cl | OCH₃ | |
| Q₂₂(R₇ = H) | H | H | OH | H | CH₃ | CH₃ | |
| Q₂₂(R₇ = H) | H | H | OH | H | CH₃ | OCH₃ | |
| Q₂₂(R₇ = H) | H | H | OH | H | OCH₃ | OCH₃ | |
| Q₂₂(R₇ = H) | H | H | OH | H | Cl | OCH₃ | |
| Q₂₃(R₇ = H) | H | H | C=O | | CH₃ | CH₃ | |
| Q₂₃(R₇ = H) | H | H | C=O | | CH₃ | OCH₃ | |
| Q₂₃(R₇ = H) | H | H | C=O | | OCH₃ | OCH₃ | |
| Q₂₃(R₇ = H) | H | H | C=O | | Cl | OCH₃ | |
| Q₂₃(R₇ = H) | H | H | OH | H | CH₃ | CH₃ | |
| Q₂₃(R₇ = H) | H | H | OH | H | CH₃ | OCH₃ | |
| Q₂₃(R₇ = H) | H | H | OH | H | OCH₃ | OCH₃ | |
| Q₂₃(R₇ = H) | H | H | OH | H | Cl | OCH₃ | |
| Q₂₄(R₇ = H, R₈ = H) | H | H | C=O | | CH₃ | CH₃ | |
| Q₂₄(R₇ = H, R₈ = H) | H | H | C=O | | CH₃ | OCH₃ | |
| Q₂₄(R₇ = H, R₈ = H) | H | H | C=O | | OCH₃ | OCH₃ | |
| Q₂₄(R₇ = H, R₈ = H) | H | H | C=O | | Cl | OCH₃ | |
| Q₂₄(R₇ = H, R₈ = H) | H | H | OH | H | CH₃ | CH₃ | |
| Q₂₄(R₇ = H, R₈ = H) | H | H | OH | H | CH₃ | OCH₃ | |
| Q₂₄(R₇ = H, R₈ = H) | H | H | OH | H | OCH₃ | OCH₃ | |
| Q₂₄(R₇ = H, R₈ = H) | H | H | OH | H | Cl | OCH₃ | |
| Q₂₅(R₇ = H, R₈ = H) | H | H | C=O | | CH₃ | CH₃ | |
| Q₂₅(R₇ = H, R₈ = H) | H | H | C=O | | CH₃ | OCH₃ | |
| Q₂₅(R₇ = H, R₈ = H) | H | H | C=O | | OCH₃ | OCH₃ | |
| Q₂₅(R₇ = H, R₈ = H) | H | H | C=O | | Cl | OCH₃ | |
| Q₂₅(R₇ = H, R₈ = H) | H | H | OH | H | CH₃ | CH₃ | |
| Q₂₅(R₇ = H, R₈ = H) | H | H | OH | H | CH₃ | OCH₃ | |
| Q₂₅(R₇ = H, R₈ = H) | H | H | OH | H | OCH₃ | OCH₃ | |
| Q₂₅(R₇ = H, R₈ = H) | H | H | OH | H | Cl | OCH₃ | |
| Q₂₆(R₇ = H, R₈ = H) | H | H | C=O | | CH₃ | CH₃ | |
| Q₂₆(R₇ = H, R₈ = H) | H | H | C=O | | CH₃ | OCH₃ | |
| Q₂₆(R₇ = H, R₈ = H) | H | H | C=O | | OCH₃ | OCH₃ | |
| Q₂₆(R₇ = H, R₈ = H) | H | H | C=O | | Cl | OCH₃ | |
| Q₂₆(R₇ = H, R₈ = H) | H | H | OH | H | CH₃ | CH₃ | |
| Q₂₆(R₇ = H, R₈ = H) | H | H | OH | H | CH₃ | OCH₃ | |
| Q₂₆(R₇ = H, R₈ = H) | H | H | OH | H | OCH₃ | OCH₃ | |
| Q₂₆(R₇ = H, R₈ = H) | H | H | OH | H | Cl | OCH₃ | |
| Q₂₇(R₇ = H, R₁₁ = H, R₁₂ = H) | H | H | C=O | | CH₃ | CH₃ | |
| Q₂₇(R₇ = H, R₁₁ = H, R₁₂ = H) | H | H | C=O | | CH₃ | OCH₃ | |
| Q₂₇(R₇ = H, R₁₁ = H, R₁₂ = H) | H | H | C=O | | OCH₃ | OCH₃ | |
| Q₂₇(R₇ = H, R₁₁ = H, R₁₂ = H) | H | H | C=O | | Cl | OCH₃ | |
| Q₂₇(R₇ = H, R₁₁ = H, R₁₂ = H) | H | H | OH | H | CH₃ | CH₃ | |
| Q₂₇(R₇ = H, R₁₁ = H, R₁₂ = H) | H | H | OH | H | CH₃ | OCH₃ | |
| Q₂₇(R₇ = H, R₁₁ = H, R₁₂ = H) | H | H | OH | H | OCH₃ | OCH₃ | |
| Q₂₇(R₇ = H, R₁₁ = H, R₁₂ = H) | H | H | OH | H | Cl | OCH₃ | |
| Q₂₈(R₁₁ = H, R₁₂ = H) | H | H | C=O | | CH₃ | CH₃ | |
| Q₂₈(R₁₁ = H, R₁₂ = H) | H | H | C=O | | CH₃ | OCH₃ | |
| Q₂₈(R₁₁ = H, R₁₂ = H) | H | H | C=O | | OCH₃ | OCH₃ | |
| Q₂₈(R₁₁ = H, R₁₂ = H) | H | H | C=O | | Cl | OCH₃ | |
| Q₂₈(R₁₁ = H, R₁₂ = H) | H | H | OH | H | CH₃ | CH₃ | |
| Q₂₈(R₁₁ = H, R₁₂ = H) | H | H | OH | H | CH₃ | OCH₃ | |
| Q₂₈(R₁₁ = H, R₁₂ = H) | H | H | OH | H | OCH₃ | OCH₃ | |
| Q₂₈(R₁₁ = H, R₁₂ = H) | H | H | OH | H | Cl | OCH₃ | |
| Q₂₉(R₁₁ = H, R₁₂ = H) | H | H | C=O | | CH₃ | CH₃ | |
| Q₂₉(R₁₁ = H, R₁₂ = H) | H | H | C=O | | CH₃ | OCH₃ | |
| Q₂₉(R₁₁ = H, R₁₂ = H) | H | H | C=O | | OCH₃ | OCH₃ | |
| Q₂₉(R₁₁ = H, R₁₂ = H) | H | H | C=O | | Cl | OCH₃ | |
| Q₂₉(R₁₁ = H, R₁₂ = H) | H | H | OH | H | CH₃ | CH₃ | |
| Q₂₉(R₁₁ = H, R₁₂ = H) | H | H | OH | H | CH₃ | OCH₃ | |
| Q₂₉(R₁₁ = H, R₁₂ = H) | H | H | OH | H | OCH₃ | OCH₃ | |
| Q₂₉(R₁₁ = H, R₁₂ = H) | H | H | OH | H | Cl | OCH₃ | |
| Q₃₀(R₇ = H, R₈ = H) | H | H | C=O | | CH₃ | CH₃ | |
| Q₃₀(R₇ = H, R₈ = H) | H | H | C=O | | CH₃ | OCH₃ | |
| Q₃₀(R₇ = H, R₈ = H) | H | H | C=O | | OCH₃ | OCH₃ | |
| Q₃₀(R₇ = H, R₈ = H) | H | H | C=O | | Cl | OCH₃ | |

TABLE IX-continued

General Formula IX

| Q | R | R₁ | R₂ | R₃ | X | Y | m.p. (°C.) |
|---|---|----|----|----|---|---|------------|
| Q₃₀(R₇ = H, R₈ = H) | H | H | OH | H | CH₃ | CH₃ | |
| Q₃₀(R₇ = H, R₈ = H) | H | H | OH | H | CH₃ | OCH₃ | |
| Q₃₀(R₇ = H, R₈ = H) | H | H | OH | H | OCH₃ | OCH₃ | |
| Q₃₀(R₇ = H, R₈ = H) | H | H | OH | H | Cl | OCH₃ | |
| Q₃₁(R₇ = H, R₈ = H) | H | H | C=O | | CH₃ | CH₃ | |
| Q₃₁(R₇ = H, R₈ = H) | H | H | C=O | | CH₃ | OCH₃ | |
| Q₃₁(R₇ = H, R₈ = H) | H | H | C=O | | OCH₃ | OCH₃ | |
| Q₃₁(R₇ = H, R₈ = H) | H | H | C=O | | Cl | OCH₃ | |
| Q₃₁(R₇ = H, R₈ = H) | H | H | OH | H | CH₃ | CH₃ | |
| Q₃₁(R₇ = H, R₈ = H) | H | H | OH | H | CH₃ | OCH₃ | |
| Q₃₁(R₇ = H, R₈ = H) | H | H | OH | H | OCH₃ | OCH₃ | |
| Q₃₁(R₇ = H, R₈ = H) | H | H | OH | H | Cl | OCH₃ | |
| Q₃₂(R₁₃ = OCH₃, R₁₄ = OCH₃) | H | H | C=O | | CH₃ | CH₃ | |
| Q₃₂(R₁₃ = OCH₃, R₁₄ = OCH₃) | H | H | C=O | | CH₃ | OCH₃ | |
| Q₃₂(R₁₃ = OCH₃, R₁₄ = OCH₃) | H | H | C=O | | OCH₃ | OCH₃ | |
| Q₃₂(R₁₃ = OCH₃, R₁₄ = OCH₃) | H | H | C=O | | Cl | OCH₃ | |
| Q₃₂(R₁₃ = OCH₃, R₁₄ = OCH₃) | H | H | OH | H | CH₃ | CH₃ | |
| Q₃₂(R₁₃ = OCH₃, R₁₄ = OCH₃) | H | H | OH | H | CH₃ | OCH₃ | |
| Q₃₂(R₁₃ = OCH₃, R₁₄ = OCH₃) | H | H | OH | H | OCH₃ | OCH₃ | |
| Q₃₂(R₁₃ = OCH₃, R₁₄ = OCH₃) | H | H | OH | H | Cl | OCH₃ | |
| Q₃₃(R₇ = H) | H | H | C=O | | CH₃ | CH₃ | |
| Q₃₃(R₇ = H) | H | H | C=O | | CH₃ | OCH₃ | |
| Q₃₃(R₇ = H) | H | H | C=O | | OCH₃ | OCH₃ | |
| Q₃₃(R₇ = H) | H | H | C=O | | Cl | OCH₃ | |
| Q₃₃(R₇ = H) | H | H | OH | H | CH₃ | CH₃ | |
| Q₃₃(R₇ = H) | H | H | OH | H | CH₃ | OCH₃ | |
| Q₃₃(R₇ = H) | H | H | OH | H | OCH₃ | OCH₃ | |
| Q₃₃(R₇ = H) | H | H | OH | H | Cl | OCH₃ | |

TABLE X

General Formula X

| Q | R | R₁ | R₂ | R₃ | X | Y | m.p. (°C.) |
|---|---|----|----|----|---|---|------------|
| Q₁(R₇ = H, R₈ = H, R₉ = H) | H | H | C=O | | CH₃ | CH₃ | |
| Q₁(R₇ = H, R₈ = H, R₉ = H) | H | H | C=O | | CH₃ | OCH₃ | |
| Q₁(R₇ = H, R₈ = H, R₉ = H) | H | H | C=O | | OCH₃ | OCH₃ | |
| Q₁(R₇ = H, R₈ = H, R₉ = H) | H | H | C=O | | Cl | OCH₃ | |
| Q₁(R₇ = H, R₈ = H, R₉ = H) | H | H | OH | H | CH₃ | CH₃ | |
| Q₁(R₇ = H, R₈ = H, R₉ = H) | H | H | OH | H | CH₃ | OCH₃ | |
| Q₁(R₇ = H, R₈ = H, R₉ = H) | H | H | OH | H | OCH₃ | OCH₃ | |
| Q₁(R₇ = H, R₈ = H, R₉ = H) | H | H | OH | H | Cl | OCH₃ | |
| Q₁(R₇ = H, R₈ = H, R₉ = H) | H | H | OCH₃ | H | OCH₃ | OCH₃ | |
| Q₁(R₇ = H, R₈ = H, R₉ = H) | H | H | OCH₂CH₃ | H | OCH₃ | OCH₃ | |
| Q₂(R₇ = H, R₈ = H, R₉ = H) | H | H | C=O | | CH₃ | CH₃ | |
| Q₂(R₇ = H, R₈ = H, R₉ = H) | H | H | C=O | | CH₃ | OCH₃ | |
| Q₂(R₇ = H, R₈ = H, R₉ = H) | H | H | C=O | | OCH₃ | OCH₃ | |
| Q₂(R₇ = H, R₈ = H, R₉ = H) | H | H | C=O | | Cl | OCH₃ | |
| Q₂(R₇ = H, R₈ = H, R₉ = H) | H | H | OH | H | CH₃ | CH₃ | |
| Q₂(R₇ = H, R₈ = H, R₉ = H) | H | H | OH | H | CH₃ | OCH₃ | |
| Q₂(R₇ = H, R₈ = H, R₉ = H) | H | H | OH | H | OCH₃ | OCH₃ | |
| Q₂(R₇ = H, R₈ = H, R₉ = H) | H | H | OH | H | Cl | OCH₃ | |
| Q₂(R₇ = H, R₈ = H, R₉ = H) | H | H | OCH₃ | H | CH₃ | OCH₃ | |
| Q₂(R₇ = H, R₈ = H, R₉ = H) | H | H | OCH₂CH₃ | H | CH₃ | CH₃ | |
| Q₃(R₇ = H, R₈ = H, R₉ = H) | H | H | C=O | | CH₃ | CH₃ | |
| Q₃(R₇ = H, R₈ = H, R₉ = H) | H | H | C=O | | CH₃ | OCH₃ | |
| Q₃(R₇ = H, R₈ = H, R₉ = H) | H | H | C=O | | OCH₃ | OCH₃ | |
| Q₃(R₇ = H, R₈ = H, R₉ = H) | H | H | C=O | | Cl | OCH₃ | |
| Q₃(R₇ = H, R₈ = H, R₉ = H) | H | H | OH | H | CH₃ | CH₃ | |
| Q₃(R₇ = H, R₈ = H, R₉ = H) | H | H | OH | H | CH₃ | OCH₃ | |
| Q₃(R₇ = H, R₈ = H, R₉ = H) | H | H | OH | H | OCH₃ | OCH₃ | |
| Q₃(R₇ = H, R₈ = H, R₉ = H) | H | H | OH | H | Cl | OCH₃ | |
| Q₃(R₇ = H, R₈ = H, R₉ = Cl) | H | H | C=O | | OCH₃ | OCH₃ | |
| Q₃(R₇ = H, R₈ = H, R₉ = CH₃) | H | H | C=O | | OCH₃ | OCH₃ | |
| Q₃(R₇ = H, R₈ = H, R₉ = CH₃) | H | H | OH | H | OCH₃ | OCH₃ | |
| Q₄(R₇ = H, R₈ = H, R₉ = H) | H | H | C=O | | CH₃ | CH₃ | |
| Q₄(R₇ = H, R₈ = H, R₉ = H) | H | H | C=O | | CH₃ | OCH₃ | |
| Q₄(R₇ = H, R₈ = H, R₉ = H) | H | H | C=O | | OCH₃ | OCH₃ | |
| Q₄(R₇ = H, R₈ = H, R₉ = H) | H | H | C=O | | Cl | OCH₃ | |
| Q₄(R₇ = H, R₈ = H, R₉ = H) | H | H | OH | H | CH₃ | CH₃ | |
| Q₄(R₇ = H, R₈ = H, R₉ = H) | H | H | OH | H | CH₃ | OCH₃ | |
| Q₄(R₇ = H, R₈ = H, R₉ = H) | H | H | OH | H | OCH₃ | OCH₃ | |
| Q₄(R₇ = H, R₈ = H, R₉ = H) | H | H | OH | H | Cl | OCH₃ | |
| Q₅(R₇ = H, R₈ = H, R₉ = H, R₁₀ = CH₃) | H | H | C=O | | CH₃ | CH₃ | |
| Q₅(R₇ = H, R₈ = H, R₉ = H, R₁₀ = CH₃) | H | H | C=O | | CH₃ | OCH₃ | |
| Q₅(R₇ = H, R₈ = H, R₉ = H, R₁₀ = CH₃) | H | H | C=O | | OCH₃ | OCH₃ | |
| Q₅(R₇ = H, R₈ = H, R₉ = H, R₁₀ = CH₃) | H | H | C=O | | Cl | OCH₃ | |
| Q₅(R₇ = H, R₈ = H, R₉ = H, R₁₀ = CH₃) | H | H | OH | H | CH₃ | CH₃ | |
| Q₅(R₇ = H, R₈ = H, R₉ = H, R₁₀ = CH₃) | H | H | OH | H | CH₃ | OCH₃ | |

TABLE X-continued

General Formula X

| Q | R | R$_1$ | R$_2$ | R$_3$ | X | Y | m.p. (°C.) |
|---|---|---|---|---|---|---|---|
| Q$_5$(R$_7$ = H, R$_8$ = H, R$_9$ = H, R$_{10}$ = CH$_3$) | H | H | OH | H | OCH$_3$ | OCH$_3$ | |
| Q$_5$(R$_7$ = H, R$_8$ = H, R$_9$ = H, R$_{10}$ = CH$_3$) | H | H | OH | H | Cl | OCH$_3$ | |
| Q$_5$(R$_7$ = H, R$_8$ = H, R$_9$ = H, R$_{10}$ = CH$_3$) | H | H | OCH$_3$ | H | Cl | OCH$_3$ | |
| Q$_5$(R$_7$ = H, R$_8$ = H, R$_9$ = H, R$_{10}$ = CH$_3$) | H | H | OCH$_2$CH$_3$ | H | OCH$_3$ | OCH$_3$ | |
| Q$_6$(R$_7$ = H, R$_8$ = H, R$_9$ = H, R$_{10}$ = CH$_3$) | H | H | C=O | | CH$_3$ | CH$_3$ | |
| Q$_6$(R$_7$ = H, R$_8$ = H, R$_9$ = H, R$_{10}$ = CH$_3$) | H | H | C=O | | CH$_3$ | OCH$_3$ | |
| Q$_6$(R$_7$ = H, R$_8$ = H, R$_9$ = H, R$_{10}$ = CH$_3$) | H | H | C=O | | OCH$_3$ | OCH$_3$ | |
| Q$_6$(R$_7$ = H, R$_8$ = H, R$_9$ = H, R$_{10}$ = CH$_3$) | H | H | C=O | | Cl | OCH$_3$ | |
| Q$_6$(R$_7$ = H, R$_8$ = H, R$_9$ = H, R$_{10}$ = CH$_3$) | H | H | OH | H | CH$_3$ | CH$_3$ | |
| Q$_6$(R$_7$ = H, R$_8$ = H, R$_9$ = H, R$_{10}$ = CH$_3$) | H | H | OH | H | CH$_3$ | OCH$_3$ | |
| Q$_6$(R$_7$ = H, R$_8$ = H, R$_9$ = H, R$_{10}$ = CH$_3$) | H | H | OH | H | OCH$_3$ | OCH$_3$ | |
| Q$_6$(R$_7$ = H, R$_8$ = H, R$_9$ = H, R$_{10}$ = CH$_3$) | H | H | OH | H | Cl | OCH$_3$ | |
| Q$_7$(R$_7$ = H, R$_8$ = H) | H | H | C=O | | CH$_3$ | CH$_3$ | |
| Q$_7$(R$_7$ = H, R$_8$ = H) | H | H | C=O | | CH$_3$ | OCH$_3$ | |
| Q$_7$(R$_7$ = H, R$_8$ = H) | H | H | C=O | | OCH$_3$ | OCH$_3$ | |
| Q$_7$(R$_7$ = H, R$_8$ = H) | H | H | C=O | | Cl | OCH$_3$ | |
| Q$_7$(R$_7$ = H, R$_8$ = H) | H | H | OH | H | CH$_3$ | CH$_3$ | |
| Q$_7$(R$_7$ = H, R$_8$ = H) | H | H | OH | H | CH$_3$ | OCH$_3$ | |
| Q$_7$(R$_7$ = H, R$_8$ = H) | H | H | OH | H | OCH$_3$ | OCH$_3$ | |
| Q$_7$(R$_7$ = H, R$_8$ = H) | H | H | OH | H | Cl | OCH$_3$ | |
| Q$_8$(R$_7$ = H, R$_8$ = H) | H | H | C=O | | OCH$_3$ | OCH$_3$ | |
| Q$_8$(R$_7$ = H, R$_8$ = H) | H | H | C=O | | Cl | OCH$_3$ | |
| Q$_8$(R$_7$ = H, R$_8$ = H) | H | H | OH | H | Cl | OCH$_3$ | |
| Q$_8$(R$_7$ = H, R$_8$ = H) | H | H | OH | H | OCH$_3$ | OCH$_3$ | |
| Q$_9$(R$_7$ = H, R$_8$ = H) | H | H | C=O | | CH$_3$ | CH$_3$ | |
| Q$_9$(R$_7$ = H, R$_8$ = H) | H | H | C=O | | CH$_3$ | OCH$_3$ | |
| Q$_9$(R$_7$ = H, R$_8$ = H) | H | H | C=O | | OCH$_3$ | OCH$_3$ | |
| Q$_9$(R$_7$ = H, R$_8$ = H) | H | H | C=O | | Cl | OCH$_3$ | |
| Q$_9$(R$_7$ = H, R$_8$ = H) | H | H | OH | H | CH$_3$ | CH$_3$ | |
| Q$_9$(R$_7$ = H, R$_8$ = H) | H | H | OH | H | CH$_3$ | OCH$_3$ | |
| Q$_9$(R$_7$ = H, R$_8$ = H) | H | H | OH | H | OCH$_3$ | OCH$_3$ | |
| Q$_9$(R$_7$ = H, R$_8$ = H) | H | H | OH | H | Cl | OCH$_3$ | |
| Q$_{10}$(R$_7$ = H, R$_8$ = H) | H | H | C=O | | CH$_3$ | OCH$_3$ | |
| Q$_{10}$(R$_7$ = H, R$_8$ = H) | H | H | C=O | | OCH$_3$ | OCH$_3$ | |
| Q$_{10}$(R$_7$ = H, R$_8$ = H) | H | H | C=O | | Cl | OCH$_3$ | |
| Q$_{10}$(R$_7$ = H, R$_8$ = H) | H | H | OH | H | CH$_3$ | CH$_3$ | |
| Q$_{10}$(R$_7$ = H, R$_8$ = H) | H | H | OH | H | OCH$_3$ | OCH$_3$ | |
| Q$_{10}$(R$_7$ = H, R$_8$ = H) | H | H | OH | H | Cl | OCH$_3$ | |
| Q$_{11}$(R$_7$ = H, R$_8$ = H) | H | H | C=O | | CH$_3$ | CH$_3$ | |
| Q$_{11}$(R$_7$ = H, R$_8$ = H) | H | H | C=O | | CH$_3$ | OCH$_3$ | |
| Q$_{11}$(R$_7$ = H, R$_8$ = H) | H | H | C=O | | OCH$_3$ | OCH$_3$ | |
| Q$_{11}$(R$_7$ = H, R$_8$ = H) | H | H | C=O | | Cl | OCH$_3$ | |
| Q$_{11}$(R$_7$ = H, R$_8$ = H) | H | H | OH | H | CH$_3$ | CH$_3$ | |
| Q$_{11}$(R$_7$ = H, R$_8$ = H) | H | H | OH | H | OCH$_3$ | OCH$_3$ | |
| Q$_{11}$(R$_7$ = H, R$_8$ = H) | H | H | OH | H | Cl | OCH$_3$ | |
| Q$_{12}$(R$_7$ = H, R$_8$ = H) | H | H | C=O | | CH$_3$ | CH$_3$ | |
| Q$_{12}$(R$_7$ = H, R$_8$ = H) | H | H | C=O | | CH$_3$ | OCH$_3$ | |
| Q$_{12}$(R$_7$ = H, R$_8$ = H) | H | H | C=O | | OCH$_3$ | OCH$_3$ | |
| Q$_{12}$(R$_7$ = H, R$_8$ = H) | H | H | C=O | | Cl | OCH$_3$ | |
| Q$_{12}$(R$_7$ = H, R$_8$ = H) | H | H | OH | H | CH$_3$ | CH$_3$ | |
| Q$_{12}$(R$_7$ = H, R$_8$ = H) | H | H | OH | H | CH$_3$ | OCH$_3$ | |
| Q$_{12}$(R$_7$ = H, R$_8$ = H) | H | H | OH | H | OCH$_3$ | OCH$_3$ | |
| Q$_{12}$(R$_7$ = H, R$_8$ = H) | H | H | OH | H | Cl | OCH$_3$ | |
| Q$_{12}$(R$_7$ = H, R$_8$ = H) | H | H | OCH$_3$ | H | OCH$_3$ | OCH$_3$ | |
| Q$_{13}$(R$_7$ = H, R$_8$ = H) | H | H | C=O | | CH$_3$ | CH$_3$ | |
| Q$_{13}$(R$_7$ = H, R$_8$ = H) | H | H | C=O | | CH$_3$ | OCH$_3$ | |
| Q$_{13}$(R$_7$ = H, R$_8$ = H) | H | H | C=O | | OCH$_3$ | OCH$_3$ | |
| Q$_{13}$(R$_7$ = H, R$_8$ = H) | H | H | C=O | | Cl | OCH$_3$ | |
| Q$_{13}$(R$_7$ = H, R$_8$ = H) | H | H | OH | H | CH$_3$ | CH$_3$ | |
| Q$_{13}$(R$_7$ = H, R$_8$ = H) | H | H | OH | H | CH$_3$ | OCH$_3$ | |
| Q$_{13}$(R$_7$ = H, R$_8$ = H) | H | H | OH | H | OCH$_3$ | OCH$_3$ | |
| Q$_{13}$(R$_7$ = H, R$_8$ = H) | H | H | OH | H | Cl | OCH$_3$ | |
| Q$_{14}$(R$_7$ = H) | H | H | C=O | | CH$_3$ | CH$_3$ | |
| Q$_{14}$(R$_7$ = H) | H | H | C=O | | CH$_3$ | OCH$_3$ | |
| Q$_{14}$(R$_7$ = H) | H | H | C=O | | OCH$_3$ | OCH$_3$ | |
| Q$_{14}$(R$_7$ = H) | H | H | C=O | | Cl | OCH$_3$ | |
| Q$_{14}$(R$_7$ = H) | H | H | OH | H | CH$_3$ | CH$_3$ | |
| Q$_{14}$(R$_7$ = H) | H | H | OH | H | CH$_3$ | OCH$_3$ | |
| Q$_{14}$(R$_7$ = H) | H | H | OH | H | OCH$_3$ | OCH$_3$ | |
| Q$_{14}$(R$_7$ = H) | H | H | OH | H | Cl | OCH$_3$ | |
| Q$_{15}$(R$_7$ = H) | H | H | C=O | | CH$_3$ | CH$_3$ | |
| Q$_{15}$(R$_7$ = H) | H | H | C=O | | CH$_3$ | OCH$_3$ | |
| Q$_{15}$(R$_7$ = H) | H | H | C=O | | OCH$_3$ | OCH$_3$ | |
| Q$_{15}$(R$_7$ = H) | H | H | C=O | | Cl | OCH$_3$ | |
| Q$_{15}$(R$_7$ = H) | H | H | OH | H | CH$_3$ | CH$_3$ | |
| Q$_{15}$(R$_7$ = H) | H | H | OH | H | CH$_3$ | OCH$_3$ | |
| Q$_{15}$(R$_7$ = H) | H | H | OH | H | OCH$_3$ | OCH$_3$ | |
| Q$_{15}$(R$_7$ = H) | H | H | OH | H | Cl | OCH$_3$ | |
| Q$_{16}$(R$_7$ = H) | H | H | C=O | | CH$_3$ | CH$_3$ | |

TABLE X-continued

| Q | R | $R_1$ | $R_2$ | $R_3$ | X | Y | m.p. (°C.) |
|---|---|---|---|---|---|---|---|
| $Q_{16}(R_7 = H)$ | H | H |  | C=O | $CH_3$ | $OCH_3$ |  |
| $Q_{16}(R_7 = H)$ | H | H |  | C=O | $OCH_3$ | $OCH_3$ |  |
| $Q_{16}(R_7 = H)$ | H | H |  | C=O | Cl | $OCH_3$ |  |
| $Q_{16}(R_7 = H)$ | H | H | OH | H | $CH_3$ | $CH_3$ |  |
| $Q_{16}(R_7 = H)$ | H | H | OH | H | $CH_3$ | $OCH_3$ |  |
| $Q_{16}(R_7 = H)$ | H | H | OH | H | $OCH_3$ | $OCH_3$ |  |
| $Q_{16}(R_7 = H)$ | H | H | OH | H | Cl | $OCH_3$ |  |
| $Q_{17}(R_7 = CH_3)$ | H | H |  | C=O | $CH_3$ | $CH_3$ |  |
| $Q_{17}(R_7 = CH_3)$ | H | H |  | C=O | $CH_3$ | $OCH_3$ |  |
| $Q_{17}(R_7 = CH_3)$ | H | H |  | C=O | $OCH_3$ | $OCH_3$ |  |
| $Q_{17}(R_7 = CH_3)$ | H | H |  | C=O | Cl | $OCH_3$ |  |
| $Q_{17}(R_7 = CH_3)$ | H | H | OH | H | $CH_3$ | $CH_3$ |  |
| $Q_{17}(R_7 = CH_3)$ | H | H | OH | H | $CH_3$ | $OCH_3$ |  |
| $Q_{17}(R_7 = CH_3)$ | H | H | OH | H | $OCH_3$ | $OCH_3$ |  |
| $Q_{17}(R_7 = CH_3)$ | H | H | OH | H | Cl | $OCH_3$ |  |
| $Q_{18}(R_7 = H)$ | H | H |  | C=O | $CH_3$ | $CH_3$ |  |
| $Q_{18}(R_7 = H)$ | H | H |  | C=O | $CH_3$ | $OCH_3$ |  |
| $Q_{18}(R_7 = H)$ | H | H |  | C=O | $OCH_3$ | $OCH_3$ |  |
| $Q_{18}(R_7 = H)$ | H | H |  | C=O | Cl | $OCH_3$ |  |
| $Q_{18}(R_7 = H)$ | H | H | OH | H | $CH_3$ | $CH_3$ |  |
| $Q_{18}(R_7 = H)$ | H | H | OH | H | $CH_3$ | $OCH_3$ |  |
| $Q_{18}(R_7 = H)$ | H | H | OH | H | $OCH_3$ | $OCH_3$ |  |
| $Q_{18}(R_7 = H)$ | H | H | OH | H | Cl | $OCH_3$ |  |
| $Q_{19}(R_7 = H, R_8 = H)$ | H | H |  | C=O | $CH_3$ | $CH_3$ |  |
| $Q_{19}(R_7 = H, R_8 = H)$ | H | H |  | C=O | $CH_3$ | $OCH_3$ |  |
| $Q_{19}(R_7 = H, R_8 = H)$ | H | H |  | C=O | $OCH_3$ | $OCH_3$ |  |
| $Q_{19}(R_7 = H, R_8 = H)$ | H | H |  | C=O | Cl | $OCH_3$ |  |
| $Q_{19}(R_7 = H, R_8 = H)$ | H | H | OH | H | $CH_3$ | $CH_3$ |  |
| $Q_{19}(R_7 = H, R_8 = H)$ | H | H | OH | H | $CH_3$ | $OCH_3$ |  |
| $Q_{19}(R_7 = H, R_8 = H)$ | H | H | OH | H | $OCH_3$ | $OCH_3$ |  |
| $Q_{19}(R_7 = H, R_8 = H)$ | H | H | OH | H | Cl | $OCH_3$ |  |
| $Q_{20}(R_7 = H, R_8 = H)$ | H | H |  | C=O | $CH_3$ | $CH_3$ |  |
| $Q_{20}(R_7 = H, R_8 = H)$ | H | H |  | C=O | $CH_3$ | $OCH_3$ |  |
| $Q_{20}(R_7 = H, R_8 = H)$ | H | H |  | C=O | $OCH_3$ | $OCH_3$ |  |
| $Q_{20}(R_7 = H, R_8 = H)$ | H | H |  | C=O | Cl | $OCH_3$ |  |
| $Q_{20}(R_7 = H, R_8 = H)$ | H | H | OH | H | $CH_3$ | $CH_3$ |  |
| $Q_{20}(R_7 = H, R_8 = H)$ | H | H | OH | H | $CH_3$ | $OCH_3$ |  |
| $Q_{20}(R_7 = H, R_8 = H)$ | H | H | OH | H | $OCH_3$ | $OCH_3$ |  |
| $Q_{20}(R_7 = H, R_8 = H)$ | H | H | OH | H | Cl | $OCH_3$ |  |
| $Q_{21}(R_7 = H, R_8 = H, R_9 = CH_3)$ | H | H |  | C=O | $CH_3$ | $CH_3$ |  |
| $Q_{21}(R_7 = H, R_8 = H, R_9 = CH_3)$ | H | H |  | C=O | $CH_3$ | $OCH_3$ |  |
| $Q_{21}(R_7 = H, R_8 = H, R_9 = CH_3)$ | H | H |  | C=O | $OCH_3$ | $OCH_3$ |  |
| $Q_{21}(R_7 = H, R_8 = H, R_9 = CH_3)$ | H | H |  | C=O | Cl | $OCH_3$ |  |
| $Q_{21}(R_7 = H, R_8 = H, R_9 = CH_3)$ | H | H | OH | H | $CH_3$ | $CH_3$ |  |
| $Q_{21}(R_7 = H, R_8 = H, R_9 = CH_3)$ | H | H | OH | H | $CH_3$ | $OCH_3$ |  |
| $Q_{21}(R_7 = H, R_8 = H, R_9 = CH_3)$ | H | H | OH | H | $OCH_3$ | $OCH_3$ |  |
| $Q_{21}(R_7 = H, R_8 = H, R_9 = CH_3)$ | H | H | OH | H | Cl | $OCH_3$ |  |
| $Q_{22}(R_7 = H)$ | H | H |  | C=O | $CH_3$ | $CH_3$ |  |
| $Q_{22}(R_7 = H)$ | H | H |  | C=O | $CH_3$ | $OCH_3$ |  |
| $Q_{22}(R_7 = H)$ | H | H |  | C=O | $OCH_3$ | $OCH_3$ |  |
| $Q_{22}(R_7 = H)$ | H | H |  | C=O | Cl | $OCH_3$ |  |
| $Q_{22}(R_7 = H)$ | H | H | OH | H | $CH_3$ | $CH_3$ |  |
| $Q_{22}(R_7 = H)$ | H | H | OH | H | $CH_3$ | $OCH_3$ |  |
| $Q_{22}(R_7 = H)$ | H | H | OH | H | $OCH_3$ | $OCH_3$ |  |
| $Q_{22}(R_7 = H)$ | H | H | OH | H | Cl | $OCH_3$ |  |
| $Q_{23}(R_7 = H)$ | H | H |  | C=O | $CH_3$ | $CH_3$ |  |
| $Q_{23}(R_7 = H)$ | H | H |  | C=O | $CH_3$ | $OCH_3$ |  |
| $Q_{23}(R_7 = H)$ | H | H |  | C=O | $OCH_3$ | $OCH_3$ |  |
| $Q_{23}(R_7 = H)$ | H | H |  | C=O | Cl | $OCH_3$ |  |
| $Q_{23}(R_7 = H)$ | H | H | OH | H | $CH_3$ | $CH_3$ |  |
| $Q_{23}(R_7 = H)$ | H | H | OH | H | $CH_3$ | $OCH_3$ |  |
| $Q_{23}(R_7 = H)$ | H | H | OH | H | $OCH_3$ | $OCH_3$ |  |
| $Q_{23}(R_7 = H)$ | H | H | OH | H | Cl | $OCH_3$ |  |
| $Q_{24}(R_7 = H, R_8 = H)$ | H | H |  | C=O | $CH_3$ | $CH_3$ |  |
| $Q_{24}(R_7 = H, R_8 = H)$ | H | H |  | C=O | $CH_3$ | $OCH_3$ |  |
| $Q_{24}(R_7 = H, R_8 = H)$ | H | H |  | C=O | $OCH_3$ | $OCH_3$ |  |
| $Q_{24}(R_7 = H, R_8 = H)$ | H | H |  | C=O | Cl | $OCH_3$ |  |
| $Q_{24}(R_7 = H, R_8 = H)$ | H | H | OH | H | $CH_3$ | $CH_3$ |  |
| $Q_{24}(R_7 = H, R_8 = H)$ | H | H | OH | H | $CH_3$ | $OCH_3$ |  |
| $Q_{24}(R_7 = H, R_8 = H)$ | H | H | OH | H | $OCH_3$ | $OCH_3$ |  |
| $Q_{24}(R_7 = H, R_8 = H)$ | H | H | OH | H | Cl | $OCH_3$ |  |
| $Q_{25}(R_7 = H, R_8 = H)$ | H | H |  | C=O | $CH_3$ | $CH_3$ |  |
| $Q_{25}(R_7 = H, R_8 = H)$ | H | H |  | C=O | $CH_3$ | $OCH_3$ |  |
| $Q_{25}(R_7 = H, R_8 = H)$ | H | H |  | C=O | $OCH_3$ | $OCH_3$ |  |
| $Q_{25}(R_7 = H, R_8 = H)$ | H | H |  | C=O | Cl | $OCH_3$ |  |
| $Q_{25}(R_7 = H, R_8 = H)$ | H | H | OH | H | $CH_3$ | $CH_3$ |  |
| $Q_{25}(R_7 = H, R_8 = H)$ | H | H | OH | H | $CH_3$ | $OCH_3$ |  |
| $Q_{25}(R_7 = H, R_8 = H)$ | H | H | OH | H | $OCH_3$ | $OCH_3$ |  |
| $Q_{25}(R_7 = H, R_8 = H)$ | H | H | OH | H | Cl | $OCH_3$ |  |
| $Q_{26}(R_7 = H, R_8 = H)$ | H | H |  | C=O | $CH_3$ | $CH_3$ |  |

TABLE X-continued

General Formula X

| Q | R | $R_1$ | $R_2$ | $R_3$ | X | Y | m.p. (°C.) |
|---|---|---|---|---|---|---|---|
| $Q_{26}(R_7 = H, R_8 = H)$ | H | H | C=O | | $CH_3$ | $OCH_3$ | |
| $Q_{26}(R_7 = H, R_8 = H)$ | H | H | C=O | | $OCH_3$ | $OCH_3$ | |
| $Q_{26}(R_7 = H, R_8 = H)$ | H | H | C=O | | Cl | $OCH_3$ | |
| $Q_{26}(R_7 = H, R_8 = H)$ | H | H | OH | H | $CH_3$ | $CH_3$ | |
| $Q_{26}(R_7 = H, R_8 = H)$ | H | H | OH | H | $CH_3$ | $OCH_3$ | |
| $Q_{26}(R_7 = H, R_8 = H)$ | H | H | OH | H | $OCH_3$ | $OCH_3$ | |
| $Q_{26}(R_7 = H, R_8 = H)$ | H | H | OH | H | Cl | $OCH_3$ | |
| $Q_{27}(R_7 = H, R_{11} = H, R_{12} = H)$ | H | H | C=O | | $CH_3$ | $CH_3$ | |
| $Q_{27}(R_7 = H, R_{11} = H, R_{12} = H)$ | H | H | C=O | | $CH_3$ | $OCH_3$ | |
| $Q_{27}(R_7 = H, R_{11} = H, R_{12} = H)$ | H | H | C=O | | $OCH_3$ | $OCH_3$ | |
| $Q_{27}(R_7 = H, R_{11} = H, R_{12} = H)$ | H | H | C=O | | Cl | $OCH_3$ | |
| $Q_{27}(R_7 = H, R_{11} = H, R_{12} = H)$ | H | H | OH | H | $CH_3$ | $CH_3$ | |
| $Q_{27}(R_7 = H, R_{11} = H, R_{12} = H)$ | H | H | OH | H | $CH_3$ | $OCH_3$ | |
| $Q_{27}(R_7 = H, R_{11} = H, R_{12} = H)$ | H | H | OH | H | $OCH_3$ | $OCH_3$ | |
| $Q_{27}(R_7 = H, R_{11} = H, R_{12} = H)$ | H | H | OH | H | Cl | $OCH_3$ | |
| $Q_{28}(R_{11} = H, R_{12} = H)$ | H | H | C=O | | $CH_3$ | $CH_3$ | |
| $Q_{28}(R_{11} = H, R_{12} = H)$ | H | H | C=O | | $CH_3$ | $OCH_3$ | |
| $Q_{28}(R_{11} = H, R_{12} = H)$ | H | H | C=O | | $OCH_3$ | $OCH_3$ | |
| $Q_{28}(R_{11} = H, R_{12} = H)$ | H | H | C=O | | Cl | $OCH_3$ | |
| $Q_{28}(R_{11} = H, R_{12} = H)$ | H | H | OH | H | $CH_3$ | $CH_3$ | |
| $Q_{28}(R_{11} = H, R_{12} = H)$ | H | H | OH | H | $CH_3$ | $OCH_3$ | |
| $Q_{28}(R_{11} = H, R_{12} = H)$ | H | H | OH | H | $OCH_3$ | $OCH_3$ | |
| $Q_{28}(R_{11} = H, R_{12} = H)$ | H | H | OH | H | Cl | $OCH_3$ | |
| $Q_{29}(R_{11} = H, R_{12} = H)$ | H | H | C=O | | $CH_3$ | $CH_3$ | |
| $Q_{29}(R_{11} = H, R_{12} = H)$ | H | H | C=O | | $CH_3$ | $OCH_3$ | |
| $Q_{29}(R_{11} = H, R_{12} = H)$ | H | H | C=O | | $OCH_3$ | $OCH_3$ | |
| $Q_{29}(R_{11} = H, R_{12} = H)$ | H | H | C=O | | Cl | $OCH_3$ | |
| $Q_{29}(R_{11} = H, R_{12} = H)$ | H | H | OH | H | $CH_3$ | $CH_3$ | |
| $Q_{29}(R_{11} = H, R_{12} = H)$ | H | H | OH | H | $CH_3$ | $OCH_3$ | |
| $Q_{29}(R_{11} = H, R_{12} = H)$ | H | H | OH | H | $OCH_3$ | $OCH_3$ | |
| $Q_{29}(R_{11} = H, R_{12} = H)$ | H | H | OH | H | Cl | $OCH_3$ | |
| $Q_{30}(R_7 = H, R_8 = H)$ | H | H | C=O | | $CH_3$ | $CH_3$ | |
| $Q_{30}(R_7 = H, R_8 = H)$ | H | H | C=O | | $CH_3$ | $OCH_3$ | |
| $Q_{30}(R_7 = H, R_8 = H)$ | H | H | C=O | | $OCH_3$ | $OCH_3$ | |
| $Q_{30}(R_7 = H, R_8 = H)$ | H | H | C=O | | Cl | $OCH_3$ | |
| $Q_{27}(R_7 = H, R_{11} = H, R_{12} = H)$ | H | H | OH | H | $CH_3$ | $CH_3$ | |
| $Q_{27}(R_7 = H, R_{11} = H, R_{12} = H)$ | H | H | OH | H | $CH_3$ | $OCH_3$ | |
| $Q_{27}(R_7 = H, R_{11} = H, R_{12} = H)$ | H | H | OH | H | $OCH_3$ | $OCH_3$ | |
| $Q_{27}(R_7 = H, R_{11} = H, R_{12} = H)$ | H | H | OH | H | Cl | $OCH_3$ | |
| $Q_{28}(R_{11} = H, R_{12} = H)$ | H | H | C=O | | $CH_3$ | $CH_3$ | |
| $Q_{28}(R_{11} = H, R_{12} = H)$ | H | H | C=O | | $CH_3$ | $OCH_3$ | |
| $Q_{28}(R_{11} = H, R_{12} = H)$ | H | H | C=O | | $OCH_3$ | $OCH_3$ | |
| $Q_{28}(R_{11} = H, R_{12} = H)$ | H | H | C=O | | Cl | $OCH_3$ | |
| $Q_{28}(R_{11} = H, R_{12} = H)$ | H | H | OH | H | $CH_3$ | $CH_3$ | |
| $Q_{28}(R_{11} = H, R_{12} = H)$ | H | H | OH | H | $CH_3$ | $OCH_3$ | |
| $Q_{28}(R_{11} = H, R_{12} = H)$ | H | H | OH | H | $OCH_3$ | $OCH_3$ | |
| $Q_{28}(R_{11} = H, R_{12} = H)$ | H | H | OH | H | Cl | $OCH_3$ | |
| $Q_{29}(R_{11} = H, R_{12} = H)$ | H | H | C=O | | $CH_3$ | $CH_3$ | |
| $Q_{29}(R_{11} = H, R_{12} = H)$ | H | H | C=O | | $CH_3$ | $OCH_3$ | |
| $Q_{29}(R_{11} = H, R_{12} = H)$ | H | H | C=O | | $OCH_3$ | $OCH_3$ | |
| $Q_{29}(R_{11} = H, R_{12} = H)$ | H | H | C=O | | Cl | $OCH_3$ | |
| $Q_{29}(R_{11} = H, R_{12} = H)$ | H | H | OH | H | $CH_3$ | $CH_3$ | |
| $Q_{29}(R_{11} = H, R_{12} = H)$ | H | H | OH | H | $CH_3$ | $OCH_3$ | |
| $Q_{29}(R_{11} = H, R_{12} = H)$ | H | H | OH | H | $OCH_3$ | $OCH_3$ | |
| $Q_{29}(R_{11} = H, R_{12} = H)$ | H | H | OH | H | Cl | $OCH_3$ | |
| $Q_{30}(R_7 = H, R_8 = H)$ | H | H | C=O | | $CH_3$ | $CH_3$ | |
| $Q_{30}(R_7 = H, R_8 = H)$ | H | H | C=O | | $CH_3$ | $OCH_3$ | |
| $Q_{30}(R_7 = H, R_8 = H)$ | H | H | C=O | | $OCH_3$ | $OCH_3$ | |
| $Q_{30}(R_7 = H, R_8 = H)$ | H | H | C=O | | Cl | $OCH_3$ | |
| $Q_{30}(R_7 = H, R_8 = H)$ | H | H | OH | H | $CH_3$ | $CH_3$ | |
| $Q_{30}(R_7 = H, R_8 = H)$ | H | H | OH | H | $CH_3$ | $OCH_3$ | |
| $Q_{30}(R_7 = H, R_8 = H)$ | H | H | OH | H | $OCH_3$ | $OCH_3$ | |
| $Q_{30}(R_7 = H, R_8 = H)$ | H | H | OH | H | Cl | $OCH_3$ | |
| $Q_{31}(R_7 = H, R_8 = H)$ | H | H | C=O | | $CH_3$ | $CH_3$ | |
| $Q_{31}(R_7 = H, R_8 = H)$ | H | H | C=O | | $CH_3$ | $OCH_3$ | |
| $Q_{31}(R_7 = H, R_8 = H)$ | H | H | C=O | | $OCH_3$ | $OCH_3$ | |
| $Q_{31}(R_7 = H, R_8 = H)$ | H | H | C=O | | Cl | $OCH_3$ | |
| $Q_{31}(R_7 = H, R_8 = H)$ | H | H | OH | H | $CH_3$ | $CH_3$ | |
| $Q_{31}(R_7 = H, R_8 = H)$ | H | H | OH | H | $CH_3$ | $OCH_3$ | |
| $Q_{31}(R_7 = H, R_8 = H)$ | H | H | OH | H | $OCH_3$ | $OCH_3$ | |
| $Q_{31}(R_7 = H, R_8 = H)$ | H | H | OH | H | Cl | $OCH_3$ | |
| $Q_{32}(R_{13} = OCH_3, R_{14} = OCH_3)$ | H | H | C=O | | $CH_3$ | $CH_3$ | |
| $Q_{32}(R_{13} = OCH_3, R_{14} = OCH_3)$ | H | H | C=O | | $CH_3$ | $OCH_3$ | |
| $Q_{32}(R_{13} = OCH_3, R_{14} = OCH_3)$ | H | H | C=O | | $OCH_3$ | $OCH_3$ | |
| $Q_{32}(R_{13} = OCH_3, R_{14} = OCH_3)$ | H | H | C=O | | Cl | $OCH_3$ | |
| $Q_{32}(R_{13} = OCH_3, R_{14} = OCH_3)$ | H | H | OH | H | $CH_3$ | $CH_3$ | |
| $Q_{32}(R_{13} = OCH_3, R_{14} = OCH_3)$ | H | H | OH | H | $CH_3$ | $OCH_3$ | |
| $Q_{32}(R_{13} = OCH_3, R_{14} = OCH_3)$ | H | H | OH | H | $OCH_3$ | $OCH_3$ | |
| $Q_{32}(R_{13} = OCH_3, R_{14} = OCH_3)$ | H | H | OH | H | Cl | $OCH_3$ | |
| $Q_{33}(R_7 = H)$ | H | H | C=O | | $CH_3$ | $CH_3$ | |

TABLE X-continued

General Formula X

| Q | R | $R_1$ | $R_2$ | $R_3$ | X | Y | m.p. (°C.) |
|---|---|---|---|---|---|---|---|
| $Q_{33}(R_7 = H)$ | H | H | C=O |  | $CH_3$ | $OCH_3$ |  |
| $Q_{33}(R_7 = H)$ | H | H | C=O |  | $OCH_3$ | $OCH_3$ |  |
| $Q_{33}(R_7 = H)$ | H | H | C=O |  | Cl | $OCH_3$ |  |
| $Q_{33}(R_7 = H)$ | H | H | OH | H | $CH_3$ | $CH_3$ |  |
| $Q_{33}(R_7 = H)$ | H | H | OH | H | $CH_3$ | $OCH_3$ |  |
| $Q_{33}(R_7 = H)$ | H | H | OH | H | $OCH_3$ | $OCH_3$ |  |
| $Q_{33}(R_7 = H)$ | H | H | OH | H | Cl | $OCH_3$ |  |

TABLE XI

General Formula XI

| Q | R | $R_1$ | $R_2$ | $R_3$ | X | Y | m.p. (°C.) |
|---|---|---|---|---|---|---|---|
| $Q_1(R_7=H,R_8=H,R_9H)$ | H | H | C=O |  | $CH_3$ | $CH_3$ |  |
| $Q_1(R_7=H,R_8=H,R_9H)$ | H | H | C=O |  | $CH_3$ | $OCH_3$ |  |
| $Q_1(R_7=H,R_8=H,R_9H)$ | H | H | C=O |  | $OCH_3$ | $OCH_3$ |  |
| $Q_1(R_7=H,R_8=H,R_9H)$ | H | H | C=O |  | Cl | $OCH_3$ |  |
| $Q_1(R_7=H,R_8=H,R_9H)$ | H | H | OH | H | $CH_3$ | $CH_3$ |  |
| $Q_1(R_7=H,R_8=H,R_9H)$ | H | H | OH | H | $CH_3$ | $OCH_3$ |  |
| $Q_1(R_7=H,R_8=H,R_9H)$ | H | H | OH | H | $OCH_3$ | $OCH_3$ |  |
| $Q_1(R_7=H,R_8=H,R_9H)$ | H | H | OH | H | Cl | $OCH_3$ |  |
| $Q_1(R_7=H,R_8=H,R_9H)$ | H | H | $OCH_3$ | H | $OCH_3$ | $OCH_3$ |  |
| $Q_1(R_7=H,R_8=H,R_9H)$ | H | H | $OCH_2CH_3$ | H | $OCH_3$ | $OCH_3$ |  |
| $Q_2(R_7=H,R_8=H,R_9H)$ | H | H | C=O |  | $CH_3$ | $CH_3$ |  |
| $Q_2(R_7=H,R_8=H,R_9H)$ | H | H | C=O |  | $CH_3$ | $OCH_3$ |  |
| $Q_2(R_7=H,R_8=H,R_9H)$ | H | H | C=O |  | $OCH_3$ | $OCH_3$ |  |
| $Q_2(R_7=H,R_8=H,R_9H)$ | H | H | C=O |  | Cl | $OCH_3$ |  |
| $Q_2(R_7=H,R_8=H,R_9H)$ | H | H | OH | H | $CH_3$ | $CH_3$ |  |
| $Q_2(R_7=H,R_8=H,R_9H)$ | H | H | OH | H | $CH_3$ | $OCH_3$ |  |
| $Q_2(R_7=H,R_8=H,R_9H)$ | H | H | OH | H | $OCH_3$ | $OCH_3$ |  |
| $Q_2(R_7=H,R_8=H,R_9H)$ | H | H | OH | H | Cl | $OCH_3$ |  |
| $Q_2(R_7=H,R_8=H,R_9H)$ | H | H | $OCH_3$ | H | $CH_3$ | $OCH_3$ |  |
| $Q_2(R_7=H,R_8=H,R_9H)$ | H | H | $OCH_2CH_3$ | H | $CH_3$ | $CH_3$ |  |
| $Q_3(R_7=H,R_8=H,R_9H)$ | H | H | C=O |  | $CH_3$ | $CH_3$ |  |
| $Q_3(R_7=H,R_8=H,R_9H)$ | H | H | C=O |  | $CH_3$ | $OCH_3$ |  |
| $Q_3(R_7=H,R_8=H,R_9H)$ | H | H | C=O |  | $OCH_3$ | $OCH_3$ |  |
| $Q_3(R_7=H,R_8=H,R_9H)$ | H | H | C=O |  | Cl | $OCH_3$ |  |
| $Q_3(R_7=H,R_8=H,R_9H)$ | H | H | OH | H | $CH_3$ | $CH_3$ |  |
| $Q_3(R_7=H,R_8=H,R_9H)$ | H | H | OH | H | $CH_3$ | $OCH_3$ |  |
| $Q_3(R_7=H,R_8=H,R_9H)$ | H | H | OH | H | $OCH_3$ | $OCH_3$ |  |
| $Q_3(R_7=H,R_8=H,R_9H)$ | H | H | OH | H | Cl | $OCH_3$ |  |
| $Q_3(R_7=H,R_8=H,R_9Cl)$ | H | H | C=O |  | $OCH_3$ | $OCH_3$ |  |
| $Q_3(R_7=H,R_8=H,R_9CH_3)$ | H | H | C=O |  | $OCH_3$ | $OCH_3$ |  |
| $Q_3(R_7=H,R_8=H,R_9=CH_3)$ | H | H | OH | H | $OCH_3$ | $OCH_3$ |  |
| $Q_4(R_7=H,R_8=H,R_9=H)$ | H | H | C=O |  | $CH_3$ | $CH_3$ |  |
| $Q_4(R_7=H,R_8=H,R_9=H)$ | H | H | C=O |  | $CH_3$ | $OCH_3$ |  |
| $Q_4(R_7=H,R_8=H,R_9=H)$ | H | H | C=O |  | $OCH_3$ | $OCH_3$ |  |
| $Q_4(R_7=H,R_8=H,R_9=H)$ | H | H | C=O |  | Cl | $OCH_3$ |  |
| $Q_4(R_7=H,R_8=H,R_9=H)$ | H | H | OH | H | $CH_3$ | $CH_3$ |  |
| $Q_4(R_7=H,R_8=H,R_9=H)$ | H | H | OH | H | $CH_3$ | $OCH_3$ |  |
| $Q_4(R_7=H,R_8=H,R_9=H)$ | H | H | OH | H | $OCH_3$ | $OCH_3$ |  |
| $Q_4(R_7=H,R_8=H,R_9=H)$ | H | H | OH | H | Cl | $OCH_3$ |  |
| $Q_5(R_7=H,R_8=H,R_9=H,R_{10}=CH_3)$ | H | H | C=O |  | $CH_3$ | $CH_3$ |  |
| $Q_5(R_7=H,R_8=H,R_9=H,R_{10}=CH_3)$ | H | H | C=O |  | $CH_3$ | $OCH_3$ |  |
| $Q_5(R_7=H,R_8=H,R_9=H,R_{10}=CH_3)$ | H | H | C=O |  | $OCH_3$ | $OCH_3$ |  |
| $Q_5(R_7=H,R_8=H,R_9=H,R_{10}=CH_3)$ | H | H | C=O |  | Cl | $OCH_3$ |  |
| $Q_5(R_7=H,R_8=H,R_9=H,R_{10}=CH_3)$ | H | H | OH | H | $CH_3$ | $CH_3$ |  |
| $Q_5(R_7=H,R_8=H,R_9=H,R_{10}=CH_3)$ | H | H | OH | H | $CH_3$ | $OCH_3$ |  |
| $Q_5(R_7=H,R_8=H,R_9=H,R_{10}=CH_3)$ | H | H | OH | H | $OCH_3$ | $OCH_3$ |  |
| $Q_5(R_7=H,R_8=H,R_9=H,R_{10}=CH_3)$ | H | H | OH | H | Cl | $OCH_3$ |  |
| $Q_5(R_7=H,R_8=H,R_9=H,R_{10}=CH_3)$ | H | H | $OCH_3$ | H | Cl | $OCH_3$ |  |
| $Q_5(R_7=H,R_8=H,R_9=H,R_{10}=CH_3)$ | H | H | $OCH_2CH_3$ | H | $OCH_3$ | $OCH_3$ |  |
| $Q_6(R_7=H,R_8=H,R_9=H,R_{10}=CH_3)$ | H | H | C=O |  | $CH_3$ | $CH_3$ |  |
| $Q_6(R_7=H,R_8=H,R_9=H,R_{10}=CH_3)$ | H | H | C=O |  | $CH_3$ | $OCH_3$ |  |
| $Q_6(R_7=H,R_8=H,R_9=H,R_{10}=CH_3)$ | H | H | C=O |  | $OCH_3$ | $OCH_3$ |  |
| $Q_6(R_7=H,R_8=H,R_9=H,R_{10}=CH_3)$ | H | H | C=O |  | Cl | $OCH_3$ |  |
| $Q_6(R_7=H,R_8=H,R_9=H,R_{10}=CH_3)$ | H | H | OH | H | $CH_3$ | $CH_3$ |  |
| $Q_6(R_7=H,R_8=H,R_9=H,R_{10}=CH_3)$ | H | H | OH | H | $CH_3$ | $OCH_3$ |  |
| $Q_6(R_7=H,R_8=H,R_9=H,R_{10}=CH_3)$ | H | H | OH | H | $OCH_3$ | $OCH_3$ |  |
| $Q_6(R_7=H,R_8=H,R_9=H,R_{10}=CH_3)$ | H | H | OH | H | Cl | $OCH_3$ |  |
| $Q_7(R_7=H,R_8=H)$ | H | H | C=O |  | $CH_3$ | $CH_3$ |  |
| $Q_7(R_7=H,R_8=H)$ | H | H | C=O |  | $CH_3$ | $OCH_3$ |  |
| $Q_7(R_7=H,R_8=H)$ | H | H | C=O |  | $OCH_3$ | $OCH_3$ |  |
| $Q_7(R_7=H,R_8=H)$ | H | H | C=O |  | Cl | $OCH_3$ |  |
| $Q_7(R_7=H,R_8=H)$ | H | H | OH | H | $CH_3$ | $CH_3$ |  |
| $Q_7(R_7=H,R_8=H)$ | H | H | OH | H | $CH_3$ | $OCH_3$ |  |
| $Q_7(R_7=H,R_8=H)$ | H | H | OH | H | $OCH_3$ | $OCH_3$ |  |
| $Q_7(R_7=H,R_8=H)$ | H | H | OH | H | Cl | $OCH_3$ |  |
| $Q_8(R_7=H,R_8=H)$ | H | H | C=O |  | $OCH_3$ | $OCH_3$ |  |

TABLE XI-continued

| Q | General Formula XI | | | | | | m.p. (°C.) |
|---|---|---|---|---|---|---|---|
| | R | R₁ | R₂ | R₃ | X | Y | |
| Q₈(R₇=H,R₈=H) | H | H | C=O | | Cl | OCH₃ | |
| Q₈(R₇=H,R₈=H) | H | H | OH | H | Cl | OCH₃ | |
| Q₈(R₇=H,R₈=H) | H | H | OH | H | OCH₃ | OCH₃ | |
| Q₉(R₇=H,R₈=H) | H | H | C=O | | CH₃ | CH₃ | |
| Q₉(R₇=H,R₈=H) | H | H | C=O | | CH₃ | OCH₃ | |
| Q₉(R₇=H,R₈=H) | H | H | C=O | | OCH₃ | OCH₃ | |
| Q₉(R₇=H,R₈=H) | H | H | C=O | | Cl | OCH₃ | |
| Q₉(R₇=H,R₈=H) | H | H | OH | H | CH₃ | CH₃ | |
| Q₉(R₇=H,R₈=H) | H | H | OH | H | CH₃ | OCH₃ | |
| Q₉(R₇=H,R₈=H) | H | H | OH | H | OCH₃ | OCH₃ | |
| Q₉(R₇=H,R₈=H) | H | H | OH | H | Cl | OCH₃ | |
| Q₁₀(R₇=H,R₈=H) | H | H | C=O | | CH₃ | OCH₃ | |
| Q₁₀(R₇=H,R₈=H) | H | H | C=O | | OCH₃ | OCH₃ | |
| Q₁₀(R₇=H,R₈=H) | H | H | C=O | | Cl | OCH₃ | |
| Q₁₀(R₇=H,R₈=H) | H | H | OH | H | CH₃ | CH₃ | |
| Q₁₀(R₇=H,R₈=H) | H | H | OH | H | OCH₃ | OCH₃ | |
| Q₁₀(R₇=H,R₈=H) | H | H | OH | H | Cl | OCH₃ | |
| Q₁₁(R₇=H,R₈=H) | H | H | C=O | | CH₃ | CH₃ | |
| Q₁₁(R₇=H,R₈=H) | H | H | C=O | | CH₃ | OCH₃ | |
| Q₁₁(R₇=H,R₈=H) | H | H | C=O | | OCH₃ | OCH₃ | |
| Q₁₁(R₇=H,R₈=H) | H | H | C=O | | Cl | OCH₃ | |
| Q₁₁(R₇=H,R₈=H) | H | H | OH | H | CH₃ | CH₃ | |
| Q₁₁(R₇=H,R₈=H) | H | H | OH | H | CH₃ | OCH₃ | |
| Q₁₁(R₇=H,R₈=H) | H | H | OH | H | OCH₃ | OCH₃ | |
| Q₁₁(R₇=H,R₈=H) | H | H | OH | H | Cl | OCH₃ | |
| Q₁₂(R₇=H,R₈=H) | H | H | C=O | | CH₃ | CH₃ | |
| Q₁₂(R₇=H,R₈=H) | H | H | C=O | | CH₃ | OCH₃ | |
| Q₁₂(R₇=H,R₈=H) | H | H | C=O | | OCH₃ | OCH₃ | |
| Q₁₂(R₇=H,R₈=H) | H | H | C=O | | Cl | OCH₃ | |
| Q₁₂(R₇=H,R₈=H) | H | H | OH | H | CH₃ | CH₃ | |
| Q₁₂(R₇=H,R₈=H) | H | H | OH | H | CH₃ | OCH₃ | |
| Q₁₂(R₇=H,R₈=H) | H | H | OH | H | OCH₃ | OCH₃ | |
| Q₁₂(R₇=H,R₈=H) | H | H | OH | H | Cl | OCH₃ | |
| Q₁₂(R₇=H,R₈=H) | H | H | OCH₃ | H | OCH₃ | OCH₃ | |
| Q₁₃(R₇=H,R₈=H) | H | H | C=O | | CH₃ | CH₃ | |
| Q₁₃(R₇=H,R₈=H) | H | H | C=O | | CH₃ | OCH₃ | |
| Q₁₃(R₇=H,R₈=H) | H | H | C=O | | OCH₃ | OCH₃ | |
| Q₁₃(R₇=H,R₈=H) | H | H | C=O | | Cl | OCH₃ | |
| Q₁₃(R₇=H,R₈=H) | H | H | OH | H | CH₃ | CH₃ | |
| Q₁₃(R₇=H,R₈=H) | H | H | OH | H | CH₃ | OCH₃ | |
| Q₁₃(R₇=H,R₈=H) | H | H | OH | H | OCH₃ | OCH₃ | |
| Q₁₃(R₇=H,R₈=H) | H | H | OH | H | Cl | OCH₃ | |
| Q₁₄(R₇=H) | H | H | C=O | | CH₃ | CH₃ | |
| Q₁₄(R₇=H) | H | H | C=O | | CH₃ | OCH₃ | |
| Q₁₄(R₇=H) | H | H | C=O | | OCH₃ | OCH₃ | |
| Q₁₄(R₇=H) | H | H | C=O | | Cl | OCH₃ | |
| Q₁₄(R₇=H) | H | H | OH | H | CH₃ | CH₃ | |
| Q₁₄(R₇=H) | H | H | OH | H | CH₃ | OCH₃ | |
| Q₁₄(R₇=H) | H | H | OH | H | OCH₃ | OCH₃ | |
| Q₁₄(R₇=H) | H | H | OH | H | Cl | OCH₃ | |
| Q₁₅(R₇=H) | H | H | C=O | | CH₃ | CH₃ | |
| Q₁₅(R₇=H) | H | H | C=O | | CH₃ | OCH₃ | |
| Q₁₅(R₇=H) | H | H | C=O | | OCH₃ | OCH₃ | |
| Q₁₅(R₇=H) | H | H | C=O | | Cl | OCH₃ | |
| Q₁₅(R₇=H) | H | H | OH | H | CH₃ | CH₃ | |
| Q₁₅(R₇=H) | H | H | OH | H | CH₃ | OCH₃ | |
| Q₁₅(R₇=H) | H | H | OH | H | OCH₃ | OCH₃ | |
| Q₁₅(R₇=H) | H | H | OH | H | Cl | OCH₃ | |
| Q₁₆(R₇=H) | H | H | C=O | | CH₃ | CH₃ | |
| Q₁₆(R₇=H) | H | H | C=O | | CH₃ | OCH₃ | |
| Q₁₆(R₇=H) | H | H | C=O | | OCH₃ | OCH₃ | |
| Q₁₆(R₇=H) | H | H | C=O | | Cl | OCH₃ | |
| Q₁₆(R₇=H) | H | H | OH | H | CH₃ | CH₃ | |
| Q₁₆(R₇=H) | H | H | OH | H | CH₃ | OCH₃ | |
| Q₁₆(R₇=H) | H | H | OH | H | OCH₃ | OCH₃ | |
| Q₁₆(R₇=H) | H | H | OH | H | Cl | OCH₃ | |
| Q₁₇(R₇=CH₃) | H | H | C=O | | CH₃ | CH₃ | |
| Q₁₇(R₇=CH₃) | H | H | C=O | | CH₃ | OCH₃ | |
| Q₁₇(R₇=CH₃) | H | H | C=O | | OCH₃ | OCH₃ | |
| Q₁₇(R₇=CH₃) | H | H | C=O | | Cl | OCH₃ | |
| Q₁₇(R₇=CH₃) | H | H | OH | H | CH₃ | CH₃ | |
| Q₁₇(R₇=CH₃) | H | H | OH | H | CH₃ | OCH₃ | |
| Q₁₇(R₇=CH₃) | H | H | OH | H | OCH₃ | OCH₃ | |
| Q₁₇(R₇=CH₃) | H | H | OH | H | Cl | OCH₃ | |
| Q₁₈(R₇=H) | H | H | C=O | | CH₃ | CH₃ | |
| Q₁₈(R₇=H) | H | H | C=O | | CH₃ | OCH₃ | |
| Q₁₈(R₇=H) | H | H | C=O | | OCH₃ | OCH₃ | |
| Q₁₈(R₇=H) | H | H | C=O | | Cl | OCH₃ | |
| Q₁₈(R₇=H) | H | H | OH | H | CH₃ | CH₃ | |
| Q₁₈(R₇=H) | H | H | OH | H | CH₃ | OCH₃ | |

TABLE XI-continued

| | General Formula XI | | | | | | |
|---|---|---|---|---|---|---|---|
| Q | R | $R_1$ | $R_2$ | $R_3$ | X | Y | m.p. (°C.) |
| $Q_{18}(R_7=H)$ | H | H | OH | H | $OCH_3$ | $OCH_3$ | |
| $Q_{18}(R_7=H)$ | H | H | OH | H | Cl | $OCH_3$ | |
| $Q_{19}(R_7=H,R_8=H)$ | H | H | C=O | | $CH_3$ | $CH_3$ | |
| $Q_{19}(R_7=H,R_8=H)$ | H | H | C=O | | $CH_3$ | $OCH_3$ | |
| $Q_{19}(R_7=H,R_8=H)$ | H | H | C=O | | $OCH_3$ | $OCH_3$ | |
| $Q_{19}(R_7=H,R_8=H)$ | H | H | C=O | | Cl | $OCH_3$ | |
| $Q_{19}(R_7=H,R_8=H)$ | H | H | OH | H | $CH_3$ | $CH_3$ | |
| $Q_{19}(R_7=H,R_8=H)$ | H | H | OH | H | $CH_3$ | $OCH_3$ | |
| $Q_{19}(R_7=H,R_8=H)$ | H | H | OH | H | $OCH_3$ | $OCH_3$ | |
| $Q_{19}(R_7=H,R_8=H)$ | H | H | OH | H | Cl | $OCH_3$ | |
| $Q_{20}(R_7=H,R_8=H)$ | H | H | C=O | | $CH_3$ | $CH_3$ | |
| $Q_{20}(R_7=H,R_8=H)$ | H | H | C=O | | $CH_3$ | $OCH_3$ | |
| $Q_{20}(R_7=H,R_8=H)$ | H | H | C=O | | $OCH_3$ | $OCH_3$ | |
| $Q_{20}(R_7=H,R_8=H)$ | H | H | C=O | | Cl | $OCH_3$ | |
| $Q_{20}(R_7=H,R_8=H)$ | H | H | OH | H | $CH_3$ | $CH_3$ | |
| $Q_{20}(R_7=H,R_8=H)$ | H | H | OH | H | $CH_3$ | $OCH_3$ | |
| $Q_{20}(R_7=H,R_8=H)$ | H | H | OH | H | $OCH_3$ | $OCH_3$ | |
| $Q_{20}(R_7=H,R_8=H)$ | H | H | OH | H | Cl | $OCH_3$ | |
| $Q_{21}(R_7=H,R_8=H,R_9=CH_3)$ | H | H | C=O | | $CH_3$ | $CH_3$ | |
| $Q_{21}(R_7=H,R_8=H,R_9=CH_3)$ | H | H | C=O | | $CH_3$ | $OCH_3$ | |
| $Q_{21}(R_7=H,R_8=H,R_9=CH_3)$ | H | H | C=O | | $OCH_3$ | $OCH_3$ | |
| $Q_{21}(R_7=H,R_8=H,R_9=CH_3)$ | H | H | C=O | | Cl | $OCH_3$ | |
| $Q_{21}(R_7=H,R_8=H,R_9=CH_3)$ | H | H | OH | H | $CH_3$ | $CH_3$ | |
| $Q_{21}(R_7=H,R_8=H,R_9=CH_3)$ | H | H | OH | H | $CH_3$ | $OCH_3$ | |
| $Q_{21}(R_7=H,R_8=H,R_9=CH_3)$ | H | H | OH | H | $OCH_3$ | $OCH_3$ | |
| $Q_{21}(R_7=H,R_8=H,R_9=CH_3)$ | H | H | OH | H | Cl | $OCH_3$ | |
| $Q_{22}(R_7=H)$ | H | H | C=O | | $CH_3$ | $CH_3$ | |
| $Q_{22}(R_7=H)$ | H | H | C=O | | $CH_3$ | $OCH_3$ | |
| $Q_{22}(R_7=H)$ | H | H | C=O | | $OCH_3$ | $OCH_3$ | |
| $Q_{22}(R_7=H)$ | H | H | C=O | | Cl | $OCH_3$ | |
| $Q_{22}(R_7=H)$ | H | H | OH | H | $CH_3$ | $CH_3$ | |
| $Q_{22}(R_7=H)$ | H | H | OH | H | $CH_3$ | $OCH_3$ | |
| $Q_{22}(R_7=H)$ | H | H | OH | H | $OCH_3$ | $OCH_3$ | |
| $Q_{22}(R_7=H)$ | H | H | OH | H | Cl | $OCH_3$ | |
| $Q_{23}(R_7=H)$ | H | H | C=O | | $CH_3$ | $CH_3$ | |
| $Q_{23}(R_7=H)$ | H | H | C=O | | $CH_3$ | $OCH_3$ | |
| $Q_{23}(R_7=H)$ | H | H | C=O | | $OCH_3$ | $OCH_3$ | |
| $Q_{23}(R_7=H)$ | H | H | C=O | | Cl | $OCH_3$ | |
| $Q_{23}(R_7=H)$ | H | H | OH | H | $CH_3$ | $CH_3$ | |
| $Q_{23}(R_7=H)$ | H | H | OH | H | $CH_3$ | $OCH_3$ | |
| $Q_{23}(R_7=H)$ | H | H | OH | H | $OCH_3$ | $OCH_3$ | |
| $Q_{23}(R_7=H)$ | H | H | OH | H | Cl | $OCH_3$ | |
| $Q_{24}(R_7=H,R_8=H)$ | H | H | C=O | | $CH_3$ | $CH_3$ | |
| $Q_{24}(R_7=H,R_8=H)$ | H | H | C=O | | $CH_3$ | $OCH_3$ | |
| $Q_{24}(R_7=H,R_8=H)$ | H | H | C=O | | $OCH_3$ | $OCH_3$ | |
| $Q_{24}(R_7=H,R_8=H)$ | H | H | C=O | | Cl | $OCH_3$ | |
| $Q_{24}(R_7=H,R_8=H)$ | H | H | OH | H | $CH_3$ | $CH_3$ | |
| $Q_{24}(R_7=H,R_8=H)$ | H | H | OH | H | $CH_3$ | $OCH_3$ | |
| $Q_{24}(R_7=H,R_8=H)$ | H | H | OH | H | $OCH_3$ | $OCH_3$ | |
| $Q_{24}(R_7=H,R_8=H)$ | H | H | OH | H | Cl | $OCH_3$ | |
| $Q_{25}(R_7=H,R_8=H)$ | H | H | C=O | | $CH_3$ | $CH_3$ | |
| $Q_{25}(R_7=H,R_8=H)$ | H | H | C=O | | $CH_3$ | $OCH_3$ | |
| $Q_{25}(R_7=H,R_8=H)$ | H | H | C=O | | $OCH_3$ | $OCH_3$ | |
| $Q_{25}(R_7=H,R_8=H)$ | H | H | C=O | | Cl | $OCH_3$ | |
| $Q_{25}(R_7=H,R_8=H)$ | H | H | OH | H | $CH_3$ | $CH_3$ | |
| $Q_{25}(R_7=H,R_8=H)$ | H | H | OH | H | $CH_3$ | $OCH_3$ | |
| $Q_{25}(R_7=H,R_8=H)$ | H | H | OH | H | $OCH_3$ | $OCH_3$ | |
| $Q_{25}(R_7=H,R_8=H)$ | H | H | OH | H | Cl | $OCH_3$ | |
| $Q_{26}(R_7=H,R_8=H)$ | H | H | C=O | | $CH_3$ | $CH_3$ | |
| $Q_{26}(R_7=H,R_8=H)$ | H | H | C=O | | $CH_3$ | $OCH_3$ | |
| $Q_{26}(R_7=H,R_8=H)$ | H | H | C=O | | $OCH_3$ | $OCH_3$ | |
| $Q_{26}(R_7=H,R_8=H)$ | H | H | C=O | | Cl | $OCH_3$ | |
| $Q_{26}(R_7=H,R_8=H)$ | H | H | OH | H | $CH_3$ | $CH_3$ | |
| $Q_{26}(R_7=H,R_8=H)$ | H | H | OH | H | $CH_3$ | $OCH_3$ | |
| $Q_{26}(R_7=H,R_8=H)$ | H | H | OH | H | $OCH_3$ | $OCH_3$ | |
| $Q_{26}(R_7=H,R_8=H)$ | H | H | OH | H | Cl | $OCH_3$ | |
| $Q_{27}(R_7=H,R_{11}=H,R_{12}=H)$ | H | H | C=O | | $CH_3$ | $CH_3$ | |
| $Q_{27}(R_7=H,R_{11}=H,R_{12}=H)$ | H | H | C=O | | $CH_3$ | $OCH_3$ | |
| $Q_{27}(R_7=H,R_{11}=H,R_{12}=H)$ | H | H | C=O | | $OCH_3$ | $OCH_3$ | |
| $Q_{27}(R_7=H,R_{11}=H,R_{12}=H)$ | H | H | C=O | | Cl | $OCH_3$ | |
| $Q_{27}(R_7=H,R_{11}=H,R_{12}=H)$ | H | H | OH | H | $CH_3$ | $CH_3$ | |
| $Q_{27}(R_7=H,R_{11}=H,R_{12}=H)$ | H | H | OH | H | $CH_3$ | $OCH_3$ | |
| $Q_{27}(R_7=H,R_{11}=H,R_{12}=H)$ | H | H | OH | H | $OCH_3$ | $OCH_3$ | |
| $Q_{27}(R_7=H,R_{11}=H,R_{12}=H)$ | H | H | OH | H | Cl | $OCH_3$ | |
| $Q_{28}(R_{11}=H,R_{12}=H)$ | H | H | C=O | | $CH_3$ | $CH_3$ | |
| $Q_{28}(R_{11}=H,R_{12}=H)$ | H | H | C=O | | $CH_3$ | $OCH_3$ | |
| $Q_{28}(R_{11}=H,R_{12}=H)$ | H | H | C=O | | $OCH_3$ | $OCH_3$ | |
| $Q_{28}(R_{11}=H,R_{12}=H)$ | H | H | C=O | | Cl | $OCH_3$ | |
| $Q_{28}(R_{11}=H,R_{12}=H)$ | H | H | OH | H | $CH_3$ | $CH_3$ | |
| $Q_{28}(R_{11}=H,R_{12}=H)$ | H | H | OH | H | $CH_3$ | $OCH_3$ | |

TABLE XI-continued

General Formula XI

| Q | R | R₁ | R₂ | R₃ | X | Y | m.p. (°C.) |
|---|---|---|---|---|---|---|---|
| Q₂₈(R₁₁=H,R₁₂=H) | H | H | OH | H | OCH₃ | OCH₃ | |
| Q₂₈(R₁₁=H,R₁₂=H) | H | H | OH | H | Cl | OCH₃ | |
| Q₂₉(R₁₁=H,R₁₂=H) | H | H | C=O | | CH₃ | CH₃ | |
| Q₂₉(R₁₁=H,R₁₂=H) | H | H | C=O | | CH₃ | OCH₃ | |
| Q₂₉(R₁₁=H,R₁₂=H) | H | H | C=O | | OCH₃ | OCH₃ | |
| Q₂₉(R₁₁=H,R₁₂=H) | H | H | C=O | | Cl | OCH₃ | |
| Q₂₉(R₁₁=H,R₁₂=H) | H | H | OH | H | CH₃ | CH₃ | |
| Q₂₉(R₁₁=H,R₁₂=H) | H | H | OH | H | CH₃ | OCH₃ | |
| Q₂₉(R₁₁=H,R₁₂=H) | H | H | OH | H | OCH₃ | OCH₃ | |
| Q₂₉(R₁₁=H,R₁₂=H) | H | H | OH | H | Cl | OCH₃ | |
| Q₃₀(R₇=H,R₈=H) | H | H | C=O | | CH₃ | CH₃ | |
| Q₃₀(R₇=H,R₈=H) | H | H | C=O | | CH₃ | OCH₃ | |
| Q₃₀(R₇=H,R₈=H) | H | H | C=O | | OCH₃ | OCH₃ | |
| Q₃₀(R₇=H,R₈=H) | H | H | C=O | | Cl | OCH₃ | |
| Q₃₀(R₇=H,R₈=H) | H | H | OH | H | CH₃ | CH₃ | |
| Q₃₀(R₇=H,R₈=H) | H | H | OH | H | CH₃ | OCH₃ | |
| Q₃₀(R₇=H,R₈=H) | H | H | OH | H | OCH₃ | OCH₃ | |
| Q₃₀(R₇=H,R₈=H) | H | H | OH | H | Cl | OCH₃ | |
| Q₃₁(R₇=H,R₈=H) | H | H | C=O | | CH₃ | CH₃ | |
| Q₃₁(R₇=H,R₈=H) | H | H | C=O | | CH₃ | OCH₃ | |
| Q₃₁(R₇=H,R₈=H) | H | H | C=O | | OCH₃ | OCH₃ | |
| Q₃₁(R₇=H,R₈=H) | H | H | C=O | | Cl | OCH₃ | |
| Q₃₁(R₇=H,R₈=H) | H | H | OH | H | CH₃ | CH₃ | |
| Q₃₁(R₇=H,R₈=H) | H | H | OH | H | CH₃ | OCH₃ | |
| Q₃₁(R₇=H,R₈=H) | H | H | OH | H | OCH₃ | OCH₃ | |
| Q₃₁(R₇=H,R₈=H) | H | H | OH | H | Cl | OCH₃ | |
| Q₃₂(R₁₃=OCH₃,R₁₄=OCH₃) | H | H | C=O | | CH₃ | CH₃ | |
| Q₃₂(R₁₃=OCH₃,R₁₄=OCH₃) | H | H | C=O | | CH₃ | OCH₃ | |
| Q₃₂(R₁₃=OCH₃,R₁₄=OCH₃) | H | H | C=O | | OCH₃ | OCH₃ | |
| Q₃₂(R₁₃=OCH₃,R₁₄=OCH₃) | H | H | C=O | | Cl | OCH₃ | |
| Q₃₂(R₁₃=OCH₃,R₁₄=OCH₃) | H | H | OH | H | CH₃ | CH₃ | |
| Q₃₂(R₁₃=OCH₃,R₁₄=OCH₃) | H | H | OH | H | CH₃ | OCH₃ | |
| Q₃₂(R₁₃=OCH₃,R₁₄=OCH₃) | H | H | OH | H | OCH₃ | OCH₃ | |
| Q₃₂(R₁₃=OCH₃,R₁₄=OCH₃) | H | H | OH | H | Cl | OCH₃ | |
| Q₃₃(R₇=H) | H | H | C=O | | CH₃ | CH₃ | |
| Q₃₃(R₇=H) | H | H | C=O | | CH₃ | OCH₃ | |
| Q₃₃(R₇=H) | H | H | C=O | | OCH₃ | OCH₃ | |
| Q₃₃(R₇=H) | H | H | C=O | | Cl | OCH₃ | |
| Q₃₃(R₇=H) | H | H | OH | H | CH₃ | CH₃ | |
| Q₃₃(R₇=H) | H | H | OH | H | CH₃ | OCH₃ | |
| Q₃₃(R₇=H) | H | H | OH | H | OCH₃ | OCH₃ | |
| Q₃₃(R₇=H) | H | H | OH | H | Cl | OCH₃ | |

TABLE XII

General Formula XII

| Q | R | R₁ | R₂ | R₃ | X | Y | m.p. (°C.) |
|---|---|---|---|---|---|---|---|
| Q₁(R₇=H,R₈=H,R₉=H) | H | H | C=O | | CH₃ | CH₃ | |
| Q₁(R₇=H,R₈=H,R₉=H) | H | H | C=O | | CH₃ | OCH₃ | |
| Q₁(R₇=H,R₈=H,R₉=H) | H | H | C=O | | OCH₃ | OCH₃ | |
| Q₁(R₇=H,R₈=H,R₉=H) | H | H | C=O | | Cl | OCH₃ | |
| Q₁(R₇=H,R₈=H,R₉=H) | H | H | OH | H | CH₃ | CH₃ | |
| Q₁(R₇=H,R₈=H,R₉=H) | H | H | OH | H | CH₃ | OCH₃ | |
| Q₁(R₇=H,R₈=H,R₉=H) | H | H | OH | H | OCH₃ | OCH₃ | |
| Q₁(R₇=H,R₈=H,R₉=H) | H | H | OH | H | Cl | OCH₃ | |
| Q₁(R₇=H,R₈=H,R₉=H) | H | H | OCH₃ | H | OCH₃ | OCH₃ | |
| Q₁(R₇=H,R₈=H,R₉=H) | H | H | OCH₂CH₃ | H | OCH₃ | OCH₃ | |
| Q₂(R₇=H,R₈=H,R₉=H) | H | H | C=O | | CH₃ | CH₃ | |
| Q₂(R₇=H,R₈=H,R₉=H) | H | H | C=O | | CH₃ | OCH₃ | |
| Q₂(R₇=H,R₈=H,R₉=H) | H | H | C=O | | OCH₃ | OCH₃ | |
| Q₂(R₇=H,R₈=H,R₉=H) | H | H | C=O | | Cl | OCH₃ | |
| Q₂(R₇=H,R₈=H,R₉=H) | H | H | OH | H | CH₃ | CH₃ | |
| Q₂(R₇=H,R₈=H,R₉=H) | H | H | OH | H | CH₃ | OCH₃ | |
| Q₂(R₇=H,R₈=H,R₉=H) | H | H | OH | H | OCH₃ | OCH₃ | |
| Q₂(R₇=H,R₈=H,R₉=H) | H | H | OH | H | Cl | OCH₃ | |
| Q₂(R₇=H,R₈=H,R₉=H) | H | H | OCH₃ | H | OCH₃ | OCH₃ | |
| Q₂(R₇=H,R₈=H,R₉=H) | H | H | OCH₂CH₃ | H | CH₃ | CH₃ | |
| Q₃(R₇=H,R₈=H,R₉=H) | H | H | C=O | | CH₃ | CH₃ | |
| Q₃(R₇=H,R₈=H,R₉=H) | H | H | C=O | | CH₃ | OCH₃ | |
| Q₃(R₇=H,R₈=H,R₉=H) | H | H | C=O | | OCH₃ | OCH₃ | |
| Q₃(R₇=H,R₈=H,R₉=H) | H | H | C=O | | Cl | OCH₃ | |
| Q₃(R₇=H,R₈=H,R₉=H) | H | H | OH | H | CH₃ | CH₃ | |
| Q₃(R₇=H,R₈=H,R₉=H) | H | H | OH | H | CH₃ | OCH₃ | |
| Q₃(R₇=H,R₈=H,R₉=H) | H | H | OH | H | OCH₃ | OCH₃ | |
| Q₃(R₇=H,R₈=H,R₉=H) | H | H | OH | H | Cl | OCH₃ | |
| Q₃(R₇=H,R₈=H,R₉=Cl) | H | H | C=O | | OCH₃ | OCH₃ | |
| Q₃(R₇=H,R₈=H,R₉=CH₃) | H | H | C=O | | OCH₃ | OCH₃ | |
| Q₃(R₇=H,R₈=H,R₉=CH₃) | H | H | OH | H | OCH₃ | OCH₃ | |

TABLE XII-continued

General Formula XII

| Q | R | R$_1$ | R$_2$ | R$_3$ | X | Y | m.p. (°C.) |
|---|---|---|---|---|---|---|---|
| Q$_4$(R$_7$=H,R$_8$=H,R$_9$=H) | H | H | C=O | | CH$_3$ | CH$_3$ | |
| Q$_4$(R$_7$=H,R$_8$=H,R$_9$=H) | H | H | C=O | | CH$_3$ | OCH$_3$ | |
| Q$_4$(R$_7$=H,R$_8$=H,R$_9$=H) | H | H | C=O | | OCH$_3$ | OCH$_3$ | |
| Q$_4$(R$_7$=H,R$_8$=H,R$_9$=H) | H | H | C=O | | Cl | OCH$_3$ | |
| Q$_4$(R$_7$=H,R$_8$=H,R$_9$=H) | H | H | OH | H | CH$_3$ | CH$_3$ | |
| Q$_4$(R$_7$=H,R$_8$=H,R$_9$=H) | H | H | OH | H | CH$_3$ | OCH$_3$ | |
| Q$_4$(R$_7$=H,R$_8$=H,R$_9$=H) | H | H | OH | H | OCH$_3$ | OCH$_3$ | |
| Q$_4$(R$_7$=H,R$_8$=H,R$_9$=H) | H | H | OH | H | Cl | OCH$_3$ | |
| Q$_5$(R$_7$=H,R$_8$=H,R$_9$=H,R$_{10}$=CH$_3$) | H | H | C=O | | CH$_3$ | CH$_3$ | |
| Q$_5$(R$_7$=H,R$_8$=H,R$_9$=H,R$_{10}$=CH$_3$) | H | H | C=O | | CH$_3$ | OCH$_3$ | |
| Q$_5$(R$_7$=H,R$_8$=H,R$_9$=H,R$_{10}$=CH$_3$) | H | H | C=O | | OCH$_3$ | OCH$_3$ | |
| Q$_5$(R$_7$=H,R$_8$=H,R$_9$=H,R$_{10}$=CH$_3$) | H | H | C=O | | Cl | OCH$_3$ | |
| Q$_5$(R$_7$=H,R$_8$=H,R$_9$=H,R$_{10}$=CH$_3$) | H | H | OH | H | CH$_3$ | CH$_3$ | |
| Q$_5$(R$_7$=H,R$_8$=H,R$_9$=H,R$_{10}$=CH$_3$) | H | H | OH | H | CH$_3$ | OCH$_3$ | |
| Q$_5$(R$_7$=H,R$_8$=H,R$_9$=H,R$_{10}$=CH$_3$) | H | H | OH | H | OCH$_3$ | OCH$_3$ | |
| Q$_5$(R$_7$=H,R$_8$=H,R$_9$=H,R$_{10}$=CH$_3$) | H | H | OH | H | Cl | OCH$_3$ | |
| Q$_5$(R$_7$=H,R$_8$=H,R$_9$=H,R$_{10}$=CH$_3$) | H | H | OCH$_3$ | H | Cl | OCH$_3$ | |
| Q$_5$(R$_7$=H,R$_8$=H,R$_9$=H,R$_{10}$=CH$_3$) | H | H | OCH$_2$CH$_3$ | H | OCH$_3$ | OCH$_3$ | |
| Q$_6$(R$_7$=H,R$_8$=H,R$_9$=H,R$_{10}$=CH$_3$) | H | H | C=O | | CH$_3$ | CH$_3$ | |
| Q$_6$(R$_7$=H,R$_8$=H,R$_9$=H,R$_{10}$=CH$_3$) | H | H | C=O | | CH$_3$ | OCH$_3$ | |
| Q$_6$(R$_7$=H,R$_8$=H,R$_9$=H,R$_{10}$=CH$_3$) | H | H | C=O | | OCH$_3$ | OCH$_3$ | |
| Q$_6$(R$_7$=H,R$_8$=H,R$_9$=H,R$_{10}$=CH$_3$) | H | H | C=O | | Cl | OCH$_3$ | |
| Q$_6$(R$_7$=H,R$_8$=H,R$_9$=H,R$_{10}$=CH$_3$) | H | H | OH | H | CH$_3$ | CH$_3$ | |
| Q$_6$(R$_7$=H,R$_8$=H,R$_9$=H,R$_{10}$=CH$_3$) | H | H | OH | H | CH$_3$ | OCH$_3$ | |
| Q$_6$(R$_7$=H,R$_8$=H,R$_9$=H,R$_{10}$=CH$_3$) | H | H | OH | H | OCH$_3$ | OCH$_3$ | |
| Q$_6$(R$_7$=H,R$_8$=H,R$_9$=H,R$_{10}$=CH$_3$) | H | H | OH | H | Cl | OCH$_3$ | |
| Q$_7$(R$_7$=H,R$_8$=H) | H | H | C=O | | CH$_3$ | CH$_3$ | |
| Q$_7$(R$_7$=H,R$_8$=H) | H | H | C=O | | CH$_3$ | OCH$_3$ | |
| Q$_7$(R$_7$=H,R$_8$=H) | H | H | C=O | | OCH$_3$ | OCH$_3$ | |
| Q$_7$(R$_7$=H,R$_8$=H) | H | H | C=O | | Cl | OCH$_3$ | |
| Q$_7$(R$_7$=H,R$_8$=H) | H | H | OH | H | CH$_3$ | CH$_3$ | |
| Q$_7$(R$_7$=H,R$_8$=H) | H | H | OH | H | CH$_3$ | OCH$_3$ | |
| Q$_7$(R$_7$=H,R$_8$=H) | H | H | OH | H | OCH$_3$ | OCH$_3$ | |
| Q$_7$(R$_7$=H,R$_8$=H) | H | H | OH | H | Cl | OCH$_3$ | |
| Q$_8$(R$_7$=H,R$_8$=H) | H | H | C=O | | OCH$_3$ | OCH$_3$ | |
| Q$_8$(R$_7$=H,R$_8$=H) | H | H | C=O | | Cl | OCH$_3$ | |
| Q$_8$(R$_7$=H,R$_8$=H) | H | H | OH | H | Cl | OCH$_3$ | |
| Q$_8$(R$_7$=H,R$_8$=H) | H | H | OH | H | OCH$_3$ | OCH$_3$ | |
| Q$_9$(R$_7$=H,R$_8$=H) | H | H | C=O | | CH$_3$ | CH$_3$ | |
| Q$_9$(R$_7$=H,R$_8$=H) | H | H | C=O | | CH$_3$ | OCH$_3$ | |
| Q$_9$(R$_7$=H,R$_8$=H) | H | H | C=O | | OCH$_3$ | OCH$_3$ | |
| Q$_9$(R$_7$=H,R$_8$=H) | H | H | C=O | | Cl | OCH$_3$ | |
| Q$_9$(R$_7$=H,R$_8$=H) | H | H | OH | H | CH$_3$ | CH$_3$ | |
| Q$_9$(R$_7$=H,R$_8$=H) | H | H | OH | H | CH$_3$ | OCH$_3$ | |
| Q$_9$(R$_7$=H,R$_8$=H) | H | H | OH | H | OCH$_3$ | OCH$_3$ | |
| Q$_9$(R$_7$=H,R$_8$=H) | H | H | OH | H | Cl | OCH$_3$ | |
| Q$_{10}$(R$_7$=H,R$_8$=H) | H | H | C=O | | CH$_3$ | OCH$_3$ | |
| Q$_{10}$(R$_7$=H,R$_8$=H) | H | H | C=O | | OCH$_3$ | OCH$_3$ | |
| Q$_{10}$(R$_7$=H,R$_8$=H) | H | H | C=O | | Cl | OCH$_3$ | |
| Q$_{10}$(R$_7$=H,R$_8$=H) | H | H | OH | H | CH$_3$ | CH$_3$ | |
| Q$_{10}$(R$_7$=H,R$_8$=H) | H | H | OH | H | OCH$_3$ | OCH$_3$ | |
| Q$_{10}$(R$_7$=H,R$_8$=H) | H | H | OH | H | Cl | OCH$_3$ | |
| Q$_{11}$(R$_7$=H,R$_8$=H) | H | H | C=O | | CH$_3$ | CH$_3$ | |
| Q$_{11}$(R$_7$=H,R$_8$=H) | H | H | C=O | | CH$_3$ | OCH$_3$ | |
| Q$_{11}$(R$_7$=H,R$_8$=H) | H | H | C=O | | OCH$_3$ | OCH$_3$ | |
| Q$_{11}$(R$_7$=H,R$_8$=H) | H | H | C=O | | Cl | OCH$_3$ | |
| Q$_{11}$(R$_7$=H,R$_8$=H) | H | H | OH | H | CH$_3$ | CH$_3$ | |
| Q$_{11}$(R$_7$=H,R$_8$=H) | H | H | OH | H | CH$_3$ | OCH$_3$ | |
| Q$_{11}$(R$_7$=H,R$_8$=H) | H | H | OH | H | OCH$_3$ | OCH$_3$ | |
| Q$_{11}$(R$_7$=H,R$_8$=H) | H | H | OH | H | Cl | OCH$_3$ | |
| Q$_{12}$(R$_7$=H,R$_8$=H) | H | H | C=O | | CH$_3$ | CH$_3$ | |
| Q$_{12}$(R$_7$=H,R$_8$=H) | H | H | C=O | | CH$_3$ | OCH$_3$ | |
| Q$_{12}$(R$_7$=H,R$_8$=H) | H | H | C=O | | OCH$_3$ | OCH$_3$ | |
| Q$_{12}$(R$_7$=H,R$_8$=H) | H | H | C=O | | Cl | OCH$_3$ | |
| Q$_{12}$(R$_7$=H,R$_8$=H) | H | H | OH | H | CH$_3$ | CH$_3$ | |
| Q$_{12}$(R$_7$=H,R$_8$=H) | H | H | OH | H | CH$_3$ | OCH$_3$ | |
| Q$_{12}$(R$_7$=H,R$_8$=H) | H | H | OH | H | OCH$_3$ | OCH$_3$ | |
| Q$_{12}$(R$_7$=H,R$_8$=H) | H | H | OH | H | Cl | OCH$_3$ | |
| Q$_{12}$(R$_7$=H,R$_8$=H) | H | H | OCH$_3$ | H | OCH$_3$ | OCH$_3$ | |
| Q$_{13}$(R$_7$=H,R$_8$=H) | H | H | C=O | | CH$_3$ | CH$_3$ | |
| Q$_{13}$(R$_7$=H,R$_8$=H) | H | H | C=O | | CH$_3$ | OCH$_3$ | |
| Q$_{13}$(R$_7$=H,R$_8$=H) | H | H | C=O | | OCH$_3$ | OCH$_3$ | |
| Q$_{13}$(R$_7$=H,R$_8$=H) | H | H | C=O | | Cl | OCH$_3$ | |
| Q$_{13}$(R$_7$=H,R$_8$=H) | H | H | OH | H | CH$_3$ | CH$_3$ | |
| Q$_{13}$(R$_7$=H,R$_8$=H) | H | H | OH | H | CH$_3$ | OCH$_3$ | |
| Q$_{13}$(R$_7$=H,R$_8$=H) | H | H | OH | H | OCH$_3$ | OCH$_3$ | |
| Q$_{13}$(R$_7$=H,R$_8$=H) | H | H | OH | H | Cl | OCH$_3$ | |
| Q$_{14}$(R$_7$=H) | H | H | C=O | | CH$_3$ | CH$_3$ | |
| Q$_{14}$(R$_7$=H) | H | H | C=O | | CH$_3$ | OCH$_3$ | |
| Q$_{14}$(R$_7$=H) | H | H | C=O | | OCH$_3$ | OCH$_3$ | |

TABLE XII-continued

General Formula XII

| Q | R | $R_1$ | $R_2$ | | $R_3$ | X | Y | m.p. (°C.) |
|---|---|---|---|---|---|---|---|---|
| $Q_{14}(R_7=H)$ | H | H | | C=O | | Cl | $OCH_3$ | |
| $Q_{14}(R_7=H)$ | H | H | OH | | H | $CH_3$ | $CH_3$ | |
| $Q_{14}(R_7=H)$ | H | H | OH | | H | $CH_3$ | $OCH_3$ | |
| $Q_{14}(R_7=H)$ | H | H | OH | | H | $OCH_3$ | $OCH_3$ | |
| $Q_{14}(R_7=H)$ | H | H | OH | | H | Cl | $OCH_3$ | |
| $Q_{15}(R_7=H)$ | H | H | | C=O | | $CH_3$ | $CH_3$ | |
| $Q_{15}(R_7=H)$ | H | H | | C=O | | $CH_3$ | $OCH_3$ | |
| $Q_{15}(R_7=H)$ | H | H | | C=O | | $OCH_3$ | $OCH_3$ | |
| $Q_{15}(R_7=H)$ | H | H | | C=O | | Cl | $OCH_3$ | |
| $Q_{15}(R_7=H)$ | H | H | OH | | H | $CH_3$ | $CH_3$ | |
| $Q_{15}(R_7=H)$ | H | H | OH | | H | $CH_3$ | $OCH_3$ | |
| $Q_{15}(R_7=H)$ | H | H | OH | | H | $OCH_3$ | $OCH_3$ | |
| $Q_{15}(R_7=H)$ | H | H | OH | | H | Cl | $OCH_3$ | |
| $Q_{16}(R_7=H)$ | H | H | | C=O | | $CH_3$ | $CH_3$ | |
| $Q_{16}(R_7=H)$ | H | H | | C=O | | $CH_3$ | $OCH_3$ | |
| $Q_{16}(R_7=H)$ | H | H | | C=O | | $OCH_3$ | $OCH_3$ | |
| $Q_{16}(R_7=H)$ | H | H | | C=O | | Cl | $OCH_3$ | |
| $Q_{16}(R_7=H)$ | H | H | OH | | H | $CH_3$ | $CH_3$ | |
| $Q_{16}(R_7=H)$ | H | H | OH | | H | $CH_3$ | $OCH_3$ | |
| $Q_{16}(R_7=H)$ | H | H | OH | | H | $OCH_3$ | $OCH_3$ | |
| $Q_{16}(R_7=H)$ | H | H | OH | | H | Cl | $OCH_3$ | |
| $Q_{17}(R_7=CH_3)$ | H | H | | C=O | | $CH_3$ | $CH_3$ | |
| $Q_{17}(R_7=CH_3)$ | H | H | | C=O | | $CH_3$ | $OCH_3$ | |
| $Q_{17}(R_7=CH_3)$ | H | H | | C=O | | $OCH_3$ | $OCH_3$ | |
| $Q_{17}(R_7=CH_3)$ | H | H | | C=O | | Cl | $OCH_3$ | |
| $Q_{17}(R_7=CH_3)$ | H | H | OH | | H | $CH_3$ | $CH_3$ | |
| $Q_{17}(R_7=CH_3)$ | H | H | OH | | H | $CH_3$ | $OCH_3$ | |
| $Q_{17}(R_7=CH_3)$ | H | H | OH | | H | $OCH_3$ | $OCH_3$ | |
| $Q_{17}(R_7=CH_3)$ | H | H | OH | | H | Cl | $OCH_3$ | |
| $Q_{18}(R_7=H)$ | H | H | | C=O | | $CH_3$ | $CH_3$ | |
| $Q_{18}(R_7=H)$ | H | H | | C=O | | $CH_3$ | $OCH_3$ | |
| $Q_{18}(R_7=H)$ | H | H | | C=O | | $OCH_3$ | $OCH_3$ | |
| $Q_{18}(R_7=H)$ | H | H | | C=O | | Cl | $OCH_3$ | |
| $Q_{18}(R_7=H)$ | H | H | OH | | H | $CH_3$ | $CH_3$ | |
| $Q_{18}(R_7=H)$ | H | H | OH | | H | $CH_3$ | $OCH_3$ | |
| $Q_{18}(R_7=H)$ | H | H | OH | | H | $OCH_3$ | $OCH_3$ | |
| $Q_{18}(R_7=H)$ | H | H | OH | | H | Cl | $OCH_3$ | |
| $Q_{19}(R_7=H,R_8=H)$ | H | H | | C=O | | $CH_3$ | $CH_3$ | |
| $Q_{19}(R_7=H,R_8=H)$ | H | H | | C=O | | $CH_3$ | $OCH_3$ | |
| $Q_{19}(R_7=H,R_8=H)$ | H | H | | C=O | | $OCH_3$ | $OCH_3$ | |
| $Q_{19}(R_7=H,R_8=H)$ | H | H | | C=O | | Cl | $OCH_3$ | |
| $Q_{19}(R_7=H,R_8=H)$ | H | H | OH | | H | $CH_3$ | $CH_3$ | |
| $Q_{19}(R_7=H,R_8=H)$ | H | H | OH | | H | $CH_3$ | $OCH_3$ | |
| $Q_{19}(R_7=H,R_8=H)$ | H | H | OH | | H | $OCH_3$ | $OCH_3$ | |
| $Q_{19}(R_7=H,R_8=H)$ | H | H | OH | | H | Cl | $OCH_3$ | |
| $Q_{20}(R_7=H,R_8=H)$ | H | H | | C=O | | $CH_3$ | $CH_3$ | |
| $Q_{20}(R_7=H,R_8=H)$ | H | H | | C=O | | $CH_3$ | $OCH_3$ | |
| $Q_{20}(R_7=H,R_8=H)$ | H | H | | C=O | | $OCH_3$ | $OCH_3$ | |
| $Q_{20}(R_7=H,R_8=H)$ | H | H | | C=O | | Cl | $OCH_3$ | |
| $Q_{20}(R_7=H,R_8=H)$ | H | H | OH | | H | $CH_3$ | $CH_3$ | |
| $Q_{20}(R_7=H,R_8=H)$ | H | H | OH | | H | $CH_3$ | $OCH_3$ | |
| $Q_{20}(R_7=H,R_8=H)$ | H | H | OH | | H | $OCH_3$ | $OCH_3$ | |
| $Q_{20}(R_7=H,R_8=H)$ | H | H | OH | | H | Cl | $OCH_3$ | |
| $Q_{21}(R_7=H,R_8=H,R_9=CH_3)$ | H | H | C=O | | | $CH_3$ | $CH_3$ | |
| $Q_{21}(R_7=H,R_8=H,R_9=CH_3)$ | H | H | C=O | | | $CH_3$ | $OCH_3$ | |
| $Q_{21}(R_7=H,R_8=H,R_9=CH_3)$ | H | H | C=O | | | $OCH_3$ | $OCH_3$ | |
| $Q_{21}(R_7=H,R_8=H,R_9=CH_3)$ | H | H | C=O | | | Cl | $OCH_3$ | |
| $Q_{21}(R_7=H,R_8=H,R_9=CH_3)$ | H | H | OH | | H | $CH_3$ | $CH_3$ | |
| $Q_{21}(R_7=H,R_8=H,R_9=CH_3)$ | H | H | OH | | H | $CH_3$ | $OCH_3$ | |
| $Q_{21}(R_7=H,R_8=H,R_9=CH_3)$ | H | H | OH | | H | $OCH_3$ | $OCH_3$ | |
| $Q_{21}(R_7=H,R_8=H,R_9=CH_3)$ | H | H | OH | | H | Cl | $OCH_3$ | |
| $Q_{22}(R_7=H)$ | H | H | | C=O | | $CH_3$ | $CH_3$ | |
| $Q_{22}(R_7=H)$ | H | H | | C=O | | $CH_3$ | $OCH_3$ | |
| $Q_{22}(R_7=H)$ | H | H | | C=O | | $OCH_3$ | $OCH_3$ | |
| $Q_{22}(R_7=H)$ | H | H | | C=O | | Cl | $OCH_3$ | |
| $Q_{22}(R_7=H)$ | H | H | OH | | H | $CH_3$ | $CH_3$ | |
| $Q_{22}(R_7=H)$ | H | H | OH | | H | $CH_3$ | $OCH_3$ | |
| $Q_{22}(R_7=H)$ | H | H | OH | | H | $OCH_3$ | $OCH_3$ | |
| $Q_{22}(R_7=H)$ | H | H | OH | | H | Cl | $OCH_3$ | |
| $Q_{23}(R_7=H)$ | H | H | | C=O | | $CH_3$ | $CH_3$ | |
| $Q_{23}(R_7=H)$ | H | H | | C=O | | $CH_3$ | $OCH_3$ | |
| $Q_{23}(R_7=H)$ | H | H | | C=O | | $OCH_3$ | $OCH_3$ | |
| $Q_{23}(R_7=H)$ | H | H | | C=O | | Cl | $OCH_3$ | |
| $Q_{23}(R_7=H)$ | H | H | OH | | H | $CH_3$ | $CH_3$ | |
| $Q_{23}(R_7=H)$ | H | H | OH | | H | $CH_3$ | $OCH_3$ | |
| $Q_{23}(R_7=H)$ | H | H | OH | | H | $OCH_3$ | $OCH_3$ | |
| $Q_{23}(R_7=H)$ | H | H | OH | | H | Cl | $OCH_3$ | |
| $Q_{24}(R_7=H,R_8=H)$ | H | H | | C=O | | $CH_3$ | $CH_3$ | |
| $Q_{24}(R_7=H,R_8=H)$ | H | H | | C=O | | $CH_3$ | $OCH_3$ | |
| $Q_{24}(R_7=H,R_8=H)$ | H | H | | C=O | | $OCH_3$ | $OCH_3$ | |

TABLE XII-continued

| Q | R | $R_1$ | $R_2$ | $R_3$ | X | Y | m.p. (°C.) |
|---|---|---|---|---|---|---|---|
| $Q_{24}(R_7=H,R_8=H)$ | H | H | | C=O | Cl | $OCH_3$ | |
| $Q_{24}(R_7=H,R_8=H)$ | H | H | OH | H | $CH_3$ | $CH_3$ | |
| $Q_{24}(R_7=H,R_8=H)$ | H | H | OH | H | $CH_3$ | $OCH_3$ | |
| $Q_{24}(R_7=H,R_8=H)$ | H | H | OH | H | $OCH_3$ | $OCH_3$ | |
| $Q_{24}(R_7=H,R_8=H)$ | H | H | OH | H | Cl | $OCH_3$ | |
| $Q_{25}(R_7=H,R_8=H)$ | H | H | | C=O | $CH_3$ | $CH_3$ | |
| $Q_{25}(R_7=H,R_8=H)$ | H | H | | C=O | $CH_3$ | $OCH_3$ | |
| $Q_{25}(R_7=H,R_8=H)$ | H | H | | C=O | $OCH_3$ | $OCH_3$ | |
| $Q_{25}(R_7=H,R_8=H)$ | H | H | | C=O | Cl | $OCH_3$ | |
| $Q_{25}(R_7=H,R_8=H)$ | H | H | OH | H | $CH_3$ | $CH_3$ | |
| $Q_{25}(R_7=H,R_8=H)$ | H | H | OH | H | $CH_3$ | $OCH_3$ | |
| $Q_{25}(R_7=H,R_8=H)$ | H | H | OH | H | $OCH_3$ | $OCH_3$ | |
| $Q_{25}(R_7=H,R_8=H)$ | H | H | OH | H | Cl | $OCH_3$ | |
| $Q_{26}(R_7=H,R_8=H)$ | H | H | | C=O | $CH_3$ | $CH_3$ | |
| $Q_{26}(R_7=H,R_8=H)$ | H | H | | C=O | $CH_3$ | $OCH_3$ | |
| $Q_{26}(R_7=H,R_8=H)$ | H | H | | C=O | $OCH_3$ | $OCH_3$ | |
| $Q_{26}(R_7=H,R_8=H)$ | H | H | | C=O | Cl | $OCH_3$ | |
| $Q_{26}(R_7=H,R_8=H)$ | H | H | OH | H | $CH_3$ | $CH_3$ | |
| $Q_{26}(R_7=H,R_8=H)$ | H | H | OH | H | $CH_3$ | $OCH_3$ | |
| $Q_{26}(R_7=H,R_8=H)$ | H | H | OH | H | $OCH_3$ | $OCH_3$ | |
| $Q_{26}(R_7=H,R_8=H)$ | H | H | OH | H | Cl | $OCH_3$ | |
| $Q_{27}(R_7=H,R_{11}=H,R_{12}=H)$ | H | H | | C=O | $CH_3$ | $CH_3$ | |
| $Q_{27}(R_7=H,R_{11}=H,R_{12}=H)$ | H | H | | C=O | $CH_3$ | $OCH_3$ | |
| $Q_{27}(R_7=H,R_{11}=H,R_{12}=H)$ | H | H | | C=O | $OCH_3$ | $OCH_3$ | |
| $Q_{27}(R_7=H,R_{11}=H,R_{12}=H)$ | H | H | | C=O | Cl | $OCH_3$ | |
| $Q_{27}(R_7=H,R_{11}=H,R_{12}=H)$ | H | H | OH | H | $CH_3$ | $CH_3$ | |
| $Q_{27}(R_7=H,R_{11}=H,R_{12}=H)$ | H | H | OH | H | $CH_3$ | $OCH_3$ | |
| $Q_{27}(R_7=H,R_{11}=H,R_{12}=H)$ | H | H | OH | H | $OCH_3$ | $OCH_3$ | |
| $Q_{27}(R_7=H,R_{11}=H,R_{12}=H)$ | H | H | OH | H | Cl | $OCH_3$ | |
| $Q_{28}(R_{11}=H,R_{12}=H)$ | H | H | | C=O | $CH_3$ | $CH_3$ | |
| $Q_{28}(R_{11}=H,R_{12}=H)$ | H | H | | C=O | $CH_3$ | $OCH_3$ | |
| $Q_{28}(R_{11}=H,R_{12}=H)$ | H | H | | C=O | $OCH_3$ | $OCH_3$ | |
| $Q_{28}(R_{11}=H,R_{12}=H)$ | H | H | | C=O | Cl | $OCH_3$ | |
| $Q_{28}(R_{11}=H,R_{12}=H)$ | H | H | OH | H | $CH_3$ | $CH_3$ | |
| $Q_{28}(R_{11}=H,R_{12}=H)$ | H | H | OH | H | $CH_3$ | $OCH_3$ | |
| $Q_{28}(R_{11}=H,R_{12}=H)$ | H | H | OH | H | $OCH_3$ | $OCH_3$ | |
| $Q_{28}(R_{11}=H,R_{12}=H)$ | H | H | OH | H | Cl | $OCH_3$ | |
| $Q_{29}(R_{11}=H,R_{12}=H)$ | H | H | | C=O | $CH_3$ | $CH_3$ | |
| $Q_{29}(R_{11}=H,R_{12}=H)$ | H | H | | C=O | $CH_3$ | $OCH_3$ | |
| $Q_{29}(R_{11}=H,R_{12}=H)$ | H | H | | C=O | $OCH_3$ | $OCH_3$ | |
| $Q_{29}(R_{11}=H,R_{12}=H)$ | H | H | | C=O | Cl | $OCH_3$ | |
| $Q_{29}(R_{11}=H,R_{12}=H)$ | H | H | OH | H | $CH_3$ | $CH_3$ | |
| $Q_{29}(R_{11}=H,R_{12}=H)$ | H | H | OH | H | $CH_3$ | $OCH_3$ | |
| $Q_{29}(R_{11}=H,R_{12}=H)$ | H | H | OH | H | $OCH_3$ | $OCH_3$ | |
| $Q_{29}(R_{11}=H,R_{12}=H)$ | H | H | OH | H | Cl | $OCH_3$ | |
| $Q_{30}(R_7=H,R_8=H)$ | H | H | | C=O | $CH_3$ | $CH_3$ | |
| $Q_{30}(R_7=H,R_8=H)$ | H | H | | C=O | $CH_3$ | $OCH_3$ | |
| $Q_{30}(R_7=H,R_8=H)$ | H | H | | C=O | $OCH_3$ | $OCH_3$ | |
| $Q_{30}(R_7=H,R_8=H)$ | H | H | | C=O | Cl | $OCH_3$ | |
| $Q_{30}(R_7=H,R_8=H)$ | H | H | OH | H | $CH_3$ | $CH_3$ | |
| $Q_{30}(R_7=H,R_8=H)$ | H | H | OH | H | $CH_3$ | $OCH_3$ | |
| $Q_{30}(R_7=H,R_8=H)$ | H | H | OH | H | $OCH_3$ | $OCH_3$ | |
| $Q_{30}(R_7=H,R_8=H)$ | H | H | OH | H | Cl | $OCH_3$ | |
| $Q_{31}(R_7=H,R_8=H)$ | H | H | | C=O | $CH_3$ | $CH_3$ | |
| $Q_{31}(R_7=H,R_8=H)$ | H | H | | C=O | $CH_3$ | $OCH_3$ | |
| $Q_{31}(R_7=H,R_8=H)$ | H | H | | C=O | $OCH_3$ | $OCH_3$ | |
| $Q_{31}(R_7=H,R_8=H)$ | H | H | | C=O | Cl | $OCH_3$ | |
| $Q_{31}(R_7=H,R_8=H)$ | H | H | OH | H | $CH_3$ | $CH_3$ | |
| $Q_{31}(R_7=H,R_8=H)$ | H | H | OH | H | $CH_3$ | $OCH_3$ | |
| $Q_{31}(R_7=H,R_8=H)$ | H | H | OH | H | $OCH_3$ | $OCH_3$ | |
| $Q_{31}(R_7=H,R_8=H)$ | H | H | OH | H | Cl | $OCH_3$ | |
| $Q_{32}(R_{13}=OCH_3,R_{14}=OCH_3)$ | H | H | | C=O | $CH_3$ | $CH_3$ | |
| $Q_{32}(R_{13}=OCH_3,R_{14}=OCH_3)$ | H | H | | C=O | $CH_3$ | $OCH_3$ | |
| $Q_{32}(R_{13}=OCH_3,R_{14}=OCH_3)$ | H | H | | C=O | $OCH_3$ | $OCH_3$ | |
| $Q_{32}(R_{13}=OCH_3,R_{14}=OCH_3)$ | H | H | | C=O | Cl | $OCH_3$ | |
| $Q_{32}(R_{13}=OCH_3,R_{14}=OCH_3)$ | H | H | OH | H | $CH_3$ | $CH_3$ | |
| $Q_{32}(R_{13}=OCH_3,R_{14}=OCH_3)$ | H | H | OH | H | $CH_3$ | $OCH_3$ | |
| $Q_{32}(R_{13}=OCH_3,R_{14}=OCH_3)$ | H | H | OH | H | $OCH_3$ | $OCH_3$ | |
| $Q_{32}(R_{13}=OCH_3,R_{14}=OCH_3)$ | H | H | OH | H | Cl | $OCH_3$ | |
| $Q_{33}(R_7=H)$ | H | H | | C=O | $CH_3$ | $CH_3$ | |
| $Q_{33}(R_7=H)$ | H | H | | C=O | $CH_3$ | $OCH_3$ | |
| $Q_{33}(R_7=H)$ | H | H | | C=O | $OCH_3$ | $OCH_3$ | |
| $Q_{33}(R_7=H)$ | H | H | | C=O | Cl | $OCH_3$ | |
| $Q_{33}(R_7=H)$ | H | H | OH | H | $CH_3$ | $CH_3$ | |
| $Q_{33}(R_7=H)$ | H | H | OH | H | $CH_3$ | $OCH_3$ | |
| $Q_{33}(R_7=H)$ | H | H | OH | H | $OCH_3$ | $OCH_3$ | |
| $Q_{33}(R_7=H)$ | H | H | OH | H | Cl | $OCH_3$ | |

TABLE XIII

General Formula XIII

| Q | R | $R_1$ | $R_2$ | $R_3$ | X | Y | m.p.(°C.) |
|---|---|---|---|---|---|---|---|
| $Q_1(R_7 = H, R_8 = H, R_9 = H)$ | H | H | C=O | | $CH_3$ | $CH_3$ | |
| $Q_1(R_7 = H, R_8 = H, R_9 = H)$ | H | H | C=O | | $CH_3$ | $OCH_3$ | |
| $Q_1(R_7 = H, R_8 = H, R_9 = H)$ | H | H | C=O | | $OCH_3$ | $OCH_3$ | |
| $Q_1(R_7 = H, R_8 = H, R_9 = H)$ | H | H | C=O | | Cl | $OCH_3$ | |
| $Q_1(R_7 = H, R_8 = H, R_9 = H)$ | H | H | OH | H | $CH_3$ | $CH_3$ | |
| $Q_1(R_7 = H, R_8 = H, R_9 = H)$ | H | H | OH | H | $CH_3$ | $OCH_3$ | |
| $Q_1(R_7 = H, R_8 = H, R_9 = H)$ | H | H | OH | H | $OCH_3$ | $OCH_3$ | |
| $Q_1(R_7 = H, R_8 = H, R_9 = H)$ | H | H | OH | H | Cl | $OCH_3$ | |
| $Q_1(R_7 = H, R_8 = H, R_9 = H)$ | H | H | $OCH_3$ | H | $OCH_3$ | $OCH_3$ | |
| $Q_1(R_7 = H, R_8 = H, R_9 = H)$ | H | H | $OCH_2CH_3$ | H | $OCH_3$ | $OCH_3$ | |
| $Q_2(R_7 = H, R_8 = H, R_9 = H)$ | H | H | C=O | | $CH_3$ | $CH_3$ | |
| $Q_2(R_7 = H, R_8 = H, R_9 = H)$ | H | H | C=O | | $CH_3$ | $OCH_3$ | |
| $Q_2(R_7 = H, R_8 = H, R_9 = H)$ | H | H | C=O | | $OCH_3$ | $OCH_3$ | |
| $Q_2(R_7 = H, R_8 = H, R_9 = H)$ | H | H | C=O | | Cl | $OCH_3$ | |
| $Q_2(R_7 = H, R_8 = H, R_9 = H)$ | H | H | OH | H | $CH_3$ | $CH_3$ | |
| $Q_2(R_7 = H, R_8 = H, R_9 = H)$ | H | H | OH | H | $CH_3$ | $OCH_3$ | |
| $Q_2(R_7 = H, R_8 = H, R_9 = H)$ | H | H | OH | H | $OCH_3$ | $OCH_3$ | |
| $Q_2(R_7 = H, R_8 = H, R_9 = H)$ | H | H | OH | H | Cl | $OCH_3$ | |
| $Q_2(R_7 = H, R_8 = H, R_9 = H)$ | H | H | OH | H | $CH_3$ | $OCH_3$ | |
| $Q_2(R_7 = H, R_8 = H, R_9 = H)$ | H | H | OH | H | $CH_3$ | $CH_3$ | |
| $Q_3(R_7 = H, R_8 = H, R_9 = H)$ | H | H | C=O | | $CH_3$ | $CH_3$ | |
| $Q_3(R_7 = H, R_8 = H, R_9 = H)$ | H | H | C=O | | $CH_3$ | $OCH_3$ | |
| $Q_3(R_7 = H, R_8 = H, R_9 = H)$ | H | H | C=O | | $OCH_3$ | $OCH_3$ | |
| $Q_3(R_7 = H, R_8 = H, R_9 = H)$ | H | H | C=O | | Cl | $OCH_3$ | |
| $Q_3(R_7 = H, R_8 = H, R_9 = H)$ | H | H | OH | H | $CH_3$ | $CH_3$ | |
| $Q_3(R_7 = H, R_8 = H, R_9 = H)$ | H | H | OH | H | $CH_3$ | $OCH_3$ | |
| $Q_3(R_7 = H, R_8 = H, R_9 = H)$ | H | H | OH | H | $OCH_3$ | $OCH_3$ | |
| $Q_3(R_7 = H, R_8 = H, R_9 = H)$ | H | H | OH | H | Cl | $OCH_3$ | |
| $Q_3(R_7 = H, R_8 = H, R_9 = Cl)$ | H | H | C=O | | $OCH_3$ | $OCH_3$ | |
| $Q_3(R_7 = H, R_8 = H, R_9 = CH_3)$ | H | H | C=O | | $OCH_3$ | $OCH_3$ | |
| $Q_3(R_7 = H, R_8 = H, R_9 = CH_3)$ | H | H | OH | H | $OCH_3$ | $OCH_3$ | |
| $Q_4(R_7 = H, R_8 = H, R_9 = H)$ | H | H | C=O | | $CH_3$ | $CH_3$ | |
| $Q_4(R_7 = H, R_8 = H, R_9 = H)$ | H | H | C=O | | $CH_3$ | $OCH_3$ | |
| $Q_4(R_7 = H, R_8 = H, R_9 = H)$ | H | H | C=O | | $OCH_3$ | $OCH_3$ | |
| $Q_4(R_7 = H, R_8 = H, R_9 = H)$ | H | H | C=O | | Cl | $OCH_3$ | |
| $Q_4(R_7 = H, R_8 = H, R_9 = H)$ | H | H | OH | H | $CH_3$ | $CH_3$ | |
| $Q_4(R_7 = H, R_8 = H, R_9 = H)$ | H | H | OH | H | $CH_3$ | $OCH_3$ | |
| $Q_4(R_7 = H, R_8 = H, R_9 = H)$ | H | H | OH | H | $OCH_3$ | $OCH_3$ | |
| $Q_4(R_7 = H, R_8 = H, R_9 = H)$ | H | H | OH | H | Cl | $OCH_3$ | |
| $Q_5(R_7 = H, R_8 = H, R_9 = H, R_{10} = CH_3)$ | H | H | C=O | | $CH_3$ | $CH_3$ | |
| $Q_5(R_7 = H, R_8 = H, R_9 = H, R_{10} = CH_3)$ | H | H | C=O | | $CH_3$ | $OCH_3$ | |
| $Q_5(R_7 = H, R_8 = H, R_9 = H, R_{10} = CH_3)$ | H | H | C=O | | $OCH_3$ | $OCH_3$ | |
| $Q_5(R_7 = H, R_8 = H, R_9 = H, R_{10} = CH_3)$ | H | H | C=O | | Cl | $OCH_3$ | |
| $Q_5(R_7 = H, R_8 = H, R_9 = H, R_{10} = CH_3)$ | H | H | OH | H | $CH_3$ | $CH_3$ | |
| $Q_5(R_7 = H, R_8 = H, R_9 = H, R_{10} = CH_3)$ | H | H | OH | H | $CH_3$ | $OCH_3$ | |
| $Q_5(R_7 = H, R_8 = H, R_9 = H, R_{10} = CH_3)$ | H | H | OH | H | $OCH_3$ | $OCH_3$ | |
| $Q_5(R_7 = H, R_8 = H, R_9 = H, R_{10} = CH_3)$ | H | H | OH | H | Cl | $OCH_3$ | |
| $Q_5(R_7 = H, R_8 = H, R_9 = H, R_{10} = CH_3)$ | H | H | $OCH_3$ | H | Cl | $OCH_3$ | |
| $Q_5(R_7 = H, R_8 = H, R_9 = H, R_{10} = CH_3)$ | H | H | $OCH_2CH_3$ | H | $OCH_3$ | $OCH_3$ | |
| $Q_6(R_7 = H, R_8 = H, R_9 = H, R_{10} = CH_3)$ | H | H | C=O | | $CH_3$ | $CH_3$ | |
| $Q_6(R_7 = H, R_8 = H, R_9 = H, R_{10} = CH_3)$ | H | H | C=O | | $CH_3$ | $OCH_3$ | |
| $Q_6(R_7 = H, R_8 = H, R_9 = H, R_{10} = CH_3)$ | H | H | C=O | | $OCH_3$ | $OCH_3$ | |
| $Q_6(R_7 = H, R_8 = H, R_9 = H, R_{10} = CH_3)$ | H | H | C=O | | Cl | $OCH_3$ | |
| $Q_6(R_7 = H, R_8 = H, R_9 = H, R_{10} = CH_3)$ | H | H | OH | H | $CH_3$ | $CH_3$ | |
| $Q_6(R_7 = H, R_8 = H, R_9 = H, R_{10} = CH_3)$ | H | H | OH | H | $CH_3$ | $OCH_3$ | |
| $Q_6(R_7 = H, R_8 = H, R_9 = H, R_{10} = CH_3)$ | H | H | OH | H | $OCH_3$ | $OCH_3$ | |
| $Q_6(R_7 = H, R_8 = H, R_9 = H, R_{10} = CH_3)$ | H | H | OH | H | Cl | $OCH_3$ | |
| $Q_7(R_7 = H, R_8 = H)$ | H | H | C=O | | $CH_3$ | $CH_3$ | |
| $Q_7(R_7 = H, R_8 = H)$ | H | H | C=O | | $CH_3$ | $OCH_3$ | |
| $Q_7(R_7 = H, R_8 = H)$ | H | H | C=O | | $OCH_3$ | $OCH_3$ | |
| $Q_7(R_7 = H, R_8 = H)$ | H | H | C=O | | Cl | $OCH_3$ | |
| $Q_7(R_7 = H, R_8 = H)$ | H | H | OH | H | $CH_3$ | $CH_3$ | |
| $Q_7(R_7 = H, R_8 = H)$ | H | H | OH | H | $CH_3$ | $OCH_3$ | |
| $Q_7(R_7 = H, R_8 = H)$ | H | H | OH | H | $OCH_3$ | $OCH_3$ | |
| $Q_7(R_7 = H, R_8 = H)$ | H | H | OH | H | Cl | $OCH_3$ | |
| $Q_8(R_7 = H, R_8 = H)$ | H | H | C=O | | $OCH_3$ | $OCH_3$ | |
| $Q_8(R_7 = H, R_8 = H)$ | H | H | C=O | | Cl | $OCH_3$ | |
| $Q_8(R_7 = H, R_8 = H)$ | H | H | OH | H | Cl | $OCH_3$ | |
| $Q_8(R_7 = H, R_8 = H)$ | H | H | OH | H | $OCH_3$ | $OCH_3$ | |
| $Q_9(R_7 = H, R_8 = H)$ | H | H | C=O | | $CH_3$ | $CH_3$ | |
| $Q_9(R_7 = H, R_8 = H)$ | H | H | C=O | | $CH_3$ | $OCH_3$ | |
| $Q_9(R_7 = H, R_8 = H)$ | H | H | C=O | | $OCH_3$ | $OCH_3$ | |
| $Q_9(R_7 = H, R_8 = H)$ | H | H | C=O | | Cl | $OCH_3$ | |
| $Q_9(R_7 = H, R_8 = H)$ | H | H | OH | H | $CH_3$ | $CH_3$ | |
| $Q_9(R_7 = H, R_8 = H)$ | H | H | OH | H | $CH_3$ | $OCH_3$ | |
| $Q_9(R_7 = H, R_8 = H)$ | H | H | OH | H | $OCH_3$ | $OCH_3$ | |
| $Q_9(R_7 = H, R_8 = H)$ | H | H | OH | H | Cl | $OCH_3$ | |
| $Q_{10}(R_7 = H, R_8 = H)$ | H | H | C=O | | $CH_3$ | $OCH_3$ | |
| $Q_{10}(R_7 = H, R_8 = H)$ | H | H | C=O | | $OCH_3$ | $OCH_3$ | |
| $Q_{10}(R_7 = H, R_8 = H)$ | H | H | C=O | | Cl | $OCH_3$ | |

TABLE XIII-continued

General Formula XIII

| Q | R | $R_1$ | $R_2$ | $R_3$ | X | Y | m.p.(°C.) |
|---|---|---|---|---|---|---|---|
| $Q_{10}(R_7 = H, R_8 = H)$ | H | H | OH | H | $CH_3$ | $CH_3$ | |
| $Q_{10}(R_7 = H, R_8 = H)$ | H | H | OH | H | $OCH_3$ | $OCH_3$ | |
| $Q_{10}(R_7 = H, R_8 = H)$ | H | H | OH | H | Cl | $OCH_3$ | |
| $Q_{11}(R_7 = H, R_8 = H)$ | H | H | C=O | | $CH_3$ | $CH_3$ | |
| $Q_{11}(R_7 = H, R_8 = H)$ | H | H | C=O | | $CH_3$ | $OCH_3$ | |
| $Q_{11}(R_7 = H, R_8 = H)$ | H | H | C=O | | $OCH_3$ | $OCH_3$ | |
| $Q_{11}(R_7 = H, R_8 = H)$ | H | H | C=O | | Cl | $OCH_3$ | |
| $Q_{11}(R_7 = H, R_8 = H)$ | H | H | OH | H | $CH_3$ | $CH_3$ | |
| $Q_{11}(R_7 = H, R_8 = H)$ | H | H | OH | H | $CH_3$ | $OCH_3$ | |
| $Q_{11}(R_7 = H, R_8 = H)$ | H | H | OH | H | $OCH_3$ | $OCH_3$ | |
| $Q_{11}(R_7 = H, R_8 = H)$ | H | H | OH | H | Cl | $OCH_3$ | |
| $Q_{12}(R_7 = H, R_8 = H)$ | H | H | C=O | | $CH_3$ | $CH_3$ | |
| $Q_{12}(R_7 = H, R_8 = H)$ | H | H | C=O | | $CH_3$ | $OCH_3$ | |
| $Q_{12}(R_7 = H, R_8 = H)$ | H | H | C=O | | $OCH_3$ | $OCH_3$ | |
| $Q_{12}(R_7 = H, R_8 = H)$ | H | H | C=O | | Cl | $OCH_3$ | |
| $Q_{12}(R_7 = H, R_8 = H)$ | H | H | OH | H | $CH_3$ | $CH_3$ | |
| $Q_{12}(R_7 = H, R_8 = H)$ | H | H | OH | H | $CH_3$ | $OCH_3$ | |
| $Q_{12}(R_7 = H, R_8 = H)$ | H | H | OH | H | $OCH_3$ | $OCH_3$ | |
| $Q_{12}(R_7 = H, R_8 = H)$ | H | H | OH | H | Cl | $OCH_3$ | |
| $Q_{12}(R_7 = H, R_8 = H)$ | H | H | $OCH_3$ | H | $OCH_3$ | $OCH_3$ | |
| $Q_{13}(R_7 = H, R_8 = H)$ | H | H | C=O | | $CH_3$ | $CH_3$ | |
| $Q_{13}(R_7 = H, R_8 = H)$ | H | H | C=O | | $CH_3$ | $OCH_3$ | |
| $Q_{13}(R_7 = H, R_8 = H)$ | H | H | C=O | | $OCH_3$ | $OCH_3$ | |
| $Q_{13}(R_7 = H, R_8 = H)$ | H | H | C=O | | Cl | $OCH_3$ | |
| $Q_{13}(R_7 = H, R_8 = H)$ | H | H | OH | H | $CH_3$ | $CH_3$ | |
| $Q_{13}(R_7 = H, R_8 = H)$ | H | H | OH | H | $CH_3$ | $OCH_3$ | |
| $Q_{13}(R_7 = H, R_8 = H)$ | H | H | OH | H | $OCH_3$ | $OCH_3$ | |
| $Q_{13}(R_7 = H, R_8 = H)$ | H | H | OH | H | Cl | $OCH_3$ | |
| $Q_{14}(R_7 = H)$ | H | H | C=O | | $CH_3$ | $CH_3$ | |
| $Q_{14}(R_7 = H)$ | H | H | C=O | | $CH_3$ | $OCH_3$ | |
| $Q_{14}(R_7 = H)$ | H | H | C=O | | $OCH_3$ | $OCH_3$ | |
| $Q_{14}(R_7 = H)$ | H | H | C=O | | Cl | $OCH_3$ | |
| $Q_{14}(R_7 = H)$ | H | H | OH | H | $CH_3$ | $CH_3$ | |
| $Q_{14}(R_7 = H)$ | H | H | OH | H | $CH_3$ | $OCH_3$ | |
| $Q_{14}(R_7 = H)$ | H | H | OH | H | $OCH_3$ | $OCH_3$ | |
| $Q_{14}(R_7 = H)$ | H | H | OH | H | Cl | $OCH_3$ | |
| $Q_{15}(R_7 = H)$ | H | H | C=O | | $CH_3$ | $CH_3$ | |
| $Q_{15}(R_7 = H)$ | H | H | C=O | | $CH_3$ | $OCH_3$ | |
| $Q_{15}(R_7 = H)$ | H | H | C=O | | $OCH_3$ | $OCH_3$ | |
| $Q_{15}(R_7 = H)$ | H | H | C=O | | Cl | $OCH_3$ | |
| $Q_{15}(R_7 = H)$ | H | H | OH | H | $CH_3$ | $CH_3$ | |
| $Q_{15}(R_7 = H)$ | H | H | OH | H | $CH_3$ | $OCH_3$ | |
| $Q_{15}(R_7 = H)$ | H | H | OH | H | $OCH_3$ | $OCH_3$ | |
| $Q_{15}(R_7 = H)$ | H | H | OH | H | Cl | $OCH_3$ | |
| $Q_{16}(R_7 = H)$ | H | H | C=O | | $CH_3$ | $CH_3$ | |
| $Q_{16}(R_7 = H)$ | H | H | C=O | | $CH_3$ | $OCH_3$ | |
| $Q_{16}(R_7 = H)$ | H | H | C=O | | $OCH_3$ | $OCH_3$ | |
| $Q_{16}(R_7 = H)$ | H | H | C=O | | Cl | $OCH_3$ | |
| $Q_{16}(R_7 = H)$ | H | H | OH | H | $CH_3$ | $CH_3$ | |
| $Q_{16}(R_7 = H)$ | H | H | OH | H | $CH_3$ | $OCH_3$ | |
| $Q_{16}(R_7 = H)$ | H | H | OH | H | $OCH_3$ | $OCH_3$ | |
| $Q_{16}(R_7 = H)$ | H | H | OH | H | Cl | $OCH_3$ | |
| $Q_{17}(R_7 = CH_3)$ | H | H | C=O | | $CH_3$ | $CH_3$ | |
| $Q_{17}(R_7 = CH_3)$ | H | H | C=O | | $CH_3$ | $OCH_3$ | |
| $Q_{17}(R_7 = CH_3)$ | H | H | C=O | | $OCH_3$ | $OCH_3$ | |
| $Q_{17}(R_7 = CH_3)$ | H | H | C=O | | Cl | $OCH_3$ | |
| $Q_{17}(R_7 = CH_3)$ | H | H | OH | H | $CH_3$ | $CH_3$ | |
| $Q_{17}(R_7 = CH_3)$ | H | H | OH | H | $CH_3$ | $OCH_3$ | |
| $Q_{17}(R_7 = CH_3)$ | H | H | OH | H | $OCH_3$ | $OCH_3$ | |
| $Q_{17}(R_7 = CH_3)$ | H | H | OH | H | Cl | $OCH_3$ | |
| $Q_{18}(R_7 = H)$ | H | H | C=O | | $CH_3$ | $CH_3$ | |
| $Q_{18}(R_7 = H)$ | H | H | C=O | | $CH_3$ | $OCH_3$ | |
| $Q_{18}(R_7 = H)$ | H | H | C=O | | $OCH_3$ | $OCH_3$ | |
| $Q_{18}(R_7 = H)$ | H | H | C=O | | Cl | $OCH_3$ | |
| $Q_{18}(R_7 = H)$ | H | H | OH | H | $CH_3$ | $CH_3$ | |
| $Q_{18}(R_7 = H)$ | H | H | OH | H | $CH_3$ | $OCH_3$ | |
| $Q_{18}(R_7 = H)$ | H | H | OH | H | $OCH_3$ | $OCH_3$ | |
| $Q_{18}(R_7 = H)$ | H | H | OH | H | Cl | $OCH_3$ | |
| $Q_{19}(R_7 = H, R_8 = H)$ | H | H | C=O | | $CH_3$ | $CH_3$ | |
| $Q_{19}(R_7 = H, R_8 = H)$ | H | H | C=O | | $CH_3$ | $OCH_3$ | |
| $Q_{19}(R_7 = H, R_8 = H)$ | H | H | C=O | | $OCH_3$ | $OCH_3$ | |
| $Q_{19}(R_7 = H, R_8 = H)$ | H | H | C=O | | Cl | $OCH_3$ | |
| $Q_{19}(R_7 = H, R_8 = H)$ | H | H | OH | H | $CH_3$ | $CH_3$ | |
| $Q_{19}(R_7 = H, R_8 = H)$ | H | H | OH | H | $CH_3$ | $OCH_3$ | |
| $Q_{19}(R_7 = H, R_8 = H)$ | H | H | OH | H | $OCH_3$ | $OCH_3$ | |
| $Q_{19}(R_7 = H, R_8 = H)$ | H | H | OH | H | Cl | $OCH_3$ | |
| $Q_{20}(R_7 = H, R_8 = H)$ | H | H | C=O | | $CH_3$ | $CH_3$ | |
| $Q_{20}(R_7 = H, R_8 = H)$ | H | H | C=O | | $CH_3$ | $OCH_3$ | |
| $Q_{20}(R_7 = H, R_8 = H)$ | H | H | C=O | | $OCH_3$ | $OCH_3$ | |
| $Q_{20}(R_7 = H, R_8 = H)$ | H | H | C=O | | Cl | $OCH_3$ | |

TABLE XIII-continued

| Q | General Formula XIII | | | | | | | |
|---|---|---|---|---|---|---|---|---|
| | R | R₁ | R₂ | | R₃ | X | Y | m.p.(°C.) |
| Q₂₀(R₇ = H,R₈ = H) | H | H | OH | | H | CH₃ | CH₃ | |
| Q₂₀(R₇ = H,R₈ = H) | H | H | OH | | H | CH₃ | OCH₃ | |
| Q₂₀(R₇ = H,R₈ = H) | H | H | OH | | H | OCH₃ | OCH₃ | |
| Q₂₀(R₇ = H,R₈ = H) | H | H | OH | | H | Cl | OCH₃ | |
| Q₂₁(R₇ = H,R₈ = H,R₉ = CH₃) | H | H | | C=O | | CH₃ | CH₃ | |
| Q₂₁(R₇ = H,R₈ = H,R₉ = CH₃) | H | H | | C=O | | CH₃ | OCH₃ | |
| Q₂₁(R₇ = H,R₈ = H,R₉ = CH₃) | H | H | | C=O | | OCH₃ | OCH₃ | |
| Q₂₁(R₇ = H,R₈ = H,R₉ = CH₃) | H | H | | C=O | | Cl | OCH₃ | |
| Q₂₁(R₇ = H,R₈ = H,R₉ = CH₃) | H | H | OH | | H | CH₃ | CH₃ | |
| Q₂₁(R₇ = H,R₈ = H,R₉ = CH₃) | H | H | OH | | H | CH₃ | OCH₃ | |
| Q₂₁(R₇ = H,R₈ = H,R₉ = CH₃) | H | H | OH | | H | OCH₃ | OCH₃ | |
| Q₂₁(R₇ = H,R₈ = H,R₉ = CH₃) | H | H | OH | | H | Cl | OCH₃ | |
| Q₂₂(R₇ = H) | H | H | | C=O | | CH₃ | CH₃ | |
| Q₂₂(R₇ = H) | H | H | | C=O | | CH₃ | OCH₃ | |
| Q₂₂(R₇ = H) | H | H | | C=O | | OCH₃ | OCH₃ | |
| Q₂₂(R₇ = H) | H | H | | C=O | | Cl | OCH₃ | |
| Q₂₂(R₇ = H) | H | H | OH | | H | CH₃ | CH₃ | |
| Q₂₂(R₇ = H) | H | H | OH | | H | CH₃ | OCH₃ | |
| Q₂₂(R₇ = H) | H | H | OH | | H | OCH₃ | OCH₃ | |
| Q₂₂(R₇ = H) | H | H | OH | | H | Cl | OCH₃ | |
| Q₂₃(R₇ = H) | H | H | | C=O | | CH₃ | CH₃ | |
| Q₂₃(R₇ = H) | H | H | | C=O | | CH₃ | OCH₃ | |
| Q₂₃(R₇ = H) | H | H | | C=O | | OCH₃ | OCH₃ | |
| Q₂₃(R₇ = H) | H | H | | C=O | | Cl | OCH₃ | |
| Q₂₃(R₇ = H) | H | H | OH | | H | CH₃ | CH₃ | |
| Q₂₃(R₇ = H) | H | H | OH | | H | CH₃ | OCH₃ | |
| Q₂₃(R₇ = H) | H | H | OH | | H | OCH₃ | OCH₃ | |
| Q₂₃(R₇ = H) | H | H | OH | | H | Cl | OCH₃ | |
| Q₂₄(R₇ = H,R₈ = H) | H | H | | C=O | | CH₃ | CH₃ | |
| Q₂₄(R₇ = H,R₈ = H) | H | H | | C=O | | CH₃ | OCH₃ | |
| Q₂₄(R₇ = H,R₈ = H) | H | H | | C=O | | OCH₃ | OCH₃ | |
| Q₂₄(R₇ = H,R₈ = H) | H | H | | C=O | | Cl | OCH₃ | |
| Q₂₄(R₇ = H,R₈ = H) | H | H | OH | | H | CH₃ | CH₃ | |
| Q₂₄(R₇ = H,R₈ = H) | H | H | OH | | H | CH₃ | OCH₃ | |
| Q₂₄(R₇ = H,R₈ = H) | H | H | OH | | H | OCH₃ | OCH₃ | |
| Q₂₄(R₇ = H,R₈ = H) | H | H | OH | | H | Cl | OCH₃ | |
| Q₂₅(R₇ = H,R₈ = H) | H | H | | C=O | | CH₃ | CH₃ | |
| Q₂₅(R₇ = H,R₈ = H) | H | H | | C=O | | CH₃ | OCH₃ | |
| Q₂₅(R₇ = H,R₈ = H) | H | H | | C=O | | OCH₃ | OCH₃ | |
| Q₂₅(R₇ = H,R₈ = H) | H | H | | C=O | | Cl | OCH₃ | |
| Q₂₅(R₇ = H,R₈ = H) | H | H | OH | | H | CH₃ | CH₃ | |
| Q₂₅(R₇ = H,R₈ = H) | H | H | OH | | H | CH₃ | OCH₃ | |
| Q₂₅(R₇ = H,R₈ = H) | H | H | OH | | H | OCH₃ | OCH₃ | |
| Q₂₅(R₇ = H,R₈ = H) | H | H | OH | | H | Cl | OCH₃ | |
| Q₂₆(R₇ = H,R₈ = H) | H | H | | C=O | | CH₃ | CH₃ | |
| Q₂₆(R₇ = H,R₈ = H) | H | H | | C=O | | CH₃ | OCH₃ | |
| Q₂₆(R₇ = H,R₈ = H) | H | H | | C=O | | OCH₃ | OCH₃ | |
| Q₂₆(R₇ = H,R₈ = H) | H | H | | C=O | | Cl | OCH₃ | |
| Q₂₆(R₇ = H,R₈ = H) | H | H | OH | | H | CH₃ | CH₃ | |
| Q₂₆(R₇ = H,R₈ = H) | H | H | OH | | H | CH₃ | OCH₃ | |
| Q₂₆(R₇ = H,R₈ = H) | H | H | OH | | H | OCH₃ | OCH₃ | |
| Q₂₆(R₇ = H,R₈ = H) | H | H | OH | | H | Cl | OCH₃ | |
| Q₂₇(R₇ = H,R₁₁ = H,R₁₂ = H) | H | H | | C=O | | CH₃ | CH₃ | |
| Q₂₇(R₇ = H,R₁₁ = H,R₁₂ = H) | H | H | | C=O | | CH₃ | OCH₃ | |
| Q₂₇(R₇ = H,R₁₁ = H,R₁₂ = H) | H | H | | C=O | | OCH₃ | OCH₃ | |
| Q₂₇(R₇ = H,R₁₁ = H,R₁₂ = H) | H | H | | C=O | | Cl | OCH₃ | |
| Q₂₇(R₇ = H,R₁₁ = H,R₁₂ = H) | H | H | OH | | H | CH₃ | CH₃ | |
| Q₂₇(R₇ = H,R₁₁ = H,R₁₂ = H) | H | H | OH | | H | CH₃ | OCH₃ | |
| Q₂₇(R₇ = H,R₁₁ = H,R₁₂ = H) | H | H | OH | | H | OCH₃ | OCH₃ | |
| Q₂₇(R₇ = H,R₁₁ = H,R₁₂ = H) | H | H | OH | | H | Cl | OCH₃ | |
| Q₂₈(R₁₁ = H,R₁₂ = H) | H | H | | C=O | | CH₃ | CH₃ | |
| Q₂₈(R₁₁ = H,R₁₂ = H) | H | H | | C=O | | CH₃ | OCH₃ | |
| Q₂₈(R₁₁ = H,R₁₂ = H) | H | H | | C=O | | OCH₃ | OCH₃ | |
| Q₂₈(R₁₁ = H,R₁₂ = H) | H | H | | C=O | | Cl | OCH₃ | |
| Q₂₈(R₁₁ = H,R₁₂ = H) | H | H | OH | | H | CH₃ | CH₃ | |
| Q₂₈(R₁₁ = H,R₁₂ = H) | H | H | OH | | H | CH₃ | OCH₃ | |
| Q₂₈(R₁₁ = H,R₁₂ = H) | H | H | OH | | H | OCH₃ | OCH₃ | |
| Q₂₈(R₁₁ = H,R₁₂ = H) | H | H | OH | | H | Cl | OCH₃ | |
| Q₂₉(R₁₁ = H,R₁₂ = H) | H | H | | C=O | | CH₃ | CH₃ | |
| Q₂₉(R₁₁ = H,R₁₂ = H) | H | H | | C=O | | CH₃ | OCH₃ | |
| Q₂₉(R₁₁ = H,R₁₂ = H) | H | H | | C=O | | OCH₃ | OCH₃ | |
| Q₂₉(R₁₁ = H,R₁₂ = H) | H | H | | C=O | | Cl | OCH₃ | |
| Q₂₉(R₁₁ = H,R₁₂ = H) | H | H | OH | | H | CH₃ | CH₃ | |
| Q₂₉(R₁₁ = H,R₁₂ = H) | H | H | OH | | H | CH₃ | OCH₃ | |
| Q₂₉(R₁₁ = H,R₁₂ = H) | H | H | OH | | H | OCH₃ | OCH₃ | |
| Q₂₉(R₁₁ = H,R₁₂ = H) | H | H | OH | | H | Cl | OCH₃ | |
| Q₃₀(R₇ = H,R₈ = H) | H | H | | C=O | | CH₃ | CH₃ | |
| Q₃₀(R₇ = H,R₈ = H) | H | H | | C=O | | CH₃ | OCH₃ | |
| Q₃₀(R₇ = H,R₈ = H) | H | H | | C=O | | OCH₃ | OCH₃ | |
| Q₃₀(R₇ = H,R₈ = H) | H | H | | C=O | | Cl | OCH₃ | |

TABLE XIII-continued

General Formula XIII

| Q | R | R$_1$ | R$_2$ | R$_3$ | X | Y | m.p.(°C.) |
|---|---|---|---|---|---|---|---|
| Q$_{30}$(R$_7$ = H,R$_8$ = H) | H | H | OH | H | CH$_3$ | CH$_3$ | |
| Q$_{30}$(R$_7$ = H,R$_8$ = H) | H | H | OH | H | CH$_3$ | OCH$_3$ | |
| Q$_{30}$(R$_7$ = H,R$_8$ = H) | H | H | OH | H | OCH$_3$ | OCH$_3$ | |
| Q$_{30}$(R$_7$ = H,R$_8$ = H) | H | H | OH | H | Cl | OCH$_3$ | |
| Q$_{31}$(R$_7$ = H,R$_8$ = H) | H | H | C=O | | CH$_3$ | CH$_3$ | |
| Q$_{31}$(R$_7$ = H,R$_8$ = H) | H | H | C=O | | CH$_3$ | OCH$_3$ | |
| Q$_{31}$(R$_7$ = H,R$_8$ = H) | H | H | C=O | | OCH$_3$ | OCH$_3$ | |
| Q$_{31}$(R$_7$ = H,R$_8$ = H) | H | H | C=O | | Cl | OCH$_3$ | |
| Q$_{31}$(R$_7$ = H,R$_8$ = H) | H | H | OH | H | CH$_3$ | CH$_3$ | |
| Q$_{31}$(R$_7$ = H,R$_8$ = H) | H | H | OH | H | CH$_3$ | OCH$_3$ | |
| Q$_{31}$(R$_7$ = H,R$_8$ = H) | H | H | OH | H | OCH$_3$ | OCH$_3$ | |
| Q$_{31}$(R$_7$ = H,R$_8$ = H) | H | H | OH | H | Cl | OCH$_3$ | |
| Q$_{32}$(R$_{13}$ = OCH$_3$,R$_{14}$ = OCH$_3$) | H | H | C=O | | CH$_3$ | CH$_3$ | |
| Q$_{32}$(R$_{13}$ = OCH$_3$,R$_{14}$ = OCH$_3$) | H | H | C=O | | CH$_3$ | OCH$_3$ | |
| Q$_{32}$(R$_{13}$ = OCH$_3$,R$_{14}$ = OCH$_3$) | H | H | C=O | | OCH$_3$ | OCH$_3$ | |
| Q$_{32}$(R$_{13}$ = OCH$_3$,R$_{14}$ = OCH$_3$) | H | H | C=O | | Cl | OCH$_3$ | |
| Q$_{32}$(R$_{13}$ = OCH$_3$,R$_{14}$ = OCH$_3$) | H | H | OH | H | CH$_3$ | CH$_3$ | |
| Q$_{32}$(R$_{13}$ = OCH$_3$,R$_{14}$ = OCH$_3$) | H | H | OH | H | CH$_3$ | OCH$_3$ | |
| Q$_{32}$(R$_{13}$ = OCH$_3$,R$_{14}$ = OCH$_3$) | H | H | OH | H | OCH$_3$ | OCH$_3$ | |
| Q$_{32}$(R$_{13}$ = OCH$_3$,R$_{14}$ = OCH$_3$) | H | H | OH | H | Cl | OCH$_3$ | |
| Q$_{33}$(R$_7$ = H) | H | H | C=O | | CH$_3$ | CH$_3$ | |
| Q$_{33}$(R$_7$ = H) | H | H | C=O | | CH$_3$ | OCH$_3$ | |
| Q$_{33}$(R$_7$ = H) | H | H | C=O | | OCH$_3$ | OCH$_3$ | |
| Q$_{33}$(R$_7$ = H) | H | H | C=O | | Cl | OCH$_3$ | |
| Q$_{33}$(R$_7$ = H) | H | H | OH | H | CH$_3$ | CH$_3$ | |
| Q$_{33}$(R$_7$ = H) | H | H | OH | H | CH$_3$ | OCH$_3$ | |
| Q$_{33}$(R$_7$ = H) | H | H | OH | H | OCH$_3$ | OCH$_3$ | |
| Q$_{33}$(R$_7$ = H) | H | H | OH | H | Cl | OCH$_3$ | |

TABLE XIV

General Formula XIV

| Q | R | R$_1$ | R$_2$ | R$_3$ | X | Y | m.p.(°C.) |
|---|---|---|---|---|---|---|---|
| Q$_1$(R$_7$ = H,R$_8$ = H,R$_9$ = H) | H | H | C=O | | CH$_3$ | CH$_3$ | |
| Q$_1$(R$_7$ = H,R$_8$ = H,R$_9$ = H) | H | H | C=O | | CH$_3$ | OCH$_3$ | |
| Q$_1$(R$_7$ = H,R$_8$ = H,R$_9$ = H) | H | H | C=O | | OCH$_3$ | OCH$_3$ | |
| Q$_1$(R$_7$ = H,R$_8$ = H,R$_9$ = H) | H | H | C=O | | Cl | OCH$_3$ | |
| Q$_1$(R$_7$ = H,R$_8$ = H,R$_9$ = H) | H | H | OH | H | CH$_3$ | CH$_3$ | |
| Q$_1$(R$_7$ = H,R$_8$ = H,R$_9$ = H) | H | H | OH | H | CH$_3$ | OCH$_3$ | |
| Q$_1$(R$_7$ = H,R$_8$ = H,R$_9$ = H) | H | H | OH | H | OCH$_3$ | OCH$_3$ | |
| Q$_1$(R$_7$ = H,R$_8$ = H,R$_9$ = H) | H | H | OH | H | Cl | OCH$_3$ | |
| Q$_1$(R$_7$ = H,R$_8$ = H,R$_9$ = H) | H | H | OCH$_3$ | H | OCH$_3$ | OCH$_3$ | |
| Q$_1$(R$_7$ = H,R$_8$ = H,R$_9$ = H) | H | H | OCH$_2$CH$_3$ | H | OCH$_3$ | OCH$_3$ | |
| Q$_2$(R$_7$ = H,R$_8$ = H,R$_9$ = H) | H | H | C=O | | CH$_3$ | CH$_3$ | |
| Q$_2$(R$_7$ = H,R$_8$ = H,R$_9$ = H) | H | H | C=O | | CH$_3$ | OCH$_3$ | |
| Q$_2$(R$_7$ = H,R$_8$ = H,R$_9$ = H) | H | H | C=O | | OCH$_3$ | OCH$_3$ | |
| Q$_2$(R$_7$ = H,R$_8$ = H,R$_9$ = H) | H | H | C=O | | Cl | OCH$_3$ | |
| Q$_2$(R$_7$ = H,R$_8$ = H,R$_9$ = H) | H | H | OH | H | CH$_3$ | CH$_3$ | |
| Q$_2$(R$_7$ = H,R$_8$ = H,R$_9$ = H) | H | H | OH | H | CH$_3$ | OCH$_3$ | |
| Q$_2$(R$_7$ = H,R$_8$ = H,R$_9$ = H) | H | H | OH | H | OCH$_3$ | OCH$_3$ | |
| Q$_2$(R$_7$ = H,R$_8$ = H,R$_9$ = H) | H | H | OH | H | Cl | OCH$_3$ | |
| Q$_2$(R$_7$ = H,R$_8$ = H,R$_9$ = H) | H | H | OCH$_3$ | H | CH$_3$ | OCH$_3$ | |
| Q$_2$(R$_7$ = H,R$_8$ = H,R$_9$ = H) | H | H | OCH$_2$CH$_3$ | H | CH$_3$ | CH$_3$ | |
| Q$_3$(R$_7$ = H,R$_8$ = H,R$_9$ = H) | H | H | C=O | | CH$_3$ | CH$_3$ | |
| Q$_3$(R$_7$ = H,R$_8$ = H,R$_9$ = H) | H | H | C=O | | CH$_3$ | OCH$_3$ | |
| Q$_3$(R$_7$ = H,R$_8$ = H,R$_9$ = H) | H | H | C=O | | OCH$_3$ | OCH$_3$ | |
| Q$_3$(R$_7$ = H,R$_8$ = H,R$_9$ = H) | H | H | C=O | | Cl | OCH$_3$ | |
| Q$_3$(R$_7$ = H,R$_8$ = H,R$_9$ = H) | H | H | OH | H | CH$_3$ | CH$_3$ | |
| Q$_3$(R$_7$ = H,R$_8$ = H,R$_9$ = H) | H | H | OH | H | CH$_3$ | OCH$_3$ | |
| Q$_3$(R$_7$ = H,R$_8$ = H,R$_9$ = H) | H | H | OH | H | OCH$_3$ | OCH$_3$ | |
| Q$_3$(R$_7$ = H,R$_8$ = H,R$_9$ = H) | H | H | OH | H | Cl | OCH$_3$ | |
| Q$_3$(R$_7$ = H,R$_8$ = H,R$_9$ = Cl) | H | H | C=O | | OCH$_3$ | OCH$_3$ | |
| Q$_3$(R$_7$ = H,R$_8$ = H,R$_9$ = CH$_3$) | H | H | C=O | | OCH$_3$ | OCH$_3$ | |
| Q$_3$(R$_7$ = H,R$_8$ = H,R$_9$ = CH$_3$) | H | H | OH | H | OCH$_3$ | OCH$_3$ | |
| Q$_4$(R$_7$ = H,R$_8$ = H,R$_9$ = H) | H | H | C=O | | CH$_3$ | CH$_3$ | |
| Q$_4$(R$_7$ = H,R$_8$ = H,R$_9$ = H) | H | H | C=O | | CH$_3$ | OCH$_3$ | |
| Q$_4$(R$_7$ = H,R$_8$ = H,R$_9$ = H) | H | H | C=O | | OCH$_3$ | OCH$_3$ | |
| Q$_4$(R$_7$ = H,R$_8$ = H,R$_9$ = H) | H | H | C=O | | Cl | OCH$_3$ | |
| Q$_4$(R$_7$ = H,R$_8$ = H,R$_9$ = H) | H | H | OH | H | CH$_3$ | CH$_3$ | |
| Q$_4$(R$_7$ = H,R$_8$ = H,R$_9$ = H) | H | H | OH | H | CH$_3$ | OCH$_3$ | |
| Q$_4$(R$_7$ = H,R$_8$ = H,R$_9$ = H) | H | H | OH | H | OCH$_3$ | OCH$_3$ | |
| Q$_4$(R$_7$ = H,R$_8$ = H,R$_9$ = H) | H | H | OH | H | Cl | OCH$_3$ | |
| Q$_5$(R$_7$ = H,R$_8$ = H,R$_9$ = H,R$_{10}$ = CH$_3$) | H | H | C=O | | CH$_3$ | CH$_3$ | |
| Q$_5$(R$_7$ = H,R$_8$ = H,R$_9$ = H,R$_{10}$ = CH$_3$) | H | H | C=O | | CH$_3$ | OCH$_3$ | |
| Q$_5$(R$_7$ = H,R$_8$ = H,R$_9$ = H,R$_{10}$ = CH$_3$) | H | H | C=O | | OCH$_3$ | OCH$_3$ | |
| Q$_5$(R$_7$ = H,R$_8$ = H,R$_9$ = H,R$_{10}$ = CH$_3$) | H | H | C=O | | Cl | OCH$_3$ | |
| Q$_5$(R$_7$ = H,R$_8$ = H,R$_9$ = H,R$_{10}$ = CH$_3$) | H | H | OH | H | CH$_3$ | CH$_3$ | |
| Q$_5$(R$_7$ = H,R$_8$ = H,R$_9$ = H,R$_{10}$ = CH$_3$) | H | H | OH | H | CH$_3$ | OCH$_3$ | |

TABLE XIV-continued

General Formula XIV

| Q | R | R$_1$ | R$_2$ | R$_3$ | X | Y | m.p.(°C.) |
|---|---|---|---|---|---|---|---|
| Q$_5$(R$_7$ = H,R$_8$ = H,R$_9$ = H,R$_{10}$ = CH$_3$) | H | H | OH | H | OCH$_3$ | OCH$_3$ | |
| Q$_5$(R$_7$ = H,R$_8$ = H,R$_9$ = H,R$_{10}$ = CH$_3$) | H | H | OH | H | Cl | OCH$_3$ | |
| Q$_5$(R$_7$ = H,R$_8$ = H,R$_9$ = H,R$_{10}$ = CH$_3$) | H | H | OCH$_3$ | H | Cl | OCH$_3$ | |
| Q$_5$(R$_7$ = H,R$_8$ = H,R$_9$ = H,R$_{10}$ = CH$_3$) | H | H | OCH$_2$CH$_3$ | H | OCH$_3$ | OCH$_3$ | |
| Q$_6$(R$_7$ = H,R$_8$ = H,R$_9$ = H,R$_{10}$ = CH$_3$) | H | H | C=O | | CH$_3$ | CH$_3$ | |
| Q$_6$(R$_7$ = H,R$_8$ = H,R$_9$ = H,R$_{10}$ = CH$_3$) | H | H | C=O | | CH$_3$ | OCH$_3$ | |
| Q$_6$(R$_7$ = H,R$_8$ = H,R$_9$ = H,R$_{10}$ = CH$_3$) | H | H | C=O | | OCH$_3$ | OCH$_3$ | |
| Q$_6$(R$_7$ = H,R$_8$ = H,R$_9$ = H,R$_{10}$ = CH$_3$) | H | H | C=O | | Cl | OCH$_3$ | |
| Q$_6$(R$_7$ = H,R$_8$ = H,R$_9$ = H,R$_{10}$ = CH$_3$) | H | H | OH | H | CH$_3$ | CH$_3$ | |
| Q$_6$(R$_7$ = H,R$_8$ = H,R$_9$ = H,R$_{10}$ = CH$_3$) | H | H | OH | H | CH$_3$ | OCH$_3$ | |
| Q$_6$(R$_7$ = H,R$_8$ = H,R$_9$ = H,R$_{10}$ = CH$_3$) | H | H | OH | H | OCH$_3$ | OCH$_3$ | |
| Q$_6$(R$_7$ = H,R$_8$ = H,R$_9$ = H,R$_{10}$ = CH$_3$) | H | H | OH | H | Cl | OCH$_3$ | |
| Q$_7$(R$_7$ = H,R$_8$ = H) | H | H | C=O | | CH$_3$ | CH$_3$ | |
| Q$_7$(R$_7$ = H,R$_8$ = H) | H | H | C=O | | CH$_3$ | OCH$_3$ | |
| Q$_7$(R$_7$ = H,R$_8$ = H) | H | H | C=O | | OCH$_3$ | OCH$_3$ | |
| Q$_7$(R$_7$ = H,R$_8$ = H) | H | H | C=O | | Cl | OCH$_3$ | |
| Q$_7$(R$_7$ = H,R$_8$ = H) | H | H | OH | H | CH$_3$ | CH$_3$ | |
| Q$_7$(R$_7$ = H,R$_8$ = H) | H | H | OH | H | CH$_3$ | OCH$_3$ | |
| Q$_7$(R$_7$ = H,R$_8$ = H) | H | H | OH | H | OCH$_3$ | OCH$_3$ | |
| Q$_7$(R$_7$ = H,R$_8$ = H) | H | H | OH | H | Cl | OCH$_3$ | |
| Q$_8$(R$_7$ = H,R$_8$ = H) | H | H | C=O | | OCH$_3$ | OCH$_3$ | |
| Q$_8$(R$_7$ = H,R$_8$ = H) | H | H | C=O | | Cl | OCH$_3$ | |
| Q$_8$(R$_7$ = H,R$_8$ = H) | H | H | OH | H | Cl | OCH$_3$ | |
| Q$_8$(R$_7$ = H,R$_8$ = H) | H | H | OH | H | OCH$_3$ | OCH$_3$ | |
| Q$_9$(R$_7$ = H,R$_8$ = H) | H | H | C=O | | CH$_3$ | CH$_3$ | |
| Q$_9$(R$_7$ = H,R$_8$ = H) | H | H | C=O | | CH$_3$ | OCH$_3$ | |
| Q$_9$(R$_7$ = H,R$_8$ = H) | H | H | C=O | | OCH$_3$ | OCH$_3$ | |
| Q$_9$(R$_7$ = H,R$_8$ = H) | H | H | C=O | | Cl | OCH$_3$ | |
| Q$_9$(R$_7$ = H,R$_8$ = H) | H | H | OH | H | CH$_3$ | CH$_3$ | |
| Q$_9$(R$_7$ = H,R$_8$ = H) | H | H | OH | H | CH$_3$ | OCH$_3$ | |
| Q$_9$(R$_7$ = H,R$_8$ = H) | H | H | OH | H | OCH$_3$ | OCH$_3$ | |
| Q$_9$(R$_7$ = H,R$_8$ = H) | H | H | OH | H | Cl | OCH$_3$ | |
| Q$_{10}$(R$_7$ = H,R$_8$ = H) | H | H | C=O | | CH$_3$ | OCH$_3$ | |
| Q$_{10}$(R$_7$ = H,R$_8$ = H) | H | H | C=O | | OCH$_3$ | OCH$_3$ | |
| Q$_{10}$(R$_7$ = H,R$_8$ = H) | H | H | C=O | | Cl | OCH$_3$ | |
| Q$_{10}$(R$_7$ = H,R$_8$ = H) | H | H | OH | H | CH$_3$ | CH$_3$ | |
| Q$_{10}$(R$_7$ = H,R$_8$ = H) | H | H | OH | H | OCH$_3$ | OCH$_3$ | |
| Q$_{10}$(R$_7$ = H,R$_8$ = H) | H | H | OH | H | Cl | OCH$_3$ | |
| Q$_{11}$(R$_7$ = H,R$_8$ = H) | H | H | C=O | | CH$_3$ | CH$_3$ | |
| Q$_{11}$(R$_7$ = H,R$_8$ = H) | H | H | C=O | | CH$_3$ | OCH$_3$ | |
| Q$_{11}$(R$_7$ = H,R$_8$ = H) | H | H | C=O | | OCH$_3$ | OCH$_3$ | |
| Q$_{11}$(R$_7$ = H,R$_8$ = H) | H | H | C=O | | Cl | OCH$_3$ | |
| Q$_{11}$(R$_7$ = H,R$_8$ = H) | H | H | OH | H | CH$_3$ | CH$_3$ | |
| Q$_{11}$(R$_7$ = H,R$_8$ = H) | H | H | OH | H | CH$_3$ | OCH$_3$ | |
| Q$_{11}$(R$_7$ = H,R$_8$ = H) | H | H | OH | H | OCH$_3$ | OCH$_3$ | |
| Q$_{11}$(R$_7$ = H,R$_8$ = H) | H | H | OH | H | Cl | OCH$_3$ | |
| Q$_{12}$(R$_7$ = H,R$_8$ = H) | H | H | C=O | | CH$_3$ | CH$_3$ | |
| Q$_{12}$(R$_7$ = H,R$_8$ = H) | H | H | C=O | | CH$_3$ | OCH$_3$ | |
| Q$_{12}$(R$_7$ = H,R$_8$ = H) | H | H | C=O | | OCH$_3$ | OCH$_3$ | |
| Q$_{12}$(R$_7$ = H,R$_8$ = H) | H | H | C=O | | Cl | OCH$_3$ | |
| Q$_{12}$(R$_7$ = H,R$_8$ = H) | H | H | OH | H | CH$_3$ | CH$_3$ | |
| Q$_{12}$(R$_7$ = H,R$_8$ = H) | H | H | OH | H | CH$_3$ | OCH$_3$ | |
| Q$_{12}$(R$_7$ = H,R$_8$ = H) | H | H | OH | H | OCH$_3$ | OCH$_3$ | |
| Q$_{12}$(R$_7$ = H,R$_8$ = H) | H | H | OH | H | Cl | OCH$_3$ | |
| Q$_{12}$(R$_7$ = H,R$_8$ = H) | H | H | OCH$_3$ | H | OCH$_3$ | OCH$_3$ | |
| Q$_{13}$(R$_7$ = H,R$_8$ = H) | H | H | C=O | | CH$_3$ | CH$_3$ | |
| Q$_{13}$(R$_7$ = H,R$_8$ = H) | H | H | C=O | | CH$_3$ | OCH$_3$ | |
| Q$_{13}$(R$_7$ = H,R$_8$ = H) | H | H | C=O | | OCH$_3$ | OCH$_3$ | |
| Q$_{13}$(R$_7$ = H,R$_8$ = H) | H | H | C=O | | Cl | OCH$_3$ | |
| Q$_{13}$(R$_7$ = H,R$_8$ = H) | H | H | OH | H | CH$_3$ | CH$_3$ | |
| Q$_{13}$(R$_7$ = H,R$_8$ = H) | H | H | OH | H | CH$_3$ | OCH$_3$ | |
| Q$_{13}$(R$_7$ = H,R$_8$ = H) | H | H | OH | H | OCH$_3$ | OCH$_3$ | |
| Q$_{13}$(R$_7$ = H,R$_8$ = H) | H | H | OH | H | Cl | OCH$_3$ | |
| Q$_{14}$(R$_7$ = H) | H | H | C=O | | CH$_3$ | CH$_3$ | |
| Q$_{14}$(R$_7$ = H) | H | H | C=O | | CH$_3$ | OCH$_3$ | |
| Q$_{14}$(R$_7$ = H) | H | H | C=O | | OCH$_3$ | OCH$_3$ | |
| Q$_{14}$(R$_7$ = H) | H | H | C=O | | Cl | OCH$_3$ | |
| Q$_{14}$(R$_7$ = H) | H | H | OH | H | CH$_3$ | CH$_3$ | |
| Q$_{14}$(R$_7$ = H) | H | H | OH | H | CH$_3$ | OCH$_3$ | |
| Q$_{14}$(R$_7$ = H) | H | H | OH | H | OCH$_3$ | OCH$_3$ | |
| Q$_{14}$(R$_7$ = H) | H | H | OH | H | Cl | OCH$_3$ | |
| Q$_{15}$(R$_7$ = H) | H | H | C=O | | CH$_3$ | CH$_3$ | |
| Q$_{15}$(R$_7$ = H) | H | H | C=O | | CH$_3$ | OCH$_3$ | |
| Q$_{15}$(R$_7$ = H) | H | H | C=O | | OCH$_3$ | OCH$_3$ | |
| Q$_{15}$(R$_7$ = H) | H | H | C=O | | Cl | OCH$_3$ | |
| Q$_{15}$(R$_7$ = H) | H | H | OH | H | CH$_3$ | CH$_3$ | |
| Q$_{15}$(R$_7$ = H) | H | H | OH | H | CH$_3$ | OCH$_3$ | |
| Q$_{15}$(R$_7$ = H) | H | H | OH | H | OCH$_3$ | OCH$_3$ | |
| Q$_{15}$(R$_7$ = H) | H | H | OH | H | Cl | OCH$_3$ | |
| Q$_{16}$(R$_7$ = H) | H | H | C=O | | CH$_3$ | CH$_3$ | |

TABLE XIV-continued

General Formula XIV

| Q | R | R$_1$ | R$_2$ | R$_3$ | X | Y | m.p.(°C.) |
|---|---|---|---|---|---|---|---|
| Q$_{16}$(R$_7$ = H) | H | H | C=O | | CH$_3$ | CH$_3$ | |
| Q$_{16}$(R$_7$ = H) | H | H | C=O | | OCH$_3$ | OCH$_3$ | |
| Q$_{16}$(R$_7$ = H) | H | H | C=O | | Cl | OCH$_3$ | |
| Q$_{16}$(R$_7$ = H) | H | H | OH | H | CH$_3$ | CH$_3$ | |
| Q$_{16}$(R$_7$ = H) | H | H | OH | H | CH$_3$ | OCH$_3$ | |
| Q$_{16}$(R$_7$ = H) | H | H | OH | H | OCH$_3$ | OCH$_3$ | |
| Q$_{16}$(R$_7$ = H) | H | H | OH | H | Cl | OCH$_3$ | |
| Q$_{17}$(R$_7$ = CH$_3$) | H | H | C=O | | CH$_3$ | CH$_3$ | |
| Q$_{17}$(R$_7$ = CH$_3$) | H | H | C=O | | CH$_3$ | OCH$_3$ | |
| Q$_{17}$(R$_7$ = CH$_3$) | H | H | C=O | | OCH$_3$ | OCH$_3$ | |
| Q$_{17}$(R$_7$ = CH$_3$) | H | H | C=O | | Cl | OCH$_3$ | |
| Q$_{17}$(R$_7$ = CH$_3$) | H | H | OH | H | CH$_3$ | CH$_3$ | |
| Q$_{17}$(R$_7$ = CH$_3$) | H | H | OH | H | CH$_3$ | OCH$_3$ | |
| Q$_{17}$(R$_7$ = CH$_3$) | H | H | OH | H | OCH$_3$ | OCH$_3$ | |
| Q$_{17}$(R$_7$ = CH$_3$) | H | H | OH | H | Cl | OCH$_3$ | |
| Q$_{18}$(R$_7$ = H) | H | H | C=O | | CH$_3$ | CH$_3$ | |
| Q$_{18}$(R$_7$ = H) | H | H | C=O | | CH$_3$ | OCH$_3$ | |
| Q$_{18}$(R$_7$ = H) | H | H | C=O | | OCH$_3$ | OCH$_3$ | |
| Q$_{18}$(R$_7$ = H) | H | H | C=O | | Cl | OCH$_3$ | |
| Q$_{18}$(R$_7$ = H) | H | H | OH | H | CH$_3$ | CH$_3$ | |
| Q$_{18}$(R$_7$ = H) | H | H | OH | H | CH$_3$ | OCH$_3$ | |
| Q$_{18}$(R$_7$ = H) | H | H | OH | H | OCH$_3$ | OCH$_3$ | |
| Q$_{18}$(R$_7$ = H) | H | H | OH | H | Cl | OCH$_3$ | |
| Q$_{19}$(R$_7$ = H,R$_8$ = H) | H | H | C=O | | CH$_3$ | CH$_3$ | |
| Q$_{19}$(R$_7$ = H,R$_8$ = H) | H | H | C=O | | CH$_3$ | OCH$_3$ | |
| Q$_{19}$(R$_7$ = H,R$_8$ = H) | H | H | C=O | | OCH$_3$ | OCH$_3$ | |
| Q$_{19}$(R$_7$ = H,R$_8$ = H) | H | H | C=O | | Cl | OCH$_3$ | |
| Q$_{19}$(R$_7$ = H,R$_8$ = H) | H | H | OH | H | CH$_3$ | CH$_3$ | |
| Q$_{19}$(R$_7$ = H,R$_8$ = H) | H | H | OH | H | CH$_3$ | OCH$_3$ | |
| Q$_{19}$(R$_7$ = H,R$_8$ = H) | H | H | OH | H | OCH$_3$ | OCH$_3$ | |
| Q$_{19}$(R$_7$ = H,R$_8$ = H) | H | H | OH | H | Cl | OCH$_3$ | |
| Q$_{20}$(R$_7$ = H,R$_8$ = H) | H | H | C=O | | CH$_3$ | CH$_3$ | |
| Q$_{20}$(R$_7$ = H,R$_8$ = H) | H | H | C=O | | CH$_3$ | OCH$_3$ | |
| Q$_{20}$(R$_7$ = H,R$_8$ = H) | H | H | C=O | | OCH$_3$ | OCH$_3$ | |
| Q$_{20}$(R$_7$ = H,R$_8$ = H) | H | H | C=O | | Cl | OCH$_3$ | |
| Q$_{20}$(R$_7$ = H,R$_8$ = H) | H | H | OH | H | CH$_3$ | CH$_3$ | |
| Q$_{20}$(R$_7$ = H,R$_8$ = H) | H | H | OH | H | CH$_3$ | OCH$_3$ | |
| Q$_{20}$(R$_7$ = H,R$_8$ = H) | H | H | OH | H | OCH$_3$ | OCH$_3$ | |
| Q$_{20}$(R$_7$ = H,R$_8$ = H) | H | H | OH | H | Cl | OCH$_3$ | |
| Q$_{21}$(R$_7$ = H,R$_8$ = H,R$_9$ = CH$_3$) | H | H | C=O | | CH$_3$ | CH$_3$ | |
| Q$_{21}$(R$_7$ = H,R$_8$ = H,R$_9$ = CH$_3$) | H | H | C=O | | CH$_3$ | OCH$_3$ | |
| Q$_{21}$(R$_7$ = H,R$_8$ = H,R$_9$ = CH$_3$) | H | H | C=O | | OCH$_3$ | OCH$_3$ | |
| Q$_{21}$(R$_7$ = H,R$_8$ = H,R$_9$ = CH$_3$) | H | H | C=O | | Cl | OCH$_3$ | |
| Q$_{21}$(R$_7$ = H,R$_8$ = H,R$_9$ = CH$_3$) | H | H | OH | H | CH$_3$ | CH$_3$ | |
| Q$_{21}$(R$_7$ = H,R$_8$ = H,R$_9$ = CH$_3$) | H | H | OH | H | CH$_3$ | OCH$_3$ | |
| Q$_{21}$(R$_7$ = H,R$_8$ = H,R$_9$ = CH$_3$) | H | H | OH | H | OCH$_3$ | OCH$_3$ | |
| Q$_{21}$(R$_7$ = H,R$_8$ = H,R$_9$ = CH$_3$) | H | H | OH | H | Cl | OCH$_3$ | |
| Q$_{22}$(R$_7$ = H) | H | H | C=O | | CH$_3$ | CH$_3$ | |
| Q$_{22}$(R$_7$ = H) | H | H | C=O | | CH$_3$ | OCH$_3$ | |
| Q$_{22}$(R$_7$ = H) | H | H | C=O | | OCH$_3$ | OCH$_3$ | |
| Q$_{22}$(R$_7$ = H) | H | H | C=O | | Cl | OCH$_3$ | |
| Q$_{22}$(R$_7$ = H) | H | H | OH | H | CH$_3$ | CH$_3$ | |
| Q$_{22}$(R$_7$ = H) | H | H | OH | H | CH$_3$ | OCH$_3$ | |
| Q$_{22}$(R$_7$ = H) | H | H | OH | H | OCH$_3$ | OCH$_3$ | |
| Q$_{22}$(R$_7$ = H) | H | H | OH | H | Cl | OCH$_3$ | |
| Q$_{23}$(R$_7$ = H) | H | H | C=O | | CH$_3$ | CH$_3$ | |
| Q$_{23}$(R$_7$ = H) | H | H | C=O | | CH$_3$ | OCH$_3$ | |
| Q$_{23}$(R$_7$ = H) | H | H | C=O | | OCH$_3$ | OCH$_3$ | |
| Q$_{23}$(R$_7$ = H) | H | H | C=O | | Cl | OCH$_3$ | |
| Q$_{23}$(R$_7$ = H) | H | H | OH | H | CH$_3$ | CH$_3$ | |
| Q$_{23}$(R$_7$ = H) | H | H | OH | H | CH$_3$ | OCH$_3$ | |
| Q$_{23}$(R$_7$ = H) | H | H | OH | H | OCH$_3$ | OCH$_3$ | |
| Q$_{23}$(R$_7$ = H) | H | H | OH | H | Cl | OCH$_3$ | |
| Q$_{24}$(R$_7$ = H,R$_8$ = H) | H | H | C=O | | CH$_3$ | CH$_3$ | |
| Q$_{24}$(R$_7$ = H,R$_8$ = H) | H | H | C=O | | CH$_3$ | OCH$_3$ | |
| Q$_{24}$(R$_7$ = H,R$_8$ = H) | H | H | C=O | | OCH$_3$ | OCH$_3$ | |
| Q$_{24}$(R$_7$ = H,R$_8$ = H) | H | H | C=O | | Cl | OCH$_3$ | |
| Q$_{24}$(R$_7$ = H,R$_8$ = H) | H | H | OH | H | CH$_3$ | CH$_3$ | |
| Q$_{24}$(R$_7$ = H,R$_8$ = H) | H | H | OH | H | CH$_3$ | OCH$_3$ | |
| Q$_{24}$(R$_7$ = H,R$_8$ = H) | H | H | OH | H | OCH$_3$ | OCH$_3$ | |
| Q$_{24}$(R$_7$ = H,R$_8$ = H) | H | H | OH | H | Cl | OCH$_3$ | |
| Q$_{25}$(R$_7$ = H,R$_8$ = H) | H | H | C=O | | CH$_3$ | CH$_3$ | |
| Q$_{25}$(R$_7$ = H,R$_8$ = H) | H | H | C=O | | CH$_3$ | OCH$_3$ | |
| Q$_{25}$(R$_7$ = H,R$_8$ = H) | H | H | C=O | | OCH$_3$ | OCH$_3$ | |
| Q$_{25}$(R$_7$ = H,R$_8$ = H) | H | H | C=O | | Cl | OCH$_3$ | |
| Q$_{25}$(R$_7$ = H,R$_8$ = H) | H | H | OH | H | CH$_3$ | CH$_3$ | |
| Q$_{25}$(R$_7$ = H,R$_8$ = H) | H | H | OH | H | CH$_3$ | OCH$_3$ | |
| Q$_{25}$(R$_7$ = H,R$_8$ = H) | H | H | OH | H | OCH$_3$ | OCH$_3$ | |
| Q$_{25}$(R$_7$ = H,R$_8$ = H) | H | H | OH | H | Cl | OCH$_3$ | |
| Q$_{26}$(R$_7$ = H,R$_8$ = H) | H | H | C=O | | CH$_3$ | CH$_3$ | |

TABLE XIV-continued

General Formula XIV

| Q | R | R₁ | R₂ | R₃ | X | Y | m.p.(°C.) |
|---|---|----|----|----|---|---|-----------|
| Q₂₆(R₇ = H,R₈ = H) | H | H | C=O | | CH₃ | OCH₃ | |
| Q₂₆(R₇ = H,R₈ = H) | H | H | C=O | | OCH₃ | OCH₃ | |
| Q₂₆(R₇ = H,R₈ = H) | H | H | C=O | | Cl | OCH₃ | |
| Q₂₆(R₇ = H,R₈ = H) | H | H | OH | H | CH₃ | CH₃ | |
| Q₂₆(R₇ = H,R₈ = H) | H | H | OH | H | CH₃ | OCH₃ | |
| Q₂₆(R₇ = H,R₈ = H) | H | H | OH | H | OCH₃ | OCH₃ | |
| Q₂₆(R₇ = H,R₈ = H) | H | H | OH | H | Cl | OCH₃ | |
| Q₂₇(R₇ = H,R₁₁ = H,R₁₂ = H) | H | H | C=O | | CH₃ | CH₃ | |
| Q₂₇(R₇ = H,R₁₁ = H,R₁₂ = H) | H | H | C=O | | CH₃ | OCH₃ | |
| Q₂₇(R₇ = H,R₁₁ = H,R₁₂ = H) | H | H | C=O | | OCH₃ | OCH₃ | |
| Q₂₇(R₇ = H,R₁₁ = H,R₁₂ = H) | H | H | C=O | | Cl | OCH₃ | |
| Q₂₇(R₇ = H,R₁₁ = H,R₁₂ = H) | H | H | OH | H | CH₃ | CH₃ | |
| Q₂₇(R₇ = H,R₁₁ = H,R₁₂ = H) | H | H | OH | H | CH₃ | OCH₃ | |
| Q₂₇(R₇ = H,R₁₁ = H,R₁₂ = H) | H | H | OH | H | OCH₃ | OCH₃ | |
| Q₂₇(R₇ = H,R₁₁ = H,R₁₂ = H) | H | H | OH | H | Cl | OCH₃ | |
| Q₂₈(R₁₁ = H,R₁₂ = H) | H | H | C=O | | CH₃ | CH₃ | |
| Q₂₈(R₁₁ = H,R₁₂ = H) | H | H | C=O | | CH₃ | OCH₃ | |
| Q₂₈(R₁₁ = H,R₁₂ = H) | H | H | C=O | | OCH₃ | OCH₃ | |
| Q₂₈(R₁₁ = H,R₁₂ = H) | H | H | C=O | | Cl | OCH₃ | |
| Q₂₈(R₁₁ = H,R₁₂ = H) | H | H | OH | H | CH₃ | CH₃ | |
| Q₂₈(R₁₁ = H,R₁₂ = H) | H | H | OH | H | CH₃ | OCH₃ | |
| Q₂₈(R₁₁ = H,R₁₂ = H) | H | H | OH | H | OCH₃ | OCH₃ | |
| Q₂₈(R₁₁ = H,R₁₂ = H) | H | H | OH | H | Cl | OCH₃ | |
| Q₂₉(R₁₁ = H,R₁₂ = H) | H | H | C=O | | CH₃ | CH₃ | |
| Q₂₉(R₁₁ = H,R₁₂ = H) | H | H | C=O | | CH₃ | OCH₃ | |
| Q₂₉(R₁₁ = H,R₁₂ = H) | H | H | C=O | | OCH₃ | OCH₃ | |
| Q₂₉(R₁₁ = H,R₁₂ = H) | H | H | C=O | | Cl | OCH₃ | |
| Q₂₉(R₁₁ = H,R₁₂ = H) | H | H | OH | H | CH₃ | CH₃ | |
| Q₂₉(R₁₁ = H,R₁₂ = H) | H | H | OH | H | CH₃ | OCH₃ | |
| Q₂₉(R₁₁ = H,R₁₂ = H) | H | H | OH | H | OCH₃ | OCH₃ | |
| Q₂₉(R₁₁ = H,R₁₂ = H) | H | H | OH | H | Cl | OCH₃ | |
| Q₃₀(R₇ = H,R₈ = H) | H | H | C=O | | CH₃ | CH₃ | |
| Q₃₀(R₇ = H,R₈ = H) | H | H | C=O | | CH₃ | OCH₃ | |
| Q₃₀(R₇ = H,R₈ = H) | H | H | C=O | | OCH₃ | OCH₃ | |
| Q₃₀(R₇ = H,R₈ = H) | H | H | C=O | | Cl | OCH₃ | |
| Q₃₀(R₇ = H,R₈ = H) | H | H | OH | H | CH₃ | CH₃ | |
| Q₃₀(R₇ = H,R₈ = H) | H | H | OH | H | CH₃ | OCH₃ | |
| Q₃₀(R₇ = H,R₈ = H) | H | H | OH | H | OCH₃ | OCH₃ | |
| Q₃₀(R₇ = H,R₈ = H) | H | H | OH | H | Cl | OCH₃ | |
| Q₃₁(R₇ = H,R₈ = H) | H | H | C=O | | CH₃ | CH₃ | |
| Q₃₁(R₇ = H,R₈ = H) | H | H | C=O | | CH₃ | OCH₃ | |
| Q₃₁(R₇ = H,R₈ = H) | H | H | C=O | | OCH₃ | OCH₃ | |
| Q₃₁(R₇ = H,R₈ = H) | H | H | C=O | | Cl | OCH₃ | |
| Q₃₁(R₇ = H,R₈ = H) | H | H | OH | H | CH₃ | CH₃ | |
| Q₃₁(R₇ = H,R₈ = H) | H | H | OH | H | CH₃ | OCH₃ | |
| Q₃₁(R₇ = H,R₈ = H) | H | H | OH | H | OCH₃ | OCH₃ | |
| Q₃₁(R₇ = H,R₈ = H) | H | H | OH | H | Cl | OCH₃ | |
| Q₃₂(R₁₃ = OCH₃,R₁₄ = OCH₃) | H | H | C=O | | CH₃ | CH₃ | |
| Q₃₂(R₁₃ = OCH₃,R₁₄ = OCH₃) | H | H | C=O | | CH₃ | OCH₃ | |
| Q₃₂(R₁₃ = OCH₃,R₁₄ = OCH₃) | H | H | C=O | | OCH₃ | OCH₃ | |
| Q₃₂(R₁₃ = OCH₃,R₁₄ = OCH₃) | H | H | C=O | | Cl | OCH₃ | |
| Q₃₂(R₁₃ = OCH₃,R₁₄ = OCH₃) | H | H | OH | H | CH₃ | CH₃ | |
| Q₃₂(R₁₃ = OCH₃,R₁₄ = OCH₃) | H | H | OH | H | CH₃ | OCH₃ | |
| Q₃₂(R₁₃ = OCH₃,R₁₄ = OCH₃) | H | H | OH | H | OCH₃ | OCH₃ | |
| Q₃₂(R₁₃ = OCH₃,R₁₄ = OCH₃) | H | H | OH | H | Cl | OCH₃ | |
| Q₃₃(R₇ = H) | H | H | C=O | | CH₃ | CH₃ | |
| Q₃₃(R₇ = H) | H | H | C=O | | CH₃ | OCH₃ | |
| Q₃₃(R₇ = H) | H | H | C=O | | OCH₃ | OCH₃ | |
| Q₃₃(R₇ = H) | H | H | C=O | | Cl | OCH₃ | |
| Q₃₃(R₇ = H) | H | H | OH | H | CH₃ | CH₃ | |
| Q₃₃(R₇ = H) | H | H | OH | H | CH₃ | OCH₃ | |
| Q₃₃(R₇ = H) | H | H | OH | H | OCH₃ | OCH₃ | |
| Q₃₃(R₇ = H) | H | H | OH | H | Cl | OCH₃ | |

TABLE XV

General Formula XV

| Q | R | R₁ | R₂ | R₃ | X | Y | m.p.(°C.) |
|---|---|----|----|----|---|---|-----------|
| Q₁(R₇ = H, R₈ = H, R₉ = H) | H | H | C=O | | CH₃ | CH₃ | |
| Q₁(R₇ = H, R₈ = H, R₉ = H) | H | H | C=O | | CH₃ | OCH₃ | |
| Q₁(R₇ = H, R₈ = H, R₉ = H) | H | H | C=O | | OCH₃ | OCH₃ | |
| Q₁(R₇ = H, R₈ = H, R₉ = H) | H | H | C=O | | Cl | OCH₃ | |
| Q₁(R₇ = H, R₈ = H, R₉ = H) | H | H | OH | H | CH₃ | CH₃ | |
| Q₁(R₇ = H, R₈ = H, R₉ = H) | H | H | OH | H | CH₃ | OCH₃ | |
| Q₁(R₇ = H, R₈ = H, R₉ = H) | H | H | OH | H | OCH₃ | OCH₃ | |
| Q₁(R₇ = H, R₈ = H, R₉ = H) | H | H | OH | H | Cl | OCH₃ | |
| Q₁(R₇ = H, R₈ = H, R₉ = H) | H | H | OCH₃ | H | OCH₃ | OCH₃ | |
| Q₁(R₇ = H, R₈ = H, R₉ = H) | H | H | OCH₂CH₃ | H | OCH₃ | OCH₃ | |

TABLE XV-continued

General Formula XV

| Q | R | $R_1$ | $R_2$ | $R_3$ | X | Y | m.p.(°C.) |
|---|---|---|---|---|---|---|---|
| $Q_2(R_7 = H, R_8 = H, R_9 = H)$ | H | H | C=O | | $CH_3$ | $CH_3$ | |
| $Q_2(R_7 = H, R_8 = H, R_9 = H)$ | H | H | C=O | | $CH_3$ | $OCH_3$ | |
| $Q_2(R_7 = H, R_8 = H, R_9 = H)$ | H | H | C=O | | $OCH_3$ | $OCH_3$ | |
| $Q_2(R_7 = H, R_8 = H, R_9 = H)$ | H | H | C=O | | Cl | $OCH_3$ | |
| $Q_2(R_7 = H, R_8 = H, R_9 = H)$ | H | H | OH | H | $CH_3$ | $CH_3$ | |
| $Q_2(R_7 = H, R_8 = H, R_9 = H)$ | H | H | OH | H | $CH_3$ | $OCH_3$ | |
| $Q_2(R_7 = H, R_8 = H, R_9 = H)$ | H | H | OH | H | $OCH_3$ | $OCH_3$ | |
| $Q_2(R_7 = H, R_8 = H, R_9 = H)$ | H | H | OH | H | Cl | $OCH_3$ | |
| $Q_2(R_7 = H, R_8 = H, R_9 = H)$ | H | H | $OCH_3$ | H | $CH_3$ | $CH_3$ | |
| $Q_2(R_7 = H, R_8 = H, R_9 = H)$ | H | H | $OCH_2CH_3$ | H | $CH_3$ | $CH_3$ | |
| $Q_3(R_7 = H, R_8 = H, R_9 = H)$ | H | H | C=O | | $CH_3$ | $CH_3$ | |
| $Q_3(R_7 = H, R_8 = H, R_9 = H)$ | H | H | C=O | | $CH_3$ | $OCH_3$ | |
| $Q_3(R_7 = H, R_8 = H, R_9 = H)$ | H | H | C=O | | $OCH_3$ | $OCH_3$ | |
| $Q_3(R_7 = H, R_8 = H, R_9 = H)$ | H | H | C=O | | Cl | $OCH_3$ | |
| $Q_3(R_7 = H, R_8 = H, R_9 = H)$ | H | H | OH | H | $CH_3$ | $CH_3$ | |
| $Q_3(R_7 = H, R_8 = H, R_9 = H)$ | H | H | OH | H | $CH_3$ | $OCH_3$ | |
| $Q_3(R_7 = H, R_8 = H, R_9 = H)$ | H | H | OH | H | $OCH_3$ | $OCH_3$ | |
| $Q_3(R_7 = H, R_8 = H, R_9 = H)$ | H | H | OH | H | Cl | $OCH_3$ | |
| $Q_3(R_7 = H, R_8 = H, R_9 = Cl)$ | H | H | C=O | | $OCH_3$ | $OCH_3$ | |
| $Q_3(R_7 = H, R_8 = H, R_9 = CH_3)$ | H | H | C=O | | $OCH_3$ | $OCH_3$ | |
| $Q_3(R_7 = H, R_8 = H, R_9 = CH_3)$ | H | H | OH | H | $OCH_3$ | $OCH_3$ | |
| $Q_4(R_7 = H, R_8 = H, R_9 = H)$ | H | H | C=O | | $CH_3$ | $CH_3$ | |
| $Q_4(R_7 = H, R_8 = H, R_9 = H)$ | H | H | C=O | | $CH_3$ | $OCH_3$ | |
| $Q_4(R_7 = H, R_8 = H, R_9 = H)$ | H | H | C=O | | $OCH_3$ | $OCH_3$ | |
| $Q_4(R_7 = H, R_8 = H, R_9 = H)$ | H | H | C=O | | Cl | $OCH_3$ | |
| $Q_4(R_7 = H, R_8 = H, R_9 = H)$ | H | H | OH | H | $CH_3$ | $CH_3$ | |
| $Q_4(R_7 = H, R_8 = H, R_9 = H)$ | H | H | OH | H | $CH_3$ | $OCH_3$ | |
| $Q_4(R_7 = H, R_8 = H, R_9 = H)$ | H | H | OH | H | $OCH_3$ | $OCH_3$ | |
| $Q_4(R_7 = H, R_8 = H, R_9 = H)$ | H | H | OH | H | Cl | $OCH_3$ | |
| $Q_5(R_7 = H, R_8 = H, R_9 = H, R_{10} = CH_3)$ | H | H | C=O | | $CH_3$ | $CH_3$ | |
| $Q_5(R_7 = H, R_8 = H, R_9 = H, R_{10} = CH_3)$ | H | H | C=O | | $CH_3$ | $OCH_3$ | |
| $Q_5(R_7 = H, R_8 = H, R_9 = H, R_{10} = CH_3)$ | H | H | C=O | | $OCH_3$ | $OCH_3$ | |
| $Q_5(R_7 = H, R_8 = H, R_9 = H, R_{10} = CH_3)$ | H | H | C=O | | Cl | $OCH_3$ | |
| $Q_5(R_7 = H, R_8 = H, R_9 = H, R_{10} = CH_3)$ | H | H | OH | H | $CH_3$ | $CH_3$ | |
| $Q_5(R_7 = H, R_8 = H, R_9 = H, R_{10} = CH_3)$ | H | H | OH | H | $CH_3$ | $OCH_3$ | |
| $Q_5(R_7 = H, R_8 = H, R_9 = H, R_{10} = CH_3)$ | H | H | OH | H | $OCH_3$ | $OCH_3$ | |
| $Q_5(R_7 = H, R_8 = H, R_9 = H, R_{10} = CH_3)$ | H | H | OH | H | Cl | $OCH_3$ | |
| $Q_5(R_7 = H, R_8 = H, R_9 = H, R_{10} = CH_3)$ | H | H | $OCH_3$ | H | Cl | $OCH_3$ | |
| $Q_5(R_7 = H, R_8 = H, R_9 = H, R_{10} = CH_3)$ | H | H | $OCH_2CH_3$ | H | $OCH_3$ | $OCH_3$ | |
| $Q_6(R_7 = H, R_8 = H, R_9 = H, R_{10} = CH_3)$ | H | H | C=O | | $OCH_3$ | $OCH_3$ | |
| $Q_6(R_7 = H, R_8 = H, R_9 = H, R_{10} = CH_3)$ | H | H | C=O | | $CH_3$ | $CH_3$ | |
| $Q_6(R_7 = H, R_8 = H, R_9 = H, R_{10} = CH_3)$ | H | H | C=O | | $CH_3$ | $OCH_3$ | |
| $Q_6(R_7 = H, R_8 = H, R_9 = H, R_{10} = CH_3)$ | H | H | C=O | | Cl | $OCH_3$ | |
| $Q_6(R_7 = H, R_8 = H, R_9 = H, R_{10} = CH_3)$ | H | H | OH | H | $CH_3$ | $CH_3$ | |
| $Q_6(R_7 = H, R_8 = H, R_9 = H, R_{10} = CH_3)$ | H | H | OH | H | $CH_3$ | $OCH_3$ | |
| $Q_6(R_7 = H, R_8 = H, R_9 = H, R_{10} = CH_3)$ | H | H | OH | H | $OCH_3$ | $OCH_3$ | |
| $Q_6(R_7 = H, R_8 = H, R_9 = H, R_{10} = CH_3)$ | H | H | OH | H | Cl | $OCH_3$ | |
| $Q_7(R_7 = H, R_8 = H)$ | H | H | C=O | | $CH_3$ | $CH_3$ | |
| $Q_7(R_7 = H, R_8 = H)$ | H | H | C=O | | $CH_3$ | $OCH_3$ | |
| $Q_7(R_7 = H, R_8 = H)$ | H | H | C=O | | $OCH_3$ | $OCH_3$ | |
| $Q_7(R_7 = H, R_8 = H)$ | H | H | C=O | | Cl | $OCH_3$ | |
| $Q_7(R_7 = H, R_8 = H)$ | H | H | OH | H | $CH_3$ | $CH_3$ | |
| $Q_7(R_7 = H, R_8 = H)$ | H | H | OH | H | $CH_3$ | $OCH_3$ | |
| $Q_7(R_7 = H, R_8 = H)$ | H | H | OH | H | $OCH_3$ | $OCH_3$ | |
| $Q_7(R_7 = H, R_8 = H)$ | H | H | OH | H | Cl | $OCH_3$ | |
| $Q_8(R_7 = H, R_8 = H)$ | H | H | C=O | | $OCH_3$ | $OCH_3$ | |
| $Q_8(R_7 = H, R_8 = H)$ | H | H | C=O | | Cl | $OCH_3$ | |
| $Q_8(R_7 = H, R_8 = H)$ | H | H | OH | H | Cl | $OCH_3$ | |
| $Q_8(R_7 = H, R_8 = H)$ | H | H | OH | H | $OCH_3$ | $OCH_3$ | |
| $Q_9(R_7 = H, R_8 = H)$ | H | H | C=O | | $CH_3$ | $CH_3$ | |
| $Q_9(R_7 = H, R_8 = H)$ | H | H | C=O | | $CH_3$ | $OCH_3$ | |
| $Q_9(R_7 = H, R_8 = H)$ | H | H | C=O | | $OCH_3$ | $OCH_3$ | |
| $Q_9(R_7 = H, R_8 = H)$ | H | H | C=O | | Cl | $OCH_3$ | |
| $Q_9(R_7 = H, R_8 = H)$ | H | H | OH | H | $CH_3$ | $CH_3$ | |
| $Q_9(R_7 = H, R_8 = H)$ | H | H | OH | H | $CH_3$ | $OCH_3$ | |
| $Q_9(R_7 = H, R_8 = H)$ | H | H | OH | H | $OCH_3$ | $OCH_3$ | |
| $Q_9(R_7 = H, R_8 = H)$ | H | H | OH | H | Cl | $OCH_3$ | |
| $Q_{10}(R_7 = H, R_8 = H)$ | H | H | C=O | | $CH_3$ | $OCH_3$ | |
| $Q_{10}(R_7 = H, R_8 = H)$ | H | H | C=O | | $OCH_3$ | $OCH_3$ | |
| $Q_{10}(R_7 = H, R_8 = H)$ | H | H | C=O | | Cl | $OCH_3$ | |
| $Q_{10}(R_7 = H, R_8 = H)$ | H | H | OH | H | $CH_3$ | $CH_3$ | |
| $Q_{10}(R_7 = H, R_8 = H)$ | H | H | OH | H | $OCH_3$ | $OCH_3$ | |
| $Q_{10}(R_7 = H, R_8 = H)$ | H | H | OH | H | Cl | OCH | |
| $Q_{11}(R_7 = H, R_8 = H)$ | H | H | C=O | | $CH_3$ | $CH_3$ | |
| $Q_{11}(R_7 = H, R_8 = H)$ | H | H | C=O | | $CH_3$ | $OCH_3$ | |
| $Q_{11}(R_7 = H, R_8 = H)$ | H | H | C=O | | $OCH_3$ | $OCH_3$ | |
| $Q_{11}(R_7 = H, R_8 = H)$ | H | H | C=O | | Cl | $OCH_3$ | |
| $Q_{11}(R_7 = H, R_8 = H)$ | H | H | OH | H | $CH_3$ | $CH_3$ | |
| $Q_{11}(R_7 = H, R_8 = H)$ | H | H | OH | H | $CH_3$ | $OCH_3$ | |
| $Q_{11}(R_7 = H, R_8 = H)$ | H | H | OH | H | $OCH_3$ | $OCH_3$ | |

TABLE XV-continued

General Formula XV

| Q | R | $R_1$ | $R_2$ | $R_3$ | X | Y | m.p.(°C.) |
|---|---|---|---|---|---|---|---|
| $Q_{11}(R_7 = H, R_8 = H)$ | H | H | OH | H | Cl | $OCH_3$ | |
| $Q_{12}(R_7 = H, R_8 = H)$ | H | H | C=O | | $CH_3$ | $CH_3$ | |
| $Q_{12}(R_7 = H, R_8 = H)$ | H | H | C=O | | $CH_3$ | $OCH_3$ | |
| $Q_{12}(R_7 = H, R_8 = H)$ | H | H | C=O | | $OCH_3$ | $OCH_3$ | |
| $Q_{12}(R_7 = H, R_8 = H)$ | H | H | C=O | | Cl | $OCH_3$ | |
| $Q_{12}(R_7 = H, R_8 = H)$ | H | H | OH | H | $CH_3$ | $CH_3$ | |
| $Q_{12}(R_7 = H, R_8 = H)$ | H | H | OH | H | $CH_3$ | $OCH_3$ | |
| $Q_{12}(R_7 = H, R_8 = H)$ | H | H | OH | H | $OCH_3$ | $OCH_3$ | |
| $Q_{12}(R_7 = H, R_8 = H)$ | H | H | OH | H | Cl | $OCH_3$ | |
| $Q_{12}(R_7 = H, R_8 = H)$ | H | H | $OCH_3$ | H | $OCH_3$ | $OCH_3$ | |
| $Q_{13}(R_7 = H, R_8 = H)$ | H | H | C=O | | $CH_3$ | $CH_3$ | |
| $Q_{13}(R_7 = H, R_8 = H)$ | H | H | C=O | | $CH_3$ | $OCH_3$ | |
| $Q_{13}(R_7 = H, R_8 = H)$ | H | H | C=O | | $OCH_3$ | $OCH_3$ | |
| $Q_{13}(R_7 = H, R_8 = H)$ | H | H | C=O | | Cl | $OCH_3$ | |
| $Q_{13}(R_7 = H, R_8 = H)$ | H | H | OH | H | $CH_3$ | $CH_3$ | |
| $Q_{13}(R_7 = H, R_8 = H)$ | H | H | OH | H | $CH_3$ | $OCH_3$ | |
| $Q_{13}(R_7 = H, R_8 = H)$ | H | H | OH | H | $OCH_3$ | $OCH_3$ | |
| $Q_{13}(R_7 = H, R_8 = H)$ | H | H | OH | H | Cl | $OCH_3$ | |
| $Q_{14}(R_7 = H)$ | H | H | C=O | | $CH_3$ | $CH_3$ | |
| $Q_{14}(R_7 = H)$ | H | H | C=O | | $CH_3$ | $OCH_3$ | |
| $Q_{14}(R_7 = H)$ | H | H | C=O | | $OCH_3$ | $OCH_3$ | |
| $Q_{14}(R_7 = H)$ | H | H | C=O | | Cl | $OCH_3$ | |
| $Q_{14}(R_7 = H)$ | H | H | OH | H | $CH_3$ | $CH_3$ | |
| $Q_{14}(R_7 = H)$ | H | H | OH | H | $CH_3$ | $OCH_3$ | |
| $Q_{14}(R_7 = H)$ | H | H | OH | H | $OCH_3$ | $OCH_3$ | |
| $Q_{14}(R_7 = H)$ | H | H | OH | H | Cl | $OCH_3$ | |
| $Q_{15}(R_7 = H)$ | H | H | C=O | | $CH_3$ | $CH_3$ | |
| $Q_{15}(R_7 = H)$ | H | H | C=O | | $CH_3$ | $OCH_3$ | |
| $Q_{15}(R_7 = H)$ | H | H | C=O | | $OCH_3$ | $OCH_3$ | |
| $Q_{15}(R_7 = H)$ | H | H | C=O | | Cl | $OCH_3$ | |
| $Q_{15}(R_7 = H)$ | H | H | OH | H | $CH_3$ | $CH_3$ | |
| $Q_{15}(R_7 = H)$ | H | H | OH | H | $CH_3$ | $OCH_3$ | |
| $Q_{15}(R_7 = H)$ | H | H | OH | H | $OCH_3$ | $OCH_3$ | |
| $Q_{15}(R_7 = H)$ | H | H | OH | H | Cl | $OCH_3$ | |
| $Q_{16}(R_7 = H)$ | H | H | C=O | | $CH_3$ | $CH_3$ | |
| $Q_{16}(R_7 = H)$ | H | H | C=O | | $CH_3$ | $OCH_3$ | |
| $Q_{16}(R_7 = H)$ | H | H | C=O | | $OCH_3$ | $OCH_3$ | |
| $Q_{16}(R_7 = H)$ | H | H | C=O | | Cl | $OCH_3$ | |
| $Q_{16}(R_7 = H)$ | H | H | OH | H | $CH_3$ | $CH_3$ | |
| $Q_{16}(R_7 = H)$ | H | H | OH | H | $CH_3$ | $OCH_3$ | |
| $Q_{16}(R_7 = H)$ | H | H | OH | H | $OCH_3$ | $OCH_3$ | |
| $Q_{16}(R_7 = H)$ | H | H | OH | H | Cl | $OCH_3$ | |
| $Q_{17}(R_7 = H)$ | H | H | C=O | | $CH_3$ | $CH_3$ | |
| $Q_{17}(R_7 = H)$ | H | H | C=O | | $CH_3$ | $OCH_3$ | |
| $Q_{17}(R_7 = H)$ | H | H | C=O | | $OCH_3$ | $OCH_3$ | |
| $Q_{17}(R_7 = H)$ | H | H | C=O | | Cl | $OCH_3$ | |
| $Q_{17}(R_7 = CH_3)$ | H | H | OH | H | $CH_3$ | $CH_3$ | |
| $Q_{17}(R_7 = CH_3)$ | H | H | OH | H | $CH_3$ | $OCH_3$ | |
| $Q_{17}(R_7 = CH_3)$ | H | H | OH | H | $OCH_3$ | $OCH_3$ | |
| $Q_{17}(R_7 = CH_3)$ | H | H | OH | H | Cl | $OCH_3$ | |
| $Q_{18}(R_7 = H)$ | H | H | C=O | | $CH_3$ | $CH_3$ | |
| $Q_{18}(R_7 = H)$ | H | H | C=O | | $CH_3$ | $OCH_3$ | |
| $Q_{18}(R_7 = H)$ | H | H | C=O | | $OCH_3$ | $OCH_3$ | |
| $Q_{18}(R_7 = H)$ | H | H | C=O | | Cl | $OCH_3$ | |
| $Q_{18}(R_7 = H)$ | H | H | OH | H | $CH_3$ | $CH_3$ | |
| $Q_{18}(R_7 = H)$ | H | H | OH | H | $CH_3$ | $OCH_3$ | |
| $Q_{18}(R_7 = H)$ | H | H | OH | H | $OCH_3$ | $OCH_3$ | |
| $Q_{18}(R_7 = H)$ | H | H | OH | H | Cl | $OCH_3$ | |
| $Q_{19}(R_7 = H, R_8 = H)$ | H | H | C=O | | $CH_3$ | $CH_3$ | |
| $Q_{19}(R_7 = H, R_8 = H)$ | H | H | C=O | | $CH_3$ | $OCH_3$ | |
| $Q_{19}(R_7 = H, R_8 = H)$ | H | H | C=O | | $OCH_3$ | $OCH_3$ | |
| $Q_{19}(R_7 = H, R_8 = H)$ | H | H | C=O | | Cl | $OCH_3$ | |
| $Q_{19}(R_7 = H, R_8 = H)$ | H | H | OH | H | $CH_3$ | $CH_3$ | |
| $Q_{19}(R_7 = H, R_8 = H)$ | H | H | OH | H | $CH_3$ | $OCH_3$ | |
| $Q_{19}(R_7 = H, R_8 = H)$ | H | H | OH | H | $OCH_3$ | $OCH_3$ | |
| $Q_{19}(R_7 = H, R_8 = H)$ | H | H | OH | H | Cl | $OCH_3$ | |
| $Q_{20}(R_7 = H, R_8 = H)$ | H | H | C=O | | $CH_3$ | $CH_3$ | |
| $Q_{20}(R_7 = H, R_8 = H)$ | H | H | C=O | | $CH_3$ | $OCH_3$ | |
| $Q_{20}(R_7 = H, R_8 = H)$ | H | H | C=O | | $OCH_3$ | $OCH_3$ | |
| $Q_{20}(R_7 = H, R_8 = H)$ | H | H | C=O | | Cl | $OCH_3$ | |
| $Q_{20}(R_7 = H, R_8 = H)$ | H | H | OH | H | $CH_3$ | $CH_3$ | |
| $Q_{20}(R_7 = H, R_8 = H)$ | H | H | OH | H | $CH_3$ | $OCH_3$ | |
| $Q_{20}(R_7 = H, R_8 = H)$ | H | H | OH | H | $OCH_3$ | $OCH_3$ | |
| $Q_{20}(R_7 = H, R_8 = H)$ | H | H | OH | H | Cl | $OCH_3$ | |
| $Q_{21}(R_7 = H, R_8 = H, R_9 = CH_3)$ | H | H | C=O | | $CH_3$ | $CH_3$ | |
| $Q_{21}(R_7 = H, R_8 = H, R_9 = CH_3)$ | H | H | C=O | | $CH_3$ | $OCH_3$ | |
| $Q_{21}(R_7 = H, R_8 = H, R_9 = CH_3)$ | H | H | C=O | | $OCH_3$ | $OCH_3$ | |
| $Q_{21}(R_7 = H, R_8 = H, R_9 = CH_3)$ | H | H | C=O | | Cl | $OCH_3$ | |
| $Q_{21}(R_7 = H, R_8 = H, R_9 = CH_3)$ | H | H | OH | H | $CH_3$ | $CH_3$ | |
| $Q_{21}(R_7 = H, R_8 = H, R_9 = CH_3)$ | H | H | OH | H | $CH_3$ | $OCH_3$ | |

TABLE XV-continued

General Formula XV

| Q | R | $R_1$ | $R_2$ | $R_3$ | X | Y | m.p.(°C.) |
|---|---|---|---|---|---|---|---|
| $Q_{21}(R_7 = H, R_8 = H, R_9 = CH_3)$ | H | H | OH | H | $OCH_3$ | $OCH_3$ | |
| $Q_{21}(R_7 = H, R_8 = H, R_9 = CH_3)$ | H | H | OH | H | Cl | $OCH_3$ | |
| $Q_{22}(R_7 = H)$ | H | H | C=O | | $CH_3$ | $CH_3$ | |
| $Q_{22}(R_7 = H)$ | H | H | C=O | | $CH_3$ | $OCH_3$ | |
| $Q_{22}(R_7 = H)$ | H | H | C=O | | $OCH_3$ | $OCH_3$ | |
| $Q_{22}(R_7 = H)$ | H | H | C=O | | Cl | $OCH_3$ | |
| $Q_{22}(R_7 = H)$ | H | H | OH | H | $CH_3$ | $CH_3$ | |
| $Q_{22}(R_7 = H)$ | H | H | OH | H | $CH_3$ | $OCH_3$ | |
| $Q_{22}(R_7 = H)$ | H | H | OH | H | $OCH_3$ | $OCH_3$ | |
| $Q_{22}(R_7 = H)$ | H | H | OH | H | Cl | $OCH_3$ | |
| $Q_{23}(R_7 = H)$ | H | H | C=O | | $CH_3$ | $CH_3$ | |
| $Q_{23}(R_7 = H)$ | H | H | C=O | | $CH_3$ | $OCH_3$ | |
| $Q_{23}(R_7 = H)$ | H | H | C=O | | $OCH_3$ | $OCH_3$ | |
| $Q_{23}(R_7 = H)$ | H | H | C=O | | Cl | $OCH_3$ | |
| $Q_{23}(R_7 = H)$ | H | H | OH | H | $CH_3$ | $CH_3$ | |
| $Q_{23}(R_7 = H)$ | H | H | OH | H | $CH_3$ | $OCH_3$ | |
| $Q_{23}(R_7 = H)$ | H | H | OH | H | $OCH_3$ | $OCH_3$ | |
| $Q_{23}(R_7 = H)$ | H | H | OH | H | Cl | $OCH_3$ | |
| $Q_{24}(R_7 = H, R_8 = H)$ | H | H | C=O | | $CH_3$ | $CH_3$ | |
| $Q_{24}(R_7 = H, R_8 = H)$ | H | H | C=O | | $CH_3$ | $OCH_3$ | |
| $Q_{24}(R_7 = H, R_8 = H)$ | H | H | C=O | | $OCH_3$ | $OCH_3$ | |
| $Q_{24}(R_7 = H, R_8 = H)$ | H | H | C=O | | Cl | $OCH_3$ | |
| $Q_{24}(R_7 = H, R_8 = H)$ | H | H | OH | H | $CH_3$ | $CH_3$ | |
| $Q_{24}(R_7 = H, R_8 = H)$ | H | H | OH | H | $CH_3$ | $OCH_3$ | |
| $Q_{24}(R_7 = H, R_8 = H)$ | H | H | OH | H | $OCH_3$ | $OCH_3$ | |
| $Q_{24}(R_7 = H, R_8 = H)$ | H | H | OH | H | Cl | $OCH_3$ | |
| $Q_{25}(R_7 = H, R_8 = H)$ | H | H | C=O | | $CH_3$ | $CH_3$ | |
| $Q_{25}(R_7 = H, R_8 = H)$ | H | H | C=O | | $CH_3$ | $OCH_3$ | |
| $Q_{25}(R_7 = H, R_8 = H)$ | H | H | C=O | | $OCH_3$ | $OCH_3$ | |
| $Q_{25}(R_7 = H, R_8 = H)$ | H | H | C=O | | Cl | $OCH_3$ | |
| $Q_{25}(R_7 = H, R_8 = H)$ | H | H | OH | H | $CH_3$ | $CH_3$ | |
| $Q_{25}(R_7 = H, R_8 = H)$ | H | H | OH | H | $CH_3$ | $OCH_3$ | |
| $Q_{25}(R_7 = H, R_8 = H)$ | H | H | OH | H | $OCH_3$ | $OCH_3$ | |
| $Q_{25}(R_7 = H, R_8 = H)$ | H | H | OH | H | Cl | $OCH_3$ | |
| $Q_{26}(R_7 = H, R_8 = H)$ | H | H | C=O | | $CH_3$ | $CH_3$ | |
| $Q_{26}(R_7 = H, R_8 = H)$ | H | H | C=O | | $CH_3$ | $OCH_3$ | |
| $Q_{26}(R_7 = H, R_8 = H)$ | H | H | C=O | | $OCH_3$ | $OCH_3$ | |
| $Q_{26}(R_7 = H, R_8 = H)$ | H | H | C=O | | Cl | $OCH_3$ | |
| $Q_{26}(R_7 = H, R_8 = H)$ | H | H | OH | H | $CH_3$ | $CH_3$ | |
| $Q_{26}(R_7 = H, R_8 = H)$ | H | H | OH | H | $CH_3$ | $OCH_3$ | |
| $Q_{26}(R_7 = H, R_8 = H)$ | H | H | OH | H | $OCH_3$ | $OCH_3$ | |
| $Q_{26}(R_7 = H, R_8 = H)$ | H | H | OH | H | Cl | $OCH_3$ | |
| $Q_{27}(R_7 = H, R_{11} = H, R_{12} = H)$ | H | H | C=O | | $CH_3$ | $CH_3$ | |
| $Q_{27}(R_7 = H, R_{11} = H, R_{12} = H)$ | H | H | C=O | | $CH_3$ | $OCH_3$ | |
| $Q_{27}(R_7 = H, R_{11} = H, R_{12} = H)$ | H | H | C=O | | $OCH_3$ | $OCH_3$ | |
| $Q_{27}(R_7 = H, R_{11} = H, R_{12} = H)$ | H | H | C=O | | Cl | $OCH_3$ | |
| $Q_{27}(R_7 = H, R_{11} = H, R_{12} = H)$ | H | H | OH | H | $CH_3$ | $CH_3$ | |
| $Q_{27}(R_7 = H, R_{11} = H, R_{12} = H)$ | H | H | OH | H | $CH_3$ | $OCH_3$ | |
| $Q_{27}(R_7 = H, R_{11} = H, R_{12} = H)$ | H | H | OH | H | $CH_3$ | $OCH_3$ | |
| $Q_{27}(R_7 = H, R_{11} = H, R_{12} = H)$ | H | H | OH | H | Cl | $OCH_3$ | |
| $Q_{28}(R_{11} = H, R_{12} = H)$ | H | H | C=O | | $CH_3$ | $CH_3$ | |
| $Q_{28}(R_{11} = H, R_{12} = H)$ | H | H | C=O | | $CH_3$ | $OCH_3$ | |
| $Q_{28}(R_{11} = H, R_{12} = H)$ | H | H | C=O | | $OCH_3$ | $OCH_3$ | |
| $Q_{28}(R_{11} = H, R_{12} = H)$ | H | H | C=O | | Cl | $OCH_3$ | |
| $Q_{28}(R_{11} = H, R_{12} = H)$ | H | H | OH | H | $CH_3$ | $CH_3$ | |
| $Q_{28}(R_{11} = H, R_{12} = H)$ | H | H | OH | H | $CH_3$ | $OCH_3$ | |
| $Q_{28}(R_{11} = H, R_{12} = H)$ | H | H | OH | H | $OCH_3$ | $OCH_3$ | |
| $Q_{28}(R_{11} = H, R_{12} = H)$ | H | H | OH | H | Cl | $OCH_3$ | |
| $Q_{29}(R_{11} = H, R_{12} = H)$ | H | H | C=O | | $CH_3$ | $CH_3$ | |
| $Q_{29}(R_{11} = H, R_{12} = H)$ | H | H | C=O | | $CH_3$ | $OCH_3$ | |
| $Q_{29}(R_{11} = H, R_{12} = H)$ | H | H | C=O | | $OCH_3$ | $OCH_3$ | |
| $Q_{29}(R_{11} = H, R_{12} = H)$ | H | H | C=O | | Cl | $OCH_3$ | |
| $Q_{29}(R_{11} = H, R_{12} = H)$ | H | H | OH | H | $CH_3$ | $CH_3$ | |
| $Q_{29}(R_{11} = H, R_{12} = H)$ | H | H | OH | H | $CH_3$ | $OCH_3$ | |
| $Q_{29}(R_{11} = H, R_{12} = H)$ | H | H | OH | H | $OCH_3$ | $OCH_3$ | |
| $Q_{29}(R_{11} = H, R_{12} = H)$ | H | H | OH | H | Cl | $OCH_3$ | |
| $Q_{30}(R_7 = H, R_8 = H)$ | H | H | C=O | | $CH_3$ | $CH_3$ | |
| $Q_{30}(R_7 = H, R_8 = H)$ | H | H | C=O | | $CH_3$ | $OCH_3$ | |
| $Q_{30}(R_7 = H, R_8 = H)$ | H | H | C=O | | $OCH_3$ | $OCH_3$ | |
| $Q_{30}(R_7 = H, R_8 = H)$ | H | H | C=O | | Cl | $OCH_3$ | |
| $Q_{30}(R_7 = H, R_8 = H)$ | H | H | OH | H | $CH_3$ | $CH_3$ | |
| $Q_{30}(R_7 = H, R_8 = H)$ | H | H | OH | H | $CH_3$ | $OCH_3$ | |
| $Q_{30}(R_7 = H, R_8 = H)$ | H | H | OH | H | $OCH_3$ | $OCH_3$ | |
| $Q_{30}(R_7 = H, R_8 = H)$ | H | H | OH | H | Cl | $OCH_3$ | |
| $Q_{31}(R_7 = H, R_8 = H)$ | H | H | C=O | | $CH_3$ | $CH_3$ | |
| $Q_{31}(R_7 = H, R_8 = H)$ | H | H | C=O | | $CH_3$ | $OCH_3$ | |
| $Q_{31}(R_7 = H, R_8 = H)$ | H | H | C=O | | $OCH_3$ | $OCH_3$ | |
| $Q_{31}(R_7 = H, R_8 = H)$ | H | H | C=O | | Cl | $OCH_3$ | |
| $Q_{31}(R_7 = H, R_8 = H)$ | H | H | OH | H | $CH_3$ | $CH_3$ | |
| $Q_{31}(R_7 = H, R_8 = H)$ | H | H | OH | H | $CH_3$ | $OCH_3$ | |

TABLE XV-continued

General Formula XV

| Q | R | R$_1$ | R$_2$ | R$_3$ | X | Y | m.p.(°C.) |
|---|---|---|---|---|---|---|---|
| Q$_{31}$(R$_7$ = H, R$_8$ = H) | H | H | OH | H | OCH$_3$ | OCH$_3$ | |
| Q$_{31}$(R$_7$ = H, R$_8$ = H) | H | H | OH | H | Cl | OCH$_3$ | |
| Q$_{32}$(R$_{13}$ = OCH$_3$, R$_{14}$ = OCH$_3$) | H | H | C=O | | CH$_3$ | CH$_3$ | |
| Q$_{32}$(R$_{13}$ = OCH$_3$, R$_{14}$ = OCH$_3$) | H | H | C=O | | CH$_3$ | OCH$_3$ | |
| Q$_{32}$(R$_{13}$ = OCH$_3$, R$_{14}$ = OCH$_3$) | H | H | C=O | | OCH$_3$ | OCH$_3$ | |
| Q$_{32}$(R$_{13}$ = OCH$_3$, R$_{14}$ = OCH$_3$) | H | H | C=O | | Cl | OCH$_3$ | |
| Q$_{32}$(R$_{13}$ = OCH$_3$, R$_{14}$ = OCH$_3$) | H | H | OH | H | CH$_3$ | CH$_3$ | |
| Q$_{32}$(R$_{13}$ = OCH$_3$, R$_{14}$ = OCH$_3$) | H | H | OH | H | CH$_3$ | OCH$_3$ | |
| Q$_{32}$(R$_{13}$ = OCH$_3$, R$_{14}$ = OCH$_3$) | H | H | OH | H | OCH$_3$ | OCH$_3$ | |
| Q$_{32}$(R$_{13}$ = OCH$_3$, R$_{14}$ = OCH$_3$) | H | H | OH | H | Cl | OCH$_3$ | |
| Q$_{33}$(R$_7$ = H) | H | H | C=O | | CH$_3$ | CH$_3$ | |
| Q$_{33}$(R$_7$ = H) | H | H | C=O | | CH$_3$ | OCH$_3$ | |
| Q$_{33}$(R$_7$ = H) | H | H | C=O | | OCH$_3$ | OCH$_3$ | |
| Q$_{33}$(R$_7$ = H) | H | H | C=O | | Cl | OCH$_3$ | |
| Q$_{33}$(R$_7$ = H) | H | H | OH | H | CH$_3$ | CH$_3$ | |
| Q$_{33}$(R$_7$ = H) | H | H | OH | H | CH$_3$ | OCH$_3$ | |
| Q$_{33}$(R$_7$ = H) | H | H | OH | H | OCH$_3$ | OCH$_3$ | |
| Q$_{33}$(R$_7$ = H) | H | H | OH | H | Cl | OCH$_3$ | |

TABLE XVI

General Formula XVI

| Q | R | R$_1$ | R$_2$ | R$_3$ | X | Y | m.p.(°C.) |
|---|---|---|---|---|---|---|---|
| Q$_1$(R$_7$ = H, R$_8$ = H, R$_9$ = H) | H | H | C=O | | CH$_3$ | CH$_3$ | |
| Q$_1$(R$_7$ = H, R$_8$ = H, R$_9$ = H) | H | H | C=O | | CH$_3$ | OCH$_3$ | |
| Q$_1$(R$_7$ = H, R$_8$ = H, R$_9$ = H) | H | H | C=O | | OCH$_3$ | OCH$_3$ | |
| Q$_1$(R$_7$ = H, R$_8$ = H, R$_9$ = H) | H | H | C=O | | Cl | OCH$_3$ | |
| Q$_1$(R$_7$ = H, R$_8$ = H, R$_9$ = H) | H | H | OH | H | CH$_3$ | CH$_3$ | |
| Q$_1$(R$_7$ = H, R$_8$ = H, R$_9$ = H) | H | H | OH | H | CH$_3$ | OCH$_3$ | |
| Q$_1$(R$_7$ = H, R$_8$ = H, R$_9$ = H) | H | H | OH | H | OCH$_3$ | OCH$_3$ | |
| Q$_1$(R$_7$ = H, R$_8$ = H, R$_9$ = H) | H | H | OH | H | Cl | OCH$_3$ | |
| Q$_1$(R$_7$ = H, R$_8$ = H, R$_9$ = H) | H | H | OCH$_3$ | H | OCH$_3$ | OCH$_3$ | |
| Q$_1$(R$_7$ = H, R$_8$ = H, R$_9$ = H) | H | H | OCH$_2$CH$_3$ | H | OCH$_3$ | OCH$_3$ | |
| Q$_2$(R$_7$ = H, R$_8$ = H, R$_9$ = H) | H | H | C=O | | CH$_3$ | CH$_3$ | |
| Q$_2$(R$_7$ = H, R$_8$ = H, R$_9$ = H) | H | H | C=O | | CH$_3$ | OCH$_3$ | |
| Q$_2$(R$_7$ = H, R$_8$ = H, R$_9$ = H) | H | H | C=O | | OCH$_3$ | OCH$_3$ | |
| Q$_2$(R$_7$ = H, R$_8$ = H, R$_9$ = H) | H | H | C=O | | Cl | OCH$_3$ | |
| Q$_2$(R$_7$ = H, R$_8$ = H, R$_9$ = H) | H | H | OH | H | CH$_3$ | CH$_3$ | |
| Q$_2$(R$_7$ = H, R$_8$ = H, R$_9$ = H) | H | H | OH | H | CH$_3$ | OCH$_3$ | |
| Q$_2$(R$_7$ = H, R$_8$ = H, R$_9$ = H) | H | H | OH | H | OCH$_3$ | OCH$_3$ | |
| Q$_2$(R$_7$ = H, R$_8$ = H, R$_9$ = H) | H | H | OH | H | Cl | OCH$_3$ | |
| Q$_2$(R$_7$ = H, R$_8$ = H, R$_9$ = H) | H | H | OCH$_3$ | H | CH$_3$ | OCH$_3$ | |
| Q$_2$(R$_7$ = H, R$_8$ = H, R$_9$ = H) | H | H | OCH$_2$CH$_3$ | H | CH$_3$ | CH$_3$ | |
| Q$_3$(R$_7$ = H, R$_8$ = H, R$_9$ = H) | H | H | C=O | | CH$_3$ | CH$_3$ | |
| Q$_3$(R$_7$ = H, R$_8$ = H, R$_9$ = H) | H | H | C=O | | CH$_3$ | OCH$_3$ | |
| Q$_3$(R$_7$ = H, R$_8$ = H, R$_9$ = H) | H | H | C=O | | OCH$_3$ | OCH$_3$ | |
| Q$_3$(R$_7$ = H, R$_8$ = H, R$_9$ = H) | H | H | C=O | | Cl | OCH$_3$ | |
| Q$_3$(R$_7$ = H, R$_8$ = H, R$_9$ = H) | H | H | OH | H | CH$_3$ | CH$_3$ | |
| Q$_3$(R$_7$ = H, R$_8$ = H, R$_9$ = H) | H | H | OH | H | CH$_3$ | OCH$_3$ | |
| Q$_3$(R$_7$ = H, R$_8$ = H, R$_9$ = H) | H | H | OH | H | OCH$_3$ | OCH$_3$ | |
| Q$_3$(R$_7$ = H, R$_8$ = H, R$_9$ = H) | H | H | OH | H | Cl | OCH$_3$ | |
| Q$_3$(R$_7$ = H, R$_8$ = H, R$_9$ = Cl) | H | H | C=O | | OCH$_3$ | OCH$_3$ | |
| Q$_3$(R$_7$ = H, R$_8$ = H, R$_9$ = CH$_3$) | H | H | C=O | | OCH$_3$ | OCH$_3$ | |
| Q$_3$(R$_7$ = H, R$_8$ = H, R$_9$ = CH$_3$) | H | H | OH | H | OCH$_3$ | OCH$_3$ | |
| Q$_4$(R$_7$ = H, R$_8$ = H, R$_9$ = H) | H | H | C=O | | CH$_3$ | CH$_3$ | |
| Q$_4$(R$_7$ = H, R$_8$ = H, R$_9$ = H) | H | H | C=O | | CH$_3$ | OCH$_3$ | |
| Q$_4$(R$_7$ = H, R$_8$ = H, R$_9$ = H) | H | H | C=O | | OCH$_3$ | OCH$_3$ | |
| Q$_4$(R$_7$ = H, R$_8$ = H, R$_9$ = H) | H | H | C=O | | Cl | OCH$_3$ | |
| Q$_4$(R$_7$ = H, R$_8$ = H, R$_9$ = H) | H | H | OH | H | CH$_3$ | CH$_3$ | |
| Q$_4$(R$_7$ = H, R$_8$ = H, R$_9$ = H) | H | H | OH | H | CH$_3$ | OCH$_3$ | |
| Q$_4$(R$_7$ = H, R$_8$ = H, R$_9$ = H) | H | H | OH | H | OCH$_3$ | OCH$_3$ | |
| Q$_4$(R$_7$ = H, R$_8$ = H, R$_9$ = H) | H | H | OH | H | Cl | OCH$_3$ | |
| Q$_5$(R$_7$ = H, R$_8$ = H, R$_9$ = H, R$_{10}$ = CH$_3$) | H | H | C=O | | CH$_3$ | CH$_3$ | |
| Q$_5$(R$_7$ = H, R$_8$ = H, R$_9$ = H, R$_{10}$ = CH$_3$) | H | H | C=O | | CH$_3$ | OCH$_3$ | |
| Q$_5$(R$_7$ = H, R$_8$ = H, R$_9$ = H, R$_{10}$ = CH$_3$) | H | H | C=O | | OCH$_3$ | OCH$_3$ | |
| Q$_5$(R$_7$ = H, R$_8$ = H, R$_9$ = H, R$_{10}$ = CH$_3$) | H | H | C=O | | Cl | OCH$_3$ | |
| Q$_5$(R$_7$ = H, R$_8$ = H, R$_9$ = H, R$_{10}$ = CH$_3$) | H | H | OH | H | CH$_3$ | CH$_3$ | |
| Q$_5$(R$_7$ = H, R$_8$ = H, R$_9$ = H, R$_{10}$ = CH$_3$) | H | H | OH | H | CH$_3$ | OCH$_3$ | |
| Q$_5$(R$_7$ = H, R$_8$ = H, R$_9$ = H, R$_{10}$ = CH$_3$) | H | H | OH | H | OCH$_3$ | OCH$_3$ | |
| Q$_5$(R$_7$ = H, R$_8$ = H, R$_9$ = H, R$_{10}$ = CH$_3$) | H | H | OH | H | OCH$_3$ | OCH$_3$ | |
| Q$_5$(R$_7$ = H, R$_8$ = H, R$_9$ = H, R$_{10}$ = CH$_3$) | H | H | OH | H | Cl | OCH$_3$ | |
| Q$_5$(R$_7$ = H, R$_8$ = H, R$_9$ = H, R$_{10}$ = CH$_3$) | H | H | OCH$_3$ | H | Cl | OCH$_3$ | |
| Q$_5$(R$_7$ = H, R$_8$ = H, R$_9$ = H, R$_{10}$ = CH$_3$) | H | H | OCH$_2$CH$_3$ | H | OCH$_3$ | OCH$_3$ | |
| Q$_6$(R$_7$ = H, R$_8$ = H, R$_9$ = H, R$_{10}$ = CH$_3$) | H | H | C=O | | CH$_3$ | CH$_3$ | |
| Q$_6$(R$_7$ = H, R$_8$ = H, R$_9$ = H, R$_{10}$ = CH$_3$) | H | H | C=O | | CH$_3$ | OCH$_3$ | |
| Q$_6$(R$_7$ = H, R$_8$ = H, R$_9$ = H, R$_{10}$ = CH$_3$) | H | H | C=O | | OCH$_3$ | OCH$_3$ | |
| Q$_6$(R$_7$ = H, R$_8$ = H, R$_9$ = H, R$_{10}$ = CH$_3$) | H | H | C=O | | Cl | OCH$_3$ | |
| Q$_6$(R$_7$ = H, R$_8$ = H, R$_9$ = H, R$_{10}$ = CH$_3$) | H | H | OH | H | CH$_3$ | CH$_3$ | |

TABLE XVI-continued

General Formula XVI

| Q | R | $R_1$ | $R_2$ | $R_3$ | X | Y | m.p.(°C.) |
|---|---|---|---|---|---|---|---|
| $Q_6(R_7 = H, R_8 = H, R_9 = H, R_{10} = CH_3)$ | H | H | OH | H | $CH_3$ | $OCH_3$ | |
| $Q_6(R_7 = H, R_8 = H, R_9 = H, R_{10} = CH_3)$ | H | H | OH | H | $OCH_3$ | $OCH_3$ | |
| $Q_6(R_7 = H, R_8 = H, R_9 = H, R_{10} = CH_3)$ | H | H | OH | H | Cl | $OCH_3$ | |
| $Q_7(R_7 = H, R_8 = H)$ | H | H | C=O | | $CH_3$ | $CH_3$ | |
| $Q_7(R_7 = H, R_8 = H)$ | H | H | C=O | | $CH_3$ | $OCH_3$ | |
| $Q_7(R_7 = H, R_8 = H)$ | H | H | C=O | | $OCH_3$ | $OCH_3$ | |
| $Q_7(R_7 = H, R_8 = H)$ | H | H | C=O | | Cl | $OCH_3$ | |
| $Q_7(R_7 = H, R_8 = H)$ | H | H | OH | H | $CH_3$ | $CH_3$ | |
| $Q_7(R_7 = H, R_8 = H)$ | H | H | OH | H | $CH_3$ | $OCH_3$ | |
| $Q_7(R_7 = H, R_8 = H)$ | H | H | OH | H | $OCH_3$ | $OCH_3$ | |
| $Q_7(R_7 = H, R_8 = H)$ | H | H | OH | H | Cl | $OCH_3$ | |
| $Q_8(R_7 = H, R_8 = H)$ | H | H | C=O | | $OCH_3$ | $OCH_3$ | |
| $Q_8(R_7 = H, R_8 = H)$ | H | H | C=O | | Cl | $OCH_3$ | |
| $Q_8(R_7 = H, R_8 = H)$ | H | H | OH | H | Cl | $OCH_3$ | |
| $Q_8(R_7 = H, R_8 = H)$ | H | H | OH | H | $OCH_3$ | $OCH_3$ | |
| $Q_9(R_7 = H, R_8 = H)$ | H | H | C=O | | $CH_3$ | $CH_3$ | |
| $Q_9(R_7 = H, R_8 = H)$ | H | H | C=O | | $CH_3$ | $OCH_3$ | |
| $Q_9(R_7 = H, R_8 = H)$ | H | H | C=O | | $OCH_3$ | $OCH_3$ | |
| $Q_9(R_7 = H, R_8 = H)$ | H | H | C=O | | Cl | $OCH_3$ | |
| $Q_9(R_7 = H, R_8 = H)$ | H | H | OH | H | $CH_3$ | $CH_3$ | |
| $Q_9(R_7 = H, R_8 = H)$ | H | H | OH | H | $CH_3$ | $OCH_3$ | |
| $Q_9(R_7 = H, R_8 = H)$ | H | H | OH | H | $OCH_3$ | $OCH_3$ | |
| $Q_9(R_7 = H, R_8 = H)$ | H | H | OH | H | Cl | $OCH_3$ | |
| $Q_{10}(R_7 = H, R_8 = H)$ | H | H | C=O | | $CH_3$ | $OCH_3$ | |
| $Q_{10}(R_7 = H, R_8 = H)$ | H | H | C=O | | $OCH_3$ | $OCH_3$ | |
| $Q_{10}(R_7 = H, R_8 = H)$ | H | H | C=O | | Cl | $OCH_3$ | |
| $Q_{10}(R_7 = H, R_8 = H)$ | H | H | OH | H | $CH_3$ | $CH_3$ | |
| $Q_{10}(R_7 = H, R_8 = H)$ | H | H | OH | H | $OCH_3$ | $OCH_3$ | |
| $Q_{10}(R_7 = H, R_8 = H)$ | H | H | OH | H | Cl | $OCH_3$ | |
| $Q_{11}(R_7 = H, R_8 = H)$ | H | H | C=O | | $CH_3$ | $CH_3$ | |
| $Q_{11}(R_7 = H, R_8 = H)$ | H | H | C=O | | $CH_3$ | $OCH_3$ | |
| $Q_{11}(R_7 = H, R_8 = H)$ | H | H | C=O | | $OCH_3$ | $OCH_3$ | |
| $Q_{11}(R_7 = H, R_8 = H)$ | H | H | C=O | | Cl | $OCH_3$ | |
| $Q_{11}(R_7 = H, R_8 = H)$ | H | H | OH | H | $CH_3$ | $CH_3$ | |
| $Q_{11}(R_7 = H, R_8 = H)$ | H | H | OH | H | $CH_3$ | $OCH_3$ | |
| $Q_{11}(R_7 = H, R_8 = H)$ | H | H | OH | H | $OCH_3$ | $OCH_3$ | |
| $Q_{11}(R_7 = H, R_8 = H)$ | H | H | OH | H | Cl | $OCH_3$ | |
| $Q_{12}(R_7 = H, R_8 = H)$ | H | H | C=O | | $CH_3$ | $CH_3$ | |
| $Q_{12}(R_7 = H, R_8 = H)$ | H | H | C=O | | $CH_3$ | $OCH_3$ | |
| $Q_{12}(R_7 = H, R_8 = H)$ | H | H | C=O | | $OCH_3$ | $OCH_3$ | |
| $Q_{12}(R_7 = H, R_8 = H)$ | H | H | C=O | | Cl | $OCH_3$ | |
| $Q_{12}(R_7 = H, R_8 = H)$ | H | H | OH | H | $CH_3$ | $CH_3$ | |
| $Q_{12}(R_7 = H, R_8 = H)$ | H | H | OH | H | $CH_3$ | $OCH_3$ | |
| $Q_{12}(R_7 = H, R_8 = H)$ | H | H | OH | H | $OCH_3$ | $OCH_3$ | |
| $Q_{12}(R_7 = H, R_8 = H)$ | H | H | OH | H | Cl | $OCH_3$ | |
| $Q_{12}(R_7 = H, R_8 = H)$ | H | H | $OCH_3$ | H | $OCH_3$ | $OCH_3$ | |
| $Q_{13}(R_7 = H, R_8 = H)$ | H | H | C=O | | $CH_3$ | $CH_3$ | |
| $Q_{13}(R_7 = H, R_8 = H)$ | H | H | C=O | | $CH_3$ | $OCH_3$ | |
| $Q_{13}(R_7 = H, R_8 = H)$ | H | H | C=O | | $OCH_3$ | $OCH_3$ | |
| $Q_{13}(R_7 = H, R_8 = H)$ | H | H | C=O | | Cl | $OCH_3$ | |
| $Q_{13}(R_7 = H, R_8 = H)$ | H | H | OH | H | $CH_3$ | -$CH_3$ | |
| $Q_{13}(R_7 = H, R_8 = H)$ | H | H | OH | H | $CH_3$ | $OCH_3$ | |
| $Q_{13}(R_7 = H, R_8 = H)$ | H | H | OH | H | $OCH_3$ | $OCH_3$ | |
| $Q_{13}(R_7 = H, R_8 = H)$ | H | H | OH | H | Cl | $OCH_3$ | |
| $Q_{14}(R_7 = H)$ | H | H | C=O | | $CH_3$ | $CH_3$ | |
| $Q_{14}(R_7 = H)$ | H | H | C=O | | $CH_3$ | $OCH_3$ | |
| $Q_{14}(R_7 = H)$ | H | H | C=O | | $OCH_3$ | $OCH_3$ | |
| $Q_{14}(R_7 = H)$ | H | H | C=O | | Cl | $OCH_3$ | |
| $Q_{14}(R_7 = H)$ | H | H | OH | H | $CH_3$ | $CH_3$ | |
| $Q_{14}(R_7 = H)$ | H | H | OH | H | $CH_3$ | $OCH_3$ | |
| $Q_{14}(R_7 = H)$ | H | H | OH | H | $OCH_3$ | $OCH_3$ | |
| $Q_{14}(R_7 = H)$ | H | H | OH | H | Cl | $OCH_3$ | |
| $Q_{15}(R_7 = H)$ | H | H | C=O | | $CH_3$ | $CH_3$ | |
| $Q_{15}(R_7 = H)$ | H | H | C=O | | $CH_3$ | $OCH_3$ | |
| $Q_{15}(R_7 = H)$ | H | H | C=O | | $OCH_3$ | $OCH_3$ | |
| $Q_{15}(R_7 = H)$ | H | H | C=O | | Cl | $OCH_3$ | |
| $Q_{15}(R_7 = H)$ | H | H | OH | H | $CH_3$ | $CH_3$ | |
| $Q_{15}(R_7 = H)$ | H | H | OH | H | $CH_3$ | $OCH_3$ | |
| $Q_{15}(R_7 = H)$ | H | H | OH | H | $OCH_3$ | $OCH_3$ | |
| $Q_{15}(R_7 = H)$ | H | H | OH | H | Cl | $OCH_3$ | |
| $Q_{16}(R_7 = H)$ | H | H | C=O | | $CH_3$ | $CH_3$ | |
| $Q_{16}(R_7 = H)$ | H | H | C=O | | $CH_3$ | $OCH_3$ | |
| $Q_{16}(R_7 = H)$ | H | H | C=O | | $OCH_3$ | $OCH_3$ | |
| $Q_{16}(R_7 = H)$ | H | H | C=O | | Cl | $OCH_3$ | |
| $Q_{16}(R_7 = H)$ | H | H | OH | H | $CH_3$ | $CH_3$ | |
| $Q_{16}(R_7 = H)$ | H | H | OH | H | $CH_3$ | $OCH_3$ | |
| $Q_{16}(R_7 = H)$ | H | H | OH | H | $OCH_3$ | $OCH_3$ | |
| $Q_{16}(R_7 = H)$ | H | H | OH | H | Cl | $OCH_3$ | |
| $Q_{17}(R_7 = CH_3)$ | H | H | C=O | | $CH_3$ | $CH_3$ | |
| $Q_{17}(R_7 = CH_3)$ | H | H | C=O | | $CH_3$ | $OCH_3$ | |

TABLE XVI-continued

General Formula XVI

| Q | R | R₁ | R₂ | R₃ | X | Y | m.p.(°C.) |
|---|---|---|---|---|---|---|---|
| Q₁₇(R₇ = CH₃) | H | H | C=O | | OCH₃ | OCH₃ | |
| Q₁₇(R₇ = CH₃) | H | H | C=O | | Cl | OCH₃ | |
| Q₁₇(R₇ = CH₃) | H | H | OH | H | CH₃ | CH₃ | |
| Q₁₇(R₇ = CH₃) | H | H | OH | H | CH₃ | OCH₃ | |
| Q₁₇(R₇ = CH₃) | H | H | OH | H | OCH₃ | OCH₃ | |
| Q₁₇(R₇ = CH₃) | H | H | OH | H | Cl | OCH₃ | |
| Q₁₈(R₇ = H) | H | H | C=O | | CH₃ | CH₃ | |
| Q₁₈(R₇ = H) | H | H | C=O | | CH₃ | OCH₃ | |
| Q₁₈(R₇ = H) | H | H | C=O | | OCH₃ | OCH₃ | |
| Q₁₈(R₇ = H) | H | H | C=O | | Cl | OCH₃ | |
| Q₁₈(R₇ = H) | H | H | OH | H | CH₃ | CH₃ | |
| Q₁₈(R₇ = H) | H | H | OH | H | CH₃ | OCH₃ | |
| Q₁₈(R₇ = H) | H | H | OH | H | OCH₃ | OCH₃ | |
| Q₁₈(R₇ = H) | H | H | OH | H | Cl | OCH₃ | |
| Q₁₉(R₇ = H, R₈ = H) | H | H | C=O | | CH₃ | CH₃ | |
| Q₁₉(R₇ = H, R₈ = H) | H | H | C=O | | CH₃ | OCH₃ | |
| Q₁₉(R₇ = H, R₈ = H) | H | H | C=O | | OCH₃ | OCH₃ | |
| Q₁₉(R₇ = H, R₈ = H) | H | H | C=O | | Cl | OCH₃ | |
| Q₁₉(R₇ = H, R₈ = H) | H | H | OH | H | CH₃ | CH₃ | |
| Q₁₉(R₇ = H, R₈ = H) | H | H | OH | H | CH₃ | OCH₃ | |
| Q₁₉(R₇ = H, R₈ = H) | H | H | OH | H | OCH₃ | OCH₃ | |
| Q₁₉(R₇ = H, R₈ = H) | H | H | OH | H | Cl | OCH₃ | |
| Q₂₀(R₇ = H, R₈ = H) | H | H | C=O | | CH₃ | CH₃ | |
| Q₂₀(R₇ = H, R₈ = H) | H | H | C=O | | CH₃ | OCH₃ | |
| Q₂₀(R₇ = H, R₈ = H) | H | H | C=O | | OCH₃ | OCH₃ | |
| Q₂₀(R₇ = H, R₈ = H) | H | H | C=O | | Cl | OCH₃ | |
| Q₂₀(R₇ = H, R₈ = H) | H | H | OH | H | CH₃ | CH₃ | |
| Q₂₀(R₇ = H, R₈ = H) | H | H | OH | H | CH₃ | OCH₃ | |
| Q₂₀(R₇ = H, R₈ = H) | H | H | OH | H | OCH₃ | OCH₃ | |
| Q₂₀(R₇ = H, R₈ = H) | H | H | OH | H | Cl | OCH₃ | |
| Q₂₁(R₇ = H, R₈ = H, R₉ = CH₃) | H | H | C=O | | CH₃ | CH₃ | |
| Q₂₁(R₇ = H, R₈ = H, R₉ = CH₃) | H | H | C=O | | CH₃ | OCH₃ | |
| Q₂₁(R₇ = H, R₈ = H, R₉ = CH₃) | H | H | C=O | | OCH₃ | OCH₃ | |
| Q₂₁(R₇ = H, R₈ = H, R₉ = CH₃) | H | H | C=O | | Cl | OCH₃ | |
| Q₂₁(R₇ = H, R₈ = H, R₉ = CH₃) | H | H | OH | H | CH₃ | CH₃ | |
| Q₂₁(R₇ = H, R₈ = H, R₉ = CH₃) | H | H | OH | H | CH₃ | OCH₃ | |
| Q₂₁(R₇ = H, R₈ = H, R₉ = CH₃) | H | H | OH | H | OCH₃ | OCH₃ | |
| Q₂₁(R₇ = H, R₈ = H, R₉ = CH₃) | H | H | OH | H | Cl | OCH₃ | |
| Q₂₂(R₇ = H) | H | H | C=O | | CH₃ | CH₃ | |
| Q₂₂(R₇ = H) | H | H | C=O | | CH₃ | OCH₃ | |
| Q₂₂(R₇ = H) | H | H | C=O | | OCH₃ | OCH₃ | |
| Q₂₂(R₇ = H) | H | H | C=O | | Cl | OCH₃ | |
| Q₂₂(R₇ = H) | H | H | OH | H | CH₃ | CH₃ | |
| Q₂₂(R₇ = H) | H | H | OH | H | CH₃ | OCH₃ | |
| Q₂₂(R₇ = H) | H | H | OH | H | OCH₃ | OCH₃ | |
| Q₂₂(R₇ = H) | H | H | OH | H | Cl | OCH₃ | |
| Q₂₃(R₇ = H) | H | H | C=O | | CH₃ | CH₃ | |
| Q₂₃(R₇ = H) | H | H | C=O | | CH₃ | OCH₃ | |
| Q₂₃(R₇ = H) | H | H | C=O | | OCH₃ | OCH₃ | |
| Q₂₃(R₇ = H) | H | H | C=O | | Cl | OCH₃ | |
| Q₂₃(R₇ = H) | H | H | OH | H | CH₃ | CH₃ | |
| Q₂₃(R₇ = H) | H | H | OH | H | CH₃ | OCH₃ | |
| Q₂₃(R₇ = H) | H | H | OH | H | OCH₃ | OCH₃ | |
| Q₂₃(R₇ = H) | H | H | OH | H | Cl | OCH₃ | |
| Q₂₄(R₇ = H, R₈ = H) | H | H | C=O | | CH₃ | CH₃ | |
| Q₂₄(R₇ = H, R₈ = H) | H | H | C=O | | CH₃ | OCH₃ | |
| Q₂₄(R₇ = H, R₈ = H) | H | H | C=O | | OCH₃ | OCH₃ | |
| Q₂₄(R₇ = H, R₈ = H) | H | H | C=O | | Cl | OCH₃ | |
| Q₂₄(R₇ = H, R₈ = H) | H | H | OH | H | CH₃ | CH₃ | |
| Q₂₄(R₇ = H, R₈ = H) | H | H | OH | H | CH₃ | OCH₃ | |
| Q₂₄(R₇ = H, R₈ = H) | H | H | OH | H | OCH₃ | OCH₃ | |
| Q₂₄(R₇ = H, R₈ = H) | H | H | OH | H | Cl | OCH₃ | |
| Q₂₅(R₇ = H, R₈ = H) | H | H | C=O | | CH₃ | CH₃ | |
| Q₂₅(R₇ = H, R₈ = H) | H | H | C=O | | CH₃ | OCH₃ | |
| Q₂₅(R₇ = H, R₈ = H) | H | H | C=O | | OCH₃ | OCH₃ | |
| Q₂₅(R₇ = H, R₈ = H) | H | H | C=O | | Cl | OCH₃ | |
| Q₂₅(R₇ = H, R₈ = H) | H | H | OH | H | CH₃ | CH₃ | |
| Q₂₅(R₇ = H, R₈ = H) | H | H | OH | H | CH₃ | OCH₃ | |
| Q₂₅(R₇ = H, R₈ = H) | H | H | OH | H | OCH₃ | OCH₃ | |
| Q₂₅(R₇ = H, R₈ = H) | H | H | OH | H | Cl | OCH₃ | |
| Q₂₆(R₇ = H, R₈ = H) | H | H | C=O | | CH₃ | CH₃ | |
| Q₂₆(R₇ = H, R₈ = H) | H | H | C=O | | CH₃ | OCH₃ | |
| Q₂₆(R₇ = H, R₈ = H) | H | H | C=O | | OCH₃ | OCH₃ | |
| Q₂₆(R₇ = H, R₈ = H) | H | H | C=O | | Cl | OCH₃ | |
| Q₂₆(R₇ = H, R₈ = H) | H | H | OH | H | CH₃ | CH₃ | |
| Q₂₆(R₇ = H, R₈ = H) | H | H | OH | H | CH₃ | OCH₃ | |
| Q₂₆(R₇ = H, R₈ = H) | H | H | OH | H | OCH₃ | OCH₃ | |
| Q₂₆(R₇ = H, R₈ = H) | H | H | OH | H | Cl | OCH₃ | |
| Q₂₇(R₇ = H, R₁₁ = H, R₁₂ = H) | H | H | C=O | | CH₃ | CH₃ | |
| Q₂₇(R₇ = H, R₁₁ = H, R₁₂ = H) | H | H | C=O | | CH₃ | OCH₃ | |

TABLE XVI-continued

General Formula XVI

| Q | R | $R_1$ | $R_2$ | $R_3$ | X | Y | m.p.(°C.) |
|---|---|---|---|---|---|---|---|
| $Q_{27}(R_7 = H, R_{11} = H, R_{12} = H)$ | H | H | C=O | | $OCH_3$ | $OCH_3$ | |
| $Q_{27}(R_7 = H, R_{11} = H, R_{12} = H)$ | H | H | C=O | | Cl | $OCH_3$ | |
| $Q_{27}(R_7 = H, R_{11} = H, R_{12} = H)$ | H | H | OH | H | $CH_3$ | $CH_3$ | |
| $Q_{27}(R_7 = H, R_{11} = H, R_{12} = H)$ | H | H | OH | H | $CH_3$ | $OCH_3$ | |
| $Q_{27}(R_7 = H, R_{11} = H, R_{12} = H)$ | H | H | OH | H | $OCH_3$ | $OCH_3$ | |
| $Q_{27}(R_7 = H, R_{11} = H, R_{12} = H)$ | H | H | OH | H | Cl | $OCH_3$ | |
| $Q_{28}(R_{11} = H, R_{12} = H)$ | H | H | C=O | | $CH_3$ | $CH_3$ | |
| $Q_{28}(R_{11} = H, R_{12} = H)$ | H | H | C=O | | $CH_3$ | $OCH_3$ | |
| $Q_{28}(R_{11} = H, R_{12} = H)$ | H | H | C=O | | $OCH_3$ | $OCH_3$ | |
| $Q_{28}(R_{11} = H, R_{12} = H)$ | H | H | C=O | | Cl | $OCH_3$ | |
| $Q_{28}(R_{11} = H, R_{12} = H)$ | H | H | OH | H | $CH_3$ | $CH_3$ | |
| $Q_{28}(R_{11} = H, R_{12} = H)$ | H | H | OH | H | $CH_3$ | $OCH_3$ | |
| $Q_{28}(R_{11} = H, R_{12} = H)$ | H | H | OH | H | $OCH_3$ | $OCH_3$ | |
| $Q_{28}(R_{11} = H, R_{12} = H)$ | H | H | OH | H | Cl | $OCH_3$ | |
| $Q_{29}(R_{11} = H, R_{12} = H)$ | H | H | C=O | | $CH_3$ | $CH_3$ | |
| $Q_{29}(R_{11} = H, R_{12} = H)$ | H | H | C=O | | $CH_3$ | $OCH_3$ | |
| $Q_{29}(R_{11} = H, R_{12} = H)$ | H | H | C=O | | $OCH_3$ | $OCH_3$ | |
| $Q_{29}(R_{11} = H, R_{12} = H)$ | H | H | C=O | | Cl | $OCH_3$ | |
| $Q_{29}(R_{11} = H, R_{12} = H)$ | H | H | OH | H | $CH_3$ | $CH_3$ | |
| $Q_{29}(R_{11} = H, R_{12} = H)$ | H | H | OH | H | $CH_3$ | $OCH_3$ | |
| $Q_{29}(R_{11} = H, R_{12} = H)$ | H | H | OH | H | $OCH_3$ | $OCH_3$ | |
| $Q_{29}(R_{11} = H, R_{12} = H)$ | H | H | OH | H | Cl | $OCH_3$ | |
| $Q_{30}(R_7 = H, R_8 = H)$ | H | H | C=O | | $CH_3$ | $CH_3$ | |
| $Q_{30}(R_7 = H, R_8 = H)$ | H | H | C=O | | $CH_3$ | $OCH_3$ | |
| $Q_{30}(R_7 = H, R_8 = H)$ | H | H | C=O | | $OCH_3$ | $OCH_3$ | |
| $Q_{30}(R_7 = H, R_8 = H)$ | H | H | C=O | | Cl | $OCH_3$ | |
| $Q_{30}(R_7 = H, R_8 = H)$ | H | H | OH | H | $CH_3$ | $CH_3$ | |
| $Q_{30}(R_7 = H, R_8 = H)$ | H | H | OH | H | $CH_3$ | $OCH_3$ | |
| $Q_{30}(R_7 = H, R_8 = H)$ | H | H | OH | H | $OCH_3$ | $OCH_3$ | |
| $Q_{30}(R_7 = H, R_8 = H)$ | H | H | OH | H | Cl | $OCH_3$ | |
| $Q_{31}(R_7 = H, R_8 = H)$ | H | H | C=O | | $CH_3$ | $CH_3$ | |
| $Q_{31}(R_7 = H, R_8 = H)$ | H | H | C=O | | $CH_3$ | $OCH_3$ | |
| $Q_{31}(R_7 = H, R_8 = H)$ | H | H | C=O | | $OCH_3$ | $OCH_3$ | |
| $Q_{31}(R_7 = H, R_8 = H)$ | H | H | C=O | | Cl | $OCH_3$ | |
| $Q_{31}(R_7 = H, R_8 = H)$ | H | H | OH | H | $CH_3$ | $CH_3$ | |
| $Q_{31}(R_7 = H, R_8 = H)$ | H | H | OH | H | $CH_3$ | $OCH_3$ | |
| $Q_{31}(R_7 = H, R_8 = H)$ | H | H | OH | H | $OCH_3$ | $OCH_3$ | |
| $Q_{31}(R_7 = H, R_8 = H)$ | H | H | OH | H | Cl | $OCH_3$ | |
| $Q_{32}(R_{13} = OCH_3, R_{14} = OCH_3)$ | H | H | C=O | | $CH_3$ | $CH_3$ | |
| $Q_{32}(R_{13} = OCH_3, R_{14} = OCH_3)$ | H | H | C=O | | $CH_3$ | $OCH_3$ | |
| $Q_{32}(R_{13} = OCH_3, R_{14} = OCH_3)$ | H | H | C=O | | $OCH_3$ | $OCH_3$ | |
| $Q_{32}(R_{13} = OCH_3, R_{14} = OCH_3)$ | H | H | C=O | | Cl | $OCH_3$ | |
| $Q_{32}(R_{13} = OCH_3, R_{14} = OCH_3)$ | H | H | OH | H | $CH_3$ | $CH_3$ | |
| $Q_{32}(R_{13} = OCH_3, R_{14} = OCH_3)$ | H | H | OH | H | $CH_3$ | $OCH_3$ | |
| $Q_{32}(R_{13} = OCH_3, R_{14} = OCH_3)$ | H | H | OH | H | $OCH_3$ | $OCH_3$ | |
| $Q_{32}(R_{13} = OCH_3, R_{14} = OCH_3)$ | H | H | OH | H | Cl | $OCH_3$ | |
| $Q_{33}(R_7 = H)$ | H | H | C=O | | $CH_3$ | $CH_3$ | |
| $Q_{33}(R_7 = H)$ | H | H | C=O | | $CH_3$ | $OCH_3$ | |
| $Q_{33}(R_7 = H)$ | H | H | C=O | | $OCH_3$ | $OCH_3$ | |
| $Q_{33}(R_7 = H)$ | H | H | C=O | | Cl | $OCH_3$ | |
| $Q_{33}(R_7 = H)$ | H | H | OH | H | $CH_3$ | $CH_3$ | |
| $Q_{33}(R_7 = H)$ | H | H | OH | H | $CH_3$ | $OCH_3$ | |
| $Q_{33}(R_7 = H)$ | H | H | OH | H | $OCH_3$ | $OCH_3$ | |
| $Q_{33}(R_7 = H)$ | H | H | OH | H | Cl | $OCH_3$ | |

TABLE XVII

General Formula XVII

| Q | R | $R_1$ | $R_2$ | $R_3$ | X | Y | m.p.(°C.) |
|---|---|---|---|---|---|---|---|
| $Q_1(R_7 = H, R_8 = H, R_9 = H)$ | H | H | C=O | | $CH_3$ | $CH_3$ | |
| $Q_1(R_7 = H, R_8 = H, R_9 = H)$ | H | H | C=O | | $CH_3$ | $OCH_3$ | |
| $Q_1(R_7 = H, R_8 = H, R_9 = H)$ | H | H | C=O | | $OCH_3$ | $OCH_3$ | |
| $Q_1(R_7 = H, R_8 = H, R_9 = H)$ | H | H | C=O | | Cl | $OCH_3$ | |
| $Q_1(R_7 = H, R_8 = H, R_9 = H)$ | H | H | OH | H | $CH_3$ | $CH_3$ | |
| $Q_1(R_7 = H, R_8 = H, R_9 = H)$ | H | H | OH | H | $CH_3$ | $OCH_3$ | |
| $Q_1(R_7 = H, R_8 = H, R_9 = H)$ | H | H | OH | H | $OCH_3$ | $OCH_3$ | |
| $Q_1(R_7 = H, R_8 = H, R_9 = H)$ | H | H | OH | H | Cl | $OCH_3$ | |
| $Q_1(R_7 = H, R_8 = H, R_9 = H)$ | H | H | $OCH_3$ | H | $OCH_3$ | $OCH_3$ | |
| $Q_1(R_7 = H, R_8 = H, R_9 = H)$ | H | H | $OHC_2CH_3$ | H | $OCH_3$ | $OCH_3$ | |
| $Q_2(R_7 = H, R_8 = H, R_9 = H)$ | H | H | C=O | | $CH_3$ | $CH_3$ | |
| $Q_2(R_7 = H, R_8 = H, R_9 = H)$ | H | H | C=O | | $CH_3$ | $OCH_3$ | |
| $Q_2(R_7 = H, R_8 = H, R_9 = H)$ | H | H | C=O | | $OCH_3$ | $OCH_3$ | |
| $Q_2(R_7 = H, R_8 = H, R_9 = H)$ | H | H | C=O | | Cl | $OCH_3$ | |
| $Q_2(R_7 = H, R_8 = H, R_9 = H)$ | H | H | OH | H | $CH_3$ | $CH_3$ | |
| $Q_2(R_7 = H, R_8 = H, R_9 = H)$ | H | H | OH | H | $CH_3$ | $OCH_3$ | |
| $Q_2(R_7 = H, R_8 = H, R_9 = H)$ | H | H | OH | H | $OCH_3$ | $OCH_3$ | |
| $Q_2(R_7 = H, R_8 = H, R_9 = H)$ | H | H | OH | H | Cl | $OCH_3$ | |
| $Q_2(R_7 = H, R_8 = H, R_9 = H)$ | H | H | $OCH_3$ | H | $CH_3$ | $OCH_3$ | |

TABLE XVII-continued

General Formula XVII

| Q | R | R$_1$ | R$_2$ | R$_3$ | X | Y | m.p.(°C.) |
|---|---|---|---|---|---|---|---|
| Q$_2$(R$_7$ = H, R$_8$ = H, R$_9$ = H) | H | H | OCH$_2$CH$_3$ | H | CH$_3$ | CH$_3$ | |
| Q$_3$(R$_7$ = H, R$_8$ = H, R$_9$ = H) | H | H | C=O | | CH$_3$ | CH$_3$ | |
| Q$_3$(R$_7$ = H, R$_8$ = H, R$_9$ = H) | H | H | C=O | | CH$_3$ | OCH$_3$ | |
| Q$_3$(R$_7$ = H, R$_8$ = H, R$_9$ = H) | H | H | C=O | | OCH$_3$ | OCH$_3$ | |
| Q$_3$(R$_7$ = H, R$_8$ = H, R$_9$ = H) | H | H | C=O | | Cl | OCH$_3$ | |
| Q$_3$(R$_7$ = H, R$_8$ = H, R$_9$ = H) | H | H | OH | H | CH$_3$ | CH$_3$ | |
| Q$_3$(R$_7$ = H, R$_8$ = H, R$_9$ = H) | H | H | OH | H | CH$_3$ | OCH$_3$ | |
| Q$_3$(R$_7$ = H, R$_8$ = H, R$_9$ = H) | H | H | OH | H | OCH$_3$ | OCH$_3$ | |
| Q$_3$(R$_7$ = H, R$_8$ = H, R$_9$ = H) | H | H | OH | H | Cl | OCH$_3$ | |
| Q$_3$(R$_7$ = H, R$_8$ = H, R$_9$ = Cl) | H | H | C=O | | OCH$_3$ | OCH$_3$ | |
| Q$_3$(R$_7$ = H, R$_8$ = H, R$_9$ = CH$_3$) | H | H | C=O | | OCH$_3$ | OCH$_3$ | |
| Q$_3$(R$_7$ = H, R$_8$ = H, R$_9$ = CH$_3$) | H | H | OH | H | OCH$_3$ | OCH$_3$ | |
| Q$_4$(R$_7$ = H, R$_8$ = H, R$_9$ = H) | H | H | C=O | | CH$_3$ | CH$_3$ | |
| Q$_4$(R$_7$ = H, R$_8$ = H, R$_9$ = H) | H | H | C=O | | CH$_3$ | OCH$_3$ | |
| Q$_4$(R$_7$ = H, R$_8$ = H, R$_9$ = H) | H | H | C=O | | OCH$_3$ | OCH$_3$ | |
| Q$_4$(R$_7$ = H, R$_8$ = H, R$_9$ = H) | H | H | C=O | | Cl | OCH$_3$ | |
| Q$_4$(R$_7$ = H, R$_8$ = H, R$_9$ = H) | H | H | OH | H | CH$_3$ | CH$_3$ | |
| Q$_4$(R$_7$ = H, R$_8$ = H, R$_9$ = H) | H | H | OH | H | CH$_3$ | OCH$_3$ | |
| Q$_4$(R$_7$ = H, R$_8$ = H, R$_9$ = H) | H | H | OH | H | OCH$_3$ | OCH$_3$ | |
| Q$_4$(R$_7$ = H, R$_8$ = H, R$_9$ = H) | H | H | OH | H | Cl | OCH$_3$ | |
| Q$_5$(R$_7$ = H, R$_8$ = H, R$_9$ = H, R$_{10}$ = CH$_3$) | H | H | C=O | | CH$_3$ | CH$_3$ | |
| Q$_5$(R$_7$ = H, R$_8$ = H, R$_9$ = H, R$_{10}$ = CH$_3$) | H | H | C=O | | CH$_3$ | OCH$_3$ | |
| Q$_5$(R$_7$ = H, R$_8$ = H, R$_9$ = H, R$_{10}$ = CH$_3$) | H | H | C=O | | OCH$_3$ | OCH$_3$ | |
| Q$_5$(R$_7$ = H, R$_8$ = H, R$_9$ = H, R$_{10}$ = CH$_3$) | H | H | C=O | | Cl | OCH$_3$ | |
| Q$_5$(R$_7$ = H, R$_8$ = H, R$_9$ = H, R$_{10}$ = CH$_3$) | H | H | OH | H | CH$_3$ | CH$_3$ | |
| Q$_5$(R$_7$ = H, R$_8$ = H, R$_9$ = H, R$_{10}$ = CH$_3$) | H | H | OH | H | CH$_3$ | OCH$_3$ | |
| Q$_5$(R$_7$ = H, R$_8$ = H, R$_9$ = H, R$_{10}$ = CH$_3$) | H | H | OH | H | OCH$_3$ | OCH$_3$ | |
| Q$_5$(R$_7$ = H, R$_8$ = H, R$_9$ = H, R$_{10}$ = CH$_3$) | H | H | OH | H | Cl | OCH$_3$ | |
| Q$_5$(R$_7$ = H, R$_8$ = H, R$_9$ = H, R$_{10}$ = CH$_3$) | H | H | OCH$_3$ | H | Cl | OCH$_3$ | |
| Q$_5$(R$_7$ = H, R$_8$ = H, R$_9$ = H, R$_{10}$ = CH$_3$) | H | H | OCH$_2$CH$_3$ | H | OCH$_3$ | OCH$_3$ | |
| Q$_6$(R$_7$ = H, R$_8$ = H, R$_9$ = H, R$_{10}$ = CH$_3$) | H | H | C=O | | CH$_3$ | CH$_3$ | |
| Q$_6$(R$_7$ = H, R$_8$ = H, R$_9$ = H, R$_{10}$ = CH$_3$) | H | H | C=O | | CH$_3$ | OCH$_3$ | |
| Q$_6$(R$_7$ = H, R$_8$ = H, R$_9$ = H, R$_{10}$ = CH$_3$) | H | H | C=O | | OCH$_3$ | OCH$_3$ | |
| Q$_6$(R$_7$ = H, R$_8$ = H, R$_9$ = H, R$_{10}$ = CH$_3$) | H | H | C=O | | Cl | OCH$_3$ | |
| Q$_6$(R$_7$ = H, R$_8$ = H, R$_9$ = H, R$_{10}$ = CH$_3$) | H | H | OH | H | CH$_3$ | CH$_3$ | |
| Q$_6$(R$_7$ = H, R$_8$ = H, R$_9$ = H, R$_{10}$ = CH$_3$) | H | H | OH | H | CH$_3$ | OCH$_3$ | |
| Q$_6$(R$_7$ = H, R$_8$ = H, R$_9$ = H, R$_{10}$ = CH$_3$) | H | H | OH | H | OCH$_3$ | OCH$_3$ | |
| Q$_6$(R$_7$ = H, R$_8$ = H, R$_9$ = H, R$_{10}$ = CH$_3$) | H | H | OH | H | Cl | OCH$_3$ | |
| Q$_7$(R$_7$ = H, R$_8$ = H) | H | H | C=O | | CH$_3$ | CH$_3$ | |
| Q$_7$(R$_7$ = H, R$_8$ = H) | H | H | C=O | | CH$_3$ | OCH$_3$ | |
| Q$_7$(R$_7$ = H, R$_8$ = H) | H | H | C=O | | OCH$_3$ | OCH$_3$ | |
| Q$_7$(R$_7$ = H, R$_8$ = H) | H | H | C=O | | Cl | OCH$_3$ | |
| Q$_7$(R$_7$ = H, R$_8$ = H) | H | H | OH | H | CH$_3$ | CH$_3$ | |
| Q$_7$(R$_7$ = H, R$_8$ = H) | H | H | OH | H | CH$_3$ | OCH$_3$ | |
| Q$_7$(R$_7$ = H, R$_8$ = H) | H | H | OH | H | OCH$_3$ | OCH$_3$ | |
| Q$_7$(R$_7$ = H, R$_8$ = H) | H | H | OH | H | Cl | OCH$_3$ | |
| Q$_8$(R$_7$ = H, R$_8$ = H) | H | H | C=O | | OCH$_3$ | OCH$_3$ | |
| Q$_8$(R$_7$ = H, R$_8$ = H) | H | H | C=O | | Cl | OCH$_3$ | |
| Q$_8$(R$_7$ = H, R$_8$ = H) | H | H | OH | H | Cl | OCH$_3$ | |
| Q$_8$(R$_7$ = H, R$_8$ = H) | H | H | OH | H | OCH$_3$ | OCH$_3$ | |
| Q$_9$(R$_7$ = H, R$_8$ = H) | H | H | C=O | | CH$_3$ | CH$_3$ | |
| Q$_9$(R$_7$ = H, R$_8$ = H) | H | H | C=O | | CH$_3$ | OCH$_3$ | |
| Q$_9$(R$_7$ = H, R$_8$ = H) | H | H | C=O | | OCH$_3$ | OCH$_3$ | |
| Q$_9$(R$_7$ = H, R$_8$ = H) | H | H | C=O | | Cl | OCH$_3$ | |
| Q$_9$(R$_7$ = H, R$_8$ = H) | H | H | OH | H | CH$_3$ | CH$_3$ | |
| Q$_9$(R$_7$ = H, R$_8$ = H) | H | H | OH | H | CH$_3$ | OCH$_3$ | |
| Q$_9$(R$_7$ = H, R$_8$ = H) | H | H | OH | H | OCH$_3$ | OCH$_3$ | |
| Q$_9$(R$_7$ = H, R$_8$ = H) | H | H | OH | H | Cl | OCH$_3$ | |
| Q$_{10}$(R$_7$ = H, R$_8$ = H) | H | H | C=O | | CH$_3$ | OCH$_3$ | |
| Q$_{10}$(R$_7$ = H, R$_8$ = H) | H | H | C=O | | OCH$_3$ | OCH$_3$ | |
| Q$_{10}$(R$_7$ = H, R$_8$ = H) | H | H | C=O | | Cl | OCH$_3$ | |
| Q$_{10}$(R$_7$ = H, R$_8$ = H) | H | H | OH | H | CH$_3$ | CH$_3$ | |
| Q$_{10}$(R$_7$ = H, R$_8$ = H) | H | H | OH | H | OCH$_3$ | OCH$_3$ | |
| Q$_{10}$(R$_7$ = H, R$_8$ = H) | H | H | OH | H | Cl | OCH$_3$ | |
| Q$_{11}$(R$_7$ = H, R$_8$ = H) | H | H | C=O | | CH$_3$ | CH$_3$ | |
| Q$_{11}$(R$_7$ = H, R$_8$ = H) | H | H | C=O | | CH$_3$ | OCH$_3$ | |
| Q$_{11}$(R$_7$ = H, R$_8$ = H) | H | H | C=O | | OCH$_3$ | OCH$_3$ | |
| Q$_{11}$(R$_7$ = H, R$_8$ = H) | H | H | C=O | | Cl | OCH$_3$ | |
| Q$_{11}$(R$_7$ = H, R$_8$ = H) | H | H | OH | H | CH$_3$ | CH$_3$ | |
| Q$_{11}$(R$_7$ = H, R$_8$ = H) | H | H | OH | H | CH$_3$ | OCH$_3$ | |
| Q$_{11}$(R$_7$ = H, R$_8$ = H) | H | H | OH | H | OCH$_3$ | OCH$_3$ | |
| Q$_{11}$(R$_7$ = H, R$_8$ = H) | H | H | OH | H | Cl | OCH$_3$ | |
| Q$_{12}$(R$_7$ = H, R$_8$ = H) | H | H | C=O | | CH$_3$ | CH$_3$ | |
| Q$_{12}$(R$_7$ = H, R$_8$ = H) | H | H | C=O | | CH$_3$ | OCH$_3$ | |
| Q$_{12}$(R$_7$ = H, R$_8$ = H) | H | H | C=O | | OCH$_3$ | OCH$_3$ | |
| Q$_{12}$(R$_7$ = H, R$_8$ = H) | H | H | C=O | | Cl | OCH$_3$ | |
| Q$_{12}$(R$_7$ = H, R$_8$ = H) | H | H | OH | H | CH$_3$ | CH$_3$ | |
| Q$_{12}$(R$_7$ = H, R$_8$ = H) | H | H | OH | H | CH$_3$ | OCH$_3$ | |
| Q$_{12}$(R$_7$ = H, R$_8$ = H) | H | H | OH | H | OCH$_3$ | OCH$_3$ | |
| Q$_{12}$(R$_7$ = H, R$_8$ = H) | H | H | OH | H | Cl | OCH$_3$ | |

TABLE XVII-continued

General Formula XVII

| Q | R | $R_1$ | $R_2$ | $R_3$ | X | Y | m.p.(°C.) |
|---|---|---|---|---|---|---|---|
| $Q_{12}(R_7 = H, R_8 = H)$ | H | H | $OCH_3$ | H | $OCH_3$ | $OCH_3$ | |
| $Q_{13}(R_7 = H, R_8 = H)$ | H | H | C=O | | $CH_3$ | $CH_3$ | |
| $Q_{13}(R_7 = H, R_8 = H)$ | H | H | C=O | | $CH_3$ | $OCH_3$ | |
| $Q_{13}(R_7 = H, R_8 = H)$ | H | H | C=O | | $OCH_3$ | $OCH_3$ | |
| $Q_{13}(R_7 = H, R_8 = H)$ | H | H | C=O | | Cl | $OCH_3$ | |
| $Q_{13}(R_7 = H, R_8 = H)$ | H | H | OH | H | $CH_3$ | $CH_3$ | |
| $Q_{13}(R_7 = H, R_8 = H)$ | H | H | OH | H | $CH_3$ | $OCH_3$ | |
| $Q_{13}(R_7 = H, R_8 = H)$ | H | H | OH | H | $OCH_3$ | $OCH_3$ | |
| $Q_{13}(R_7 = H, R_8 = H)$ | H | H | OH | H | Cl | $OCH_3$ | |
| $Q_{14}(R_7 = H)$ | H | H | C=O | | $CH_3$ | $CH_3$ | |
| $Q_{14}(R_7 = H)$ | H | H | C=O | | $CH_3$ | $OCH_3$ | |
| $Q_{14}(R_7 = H)$ | H | H | C=O | | $OCH_3$ | $OCH_3$ | |
| $Q_{14}(R_7 = H)$ | H | H | C=O | | Cl | $OCH_3$ | |
| $Q_{14}(R_7 = H)$ | H | H | OH | H | $CH_3$ | $CH_3$ | |
| $Q_{14}(R_7 = H)$ | H | H | OH | H | $CH_3$ | $OCH_3$ | |
| $Q_{14}(R_7 = H)$ | H | H | OH | H | $OCH_3$ | $OCH_3$ | |
| $Q_{14}(R_7 = H)$ | H | H | OH | H | Cl | $OCH_3$ | |
| $Q_{15}(R_7 = H)$ | H | H | C=O | | $CH_3$ | $CH_3$ | |
| $Q_{15}(R_7 = H)$ | H | H | C=O | | $CH_3$ | $OCH_3$ | |
| $Q_{15}(R_7 = H)$ | H | H | C=O | | $OCH_3$ | $OCH_3$ | |
| $Q_{15}(R_7 = H)$ | H | H | C=O | | Cl | $OCH_3$ | |
| $Q_{15}(R_7 = H)$ | H | H | OH | H | $CH_3$ | $CH_3$ | |
| $Q_{15}(R_7 = H)$ | H | H | OH | H | $CH_3$ | $OCH_3$ | |
| $Q_{15}(R_7 = H)$ | H | H | OH | H | $OCH_3$ | $OCH_3$ | |
| $Q_{15}(R_7 = H)$ | H | H | OH | H | Cl | $OCH_3$ | |
| $Q_{16}(R_7 = H)$ | H | H | C=O | | $CH_3$ | $CH_3$ | |
| $Q_{16}(R_7 = H)$ | H | H | C=O | | $CH_3$ | $OCH_3$ | |
| $Q_{16}(R_7 = H)$ | H | H | C=O | | $OCH_3$ | $OCH_3$ | |
| $Q_{16}(R_7 = H)$ | H | H | C=O | | Cl | $OCH_3$ | |
| $Q_{16}(R_7 = H)$ | H | H | OH | H | $CH_3$ | $CH_3$ | |
| $Q_{16}(R_7 = H)$ | H | H | OH | H | $CH_3$ | $OCH_3$ | |
| $Q_{16}(R_7 = H)$ | H | H | OH | H | $OCH_3$ | $OCH_3$ | |
| $Q_{16}(R_7 = H)$ | H | H | OH | H | Cl | $OCH_3$ | |
| $Q_{17}(R_7 = CH_3)$ | H | H | C=O | | $CH_3$ | $CH_3$ | |
| $Q_{17}(R_7 = CH_3)$ | H | H | C=O | | $CH_3$ | $OCH_3$ | |
| $Q_{17}(R_7 = CH_3)$ | H | H | C=O | | $OCH_3$ | $OCH_3$ | |
| $Q_{17}(R_7 = CH_3)$ | H | H | C=O | | Cl | $OCH_3$ | |
| $Q_{17}(R_7 = CH_3)$ | H | H | OH | H | $CH_3$ | $CH_3$ | |
| $Q_{17}(R_7 = CH_3)$ | H | H | OH | H | $CH_3$ | $OCH_3$ | |
| $Q_{17}(R_7 = CH_3)$ | H | H | OH | H | $OCH_3$ | $OCH_3$ | |
| $Q_{17}(R_7 = CH_3)$ | H | H | OH | H | Cl | $OCH_3$ | |
| $Q_{18}(R_7 = H)$ | H | H | C=O | | $CH_3$ | $CH_3$ | |
| $Q_{18}(R_7 = H)$ | H | H | C=O | | $CH_3$ | $OCH_3$ | |
| $Q_{18}(R_7 = H)$ | H | H | C=O | | $OCH_3$ | $OCH_3$ | |
| $Q_{18}(R_7 = H)$ | H | H | C=O | | Cl | $OCH_3$ | |
| $Q_{18}(R_7 = H)$ | H | H | OH | H | $CH_3$ | $CH_3$ | |
| $Q_{18}(R_7 = H)$ | H | H | OH | H | $CH_3$ | $OCH_3$ | |
| $Q_{18}(R_7 = H)$ | H | H | OH | H | $OCH_3$ | $OCH_3$ | |
| $Q_{18}(R_7 = H)$ | H | H | OH | H | Cl | $OCH_3$ | |
| $Q_{19}(R_7 = H, R_8 = H)$ | H | H | C=O | | $CH_3$ | $CH_3$ | |
| $Q_{19}(R_7 = H, R_8 = H)$ | H | H | C=O | | $CH_3$ | $OCH_3$ | |
| $Q_{19}(R_7 = H, R_8 = H)$ | H | H | C=O | | $OCH_3$ | $OCH_3$ | |
| $Q_{19}(R_7 = H, R_8 = H)$ | H | H | C=O | | Cl | $OCH_3$ | |
| $Q_{19}(R_7 = H, R_8 = H)$ | H | H | OH | H | $CH_3$ | $CH_3$ | |
| $Q_{19}(R_7 = H, R_8 = H)$ | H | H | OH | H | $CH_3$ | $OCH_3$ | |
| $Q_{19}(R_7 = H, R_8 = H)$ | H | H | OH | H | $OCH_3$ | $OCH_3$ | |
| $Q_{19}(R_7 = H, R_8 = H)$ | H | H | OH | H | Cl | $OCH_3$ | |
| $Q_{20}(R_7 = H, R_8 = H)$ | H | H | C=O | | $CH_3$ | $CH_3$ | |
| $Q_{20}(R_7 = H, R_8 = H)$ | H | H | C=O | | $CH_3$ | $OCH_3$ | |
| $Q_{20}(R_7 = H, R_8 = H)$ | H | H | C=O | | $OCH_3$ | $OCH_3$ | |
| $Q_{20}(R_7 = H, R_8 = H)$ | H | H | C=O | | Cl | $OCH_3$ | |
| $Q_{20}(R_7 = H, R_8 = H)$ | H | H | OH | H | $CH_3$ | $CH_3$ | |
| $Q_{20}(R_7 = H, R_8 = H)$ | H | H | OH | H | $CH_3$ | $OCH_3$ | |
| $Q_{20}(R_7 = H, R_8 = H)$ | H | H | OH | H | $OCH_3$ | $OCH_3$ | |
| $Q_{20}(R_7 = H, R_8 = H)$ | H | H | OH | H | Cl | $OCH_3$ | |
| $Q_{21}(R_7 = H, R_8 = H, R_9 = CH_3)$ | H | H | C=O | | $CH_3$ | $CH_3$ | |
| $Q_{21}(R_7 = H, R_8 = H, R_9 = CH_3)$ | H | H | C=O | | $CH_3$ | $OCH_3$ | |
| $Q_{21}(R_7 = H, R_8 = H, R_9 = CH_3)$ | H | H | C=O | | $OCH_3$ | $OCH_3$ | |
| $Q_{21}(R_7 = H, R_8 = H, R_9 = CH_3)$ | H | H | C=O | | Cl | $OCH_3$ | |
| $Q_{21}(R_7 = H, R_8 = H, R_9 = CH_3)$ | H | H | OH | H | $CH_3$ | $CH_3$ | |
| $Q_{21}(R_7 = H, R_8 = H, R_9 = CH_3)$ | H | H | OH | H | $CH_3$ | $OCH_3$ | |
| $Q_{21}(R_7 = H, R_8 = H, R_9 = CH_3)$ | H | H | OH | H | $OCH_3$ | $OCH_3$ | |
| $Q_{21}(R_7 = H, R_8 = H, R_9 = CH_3)$ | H | H | OH | H | Cl | $OCH_3$ | |
| $Q_{22}(R_7 = H)$ | H | H | C=O | | $CH_3$ | $CH_3$ | |
| $Q_{22}(R_7 = H)$ | H | H | C=O | | $CH_3$ | $OCH_3$ | |
| $Q_{22}(R_7 = H)$ | H | H | C=O | | $OCH_3$ | $OCH_3$ | |
| $Q_{22}(R_7 = H)$ | H | H | C=O | | Cl | $OCH_3$ | |
| $Q_{22}(R_7 = H)$ | H | H | OH | H | $CH_3$ | $CH_3$ | |
| $Q_{22}(R_7 = H)$ | H | H | OH | H | $CH_3$ | $OCH_3$ | |
| $Q_{22}(R_7 = H)$ | H | H | OH | H | $OCH_3$ | $OCH_3$ | |

TABLE XVII-continued

General Formula XVII

| Q | R | $R_1$ | $R_2$ | $R_3$ | X | Y | m.p.(°C.) |
|---|---|---|---|---|---|---|---|
| $Q_{22}(R_7 = H)$ | H | H | OH | H | Cl | $OCH_3$ | |
| $Q_{23}(R_7 = H)$ | H | H | C=O | | $CH_3$ | $CH_3$ | |
| $Q_{23}(R_7 = H)$ | H | H | C=O | | $CH_3$ | $OCH_3$ | |
| $Q_{23}(R_7 = H)$ | H | H | C=O | | $OCH_3$ | $OCH_3$ | |
| $Q_{23}(R_7 = H)$ | H | H | C=O | | Cl | $OCH_3$ | |
| $Q_{23}(R_7 = H)$ | H | H | OH | H | $CH_3$ | $CH_3$ | |
| $Q_{23}(R_7 = H)$ | H | H | OH | H | $CH_3$ | $OCH_3$ | |
| $Q_{23}(R_7 = H)$ | H | H | OH | H | $OCH_3$ | $OCH_3$ | |
| $Q_{23}(R_7 = H)$ | H | H | OH | H | Cl | $OCH_3$ | |
| $Q_{24}(R_7 = H, R_8 = H)$ | H | H | C=O | | $CH_3$ | $CH_3$ | |
| $Q_{24}(R_7 = H, R_8 = H)$ | H | H | C=O | | $CH_3$ | $OCH_3$ | |
| $Q_{24}(R_7 = H, R_8 = H)$ | H | H | C=O | | $OCH_3$ | $OCH_3$ | |
| $Q_{24}(R_7 = H, R_8 = H)$ | H | H | C=O | | Cl | $OCH_3$ | |
| $Q_{24}(R_7 = H, R_8 = H)$ | H | H | OH | H | $CH_3$ | $CH_3$ | |
| $Q_{24}(R_7 = H, R_8 = H)$ | H | H | OH | H | $CH_3$ | $OCH_3$ | |
| $Q_{24}(R_7 = H, R_8 = H)$ | H | H | OH | H | $OCH_3$ | $OCH_3$ | |
| $Q_{24}(R_7 = H, R_8 = H)$ | H | H | OH | H | Cl | $OCH_3$ | |
| $Q_{25}(R_7 = H, R_8 = H)$ | H | H | C=O | | $CH_3$ | $CH_3$ | |
| $Q_{25}(R_7 = H, R_8 = H)$ | H | H | C=O | | $CH_3$ | $OCH_3$ | |
| $Q_{25}(R_7 = H, R_8 = H)$ | H | H | C=O | | $OCH_3$ | $OCH_3$ | |
| $Q_{25}(R_7 = H, R_8 = H)$ | H | H | C=O | | Cl | $OCH_3$ | |
| $Q_{25}(R_7 = H, R_8 = H)$ | H | H | OH | H | $CH_3$ | $CH_3$ | |
| $Q_{25}(R_7 = H, R_8 = H)$ | H | H | OH | H | $CH_3$ | $OCH_3$ | |
| $Q_{25}(R_7 = H, R_8 = H)$ | H | H | OH | H | $OCH_3$ | $OCH_3$ | |
| $Q_{25}(R_7 = H, R_8 = H)$ | H | H | OH | H | Cl | $OCH_3$ | |
| $Q_{26}(R_7 = H, R_8 = H)$ | H | H | C=O | | $CH_3$ | $CH_3$ | |
| $Q_{26}(R_7 = H, R_8 = H)$ | H | H | C=O | | $CH_3$ | $OCH_3$ | |
| $Q_{26}(R_7 = H, R_8 = H)$ | H | H | C=O | | $OCH_3$ | $OCH_3$ | |
| $Q_{26}(R_7 = H, R_8 = H)$ | H | H | C=O | | Cl | $OCH_3$ | |
| $Q_{26}(R_7 = H, R_8 = H)$ | H | H | OH | H | $CH_3$ | $CH_3$ | |
| $Q_{26}(R_7 = H, R_8 = H)$ | H | H | OH | H | $CH_3$ | $OCH_3$ | |
| $Q_{26}(R_7 = H, R_8 = H)$ | H | H | OH | H | $OCH_3$ | $OCH_3$ | |
| $Q_{26}(R_7 = H, R_8 = H)$ | H | H | OH | H | Cl | $OCH_3$ | |
| $Q_{27}(R_7 = H, R_{11} = H, R_{12} = H)$ | H | H | C=O | | $CH_3$ | $CH_3$ | |
| $Q_{27}(R_7 = H, R_{11} = H, R_{12} = H)$ | H | H | C=O | | $CH_3$ | $OCH_3$ | |
| $Q_{27}(R_7 = H, R_{11} = H, R_{12} = H)$ | H | H | C=O | | $OCH_3$ | $OCH_3$ | |
| $Q_{27}(R_7 = H, R_{11} = H, R_{12} = H)$ | H | H | C=O | | Cl | $OCH_3$ | |
| $Q_{27}(R_7 = H, R_{11} = H, R_{12} = H)$ | H | H | OH | H | $CH_3$ | $CH_3$ | |
| $Q_{27}(R_7 = H, R_{11} = H, R_{12} = H)$ | H | H | OH | H | $CH_3$ | $OCH_3$ | |
| $Q_{27}(R_7 = H, R_{11} = H, R_{12} = H)$ | H | H | OH | H | $OCH_3$ | $OCH_3$ | |
| $Q_{27}(R_7 = H, R_{11} = H, R_{12} = H)$ | H | H | OH | H | Cl | $OCH_3$ | |
| $Q_{28}(R_{11} = H, R_{12} = H)$ | H | H | C=O | | $CH_3$ | $CH_3$ | |
| $Q_{28}(R_{11} = H, R_{12} = H)$ | H | H | C=O | | $CH_3$ | $OCH_3$ | |
| $Q_{28}(R_{11} = H, R_{12} = H)$ | H | H | C=O | | $OCH_3$ | $OCH_3$ | |
| $Q_{28}(R_{11} = H, R_{12} = H)$ | H | H | C=O | | Cl | $OCH_3$ | |
| $Q_{28}(R_{11} = H, R_{12} = H)$ | H | H | OH | H | $CH_3$ | $CH_3$ | |
| $Q_{28}(R_{11} = H, R_{12} = H)$ | H | H | OH | H | $CH_3$ | $OCH_3$ | |
| $Q_{28}(R_{11} = H, R_{12} = H)$ | H | H | OH | H | $OCH_3$ | $OCH_3$ | |
| $Q_{28}(R_{11} = H, R_{12} = H)$ | H | H | OH | H | Cl | $OCH_3$ | |
| $Q_{29}(R_{11} = H, R_{12} = H)$ | H | H | C=O | | $CH_3$ | $CH_3$ | |
| $Q_{29}(R_{11} = H, R_{12} = H)$ | H | H | C=O | | $CH_3$ | $OCH_3$ | |
| $Q_{29}(R_{11} = H, R_{12} = H)$ | H | H | C=O | | $OCH_3$ | $OCH_3$ | |
| $Q_{29}(R_{11} = H, R_{12} = H)$ | H | H | C=O | | Cl | $OCH_3$ | |
| $Q_{29}(R_{11} = H, R_{12} = H)$ | H | H | OH | H | $CH_3$ | $CH_3$ | |
| $Q_{29}(R_{11} = H, R_{12} = H)$ | H | H | OH | H | $CH_3$ | $OCH_3$ | |
| $Q_{29}(R_{11} = H, R_{12} = H)$ | H | H | OH | H | $OCH_3$ | $OCH_3$ | |
| $Q_{29}(R_{11} = H, R_{12} = H)$ | H | H | OH | H | Cl | $OCH_3$ | |
| $Q_{30}(R_7 = H, R_8 = H)$ | H | H | C=O | | $CH_3$ | $CH_3$ | |
| $Q_{30}(R_7 = H, R_8 = H)$ | H | H | C=O | | $CH_3$ | $OCH_3$ | |
| $Q_{30}(R_7 = H, R_8 = H)$ | H | H | C=O | | $OCH_3$ | $OCH_3$ | |
| $Q_{30}(R_7 = H, R_8 = H)$ | H | H | C=O | | Cl | $OCH_3$ | |
| $Q_{30}(R_7 = H, R_8 = H)$ | H | H | OH | H | $CH_3$ | $CH_3$ | |
| $Q_{30}(R_7 = H, R_8 = H)$ | H | H | OH | H | $CH_3$ | $OCH_3$ | |
| $Q_{30}(R_7 = H, R_8 = H)$ | H | H | OH | H | $OCH_3$ | $OCH_3$ | |
| $Q_{30}(R_7 = H, R_8 = H)$ | H | H | OH | H | Cl | $OCH_3$ | |
| $Q_{31}(R_7 = H, R_8 = H)$ | H | H | C=O | | $CH_3$ | $CH_3$ | |
| $Q_{31}(R_7 = H, R_8 = H)$ | H | H | C=O | | $CH_3$ | $OCH_3$ | |
| $Q_{31}(R_7 = H, R_8 = H)$ | H | H | C=O | | $OCH_3$ | $OCH_3$ | |
| $Q_{31}(R_7 = H, R_8 = H)$ | H | H | C=O | | Cl | $OCH_3$ | |
| $Q_{31}(R_7 = H, R_8 = H)$ | H | H | OH | H | $CH_3$ | $CH_3$ | |
| $Q_{31}(R_7 = H, R_8 = H)$ | H | H | OH | H | $CH_3$ | $OCH_3$ | |
| $Q_{31}(R_7 = H, R_8 = H)$ | H | H | OH | H | $OCH_3$ | $OCH_3$ | |
| $Q_{31}(R_7 = H, R_8 = H)$ | H | H | OH | H | Cl | $OCH_3$ | |
| $Q_{32}(R_{13} = OCH_3, R_{14} = OCH_3)$ | H | H | C=O | | $CH_3$ | $CH_3$ | |
| $Q_{32}(R_{13} = OCH_3, R_{14} = OCH_3)$ | H | H | C=O | | $CH_3$ | $OCH_3$ | |
| $Q_{32}(R_{13} = OCH_3, R_{14} = OCH_3)$ | H | H | C=O | | $OCH_3$ | $OCH_3$ | |
| $Q_{32}(R_{13} = OCH_3, R_{14} = OCH_3)$ | H | H | C=O | | Cl | $OCH_3$ | |
| $Q_{32}(R_{13} = OCH_3, R_{14} = OCH_3)$ | H | H | OH | H | $CH_3$ | $CH_3$ | |
| $Q_{32}(R_{13} = OCH_3, R_{14} = OCH_3)$ | H | H | OH | H | $CH_3$ | $OCH_3$ | |
| $Q_{32}(R_{13} = OCH_3, R_{14} = OCH_3)$ | H | H | OH | H | $OCH_3$ | $OCH_3$ | |

TABLE XVII-continued

General Formula XVII

| Q | R | R₁ | R₂ | R₃ | X | Y | m.p.(°C.) |
|---|---|----|----|----|---|---|-----------|
| $Q_{32}(R_{13} = OCH_3, R_{14} = OCH_3)$ | H | H | OH | H | Cl | OCH₃ | |
| $Q_{33}(R_7 = H)$ | H | H | C=O | | CH₃ | CH₃ | |
| $Q_{33}(R_7 = H)$ | H | H | C=O | | CH₃ | OCH₃ | |
| $Q_{33}(R_7 = H)$ | H | H | C=O | | OCH₃ | OCH₃ | |
| $Q_{33}(R_7 = H)$ | H | H | C=O | | Cl | OCH₃ | |
| $Q_{33}(R_7 = H)$ | H | H | OH | H | CH₃ | CH₃ | |
| $Q_{33}(R_7 = H)$ | H | H | OH | H | CH₃ | OCH₃ | |
| $Q_{33}(R_7 = H)$ | H | H | OH | H | OCH₃ | OCH₃ | |
| $Q_{33}(R_7 = H)$ | H | H | OH | H | Cl | OCH₃ | |

TABLE XVIII

General Formula XVIII

| Q | R | R₁ | R₂ | R₃ | X | Y | m.p.(°C.) |
|---|---|----|----|----|---|---|-----------|
| $Q_1(R_7 = H, R_8 = H, R_9 = H)$ | H | H | C=O | | CH₃ | CH₃ | |
| $Q_1(R_7 = H, R_8 = H, R_9 = H)$ | H | H | C=O | | CH₃ | OCH₃ | |
| $Q_1(R_7 = H, R_8 = H, R_9 = H)$ | H | H | C=O | | OCH₃ | OCH₃ | |
| $Q_1(R_7 = H, R_8 = H, R_9 = H)$ | H | H | C=O | | Cl | OCH₃ | |
| $Q_1(R_7 = H, R_8 = H, R_9 = H)$ | H | H | OH | H | CH₃ | CH₃ | |
| $Q_1(R_7 = H, R_8 = H, R_9 = H)$ | H | H | OH | H | CH₃ | OCH₃ | |
| $Q_1(R_7 = H, R_8 = H, R_9 = H)$ | H | H | OH | H | OCH₃ | OCH₃ | |
| $Q_1(R_7 = H, R_8 = H, R_9 = H)$ | H | H | OH | H | Cl | OCH₃ | |
| $Q_1(R_7 = H, R_8 = H, R_9 = H)$ | H | H | OCH₃ | H | OCH₃ | OCH₃ | |
| $Q_1(R_7 = H, R_8 = H, R_9 = H)$ | H | H | OCH₂CH₃ | H | OCH₃ | OCH₃ | |
| $Q_2(R_7 = H, R_8 = H, R_9 = H)$ | H | H | C=O | | CH₃ | CH₃ | |
| $Q_2(R_7 = H, R_8 = H, R_9 = H)$ | H | H | C=O | | CH₃ | OCH₃ | |
| $Q_2(R_7 = H, R_8 = H, R_9 = H)$ | H | H | C=O | | OCH₃ | OCH₃ | |
| $Q_2(R_7 = H, R_8 = H, R_9 = H)$ | H | H | C=O | | Cl | OCH₃ | |
| $Q_2(R_7 = H, R_8 = H, R_9 = H)$ | H | H | OH | H | CH₃ | CH₃ | |
| $Q_2(R_7 = H, R_8 = H, R_9 = H)$ | H | H | OH | H | CH₃ | OCH₃ | |
| $Q_2(R_7 = H, R_8 = H, R_9 = H)$ | H | H | OH | H | OCH₃ | OCH₃ | |
| $Q_2(R_7 = H, R_8 = H, R_9 = H)$ | H | H | OH | H | Cl | OCH₃ | |
| $Q_2(R_7 = H, R_8 = H, R_9 = H)$ | H | H | OCH₃ | H | CH₃ | CH₃ | |
| $Q_2(R_7 = H, R_8 = H, R_9 = H)$ | H | H | OCH₂CH₃ | H | CH₃ | CH₃ | |
| $Q_3(R_7 = H, R_8 = H, R_9 = H)$ | H | H | C=O | | CH₃ | CH₃ | |
| $Q_3(R_7 = H, R_8 = H, R_9 = H)$ | H | H | C=O | | CH₃ | OCH₃ | |
| $Q_3(R_7 = H, R_8 = H, R_9 = H)$ | H | H | C=O | | OCH₃ | OCH₃ | |
| $Q_3(R_7 = H, R_8 = H, R_9 = H)$ | H | H | C=O | | Cl | OCH₃ | |
| $Q_3(R_7 = H, R_8 = H, R_9 = H)$ | H | H | OH | H | CH₃ | CH₃ | |
| $Q_3(R_7 = H, R_8 = H, R_9 = H)$ | H | H | OH | H | CH₃ | OCH₃ | |
| $Q_3(R_7 = H, R_8 = H, R_9 = H)$ | H | H | OH | H | OCH₃ | OCH₃ | |
| $Q_3(R_7 = H, R_8 = H, R_9 = H)$ | H | H | OH | H | Cl | OCH₃ | |
| $Q_3(R_7 = H, R_8 = H, R_9 = Cl)$ | H | H | C=O | | OCH₃ | OCH₃ | |
| $Q_3(R_7 = H, R_8 = H, R_9 = CH_3)$ | H | H | C=O | | OCH₃ | OCH₃ | |
| $Q_3(R_7 = H, R_8 = H, R_9 = CH_3)$ | H | H | OH | H | OCH₃ | OCH₃ | |
| $Q_4(R_7 = H, R_8 = H, R_9 = H)$ | H | H | C=O | | CH₃ | CH₃ | |
| $Q_4(R_7 = H, R_8 = H, R_9 = H)$ | H | H | C=O | | CH₃ | OCH₃ | |
| $Q_4(R_7 = H, R_8 = H, R_9 = H)$ | H | H | C=O | | OCH₃ | OCH₃ | |
| $Q_4(R_7 = H, R_8 = H, R_9 = H)$ | H | H | C=O | | Cl | OCH₃ | |
| $Q_4(R_7 = H, R_8 = H, R_9 = H)$ | H | H | OH | H | CH₃ | CH₃ | |
| $Q_4(R_7 = H, R_8 = H, R_9 = H)$ | H | H | OH | H | CH₃ | OCH₃ | |
| $Q_4(R_7 = H, R_8 = H, R_9 = H)$ | H | H | OH | H | OCH₃ | OCH₃ | |
| $Q_4(R_7 = H, R_8 = H, R_9 = H)$ | H | H | OH | H | Cl | OCH₃ | |
| $Q_5(R_7 = H, R_8 = H, R_9 = H, R_{10} = CH_3)$ | H | H | C=O | | CH₃ | CH₃ | |
| $Q_5(R_7 = H, R_8 = H, R_9 = H, R_{10} = CH_3)$ | H | H | C=O | | CH₃ | OCH₃ | |
| $Q_5(R_7 = H, R_8 = H, R_9 = H, R_{10} = CH_3)$ | H | H | C=O | | OCH₃ | OCH₃ | |
| $Q_5(R_7 = H, R_8 = H, R_9 = H, R_{10} = CH_3)$ | H | H | C=O | | Cl | OCH₃ | |
| $Q_5(R_7 = H, R_8 = H, R_9 = H, R_{10} = CH_3)$ | H | H | OH | H | CH₃ | CH₃ | |
| $Q_5(R_7 = H, R_8 = H, R_9 = H, R_{10} = CH_3)$ | H | H | OH | H | CH₃ | OCH₃ | |
| $Q_5(R_7 = H, R_8 = H, R_9 = H, R_{10} = CH_3)$ | H | H | OH | H | OCH₃ | OCH₃ | |
| $Q_5(R_7 = H, R_8 = H, R_9 = H, R_{10} = CH_3)$ | H | H | OH | H | Cl | OCH₃ | |
| $Q_5(R_7 = H, R_8 = H, R_9 = H, R_{10} = CH_3)$ | H | H | OCH₃ | H | Cl | OCH₃ | |
| $Q_5(R_7 = H, R_8 = H, R_9 = H, R_{10} = CH_3)$ | H | H | OCH₂CH₃ | H | OCH₃ | OCH₃ | |
| $Q_6(R_7 = H, R_8 = H, R_9 = H, R_{10} = CH_3)$ | H | H | C=O | | CH₃ | CH₃ | |
| $Q_6(R_7 = H, R_8 = H, R_9 = H, R_{10} = CH_3)$ | H | H | C=O | | CH₃ | OCH₃ | |
| $Q_6(R_7 = H, R_8 = H, R_9 = H, R_{10} = CH_3)$ | H | H | C=O | | OCH₃ | OCH₃ | |
| $Q_6(R_7 = H, R_8 = H, R_9 = H, R_{10} = CH_3)$ | H | H | C=O | | Cl | OCH₃ | |
| $Q_6(R_7 = H, R_8 = H, R_9 = H, R_{10} = CH_3)$ | H | H | OH | H | CH₃ | CH₃ | |
| $Q_6(R_7 = H, R_8 = H, R_9 = H, R_{10} = CH_3)$ | H | H | OH | H | CH₃ | OCH₃ | |
| $Q_6(R_7 = H, R_8 = H, R_9 = H, R_{10} = CH_3)$ | H | H | OH | H | OCH₃ | OCH₃ | |
| $Q_6(R_7 = H, R_8 = H, R_9 = H, R_{10} = CH_3)$ | H | H | OH | H | Cl | OCH₃ | |
| $Q_7(R_7 = H, R_8 = H)$ | H | H | C=O | | CH₃ | CH₃ | |
| $Q_7(R_7 = H, R_8 = H)$ | H | H | C=O | | CH₃ | OCH₃ | |
| $Q_7(R_7 = H, R_8 = H)$ | H | H | C=O | | OCH₃ | OCH₃ | |
| $Q_7(R_7 = H, R_8 = H)$ | H | H | C=O | | Cl | OCH₃ | |
| $Q_7(R_7 = H, R_8 = H)$ | H | H | OH | H | CH₃ | CH₃ | |
| $Q_7(R_7 = H, R_8 = H)$ | H | H | OH | H | CH₃ | OCH₃ | |
| $Q_7(R_7 = H, R_8 = H)$ | H | H | OH | H | OCH₃ | OCH₃ | |

TABLE XVIII-continued

General Formula XVIII

| Q | R | $R_1$ | $R_2$ | $R_3$ | X | Y | m.p.(°C.) |
|---|---|---|---|---|---|---|---|
| $Q_7(R_7 = H, R_8 = H)$ | H | H | OH | H | Cl | $OCH_3$ | |
| $Q_8(R_7 = H, R_8 = H)$ | H | H | C=O | | $OCH_3$ | $OCH_3$ | |
| $Q_8(R_7 = H, R_8 = H)$ | H | H | C=O | | Cl | $OCH_3$ | |
| $Q_8(R_7 = H, R_8 = H)$ | H | H | OH | H | Cl | $OCH_3$ | |
| $Q_8(R_7 = H, R_8 = H)$ | H | H | OH | H | $OCH_3$ | $OCH_3$ | |
| $Q_9(R_7 = H, R_8 = H)$ | H | H | C=O | | $CH_3$ | $CH_3$ | |
| $Q_9(R_7 = H, R_8 = H)$ | H | H | C=O | | $CH_3$ | $OCH_3$ | |
| $Q_9(R_7 = H, R_8 = H)$ | H | H | C=O | | $OCH_3$ | $OCH_3$ | |
| $Q_9(R_7 = H, R_8 = H)$ | H | H | C=O | | Cl | $OCH_3$ | |
| $Q_9(R_7 = H, R_8 = H)$ | H | H | OH | H | $CH_3$ | $CH_3$ | |
| $Q_9(R_7 = H, R_8 = H)$ | H | H | OH | H | $CH_3$ | $OCH_3$ | |
| $Q_9(R_7 = H, R_8 = H)$ | H | H | OH | H | $OCH_3$ | $OCH_3$ | |
| $Q_9(R_7 = H, R_8 = H)$ | H | H | OH | H | Cl | $OCH_3$ | |
| $Q_{10}(R_7 = H, R_8 = H)$ | H | H | C=O | | $CH_3$ | $OCH_3$ | |
| $Q_{10}(R_7 = H, R_8 = H)$ | H | H | C=O | | $OCH_3$ | $OCH_3$ | |
| $Q_{10}(R_7 = H, R_8 = H)$ | H | H | C=O | | Cl | $OCH_3$ | |
| $Q_{10}(R_7 = H, R_8 = H)$ | H | H | OH | H | $CH_3$ | $CH_3$ | |
| $Q_{10}(R_7 = H, R_8 = H)$ | H | H | OH | H | $OCH_3$ | $OCH_3$ | |
| $Q_{10}(R_7 = H, R_8 = H)$ | H | H | OH | H | Cl | $OCH_3$ | |
| $Q_{11}(R_7 = H, R_8 = H)$ | H | H | C=O | | $CH_3$ | $CH_3$ | |
| $Q_{11}(R_7 = H, R_8 = H)$ | H | H | C=O | | $CH_3$ | $OCH_3$ | |
| $Q_{11}(R_7 = H, R_8 = H)$ | H | H | C=O | | $OCH_3$ | $OCH_3$ | |
| $Q_{11}(R_7 = H, R_8 = H)$ | H | H | C=O | | Cl | $OCH_3$ | |
| $Q_{11}(R_7 = H, R_8 = H)$ | H | H | OH | H | $CH_3$ | $CH_3$ | |
| $Q_{11}(R_7 = H, R_8 = H)$ | H | H | OH | H | $CH_3$ | $OCH_3$ | |
| $Q_{11}(R_7 = H, R_8 = H)$ | H | H | OH | H | $OCH_3$ | $OCH_3$ | |
| $Q_{11}(R_7 = H, R_8 = H)$ | H | H | OH | H | Cl | $OCH_3$ | |
| $Q_{12}(R_7 = H, R_8 = H)$ | H | H | C=O | | $CH_3$ | $CH_3$ | |
| $Q_{12}(R_7 = H, R_8 = H)$ | H | H | C=O | | $CH_3$ | $OCH_3$ | |
| $Q_{12}(R_7 = H, R_8 = H)$ | H | H | C=O | | $OCH_3$ | $OCH_3$ | |
| $Q_{12}(R_7 = H, R_8 = H)$ | H | H | C=O | | Cl | $OCH_3$ | |
| $Q_{12}(R_7 = H, R_8 = H)$ | H | H | OH | H | $CH_3$ | $CH_3$ | |
| $Q_{12}(R_7 = H, R_8 = H)$ | H | H | OH | H | $CH_3$ | $OCH_3$ | |
| $Q_{12}(R_7 = H, R_8 = H)$ | H | H | OH | H | $OCH_3$ | $OCH_3$ | |
| $Q_{12}(R_7 = H, R_8 = H)$ | H | H | OH | H | Cl | $OCH_3$ | |
| $Q_{12}(R_7 = H, R_8 = H)$ | H | H | $OCH_3$ | H | $OCH_3$ | $OCH_3$ | |
| $Q_{13}(R_7 = H, R_8 = H)$ | H | H | C=O | | $CH_3$ | $CH_3$ | |
| $Q_{13}(R_7 = H, R_8 = H)$ | H | H | C=O | | $CH_3$ | $OCH_3$ | |
| $Q_{13}(R_7 = H, R_8 = H)$ | H | H | C=O | | $OCH_3$ | $OCH_3$ | |
| $Q_{13}(R_7 = H, R_8 = H)$ | H | H | C=O | | Cl | $OCH_3$ | |
| $Q_{13}(R_7 = H, R_8 = H)$ | H | H | OH | H | $CH_3$ | $CH_3$ | |
| $Q_{13}(R_7 = H, R_8 = H)$ | H | H | OH | H | $CH_3$ | $OCH_3$ | |
| $Q_{13}(R_7 = H, R_8 = H)$ | H | H | OH | H | $OCH_3$ | $OCH_3$ | |
| $Q_{13}(R_7 = H, R_8 = H)$ | H | H | OH | H | Cl | $OCH_3$ | |
| $Q_{14}(R_7 = H)$ | H | H | C=O | | $CH_3$ | $CH_3$ | |
| $Q_{14}(R_7 = H)$ | H | H | C=O | | $CH_3$ | $OCH_3$ | |
| $Q_{14}(R_7 = H)$ | H | H | C=O | | $OCH_3$ | $OCH_3$ | |
| $Q_{14}(R_7 = H)$ | H | H | C=O | | Cl | $OCH_3$ | |
| $Q_{14}(R_7 = H)$ | H | H | OH | H | $CH_3$ | $CH_3$ | |
| $Q_{14}(R_7 = H)$ | H | H | OH | H | $CH_3$ | $OCH_3$ | |
| $Q_{14}(R_7 = H)$ | H | H | OH | H | $OCH_3$ | $OCH_3$ | |
| $Q_{14}(R_7 = H)$ | H | H | OH | H | Cl | $OCH_3$ | |
| $Q_{15}(R_7 = H)$ | H | H | C=O | | $CH_3$ | $CH_3$ | |
| $Q_{15}(R_7 = H)$ | H | H | C=O | | $CH_3$ | $OCH_3$ | |
| $Q_{15}(R_7 = H)$ | H | H | C=O | | $OCH_3$ | $OCH_3$ | |
| $Q_{15}(R_7 = H)$ | H | H | C=O | | Cl | $OCH_3$ | |
| $Q_{15}(R_7 = H)$ | H | H | OH | H | $CH_3$ | $CH_3$ | |
| $Q_{15}(R_7 = H)$ | H | H | OH | H | $CH_3$ | $OCH_3$ | |
| $Q_{15}(R_7 = H)$ | H | H | OH | H | $OCH_3$ | $OCH_3$ | |
| $Q_{15}(R_7 = H)$ | H | H | OH | H | Cl | $OCH_3$ | |
| $Q_{16}(R_7 = H)$ | H | H | C=O | | $CH_3$ | $CH_3$ | |
| $Q_{16}(R_7 = H)$ | H | H | C=O | | $CH_3$ | $OCH_3$ | |
| $Q_{16}(R_7 = H)$ | H | H | C=O | | $OCH_3$ | $OCH_3$ | |
| $Q_{16}(R_7 = H)$ | H | H | C=O | | Cl | $OCH_3$ | |
| $Q_{16}(R_7 = H)$ | H | H | OH | H | $CH_3$ | $CH_3$ | |
| $Q_{16}(R_7 = H)$ | H | H | OH | H | $CH_3$ | $OCH_3$ | |
| $Q_{16}(R_7 = H)$ | H | H | OH | H | $OCH_3$ | $OCH_3$ | |
| $Q_{16}(R_7 = H)$ | H | H | OH | H | Cl | $OCH_3$ | |
| $Q_{17}(R_7 = CH_3)$ | H | H | C=O | | $CH_3$ | $CH_3$ | |
| $Q_{17}(R_7 = CH_3)$ | H | H | C=O | | $CH_3$ | $OCH_3$ | |
| $Q_{17}(R_7 = CH_3)$ | H | H | C=O | | $OCH_3$ | $OCH_3$ | |
| $Q_{17}(R_7 = CH_3)$ | H | H | C=O | | Cl | $OCH_3$ | |
| $Q_{17}(R_7 = CH_3)$ | H | H | OH | H | $CH_3$ | $CH_3$ | |
| $Q_{17}(R_7 = CH_3)$ | H | H | OH | H | $CH_3$ | $OCH_3$ | |
| $Q_{17}(R_7 = CH_3)$ | H | H | OH | H | $OCH_3$ | $OCH_3$ | |
| $Q_{17}(R_7 = CH_3)$ | H | H | OH | H | Cl | $OCH_3$ | |
| $Q_{18}(R_7 = H)$ | H | H | C=O | | $CH_3$ | $CH_3$ | |
| $Q_{18}(R_7 = H)$ | H | H | C=O | | $CH_3$ | $OCH_3$ | |
| $Q_{18}(R_7 = H)$ | H | H | C=O | | $OCH_3$ | $OCH_3$ | |
| $Q_{18}(R_7 = H)$ | H | H | C=O | | Cl | $OCH_3$ | |

TABLE XVIII-continued

| | General Formula XVIII | | | | | | | |
|---|---|---|---|---|---|---|---|---|
| Q | R | $R_1$ | $R_2$ | | $R_3$ | X | Y | m.p.(°C.) |
| $Q_{18}(R_7 = H)$ | H | H | OH | | H | $CH_3$ | $CH_3$ | |
| $Q_{18}(R_7 = H)$ | H | H | OH | | H | $CH_3$ | $OCH_3$ | |
| $Q_{18}(R_7 = H)$ | H | H | OH | | H | $OCH_3$ | $OCH_3$ | |
| $Q_{18}(R_7 = H)$ | H | H | OH | | H | Cl | $OCH_3$ | |
| $Q_{19}(R_7 = H, R_8 = H)$ | H | H | | C=O | | $CH_3$ | $CH_3$ | |
| $Q_{19}(R_7 = H, R_8 = H)$ | H | H | | C=O | | $CH_3$ | $OCH_3$ | |
| $Q_{19}(R_7 = H, R_8 = H)$ | H | H | | C=O | | $OCH_3$ | $OCH_3$ | |
| $Q_{19}(R_7 = H, R_8 = H)$ | H | H | | C=O | | Cl | $OCH_3$ | |
| $Q_{19}(R_7 = H, R_8 = H)$ | H | H | OH | | H | $CH_3$ | $CH_3$ | |
| $Q_{19}(R_7 = H, R_8 = H)$ | H | H | OH | | H | $CH_3$ | $OCH_3$ | |
| $Q_{19}(R_7 = H, R_8 = H)$ | H | H | OH | | H | $OCH_3$ | $OCH_3$ | |
| $Q_{19}(R_7 = H, R_8 = H)$ | H | H | OH | | H | Cl | $OCH_3$ | |
| $Q_{20}(R_7 = H, R_8 = H)$ | H | H | | C=O | | $CH_3$ | $CH_3$ | |
| $Q_{20}(R_7 = H, R_8 = H)$ | H | H | | C=O | | $CH_3$ | $OCH_3$ | |
| $Q_{20}(R_7 = H, R_8 = H)$ | H | H | | C=O | | $OCH_3$ | $OCH_3$ | |
| $Q_{20}(R_7 = H, R_8 = H)$ | H | H | | C=O | | Cl | $OCH_3$ | |
| $Q_{20}(R_7 = H, R_8 = H)$ | H | H | OH | | H | $CH_3$ | $CH_3$ | |
| $Q_{20}(R_7 = H, R_8 = H)$ | H | H | OH | | H | $CH_3$ | $OCH_3$ | |
| $Q_{20}(R_7 = H, R_8 = H)$ | H | H | OH | | H | $OCH_3$ | $OCH_3$ | |
| $Q_{20}(R_7 = H, R_8 = H)$ | H | H | OH | | H | Cl | $OCH_3$ | |
| $Q_{21}(R_7 = H, R_8 = H, R_9 = CH_3)$ | H | H | | C=O | | $CH_3$ | $CH_3$ | |
| $Q_{21}(R_7 = H, R_8 = H, R_9 = CH_3)$ | H | H | | C=O | | $CH_3$ | $OCH_3$ | |
| $Q_{21}(R_7 = H, R_8 = H, R_9 = CH_3)$ | H | H | | C=O | | $OCH_3$ | $OCH_3$ | |
| $Q_{21}(R_7 = H, R_8 = H, R_9 = CH_3)$ | H | H | | C=O | | Cl | $OCH_3$ | |
| $Q_{21}(R_7 = H, R_8 = H, R_9 = CH_3)$ | H | H | OH | | H | $CH_3$ | $CH_3$ | |
| $Q_{21}(R_7 = H, R_8 = H, R_9 = CH_3)$ | H | H | OH | | H | $CH_3$ | $OCH_3$ | |
| $Q_{21}(R_7 = H, R_8 = H, R_9 = CH_3)$ | H | H | OH | | H | $OCH_3$ | $OCH_3$ | |
| $Q_{21}(R_7 = H, R_8 = H, R_9 = CH_3)$ | H | H | OH | | H | Cl | $OCH_3$ | |
| $Q_{22}(R_7 = H)$ | H | H | | C=O | | $CH_3$ | $CH_3$ | |
| $Q_{22}(R_7 = H)$ | H | H | | C=O | | $CH_3$ | $OCH_3$ | |
| $Q_{22}(R_7 = H)$ | H | H | | C=O | | $OCH_3$ | $OCH_3$ | |
| $Q_{22}(R_7 = H)$ | H | H | | C=O | | Cl | $OCH_3$ | |
| $Q_{22}(R_7 = H)$ | H | H | OH | | H | $CH_3$ | $CH_3$ | |
| $Q_{22}(R_7 = H)$ | H | H | OH | | H | $CH_3$ | $OCH_3$ | |
| $Q_{22}(R_7 = H)$ | H | H | OH | | H | $OCH_3$ | $OCH_3$ | |
| $Q_{22}(R_7 = H)$ | H | H | OH | | H | Cl | $OCH_3$ | |
| $Q_{23}(R_7 = H)$ | H | H | | C=O | | $CH_3$ | $CH_3$ | |
| $Q_{23}(R_7 = H)$ | H | H | | C=O | | $CH_3$ | $OCH_3$ | |
| $Q_{23}(R_7 = H)$ | H | H | | C=O | | $OCH_3$ | $OCH_3$ | |
| $Q_{23}(R_7 = H)$ | H | H | | C=O | | Cl | $OCH_3$ | |
| $Q_{23}(R_7 = H)$ | H | H | OH | | H | $CH_3$ | $CH_3$ | |
| $Q_{23}(R_7 = H)$ | H | H | OH | | H | $CH_3$ | $OCH_3$ | |
| $Q_{23}(R_7 = H)$ | H | H | OH | | H | $OCH_3$ | $OCH_3$ | |
| $Q_{23}(R_7 = H)$ | H | H | OH | | H | Cl | $OCH_3$ | |
| $Q_{24}(R_7 = H, R_8 = H)$ | H | H | | C=O | | $CH_3$ | $CH_3$ | |
| $Q_{24}(R_7 = H, R_8 = H)$ | H | H | | C=O | | $CH_3$ | $OCH_3$ | |
| $Q_{24}(R_7 = H, R_8 = H)$ | H | H | | C=O | | $OCH_3$ | $OCH_3$ | |
| $Q_{24}(R_7 = H, R_8 = H)$ | H | H | | C=O | | Cl | $OCH_3$ | |
| $Q_{24}(R_7 = H, R_8 = H)$ | H | H | OH | | H | $CH_3$ | $CH_3$ | |
| $Q_{24}(R_7 = H, R_8 = H)$ | H | H | OH | | H | $CH_3$ | $OCH_3$ | |
| $Q_{24}(R_7 = H, R_8 = H)$ | H | H | OH | | H | $OCH_3$ | $OCH_3$ | |
| $Q_{24}(R_7 = H, R_8 = H)$ | H | H | OH | | H | Cl | $OCH_3$ | |
| $Q_{25}(R_7 = H, R_8 = H)$ | H | H | | C=O | | $CH_3$ | $CH_3$ | |
| $Q_{25}(R_7 = H, R_8 = H)$ | H | H | | C=O | | $CH_3$ | $OCH_3$ | |
| $Q_{25}(R_7 = H, R_8 = H)$ | H | H | | C=O | | $OCH_3$ | $OCH_3$ | |
| $Q_{25}(R_7 = H, R_8 = H)$ | H | H | | C=O | | Cl | $OCH_3$ | |
| $Q_{25}(R_7 = H, R_8 = H)$ | H | H | OH | | H | $CH_3$ | $CH_3$ | |
| $Q_{25}(R_7 = H, R_8 = H)$ | H | H | OH | | H | $CH_3$ | $OCH_3$ | |
| $Q_{25}(R_7 = H, R_8 = H)$ | H | H | OH | | H | $OCH_3$ | $OCH_3$ | |
| $Q_{25}(R_7 = H, R_8 = H)$ | H | H | OH | | H | Cl | $OCH_3$ | |
| $Q_{26}(R_7 = H, R_8 = H)$ | H | H | | C=O | | $CH_3$ | $CH_3$ | |
| $Q_{26}(R_7 = H, R_8 = H)$ | H | H | | C=O | | $CH_3$ | $OCH_3$ | |
| $Q_{26}(R_7 = H, R_8 = H)$ | H | H | | C=O | | $OCH_3$ | $OCH_3$ | |
| $Q_{26}(R_7 = H, R_8 = H)$ | H | H | | C=O | | Cl | $OCH_3$ | |
| $Q_{26}(R_7 = H, R_8 = H)$ | H | H | OH | | H | $CH_3$ | $CH_3$ | |
| $Q_{26}(R_7 = H, R_8 = H)$ | H | H | OH | | H | $CH_3$ | $OCH_3$ | |
| $Q_{26}(R_7 = H, R_8 = H)$ | H | H | OH | | H | $OCH_3$ | $OCH_3$ | |
| $Q_{26}(R_7 = H, R_8 = H)$ | H | H | OH | | H | Cl | $OCH_3$ | |
| $Q_{27}(R_7 = H, R_{11} = H, R_{12} = H)$ | H | H | | C=O | | $CH_3$ | $CH_3$ | |
| $Q_{27}(R_7 = H, R_{11} = H, R_{12} = H)$ | H | H | | C=O | | $CH_3$ | $OCH_3$ | |
| $Q_{27}(R_7 = H, R_{11} = H, R_{12} = H)$ | H | H | | C=O | | $OCH_3$ | $OCH_3$ | |
| $Q_{27}(R_7 = H, R_{11} = H, R_{12} = H)$ | H | H | | C=O | | Cl | $OCH_3$ | |
| $Q_{27}(R_7 = H, R_{11} = H, R_{12} = H)$ | H | H | OH | | H | $CH_3$ | $CH_3$ | |
| $Q_{27}(R_7 = H, R_{11} = H, R_{12} = H)$ | H | H | OH | | H | $CH_3$ | $OCH_3$ | |
| $Q_{27}(R_7 = H, R_{11} = H, R_{12} = H)$ | H | H | OH | | H | $OCH_3$ | $OCH_3$ | |
| $Q_{27}(R_7 = H, R_{11} = H, R_{12} = H)$ | H | H | OH | | H | Cl | $OCH_3$ | |
| $Q_{28}(R_{11} = H, R_{12} = H)$ | H | H | | C=O | | $CH_3$ | $CH_3$ | |
| $Q_{28}(R_{11} = H, R_{12} = H)$ | H | H | | C=O | | $CH_3$ | $OCH_3$ | |
| $Q_{28}(R_{11} = H, R_{12} = H)$ | H | H | | C=O | | $OCH_3$ | $OCH_3$ | |
| $Q_{28}(R_{11} = H, R_{12} = H)$ | H | H | | C=O | | Cl | $OCH_3$ | |

TABLE XVIII-continued

General Formula XVIII

| Q | R | $R_1$ | $R_2$ | $R_3$ | X | Y | m.p.(°C.) |
|---|---|---|---|---|---|---|---|
| $Q_{28}(R_{11} = H, R_{12} = H)$ | H | H | OH | H | $CH_3$ | $CH_3$ | |
| $Q_{28}(R_{11} = H, R_{12} = H)$ | H | H | OH | H | $CH_3$ | $OCH_3$ | |
| $Q_{28}(R_{11} = H, R_{12} = H)$ | H | H | OH | H | $OCH_3$ | $OCH_3$ | |
| $Q_{28}(R_{11} = H, R_{12} = H)$ | H | H | OH | H | Cl | $OCH_3$ | |
| $Q_{29}(R_{11} = H, R_{12} = H)$ | H | H | C=O | | $CH_3$ | $CH_3$ | |
| $Q_{29}(R_{11} = H, R_{12} = H)$ | H | H | C=O | | $CH_3$ | $OCH_3$ | |
| $Q_{29}(R_{11} = H, R_{12} = H)$ | H | H | C=O | | $OCH_3$ | $OCH_3$ | |
| $Q_{29}(R_{11} = H, R_{12} = H)$ | H | H | C=O | | Cl | $OCH_3$ | |
| $Q_{29}(R_{11} = H, R_{12} = H)$ | H | H | OH | H | $CH_3$ | $CH_3$ | |
| $Q_{29}(R_{11} = H, R_{12} = H)$ | H | H | OH | H | $CH_3$ | $OCH_3$ | |
| $Q_{29}(R_{11} = H, R_{12} = H)$ | H | H | OH | H | $OCH_3$ | $OCH_3$ | |
| $Q_{29}(R_{11} = H, R_{12} = H)$ | H | H | OH | H | Cl | $OCH_3$ | |
| $Q_{30}(R_7 = H, R_8 = H)$ | H | H | C=O | | $CH_3$ | $CH_3$ | |
| $Q_{30}(R_7 = H, R_8 = H)$ | H | H | C=O | | $CH_3$ | $OCH_3$ | |
| $Q_{30}(R_7 = H, R_8 = H)$ | H | H | C=O | | $OCH_3$ | $OCH_3$ | |
| $Q_{30}(R_7 = H, R_8 = H)$ | H | H | C=O | | Cl | $OCH_3$ | |
| $Q_{30}(R_7 = H, R_8 = H)$ | H | H | OH | H | $CH_3$ | $CH_3$ | |
| $Q_{30}(R_7 = H, R_8 = H)$ | H | H | OH | H | $CH_3$ | $OCH_3$ | |
| $Q_{30}(R_7 = H, R_8 = H)$ | H | H | OH | H | $OCH_3$ | $OCH_3$ | |
| $Q_{30}(R_7 = H, R_8 = H)$ | H | H | OH | H | Cl | $OCH_3$ | |
| $Q_{31}(R_7 = H, R_8 = H)$ | H | H | C=O | | $CH_3$ | $CH_3$ | |
| $Q_{31}(R_7 = H, R_8 = H)$ | H | H | C=O | | $CH_3$ | $OCH_3$ | |
| $Q_{31}(R_7 = H, R_8 = H)$ | H | H | C=O | | $OCH_3$ | $OCH_3$ | |
| $Q_{31}(R_7 = H, R_8 = H)$ | H | H | C=O | | Cl | $OCH_3$ | |
| $Q_{31}(R_7 = H, R_8 = H)$ | H | H | OH | H | $CH_3$ | $CH_3$ | |
| $Q_{31}(R_7 = H, R_8 = H)$ | H | H | OH | H | $CH_3$ | $OCH_3$ | |
| $Q_{31}(R_7 = H, R_8 = H)$ | H | H | OH | H | $OCH_3$ | $OCH_3$ | |
| $Q_{31}(R_7 = H, R_8 = H)$ | H | H | OH | H | Cl | $OCH_3$ | |
| $Q_{32}(R_{13} = OCH_3, R_{14} = OCH_3)$ | H | H | C=O | | $CH_3$ | $CH_3$ | |
| $Q_{32}(R_{13} = OCH_3, R_{14} = OCH_3)$ | H | H | C=O | | $CH_3$ | $OCH_3$ | |
| $Q_{32}(R_{13} = OCH_3, R_{14} = OCH_3)$ | H | H | C=O | | $OCH_3$ | $OCH_3$ | |
| $Q_{32}(R_{13} = OCH_3, R_{14} = OCH_3)$ | H | H | C=O | | Cl | $OCH_3$ | |
| $Q_{32}(R_{13} = OCH_3, R_{14} = OCH_3)$ | H | H | OH | H | $CH_3$ | $CH_3$ | |
| $Q_{32}(R_{13} = OCH_3, R_{14} = OCH_3)$ | H | H | OH | H | $CH_3$ | $OCH_3$ | |
| $Q_{32}(R_{13} = OCH_3, R_{14} = OCH_3)$ | H | H | OH | H | $OCH_3$ | $OCH_3$ | |
| $Q_{32}(R_{13} = OCH_3, R_{14} = OCH_3)$ | H | H | OH | H | Cl | $OCH_3$ | |
| $Q_{33}(R_7 = H)$ | H | H | C=O | | $CH_3$ | $CH_3$ | |
| $Q_{33}(R_7 = H)$ | H | H | C=O | | $CH_3$ | $OCH_3$ | |
| $Q_{33}(R_7 = H)$ | H | H | C=O | | $OCH_3$ | $OCH_3$ | |
| $Q_{33}(R_7 = H)$ | H | H | C=O | | Cl | $OCH_3$ | |
| $Q_{33}(R_7 = H)$ | H | H | OH | H | $CH_3$ | $CH_3$ | |
| $Q_{33}(R_7 = H)$ | H | H | OH | H | $CH_3$ | $OCH_3$ | |
| $Q_{33}(R_7 = H)$ | H | H | OH | H | $OCH_3$ | $OCH_3$ | |
| $Q_{33}(R_7 = H)$ | H | H | OH | H | Cl | $OCH_3$ | |

TABLE XIX

General Formula XIX

| Q | $R_1$ | $R_2$ | $R_3$ | $X_1$ | $Y_1$ | m.p.(°C.) |
|---|---|---|---|---|---|---|
| $Q_1(R_7 = H, R_8 = H, R_9 = H)$ | H | C=O | | $CH_3$ | O | |
| $Q_1(R_7 = H, R_8 = H, R_9 = H)$ | H | C=O | | $CH_3$ | $CH_2$ | |
| $Q_1(R_7 = H, R_8 = H, R_9 = H)$ | H | C=O | | $OCH_3$ | O | |
| $Q_1(R_7 = H, R_8 = H, R_9 = H)$ | H | C=O | | $OCH_3$ | $CH_2$ | |
| $Q_1(R_7 = H, R_8 = H, R_9 = H)$ | H | C=O | | $OCH_2CH_3$ | O | |
| $Q_1(R_7 = H, R_8 = H, R_9 = H)$ | H | C=O | | $OCF_2H$ | $CH_2$ | |
| $Q_1(R_7 = H, R_8 = H, R_9 = H)$ | H | C=O | | $OCF_2H$ | O | |
| $Q_1(R_7 = H, R_8 = H, R_9 = H)$ | H | C=O | | $OCF_2H$ | $CH_2$ | |

TABLE XX

General Formula XX

| Q | $R_1$ | $R_2$ | $R_3$ | $X_1$ | m.p.(°C.) |
|---|---|---|---|---|---|
| $Q_1(R_7 = H, R_8 = H, R_9 = H)$ | H | C=O | | $CH_3$ | |
| $Q_1(R_7 = H, R_8 = H, R_9 = H)$ | H | C=O | | $OCH_3$ | |
| $Q_1(R_7 = H, R_8 = H, R_9 = H)$ | H | C=O | | $OCH_2CH_3$ | |
| $Q_1(R_7 = H, R_8 = H, R_9 = H)$ | H | C=O | | $OCF_2H$ | |
| $Q_1(R_7 = H, R_8 = H, R_9 = H)$ | H | OH | H | $OCH_3$ | |
| $Q_1(R_7 = H, R_8 = H, R_9 = H)$ | H | $OCH_3$ | H | $OCH_3$ | |

TABLE XXI

General Formula XXI

| Q | $R_1$ | $R_2$ | $R_3$ | $X_1$ | $Y_2$ | m.p.(°C.) |
|---|---|---|---|---|---|---|
| $Q_1(R_7 = H, R_8 = H, R_9 = H)$ | H | C=O | | $CH_3$ | H | |

TABLE XXI-continued

General Formula XXI

| Q | $R_1$ | $R_2$ | $R_3$ | $X_1$ | $Y_2$ | m.p.(°C.) |
|---|---|---|---|---|---|---|
| $Q_1(R_7 = H, R_8 = H, R_9 = H)$ | H | C=O | | $CH_3$ | $CH_3$ | |
| $Q_1(R_7 = H, R_8 = H, R_9 = H)$ | H | C=O | | $OCH_3$ | H | |
| $Q_1(R_7 = H, R_8 = H, R_9 = H)$ | H | C=O | | $OCH_3$ | H | |
| $Q_1(R_7 = H, R_8 = H, R_9 = H)$ | H | C=O | | $OCH_3$ | $CH_3$ | |
| $Q_1(R_7 = H, R_8 = H, R_9 = H)$ | H | C=O | | $OCH_2CH_3$ | H | |
| $Q_1(R_7 = H, R_8 = H, R_9 = H)$ | H | C=O | | $OCH_2CH_3$ | $CH_3$ | |
| $Q_1(R_7 = H, R_8 = H, R_9 = H)$ | H | C=O | | $OCF_2H$ | H | |
| $Q_1(R_7 = H, R_8 = H, R_9 = H)$ | H | C=O | | $OCF_2H$ | $CH_3$ | |
| $Q_1(R_7 = H, R_8 = H, R_9 = H)$ | H | OH | H | $OCH_3$ | $CH_3$ | |
| $Q_1(R_7 = H, R_8 = H, R_9 = H)$ | H | $OCH_3$ | H | $OCH_3$ | $CH_3$ | |

TABLE XXII

General Formula XXII

| Q | $R_1$ | $R_2$ | $R_3$ | $X_2$ | $Y_3$ | m.p.(°C.) |
|---|---|---|---|---|---|---|
| $Q_1(R_7 = H, R_8 = H, R_9 = H)$ | H | C=O | | $CH_3$ | $CH_3$ | |
| $Q_1(R_7 = H, R_8 = H, R_9 = H)$ | H | C=O | | $CH_3$ | $CH_2CH_3$ | |
| $Q_1(R_7 = H, R_8 = H, R_9 = H)$ | H | C=O | | $CH_3$ | $CH_2CF_3$ | |
| $Q_1(R_7 = H, R_8 = H, R_9 = H)$ | H | C=O | | $OCH_3$ | $OCH_3$ | |
| $Q_1(R_7 = H, R_8 = H, R_9 = H)$ | H | C=O | | $OCH_3$ | $CH_3$ | |
| $Q_1(R_7 = H, R_8 = H, R_9 = H)$ | Cl | C=O | | $OCH_3$ | $CH_3$ | |
| $Q_1(R_7 = H, R_8 = H, R_9 = H)$ | $OCH_3$ | C=O | | $CH_3$ | $CH_3$ | |

TABLE XXIII

General Formula XXIII

| Q | $R_1$ | $R_2$ | $R_3$ | $X_3$ | m.p.(°C.) |
|---|---|---|---|---|---|
| $Q_1(R_7 = H, R_8 = H, R_9 = H)$ | H | C=O | | $CH_3$ | |
| $Q_1(R_7 = H, R_8 = H, R_9 = H)$ | H | C=O | | $OCH_3$ | |
| $Q_1(R_7 = H, R_8 = H, R_9 = H)$ | H | OH | H | $OCH_3$ | |
| $Q_1(R_7 = H, R_8 = H, R_9 = H)$ | H | OH | H | $CH_3$ | |
| $Q_1(R_7 = H, R_8 = H, R_9 = H)$ | H | $OCH_3$ | H | $OCH_3$ | |
| $Q_1(R_7 = H, R_8 = H, R_9 = H)$ | H | $OCH_3$ | H | $CH_3$ | |

TABLE XXIV

General Formula XXIV

| Q | $R_1$ | $n_1$ | $n_2$ | X | Y | m.p.(°C.) |
|---|---|---|---|---|---|---|
| $Q_1(R_7 = R_8 = R_9 = H)$ | H | 1 | 0 | $OCH_3$ | $OCH_3$ | |
| $Q_1(R_7 = R_8 = R_9 = H)$ | H | 0 | 1 | $OCH_3$ | $OCH_3$ | |
| $Q_2(R_7 = R_8 = R_9 = H)$ | H | 0 | 1 | $OCH_3$ | $OCH_3$ | |
| $Q_3(R_7 = R_8 = R_9 = H)$ | H | 1 | 0 | $OCH_3$ | $OCH_3$ | |
| $Q_3(R_7 = R_8 = R_9 = H)$ | H | 0 | 1 | $OCH_3$ | $OCH_3$ | |
| $Q_4(R_7 = R_8 = R_9 = H)$ | H | 0 | 1 | $OCH_3$ | $OCH_3$ | |
| $Q_7(R_7 = R_8 = H)$ | H | 0 | 2 | $OCH_3$ | $OCH_3$ | |
| $Q_7(R_7 = R_8 = H)$ | H | 1 | 1 | $OCH_3$ | $OCH_3$ | |
| $Q_8(R_7 = R_8 = H)$ | H | 0 | 1 | $CH_3$ | $OCH_3$ | |
| $Q_9(R_7 = R_8 = H)$ | H | 0 | 1 | $CH_3$ | $OCH_3$ | |
| $Q_{10}(R_7 = R_8 = H)$ | H | 0 | 1 | $OCH_3$ | $OCH_3$ | |
| $Q_{10}(R_7 = R_8 = H)$ | H | 0 | 1 | $CH_3$ | $OCH_3$ | |
| $Q_{11}(R_7 = R_8 = H)$ | H | 0 | 1 | $OCH_3$ | $OCH_3$ | |
| $Q_{12}(R_7 = R_8 = H)$ | H | 0 | 1 | $OCH_3$ | $OCH_3$ | |
| $Q_{14}(R_7 = H)$ | H | 0 | 1 | $OCH_3$ | $OCH_3$ | |
| $Q_{14}(R_7 = H)$ | H | 1 | 0 | $OCH_3$ | $OCH_3$ | |
| $Q_{15}(R_7 = H)$ | H | 0 | 1 | $CH_3$ | $OCH_3$ | |
| $Q_{16}(R_7 = H)$ | H | 0 | 1 | $CH_3$ | $OCH_3$ | |
| $Q_{17}(R_7 = H)$ | H | 0 | 1 | $OCH_3$ | $OCH_3$ | |
| $Q_{18}(R_7 = H)$ | H | 0 | 1 | $OCH_3$ | $OCH_3$ | |
| $Q_{19}(R_7 = R_8 = H)$ | H | 0 | 1 | $OCH_3$ | $OCH_3$ | |
| $Q_{20}(R_7 = R_8 = H)$ | H | 0 | 1 | $OCH_3$ | $OCH_3$ | |
| $Q_{24}(R_7 = R_8 = H)$ | H | 0 | 1 | $OCH_3$ | $OCH_3$ | |
| $Q_{24}(R_7 = R_8 = H)$ | H | 0 | 1 | $CH_3$ | $OCH_3$ | |
| $Q_{26}(R_7 = R_8 = H)$ | H | 0 | 1 | $OCH_3$ | $OCH_3$ | |
| $Q_{27}(R_{11} = R_7 = R_{12} = H)$ | H | 0 | 1 | $OCH_3$ | $OCH_3$ | |
| $Q_{30}(R_7 = R_8 = H)$ | H | 0 | 1 | $OCH_3$ | $OCH_3$ | |
| $Q_{31}(R_7 = R_8 = H)$ | H | 0 | 1 | $OCH_3$ | $OCH_3$ | |
| $Q_{32}(R_{13} = R_{14} = H)$ | H | 0 | 1 | $OCH_3$ | $OCH_3$ | |
| $Q_{33}(R_7 = H)$ | H | 0 | 1 | $OCH_3$ | $OCH_3$ | |
| $Q_{34}$ | H | 0 | 1 | $OCH_3$ | $OCH_3$ | |
| $Q_{34}$ | H | 1 | 0 | $OCH_3$ | $OCH_3$ | |
| $Q_{34}$ | H | 0 | 1 | $CH_3$ | $OCH_3$ | |
| $Q_{35}$ | H | 0 | 1 | $OCH_3$ | $OCH_3$ | |

TABLE XXIV-continued

General Formula XXIV

| Q | $R_1$ | $n_1$ | $n_2$ | X | Y | m.p.(°C.) |
|---|---|---|---|---|---|---|
| $Q_{36}(R_7 = R_8 = H, R_{10} = R_{15} = H)$ | H | 0 | 1 | $OCH_3$ | $OCH_3$ | |
| $Q_{37}(R_{16} = R_{15} = R_{16} = H)$ | H | 0 | 1 | $OCH_3$ | $OCH_3$ | |
| $Q_{38}(R_7 = R_8 = H, R_{10}\ R_{15} = H)$ | H | 0 | 1 | $OCH_3$ | $OCH_3$ | |

TABLE XXV

General Formula XXV

| Q | $R_1$ | $n_1$ | $n_2$ | X | Y | m.p.(°C.) |
|---|---|---|---|---|---|---|
| $Q_1(R_7 = R_8 = R_9 = H)$ | H | 1 | 0 | $OCH_3$ | $OCH_3$ | |
| $Q_1(R_7 = R_8 = R_9 = H)$ | H | 0 | 1 | $OCH_3$ | $OCH_3$ | |
| $Q_2(R_7 = R_8 = R_9 = H)$ | H | 0 | 1 | $OCH_3$ | $OCH_3$ | |
| $Q_3(R_7 = R_8 = R_9 = H)$ | H | 1 | 0 | $OCH_3$ | $OCH_3$ | |
| $Q_3(R_7 = R_8 = R_9 = H)$ | H | 0 | 1 | $OCH_3$ | $OCH_3$ | |
| $Q_4(R_7 = R_8 = R_9 = H)$ | H | 0 | 1 | $OCH_3$ | $OCH_3$ | |
| $Q_7(R_7 = R_8 = H)$ | H | 0 | 2 | $OCH_3$ | $OCH_3$ | |
| $Q_7(R_7 = R_8 = H)$ | H | 1 | 1 | $OCH_3$ | $OCH_3$ | |
| $Q_8(R_7 = R_8 = H)$ | H | 0 | 1 | $CH_3$ | $OCH_3$ | |
| $Q_9(R_7 = R_8 = H)$ | H | 0 | 1 | $CH_3$ | $OCH_3$ | |
| $Q_{10}(R_7 = R_8 = H)$ | H | 0 | 1 | $OCH_3$ | $OCH_3$ | |
| $Q_{10}(R_7 = R_8 = H)$ | H | 0 | 1 | $CH_3$ | $OCH_3$ | |
| $Q_{11}(R_7 = R_8 = H)$ | H | 0 | 1 | $OCH_3$ | $OCH_3$ | |
| $Q_{12}(R_7 = R_8 = H)$ | H | 0 | 1 | $OCH_3$ | $OCH_3$ | |
| $Q_{14}(R_7 = H)$ | H | 0 | 1 | $OCH_3$ | $OCH_3$ | |
| $Q_{14}(R_7 = H)$ | H | 1 | 0 | $OCH_3$ | $OCH_3$ | |
| $Q_{15}(R_7 = H)$ | H | 0 | 1 | $CH_3$ | $OCH_3$ | |
| $Q_{16}(R_7 = H)$ | H | 0 | 1 | $CH_3$ | $OCH_3$ | |
| $Q_{17}(R_7 = H)$ | H | 0 | 1 | $CH_3$ | $OCH_3$ | |
| $Q_{18}(R_7 = H)$ | H | 0 | 1 | $OCH_3$ | $OCH_3$ | |
| $Q_{19}(R_7 = R_8 = H)$ | H | 0 | 1 | $OCH_3$ | $OCH_3$ | |
| $Q_{20}(R_7 = R_8 = H)$ | H | 0 | 1 | $OCH_3$ | $OCH_3$ | |
| $Q_{24}(R_7 = R_8 = H)$ | H | 0 | 1 | $OCH_3$ | $OCH_3$ | |
| $Q_{24}(R_7 = R_8 = H)$ | H | 0 | 1 | $CH_3$ | $OCH_3$ | |
| $Q_{26}(R = R = H)$ | H | 0 | 1 | $OCH_3$ | $OCH_3$ | |
| $Q_{27}(R_{11}R_7 = R_{12} = H)$ | H | 0 | 1 | $OCH_3$ | $OCH_3$ | |
| $Q_{30}(R_7 = R_8 = H)$ | H | 0 | 1 | $OCH_3$ | $OCH_3$ | |
| $Q_{31}(R_7 = R_8 = H)$ | H | 0 | 1 | $OCH_3$ | $OCH_3$ | |
| $Q_{32}(R_{13} = R_{14} = H)$ | H | 0 | 1 | $OCH_3$ | $OCH_3$ | |
| $Q_{33}(R = H)$ | H | 0 | 1 | $OCH_3$ | $OCH_3$ | |
| $Q_{34}$ | H | 0 | 1 | $OCH_3$ | $OCH_3$ | |
| $Q_{34}$ | H | 1 | 0 | $OCH_3$ | $OCH_3$ | |
| $Q_{34}$ | H | 0 | 1 | $CH_3$ | $OCH_3$ | |
| $Q_{35}$ | H | 0 | 1 | $OCH_3$ | $OCH_3$ | |
| $Q_{35}$ | H | 0 | 1 | $CH_3$ | $OCH_3$ | |

TABLE XXV-continued
General Formula XXV

| Q | $R_1$ | $n_1$ | $n_2$ | X | Y | m.p. (°C.) |
|---|---|---|---|---|---|---|
| $Q_{36}(R_7 = R_8 = H, R_{10} = R_{15} = H)$ | H | 0 | 1 | $OCH_3$ | $OCH_3$ | |
| $Q_{37}(R_{10} = R_{15} = R_{16} = H)$ | H | 0 | 1 | $OCH_3$ | $OCH_3$ | |
| $Q_{38}(R_7 = R_8 = H, R_{10} = R_{15} = H)$ | H | 0 | 1 | $OCH_3$ | $OCH_3$ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Weight Percent | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 5-50 | 40-95 | 0-15 |
| Aqueous Suspension | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

J. B. Buchanan, U.S. Pat. No. 3,576,834, Apr. 27, 1971, Col. 5 Line 36 through Col. 7 Line 70 and Ex. 1-4, 17, 106, 123-140.

R. R. Shaffer, U.S. Pat. No. 3,560,616, Feb. 2, 1971, Col. 3 Line 48 through Col. 7 Line 26 and Examples 3-9, 11-18.

E. Somers, "Formulation", Chapter 6 in Torgeson, "Fungicides", Vol. I, Academic Press, New York, 1967.

In the following examples, all parts are by weight unless otherwise indicated.

EXAMPLE 13

| Wettable Powder | |
|---|---|
| N—[(4,6-dimethoxypyrimidin-2-yl)aminocarbonyl]-2-(2-thienylcarbonyl)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended and hammer-milled

EXAMPLE 14

| High Strength Concentrate | |
|---|---|
| N—[(4-methoxy-6-methyl-1,3,5-triazin-2-yl)aminocarbonyl]-2-(2-thienylcarbonyl)benzenesulfonamide | 98.5% |
| silica aerogel | 0.5% |
| synthetic amorphous silica | 1.0% |

The ingredients are blended and ground in a hammer-mill to produce a material essentially all passing a U.S.S. No. 50 screen (0.3 mm opening). The concentrate may then be formulated in a variety of ways.

EXAMPLE 15

| Dust | |
|---|---|
| wettable powder of Example 13 | 10% |

-continued

| Dust | |
|---|---|
| pyrophyllite (powder) | 90% |

The wettable powder and the pyrophyllite diluent are thoroughly blended and then packaged. The product is suitable for use as a dust.

EXAMPLE 16

| Aqueous Suspension | |
|---|---|
| N—[(4,6-dimethoxypyrimidin-2-yl)aminocarbonyl]-2-hydroxy(2-thienyl)methyl]benzenesulfonamide | 50.1% |
| dodecylphenol polyethylene glycol ether | 0.5% |
| crude calcium ligninsulfonate | 5.0% |
| xanthen gum thickener | 0.2% |
| paraformaldehyde | 0.2% |
| water | 44.0% |

The ingredients are ground together in a sand ball or roller mill to product particles essentially all under five microns in size.

EXAMPLE 17

| Granule | |
|---|---|
| wettable powder of Example 13 | 15% |
| gypsum | 69% |
| sugar | 16% |

The ingredients are blended in a rotating or fluid bed mixer and water sprayed on to accomplish granulation. When most of the material has reached the desired range or 1.0 to 0.42 mm (U.S.S. #18 to 40 sieves), the granules are removed, dried, and screened. Oversize material is crushed to produce additional material in the desired range. These granules contain 12% active ingredient.

EXAMPLE 18

| Solution | |
|---|---|
| N—[(4,6-dimethoxypyrimidin-2-yl)aminocarbonyl]-2-(2-thienylcarbonyl)benzenesulfonamide | 30% |
| dimethylformamide | 70% |

The ingredients are comined and stirred to produce a solution, which can be used for low volume applications.

EXAMPLE 19

| Emulsifiable Concentrate | |
|---|---|
| N—[(4-methoxy-6-methyl-1,3,5-triazin-2-yl)aminocarbonyl]-2-(2-thienylcarbonyl)benzenesulfonamide | 10% |
| blend of oil soluble sulfonates and polyoxyethylene ethers | 4% |
| xylene | 86% |

The ingredients are combined and stirred until the active is dissolved. A fine screen filter is included in packaging operation to insure the absence of any extraneous material in the product.

UTILITY

Test results indicate that the compounds of the present invention are highly active preemergent or postemergent herbicides or plant growth regulants. Many of them have utility for broad-spectrum pre- and or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice, wheat, barley and corn. Alternatively, the subject compounds are useful to modify plant growth.

The rates of application for the compounds of the invention are determined by a number of factors, including their use as plant growth modifiers or herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

the herbicidal properties of the subject compounds were discovered in a number of greenhouse tests. The test procedures and results follow.

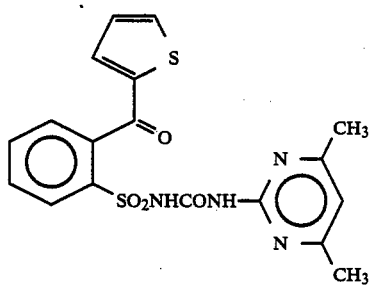

Compound 1

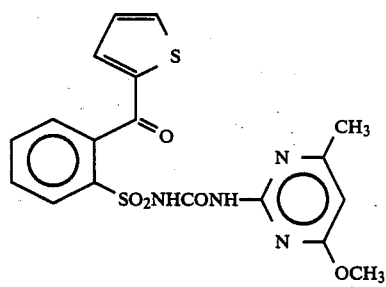

Compound 2

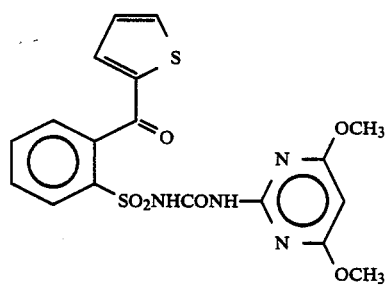

Compound 3

-continued
Compound 4
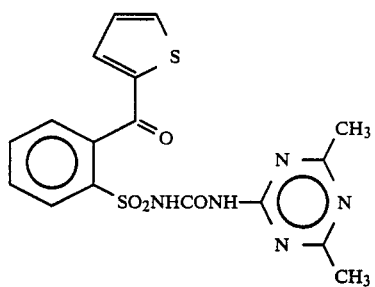
Compound 5
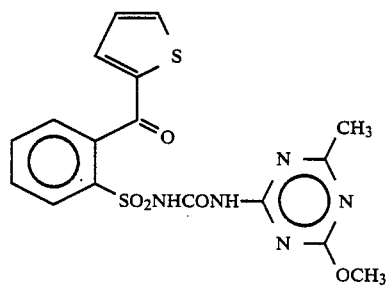
Compound 6
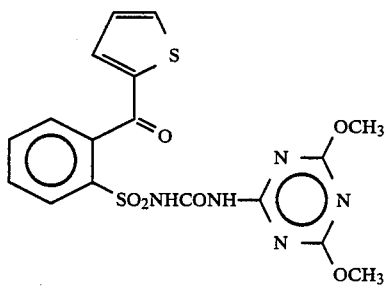
Compound 7
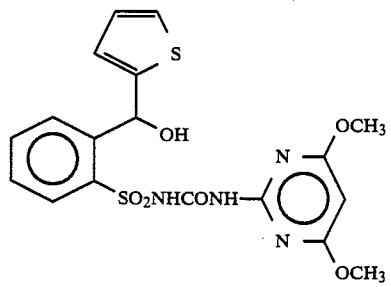
Compound 8
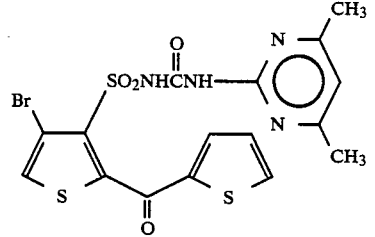
Compound 9
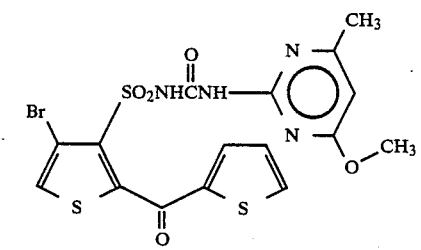
-continued
Compound 10
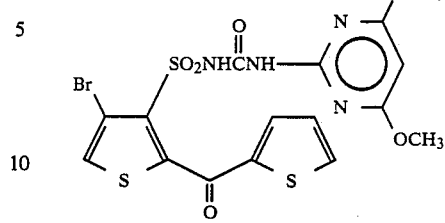
Compound 11
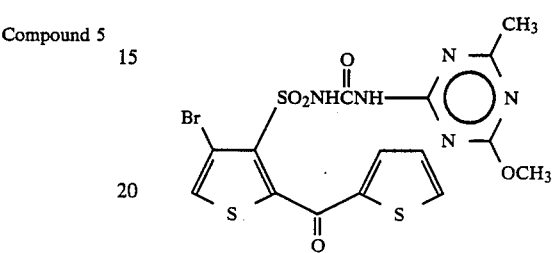
Compound 12
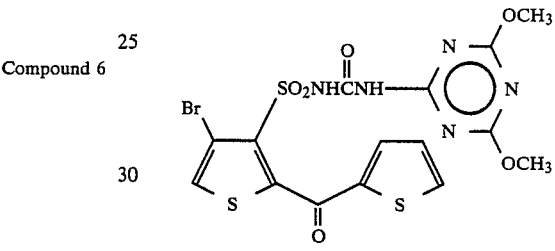
Compound 13
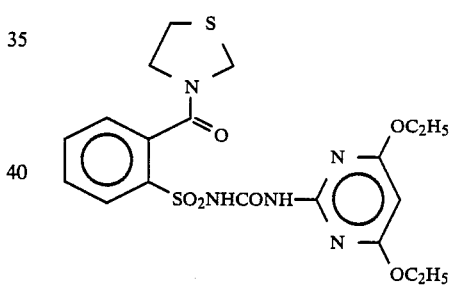
Compound 14
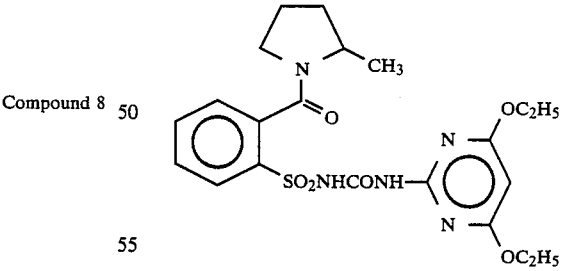
Compound 15
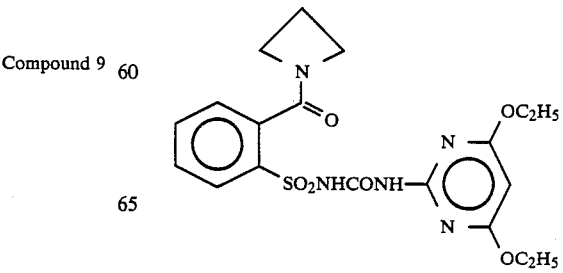

-continued
Compound 16
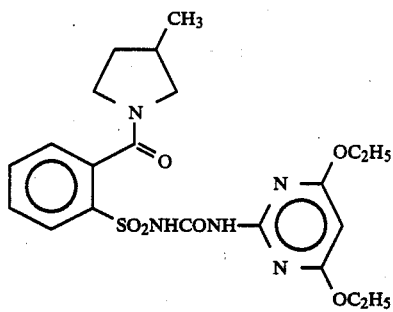
Compound 17
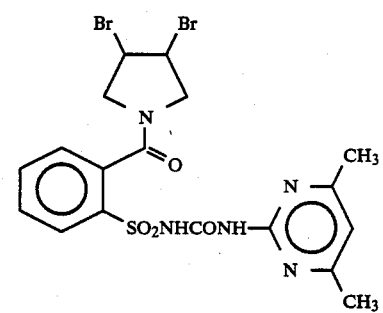
Compound 18
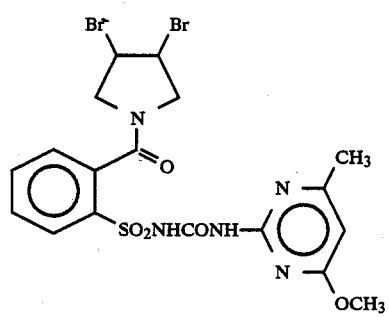
Compound 19
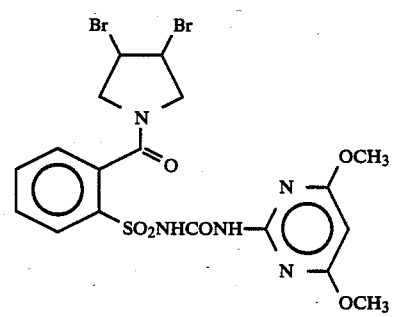
Compound 20
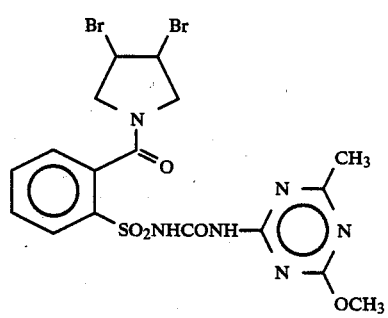
-continued
Compound 21
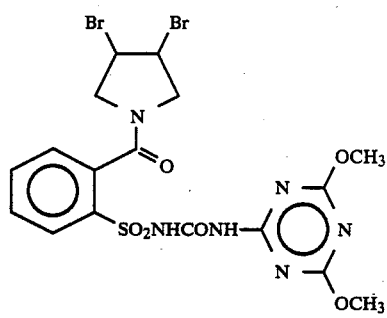
Compound 22
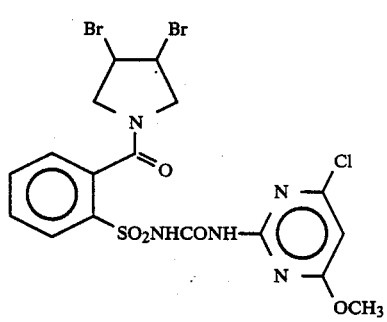
Compound 23
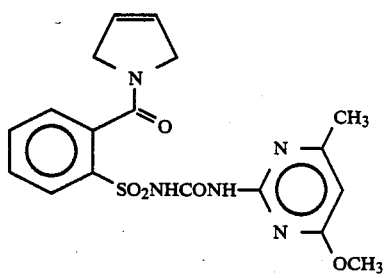
Compound 24
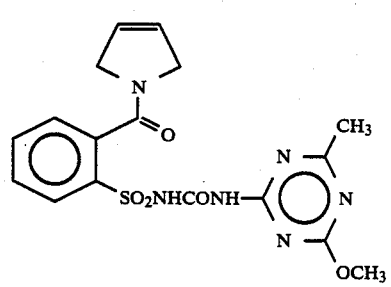
Compound 25
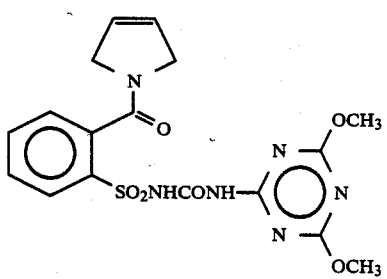

Compound 26

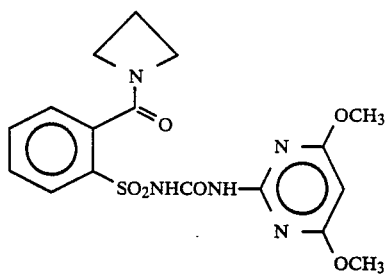

Compound 27

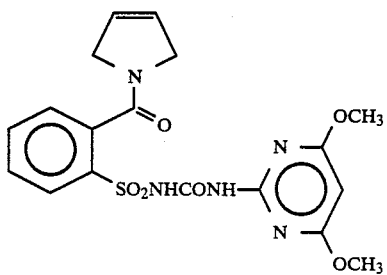

Compound 28

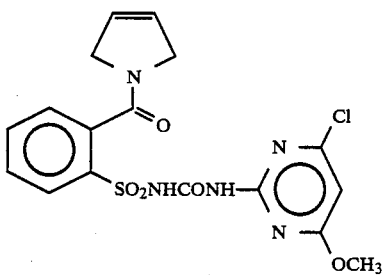

TEST A

Seeds of crabgrass (Digitaria spp.), barnyardgrass (*Echinochloa crusgalli*), wild oats (*Avena fatua*), cheatgrass (*Bromus secalimus*), velvetleaf (*Abutilon theophrasti*), moringglory (Ipomoea spp), cocklebur (*Xanthium pennsylvanicum*), sorghum, corn, soybean, sugarbeet, cotton, rice, wheat, and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis
B=burn
D=defoliation
E=emergence inhibition
G=greowth retardation
H=formative effect
U=unusual pigmentation
X=axillary stimulation
S=albinism
6Y=abscised buds or flowers.

TABLE A

| Rate (kg/ha) | Compound 1 (0.05) | Compound 2 (0.05) |
|---|---|---|
| POSTEMERGENCE | | |
| Morningglory | 4C,8H | 6C,9H |
| Cocklebur | 4C,9G | 6C,9H |
| Velvetleaf | 4C,8H | 9C |
| Nutsedge | 0 | 2C,8G |
| Crabgrass | 0 | 0 |
| Barnyardgrass | 0 | 3C,8H |
| Wild Oats | 0 | 2C,4H |
| Wheat | 0 | 3G |
| Corn | 2G | 3C,8H |
| Soybean | 2C,9G | 5C,9H |
| Rice | 6G | 5C,9G |
| Sorghum | 2C,2H | 5C,9H |
| Cheatgrass | 5G | 6G |
| Sugar Beets | 3C,8H | 4C,8H |
| Cotton | 3C,9H | 5C,9G |
| PREEMERGENCE | | |
| Morningglory | 4C,5H | 9G |
| Cocklebur | 2C,2H | 4C,8H |
| Velvetleaf | 3C,7G | 5C,9G |
| Nutsedge | 0 | 9G |
| Crabgrass | 0 | 2G |
| Barnyardgrass | 2C,3H | 4C,9H |
| Wild Oats | 0 | 3C,8G |
| Wheat | 0 | 3C,8H |
| Corn | 2C,4G | 3C,9H |
| Soybean | 2C,2H | 4C,8H |
| Rice | 2C | 5C,8H |
| Sorghum | 2C,5H | 2C,8G |
| Cheatgrass | 2C,7G | 9C |
| Sugar Beets | 6H | 9C |
| Cotton | 3G | 8H |

| Rate (kg/ha) | Compound 3 (0.05) | Compound 4 (0.05) |
|---|---|---|
| POSTEMERGENCE | | |
| Morningglory | 5C,9G | 2C,3H |
| Cocklebur | 5C,9H | 2H |
| Velvetleaf | 6C,9G | 2C,2G |
| Nutsedge | 2C,6G | 0 |
| Crabgrass | 0 | 0 |
| Barnyardgrass | 0 | 0 |
| Wild Oats | 0 | 0 |
| Wheat | 3G | 0 |
| Corn | 3C,8H | 0 |
| Soybean | 3C,9G | 3C,6H |
| Rice | 3C,9G | 0 |
| Sorghum | 3C,8H | 0 |
| Cheatgrass | 5C,8G | 0 |
| Sugar Beets | 9C | 3C,7H |
| Cotton | 9C | 1C |
| PREEMERGENCE | | |
| Morningglory | 8G | 2C |
| Cocklebur | 3C,9H | 0 |
| Velvetleaf | 4C,9G | 0 |
| Nutsedge | 10E | 0 |
| Crabgrass | 2G | 0 |
| Barnyardgrass | 3C,5G | 0 |
| Wild Oats | 2C,6G | 0 |
| Wheat | 6G | 0 |
| Corn | 8G | 0 |
| Soybean | 2C,7H | 2C |
| Rice | 9H | 0 |
| Sorghum | 3C,9H | 0 |
| Cheatgrass | 10E | 0 |
| Sugar Beets | 9G | 5H |
| Cotton | 8G | 0 |

| Rate (kg/ha) | Compound 5 (0.05) | Compound 6 (0.05) |
|---|---|---|
| POSTEMERGENCE | | |
| Morningglory | 10C | 9C |
| Cocklebur | 10C | 10C |
| Velvetleaf | 9C | 9C |
| Nutsedge | 3G | 2C,5G |
| Crabgrass | 3G | 0 |
| Barnyardgrass | 0 | 0 |
| Wild Oats | 0 | 0 |

TABLE A-continued

| | | |
|---|---|---|
| Wheat | 0 | 0 |
| Corn | 2C,6H | 2C,3H |
| Soybean | 4C,9G | 4C,9G |
| Rice | 1C,4G | 1C |
| Sorghum | 2C,6G | 2C,4G |
| Cheatgrass | 4G | 2G |
| Sugar Beets | 10C | 9C |
| Cotton | 5C,9G | 9C |
| PREEMERGENCE | | |
| Morningglory | 9G | 5C,9G |
| Cocklebur | 9H | 9H |
| Velvetleaf | 5C,9G | 4C,8H |
| Nutsedge | 0 | 5G |
| Crabgrass | 0 | 0 |
| Barnyardgrass | 2G | 1C |
| Wild Oats | 0 | 0 |
| Wheat | 0 | 0 |
| Corn | 2C,7G | 3C,7G |
| Soybean | 3C,7H | 4C,8H |
| Rice | 7G | 6G |
| Sorghum | 4G | 3G |
| Cheatgrass | 3C,8G | 5G |
| Sugar Beets | 5C,9G | 9C |
| Cotton | 8G | 3C,8G |

| | Compound 7 | Compound 8 |
|---|---|---|
| Rate (kg/ha) | (0.05) | (0.05) |
| POSTEMERGENCE | | |
| Morningglory | 5C,9G | 3C,5G |
| Cocklebur | 4C,9H | 9C |
| Velvetleaf | 4C,9H | 9C |
| Nutsedge | 3C,9G | 2C,5G |
| Crabgrass | 2H | 0 |
| Barnyardgrass | 3C,7H | 1C,3H |
| Cheatgrass | 7G | 0 |
| Wild Oats | 0 | 0 |
| Wheat | 0 | 0 |
| Corn | 3C,8H | 2C,5H |
| Soybean | 4C,9G | 3C,6G |
| Rice | 8G | 5G |
| Sorghum | 3C,HG | 6G |
| Sugar Beets | 2C,6G | 5H |
| Cotton | 5C,9G | 4G |
| PREEMERGENCE | | |
| Morningglory | 9C | 9G |
| Cocklebur | 3C,8H | 3C,8H |
| Velvetleaf | 9G | 5C,9G |
| Nutsedge | 3G | 0 |
| Crabgrass | 0 | 0 |
| Barnyardgrass | 1C | 0 |
| Cheatgrass | 2G | 5G |
| Wild Oats | 0 | 0 |
| Wheat | 0 | 0 |
| Corn | 2C,7G | 2C,7G |
| Soybean | 3C,7H | 3C,6G |
| Rice | 2C,6G | 4G |
| Sorghum | 3C,8H | 2C,7H |
| Sugar Beets | 9G | 9G |
| Cotton | 9G | 8G |

| | Compound 9 | Compound 10 |
|---|---|---|
| Rate (kg/ha) | (0.05) | (0.05) |
| POSTEMERGENCE | | |
| Morningglory | 2C,7G | 9C |
| Cocklebur | 9C | 5C,9G |
| Velvetleaf | 5C,9G | 4C,9G |
| Nutsedge | 4C,9G | 10C |
| Crabgrass | 0 | 0 |
| Barnyardgrass | 3H | 3C,7H |
| Cheatgrass | 0 | 0 |
| Wild Oats | 0 | 0 |
| Wheat | 2G | 0 |
| Corn | 2C,5H | 3C,7H |
| Soybean | 3C,8H | 5C,9G |
| Rice | 3G | 6G |
| Sorghum | 2C,8H | 3H |
| Sugar Beets | 3C,7G | 9C |
| Cotton | 5C,9G | 9C |
| PREEMERGENCE | | |
| Morningglory | 9G | 9G |
| Cocklebur | 10C | 9H |
| Velvetleaf | 4C,9G | 9G |
| Nutsedge | 6G | 5G |
| Crabgrass | 0 | 0 |
| Barnyardgrass | 3C,6H | 3G |
| Cheatgrass | 3C,8G | 0 |
| Wild Oats | 0 | 0 |
| Wheat | 4G | 0 |
| Corn | 2C,8G | 3C,7G |
| Soybean | 3C,8H | 2C,6G |
| Rice | 8G | 6G |
| Sorghum | 3C,7H | 3G |
| Sugar Beets | 10E | 10C |
| Cotton | 10C | 9C |

| | Compound 11 | Compound 12 |
|---|---|---|
| Rate (kg/ha) | (0.05) | (0.05) |
| POSTEMERGENCE | | |
| Morningglory | 5C,9G | 5C,9G |
| Cocklebur | 5C,8G | 9C |
| Velvetleaf | 5C,9G | 2C,5G |
| Nutsedge | 0 | 2C |
| Crabgrass | 0 | 0 |
| Barnyardgrass | 2C,4H | 2H |
| Cheatgrass | 3C,6G | 0 |
| Wild Oats | 0 | 0 |
| Wheat | 0 | 0 |
| Corn | 3C,9H | 1C,4G |
| Soybean | 4C,9G | 4C,9G |
| Rice | 4G | 0 |
| Sorghum | 5C,9G | 2C,4H |
| Sugar Beets | 5C,9G | 7G |
| Cotton | 2C,6G | 3C,8G |
| PREEMERGENCE | | |
| Morningglory | 9G | 9H |
| Cocklebur | 8H | 9H |
| Velvetleaf | 5C,9G | 5C,9G |
| Nutsedge | 0 | 0 |
| Crabgrass | 2C | 0 |
| Barnyardgrass | 3C,7H | 1C |
| Cheatgrass | 3C,8G | 3G |
| Wild Oats | 2C,3G | 0 |
| Wheat | 3G | 0 |
| Corn | 5C,9H | 2C,8H |
| Soybean | 4C,9G | 3C,8H |
| Rice | 5C,9H | 3C,7G |
| Sorghum | 5C,9H | 3C,9H |
| Sugar Beets | 6C,9G | 5C,9G |
| Cotton | 8G | 8G |

| | Cmpd. 13 | Cmpd. 14 | Compound 15 | |
|---|---|---|---|---|
| Rate kg/ha | 0.4 | 0.4 | 0.4 | 0.05 |
| POSTEMERGENCE | | | | |
| Morningglory | 3G | 1C | 2C,3G | 1C,5G |
| Cocklebur | 0 | 0 | 0 | 2G |
| Velvetleaf | 8G | 9G | 9C | 2C,8G |
| Nutsedge | 4G | 8G | 2C,9G | 5G |
| Crabgrass | 0 | 0 | 3C,9G | 4G |
| Barnyardgrass | 0 | 0 | 3C,9H | 3C,7H |
| Cheatgrass | 3G | 4G | 7G | 2C |
| Wild Oats | 0 | 0 | 8G | 2C,4G |
| Wheat | 0 | 2G | 9G | 2C,8G |
| Corn | 1C,1H | 0 | 3C,7H | 0 |
| Soybean | 3H | 4H | 2C,1H | 2C,5G |
| Rice | 8H | 7G | 9G | 4C,9G |
| Sorghum | 0 | 0 | 3C,9H | 4G |
| Sugar beet | 6G | 3C,8G | 3C,6G | 1C,1H |
| Cotton | 5G | 9G | 5C,9G | 2G |
| PREEMERGENCE | | | | |
| Morningglory | 3G | 0 | 9G | 8G |
| Cocklebur | 3G | 3G | 5H | — |
| Velvetleaf | 5G | 5G | 5C,9G | 2H |
| Nutsedge | 0 | 3G | 9G | 3G |
| Crabgrass | 0 | 2G | 2G | 2G |
| Barnyardgrass | 1C | 0 | 3C,8H | 1H |
| Cheatgrass | 7G | 8G | 9H | 3G |
| Wild Oats | 3G | 0 | 3C,7G | 2C,5G |
| Wheat | 4G | 0 | 3C,9H | 2C,8G |
| Corn | 7G | 7G | 2C,9G | 2C,5G |
| Soybean | 1C | 0 | 2C,5H | 2H |
| Rice | 2C,8H | 7H | 10E | 3C,8H |
| Sorghum | 3C,9H | 5G | 9H | 3C,6G |

TABLE A-continued

| | Cmpd. 16 | Cmpd. 17 | Cmpd. 18 | Cmpd. 19 |
|---|---|---|---|---|
| Sugar beet | 8G | 8G | 7G | — |
| Cotton | 0 | 0 | 8G | 0 |
| Rate kg/ha | 2 | 0.05 | 0.05 | 0.05 |
| POSTEMERGENCE | | | | |
| Morningglory | 2C,7G | 3C,7G | 10C | 10C |
| Cocklebur | 2C,7G | 3C,8G | 10C | 10C |
| Velvetleaf | 2C,6G | 3C,8H | 10C | 10C |
| Nutsedge | 2G | 4G | 3C,8G | 5C,9G |
| Crabgrass | 3C | 2C,4G | 3C,5G | 4G |
| Barnyardgrass | 2C,5H | 3C,6H | 3C,9H | 4C,9H |
| Cheatgrass | 5G | 5G | 2C,8G | 3C,9G |
| Wild Oats | 0 | 2C | 3C,8G | 3C,9G |
| Wheat | 0 | 5G | 9G | 2C,9G |
| Corn | 2H | 1C,4G | 3C,9H | 3C,9H |
| Soybean | 4C,9G | 3H,4G | 5C,9G | 5C,9G |
| Rice | 5C,9G | 4C,9G | 5C,9G | 9C |
| Sorghum | 2C,3H | 3C,7G | 4C,9H | 9H |
| Sugar beet | 5C,9G | 2C,3G | 3C,7G | 4C,9G |
| Cotton | 7G | 4C,8G | 4C,9G | 4C,9G |
| PREEMERGENCE | | | | |
| Morningglory | 5G | 3G | 9G | 9G |
| Cocklebur | 2G | 2C | 9H | 9H |
| Velvetleaf | 5G | 2C | 9C | 5C,9G |
| Nutsedge | 5G | 0 | 4G | 4C,8G |
| Crabgrass | 0 | 0 | 5G | 2G |
| Barnyardgrass | 1C | 1C | 5G | 3C,7H |
| Cheatgrass | 7G | 0 | 9H | 8H |
| Wild Oats | 2G | 0 | 3C,8G | 3C,8H |
| Wheat | 4G | 0 | 3C,8H | 9H |
| Corn | 7G | 0 | 3C,9G | 2C,8G |
| Soybean | 2H | 2C,2H | 3C,6H | 3C,6H |
| Rice | 7H | 2G | 3C,9H | 9H |
| Sorghum | 3C,4G | 2C | 3C,9H | 5C,9H |
| Sugar beet | 7G | 8G | 5C,9G | 5C,9G |
| Cotton | 5G | 0 | 9G | 9G |

| | Cmpd. 20 | Cmpd. 21 | Cmpd. 22 | Cmpd. 23 |
|---|---|---|---|---|
| Rate kg/ha | 0.05 | 0.05 | 0.05 | 0.05 |
| POSTEMERGENCE | | | | |
| Morningglory | 4C,9H | 10C | 3C,8G | 9C |
| Cocklebur | 4C,9G | 9C | 3C,9H | 10C |
| Velvetleaf | 5C,9H | 3C,8H | 3C,8H | 10C |
| Nutsedge | 4G | 2G | 0 | 4C,9G |
| Crabgrass | 4G | 2G | 2G | 4C,8G |
| Barnyardgrass | 3C,5H | 2C,5H | 2H | 4C,9H |
| Cheatgrass | 2C | 2G | 0 | 2C,9G |
| Wild Oats | 2C,6G | 2C,6G | 0 | 4C,9G |
| Wheat | 0 | 0 | 0 | 9G |
| Corn | 3C,9G | 3C,9H | 1C,2H | 4C,9G |
| Soybean | 5C,9G | 5C,9G | 0 | 4C,9G |
| Rice | 5C,9G | 5C,9G | 4C,9G | 6C,9G |
| Sorghum | 3C,9H | 4C,9H | 2C,6G | 3C,9G |
| Sugar beet | 9C | 9C | 2C,6H | 5C,9G |
| Cotton | 3C,9H | 4C,9G | 3C,9G | 5C,9H |
| PREEMERGENCE | | | | |
| Morningglory | 3C,8H | 5C,9G | 3C,7H | 9G |
| Cocklebur | 3C,4H | 9H | — | 9H |
| Velvetleaf | 3C,4H | 4C,4H | 0 | 4C,9G |
| Nutsedge | 0 | 4G | 0 | 4C,9G |
| Crabgrass | 4G | 5G | 2G | 2C,5G |
| Barnyardgrass | 1C | 1C | 0 | 4C,9H |
| Cheatgrass | 0 | 2C,5G | 0 | 4C,9H |
| Wild Oats | 0 | 0 | 0 | 4C,9G |
| Wheat | 0 | 0 | 0 | 4C,9H |
| Corn | 3C,7G | 3C,7G | 0 | 2C,9G |
| Soybean | 3C,7H | 3C,6G | 0 | 3C,7H |
| Rice | 6G | 2C,7G | 5G | 5C,9H |
| Sorghum | 3C,8H | 3C,7H | 2C | 10H |
| Sugar beet | 5C,9G | 5C,9G | 5G | 5C,9G |
| Cotton | 2C,8G | 2C,8G | 5G | 9G |

| | Cmpd. 24 | Cmpd. 25 | Compound 26 | |
|---|---|---|---|---|
| Rate kg/ha | 0.05 | 0.05 | 0.05 | 0.01 |
| POSTEMERGENCE | | | | |
| Morningglory | 4C,9G | 9C | 10C | 10C |
| Cocklebur | 5C,9G | 9C | 9C | 9G |
| Velvetleaf | 4C,9G | 5C,9H | 9C | 9C |
| Nutsedge | 4G | 0 | 9C | 4C,9G |
| Crabgrass | 5G | 6G | 4C,9G | 2C,7G |
| Barnyardgrass | 3C,8H | 4C,9H | 9C | 9C |
| Cheatgrass | 2C,5G | 2G | 9C | 9G |
| Wild Oats | 9G | 2C,5G | 6C,9G | 4C,9G |
| Wheat | 3G | 5G | 9C | 4C,9G |
| Corn | 4C,9H | 3C,9H | 4U,9G | 4C,8H |
| Soybean | 5C,9G | 5C,9G | 4C,9G | 3C,8G |
| Rice | 5C,9G | 5C,9G | 9C | 9C |
| Sorghum | 3C,9H | 2C,9H | 6C,9G | 3U,9G |
| Sugar beet | 9C | 9C | 9C | 9C |
| Cotton | 5C,9H | 4C,9H | 10C | 9C |
| PREEMERGENCE | | | | |
| Morningglory | 9G | 2C,8H | 9G | 4C,9G |
| Cocklebur | 8H | 8H | 9H | 8G |
| Velvetleaf | 3C,5H | 2C,5G | 5C,9G | 4C,9G |
| Nutsedge | 5G | 0 | 10E | 5C,9G |
| Crabgrass | 0 | 0 | 3C,8G | 5G |
| Barnyardgrass | 3C,3H | 2C | 9H | 5C,9H |
| Cheatgrass | 0 | 0 | 9H | 8G |
| Wild Oats | 1C | 0 | 5C,9G | 4C,8G |
| Wheat | 0 | 0 | 10H | 5C,9H |
| Corn | 3C,7G | 3C,8H | 2U,9G | 8G |
| Soybean | 3C,6H | 3C,6H | 2C,8G | 3G |
| Rice | 4C,9H | 2C,8H | 10E | 5C,9H |
| Sorghum | 4C,8G | 2C,8H | 10E | 9H |
| Sugar beet | 5C,9G | 4C,8G | 4C,9G | 8G |
| Cotton | 3C,8G | 2C,8G | 9G | 9G |

| | Cmpd. 27 | Cmpd. 28 |
|---|---|---|
| Rate kg/ha | 0.05 | 0.05 |
| POSTEMERGENCE | | |
| Morningglory | 10C | 4C,9G |
| Cocklebur | 9C | 5C,9G |
| Velvetleaf | 9C | 4C,8H |
| Nutsedge | 9C | 2C,6G |
| Crabgrass | 2C,8G | 4G |
| Barnyardgrass | 9C | 2C,5H |
| Cheatgrass | 9C | 6G |
| Wild Oats | 4C,8G | 0 |
| Wheat | 4C,8G | 5G |
| Corn | 7U,9C | 3C,8H |
| Soybean | 6C,9G | 1H |
| Rice | 6C,9G | 5C,9G |
| Sorghum | 6C,9G | 4C,9H |
| Sugar beet | 9C | 4C,8G |
| Cotton | 10C | 4C,9G |
| PREEMERGENCE | | |
| Morningglory | 9G | 8H |
| Cocklebur | 9H | 8H |
| Velvetleaf | 5C,9G | 7G |
| Nutsedge | 10E | 5G |
| Crabgrass | 5G | 0 |
| Barnyardgrass | 3C,9H | 0 |
| Cheatgrass | 4C,9H | 0 |
| Wild Oats | 3C,9G | 0 |
| Wheat | 3C,9H | 0 |
| Corn | 3C,9G | 2C,6G |
| Soybean | 2H,6G | 2G |
| Rice | 10E | 3C,9H |
| Sorghum | 4C,9H | 3C,8H |
| Sugar beet | 9G | 4C,9G |
| Cotton | 8G | 8G |

TEST B

Postemergence

Two round pans (25 cm diameter by 12.5 cm deep) were filled with Sassafras sandy loam soil. One pan was planted with blackgrass (*Alopecurus myosuroides*), sugarbeets, nutsedge (*Cyperus rotundus*) tubers, rape (*Brassica napus*), crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn soybean, wild oats (*Avena fatua*), cocklebur (*Xanthium pensylvanicum*), morningglory (*Ipomoea hederacea*), johnsongrass (*Sorghum halepense*) and barnyardgrass (*Echino-

*chloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with Sassafras sandy loam soil. One pan was planted with blackgrass, sugarbeets, nutsedge tubers, rape, crabgrass, sicklepod, teaweed, jimsonweed velvetleaf, and giant foxtail. The other pan was planted with wheat, cotton rice, corn, soybeans, wild oats, cocklebur, morningglory, johnsongrass and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 100 where 0=no effect and 100=complete control. A dash (-) response means no test.

Response ratings are contained in Table B.

TABLE B

| | Compound 2 | | | |
|---|---|---|---|---|
| Rate g/ha | 0.004 | 0.016 | 0.062 | 0.250 |
| POSTEMERGENCE | | | | |
| Nutsedge | — | 30 | 80 | — |
| Crabgrass | — | 0 | 0 | — |
| Cassia | — | 0 | 80 | — |
| Teaweed | — | 0 | 0 | — |
| Rape | — | 80 | 90 | — |
| Jimsonweed | — | 0 | 50 | — |
| Velvetleaf | — | 70 | 90 | — |
| Blackgrass | — | 60 | 80 | — |
| Rice | — | 50 | 70 | — |
| Sugar Beet | — | 0 | 20 | — |
| Wheat | — | 0 | 0 | — |
| Wild Oats | — | 0 | 0 | — |
| Cocklebur | — | 60 | 80 | — |
| Morningglory | — | 30 | 90 | — |
| Cotton | — | 40 | 80 | — |
| Johnsongrass | — | 20 | 90 | — |
| Barnyardgrass | — | 0 | 60 | — |
| Giant Foxtail | — | 0 | 0 | — |
| Soybean | — | 90 | 90 | — |
| Corn | — | 50 | 90 | — |
| PREEMERGENCE | | | | |
| Nutsedge | — | 40 | 80 | 90 |
| Crabgrass | — | 0 | 20 | 60 |
| Cassia | — | 0 | 20 | 60 |
| Teaweed | — | 30 | 70 | 90 |
| Rape | — | 80 | 90 | 100 |
| Jimsonweed | — | 70 | 90 | 100 |
| Velvetleaf | — | 50 | 90 | 100 |
| Blackgrass | — | 70 | 90 | 100 |
| Rice | — | 80 | 90 | 100 |
| Sugar Beet | — | 50 | 90 | 100 |
| Wheat | — | 0 | 20 | 60 |
| Wild Oats | — | 0 | 70 | 90 |
| Cocklebur | — | 40 | 60 | 80 |
| Morningglory | — | 40 | 70 | 80 |
| Cotton | — | 10 | 70 | 80 |
| Johnsongrass | — | 80 | 90 | 90 |
| Barnyardgrass | — | 60 | 90 | 90 |
| Giant Foxtail | — | 0 | 40 | 70 |
| Soybean | — | 50 | 90 | 90 |
| Corn | — | 50 | 80 | 90 |

| | Compound 3 | | | |
|---|---|---|---|---|
| Rate g/ha | 0.004 | 0.016 | 0.062 | 0.250 |
| POSTEMERGENCE | | | | |
| Nutsedge | — | 80 | 90 | — |
| Crabgrass | 0 | 0 | 0 | — |
| Cassia | 50 | 90 | 90 | — |
| Teaweed | 0 | 0 | 60 | — |
| Rape | 80 | 90 | 100 | — |

TABLE B-continued

| | | | | |
|---|---|---|---|---|
| Jimsonweed | 0 | 30 | 80 | — |
| Velvetleaf | 60 | 90 | 100 | — |
| Blackgrass | 0 | 20 | 60 | — |
| Rice | 0 | 20 | 60 | — |
| Sugar Beet | 0 | 0 | 30 | — |
| Wheat | 0 | 0 | 0 | — |
| Wild Oats | 0 | 0 | 0 | — |
| Cocklebur | 30 | 70 | 90 | — |
| Morningglory | 50 | 90 | 100 | — |
| Cotton | 0 | 50 | 80 | — |
| Johnsongrass | 0 | 50 | 80 | — |
| Barnyardgrass | 0 | 0 | 20 | — |
| Giant Foxtail | 0 | 0 | 0 | — |
| Soybean | 50 | 80 | 90 | — |
| Corn | 30 | 60 | 70 | — |
| PREEMERGENCE | | | | |
| Nutsedge | — | 70 | 90 | 100 |
| Crabgrass | — | 0 | 0 | 20 |
| Cassia | — | 0 | 20 | 80 |
| Teaweed | — | 0 | 30 | 70 |
| Rape | — | 70 | 90 | 100 |
| Jimsonweed | — | 30 | 70 | 90 |
| Velvetleaf | — | 40 | 60 | 80 |
| Blackgrass | — | 70 | 80 | 90 |
| Rice | — | 70 | 90 | 100 |
| Sugar Beet | — | 30 | 40 | 100 |
| Wheat | — | 0 | 20 | 70 |
| Wild Oats | — | 20 | 60 | 80 |
| Cocklebur | — | 0 | 60 | 80 |
| Morningglory | — | 20 | 70 | 80 |
| Cotton | — | 0 | 0 | 60 |
| Johnsongrass | — | 0 | 60 | 80 |
| Barnyardgrass | — | 0 | 40 | 90 |
| Giant Foxtail | — | 0 | 0 | 20 |
| Soybean | — | 20 | 90 | 100 |
| Corn | — | 20 | 90 | 100 |

| | Compound 5 | | | |
|---|---|---|---|---|
| Rate g/ha | 0.004 | 0.016 | 0.062 | 0.250 |
| POSTEMERGENCE | | | | |
| Nutsedge | 0 | — | 50 | — |
| Crabgrass | 0 | 0 | 0 | — |
| Cassia | 20 | 60 | 80 | — |
| Teaweed | 0 | 0 | 30 | — |
| Rape | 90 | 90 | 100 | — |
| Jimsonweed | 60 | 70 | 80 | — |
| Velvetleaf | — | — | — | — |
| Blackgrass | 0 | 20 | 70 | — |
| Rice | 0 | 0 | 0 | — |
| Sugar Beet | 50 | 90 | 90 | — |
| Wheat | 0 | 0 | 0 | — |
| Wild Oats | 0 | 0 | 0 | — |
| Cocklebur | 80 | 90 | 100 | — |
| Morningglory | 70 | 80 | 90 | — |
| Cotton | 50 | 80 | 90 | — |
| Johnsongrass | 0 | 0 | 0 | — |
| Barnyardgrass | 0 | 0 | 0 | — |
| Giant Foxtail | 0 | 0 | 0 | — |
| Soybean | 90 | 90 | 100 | — |
| Corn | 0 | 30 | 50 | — |
| PREEMERGENCE | | | | |
| Nutsedge | — | 20 | 70 | 90 |
| Crabgrass | — | 0 | 0 | 50 |
| Cassia | — | 40 | 90 | 90 |
| Teaweed | — | 40 | 80 | 90 |
| Rape | — | 80 | 90 | 100 |
| Jimsonweed | — | 60 | 90 | 100 |
| Velvetleaf | — | 40 | 80 | 100 |
| Blackgrass | — | 50 | 70 | 90 |
| Rice | — | 50 | 90 | 100 |
| Sugar Beet | — | 60 | 90 | 100 |
| Wheat | — | 0 | 0 | 0 |
| Wild Oats | — | 0 | 0 | 60 |
| Cocklebur | — | 70 | 90 | 90 |
| Morningglory | — | 40 | 90 | 90 |
| Cotton | — | 0 | 80 | 90 |
| Johnsongrass | — | 0 | 0 | 30 |
| Barnyardgrass | — | 0 | 0 | 70 |
| Giant Foxtail | — | 0 | 0 | 20 |
| Soybean | — | 80 | 100 | 100 |
| Corn | — | 0 | 80 | 100 |

TABLE B-continued

| | Compound 6 | | | |
|---|---|---|---|---|
| Rate g/ha | 0.001 | 0.004 | 0.016 | 0.062 |
| POSTEMERGENCE | | | | |
| Nutsedge | 0 | 0 | 0 | 40 |
| Crabgrass | 0 | 0 | 0 | 0 |
| Cassia | 0 | 80 | 80 | 90 |
| Teaweed | 0 | 0 | 0 | 0 |
| Rape | 60 | 90 | 100 | 100 |
| Jimsonweed | 20 | 60 | 80 | 80 |
| Velvetleaf | 0 | 0 | — | 100 |
| Blackgrass | 0 | 0 | 0 | 0 |
| Rice | 0 | 0 | 0 | 0 |
| Sugar Beet | 40 | 90 | 90 | 100 |
| Wheat | 0 | 0 | 0 | 0 |
| Wild Oats | 0 | 0 | 0 | 0 |
| Cocklebur | 40 | 90 | 100 | 100 |
| Morningglory | 70 | 90 | 100 | 100 |
| Cotton | 50 | 90 | 90 | 100 |
| Johnsongrass | 0 | 0 | 0 | 20 |
| Barnyardgrass | 0 | 0 | 0 | 0 |
| Giant Foxtail | 0 | 0 | 0 | 0 |
| Soybean | 90 | 90 | 100 | 90 |
| Corn | 0 | 0 | 80 | 80 |
| Rate g/ha | 0.001 | 0.016 | 0.062 | 0.250 |
| PREEMERGENCE | | | | |
| Nutsedge | — | 60 | 90 | 100 |
| Crabgrass | — | 0 | 0 | 40 |
| Cassia | — | 50 | 90 | 90 |
| Teaweed | — | 50 | 70 | 90 |
| Rape | — | 90 | 90 | 100 |
| Jimsonweed | — | 80 | 90 | 90 |
| Velvetleaf | — | 50 | 80 | 90 |
| Blackgrass | — | 50 | 70 | 80 |
| Rice | — | 70 | 90 | 100 |
| Sugar Beet | — | 70 | 80 | 100 |
| Wheat | — | 0 | 0 | 0 |
| Wild Oats | — | 0 | 0 | 30 |
| Cocklebur | — | 70 | 90 | 90 |
| Morningglory | — | 50 | 80 | 90 |
| Cotton | — | 60 | 80 | 90 |
| Johnsongrass | — | 0 | 0 | 40 |
| Barnyardgrass | — | 0 | 0 | 50 |
| Giant Foxtail | — | 0 | 0 | 40 |
| Soybean | — | 60 | 90 | 100 |
| Corn | — | 20 | 90 | 100 |

| | Compound 7 | | | |
|---|---|---|---|---|
| Rate g/ha | 0.001 | 0.004 | 0.016 | 0.062 |
| POSTEMERGENCE | | | | |
| Nutsedge | 0 | 0 | 0 | 30 |
| Crabgrass | 0 | 0 | 0 | 0 |
| Cassia | 0 | 0 | 20 | 50 |
| Teaweed | 0 | 0 | 0 | 30 |
| Rape | 90 | 100 | 100 | 100 |
| Jimsonweed | 0 | 0 | 20 | 50 |
| Velvetleaf | 0 | 20 | 70 | 100 |
| Blackgrass | 0 | 20 | 60 | 80 |
| Rice | 0 | 0 | 40 | 90 |
| Sugar Beet | 0 | 50 | 100 | 100 |
| Wheat | 0 | 0 | 0 | 0 |
| Wild Oats | 0 | 0 | 0 | 0 |
| Cocklebur | 0 | 0 | 30 | 60 |
| Morningglory | 0 | 0 | 50 | 70 |
| Cotton | 0 | 20 | 50 | 90 |
| Johnsongrass | 0 | 0 | 0 | 30 |
| Barnyardgrass | 0 | 0 | 0 | 20 |
| Giant Foxtail | 0 | 0 | 0 | 0 |
| Corn | 20 | 50 | 70 | 100 |
| Soybean | 30 | 80 | 100 | 100 |
| Rate g/ha | 0.001 | 0.016 | 0.062 | 0.250 |
| PREEMERGENCE | | | | |
| Nutsedge | — | 0 | 70 | 90 |
| Crabgrass | — | 0 | 20 | 60 |
| Cassia | — | 0 | 20 | 60 |
| Teaweed | — | 0 | 30 | 60 |
| Rape | — | 0 | 60 | 90 |
| Jimsonweed | — | 60 | 60 | 80 |
| Velvetleaf | — | 30 | 60 | 90 |
| Blackgrass | — | 70 | 80 | 80 |
| Rice | — | 80 | 90 | 90 |
| Sugar Beet | — | 0 | 0 | 80 |
| Wheat | — | 0 | 0 | 0 |
| Wild Oats | — | 0 | 50 | 60 |
| Cocklebur | — | 0 | 20 | 80 |
| Morningglory | — | 0 | 50 | 80 |
| Cotton | — | 0 | 20 | 40 |
| Johnsongrass | — | 50 | 70 | 80 |
| Barnyardgrass | — | 0 | 20 | 70 |
| Giant Foxtail | — | 0 | 20 | 90 |
| Corn | — | 0 | 20 | 60 |
| Soybean | — | 0 | 50 | 70 |

What is claimed is:

1. A compound of the formula

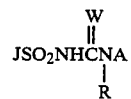

wherein
W is O or S;
J is

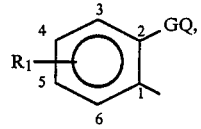

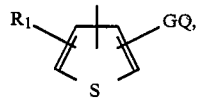

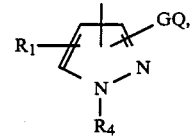

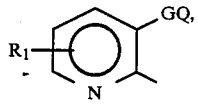

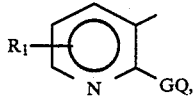

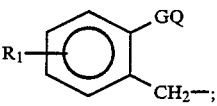

Q is

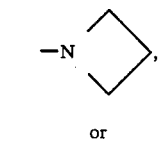

or

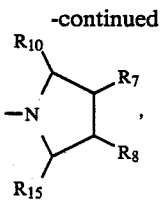

G is a C$_1$-C$_3$ alkyl radical in which one of the carbons must be substituted with R$_2$ and/or R$_3$, and the remaining carbon atoms may optionally be substituted with 1 or 2 substituents selected from CH$_3$, F and Cl;

R is H or CH$_3$;

R$_1$ is H, C$_1$-C$_3$ alkyl, C$_1$-C$_3$ haloalkyl, halogen, nitro, C$_1$-C$_3$ alkoxy, SO$_2$NR$^I$R$^{II}$, C$_1$-C$_3$ alkylthio, C$_1$-C$_3$ alkylsulfinyl, C$_1$-C$_3$ alkylsulfonyl, CO$_2$R$^{III}$, CH$_2$OCH$_3$, CH$_2$SCH$_3$, CH$_2$CN, NH$_2$, NHCH$_3$ or N(CH$_3$)$_2$;

R$_2$ is OH, OCH$_3$ or OC$_2$H$_5$;

R$_3$ is OCH$_3$ or OC$_2$H$_5$; or

R$_2$ and R$_3$ can be taken together to form a carbonyl group, or the 5- or 6-membered ring ketal or thioketal thereof;

R$^I$ is H, C$_1$-C$_4$ alkyl, C$_2$-C$_3$ cyanoalkyl, methoxy, or ethoxy;

R$^{II}$ is H, C$_1$-C$_4$ alkyl or C$_3$-C$_4$ alkenyl; or

R$^I$ and R$^{II}$ may be taken together as —(CH$_2$)$_3$—, —(CH$_2$)$_4$—, —(CH$_2$)$_5$— or —CH$_2$CH$_2$OCH$_2$CH$_2$—;

R$^{III}$ is C$_1$-C$_4$ alkyl, C$_3$-C$_4$ alkenyl, C$_3$-C$_4$ alkynyl, C$_3$-C$_4$ haloalkyl, C$_2$-C$_3$ cyanoalkyl, C$_5$-C$_6$ cycloalkyl, C$_4$-C$_7$ cycloalkylalkyl or C$_2$-C$_4$ alkoxyalkyl;

R$_7$ and R$_8$ are independently H, CH$_3$, Cl or Br;

R$_{10}$ and R$_{15}$ are independently H or CH$_3$;

A is

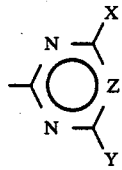 A-1

X is H, C$_1$-C$_4$ alkyl, C$_1$-C$_4$ alkoxy, C$_1$-C$_4$ haloalkoxy, C$_1$-C$_4$ haloalkyl, C$_1$-C$_4$ haloalkylthio, C$_1$-C$_4$ alkylthio, halogen, C$_2$-C$_5$ alkoxyalkyl, C$_2$-C$_5$ alkoxyalkoxy, amino, C$_1$-C$_3$ alkylamino or di(C$_1$-C$_3$ alkyl)amino;

Y is H, C$_1$-C$_4$ alkyl, C$_1$-C$_4$ alkoxy, C$_1$-C$_4$ haloalkoxy, C$_1$-C$_4$ haloalkylthio, C$_1$-C$_4$ alkylthio, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$-C$_4$ alkenyloxy, C$_3$-C$_4$ alkynyloxy, C$_2$-C$_5$ alkylthioalkyl, C$_1$-C$_4$ haloalkyl, C$_3$-C$_5$ cycloalkyl, C$_2$-C$_4$ alkynyl, C(O)R$_4$,

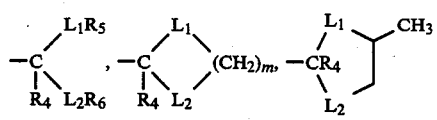

or N(OCH$_3$)CH$_3$;

m is 2 or 3;

L$_1$ and L$_2$ are independently O or S;

R$_5$ and R$_6$ are independently C$_1$-C$_2$ alkyl;

R$_4$ is H or CH$_3$; and

Z is CH;

and their agriculturally suitable salts; provided that
(a) when X is Cl, F, Br, or I, Y is OCH$_3$, OCH$_2$CH$_3$, N(OCH$_3$)CH$_3$, NHCH$_3$, N(CH$_3$)$_2$ or OCF$_2$H;
(b) when J is J-2 or J-3, then GQ and the sulfonylurea bridge must be on adjacent carbon atoms;
(c) when Q is bonded to G through nitrogen, then the adjacent carbon atom of G cannot be substituted with OH, F or Cl;
(d) when G is C$_1$ alkyl in the form of a carbonyl group, then Q is other than

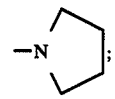

(e) when the total number of carbon atoms of X and Y is greater than four, then the total number of carbon atoms of R$_1$ and GQ must be less than or equal to ten;
(f) when W is S, then R is H, and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$ or CH(OCH$_3$)$_2$; and
(g) when R$_3$ is OCH$_3$ or OC$_2$H$_5$, the R$_2$ is other than OH.

2. The compounds of claim 1 wherein
G is a carbonyl group or CHR$_2$; and
R$_1$ is H, C$_1$-C$_3$ alkyl, C$_1$-C$_3$ haloalkyl, halogen, nitro, C$_1$-C$_3$ alkoxy, SO$_2$NR$^I$R$^{II}$, C$_1$-C$_3$ alkylthio, C$_1$-C$_3$ alkylsulfinyl, C$_1$-C$_3$ alkylsulfonyl or CO$_2$R$^{III}$.

3. The compounds of claim 1 wherein W is O and R is H.

4. The compound of claim 3 where G is a carbonyl group, or is a single carbon atom substituted with OH, OCH$_3$ or OC$_2$H$_5$; and R$_1$ is H, CH$_3$, OCH$_3$, SCH$_3$, SO$_2$CH$_3$, F, Cl, Br, NO$_2$, CH$_2$CN, CF$_3$ or OCF$_2$H.

5. The compounds of claim 4 where
X is CH$_3$, OCH$_3$, OCH$_2$CH$_3$, Cl, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br; and
Y is H, C$_1$-C$_3$ alkyl, OCH$_3$, OC$_2$H$_5$, CH$_2$OCH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, SCF$_2$H, C(O)R$_4$,

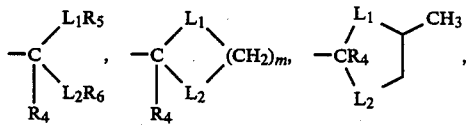

OCF$_2$H, cyclopropyl, C≡CH or C≡CCH$_3$.

6. The compounds of claim 5 where
R$_1$ is H, CH$_3$, OCH$_3$, SCH$_3$ or Cl; and
G is a carbonyl group or a single carbon atom substituted with OH.

7. The compounds of claim 6 where
X is CH$_3$, OCH$_3$, Cl or OCF$_2$H; and
Y is CH$_3$, OCH$_3$, C$_2$H$_5$, CH$_2$OCH$_3$, NHCH$_3$, CH(OCH$_3$)$_2$ or cyclopropyl.

8. The compounds of claim 7 where
J is J-1; and
R$_1$ is in the 5-position.

9. The compounds of claim 7 where J is J-2 and R1 is H.

10. An agriculturally suitable composition for controlling the growth of undesired vegetation comprising an effective amount of a compound of claim 1 and at least one of the following: surfactant, solid or liquid diluent.

11. An agriculturally suitable composition for controlling the growth of undesired vegetation comprising an effective amount of a compound of claim 2 and at least one of the following: surfactant, solid or liquid diluent.

12. An agriculturally suitable composition for controlling the growth of undesired vegetation comprising an effective amount of a compound of claim 3 and at least one of the following: surfactant, solid or liquid diluent.

13. An agriculturally suitable composition for controlling the growth of undesired vegetation comprising an effective amount of a compound of claim 4 and at least one of the following: surfactant, solid or liquid diluent.

14. An agriculturally suitable composition for controlling the growth of undesired vegetation comprising an effective amount of a compound of claim 5 and at least one of the following: surfactant, solid or liquid diluent.

15. An agriculturally suitable composition for controlling the growth of undesired vegetation comprising an effective amount of a compound of claim 6 and at least one of the following: surfactant, solid or liquid diluent.

16. An agriculturally suitable composition for controlling the growth of undesired vegetation comprising an effective amount of a compound of claim 7 and at least one of the following: surfactant, solid or liquid diluent.

17. An agriculturally suitable composition for controlling the growth of undesired vegetation comprising an effective amount of a compound of claim 8 and at least one of the following: surfactant, solid or liquid diluent.

18. An agriculturally suitable composition for controlling the growth of undesired vegetation comprising an effective amount of a compound of claim 9 and at least one of the following: surfactant, solid or liquid diluent.

19. A method for controlling the growth of undesired vegetation which comprises applying to the locus to be protected an effective amount of a compound of claim 1.

20. A method for controlling the growth of undesired vegetation which comprises applying to the locus to be protected an effective amount of a compound of claim 2.

21. A method for controlling the growth of undesired vegetation which comprises applying to the locus to be protected an effective amount of a compound of claim 3.

22. A method for controlling the growth of undesired vegetation which comprises applying to the locus to be protected an effective amount of a compound of claim 4.

23. A method for controlling the growth of undesired vegetation which comprises applying to the locus to be protected an effective amount of a compound of claim 5.

24. A method for controlling the growth of undesired vegetation which comprises applying to the locus to be protected an effective amount of a compound of claim 6.

25. A method for controlling the growth of undesired vegetation which comprises applying to the locus to be protected an effective amount of a compound of claim 7.

26. A method for controlling the growth of undesired vegetation which comprises applying to the locus to be protected an effective amount of a compound of claim 8.

27. A method for controlling the growth of undesired vegetation which comprises applying to the locus to be protected an effective amount of a compound of claim 9.

* * * * *